US012370238B2

(12) United States Patent
Dias et al.

(10) Patent No.: US 12,370,238 B2
(45) **Date of Patent: *Jul. 29, 2025**

(54) COMPOSITION AND METHODS FOR TREATMENT OF PRIMARY CILIARY DYSKINESIA

(71) Applicant: Translate Bio, Inc., Waltham, MA (US)

(72) Inventors: Anusha Dias, Cambridge, MA (US); Darshan Parekh, Cambridge, MA (US); Jeffrey S. Dubins, Cambridge, MA (US); Christian Cobaugh, Cambridge, MA (US); Shrirang Karve, Cambridge, MA (US); Zarna Patel, Cambridge, MA (US); Sara J. Dunaj, Cambridge, MA (US); Frank DeRosa, Cambridge, MA (US); Michael Heartlein, Cambridge, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/062,435

(22) Filed: Dec. 6, 2022

(65) Prior Publication Data

US 2023/0226147 A1 Jul. 20, 2023

Related U.S. Application Data

(63) Continuation of application No. 16/736,417, filed on Jan. 7, 2020, now Pat. No. 11,559,561.

(60) Provisional application No. 62/789,414, filed on Jan. 7, 2019.

(51) Int. Cl.

| | |
|---|---|
| ***A61K 9/127*** | (2025.01) |
| ***A61K 9/00*** | (2006.01) |
| ***A61K 9/1272*** | (2025.01) |
| ***A61K 31/7105*** | (2006.01) |
| ***A61K 31/711*** | (2006.01) |
| ***A61K 38/17*** | (2006.01) |
| ***A61P 11/00*** | (2006.01) |

(52) U.S. Cl.

CPC ........ *A61K 38/1709* (2013.01); *A61K 9/0053* (2013.01); *A61K 9/1272* (2013.01); *A61K 31/7105* (2013.01); *A61K 31/711* (2013.01); *A61P 11/00* (2018.01)

(58) Field of Classification Search

CPC ................ A61K 9/1271; A61K 9/1272; A61K 31/7105; A61K 31/711; A61K 38/1709; A61K 9/0053; A61P 11/00; C07K 14/47

See application file for complete search history.

(56) References Cited

U.S. PATENT DOCUMENTS

| | | | |
|---|---|---|---|
| 11,510,997 B2 | 11/2022 | Lockhart et al. | |
| 11,559,561 B2 * | 1/2023 | Dias | A61K 9/1272 |
| 2009/0068208 A1 * | 3/2009 | Hessel | A61P 11/06 424/184.1 |
| 2020/0215157 A1 | 7/2020 | Dias et al. | |
| 2022/0087935 A1 | 3/2022 | Dias et al. | |

FOREIGN PATENT DOCUMENTS

| | | |
|---|---|---|
| JP | 2019-520422 A | 7/2019 |
| WO | WO 2015/148247 A1 | 10/2015 |
| WO | WO 2016/149508 A1 | 9/2016 |
| WO | WO 2017/205767 A1 | 11/2017 |
| WO | WO 2018/165257 A1 | 9/2018 |
| WO | WO 2019/207060 A1 | 10/2019 |

OTHER PUBLICATIONS

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research Efficacy and Mechanism Evaluation, vol. 3, No. 5, Jul. 2016, pp. 1-210, DOI: 10.3310/eme03050 (240 pages).

Final Office Action for U.S. Appl. No. 16/736,417 dated May 20, 2022 (8 pages).

Hornef et al., "DNAH5 Mutations Are a Common Cause of Primary Ciliary Dyskinesia with Outer Dynein Arm Defects", American Journal of Respiratory and Critical Care Medicine, vol. 174, No. 2, 2006, pp. 120-126, DOI: 10.1164/rccm.200601-084OC (7 pages).

International Preliminary Report on Patentability for PCT/US2020/012529 dated Jun. 16, 2021 (6 pages).

International Search Report and Written Opinion for PCT/US2020/012529 dated Mar. 30, 2020 (11 pages).

Lai et al., "Gene editing of DNAH11 restores normal cilia motility in primary ciliary dyskinesia", Journal of Medical Genetics, vol. 0, 2016, pp. 1-8, DOI: 10.1136//jmedgenet-2015-103539 (9 pages).

Non-Final Office Action for U.S. Appl. No. 16/736,417 dated Oct. 20, 2021 (10 pages).

Notice of Allowance for U.S. Appl. No. 16/736,417 dated Sep. 8, 2022 (7 pages).

Sequence Alignment: WO 2017/205767, SEQ ID No. 17, vs. U.S. Appl. No. 16/736,417, SEQ ID No. 16, alignment performed Oct. 14, 2021 (23 pages).

(Continued)

*Primary Examiner* — Jeanette M Lieb

(74) *Attorney, Agent, or Firm* — LATHROP GPM LLP; James H. Velema, Esq.

(57) ABSTRACT

The present invention provides, among other things, methods and compositions for treating primary ciliary dyskinesia (PCD) based on mRNA therapy. The compositions used in treatment of PCD comprise an mRNA comprising a dynein axonemal heavy chain 5 (DNAH5) coding sequence and are administered at an effective dose and an administration interval such that at least one symptom or feature of PCD is reduced in intensity, severity, or frequency or has a delayed onset. mRNAs with optimized DNAH5 coding sequences are provided that can be administered without the need for modifying the nucleotides of the mRNA to achieve sustained in vivo function.

16 Claims, 4 Drawing Sheets

Specification includes a Sequence Listing.

(56) References Cited

OTHER PUBLICATIONS

Sequence Alignment: WO 2017/205767, SEQ ID No. 18, vs. U.S. Appl. No. 16/736,417, SEQ ID No. 16, alignment performed Oct. 14, 2021 (23 pages).

Munye et al., "Towards gene therapy for primary ciliary dyskinesia", Cilia, 2012, 1(Suppl 1): p. 109, ePublished Nov. 16, 2012.

U.S. Appl. No. 16/736,417 2020/0215157 U.S. Pat. No. 11,559,561, filed Jan. 7, 2020, Jul. 9, 2020 Jan. 24, 2023, Anusha Dias, Composition and Methods for Treatment of Primary Ciliary Dyskinesia.

U.S. Appl. No. 17/420,346 2022/0087935, filed Jan. 7, 2020 Mar. 24, 2022, Anusha Dias, Composition and Methods for Treatment of Primary Ciliary Dyskinesia.

U.S. Appl. No. 18/062,435 2023/0226147, filed Dec. 6, 2022 Jul. 20, 2023, Anusha Dias, Composition and Methods for Treatment of Primary Ciliary Dyskinesia.

Munye et al., "Minicircle DNA Provides Enhanced and Prolonged Transgene Expression Following Airway Gene Transfer", Science Reports, Mar. 15, 2016, 6:23125.

* cited by examiner

SEQUENCE LISTING

```
Sequence total quantity: 31
SEQ ID NO: 1           moltype = AA  length = 4624
FEATURE                Location/Qualifiers
source                 1..4624
                       mol_type = protein
                       organism = Homo sapiens
SEQUENCE: 1
MFRIGRRQLW KHSVTRVLTQ RLKGEKEAKR ALLDARHNYL FAIVASCLDL NKTEVEDAIL  60
EGNQIERIDQ LFAVGGLRHL MFYYQDVEEA ETGQLGSLGG VNLVSGKIKK PKVFVTEGND  120
VALTGVCVFF IRTDPSKAIT PDNIHQEVSF NMLDAADGGL LNSVRRLLSD IFIPALRATS  180
HGWGELEGLQ DAANIRQEFL SSLEGFVNVL SGAQESLKEK VNLRKCDILE LKTLKEPTDY  240
LTLANNPETL GKIEDCMKVW IKQTEQVLAE NNQLLKEADD VGPRAELEHW KKRLSKFNYL  300
LEQLKSPDVK AVLAVLAAAK SKLLKTWREM DIRITDATNE AKDNVKYLYT LEKCCDPLYS  360
SDPLSMMDAI PTLINAIKMI YSISHYYNTS EKITSLFVKV TNQIISACKA YITNNGTASI  420
WNQPQDVVEE KILSAIKLKQ EYQLCFHKTK QKLKQNPNAK QFDFSEMYIF GKFETFHRRL  480
AKIIDIFTTL KTYSVLQDST IEGLEDMATK YQGIVATIKK KEYNFLDQRK MDFDQDYEEF  540
```

-continued

```
CKQTNDLHNE LRKFMDVTFA KIQNTNQALR MLKKFERLNI PNLGIDDKYQ LILENYGADI  600
DMISKLYTKQ KYDPPLARNQ PPIAGKILWA RQLFHRIQQP MQLFQQHPAV LSTAEAKPII  660
RSYNRMAKVL LEFEVLFHRA WLRQIEEIHV GLEASLLVKA PGTGELFVNF DPQILILFRE  720
TECMAQMGLE VSPLATSLFQ KRDRYKRNFS NMKMMLAEYQ RVKSKIPAAI EQLIVPHLAK  780
VDEALQPGLA ALTWTSLNIE AYLENTFAKI KDLELLLDRV NDLIEFRIDA ILEEMSSTPL  840
CQLPQEEPLT CEEFLQMTKD LCVNGAQILH FKSSLVEEAV NELVNMLLDV EVLSEEESEK  900
ISNENSVNYK NESSAKREEG NFDTLTSSIN ARANALLLTT VTRKKKETEM LGEEARELLS  960
HFNHQNMDAL LKVTRNTLEA IRKRIHSSHT INFRDSNSAS NMKQNSLPIF RASVTLAIPN  1020
IVMAPALEDV QQTLNKAVEC IISVPKGVRQ WSSELLSKKK IQERKMAALQ SNEDSDSDVE  1080
MGENELQDTL EIASVNLPIP VQTKNYYKNV SENKEIVKLV SVLSTIINST KKEVITSMDC  1140
FKRYNHIWQK GKEEAIKTFI TQSPLLSEFE SQILYFQNLE QEINAEPEYV CVGSIALYTA  1200
DLKFALTAET KAWMVVIGRH CNKKYRSEME NIFMLIEEFN KKLNRPIKDL DDIRIAMAAL  1260
KEIREEQISI DFQVGPIEES YALLNRYGLL IAREEIDKVD TLHYAWEKLL ARAGEVQNKL  1320
VSLQPSFKKE LISAVEVFLQ DCHQFYLDYD LNGPMASGLK PQEASDRLIM FQNQFDNIYR  1380
KYITYTGGEE LFGLPATQYP QLLEIKKQLN LLQKIYTLYN SVIETVNSYY DILWSEVNIE  1440
KINNELLEFQ NRCRKLPRAL KDWQAFLDLK KIIDDFSECC PLLEYMASKA MMERHWERIT  1500
TLTGHSLDVG NESFKLRNIM EAPLLKYKEE IEDICISAVK ERDIEQKLKQ VINEWDNKTF  1560
TFGSFKTRGE LLLRGDSTSE IIANMEDSLM LLGSLLSNRY NMPFKAQIQK WVQYLSNSTD  1620
IIESWMTVQN LWIYLEAVFV GGDIAKQLPK EAKRFSNIDK SWVKIMTRAH EVPSVVQCCV  1680
GDETLGQLLP HLLDQLEICQ KSLTGYLEKK RLCFPRFFFV SDPALLEILG QASDSHTIQA  1740
HLLNVFDNIK SVKFHEKIYD RILSISSQEG ETIELDKPVM AEGNVEVWLN SLLEESQSSL  1800
HLVIRQAAAN IQETGFQLTE FLSSFPAQVG LLGIQMIWTR DSEEALRNAK FDKKIMQKTN  1860
QAFLELLNTL IDVTTRDLSS TERVKYETLI TIHVHQRDIF DDLCHMHIKS PMDFEWLKQC  1920
RFYFNEDSDK MMIHITDVAF IYQNEFLGCT DRLVITPLTD RCYITLAQAL GMSMGGAPAG  1980
PAGTGKTETT KDMGRCLGKY VVVFNCSDQM DFRGLGRIFK GLAQSGSWGC FDEFNRIDLP  2040
VLSVAAQQIS IILTCKKEHK KSFIFTDGDN VTMNPEFGLF LTMNPGYAGR QELPENLKIN  2100
FRSVAMMVPD RQIIIRVKLA SCGFIDNVVL ARKFFTLYKL CEEQLSKQVH YDFGLRNILS  2160
VLRTLGAAKR ANPMDTESTI VMRVLRDMNL SKLIDEDEPL FLSLIEDLFP NILLDKAGYP  2220
ELEAAISRQV EEAGLINHPP WKLKVIQLFE TQRVRHGMMT LGPSGAGKTT CIHTLMRAMT  2280
DCGKPHREMR MNPKAITAPQ MFGRLDVATN DWTDGIFSTL WRKTLRAKKG EHIWIILDGP  2340
VDAIWIENLN SVLDDNKTLT LANGDRIPMA PNCKIIFEPH NIDNASPATV SRNGMVFMSS  2400
SILDWSPILE GFLKKRSPQE AEILRQLYTE SFPDLYRFCI QNLEYKMEVL EAFVITQSIN  2460
MLQGLIPLKE QGGEVSQAHL GRLFVFALLW SAGAALELDG RRRLELWLRS RPTGTLELPP  2520
PAGPGDTAFD YYVAPDGTWT HWNTRTQEYL YPSDTTPEYG SILVPNVDNV RTDFLIQTIA  2580
KQGKAVLLIG EQGTAKTVII KGFMSKYDPE CHMIKSLNFS SATTPLMFQR TIESYVDKRM  2640
GTTYGPPAGK KMTVFIDDVN MPIINEWGDQ VTNEIVRQLM EQNGFYNLEK PGEFTSIVDI  2700
QFLAAMIHPG GGRNDIPQRL KRQFSIFNCT LPSEASVDKI FGVIGVGHYC TQRGFSEEVR  2760
DSVTKLVPLT RRLWQMTKIK MLPTPAKFHY VFNLRDLSRV WQGMLNTTSE VIKEPNDLLK  2820
LWKHECKRVI ADRFTVSSDV TWFDKALVSL VEEEFGEEKK LLVDCGIDTY FVDFLRDAPE  2880
AAGETSEEAD AETPKIYEPI ESFSHLKERL NMFLQLYNES IRGAGMDMVF FADAMVHLVK  2940
ISRVIRTPQG NALLVGVGGS GKQSLTRLAS FIAGYVSFQI TLTRSYNTSN LMEDLKVLYR  3000
TAGQQGKGIT FIFTDNEIKD ESFLEYMNNV LSSGEVSNLF ARDEIDEINS DLASVMKKEF  3060
PRCLPTNENL HDYFMSRVRQ NLHIVLCFSP VGEKFRNRAL KFPALISGCT IDWFSRWPKD  3120
ALVAVSEHFL TSYDIDCSLE IKKEVVQCMG SFQDGVAEKC VDYFQRFRRS THVTPKSYLS  3180
FIQGYKFIYG EKHVEVRTLA NRMNTGLEKL KEASESVAAL SKELEAKEKE LQVANDKADM  3240
VLKEVTMKAQ AAEKVKAEVQ KVKDRAQAIV DSISKDKAIA EEKLEAAKPA LEEAEAALQT  3300
IRPSDIATVR TLGRPPHLIM RIMDCVLLLF QRKVSAVKID LEKSCTMPSW QESLKLMTAG  3360
NFLQNLQQFP KDTINEEVIE FLSPYFEMPD YNIETAKRVC GNVAGLCSWT KAMASFFSIN  3420
KEVLPLKANL VVQENRHLLA MQDLQKAQAE LDDKQAELDV VQAEYEQAMT EKQTLLEDAE  3480
RCRHKMQTAS TLISGLAGEK ERWTEQSQEF AAQTKRLVGD VLLATAFLSY SGPFNQEFRD  3540
LLLNDWRKEM KARKIPFGKN LNLSEMLIDA PTISEWNLQG LPNDDLSIQN GIIVTKASRY  3600
PLLIDPQTQG KIWIKNKESR NELQITSLNH KYFRNHLEDS LSLGRPLLIE DVGEELDPAL  3660
DNVLERNFIK TGSTFKVKVG DKEVDVLDGF RLYITTKLPN PAYTPEISAR TSIIDFTVTM  3720
KGLEDQLLGR VILTEKQELE KERTHLMEDV TANKRRMKEL EDNLLYRLTS TQGSLVEDES  3780
LIVVLSNTKR TAEEVTQKLE ISAETEVQIN SAREEYRPVA TRGSILYFLI TEMRLVNEMY  3840
QTSLRQFLGL FDLSLARSVK SPITSKRIAN IIEHMTYEVY KYAARGLYEE HKFLFTLLLT  3900
LKIDIQRNRV KHEEFLTLIK GGASLDLKAC PPKPSKWILD ITWLNLVELS KLRQFSDVLD  3960
QISRNEKMWK IWFDKENPEE EPLPNAYDKS LDCFRRLLLI RSWCPDRTIA QARKYIVDSM  4020
GEKYAEGVIL DLEKTWEESD PRTPLICLLS MGSDPTDSII ALGKRLKIET RYVSMGQGQE  4080
VHARKLLQQT MANGGWALLQ NCHLGLDFMD ELMDIIIETE LVHDAFRLWM TTEAHKQFPI  4140
TLLQMSIKFA NDPPQGLRAG LKRTYSGVSQ DLLDVSSGSQ WKPMLYAVAF LHSTVQERRK  4200
FGALGWNIPY EFNQADFNAT VQFIQNHLDD MDVKKGVSWT TIRYMIGEIQ YGGRVTDDYD  4260
KRLLNTFAKV WFSENMFGPD FSFYQGYNIP KCSTVDNYLQ YIQSLPAYDS PEVFGLHPNA  4320
DITYQSKLAK DVLDTILGIQ PKDTSGGGDE TREAVVARLA DDMLEKLPPD YVPFEVKERL  4380
QKMGPFQPMN IFLRQEIDRM QRVLSLVRST LTELKLAIDG TIIMSENLRD ALDCMFDARI  4440
PAWWKKASWI SSTLGFWFTE LIERNSQFTS WVFNGRPHCF WMTGFFNPQG FLTAMRQEIT  4500
RANKGWALDN MVLCNEVTKW MKDDISAPPT EGVYVYGLYL EGAGWDKRNM KLIESKPKVL  4560
FELMPVIRIY AENNTLRDPR FYSCPIYKKP VRTDLNYIAA VDLRTAQTPE HWVLRGVALL  4620
CDVK                                                              4624
```

```
SEQ ID NO: 2          moltype = RNA  length = 140
FEATURE               Location/Qualifiers
misc_feature          1..140
                      note = Synthetic polynucleotide
source                1..140
                      mol_type = other RNA
                      organism = synthetic construct
SEQUENCE: 2
agacagatcg cctggagacg ccatccacgc tgttttgacc tccatagaag acaccgggac  60
```

```
cgatccagcc tccgcggccg ggaacggtgc attggaacgc ggattccccg tgccaagagt  120
gactcaccgt ccttgacacg                                              140

SEQ ID NO: 3           moltype = RNA  length = 140
FEATURE                Location/Qualifiers
misc_feature           1..140
                       note = Synthetic polynucleotide
source                 1..140
                       mol_type = other RNA
                       organism = synthetic construct
SEQUENCE: 3
ggacagatcg cctggagacg ccatccacgc tgttttgacc tccatagaag acaccgggac  60
cgatccagcc tccgcggccg ggaacggtgc attggaacgc ggattccccg tgccaagagt  120
gactcaccgt ccttgacacg                                              140

SEQ ID NO: 4           moltype = RNA  length = 105
FEATURE                Location/Qualifiers
misc_feature           1..105
                       note = Synthetic polynucleotide
source                 1..105
                       mol_type = other RNA
                       organism = synthetic construct
SEQUENCE: 4
cgggtggcat ccctgtgacc cctccccagt gcctctcctg gccctggaag ttgccactcc  60
agtgcccacc agccttgtcc taataaaatt aagttgcatc aagct                  105

SEQ ID NO: 5           moltype = RNA  length = 105
FEATURE                Location/Qualifiers
misc_feature           1..105
                       note = Synthetic polynucleotide
source                 1..105
                       mol_type = other RNA
                       organism = synthetic construct
SEQUENCE: 5
gggtggcatc cctgtgaccc ctccccagtg cctctcctgg ccctggaagt tgccactcca  60
gtgcccacca gccttgtcct aataaaatta agttgcatca aagct                  105

SEQ ID NO: 6           moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 6
atgttcagaa ttggacgccg ccagctctgg aagcattccg tcacccgggt cctgactcag  60
aggctgaagg gggaaaagga agcgaaacgc gccctgctgg acgcccgcca taactacctc  120
tttgccatcg tggcctcctg cctggacctc aacaagacag aagtcgagga cgccattctc  180
gaagggaacc agattgagcg gatcgaccaa ctcttcgccg tcggaggact tcggcacctc  240
atgttctact accaggacgt ggaggaggca gaaaccggcc agctcggcag cctgggtgga  300
gtgaacctcg tgtcggggaa gattaagaag ccaaaagtgt tcgtgaccga aggaaatgac  360
gtggcactca ccggagtgtg cgtgttcttc attcggacag acccctcgaa ggcgattacc  420
ccagacaata tccaccaaga agtgtcgttc aacatgctgg acgctgcgga tggcgggctg  480
ttgaactccg tgcggcggtt gctgtccgac attttcattc cggccctgcg agctacttcg  540
cacggctggg gcgaactgga gggcttgcag gatgcggcta acattcggca ggagttcctt  600
tcctctctgg aaggcttcgt caacgtcctg tccggcgctc aggagtcact gaaggagaag  660
gtgaacctta gaaaatgcga catcctggag ctcaagaccc tgaaggagcc caccgattac  720
cttaccctgg ccaacaaccc tgaaacactg ggaaagattg aggattgcat gaaggtctgg  780
attaagcaga ctgaacaagt gctggccgaa aacaaccagc tgctgaagga agccgacgat  840
gtggggcctc gcgcggagct tgaacactgg aagaagagac tctcgaagtt caactacctc  900
ctggagcaat tgaagtcccc tgatgtgaag gccgtgctgg ccgtcctggc cgccgccaag  960
tccaagctgc tcaagacctg gagggaaatg gacataagaa ttactgacgc gaccaatgag  1020
gccaaggaca acgtgaaata cttgtacacc ctggaaaagt gctgcgaccc gctctactcc  1080
tccgacccgc tcagcatgat ggacgccatt ccgaccctta tcaacgcgat caagatgatc  1140
tactccattt cccactacta caacacctcc gagaagatta cttcgctgtt cgtcaaggtg  1200
accaaccaga tcatctcagc ctgcaaggcc tacattacca acaacggaac cgcctccatc  1260
tggaaccagc cgcaggacgt ggtggaagaa aaaatccttt ccgccattaa gctcaagcag  1320
gaataccagt tgtgcttcca caagaccaag cagaagctca agcagaaccc taacgccaag  1380
cagttcgact tctccgaaat gtacatcttc ggcaaatttg agacattcca ccgccggctc  1440
gctaagatca ttgacatttt caccacgctc aagacctact ccgtcctgca agactcgacc  1500
attgagggac ttgaggacat ggcgaccaag taccagggca tcgtcgccac catcaagaag  1560
aaggagtaca acttcctcga ccaaaggaag atggacttcg accaggatta cgaggaattc  1620
tgcaaacaga ctaacgacct ccacaacgag ctgcgcaagt tcatggacgt caccttcgcg  1680
aagattcaga acaccaacca agcgctgagg atgcttaaaa agttcgaacg gctcaacatc  1740
cccaacctgg ggatcgatga caagtaccaa ctcatcctgg aaaactacgg cgccgatatc  1800
gacatgatct ccaagctgta taccaagcag aagtacgacc ccccgctggc acgcaaccaa  1860
ccccccattg ccgggaagat tctgtgggcg aggcaactgt tccacagaat tcagcaaccc  1920
atgcaactct tccagcagca ccccgccgtg ctctcgaccg ccgaagccaa acccatcatt  1980
cggtcctaca accgcatggc caaggtcctt ttggagttcg aagtcctgtt ccaccgcgcg  2040
```

-continued

```
tggctccggc agattgagga gattcatgtg gggcttgagg ccagcctgct cgtcaaggct  2100
cccggcactg gagaactgtt cgtgaatttt gacccgcaaa tcctgatcct gttcagggag  2160
acagagtgta tggcccagat gggccttgaa gtgtctccgc tcgccacctc actgttccag  2220
aagcgcgaca gatacaagag aaacttcagc aacatgaaga tgatgctggc cgagtaccag  2280
agagtcaagt ccaagatccc cgcagccatc gagcagctca ttgtgccgca ccttgcgaag  2340
gtcgacgagg cacttcagcc aggactcgcc gccctgactt ggacttccct caacatcgaa  2400
gcctacctgg agaacacctt cgcgaagatc aaagacttgg aactgctgct ggatagagtc  2460
aacgatctga tcgagttcag aattgacgcc atcctggaag aaatgtctag caccccgctc  2520
tgtcaacttc ctcaggaaga acccctcact tgcgaagagt tcctgcagat gactaaggat  2580
ctgtgcgtga atggggccca gatcctgcac ttcaagtcgt ccctggtgga ggaagccgtg  2640
aacgagctgg tcaacatgct cctggacgtc gaggtgctgt ccgaggagga gtcggagaag  2700
attagcaacg aaaacagcgt gaactacaaa aacgaatcct ccgccaagag agaagaggga  2760
aacttcgaca ccctgacctc ctcgataaat gcgcgggcca acgccctgct cctgaccacc  2820
gtcactcgga agaaaaagga aactgagatg ctgggcgaag aggcccggga gctgctctcc  2880
cacttcaacc accaaaacat ggacgccctg ctcaaggtga cccgcaacac cctggaggcc  2940
attcgaaagc ggattcattc ctcccacacg attaacttcc gggacagcaa ctccgcgtcc  3000
aacatgaagc agaactccct cccaatcttc agggcttcgg tgaccctcgc cattcccaac  3060
atcgtgatgg cgcctgccct cgaggacgtg cagcagacgc tgaacaaggc agtcgagtgc  3120
attatctccg tgcccaaggg cgtgcgccag tggtccagcg agttgcttag caagaaaaag  3180
atccaagagc gcaagatggc cgccctgcaa tcaaacgaag attcggactc cgacgtggaa  3240
atgggagaaa acgaactgca ggacaccctc gagatcgcct ccgtgaactt gcccatcccg  3300
gtgcaaacca agaactacta taagaacgtg tccgaaaaca aggaaatcgt caagctcgtg  3360
agcgtcctct cgaccatcat caactccacc aagaaagagg tgatcacctc catggactgc  3420
ttcaagcgct acaaccacat ctggcagaaa gggaaagaag aggccattaa gaccttcatc  3480
acccagtcac cactgctgtc agagttcgag tcgcagatcc tgtacttcca gaacctcgag  3540
caggaaatca acgcggaacc agaatacgtc tgcgtcggat cgattgccct gtacacggca  3600
gacctgaagt tcgcactcac tgcagagact aaagcctgga tggtcgtgat cgggcgccat  3660
tgcaacaaga agtatagaag cgagatggaa aacatattca tgctgatcga ggaattcaac  3720
aagaaattga accggcctat caaggacctg gacgacatcc gcatcgccat ggccgccctg  3780
aaggagattc gcgaggaaca aatttcgata gatttccaag tgggacccat tgaggagtcc  3840
tacgccctgc tgaaccggta cggactgctg atcgctagag aggagattga caaggtggac  3900
accctgcact acgcctggga aaagctgctg gccagggccg gtgaagtgca gaacaagctg  3960
gtcagcctcc agccttcctt caagaaggaa ctgatttccg cggtcgaagt gttcctgcaa  4020
gactgccacc agttctacct ggactatgac ctcaacggac cgatggccag cggtctgaaa  4080
ccgcaggagg cctccgaccg cctgatcatg ttccaaaacc agttcgacaa catataccgg  4140
aaatacatca cttacactgg aggagaagaa ctcttcggcc tgcccgccac ccaataccct  4200
caactgctgg agatcaagaa gcagctgaat ctgctgcaaa agatctacac cctctacaac  4260
tccgtcattg agactgtgaa ttcatactac gatatcctgt ggtccgaagt gaacatcgaa  4320
aagattaaca acgagctcct ggagtttcag aacagatgcc ggaagctgcc gcgggccctc  4380
aaggattggc aggctttcct tgacctgaag aagataatcg acgacttctc ggagtgttgc  4440
cccctcctcg agtacatggc ctcgaaggcc atgatggaac gccactggga aaggatcact  4500
actctgactg ggcacagcct ggatgtgggt aacgagtcct tcaagctgcg gaacatcatg  4560
gaggccccgc ttctgaaata caaggaggaa atcgaggaca tctgcatctc ggccgtcaag  4620
gaacgcgaca ttgagcaaaa gctgaagcaa gtgatcaacg agtgggacaa caagactttc  4680
accttcggat ccttcaaaac ccggggagag ctcctgctga gaggagactc cacttccgaa  4740
atcattgcga acatggagga ctccctcatg ctcctcgggt cgctcctgag caacagatac  4800
aacatgccgt tcaaggccca gatccagaag tgggtgcagt acctgtcgaa ctccactgac  4860
atcattgaga gctggatgac tgtgcagaac ctctggatct acttagaggc cgtgttcgtg  4920
ggaggcgaca ttgctaagca gctcccaaag gaagcaaagc gcttcagcaa catcgacaag  4980
tcgtgggtga agattatgac ccgcgcgcat gaggtgccca gcgtggtgca gtgttgcgtg  5040
ggcgatgaaa cgctgggcca gcttctgccg catctgctgg accagctgga gatttgccag  5100
aagtccctca ccggatacct ggagaagaag cggctgtgct tcccccggtt cttcttcgtg  5160
tccgaccctg ccctgctgga aattcttgga caggcctctg acagccatac tatccaggcc  5220
cacctcctga acgtgttcga caacatcaag tccgtgaagt tccacgaaaa gatatatgac  5280
cgcatcctgt cgattagcag ccaggaaggg gaaaccatcg agctcgacaa gcctgtgatg  5340
gccgaaggaa acgtcgaggt gtggctgaac tcgctcctgg aggagagcca gagcagcctg  5400
cacctcgtta taagacaggc cgccgccaac atccaggaga ctggattcca gctcactgaa  5460
ttcttgtcgt ccttccctgc ccaagtgggc ttgctgggaa ttcaaatgat ctggacccgc  5520
gactccgaag aggccctcag gaacgccaag ttcgacaaaa agatcatgca gaaaaccaat  5580
caggcgttcc tggagcttct gaacaccctc attgatgtga ccactaggga cctgtcaagc  5640
accgaacggg tgaagtacga aaccctcatc accatccacg tccatcagcg ggatattttc  5700
gatgacctgt gtcacatgca tatcaagtcc cctatggact tcgaatggct gaagcaatgc  5760
cgcttctact tcaatgagga ctcggacaag atgatgatcc atatcacaga tgtcgccttc  5820
atctaccaga acgaattcct gggatgcacc gaccgcttgg tgatcacccc cctcactgac  5880
cggtgctaca ttaccttggc ccaggccctg ggaatgtcca tgggaggggc gcctgccggg  5940
ccagccggca ccggaaaaac cgaaacaaca aaggacatgg gccgctgcct ggggaagtac  6000
gtggtggtgt tcaattgctc cgatcaaatg gacttcagag gtctggggcg gatcttcaag  6060
ggtctggctc agtccggctc ctggggatgc ttcgacgaat tcaaccggat cgacttgccg  6120
gtgctgagcg tcgccgccca gcagatctcc atcatcctga cctgtaagaa ggaacacaag  6180
aagtcgttca ttttcaccga cggagacaac gtgacgatga acccggagtt cgggctattc  6240
ttgaccatga acccgggtta cgccggccga caagagctgc ccgaaaactt gaagatcaac  6300
ttccgcagcg tggctatgat ggtcccggat cggcagatta ttattagagt gaagctggct  6360
tcgtgcggat tcatcgataa cgtcgtgctg gcccggaagt tcttcacgct gtacaagctc  6420
tgcgaggaac agctgagcaa gcaagtccac tacgacttcg ggctgcgcaa cattctctcc  6480
gtgctgcgca ctctgggagc ggccaagcgg gcgaacccta tggataccga gagcaccatt  6540
gtcatgcgcg tgctccggga catgaacctc tcaaagttga tcgacgagga cgagcctctc  6600
ttcctctccc tgatcgagga cctctttccc aacatcctgc tcgataaggc cgggtacccc  6660
gagctggagg ccgccattag ccgccaggtg gaagaggctg gcctcatcaa ccaccctcct  6720
tggaagttga aggtcataca gctgttcgaa actcagcgcg tgcgacatgg catgatgacc  6780
```

-continued

```
ctgggacctt cgggagccgg caaaactact tgcatccaca ccctgatgcg ggctatgacc  6840
gactgcggga agcctcaccg ggagatgagg atgaacccga aggccatcac cgccccgcaa  6900
atgttcggcc ggctggacgt ggccactaat gattggaccg acgggatctt ctcaaccctc  6960
tggcgcaaaa ccctgcgcgc aaagaaggga gagcacatct ggatcatcct ggatggcccg  7020
gtcgatgcca tctggattga gaacctgaac agcgtgctgg acgacaacaa gactctcact  7080
ctcgcgaacg gcgacagaat tcccatggcc ccgaactgca agatcatttt cgagccacac  7140
aacattgaca acgcctcccc ggctaccgtg tcgagaaacg gaatggtgtt tatgtccagc  7200
tcgatcctcg attggtcccc catcctggaa ggcttcctga agaagaggtc gccgcaagag  7260
gccgaaattt tgagacagct gtacaccgaa tccttcccgg acctgtaccg cttctgcatc  7320
cagaacctcg agtacaagat ggaagtgctg gaggcattcg tgatcactca gagcattaac  7380
atgctgcagg gactcatccc tcttaaggaa caggggggcg aagtctctca ggctcacctc  7440
ggccggctgt tcgtgttcgc cctcctctgg agcgcgggtg cggccctgga gctggatggc  7500
cgccgcagac tcgagctgtg gctgagatcc agacccaccg gaactctcga gttgccccccg  7560
cccgccggcc ccggagatac ggccttcgac tactacgtgg cccccgacgg gacgtggact  7620
cattggaaca cacgcacaca ggaatacctg taccctagcg acaccactcc ggaatacgga  7680
tcgatcctgg tgcccaacgt ggataacgtg aggaccgatt tccttataca aaccatcgcc  7740
aagcaaggaa aggcggtcct cctcatcggg gagcagggga ccgccaagac cgtgatcatt  7800
aagggattca tgtccaagta cgaccccgaa tgccacatga tcaagtctct caactttagc  7860
tccgccacca ccccactgat gttccaacgg actatcgaaa gctacgtcga caagcgcatg  7920
ggaactactt acggccctcc ggcaggaaag aaaatgaccg tgttcatcga cgacgtcaac  7980
atgcccatca ttaacgaatg gggggaccag gtgacgaacg agatcgtgcg ccagctcatg  8040
gaacaaaacg gtttctacaa ccttgagaag cccggagagt ttacttcaat tgtggacatc  8100
cagttcctcg cggcaatgat tcatcccggc ggaggaagaa acgacatccc gcagcgcctc  8160
aaacgccagt tctcgatctt caactgcacg ctgccgtccg aggctagcgt cgacaagata  8220
tttggcgtga ttggtgtggg acattactgc acccagaggg gattctcgga ggaagtgcgg  8280
gacagcgtga ccaagctggt gccgctgact aggcggctct ggcagatgac caagatcaag  8340
atgctcccta cacccgccaa gttccactac gtgttcaatc tgcgcgacct gtcacgcgtg  8400
tggcagggaa tgctgaacac tacctccgaa gtcatcaagg aaccgaacga tctccttaaa  8460
ctttggaagc acgaatgcaa gcgcgtaatc gcagaccggt tcaccgtgag ctccgatgtg  8520
acctggttcg acaaggccct ggtgtccctc gtggaggaag agttcggaga ggaaaagaaa  8580
cttctcgtag actgcggtat agatacgtac ttcgtggact tcctgcgcga cgcccccgaa  8640
gccgccggcg aaacctccga agaagctgac gccgaaacac caaagatata cgagcctatc  8700
gaatccttca gccatctgaa ggagagactc aacatgttcc tgcaattgta taatgagtcc  8760
atccgcggcg ccggcatgga catggtgttc tttgcggatg ccatggtgca cctggtgaag  8820
atctcgcggg tgattcggac tccccagggc aacgcgctgc tcgtgggcgt gggggctcc  8880
gggaagcaga gccttacccg gctggcctcc ttcattgccg gctatgtgag cttccagatc  8940
actctgactc gctcgtacaa taccagcaac ctcatggagg atctcaaggt cctgtaccgg  9000
accgccggac aacagggcaa gggtatcacc ttcatcttta ccgacaacga gatcaaggat  9060
gagtccttcc tggagtacat gaacaacgtg ctgtcctccg gtgaagtctc caacctcttt  9120
gcccgggacg agattgatga gatcaactcg gacttggcgt cagtgatgaa gaaggaattc  9180
ccgaggtgtc tgcctaccaa cgagaacctc cacgactact tcatgagccg ggtgcggcag  9240
aatctgcaca tcgtgctttg cttcagcccg gtgggagaaa agtttcggaa ccgcgccctc  9300
aagttcccgg cccttatctc gggatgcacc attgactggt tttcacggtg gccgaaggat  9360
gctctggtcg cggtgtccga acacttcctt acttcgtacg acattgactg ctccctggaa  9420
atcaagaaag aagtggtcca gtgtatgggc tccttccagg acggtgtcgc cgaaaagtgc  9480
gtggactact tccagcgctt ccgcagatcc acgcacgtga cccctaagtc ctacctgtcg  9540
ttcatccaag gatacaagtt catctacggg gaaaagcacg tcgaagtgcg gaccctggcc  9600
aaccgaatga acacaggact ggaaaagctg aaggaggcgt ccgagtccgt ggctgccctg  9660
agcaaggagc tggaagctaa agagaaggag ctccaggtcg ccaacgacaa ggccgacatg  9720
gtcctgaagg aggtgaccat gaaggctcaa gccgccgaga aagtcaaggc ggaggtgcaa  9780
aaggtcaagg atagagcgca agccatcgtg gactccatct ccaaagacaa ggctattgcg  9840
gaggagaagc tcgaggccgc caagcctgcc ttggaagagg ccgaagccgc tctgcagacc  9900
attcggccga gcgatatagc caccgtgcgg acgctgggac ggcctcctca cctgattatg  9960
cggatcatgg actgtgtgct cctgctgttt caacggaagg tgtccgccgt gaagatcgat  10020
ctcgagaaat cctgcactat gccgagctgg caggagtccc tgaagctgat gaccgccggc  10080
aacttcctcc agaacctcca gcagttccca aaagatacca ttaacgagga ggtgatcgaa  10140
ttcctgagcc cgtacttcga aatgcccgat tacaacatcg aaaccgccaa gagggtgtgc  10200
ggcaacgtgg ctgggctctg ctcgtggact aaggccatgg cctccttctt ctcaatcaac  10260
aaggaagtgc tgcccctgaa ggccaacctc gtggtgcagg aaaatcgcca ccttctcgcc  10320
atgcaggatc tgcagaaggc acaggctgaa ctggacgaca aacaggcaga gctggatgtg  10380
gtgcaggccg agtacgaaca ggccatgacg gagaagcaaa ccctgttgga ggatgcggag  10440
agatgcagac ataagatgca gactgcctcc accctgattt caggcctggc cggagaaaag  10500
gaacgctgga ctgaacaatc ccaggaattc gcggcccaga caaagagact cgtgggagat  10560
gtgctgcttg cgactgcctt tctgagctac tctggaccgt tcaaccagga attccgggac  10620
ctcctgctca acgactggcg caaggagatg aaggcccgga agatcccctt cgggaagaac  10680
ctcaacctga gcgagatgct gatcgacgcc cccaccatct ccgagtggaa cctccaggga  10740
ctgcctaacg acgacctctc cattcagaac ggcatcatcg tgactaaggc gtcccgctac  10800
ccgctgctca ttgaccctca gacccaggga aagatttgga tcaaaaataa ggagtcccgc  10860
aacgagctgc agatcacctc cctgaaccac aagtactttc gcaaccatct ggaagattcc  10920
ctcagcctgg gacggccgct tctgatagag gatgtgggag aagaactgga cccggctctc  10980
gacaacgtcc tggagaggaa cttcatcaag accgggtcca ccttcaaggt gaaggtgggc  11040
gacaaggagg tggacgtcct ggatggattc cgcctgtaca ttaccactaa gctcccaaac  11100
cccgcttaca ctcctgagat cagcgcgcgg accagcatca ttgatttcac cgtgactatg  11160
aagggccttg aggaccagct gctgggtcgc gtgatcttga ccgagaagca ggaacttgaa  11220
aaggaacgca ctcacctcat ggaggacgtg accgccaata agcgccggat gaaggaactg  11280
gaagataact tgctgtacag gcttacttcc actcagggtt ccctggtgga ggacgagtcg  11340
ctgattgtgg tgctgagcaa caccaagcgg actgccgaag aagtgaccca aaaactggag  11400
atctcggcgg aaaccgaggt gcagatcaat agcgcgcggg aggagtaccg gccagtcgca  11460
accagagggt ccatcctgta cttcctgatt accgaaatga ggctggtcaa cgaaatgtac  11520
```

-continued

```
cagacgtccc tgaggcagtt cctggggttg ttcgacctga gccttgcccg ctcggtgaag  11580
tcaccaatca cttccaagag aattgccaac attattgagc acatgaccta cgaggtctat  11640
aagtacgccg cgcggggact gtacgaggaa cacaaattcc tgttcactct gctgctcacc  11700
ctgaaaatcg atattcagcg gaaccgcgtc aagcacgagg agttcctcac cctgattaag  11760
ggaggagcca gcctggacct gaaggcgtgc cctcctaagc cctccaagtg gattcttgac  11820
atcacctggc tgaacctggt ggaactcagc aagttgcggc aattctccga cgtgcttgac  11880
caaatttccc gcaacgagaa gatgtggaag atttggttcg acaaagagaa cccggaggaa  11940
gaacccctgc ctaacgccta cgacaagtcg ctcgattgtt tccggcgcct cctgctgatt  12000
aggagctggt gccctgacag gaccattgcc caagctcgga agtacattgt ggactccatg  12060
ggcgagaagt atgccgaagg ggtcattctc gacctggaga aaacttggga agagtccgac  12120
ccgagaactc cactgatctg cctcctgtcc atgggctccg accccaccga tagcatcatc  12180
gcgctgggaa agcggctgaa gatcgaaact agatacgtga gcatgggaca agggcaggag  12240
gtgcacgcga ggaagctcct ccaacaaacc atggccaacg gaggctgggc cttgctgcag  12300
aactgtcacc tcggactcga ctttatggac gagctgatgg acattatcat cgagactgaa  12360
cttgtgcatg acgccttcag actgtggatg accaccgaag cccacaagca gttcccgatt  12420
acactgctcc aaatgtccat caaattcgca aacgacccgc ctcagggact ccgggccgga  12480
ctgaagcgga cctactcggg agtgtcccaa gacctcctgg atgtgagctc agggagccaa  12540
tggaagccaa tgctctacgc cgtggccttc ctgcattcga ccgtgcagga acggcgcaag  12600
ttcggcgccc tgggctggaa catcccgtac gaattcaacc aggccgactt caatgccacc  12660
gtgcagttca tccagaacca ccttgacgac atggacgtga agaagggagt gtcgtggact  12720
accatccgct acatgattgg cgaaattcag tatggcggcc gcgtgaccga cgactacgat  12780
aagagactcc tcaacacctt cgccaaggtc tggttctcgg aaaacatgtt cggtccagac  12840
ttctccttct accaaggata caacatcccc aagtgctcca ccgtggataa ttaccttcag  12900
tacatccagt cgctgccggc ctacgattca ccggaagtgt tcggactgca tcctaacgcg  12960
gacattactt accagagcaa gctcgccaag gatgtcctgg acactatcct gggaattcag  13020
cctaaggata cttcaggagg gggagatgag actagagagg cggtggtcgc tcgcctggcc  13080
gacgacatgt tggaaaagct cccgcctgat tacgtgccgt tcgaggtgaa agagcggctg  13140
cagaagatgg gacctttcca accgatgaac atttttctga gacaggagat cgaccggatg  13200
cagagagtgc tgtccctcgt gcggtccacc ctgaccgaac tgaagttggc tatcgacggg  13260
accattatta tgtcggagaa cctccgggac gccctggact gcatgttcga tgcgcggatt  13320
ccggcctggt ggaagaaggc atcctggatt tccagcaccc tgggcttctg gtttaccgaa  13380
ctgattgaaa gaaattcgca attcacttcc tgggtgttca acgggcgccc gcactgtttt  13440
tggatgaccg gcttcttcaa cccccaggga tttctcactg cgatgaggca ggaaattacc  13500
cgcgcgaaca agggatgggc cctggataac atggtgctct gcaacgaggt gaccaaatgg  13560
atgaaggatg acatttccgc ccccccgacc gaaggagtct acgtctacgg cctgtacctc  13620
gagggtgccg ggtgggacaa gcgaaatatg aagttgatcg aatcaaagcc aaaggtcttg  13680
ttcgaactga tgccggtgat cagaatatac gccgagaaca acaccttgcg cgaccccagg  13740
ttctactcct gccctatcta caagaagcca gtgcgcaccg acctcaacta catcgccgcc  13800
gtcgacctcc ggactgccca aaccccggaa cactgggtgc tgcgcggtgt ggccctgctc  13860
tgcgatgtca agtag                                                  13875

SEQ ID NO: 7           moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 7
atgttccgaa tcggccggcg ccagctgtgg aagcactcag tgacccgcgt cctgacccag  60
agactgaagg gagaaaagga ggccaaacgg gccctcctgg acgcgcggca caactacctg  120
ttcgctatcg tggcctcgtg tctcgacctc aacaagaccg aggtggaaga tgcaatcctg  180
gagggcaatc aaattgagcg gattgatcag ctgttcgcag tgggcggctt gcggcacctg  240
atgttttact accaagacgt ggaggaggcc gaaactgggc agctgggaag cctgggcgga  300
gtgaacctgg tgtccggcaa aatcaaaaag cccaaggtct ttgtcactga agggaacgac  360
gtggccctca ccggagtgtg cgtgttcttc atccggacgg accctagcaa agccatcacc  420
ccggacaaca tccaccagga agtgtccttt aacatgctgg acgcggccga cgggggcctc  480
cttaactcgg tccggcgcct cctttccgac atcttcatcc cggctctgcg ggctacgtcc  540
cacggttggg gagaactgga aggactgcag gacgccgcta acatccgcca agagttcctc  600
tcatccctcg agggttttgt caatgtgctg tcgggcgccc aggaatcgct gaaggagaag  660
gtgaacctcc gcaagtgcga tattctggag ctcaagaccc tcaaggaacc gactgactac  720
ctcactctgg ccaacaaccc cgaaactctg ggaaaattg aggactgcat gaaggtgtgg  780
atcaagcaga ccgaacaggt cctggccgaa aacaaccagc tgctgaaaga ggccgatgac  840
gtgggacccc gggccgagct ggagcactgg aagaagcgcc tctcaaagtt caactacctt  900
ctcgagcaac tgaagtcccc tgacgtgaag gctgtgctgg cggtgcttgc cgcggctaaa  960
tcaaagctcc tgaaaacctg gagagaaatg gatattagaa tcaccgacgc gaccaatgaa  1020
gcgaaggaca acgtgaagta cctgtacacg ctggaaaaat gctgcgaccc cctctattcc  1080
tccgacccgc tgtccatgat ggatgcaatt cccacccctga tcaacgccat caagatgatc  1140
tactcgattt cacactacta caatacttcc gagaagatca ccagcctgtt cgtcaaggtc  1200
actaaccaaa tcatcagcgc atgcaaggcc tacatcacca acaacggaac cgcgtccatt  1260
tggaaccagc cacaggatgt ggtcgaggaa aagatccttt ccgcaattaa gctcaagcag  1320
gaataccagc tgtgcttcca caagactaag cagaaactga aacaaaaccc gaacgcaaag  1380
cagttcgact ttagcgagat gtacattttc ggaaagttcg aaaccttcca tagacggctg  1440
gctaagatca tcgatatctt caccaccctc aagacctact cggtgttgca ggacagcacc  1500
atcgaaggtc tggaggacat ggcgactaag taccagggaa tcgtcgccac tatcaagaag  1560
aaggagtaca acttcctgga tcagcggaag atggacttcg accaggatta cgaagagttc  1620
tgcaagcaga ccaatgacct ccacaacgag ctgcggaagt tcatggatgt gactttcgcc  1680
aaaattcaga acaccaacca ggcgcttcgg atgctgaaga agttcgaaag gcttaacatc  1740
cccaacctgg gcatcgatga taaataccag ttgatccttg agaactacgg agccgacatc  1800
```

-continued

```
gacatgatta gcaagctgta caccaaacaa aaatacgacc ctcctctggc cagaaaccaa  1860
cctccgattg ctggaaagat tctctgggcc cggcagctgt tccaccgcat ccagcagcct  1920
atgcagctgt ttcaacagca cccggccgtc ctgtccaccg ctgaagccaa gccgatcatc  1980
aggtcctata acaggatggc caaggtgctg ctggagttcg aggtgctgtt ccaccgagcc  2040
tggctgcggc aaattgaaga aatccacgtg ggactggaag cctccctcct ggtgaaggcc  2100
ccagggaccg gcgaactgtt cgtgaatttc gaccctcaga tcctgattct gttccgggaa  2160
accgaatgca tggcccagat gggcctggag gtgtccccc tggcaacctc actgttccaa  2220
aagcgcgaca ggtacaagag gaacttctcc aatatgaaga tgatgctcgc agagtaccag  2280
agagtcaagt ccaagatccc cgcagccatt gagcagctga ttgtcccgca ccttgctaag  2340
gtggacgaag cgctccagcc cggcctcgcc gccctgacct ggacttcctt gaatatcgag  2400
gcgtatctcg aaaacacttt cgctaaaatc aaggacctgg aattgctgct ggacagggtc  2460
aacgatctca tcgagttcag aattgacgcg atcctggagg aaatgtcctc gacccctctg  2520
tgccagcttc ctcaggagga gccactgacc tgtgaggagt tcctgcagat gaccaaggac  2580
ctgtgtgtga acggagccca gatcctccac tttaagagca gcttggtgga agaagccgtg  2640
aacgaattgg tgaacatgct cctggacgtg gaggtgctgt ccgaagagga gtccgagaag  2700
atttcgaacg agaactcagt gaactacaag aacgaatcct cagcgaagag agaggaaggc  2760
aactttgaca ctctgacctc ctcgattaat gcacgggcca acgctctgct gttgaccacc  2820
gtgactcgga aaaagaagga aaccgagatg ctgggtgaag aggcccgcga acttctctcg  2880
cacttcaatc accaaaacat ggacgccctg ttgaaggtca ccaggaacac cctggaagcc  2940
atcaggaaga gaattcactc ctcgcacact atcaacttca gagattcaaa ttccgcatcc  3000
aacatgaagc agaacagcct gccgatcttc cgcgcgagcg tgacccttgc catcccaaac  3060
atcgtgatgg ccccagctct cgaggacgtg cagcagactc tgaacaaagc tgtggaatgc  3120
attatttccg tgcccaaggg agtgagacaa tggtcatccg aactgctgag caagaagaag  3180
atccaagagc gcaagatggc cgcactccag agcaacgagg attccgatag cgacgtggaa  3240
atgggcgaga acgaactgca ggataccctg gagatcgcca gcgtcaacct tcccatcccg  3300
gtgcagacca agaactatta caagaacgtg tcggaaaaca aggaaatcgt gaaactcgtg  3360
tccgtgctct ccactattat caacagcact aagaaggaag tcatcacttc aatggattgt  3420
ttcaagaggt acaaccacat ctggcaaaag ggcaaagaag aagccatcaa gacttttatt  3480
acccaaagcc ccctgctgtc agagttcgag agccagatcc tgtacttcca gaacctggaa  3540
caagaaatca acgccgaacc ggagtacgtg tgcgtgggta gcatcgccct ttacactgct  3600
gacctgaagt tcgcactgac cgcagagact aaagcatgga tggtggtgat cggacggcac  3660
tgcaacaaga agtaccgctc cgaaatggag aacatcttca tgcttatcga ggagttcaac  3720
aagaagctca accggccgat caaggacctg gatgacattc ggattgcgat ggccgccctg  3780
aaagagatta gagaagaaca aatctccatc gatttccaag tcggacccat tgaagaatcc  3840
tacgccctgc tgaaccgcta cggattgctg atcgcccgcg aggaaatcga caaggtggac  3900
accctgcatt acgcctggga aaagctgctg gccagagcag gagaagtgca aaacaagctc  3960
gtgtccctgc agccgtcgtt taagaaagag ctcatttcgg ccgtggaagt gttcctgcag  4020
gactgtcacc agttctatct ggactacgat ctcaatggac ctatggcttc cgggttgaag  4080
ccgcaggaag cctctgaccg cctcattatg ttccagaatc agttcgacaa tatctaccgc  4140
aagtacatta catacaccgg cggagaagaa ctgttcgggc tcccagcgac ccagtacccc  4200
cagctcctcg agatcaaaaa gcagctgaac cttctgcaga aaatctacac tctatacaac  4260
tccgtgatcg aaactgtcaa ttcctactac gatatcctgt ggtcggaagt caacattgag  4320
aagatcaaca atgaactgct cgaattccag aaccgctgca ggaagctgcc gcgggccctc  4380
aaggattggc aggccttcct ggacctgaag aagatcatcg acgacttctc cgaatgttgc  4440
cccctcctgg aatacatggc atccaaggcc atgatggagc ggcactggga aaggattacc  4500
acactcaccg gccactcact ggacgtcggg aacgagtcct tcaagctccg gaacattatg  4560
gaggcccccc tgctgaagta caaggaggag attgaggata tctgcatttc ggccgtgaag  4620
gaaagagaca tagagcagaa gctgaagcaa gtgatcaacg aatgggacaa caagacgttc  4680
actttcggat ccttcaagac gaggggtgaa ctgctgctcc ggggagacag cacctccgag  4740
atcatcgcaa acatggagga ctcgctgatg ctgctggggt ccctgctgtc caaccggtac  4800
aatatgcctt tcaaggccca gattcagaag tgggtccagt acttgagcaa ctcgaccgac  4860
atcatcgagt cctggatgac tgtccaaaac ctgtggatct acctcgaagc ggtgttcgtg  4920
ggaggtgaca ttgccaaaca gctccccaag gaagcgaagc gcttttcgaa cattgacaag  4980
tcctgggtga agatcatgac tcgggctcac gaagtgccgt ccgtcgtcca gtgttgcgtg  5040
ggcgacgaaa ccctgggaca gttgctcccc catctgctgg atcagctcga aatttgccag  5100
aagtcgctga ctggatacct cgagaagaag agattgtgct tcccgagatt cttcttcgtg  5160
tcggacccgg ccctgctgga gatcctgggc caggcctccg atagccacac tattcaagcg  5220
cacctcttga acgtgttcga caatatcaag agcgtgaagt tccacgaaaa gatctatgac  5280
cggatcctgt caattagcag ccaagaagga gaaaccattg aactggacaa gcccgtgatg  5340
gctgagggca acgtggaagt gtggctgaac agcctcttgg aagagtcgca gtcaagcctc  5400
catctggtga tcagacaggc agccgccaac atccaggaaa ccggtttcca actgactgag  5460
ttcctgtcat ccttcccggc tcaagtcggg ctgctcggaa tccagatgat ttggacccgg  5520
gactccgagg aagccctcag gaatgccaag ttcgataaga agatcatgca aaagaccaac  5580
caggcatttt tggagctcct gaacaccctg atcgacgtca caacccggga cctgtccagc  5640
accgagcggg tcaagtacga aaccttgatc accattcacg tgcaccagag agacatcttc  5700
gatgacctgt gtcacatgca catcaagtcc cccatggact tcgaatggct gaagcagtgc  5760
cggttctact ttaacgagga cagcgataag atgatgatcc acatcaccga cgtggccttc  5820
atctaccaaa acgagtttct tggatgcacc gaccgcctgg tcatcacccc cctgacggac  5880
cggtgttaca tcacgctcgc ccaagcactg ggcatgagca tgggcggcgc cccagctgga  5940
cccgcgggaa ctggaaagac tgaaaccacc aaggacatgg gccggtgcct gggaaagtac  6000
gtcgtggtgt ttaactgctc cgatcagatg gacttcagag gcctcggccg catctttaag  6060
gggctggccc agtccggctc ctggggctgc ttcgacgagt tcaacaggat cgatctgccg  6120
gtcctgagcg tggctgcgca gcagatctcc attatcctga cttgcaagaa ggaacacaag  6180
aagtccttta tcttcactga tggcgataac gtcactatga accccgagtt cgggctgttc  6240
ctgaccatga accccggata cgccggtcgg caggagctgc ctgagaacct caagatcaac  6300
ttccggtccg tggccatgat ggtgcccgac cgccagatta tcatacgggt gaagctcgcc  6360
tcatgcggct ttatcgacaa cgtggtgctg gcccggaagt tctttaccct gtacaagctg  6420
tgcgaggaac agctgtcgaa gcaagtccac tacgacttcg gcctgcgcaa catcttgtcc  6480
gtcctgcgca ccctgggcgc ggccaagcgg gccaacccca tggatactga gagcaccatt  6540
```

-continued

```
gtcatgcgcg tgctccggga tatgaacttg agcaagctga ttgatgagga cgagccgctt  6600
tttctgtccc tgattgaaga cttgtttcca aacatcctgc tggacaaagc cggataccca  6660
gagctggagg cagcgatctc ccgccaagtg gaagaagccg gactgatcaa ccacccgcct  6720
tggaaattga aagtgatcca actgttcgaa actcagcggg tccggcacgg catgatgacc  6780
ttgggcccct cgggggcggg aaagacgact tgcatcccata ctttgatgcg ggctatgacg  6840
gattgcggga agccgcatag ggaaatgcgg atgaacccca aggccatcac cgctccacaa  6900
atgttcggta ggcttgacgt ggccaccaac gattggaccg atggcatctt ctcaactctg  6960
tggagaaaga ccctgcgggc taagaagggg gagcatattt ggattatcct cgacggccca  7020
gtggacgcca tctggatcga aaaccttaac tccgtgctcg acgacaacaa gaccctgacc  7080
ctggccaacg gcgaccgcat cccgatggct ccgaactgca agatcatctt cgaaccgcac  7140
aacatcgaca acgcctcccc ggccaccgtg tccagaaacg gaatggtgtt catgtcctcc  7200
tctatcttgg actggtcgcc gatcctggag ggattcctga agaagagaag cccgcaagaa  7260
gccgagatcc tgcgccaact gtatactgaa tcgttccccg atctgtaccg gttttgcatc  7320
caaaacctgg agtacaagat ggaggtgctc gaggcgttcg tgatcactca gagcattaac  7380
atgttgcaag gcctgatccc gctcaaggag caggggggcg aagtgtccca ggcccacctg  7440
gggcggctgt tcgtgttcgc cctcctgtgg tcagccggag cggcgctgga gcttgacgga  7500
cgccgcagac tggaactgtg gctgcggtcc cgaccgactg ggactctgga gttgcctccg  7560
ccggccggcc ctggcgatac agcgttcgac tattacgtgg cccctgatgg aacttggacc  7620
cattggaaca ctaggaccca ggaatacctc tacccgagcg acaccacccc agaatacggg  7680
tcaatcctgg tcccgaacgt ggataatgtc cggactgatt tcttgatcca gaccatcgcg  7740
aagcagggaa aagccgtgct gctgattgga gaacagggta ccgctaagac tgtgattatc  7800
aagggattca tgtccaagta cgacccggaa tgtcacatga ttaagtcctt gaacttctca  7860
tcggccacca ccccccctgat gttccagcgg accatcgagt cctacgtgga caagcggatg  7920
ggaactacct acggaccgcc ggcagggaag aagatgaccg tgttcattga cgacgtcaac  7980
atgccaatca tcaatgaatg gggcgatcaa gtcaccaacg agatcgtccg ccagctgatg  8040
gaacagaacg gcttctacaa cctcgaaaaa ccgggagaat tcactagcat cgtggacatc  8100
caatttctcg cagccatgat ccaccctggt ggcgggcgga acgatattcc ccagagactg  8160
aagcgccagt ttagcatctt caactgcact ttgcctagcg aagccagcgt cgacaagatc  8220
ttcggcgtga taggagtggg acactactgc actcagcggg gattctcaga agaagtccgg  8280
gactccgtga ctaagctcgt gcctctgaca aggcggctgt ggcagatgac taagatcaag  8340
atgctgccga cccccgcaaa gttccactac gtgtttaacc ttcgggacct gtccagagtc  8400
tggcagggga tgctcaacac cacctcggag gtcattaagg aacccaacga tcttctgaag  8460
ttgtggaagc acgagtgcaa gagggtcatc gccgacagat tcactgtgtc ctcagacgtc  8520
acttggttcg acaaggccct cgtgtccctt gtggaggaag aattcggaga agagaagaag  8580
ttgctcgtgg actgcggcat tgatacttac ttcgtggact tcctccggga tgcgccggag  8640
gccgccggag aaacctctga ggaggccgac gctgaaaccc ccaaaatcta cgagcctatc  8700
gagtcgttct cccatctgaa ggagcggctg aacatgttct tgcagctgta caacgagtcc  8760
atccgggggg ccggaatgga catggtgttt tttgccgatg cgatggtgca cctggtgaag  8820
atttccagag tgatccgcac cccccaggga aacgcactcc ttgtgggagt gggaggatcc  8880
ggcaaacaga gcctgactcg cttggcgtcg ttcatcgcgg gatacgtgtc gttccagatc  8940
accctgactc gcagctacaa cacctcgaac ctcatggagg acctcaaggt cctgtacagg  9000
accgcaggcc aacaaggcaa aggaattacc ttcattttca ccgacaacga aatcaaggac  9060
gaatcattcc tggagtacat gaacaacgtg ctgagctcag gagaggtgtc aaacctgttc  9120
gcccgcgacg agatcgacga gatcaactcg gatctggctt ccgtgatgaa aaaggaattc  9180
cctcggtgtc tgcctaccaa tgagaacctc catgactact tcatgagccg cgtgcggcag  9240
aacttgcata tcgtcctgtg cttttccccc gtcggagaaa agttcagaaa cagggccctg  9300
aagttcccgg cgctcatctc cggctgcacc attgattggt ttagccgctg gccaaaggac  9360
gcactcgtgg ccgtgtcgga acatttcctc acatcctacg acatcgattg ctcgcttgag  9420
atcaaaaagg aggtggtgca gtgcatgggc tcgttccaag acggcgtggc tgaaaagtgt  9480
gtggactact tccagaggtt ccgacggtcc actcacgtga ccccaaagtc ctacctgagc  9540
ttcatccagg gatacaagtt catctacgga gagaagcatg tcgaagtgcg caccttggcg  9600
aaccggatga acaccgggct cgaaaagctg aaggaggcct ctgaatccgt cgccgccctg  9660
tccaaagagc tggaggccaa ggaaaaggaa ctgcaagtcg ccaacgataa ggccgacatg  9720
gtcctgaagg aagtcaccat gaaggctcag gccgcgcgaga aggtcaaagc agaggtgcag  9780
aaggtgaagg atcgcgcgca ggccattgtg gacagcattt caaaggacaa ggccatcgcc  9840
gaggaaaaac tggaagccgc gaagccggcc ttggaagagg cagaggccgc gctgcagacc  9900
atacggccct ctgacattgc caccgtgcgg accctcgggc ggcccccgca tctgatcatg  9960
agaattatgg actgcgtgct gctgctgttc caacggaaag tgtccgccgt gaagattgac  10020
ctggagaagt cctgcactat gccgagctgg caggagtcgc tgaagctcat gactgcggga  10080
aacttcctgc agaacctcca acaatttccc aaagacacca ttaacgagga agtgattgag  10140
ttcctgtccc catacttcga gatgcccgac tacaacatcg agactgccaa gagggtgtgc  10200
ggaaacgtgg ccggcctctg ctcgtggacc aaggccatgg cgtcgttttt cagcatcaac  10260
aaggaggtgt tgcctcttaa ggccaacctg gtggtgcaag agaaccggca tctcttggcc  10320
atgcaggacc tccagaaggc ccaggcagag ttggacgaca agcaggccga gctggacgtc  10380
gtccaagccg agtacgaaca ggccatgacc gaaaagcaga ccctcctgga ggatgctgaa  10440
cgctgccgcc acaagatgca gactgccagc actctgatct ccggacttgc cggagaaaag  10500
gagcgctgga ccgagcagtc ccaggagttc gcagcccaga cgaagcgcct cgtgggggac  10560
gtgctgctgg cgaccgcctt cctctcgtac tcgggcccgt tcaaccagga gtttcgggat  10620
cttctgttga acgattggcg caaggagatg aaagccagaa aaatcccgtt cggtaaaaac  10680
ctcaatctga gcgagatgct gatcgatgcc ccccaccatct ccgaatggaa ccttcaggga  10740
ctgccgaacg atgatttgtc aatccagaac ggtatcattg tcactaaggc ctcccgctac  10800
cccttattga ttgatcctca gacccagggg aagatttgga tcaaaaacaa ggaatcgcgg  10860
aacgagctgc agatcacatc tctgaaccac aagtacttcc gaaaccactt ggaagattcc  10920
ctgtccctgg gccggcccct gctgattgag gacgtgggcg aagaactcga cccggccctg  10980
gataatgtgc tggaacggaa tttcattaag accggtagca ctttcaaggt gaaagtggga  11040
gataaggagg tggacgtcct ggacggattc cgcttgtaca tcacgaccaa gctgcctaac  11100
cccgcgtaca ctccggaaat cagcgcgagg acgtcgatca tcgatttcac tgtgaccatg  11160
aagggtctgg aagatcagct tctgggacgg gtcatcctga ctgagaagca ggaactggaa  11220
aaagagagaa cccacctgat ggaagatgtg accgccaata agcgcaggat gaaagagctc  11280
```

```
gaggacaacc tcctttaccg cctgacctcc acccagggtt ccttggtgga ggatgaatcg  11340
ctgattgtgg tgctgtcgaa caccaagagg accgccgaag aagtgaccca aaagttggaa  11400
atctccgccg aaaccgaagt gcagatcaac tcggctcggg aggagtaccg gccggtggcc  11460
actcgaggat caattctgta cttcctgatc accgagatgc ggctcgtgaa cgagatgtat  11520
cagactagcc tccgccagtt ccttggcttg ttcgacctgt cgctggcgag aagcgtgaag  11580
tccccaatta cctcgaaacg gatcgccaac attattgaac atatgactta cgaagtgtac  11640
aaatacgcgg cacgggggct ctacgaagaa cacaagtttc tcttcacgct gctgctgact  11700
ctgaagatcg atattcagcg caaccgggtg aagcacgaag agttcctgac cctgattaag  11760
ggtggcgcct ccctggacct caaggcctgc ccccccaagc cgtccaagtg gatcctcgac  11820
attacctggc tcaacctcgt ggaactttca aagctcagac agttctccga cgtgctcgat  11880
cagatctcca ggaacgagaa gatgtggaag atttggttcg ataaggaaaa tcccgaagag  11940
gagcctcttc ctaacgcgta cgacaagtcc ctggattgct tccgccggct gctcctgatc  12000
cggtcgtggt gtccagaccg gactattgcc caagcccgga aatacatcgt ggactcaatg  12060
ggcgagaagt acgcagaggg tgtgatcctg gacctggaaa agacctggga agagtccgat  12120
ccgagaactc ctctgatctg cctgctgtcc atgggttcag accccaccga ctcgatcatc  12180
gccctcggaa agcgcctgaa gatcgaaacc cgatacgtca gcatgggcca aggccaggag  12240
gtccacgccc gcaaactgct gcagcagacc atggctaacg gaggatgggc gctgctgcag  12300
aattgtcacc tgggacttga cttcatggat gagctgatgg acatcatcat cgaaaccgag  12360
ctcgtgcacg atgcattccg gctgtggatg acaactgagg cgcacaagca gttcccgatt  12420
accttgctgc agatgtctat taagttcgcg aacgatccgc cccagggact gagagccgga  12480
ctcaagcgca cctacagcgg cgtgtcccaa gacttgttgg acgtgtcctc gggaagccag  12540
tggaagccga tgctctacgc cgtggcgttc ctccattcaa ccgtccagga gcgcagaaag  12600
ttcggcgcac tgggatggaa catcccttac gaattcaacc aggcggattt taacgccacc  12660
gtgcagttca ttcagaacca cctggacgac atggacgtga agaagggggt gtcatggacc  12720
actatccggt acatgatcgg agagatacag tatggaggtc gggtgaccga cgactacgac  12780
aagcgcttgc tgaacacctt cgccaaggtc tggttctccg agaacatgtt cggacccgat  12840
ttcagcttct accagggata caacatccct aagtgctcca ccgtcgacaa ctacctccag  12900
tacattcagt ccctgccagc ctacgacagc ccggaggtgt tcggactcca ccccaacgca  12960
gacatcacct accagtccaa gctcgccaag gatgtgttgg acaccatcct gggaatccag  13020
cctaaggaca cgagcggcgg gggggatgaa actcgggagg ctgtggtggc acggctggcc  13080
gacgatatgc tggaaaagct cccacctgac tacgtgccgt tcgaagtgaa ggagcggctc  13140
cagaagatgg gcccgttcca gcccatgaac atcttcctgc ggcaagaaat tgaccggatg  13200
cagagagtgc tgtccctggt ccggtcaacc ctgactgaac tgaagctggc catcgacgga  13260
accatcatca tgtccgagaa cctcagagat gcgctggatt gcatgttcga cgcccggatc  13320
cctgcctggt ggaaaaaggc ctcctggatc tccagcactt tgggattctg gttcaccgaa  13380
ctgatcgaaa gaaactcaca attcacttcc tgggtgttta acggcagacc acactgtttc  13440
tggatgaccg gcttcttcaa cccacaagga ttcctgacag cgatgagaca ggaaatcacc  13500
cgcgccaaca agggctgggc cctggacaac atggtgctgt gcaacgaagt gaccaagtgg  13560
atgaaggacg acatttccgc accgcctact gaaggggtgt acgtgtacgg cctgtacctg  13620
gagggcgctg gatgggacaa gcggaacatg aaactgattg aatccaagcc caaggtcctg  13680
ttcgaactca tgccagtcat taggatctac gcggagaaca acacgctccg ggacccgagg  13740
ttttactcct gccccatcta taagaagccc gtgcggaccg atctgaacta cattgcggcg  13800
gtggacctca ggaccgcgca gacccctgaa cattgggtgc tccgcggcgt ggcccttctg  13860
tgtgacgtga agtag                                                    13875
```

```
SEQ ID NO: 8            moltype = DNA  length = 13875
FEATURE                 Location/Qualifiers
misc_feature            1..13875
                        note = Synthetic polynucleotide
source                  1..13875
                        mol_type = other DNA
                        organism = synthetic construct
SEQUENCE: 8
atgttcagaa tcgggcggcg gcaactgtgg aagcattcag taactcgcgt cctgactcag  60
agactgaagg gagaaaagga ggcaaaaagg gccttgctgg acgcccgcca caactacctc  120
ttcgcgattg tggcctcatg cctggacctg aataagactg aagtggagga cgctatcctc  180
gagggaaacc aaatagagag aatcgaccaa ttgttcgccg tgggtggact ccggcacctg  240
atgttctact accaagacgt ggaggaagcg gaaaccggac agctgggatc actgggggc  300
gtgaacctcg tgagcggaaa gatcaagaag cccaaggtgt tcgtcaccga aggcaacgat  360
gtggcgctca ccggcgtgtg cgtgtttttc attcgcaccg acccatcgaa ggccattact  420
cccgataaca tccatcaaga ggtgtccttc aacatgctgg acgctgccga tggaggactc  480
ctcaacagcg tgcgccggct cctctccgac attttcatcc ccgcgctgag agctaccagc  540
cacggatggg gggaactcga gggactgcag gacgccgcaa acattcgcca agaattcctc  600
tcctcattgg agggcttcgt gaacgtgctc agcggcgctc aggaaagcct gaaagaaaag  660
gtcaatctcc gcaagtgcga catcctagag ctcaaaacgc tgaaagagcc cacagactac  720
ctcactcttg ccaataaccc tgaaaccctg ggaaagatcg aggactgcat gaaggtctgg  780
attaagcaaa cagaacaagt cctggccgag aacaaccagc tcctgaagga ggcggatgac  840
gtgggcccgc gggcagaatt agagcactgg aagaaacgcc tcagcaagtt taattacctc  900
ctggagcaat tgaagtcccc tgacgtgaag gccgtgctcg cagtgttggc agcggcaaag  960
tccaagctgc tgaaaacttg gcgggagatg gacattagaa ttactgacgc gacgaacgag  1020
gcaaaggata acgtcaaata cttgtacacg ctcgagaagt gctgcgaccc gttgtattcc  1080
tcagacccac tgagcatgat ggacgccatt cccacccctca tcaacgccat taagatgatt  1140
tactcaattt cccattacta caacacctca gagaagatta cttcactctt cgtgaaggtg  1200
accaaccaaa ttatctccgc ctgcaaggcc tacatcacta acaacgggac agcttcgatc  1260
tggaaccagc cgcaggatgt cgtggaggag aagatcctgt cggccatcaa acttaagcag  1320
gagtaccaac tgtgctttca caaaaccaag cagaagctga agcaaaatcc aaacgccaag  1380
caattcgact tctccgagat gtacatcttc ggcaagttcg aaaccttcca caggagactg  1440
gccaaaatca ttgatatttt cactaccctt aagacctaca gcgtgctcca agacagcact  1500
atcgagggac tggaggacat ggccaccaag taccaaggca tcgtcgccac cattaaaaaa  1560
```

-continued

```
aaggaataca acttcctgga tcagcggaag atggacttcg atcaggatta tgaagagttc  1620
tgcaaacaga ccaatgatct ccacaacgaa ctgcggaagt ttatggacgt gaccttcgca  1680
aaaatccaga acaccaacca ggcgctgcgc atgctgaaga agttcgagag attgaacatc  1740
ccgaatctcg gcatcgacga taagtaccag ctcatcctgg aaaactacgg ggccgacatc  1800
gacatgatct ccaagctgta cactaagcag aaatacgacc cgccactggc gagaaaccag  1860
ccccccattg ccggcaagat cctctgggcc cgacagcttt tccaccgaat ccagcaaccc  1920
atgcagcttt tccagcaaca ccccgccgtg ctctcaaccg ccgaggccaa gccgatcatt  1980
agaagctaca acagaatggc gaaggtgctg ctcgaattcg aggtgttgtt ccaccgggca  2040
tggttgaggc agatcgagga aatacacgtg ggactggagg cctcgctgtt ggtgaaggcc  2100
ccagggaccg gagaactgtt cgtcaacttc gacccgcaaa tcctgatcct gttccgcgaa  2160
actgaatgca tggctcagat gggattggaa gtcagccccc tcgcgacttc cctcttccaa  2220
aagagagata gatacaaacg gaacttctcc aatatgaaga tgatgctggc ggaataccag  2280
agagtgaaat ccaaaattcc ggccgctatt gagcagctga ttgtgcctca ccttgccaag  2340
gtcgacgaag cgttgcagcc tggcctggcc gctctcactt ggaccagcct gaacatcgag  2400
gcctacttgg aaaacacctt cgccaaaatt aaggacctcg aactcctgct cgaccgggtg  2460
aacgacttga tcgagtttag gattgatgcc attctggagg agatgagctc cactccgttg  2520
tgtcaactgc cacaggagga accccctcaca tgcgaggaat tcctgcaaat gactaaggac  2580
ctgtgcgtca acggggccca aatcctgcac ttcaaatcct ccctggtcga ggaagcagtc  2640
aacgagttgg tgaacatgct cctggatgtg gaggtgctgt ccgaggagga gtccgagaag  2700
atctccaacg aaaactccgt gaactataag aatgaatcct ccgcaaagcg ggaggagggg  2760
aatttcgata ccctgacttc ctccatcaac gcccgcgcca acgccttgct gctaactacc  2820
gtgactagaa agaagaaaga aactgaaatg ctgggggagg aggcacgcga actcctgtcc  2880
cactttaacc accagaacat ggacgccctg ctgaaggtca cccggaacac cttggaggcc  2940
attcgcaagc ggatccatag cagccacacc attaacttca gagactcaaa ctcggcatcc  3000
aacatgaagc agaattcact cccgatcttc agggcaagcg tgactttggc tatcccgaac  3060
attgtcatgg cgcctgctct ggaggacgtc cagcagacgc tgaacaaggc cgtggaatgc  3120
atcatcagcg tcccgaaggg tgtgagacag tggtcctccg aattgttgtc aaagaagaag  3180
atccaagaga ggaagatggc ggcgctccag tccaatgaag atagcgatag cgacgtggag  3240
atgggcgaga acgaactcca ggatacccctg gagatcgcgt ccgtcaacct ccctatcccg  3300
gtccagacca agaactacta caagaatgtc tcggaaaaca aggagatcgt gaagctcgtg  3360
tcggtcctgt ccaccattat caactccacc aagaaggagg tcattactag catggactgc  3420
ttcaagcgct ataaccacat ctggcaaaag gggaaggaag aggccatcaa gacctttatc  3480
acccagtcgc cgctcttgtc agagtttgag tcacagattc tgtacttcca gaacctggaa  3540
caggagatta atgctgaacc agagtacgtg tgcgtgggct ccatcgcgct gtatactgcg  3600
gacctcaagt tcgcgttgac cgcagaaact aaggcctgga tggtggtcat cggcagacac  3660
tgcaataaga agtaccgcag cgaaatggaa aacatcttca tgttgattga agagttcaac  3720
aagaagctca accggcccat taaggacctc gatgatattc gcatcgccat ggcggccctc  3780
aaagaaatcc gggaggagca aatctccatc gacttccagg tcggccccat tgaagagagc  3840
tacgcactgc tgaaccgcta tggactgtta atcgcccggg aagaaatcga taaggtggat  3900
accctgcatt acgcttggga aaagttgctg gcccgggcag gagaggtgca gaacaagctc  3960
gtgagcctcc aaccctcctt caaaaaagaa ctgatcagcg cggtggaagt gtttctccag  4020
gactgccacc agttctacct cgactatgac ctgaacggcc ccatggctag cggcttgaag  4080
cctcaggagg cctcagaccg cctgatcatg tttcagaacc aattcgataa catctaccgg  4140
aagtacatta cctataccgg cggcgaggag ttgtttggat tgccagccac ccagtaccct  4200
caactcctgg agatcaaaaa gcaactgaac ttgctccaga agatctacac cctctacaac  4260
tcggtcatcg aaactgtgaa ctcgtactac gacattcttt ggagcgaggt caacatcgaa  4320
aagatcaata acgaactcct ggaattccag aaccgatgca ggaagctgcc ccgggccctg  4380
aaagattggc aagccttctt ggacctgaag aagattattg atgacttctc agaatgttgc  4440
cccctcctgg agtacatggc ctccaaggcc atgatggaac ggcattggga gcggattact  4500
acccttacgg gccacagcct ggacgtcggc aacgagagct tcaaactgag aaacatcatg  4560
gaggccccac tcctgaagta caaggaagag attgaggata tttgcatttc cgccgtgaag  4620
gaacgcgaca tcgaacagaa acttaagcaa gtcattaacg agtgggacaa caaaaccttc  4680
acgttcggat ccttcaagac gagaggcgag ctcctcctga ggggagactc aaccagcgaa  4740
attatcgcca acatggagga ctccctgatg ctcctggggt cgctgctgtc gaacaggtac  4800
aacatgccct tcaaggccca gatccagaag tgggtccagt acctcagcaa ctccaccgac  4860
atcatcgagt cctggatgac tgtgcagaac ttgtggatct acctggaggc cgtgttcgtg  4920
ggaggagata tcgccaaaca attgcctaag gaagccaaga ggttctcgaa tattgacaag  4980
agctgggtga agatcatgac cagggcacac gaagtgcctt cggtggtgca atgttgcgtg  5040
ggggatgaaa ctctcggaca gttgctgcct cacctcctgg accaactcga gatttgtcag  5100
aagtccctga ctggatacct cgagaagaaa cgcttgtgct tcccaaggtt tttcttcgtg  5160
tcggatcctg ccctcttgga aatcctcggt caggcctcag actcacacac cattcaagcc  5220
cacctcctta acgtctttga taacattaag agcgtcaagt tccatgagaa aatctacgac  5280
cggatcctct ccatttcgtc ccaagaggga gaaacgattg aacttgacaa gccagtgatg  5340
gccgaaggga atgtcgaggt gtggctcaac agcctcctgg aagaatccca aagctccctt  5400
catcttgtga tccggcaggc cgccgccaat atccaggaaa ccggattcca actcaccgag  5460
ttcctttcct ccttccccgc acaagtggga ctgctcggca ttcaaatgat ctggacgcgg  5520
gattccgagg aggccctgag gaacgccaag ttcgacaaga agatcatgca aaaaacaaac  5580
caggccttcc tcgaacttct caataccctg atcgatgtga ccactagaga tctctcctcg  5640
acggaacggg tgaaatacga aaccctcatc accatccacg tgcaccagag agatattttc  5700
gacgacctct gccacatgca tattaagtcg ccaatggact tcgaatggtt gaaacaatgc  5760
agattttact ttaacgagga cagcgataag atgatgatcc atatcaccga cgtcgccttc  5820
atctaccaga acgaattcct gggatgcacc gataggctgg tgattacccc gctgactgac  5880
cggtgctaca ttaccctggc ccaggccctg ggaatgagca tgggcggcgc ccctgccgga  5940
ccggcgggca ccggcaagac cgaaaccacc aaggatatgg gacggtgcct cggaaagtac  6000
gtggtggtgt ttaactgctc ggaccagatg gatttccgcg gactgggcag gatcttcaaa  6060
ggcctggctc agagcggttc atggggctgc ttcgacgagt tcaaccgaat tgacttgccg  6120
gtgctgtccg tcgcagcgca gcaaatctcg atcatcctga cttgtaagaa ggaacataaa  6180
aagtccttca tttttaccga cggagacaac gtgacaatga acccggagtt cggactgttc  6240
ctgactatga accctgggta cgccgggcgc caggagctcc ctgaaaacct taagatcaac  6300
```

-continued

```
ttccgctccg tggcaatgat ggtgcctgac agacagatta tcattcgcgt gaagctggcg  6360
tcatgcggct tcatcgacaa cgtggtgctg gcgaggaagt ttttcacact gtacaaactt  6420
tgcgaggagc agctctccaa acaggtgcac tacgacttcg gactgagaaa catcctgagc  6480
gtcctgagga ccctgggggc tgctaagcgc gccaacccca tggataccga atccaccatt  6540
gtcatgcggg tcctgaggga catgaacctg tccaagctca tcgacgagga tgaacccctg  6600
ttcctgagcc tgattgaaga tctgtttcca aacatcttgc tggacaaggc gggttacccc  6660
gagctggaag ccgccatctc ccgccaagtg gaggaggctg gactcattaa ccacccaccc  6720
tggaagctca aggtcatcca actgttcgaa acgcagagag tgcgacacgg catgatgaca  6780
ctggggccat caggtgcagg aaagaccacg tgcatccaca ccttgatgcg ggcgatgacc  6840
gactgcggga agccacatcg ggagatgcgc atgaacccga aggcgatcac tgcacctcaa  6900
atgttcggac ggctcgacgt ggccactaac gactggaccg acgggatttt ctcgaccttg  6960
tggcgcaaga ccctacgggc caagaaagga gagcacatct ggattatcct ggatggtcca  7020
gtggatgcga tctggatcga gaaccttaac tccgtgctgg acgacaacaa gaccctgacc  7080
ctggctaacg gcgaccggat cccaatggcg cccaactgca aaatcatctt cgaaccccac  7140
aacattgaca acgcctcgcc cgccactgtg tcgcggaacg ggatggtgtt catgtcgtcg  7200
tccatcttgg actggtcccc cattctcgaa ggcttcctga agaagcgcag ccctcaagaa  7260
gccgagatac tccgccaact ctacaccgag tcgttcccgg atttgtaccg gttctgtatc  7320
cagaacttgg agtacaagat ggaggtgctt gaggcattcg tgatcaccca atcgatcaac  7380
atgctgcaag gactcatccc cctgaaagaa cagggaggtg aagtctccca agctcacctg  7440
ggacgcctct tcgtgttcgc gctgctttgg agcgcgggag ccgcgctcga gctcgacggg  7500
cggcgcaggc tggagctctg gctgcgctcc cgcccgaccg gaaccctgga gctgccgccc  7560
ccggccggcc cgggcgacac cgcctttgac tactacgtgg cccccgacgg gacctggact  7620
cactggaaca ctagaaccca ggaatacctt taccoctccg acactactcc cgaatacgga  7680
agcatccttg tgccgaacgt ggacaacgtg cgcaccgact tcctaattca gaccatcgcc  7740
aagcagggaa aggccgtgct gcttattgga gaacagggta ccgcaaagac cgtgatcatc  7800
aagggattca tgtcaaagta cgaccctgaa tgtcacatga ttaagtcact taacttctcc  7860
agcgccacca cccctctgat gttccagaga accatcgaga gctacgtgga caaacgcatg  7920
ggcaccacgt acggtccccc ggccggaaag aagatgaccg tattcatcga cgacgtgaac  7980
atgccgatca ttaacgaatg gggagatcag gtgaccaacg aaatcgtgcg ccagttaatg  8040
gagcagaacg gtttctacaa ccttgaaaaa cccggagagt tcacttcaat cgtggacatc  8100
cagttcctgg ccgccatgat ccacccgggc ggaggtagaa acgacatccc gcagagactg  8160
aagagacagt tctcaatctt caactgcacc ctgccctccg aagcatcagt cgataagatt  8220
ttcggggtga tcggagtggg ccactactgc acgcagaggg gtttctcaga ggaggtgcgc  8280
gactccgtga ccaaactggt cccactcact cgaaggctgt ggcagatgac caagattaag  8340
atgctcccta ctcctgccaa gttccattac gtctttaacc ttcgggactt gtcccgggtc  8400
tggcagggaa tgctgaatac cacctccgaa gtgattaagg aacctaacga cctcctgaag  8460
ctctggaaac acgagtgcaa gagggtgatc gccgatagat tcaccgtgtc ctccgacgtg  8520
acctggttcg acaaggccct cgtgtccttg gtggaagaag agttcggtga agaaaagaag  8580
ctcctcgtgg actgcggaat cgacacctac ttcgtcgact tcctcagaga tgcccccgag  8640
gctgccggag aaacctcaga agaggccgat gcggagactc cgaagattta cgaacccatc  8700
gaatccttca gccacttgaa ggagaggctc aacatgttcc tgcagctcta caacgaaagc  8760
atcaggggag ctggcatgga catggtgttc ttcgccgacg cgatggtgca ccttgtcaag  8820
atctcccggg tcattcgaac gccgcaggga aacgcattgc tcgtgggcgt cggaggttcc  8880
ggaaaacagt ccctcacgag gctggcgtcc ttcattgcgg gatacgtgag cttccaaatt  8940
accctcaccc gcagctacaa tacctccaac cttatggagg acttgaaggt cttgtaccgc  9000
actgccggac agcagggaaa ggggatcacc ttcatcttca ccgacaacga aatcaaggat  9060
gagagcttct tggagtacat gaacaacgtc ctttcgtccg gagaagtgtc caacctcttc  9120
gctcgcgatg aaatcgacga gatcaactcc gacctcgcca gcgtcatgaa aaaagaattc  9180
cctcgctgtc tccccaccaa cgagaacctc cacgattact ttatgtcccg ggtccgccaa  9240
aacttgcata ttgtgctgtg cttctcgccc gtgggggaga agtttcggaa ccgggcgctg  9300
aagttccccg ccctgattag cggatgtact atcgactggt tctcgagatg gcccaaagac  9360
gccctggtcg ccgtgagcga acatttcctg acttcctacg acatcgactg cagcctcgaa  9420
atcaagaagg aagtggtgca gtgcatgggg tcatttcagg atggagtggc cgagaagtgc  9480
gtcgactact tccagagatt ccggcggtca acccatgtga cgcccaaaag ctacctttcg  9540
ttcatccagg gctacaagtt catctacggg gaaaagcatg tcgaagtgcg gacccttgca  9600
aaccgcatga acaccggcct tgagaagttg aaagaggcct cggaatccgt ggccgcgctc  9660
agcaaagaac tggaagctaa ggagaaggaa ctccaagtcg ccaacgataa agcggacatg  9720
gtgctgaagg aagtgaccat gaaggcccag gccgccgaga aggtcaaggc cgaggtccag  9780
aaggtgaagg accgcgcaca agcaatcgtg gatagcatct ccaaggacaa agcaatcgca  9840
gaagagaagc tcgaggcggc aaagcccgcg ctcgaagagg cggaagcggc gctgcagact  9900
atccggccgt ccgacattgc aaccgtgaga accctgggcc gcccccccaca cctcatcatg  9960
cgcattatgg actgcgtgct cttgctcttt caacggaagg tgtccgccgt gaagatcgac  10020
cttgagaagt cctgcaccat gccaagctgg caggagtcgc tgaaactcat gaccgccgga  10080
aacttcctgc agaacttgca acagttcccg aaagacacca tcaacgaaga agtcatcgag  10140
ttcctttccc cgtacttcga aatgcctgat tacaacattg aaaccgccaa gagagtgtgc  10200
ggaaatgtcg cgggcctgtg ctcgtggacc aaggccatgg cgtcgttctt tagcatcaac  10260
aaggaggtgc tcccccctgaa ggccaacctc gtggtgcagg aaaatcgcca cttgctggcc  10320
atgcaagatc ttcagaaggc tcaagcggag ctggacgata aacaggccga acttgacgtg  10380
gtccaggccg agtacgagca ggctatgacg gaaaagcaga ccctcctgga ggatgcagaa  10440
cgctgcaggc acaagatgca gaccgcctcc acccttattt ccggcctggc gggcgaaaag  10500
gagcggtgga ccgagcagtc ccaggaattc gcagctcaga ccaagcggct cgtgggcgat  10560
gtgctgctgg ccactgcctt cttgagctac tccggcccct tcaaccagga atttcgggac  10620
ctcctgctga acgactggag gaaggagatg aaggcgcgga agatcccatt cgggaagaac  10680
ttgaacctct ccgagatgct catcgacgct cccaccatca gcgaatggaa cctccaggga  10740
ctgcccaacg atgaccttag cattcaaaac ggaatcatcg tgaccaaggc ctcgcgctac  10800
ccgctgctta tcgacccaca aactcaagga aagatttgga ttaagaacaa ggagtcacgc  10860
aacgagctgc agatcacctc cctgaaccat aaatacttta gaaaccatct cgaggattcc  10920
ctgagcctgg gcagacccct tctcatcgag gacgtgggcg aggagctcga tccagcgctg  10980
gacaacgtcc tggagagaaa cttcattaag accggatcca cgttcaaggt caaggtcggc  11040
```

-continued

```
gacaaggaag tggatgtcct ggacggcttc cgcctgtaca tcaccaccaa attgcctaac  11100
cccgcataca ccccggaaat ctcagctcgc acgtcgatca ttgattttac cgtcactatg  11160
aaaggactgg aggaccagct gctgggcaga gtcattctca ccgaaaagca agagctggaa  11220
aaggaacgca cccatctcat ggaggacgtg actgcgaata agcggcggat gaaagagctg  11280
gaagataact tgctgtaccg cctgacttcc actcaggggt ccctcgtcga agatgagtca  11340
ctgatcgtgg tcctgtcaaa cacgaagagg accgccgagg aagtaaccca gaagctggag  11400
atttccgccg aaaccgaagt gcagatcaac tccgcaagag aggaatatag acccgtagct  11460
acgcggggga gcattctgta cttcctcatc acggagatga gacttgtcaa cgaaatgtac  11520
cagacctcat tgcggcagtt cctcggactg tttgacctgt ccctcgcaag aagcgtcaag  11580
tccccaatta cttcaaagcg catcgcgaac attattgagc acatgactta cgaagtgtac  11640
aagtacgcgg ccaggggggtt gtatgaggag cacaagtttc tcttcaccct gctgctgacc  11700
ttgaagatcg acattcaacg gaatagagtg aagcatgaag agttcctgac cctcatcaaa  11760
ggcggcgctt ccctcgatct gaaggcttgc cctccgaaac cgtcaaaatg gatcctggac  11820
attacctggc tgaaccttgt cgagctgtcc aagttgcgcc aattctccga cgtgctggac  11880
cagatctccc ggaacgagaa gatgtggaag atctggttcg acaaggaaaa cccagaggag  11940
gagcctctgc ccaacgccta tgacaaaagc ctggactgct tccggcggct ccttctcatt  12000
cgctcttggt gtcccgaccg gaccattgcc caggcccgca agtacatcgt ggattcaatg  12060
ggggagaagt acgctgaggg ggtgatcctt gacctggaga aaacttggga ggagagcgat  12120
ccgcggaccc cgctgatttg cttgctttca atgggatctg accccaccga ctccatcatc  12180
gccctgggaa agaggcttaa gatcgaaact cgctacgtca gcatgggaca aggacaggag  12240
gtgcacgccc ggaagctgct ccagcagacc atggccaacg ggggatgggc gctgctgcag  12300
aactgccacc ttggactgga tttcatggac gaactcatgg acatcattat cgagactgaa  12360
ttggtccatg acgccttcag actgtggatg actactgagg cccataagca gttccccatc  12420
acacttctgc agatgagcat caagttcgcg aacgatcctc ctcaaggcct gagagccgga  12480
ttgaaaagga cgtactccgg ggtgtcccaa gacctcctgg atgtgtcctc cggatcccaa  12540
tggaagccaa tgctctacgc ggtggcgttc cttcacagca ctgtgcagga gaggcggaag  12600
tttggagccc tgggatggaa cattccatac gagttcaacc aagccgactt caacgcgact  12660
gtgcaattca tccagaacca cctggacgat atggatgtga aaaagggggt gtcctggacg  12720
accatccgct acatgatcgg ggagatccag tacgggggaa gagtgaccga tgattacgac  12780
aagaggctcc tgaacacttt cgccaaggtc tggttctccg aaaacatgtt cggccccgac  12840
ttctcgttct accaggggta taacattccg aagtgctcga cggtggataa ctacctccag  12900
tacattcaat cgctgccggc ctacgactcc cccgaggtgt tcggcctcca ccccaacgcc  12960
gacattacct accagagcaa gctggctaag gacgtgctag acaccatact ggggatccaa  13020
ccgaaggata cttccggcgg aggggatgaa acccgcgaag cagtggtggc acggctggct  13080
gacgacatgc tggagaaact gccccctgac tacgtcccct ttgaggtcaa ggaaaggctc  13140
cagaagatgg gacctttcca gccaatgaac atcttcttgc ggcaagagat cgaccggatg  13200
cagagagtgc tctccctcgt gcgctcaacc ctcactgagc tcaagctggc aatcgacggt  13260
accattatca tgtcggagaa cctccgggac gcactggact gcatgttcga tgcgcggatc  13320
cctgcgtggt ggaagaaggc ctcctggatc tcgtcaaccc tggggttctg gttcaccgag  13380
ctgattgaaa ggaactccca attcacctcc tgggtcttta acggccgccc gcactgcttc  13440
tggatgaccg gctttttcaa cccccaggga tttctcaccg ccatgcggca ggaaatcacc  13500
agggccaaca agggctgggc gttggataac atggtgctgt gcaacgaagt gaccaagtgg  13560
atgaaagatg acatttcagc cccgccgacc gaaggcgtct acgtctacgg gctctacttg  13620
gaaggggccg gatgggacaa gcggaatatg aaactcattg agtccaagcc caaggtcctg  13680
ttcgagctga tgccagtgat ccgcatctac gccgaaaata acaccctccg ggatccgagg  13740
ttctactcgt gcccaattta caagaagccc gtgcggaccg acctgaatta catcgccgct  13800
gtcgaccttc gcactgccca aactccggaa cactgggtgc tgcggggagt cgccctgctt  13860
tgcgacgtga agtag                                                   13875
```

```
SEQ ID NO: 9           moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 9
atgtttagga ttggtcggcg ccagctgtgg aaacatagcg tcactcgcgt cctcacgcaa  60
agacttaaag gagaaaagga ggcaaaacgg gcgttgctcg acgctcggca taactacctg  120
tttgcaatcg tcgcatcgtg tcttgatctt aacaagacgg aggtggaaga cgctattctg  180
gaaggtaatc agatcgagag aattgaccag ttgttcgctg tgggcggtct tcgccacctt  240
atgttctatt atcaagatgt cgaagaggcg gagactgggc agttggggag cttgggtgga  300
gtcaatttgg tcagcggtaa aatcaaaaaa ccaaaagtgt tcgtcacgga gggcaatgac  360
gtcgcgctga cgggtgtctg cgtcttcttt atccggacgg accccagcaa ggctatcacg  420
ccagataaca tccatcagga ggtgtcattc aatatgttgg atgccgcaga tggaggactc  480
cttaattccg tgaggcgcct tctttccgac atttttattc cggctctgcg cgccacctcg  540
catggttggg gagagctcga gggacttcaa gatgcagcga atattcggca agaattttg  600
tcctccctgg aaggattcgt caatgtgctt tcgggagcac aggagtccct taaagaaaaa  660
gtcaatttgc ggaagtgtga catcctggag cttaaaactt tgaaagaacc cacggactat  720
cttactttgg cgaacaatcc agaaacgttg gggaagattg aagactgtat gaaagtgtgg  780
attaaacaga ctgaacaggt gttggcagaa aataatcaat tgctcaaaga agccgacgat  840
gtgggcccga gagcggaact cgaacattgg aaaaagagac tgagcaagtt taattacctt  900
cttgaacagc ttaaatcccc ggacgtcaaa gcagtgctgg cagtgttggc ggctgctaag  960
tcgaaacttt tgaaaacttg gcgggagatg gacattcgga ttacggatgc cacgaacgag  1020
gccaaagata atgtgaaata tctttatacc ctcgagaagt gctgcgaccc actttattca  1080
tccgaccccgc tctcaatgat ggacgctatt cctaccctga tcaacgcaat taagatgatt  1140
tactcaattt cgcattacta caataccagc gagaaaatca cttcgttgtt cgtgaaagtg  1200
accaatcaaa tcattagcgc atgcaaggcc tatatcacga acaatggcac ggcctcaatc  1260
tggaaccaac cgcaagatgt ggtcgaggaa aagattttgt cggcaattaa gttgaagcaa  1320
```

-continued

```
gaataccagc tctgctttca taaaaccaag caaaagttga aacaaaaccc caatgccaaa  1380
caattcgact tcagcgaaat gtacatcttt gggaaattcg agacgtttca caggcggctg  1440
gcaaaaatca tcgatatctt taccacgctt aaaacgtact cggtcctcca agattcgacg  1500
atcgaggggt tggaggacat ggcgacgaag tatcaaggta ttgtggcaac tatcaagaaa  1560
aaagagtata acttcttgga ccagagaaaa atggactttg accaagatta cgaggagttc  1620
tgtaagcaaa ccaacgattt gcacaacgag cttcgcaagt tcatggacgt cacctttgcg  1680
aaaatccaga acaccaatca ggcgctccgc atgctgaaaa agtttgaacg gctcaacatt  1740
cccaatcttg gaattgacga caagtatcaa ctcattctcg aaaattatgg ggcagatatc  1800
gatatgatca gcaagttgta taccaagcag aaatatgacc cgccgttggc taggaatcag  1860
ccgcccatcg ctggcaaaat cctttgggca cgccagctct tccatcggat tcagcagccc  1920
atgcaactgt ttcaacagca tcccgcggtc ctgtcgaccg ccgaagccaa gccaattatt  1980
cggtcgtata acagaatggc taaggtcttg ctcgagttcg aagtcctgtt ccaccgcgct  2040
tggctgcgcc aaattgagga aattcacgtc ggtcttgaag caagcctttt ggtcaaagct  2100
cctggcactg gcgaactctt tgtcaatttt gacccgcaga ttttgattct gttcagagaa  2160
actgagtgta tggctcagat gggactcgaa gtgagccctt tggccacttc cctgtttcaa  2220
aagagagata ggtataagcg caacttctcg aatatgaaga tgatgcttgc tgaatatcaa  2280
agggtgaaaa gcaagattcc cgcggcgatt gaacagctca ttgtgccgca cctcgcgaag  2340
gtggatgagg cattgcaacc cggacttgcg gcgttgacct ggacttcgct caacattgaa  2400
gcctacttgg agaacacttt tgccaaaatc aaagatctgg agcttttgct cgacagggtg  2460
aatgatttga tcgagttcag aatcgacgcg atcctggaag agatgtcatc cactccactg  2520
tgtcagttgc ctcaggagga accacttacc tgcgaagaat ttctgcagat gacgaaagac  2580
ctctgtgtca acggcgcaca aattttgcac tttaaatcat cattggtgga agaagcggtc  2640
aatgaacttg tgaacatgtt gcttgatgtg gaagtgttgt ccgaggagga atcggagaaa  2700
atttcgaacg aaaattcggt caactacaag aatgaatcgt ccgcgaaacg cgaggagggg  2760
aattttgaca ctctgacctc ctcaattaat gccagagcca atgccctctt gctgactacc  2820
gtgacgagaa agaagaagga gaccgagatg cttggagagg aagctaggga attgctctcc  2880
cactttaacc atcagaacat ggacgcgttg ctcaaggtga cgcgcaatac tcttgaggcc  2940
attaggaagc gcatccactc gtcccacacg atcaacttcc gggattcaaa ctccgcttcc  3000
aatatgaaac agaactcgct cccgatcttt agagcttcag tgactctggc cattcctaat  3060
attgtcatgg cacctgcttt ggaggacgtc cagcaaacgc tcaacaaggc cgtcgagtgt  3120
attatttcgg tcccgaaggg agtcagacag tggtcctcag aactcttgtc caagaagaag  3180
atccaagaac gcaaaatggc agcccttcaa tccaacgaag attcggattc agatgtggaa  3240
atgggcgaaa atgagctcca ggataccctg gaaattgcat cggtcaatct tccaatccct  3300
gtccagacta agaactatta taagaatgtc tcagaaaaca aagaaatcgt caagttggtg  3360
tcagtcctgt cgacgatcat taatagcact aagaaggaag tgattacgtc gatggactgc  3420
ttcaaaaggt ataaccatat ctggcagaaa ggcaaggaag aagcaattaa aacctttatc  3480
acgcagtcac cgctgctgtc agagtttgag agccagattt tgtacttcca gaatcttgag  3540
caagaaatta atgcagagcc ggagtatgtc tgcgtcggtt ccatcgctct gtacacggcc  3600
gatttgaagt ttgctcttac cgcagaaacg aaagcatgga tggtggtgat cggcagacat  3660
tgtaataaga aataccggtc ggagatggaa aatatcttta tgcttattga ggaattcaat  3720
aaaaaattga accggcctat taaggatctg gatgatatcc gcatcgccat ggccgccctg  3780
aaagagatta gagaagaaca aatctcaatc gatttccagg tgggccccat cgaagaatca  3840
tatgcgctcc ttaataggta cggactgctc attgccagag aggagatcga caaagtcgac  3900
accctccatt acgcttggga gaagctgctc gccagagcgg gggaagtgca aaacaaactt  3960
gtgagcttgc aaccgtcctt taagaaagaa ctcatttcag ccgtcgaggt gtttctgcaa  4020
gattgtcatc aattctacct cgattatgat ctgaacggtc caatggcttc gggactgaaa  4080
ccccaggaag ccagcgaccg gctgattatg ttccagaacc agtttgacaa catttatcgg  4140
aaatacatta cgtacacggg gggtgaggaa cttttcggtc tgccagcaac gcagtatcct  4200
cagctgttgg aaattaaaaa acaactgaac ctgctccaaa agatttacac cctctacaat  4260
tcagtcattg agaccgtgaa ctcatactac gacattctct ggtcagaggt gaatatcgag  4320
aagattaata atgaactcct tgaattccag aacaggtgca ggaagcttcc acgggcactc  4380
aaggattggc aggcgttctt ggatctcaaa aaaattattg acgatttctc agagtgttgc  4440
cctcttctgg agtatatggc ctcgaaagcg atgatggaaa ggcattggga aaggattacc  4500
accttgacgg gccacagcct tgatgtcggg aatgagtcat ttaaactcag aaacattatg  4560
gaagcccctt tgctgaagta taaggaggag atcgaggata tctgcattag cgctgtgaaa  4620
gagcgcgata tcgagcagaa attgaagcaa gtgattaacg aatgggacaa caaaacgttc  4680
acgtttggga gcttcaagac cagaggggaa ctcctcctgc ggggcgactc cacttccgaa  4740
attatcgcga acatggaaga ctcgcttatg cttctcggct cgctgttgtc caacaggtac  4800
aatatgccat ttaaggcaca gattcaaaaa tgggtgcaat acctcagcaa ctcgacggat  4860
attatcgagt catggatgac cgtgcaaaac ttgtggattt atctggaagc ggtgtttgtg  4920
ggaggagaca tcgctaaaca gctcccgaaa gaagcaaagc gcttttcgaa cattgacaaa  4980
agctgggtga aaattatgac gagggcccac gaagtgccct ccgtcgtgca atgttgtgtc  5040
ggcgacgaga ccctcggcca gctgcttccc cacctcctcg atcagctcga aatttgtcag  5100
aaatcgttga cgggatatct tgagaaaaaa aggttgtgct tcccgagatt ttttttcgtg  5160
agcgaccccg ctctcttgga gattttgggt caggcctccg attcgcatac catccaagca  5220
catctgctca acgtctttga caacattaag tcagtgaagt ttcatgaaaa gatttacgat  5280
agaatcctta gcatctcatc ccaagaggga gaaactattg aactggacaa gcccgtgatg  5340
gcagagggga acgtcgaggt ctggcttaat tcgttgctgg aagagtccca atcatcactg  5400
catcttgtca ttcgccaagc cgcggccaat atccaggaaa cggggttcca gctcactgaa  5460
ttcctttcaa gcttcccggc tcaggtcgga ctgttgggaa ttcaaatgat ttggacgcgg  5520
gattccgaag aggctttgag aaacgcgaag tttgacaaaa aaattatgca aaagaccaat  5580
caggctttct tggaactcct taatacgttg attgacgtca ccactagaga tttgtcatcg  5640
acggagcggg tgaagtacga aaccctgatc acgatccacg tgcatcagag agacatcttc  5700
gacgacttgt gtcatatgca cattaagagc ccaatggact ttgaatggct gaaacaatgt  5760
agattctact tcaacgagga ctccgataaa atgatgattc atatcacgga cgtggcattt  5820
atctatcaaa acgaattctt gggatgcact gatagactcg tgattactcc ccttaccgac  5880
agatgttata ttactttggc gcaagcactg ggcatgtcaa tgggtggcgc accggccgga  5940
cccgctggca ctggtaaaac cgaaaccacc aaggatatgg ggcggtgtct ggggaaatac  6000
gtcgtggtgt ttaattgctc cgaccagatg gatttccgcg gcctcggccg catctttaag  6060
```

-continued

```
ggcctcgccc aatcgggctc atgggggtgc tttgacgagt tcaatagaat tgacctgcct  6120
gtcttgtcgg tcgcagccca acaaatttca attatcttga cctgcaaaaa ggagcataaa  6180
aaatcgttta tctttactga cggggataat gtcactatga atccggagtt cggactcttt  6240
ttgacgatga acccgggtta cgccggaaga caagaactgc ctgagaatct caaaatcaat  6300
tttagatccg tggcaatgat ggtccccgac cgccaaatta ttattagagt caaacttgcc  6360
tcgtgtgggt tcattgataa cgtcgtgctc gcccggaaat tttttaccct gtacaaactg  6420
tgtgaagaac aactttcgaa gcaggtgcat tatgatttcg ggcttcggaa tatcctgagc  6480
gtgctccgga cgctgggtgc agcgaaaagg gccaacccaa tggacaccga gtcaactatt  6540
gtgatgcggg tccttagaga catgaatttg tccaaactga ttgatgagga cgagcctctg  6600
ttcctttcgc tgatcgagga tcttttcccg aacattcttc tggataaagc tggatatcct  6660
gaattggaag cggcaatcag cagacaggtg gaggaagcag gtttgatcaa ccatccccct  6720
tggaaattga aagtcatcca gttgttcgag acgcagcgcg tcaggcacgg tatgatgacc  6780
ctggggccct caggcgcagg gaagactacg tgtatccaca ctttgatgag ggcgatgact  6840
gattgcggta agccccacag ggaaatgaga atgaatccaa aagcaattac tgctccacag  6900
atgtttggtc ggctcgacgt ggccacgaat gattggacgg acggaatttt tagcactttg  6960
tggagaaaaa ctctcagagc taaaaagggt gaacatatct ggattattct cgatggcccg  7020
gtggatgcga tttggatcga gaatctgaat tcagtgctgg acgacaataa aactttgacg  7080
ctcgcgaacg gtgatcggat tcccatggcc cctaattgta aaattatttt cgaacctcac  7140
aacattgata atgctagccc ggccactgtc tccaggaacg ggatggtgtt tatgtcgtcg  7200
tccattttgg actggtcccc gattctggag ggcttcctga agaaaaggag cccacaggag  7260
gcagaaattt tgagacagtt gtacactgag tccttcccag atctctatcg gttctgcatc  7320
cagaacctcg aatacaaaat ggaggtgctc gaggcctttg tcattaccca gtcaattaat  7380
atgttgcagg ggcttattcc ccttaaggag caggggggtg aggtgagcca ggcccatctg  7440
gggcgcttgt tcgtctttgc tcttctgtgg tcggccgggg ctgctctgga gcttgacggc  7500
cggagacggt tggaattgtg gctgaggagc agacctacgg gtacgctcga attgcccccg  7560
ccagccgggc ccggggacac ggcgttcgat tactacgtcg cgcccgatgg gacttggacc  7620
cactggaaca ctcggacgca agagtatttg tatccctccg ataccacccc ggaatacggt  7680
agcatcctcg tgcctaacgt cgataacgtc cgcacggact ttcttatcca aaccatcgcg  7740
aagcagggca aggcagtgct gttgattggg gagcaaggca ctgccaaaac ggtgatcatc  7800
aaaggtttca tgtcgaagta tgatccagaa tgccatatga ttaaatcgct gaacttcagc  7860
tccgcgacta ccccgctcat gtttcaacgc accatcgagt cgtacgtcga taagaggatg  7920
ggcaccacgt acggtccgcc agccggtaaa aaaatgaccg tctttattga tgatgtgaat  7980
atgcctatca ttaatgagtg gggtgatcag gtcactaatg aaatcgtgcg ccagcttatg  8040
gaacagaatg gcttttacaa tctcgagaaa cccggcgaat tcacttcaat tgtggatatc  8100
caatttctgg ctgccatgat tcacccaggt ggaggaagga atgacattcc gcagagactc  8160
aaacggcagt tcagcatttt taattgcact ctcccttcgg aggcgtcagt ggacaagatc  8220
tttggagtca tcggggtcgg tcattactgt acccagagag gattttcgga ggaggtccgc  8280
gactcggtca ccaagcttgt ccctcttact aggcgcctct ggcaaatgac taagatcaag  8340
atgcttccca ccccggcgaa attccactac gtgtttaatc ttagggacct gtcccgggtc  8400
tggcagggca tgttgaacac tacgtcggag gtgattaagg aacccaacga tttgcttaaa  8460
ctgtggaagc acgagtgcaa acgcgtcatc gctgaccgct ttactgtgtc ctcagacgtg  8520
acctggtttg acaaagcctt ggtctccttg gtcgaggagg aatttggtga ggaaaaaaaa  8580
ttgctggtgg attgcggaat tgacacttac ttcgtggatt tcctccgcga tgcaccagaa  8640
gctgccggtg aaacctcgga ggaagcggac gccgagaccc ccaaaattta cgaaccgatt  8700
gaatcgttct cccacttgaa agagcggctc aacatgtttc tccaactgta taacgagtcg  8760
atcaggggag ctgggatgga catggtgttc ttcgccgatg ccatggtcca ccttgtcaag  8820
atctcgcggg tcatccgcac gcctcaaggt aacgctctct tggtcggtgt gggagggagc  8880
ggcaaacaaa gcctcactcg cctcgcgtcg ttcattgcag gttatgtctc atttcaaatt  8940
actctcaccc gctcctataa tacttcgaat ttgatggagg atttgaaggt cctttatagg  9000
accgctgggc aacaaggcaa aggaatcacc ttcatcttca ccgacaacga aattaaggac  9060
gaatcctttt tggaatatat gaataatgtc ctcagctcgg gagaagtgag caacctgttt  9120
gcaagagatg agattgatga aatcaattcc gaccttgctt ccgtgatgaa aaaggagttc  9180
ccaaggtgcc tgcccaccaa tgagaatctt cacgactact ttatgagccg cgtccggcaa  9240
aatctgcata tcgtgttgtg tttctcaccc gtcggtgaga agtttagaaa tcgcgccctc  9300
aagtttccgg ctttgatctc aggctgcacc attgattggt tttccagatg gccgaaggat  9360
gcactggtgg cagtctccga acatttcctg acttcatacg atattgactg ttcactggaa  9420
attaagaagg aagtggtcca atgcatggga tcattccagg atggcgtcgc agaaaagtgt  9480
gtggattact tccaaaggtt tcggaggagc acccacgtca cgcccaaatc atatttgtca  9540
ttcattcagg gctacaaatt tatctacggc gaaaagcacg tcgaggtccg gactttggca  9600
aacaggatga acaccggcct tgaaaaactg aaggaagcta gcgagtccgt ggctgcactc  9660
tcgaaggagc tggaggccaa agaaaaagag ctgcaagtcg ctaatgacaa ggccgacatg  9720
gtcttgaaag aggtgactat gaaagcgcag gctgctgaga aggtgaaggc tgaggtgcaa  9780
aaggtgaaag accgggctca ggccatcgtg gactcaattt caaaggataa ggctatcgct  9840
gaggaaaagt tggaagccgc taagcccgca ttggaggagg cagaggctgc gcttcaaacc  9900
atcaggccct ccgacattgc gactgtgagg accctgggaa ggccgcccca tctcatcatg  9960
cggattatgg actgtgtgct cctcctcttc caacgcaagg tctcagcagt caaaatcgat  10020
cttgaaaaaa gctgtacgat gccctcctgg caagagtcgc ttaaacttat gactgcgggc  10080
aattttctcc agaatcttca acagttccct aaagacacca ttaacgaaga agtcattgaa  10140
tttctttcgc cgtatttcga gatgcccgac tataatatcg agactgccaa acgcgtgtgt  10200
ggaaacgtcg cgggactgtg tagctggacg aaagcaatgg caagcttctt ttcgattaat  10260
aaagaagtcc tgccactgaa agccaatctc gtggtccaag aaaaccgcca ccttttggca  10320
atgcaagatc tccaaaaggc tcaagccgaa ttggacgata agcaagccga gctggacgtg  10380
gtccaggccg aatacgaaca agcaatgacg gagaagcaga cgttgctgga ggacgcagaa  10440
cggtgcaggc ataagatgca gacggcttcg acgcttattt cgggtcttgc cggagaaaag  10500
gaaaggtgga ccgagcaatc gcaagagttc gcagcccaaa ctaaaagact tgtgggagac  10560
gtcttgctcg ccactgcctt tttgtcatac agcggcccat tcaaccagga gttcagggac  10620
ctcttgctta acgattggag aaaggaaatg aaggctcgca aaatcccgtt tggaaagaac  10680
ctgaatttga gcgaaatgct tattgacgca ccgaccattt ccgagtggaa tctgcaaggc  10740
ctcccgaatg acgatcttag catccaaaac ggtattattg tgaccaaggc ctccaggtat  10800
```

-continued

```
ccactgttga tcgacccgca aactcaagga aagatctgga ttaaaaacaa ggaatcgcgg  10860
aacgaacttc agatcactag cctgaaccac aagtacttcc gcaaccatct cgaggattcc  10920
ctcagcctgg gccgccccct tctgatcgaa gacgtcggtg aggagctcga tcctgcgctc  10980
gataacgtcc tcgagaggaa ctttatcaaa acgggatcaa cgttcaaggt gaaagtcgga  11040
gacaaggaag tggatgtcct ggacgggttt cgcctctaca ttacgactaa gttgccaaac  11100
cctgcttaca cgcccgagat ctcggcaagg acgtcaatca ttgattttac cgtgaccatg  11160
aaaggcctcg aggatcagct tctcgggcgg gtgattctga ctgaaaagca ggaactcgaa  11220
aaagaaagaa cgcatcttat ggaggatgtg accgcgaata aacgccggat gaaagagctc  11280
gaagataacc ttctctacag gcttacctca acgcaaggtt ccctggtcga ggacgaatca  11340
cttattgtcg tgctgtccaa cactaagagg accgcggaag aggtgacgca gaagttggaa  11400
atttcagcag aaacggaagt gcagattaat tcggctcgcg aagaatatag accagtcgca  11460
actcgcggat cgattctcta ttttttgatc actgagatgc ggcttgtcaa tgaaatgtat  11520
caaacctcgc tgcgccagtt tcttggattg tttgacctgt cactcgcacg gagcgtcaaa  11580
tcgcccatca cgtcaaagcg cattgcgaat atcatcgaac atatgaccta cgaggtctat  11640
aagtatgccg cacggggatt gtacgaagag cacaagttcc tctttactct gctgctgacc  11700
cttaaaatcg acattcagag gaacagagtc aagcacgagg aattccttac gctgattaag  11760
ggaggagctt cactcgattt gaaggcgtgc ccacccaaac cgtccaagtg gattcttgac  11820
attacctggc tgaacctcgt cgagttgtcc aaattgaggc agttctcaga tgtcctggat  11880
cagatctcgc ggaacgagaa aatgtggaaa atttggtttg ataaggaaaa cccggaggag  11940
gagcccctgc cgaatgcgta cgacaaatca cttgattgtt ttagaaggct ccttttgatt  12000
cggtcatggt gccctgacag gacgatcgcc caagctagaa agtacattgt ggactcgatg  12060
ggggaaaagt atgcagaggg agtcatcctg gatcttgaaa agacctggga agagtcagac  12120
cctagaactc ctcttatctg tctgctttcc atgggctcgg atccgacgga ttcaatcatc  12180
gcactcggca agcgcctcaa aatcgagacg cggtacgtgt caatgggtca aggacaagag  12240
gtgcatgcac gcaagttgct gcaacagacc atggcgaacg gtgggtgggc cctgcttcaa  12300
aactgccacc ttgggctgga cttcatggac gaattgatgg atattattat cgagacggag  12360
ttggtgcatg acgcttttag actctggatg actacggaag cccataagca gttccccatc  12420
accctgttgc agatgtcgat taagttcgca aatgatcccc cccagggttt gcgggctggt  12480
ctgaaaagga cgtattcggg agtgtcgcaa gatttgttgg atgtctcctc cgggtcgcaa  12540
tggaaaccaa tgttgtatgc cgtggccttc cttcattcca cggtgcaaga gcgccgcaaa  12600
ttcggggcgc ttggatggaa catcccttat gagttcaatc aagcagattt caatgccacc  12660
gtgcaattca tccagaatca ccttgacgat atggatgtga aaaagggtgt ctcatggacc  12720
acgatccgct atatgatcgg tgagattcag tatggcggtc gcgtgacgga cgattatgat  12780
aagcggttgt tgaacacctt cgcgaaagtg tggttcagcg agaatatgtt cggacctgac  12840
ttctccttct accaaggcta taacattcca aagtgttcga ccgtcgataa ctacctccag  12900
tacattcaaa gccttcccgc atatgacagc cctgaggtct tcggtttgca cccgaatgcc  12960
gacattactt atcagagcaa gctggcaaag gacgtcctgg acaccatcct gggaatccag  13020
ccaaaagaca cgagcggtgg aggagacgag acgagggagg ccgtcgtggc cagattggca  13080
gacgacatgt tggagaaact gcctcccgac tatgtcccct ttgaggtgaa agaacggctg  13140
cagaaaatgg gtcctttcca gccgatgaac attttcctga ggcaggaaat tgatcggatg  13200
caaagagtgc tttcccttgt cagatcgacc ctgacggaac tgaaacttgc tatcgatggc  13260
actatcatta tgtcggagaa cttgagggat gccttggatt gcatgttcga tgcgagaatc  13320
ccggcatggt ggaagaaagc ttcatggatt tcatccactc tcgggttctg gttcacggaa  13380
cttatcgaga gaaactcaca gtttaccagc tgggtgttca acggtagacc acattgcttt  13440
tggatgactg gtttcttcaa cccgcagggc tttttgaccg ccatgaggca ggagattacc  13500
cgcgcaaata aaggttgggc tttggacaac atggtcctct gcaacgaagt cactaaatgg  13560
atgaaggacg atatctccgc gccgccaacg gagggcgtgt acgtctacgg gttgtatttg  13620
gagggagccg gatgggataa aagaaacatg aagcttatcg aaagcaagcc taaggtgttg  13680
ttcgaactca tgccagtgat cagaatttat gcggaaaaca atacgcttcg ggacccgcgg  13740
ttttattcct gccctatcta taaaaagcct gtccggaccg acctcaacta tattgcagcc  13800
gtggatctgc ggaccgccca aaccccgaa cattgggtgc tgagggggt ggcgcttctc  13860
tgcgacgtga aatag                                                  13875
```

```
SEQ ID NO: 10          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 10
atgttccgga ttggtcgccg ccagctttgg aagcacagcg tcactcgcgt cctgactcag  60
aggctgaagg gtgaaaaaga ggccaaaagg gccctgctcg atgcaagaca caattatctc  120
tttgcaattg tggcatcatg cctcgatctt aataagactg aagtcgagga cgcgattctt  180
gaagggaatc aaatcgaaag gattgatcag ctcttcgctg tgggtgggct tagacatctt  240
atgttttact accaggacgt cgaagaagca gaaaccggcc aattggggag cctcggtggt  300
gtcaatctgg tctccggaaa gattaaaaaa ccgaaggtct tcgtcactga gggtaacgac  360
gtcgcgctca cgggagtctg cgtctttttt attagaactg acccttcaaa agccatcacc  420
cccgacaaca ttcaccagga ggtgtcattc aacatgctgg acgcagcaga cggaggtctt  480
ctgaattcag tcaggcggct tctttccgat attttcattc cggcgcttcg ggccacctcg  540
cacggatggg gcgaactcga aggcctccag gatgctgcga acattagaca ggaattcctc  600
agctcgttgg agggatttgt gaacgtgttg tcaggggcac aggaaagcct gaaagagaag  660
gtgaacctca ggaaatgtga catccttgaa ctgaaaaccc ttaaggagcc aactgattat  720
ttgactctgg ctaataatcc tgaaaccctt ggtaaaatcg aggattgtat gaaagtgtgg  780
atcaaacaga ccgaacaagt cttggccgag aacaatcaac tgctcaagga ggcagacgac  840
gtgggtcctc gggcagaact tgagcattgg aaaaaacggc tgtccaagtt caattatctg  900
cttgaacagc ttaaaagccc ggacgtcaaa gccgtgcttg ctgtcctggc cgccgctaaa  960
tcgaaacttt tgaaaacttg gcgggaaatg gatatccgga ttaccgatgc tactaacgag  1020
gctaaagaca atgtgaagta cttgtacacg ttggagaagt gttgtgatcc tttgtattcc  1080
```

```
tcagatccgc tcagcatgat ggacgcgatt ccaaccctta ttaatgcaat taagatgatt  1140
tattcgatca gccattatta caatacctca gagaaaatta cctcactgtt cgtcaaagtg  1200
acgaatcaga ttatctccgc gtgtaaagca tatattacca acaacggcac tgcatcaatc  1260
tggaatcaac cacaagacgt cgtcgaagaa aaaattcttt ccgctatcaa gctgaaacaa  1320
gaatatcagc tctgctttca caaaactaaa caaaaactca aacagaaccc caatgccaaa  1380
cagtttgatt ttagcgaaat gtatatcttt ggaaagtttg agacgttcca tcggaggttg  1440
gcgaagatta tcgatatctt caccacgctc aagacttatt cagtgctcca ggattcaacc  1500
atcgaaggat tggaggatat ggctacgaag taccaaggaa ttgtcgcaac tatcaaaaaa  1560
aaggaatata acttcttgga tcagcgcaaa atggatttcg atcaggatta cgaggagttt  1620
tgtaagcaaa cgaatgacct ccacaatgaa ctcaggaaat tcatggacgt gacgttcgcc  1680
aaaattcaaa atactaatca agctttgagg atgctcaaga agttcgaaag gcttaacatc  1740
ccaaatcttg gaattgacga taaataccaa cttatcctcg agaactatgg agctgatatc  1800
gacatgattt ccaaattgta cacgaagcag aagtatgacc ctccccttgc ccggaatcag  1860
cctccgattg caggtaagat cctgtgggcc cgccagctgt ttcacaggat ccaacaacct  1920
atgcagcttt ttcagcagca ccccgcagtc ctgtcgaccg ctgaggccaa acctattatt  1980
agatcatata accgcatggc taaagtcctc ctggagttcg aggtcctgtt ccatagagcc  2040
tggcttaggc agatcgagga aatccacgtc ggcttggagg cttccctgct tgtcaaggcc  2100
ccggggacgg gcgagctctt cgtgaatttt gatccacaga ttttgatttt gtttcgcgag  2160
acggaatgca tggcacaaat gggtctggaa gtctcgccac ttgctacctc gttgtttcag  2220
aaaagagata ggtacaagcg caacttttcg aacatgaaga tgatgctcgc agaatatcaa  2280
cgggtgaagt ccaaaatccc ggccgcaatc gagcagctca tcgtcccgca cctcgctaaa  2340
gtcgacgaag ccttgcaacc tggactggca gcgctcacgt ggacgtcgct caatatcgag  2400
gcctacctcg aaaatacgtt tgctaagatc aaagacctcg aattgctcct tgatcgggtc  2460
aacgatctga ttgagtttag gattgacgca atcctggagg aaatgtcgtc aacccctctc  2520
tgtcagctcc cgcaagaaga gccacttacg tgcgaggaat tttgcaaat gacgaaagac  2580
ctgtgcgtca atggagccca gattcttcac ttcaagtcgt cattggtgga ggaggccgtg  2640
aatgagctcg tcaacatgtt gctcgatgtg gaagtgcttt cggaggagga gtcggaaaaa  2700
atctccaatg agaatagcgt caactataag aacgaatcaa gcgcaaagcg ggaagagggt  2760
aacttcgata ccctgactag ctcaattaac gctagagcga acgctttgct ccttacgacg  2820
gtgactcgga aaaaaaaaga gaccgagatg ttgggtgagg aggccaggga gctgctctcg  2880
cacttcaacc atcagaacat ggacgcactc cttaaggtga ccaggaatac tttggaggct  2940
atccgcaaga ggatccattc gagccatact atcaacttcc gcgactccaa tagcgcgtcg  3000
aacatgaaac aaaattcact tccaatcttc agagcgagcg tcacgcttgc cattcctaat  3060
atcgtcatgg ctcctgcact ggaagatgtg cagcaaactt tgaacaaggc cgtggagtgt  3120
atcatttcgg tcccgaaggg ggtgagacaa tggagcagcg agcttcttag caaaaaaaag  3180
attcaagaac gcaagatggc agccctccag tccaacgaag attcagattc agacgtcgaa  3240
atgggtgaaa atgagttgca agatacgttg gaaatcgcga gcgtgaatct tcccattccc  3300
gtccagacta aaaactatta caagaacgtc agcgaaaata aggagattgt caaacttgtc  3360
tcggtccttt caactattat taactcgacg aaaaaagagg tgatcacttc aatggattgc  3420
tttaaaaggt ataaccatat ctggcagaag ggtaaggagg aagcaatcaa aacgttcatc  3480
acccagagcc cccttctctc agaatttgaa agccaaatcc tctatttcca aaaccttgag  3540
caagaaatca acgcggagcc tgaatacgtc tgcgtggggt caattgcgct gtatacggcg  3600
gacctcaagt tcgcgctgac cgcggaaacc aaggcatgga tggtggtcat cggaaggcat  3660
tgtaacaaaa aatatcgctc ggagatggag aacatcttca tgttgatcga ggagttcaac  3720
aagaaactga acagaccgat taaggacctg gatgacatca ggattgccat ggcggcgctc  3780
aaagaaatta gagaggaaca aatttccatc gatttccagg tcggcccaat cgaagaatcc  3840
tatgcattgc tcaacaggta tggccttctg atcgcccgcg aggagattga caaagtggac  3900
acgctgcatt atgcttggga aaaacttctt gctagggcgg gagaagtcca aaacaagctc  3960
gtgagccttc agccaagctt caagaaagag ctgatcagcg ccgtcgaggt gtttcttcag  4020
gattgtcatc aattttacct cgactacgat ttgaatggtc ccatggcatc gggtctgaaa  4080
ccacaagagg cttcggatcg gctcatcatg tttcaaaatc agtttgataa tatctacaga  4140
aaatacatta cgtacacggg aggtgaagag cttttcggac ttcctgcaac tcaatatccg  4200
caacttcttg agatcaaaaa gcaacttaac cttctccaga aaatttatac tctgtataat  4260
tcagtcattg agactgtcaa cagctactac gacatcttgt ggtcagaggt caatattgag  4320
aaaatcaata atgagttgct tgaatttcag aatagatgtc ggaagcttcc tcgggccctc  4380
aaagactggc aggcttttt ggaccttaaa aaaatcatcg atgatttctc cgaatgttgc  4440
cccttgctcg agtatatggc tagcaaagcg atgatggaac gccattggga gcggatcacg  4500
acgcttactg gacatagcct ggatgtcggc aacgaatcct ttaaacttcg gaacatcatg  4560
gaggcgccgc ttcttaaata taaggaggaa attgaggaca tttgtatttc ggcggtgaaa  4620
gaaagggaca ttgagcagaa actgaaacag gtgattaacg agtgggacaa taagactttc  4680
actttcggtt cctttaaaac gagaggtgaa ctcctgctga gaggagactc gacgtcagag  4740
attattgcta atatggaaga ttcacttatg ctgttgggct cacttctctc aaataggtat  4800
aacatgccgt ttaaagcaca gatccagaaa tgggtgcaat accttagcaa ctccactgat  4860
attattgaga gctggatgac tgtgcaaaac ttgtggatct atcttgaggc agtgtttgtg  4920
gggggtgata tcgcgaaaca actgcctaaa gaggccaagc ggttctcaaa catcgataaa  4980
tcgtgggtca aaattatgac gcgggcacac gaggtcccta gcgtcgtcca atgctgtgtg  5040
ggggacgaga ctctcgggca actgcttccg cacctgctgg atcagctgga gatctgtcag  5100
aaatcgctga ctggatacct cgaaaagaaa cgcttgtgtt tccccaggtt ctttttgtg  5160
tcagaccctg ccttgttgga aattttgggg caggcaagcg acagccacac tattcaagcc  5220
cacttgttga acgtctttga taacattaaa tccgtgaagt ttcatgagaa aatttacgat  5280
agaatcttgt cgattagcag ccaggagggt gaaactatcg agctggataa acctgtcatg  5340
gctgagggta atgtcgaagt ctggttgaac agccttctgg aggagtccca gagctcactc  5400
catttggtca ttagacaggc tgcagctaat atccaggaga ctggatttca actgacggag  5460
tttctctcaa gctttcctgc tcaggtgggt ctgcttggaa tccaaatgat ctggacccgc  5520
gattcggagg aggctctgcg gaacgctaag ttcgataaaa agattatgca gaaaacgaat  5580
caggcatttc tggaactctt gaataccctg attgacgtga cgactcgcga ccttagctca  5640
accgagaggg tcaaatatga gaccctcatt accattcatg tgcatcaacg cgatattttt  5700
gacgacctct gccacatgca tattaaatca ccgatggact tcgagtggct gaagcaatgc  5760
agattttatt tcaacgagga ttcggataaa atgatgatcc atatcacgga tgtcgccttc  5820
```

```
atctaccaga atgagttcct tggatgcact gaccgcttgg tcatcactcc attgaccgac  5880
cgctgctaca ttactcttgc ccaggctttg gggatgtcga tgggtggggc cccagcgggc  5940
cctgcaggta cgggcaaaac ggaaactacg aaggacatgg ggaggtgcct tgggaagtac  6000
gtggtcgtgt tcaattgctc agatcagatg gattttaggg ggctcggaag aattttcaaa  6060
ggcctggctc agtccggctc ctgggggtgt ttcgacgaat ttaatcggat tgacttgcct  6120
gtgctttccg tggctgccca gcaaatcagc attattctca cgtgtaagaa ggagcacaag  6180
aaatcattta ttttcactga cggagataac gtgaccatga atcctgaatt cggccttttc  6240
ctcacgatga acccaggtta tgcgggtcgg caggagttgc ctgaaaattt gaagattaac  6300
tttcgctccg tcgctatgat ggtcccggac cggcaaatca ttattagagt gaagttggcc  6360
tcgtgcgggt tcatcgacaa cgtcgtgctg gcaagaaaat tctttacgct ctataagctc  6420
tgcgaagaac agctttcaaa acaggtccat tacgactttg gactcagaaa tattctctca  6480
gtgctcagga cgttgggtgc cgcaaagagg gccaatccca tggataccga atcaaccatc  6540
gtgatgagag tcctgagaga catgaatttg tccaagctta tcgacgagga cgaaccgctc  6600
ttcctgagct tgatcgagga ccttttccca aacattttgc tcgataaagc gggctaccca  6660
gaattggaag ccgccatttc gcggcaagtc gaggaagcag gtctgatcaa tcatccgcct  6720
tggaagctga aagtcattca attgttcgaa acccaacggg tccggcatgg gatgatgacc  6780
ctcggtccat cgggcgcggg taaaactacc tgtatccaca ctctcatgag ggcaatgacc  6840
gactgtggaa agccacaccg ggagatgagg atgaacccta aagctattac cgcgccccag  6900
atgttcggaa gactcgatgt ggccaccaat gattggacgg atgggatttt ttcgactttg  6960
tggcggaaga ctttgcgggc caagaagggg gaacacatct ggatcattct tgacggaccg  7020
gtggatgcca tttggatcga aaatctgaat tcggtgttgg acgataataa aactctgacc  7080
cttgcgaatg gtgatcgcat tccgatggcg cccaactgca aaattatctt cgagccccat  7140
aatatcgata atgcttcgcc agctactgtg tccaggaacg ggatggtgtt tatgtcatcc  7200
tcgatcctgg attggagccc aatcctggag gggtttctca aaaaacggtc gcctcaggag  7260
gccgaaattc tcagacagct ttacaccgag tccttcccgg atctctacag gttctgcatc  7320
caaaatctcg aatataagat ggaagtcctc gaagccttcg tgatcaccca atccatcaat  7380
atgcttcagg gactcatccc ccttaaggag caaggaggag aggtgtcgca ggcccatctg  7440
ggaagacttt ttgtcttcgc attgttgtgg agcgccgggg cagctctcga acttgacgga  7500
cgcaggcgcc tggaactttg gcttaggtcc aggcccaccg gaacgctgga acttcctccg  7560
cctgctggcc ccggggacac tgcttttgac tattatgtcg cccctgacgg tacctggacg  7620
cactggaaca ccaggactca ggaatatctg taccettcag acaccacgcc cgagtacggg  7680
tccatcttgg tccctaacgt cgacaacgtg agaactgact ttcttatcca gactatcgcg  7740
aagcaaggca aagcagtcct cctgatcggc gaacaaggaa cggctaagac ggtcatcatt  7800
aagggtttca tgtcaaagta tgatcctgag tgccacatga ttaaatcgtt gaatttttcc  7860
tcggcgacga cgcccttgat gtttcaacgc actattgagt cgtacgtgga taaaagaatg  7920
gggaccacgt acgggccccc ggcgggaaag aagatgactg tgttcatcga cgacgtcaat  7980
atgccgatca tcaacgagtg gggggaccag gtcacgaacg agatcgtgag gcaattgatg  8040
gaacagaatg gtttctacaa tcttgagaag cctggagagt tcacttcaat cgtcgatatt  8100
cagtttctgg ccgctatgat ccatccagga ggtggtcgga atgacattcc gcagaggctc  8160
aaaaggcagt tttcgatttt taattgcact ttgcccagcg aggccagcgt ggataaaatc  8220
ttcggggtga ttggagtggg tcattactgt actcagcggg gattctccga ggaggtgaga  8280
gactcggtca cgaagcttgt cccattgact cggcggcttt ggcaaatgac caagattaag  8340
atgctgccaa ctcccgccaa attccattat gtgttcaatc tcagggacct ttcgcgcgtg  8400
tggcaaggca tgctcaacac cactagcgag gtcattaaag agcccaacga cctttgaaa  8460
ttgtggaagc atgagtgcaa acgcgtcatc gcagacagat ttacggtgtc ctcagacgtg  8520
acttggttcg acaaagccct cgtgtccctg gtggaagagg aatttggaga ggaaaaaaag  8580
ctgctggtgg actgcggtat tgatacttat ttcgtggact ttcttcggga cgcaccggaa  8640
gcagccggag aaacgtcgga ggaagctgac gccgagactc ctaagatcta tgagcccatc  8700
gagagcttta gccacctcaa agaaaggctt aacatgttcc tccaattgta taatgagtcg  8760
attagaggtg ccggcatgga tatggtgttc tttgctgatg cgatggtgca cctcgtcaaa  8820
atttcgcggg tgatccggac tccacaggga aatgccctgc ttgtgggcgt cggcggatca  8880
gggaaacagt cgctcacgcg cttggcaagc tttatcgccg gttacgtctc attccagatc  8940
actctgacga gatcatataa tacttcgaac ttgatggaag atttgaaagt gttgtaccgc  9000
acggcgggcc aacaagggaa agggattacg ttcattttca ccgataacga aatcaaagac  9060
gaatcgtttc tcgaatacat gaacaacgtc ctgagctccg gggaggtgtc caatctgttt  9120
gctagggatg agattgacga aattaattca gaccttgcaa gcgtgatgaa gaaagagttc  9180
ccgcgctgcc tccccacgaa cgaaaacctg cacgattatt tcatgagcag agtccgccag  9240
aaccttcata tcgtgctttg ttttagccca gtcggagaga agtttcggaa tagagcactt  9300
aaatttccgg cgctgatctc cgggtgcacc atcgattggt tttcccgctg gcctaaagac  9360
gctctggtcg ccgtgtccga gcactttctc acttcgtatg atattgattg ctcactcgaa  9420
atcaagaagg aggtggtgca gtgcatgggg agcttccaag atggtgtggc agagaagtgc  9480
gtcgattact tccaaaggtt tagacgctcg actcacgtca ctcctaagtc atatctgagc  9540
tttattcaag gttataaatt tatctacggc gaaaagcacg tcgaggtccg gacccttgct  9600
aacagaatga acacggggct tgaaaagttg aaggaagctt cagaatcggt ggcagcactc  9660
tccaaggaac tcgaggccaa agagaaagaa cttcaagtcg caaacgataa agcggatatg  9720
gtcctcaaag aagtgaccat gaaggcacaa gcggcagaaa aagtgaaggc ggaggtgcaa  9780
aaagtgaagg atcgcgcgca agcaatcgtc gatagcatct caaaagacaa ggctattgcg  9840
gaggagaagc tggaggccgc caagcctgct ctggaggaag cagaggcagc tcttcagacc  9900
attcgcccta gcgatatcgc taccgtgaga actcttggta ggccccccca cttgattatg  9960
aggattatgg attgcgtgct tctccttttt caacggaagg tgtcggcggt gaagatcgac  10020
ttggagaagt catgtactat gccgagctgg caagaatcat tgaaattgat gaccgcagga  10080
aacttcttgc agaacctcca acagttccca aaggatacca tcaatgaaga agtcattgaa  10140
tttctctccc catattttga aatgccagac tataatattg aaacggccaa aagggtgtgt  10200
ggaaacgtgg cgggactgtg ctcctggacg aaggcaatgg cgtcgttttt ctcgatcaac  10260
aaggaggtgc ttccgttgaa agcaaacctc gtggtccaag agaaccggca cctgctggcc  10320
atgcaggacc ttcagaaggc tcaagccgag ctggacgaca agcaggcaga actggacgtc  10380
gtgcaagccg aatacgagca agcaatgacg gaaaagcaga cgttgttgga agatgcggaa  10440
cgctgccggc ataaaatgca gacggcttcg acgcttattt ccggactcgc tggggagaaa  10500
gaaaggtgga cggaacagtc acaagaattt gccgcccaaa ctaagagact ggtgggagac  10560
```

```
gtgcttctgg caactgcctt tctgtcgtac agcggcccat tcaatcagga attccgggat  10620
ctgttgctga atgattggag aaaagagatg aaagcccgga agatcccctt cgggaaaaat  10680
cttaatctct ccgaaatgct cattgatgcc cctaccatta gcgagtggaa tctccaagga  10740
ttgccgaatg acgatctgtc aattcaaaac ggcatcattg tgacgaaggc ctccaggtac  10800
ccacttctta tcgatccgca aacccagggg aaaatctgga ttaagaataa agaatcgcgg  10860
aacgagctcc agattacctc acttaatcac aaatatttca ggaaccacct tgaggattca  10920
ctgtcgctcg ggcggcctct gttgattgag gatgtgggtg aggaactgga tccagctttg  10980
gataatgtcc ttgaacgcaa cttcattaag accggatcaa cctttaaagt caaggtcggc  11040
gataaagagg tggatgtgct ggacggcttt agactctata ttacgactaa gcttcctaat  11100
cctgcgtaca cgccagaaat ttccgcgagg accagcatca tcgacttcac cgtcacgatg  11160
aagggactcg aggaccaatt gctggggagg gtcatcctca ctgaaaagca agaacttgag  11220
aaagagagaa cgcacctcat ggaagatgtg actgctaaca agagacggat gaaggaattg  11280
gaagataatt tgctgtatcg gctgacttca acccagggct cgctggtgga agacgaaagc  11340
cttattgtcg tcttgtcgaa tactaagcgc actgctgagg aagtcactca aaaactcgaa  11400
atttcagcgg agaccgaggt ccagatcaac tcggccaggg aggagtacag gccagtggcc  11460
actagaggtt cgatcttgta ttttcttatt accgagatgc ggctggtgaa tgaaatgtac  11520
caaacgtccc tgcggcaatt ccttggcctt ttcgacttga gccttgctcg ctcggtcaaa  11580
tcaccaatta cttccaaacg catcgcgaat atcattgagc acatgactta cgaagtgtac  11640
aagtacgcgg ccaggggact gtatgaggaa cacaaattcc tttttacgct cctcctcact  11700
ctcaaaattg atatccaacg caacagggtg aagcatgaag agtttcttac tttgatcaag  11760
ggaggtgcct cactcgacct caaggcctgc cctcccaaac cgtccaaatg gatcttggat  11820
attacttggt tgaacctcgt ggagcttagc aagctgcggc aattctcaga tgtcctcgat  11880
caaatttcac ggaatgaaaa aatgtggaag atttggtttg acaaagagaa ccccgaggag  11940
gaacctcttc ccaatgccta cgacaaaagc ctggactgtt ttaggcggct tctcttgatc  12000
aggtcatggt gtccggatcg cactatcgct caagcgcgga agtatatcgt cgactccatg  12060
ggtgaaaagt acgcagaggg ggtcatcctc gatctggaga aaacctggga agagtcagac  12120
ccaagaactc cgttgatttg cctcttgtca atgggctccg accctaccga ctccatcatc  12180
gcgctgggta aaaggctcaa aatcgaaacc cggtatgtca gcatggggca aggtcaggag  12240
gtgcacgcgc ggaagcttct ccaacagacg atggcaaatg gggttgggc acttcttcag  12300
aactgccact tgggcctcga cttcatggat gaactgatgg acattattat tgagacggag  12360
ctggtccacg atgcattccg cctctggatg accacggaag cccacaaaca atttcctatc  12420
acgctgctgc agatgtccat taagtttgca aatgatcccc cccaaggtct tcgcgcaggc  12480
cttaagagaa cgtattcagg agtgtcacag gatctccttg atgtctcatc ggggtcacaa  12540
tggaaaccga tgctgtacgc ggtcgctttc cttcactcca ctgtgcagga gcggaggaag  12600
tttggagcgt tgggatggaa tatcccctac gaatttaacc aagccgactt taatgctact  12660
gtgcaattta ttcaaaacca tcttgacgac atggacgtca aaaagggagt gagctggact  12720
accatcagat acatgatcgg tgagattcag tatggaggga gggtcaccga cgactatgac  12780
aaacggcttt tgaacacgtt cgcaaaagtg tggttttcag agaacatgtt tggcccggat  12840
ttctcatttt atcaagggta taatatccct aagtgctcaa ccgtcgataa ctatctccag  12900
tatatccaga gccttcccgc ttatgattcc ccagaggtgt ttgggttgca cccgaatgcg  12960
gatatcactt accagagcaa acttgctaag gacgtgcttg atacgattct cggtattcaa  13020
cccaaagata cgagcggagg aggagacgaa accagggaag ccgtggtcgc taggctcgct  13080
gacgacatgc tcgagaaact tccgcccgac tacgtcccgt ttgaagtcaa ggaaaggttg  13140
cagaagatgg gtcccttcca gccaatgaac attttcctcc ggcaggagat tgatcgcatg  13200
cagagagtgc tgtcattggt ccggtcgacg ctcactgaac ttaaacttgc cattgacggg  13260
actatcatca tgagcgaaaa tctgcgggat gcattggatt gcatgtttga tgcgcggatc  13320
ccagcgtggt ggaagaaagc ttcctggatc agcagcactc tcgggttttg gtttaccgag  13380
ctcattgaaa gaaattcgca gttcacgtca tgggtcttta acgggcgccc tcattgcttt  13440
tggatgacgg gcttctttaa cccgcagggt tttctcacgg ctatgaggca ggaaatcact  13500
agggcaaata aaggctgggc gcttgacaac atggtcctgt gtaatgaggt gactaaatgg  13560
atgaaggacg acatcagcgc tccccctacg gagggtgtgt atgtgtacgg cctctatttg  13620
gaaggtgctg gatgggataa gcgcaatatg aaacttattg agagcaaacc taaggtgctg  13680
tttgagctga tgcccgtgat ccggatctat gctgaaaata acacgttgag ggaccccagg  13740
ttctattcgt gtccgatcta caaaaagccg gtccgcaccg atttgaatta cattgctgct  13800
gtcgatcttc ggacggccca gacgcctgaa cattgggtcc tcaggggtgt ggcgctgctg  13860
tgtgatgtca aatag                                                   13875
```

```
SEQ ID NO: 11           moltype = DNA  length = 13875
FEATURE                 Location/Qualifiers
misc_feature            1..13875
                        note = Synthetic polynucleotide
source                  1..13875
                        mol_type = other DNA
                        organism = synthetic construct
SEQUENCE: 11
```

```
atgtttcgga ttggcaggcg ccagctgtgg aagcactcag tgactcgggt ccttacgcag  60
cggttgaaag gcgagaagga ggcaaaacgg gcactgttgg acgcaaggca caactatttg  120
ttcgcaattg tggcatcgtg cttggatctt aacaaaacgg aggtcgaaga cgcgatcctg  180
gaggggaatc agattgagag gatcgaccaa ttgttcgccg tcggagggtt gcggcacttg  240
atgttctact atcaagacgt cgaggaggct gagaccggcc agctcgggag cttgggagga  300
gtcaaccttg tgtcgggcaa aatcaaaaaa cccaaggtct tcgtgacgga ggggaatgat  360
gtcgcactga ccggtgtgtg cgtcttcttt atccgcaccg atccgtcaaa agcaattacc  420
cccgacaata tccatcagga agtgtcgttc aatatgctcg atgcggctga tggtggcctc  480
cttaattcag tcagaaggct tctctcagat atttttattc ccgccctccg ggctacgtcg  540
catggctggg gggagctgga ggggcttcaa gacgcagcta atattagaca ggagtttctt  600
tcctcactcg agggcttcgt caatgtcctg tccggcgcgc aggaatcact caaagaaaaa  660
gtcaacctca gaaaatgtga tatcctcgaa cttaaaaccc ttaaagaacc gaccgattac  720
ctcacgttgg caaataaccc cgaaactctg ggcaaaattg aagattgcat gaaagtgtgg  780
atcaagcaaa ctgagcaggt cctcgccgag aataaccagc tgctgaagga ggcggatgac  840
```

-continued

```
gtgggacctc gcgcggaact ggaacactgg aagaaacggc tttcaaaatt caactacctt  900
ctggaacagc ttaaatcccc tgatgtgaag gccgtcctgg ccgtgctcgc ggccgccaaa  960
agcaagctgt tgaagacttg gcgggagatg gacatcagaa tcacggacgc gaccaacgaa  1020
gccaaggaca atgtcaagta cctctacacg cttgagaaat gttgtgatcc cctctattca  1080
agcgatcctc ttagcatgat ggacgctatc ccaactctta tcaacgctat taaaatgatc  1140
tatagcatta gccactatta taacacttca gagaaaatca cgagcctctt cgtgaaggtc  1200
actaatcaaa tcatttccgc ttgtaaagcc tacattacta ataacggaac ggcatcgatc  1260
tggaaccagc cgcaagacgt ggtggaggaa aaaatccttt ccgcaattaa gcttaaacag  1320
gagtatcagc tttgctttca caagacgaaa cagaagttga aacaaaaccc aaacgcaaag  1380
caattcgatt tctcagagat gtatattttc ggaaagttcg aaacgtttca caggagactg  1440
gcgaaaatta tcgacatctt cactacgctt aaaacgtact cggtgctcca ggacagcact  1500
atcgagggtc ttgaggacat ggccaccaag tatcagggga tcgtcgccac cattaagaag  1560
aaggagtaca acttccttga ccaacggaaa atggattttg accaagatta tgaagaattc  1620
tgcaaacaaa ccaatgattt gcataacgaa cttcgcaaat tcatggacgt cacgtttgcg  1680
aaaatccaga atactaacca ggcgctgcgc atgctcaaaa agtttgagag gctgaacatc  1740
ccgaatctcg ggatcgacga caagtatcag ctcattcttg agaactacgg cgccgacatt  1800
gatatgatct cgaaactcta cacgaagcag aaatatgatc cgccgctcgc taggaaccag  1860
cctcctattg ccggaaagat tctctgggcg cgccagctgt tccatcgcat tcagcaacca  1920
atgcagcttt tccagcagca tcctgctgtg ctgtccaccg cagaggcgaa acctattatt  1980
agatcataca acaggatggc caaagtgttg ctggaatttg aggtgctgtt ccaccgggcc  2040
tggctgcgcc aaatcgagga gattcacgtg ggcttgaggc catccctctt ggtgaaagct  2100
ccaggtaccg gggaactgtt cgtcaatttt gacccgcaaa ttttgattct ttttcgggag  2160
actgaatgta tggctcagat gggtttggag gtgtcaccct tggcaactag cctgtttcag  2220
aagagagatc gctataaaag gaacttcagc aacatgaaga tgatgctcgc agagtaccag  2280
cgcgtcaagt ccaagatccc agccgctatc gagcagctga tcgtccccca cctcgctaaa  2340
gtggacgaag cgttgcagcc tgggctcgca gcacttacgt ggactagcct caacatcgaa  2400
gcttatttgg agaatacttt cgcaaagatc aaggacctgg agcttctgct tgatagggtc  2460
aacgatttga tcgagttcag aattgatgct attctcgagg agatgtcctc aacgccgttg  2520
tgccagctcc cacaggaaga accattgact tgcgaggagt tcctgcaaat gaccaaggac  2580
ttgtgtgtca acggtgcgca gattttgcat tttaagtcaa gcttggtgga agaggcggtg  2640
aacgagcttg tcaacatgct cttggacgtc gaggtgttgt cagaggaaga atcggaaaaa  2700
atctcgaatg aaaattccgt gaactataaa aacgaatcgt ccgccaagcg ggaagaaggg  2760
aacttcgata ccctcacctc aagcattaac gcgagggcta acgccctcct gctcactact  2820
gtgacgcgga aaaaaaagga aactgaaatg ctgggtgaag aggctcgcga acttttgtca  2880
cattttaatc accagaatat ggacgctctg ctcaaggtca ctcgcaacac tcttgaagcc  2940
atccgcaaac gcatccattc aagccacacg atcaacttca gggattccaa ctcggcaagc  3000
aacatgaaac agaactcact gcccattttt cgggcgtcag tgacgctcgc gatcccgaat  3060
atcgtcatgg cccctgccct tgaagatgtc caacaaactc tcaacaaagc ggtggaatgt  3120
attatttcag tgcctaaggg tgtcaggcaa tggagctcag agcttctgtc gaaaaaaaaa  3180
atccaggaga ggaaaatggc cgctttgcag agcaatgagg actcggattc cgacgtcgaa  3240
atgggggaaa acgaactgca agacacgctg gaaattgcat cagtcaacct tccaattcct  3300
gtccaaacta aaaactatta taagaacgtc tcggaaaata aggagattgt caaactggtg  3360
agcgtgttga gcactattat taatagcacg aagaaagaag tgatcacgtc catggactgc  3420
ttcaagaggt ataaccatat ctggcagaaa ggtaaagagg aagccattaa gacttttatt  3480
acgcaaagcc ccttgttgag cgagtttgag tcccagattc tctacttcca gaatctcgag  3540
caggagatca acgctgaacc cgagtatgtc tgtgtgggta gcattgcctt gtatactgcc  3600
gacctcaagt ttgctctcac ggctgaaact aaagcgtgga tggtcgtgat cgggaggcat  3660
tgtaacaaga agtaccgcag cgaaatggaa aatattttta tgctgatcga agagttcaac  3720
aaaaaactta atcggcccat caaagacttg gatgacattc ggattgcgat ggccgctctc  3780
aaagaaatca gggaggagca gatctccatt gactttcagg tcgggcctat tgaggagtcc  3840
tacgcactcc tgaacagata tggtctgctc atcgctcggg aagaaatcga caaagtggat  3900
accctgcatt atgcatggga aaaattgttg gcacgcgcag ggaggtccca gaacaaactt  3960
gtgagcctcc aaccttcgtt taaaaaggag ctgatctccg cagtggaggt ctttttgcag  4020
gactgtcatc aattctatct tgattatgac ctcaatgggc ctatggcgag cgggctcaag  4080
cctcaagaag catccgatcg cttgattatg ttccagaatc agtttgacaa tatctaccgg  4140
aagtatatta cttataccgg cggtgaagaa ttgttcggtc ttcctgcgac ccagtacccg  4200
cagcttctcg aaattaagaa gcaactgaat ctcctccaaa aaatttacac gctttacaac  4260
agcgtgatcg aaaccgtgaa ctcgtattac gatatcctct ggtcggaagt caacattgaa  4320
aaaattaaca atgaactgct ggaatttcag aatagatgca gaaaattgcc acgggctctg  4380
aaagattggc aggccttttt ggacttgaag aaaattatcg acgacttttc cgagtgctgc  4440
cccttgctgg aatatatggc ttccaaggcg atgatggaaa gacactggga aaggatcacg  4500
actctcaccg gtcactcgct tgatgtggga aacgaaagct ttaagctcag aaatatcatg  4560
gaggcaccgc tgttgaagta taaggaggag attgaagata tttgtatttc ggccgtgaag  4620
gaacgggaca tcgagcagaa actgaagcag gtgatcaatg aatgggataa caagactttt  4680
acctttgggt cctttaagac ccggggcgag ctccttctta gaggcgactc gacttccgaa  4740
atcatcgcaa atatggaaga ttccctgatg ctccttggat cattgttgtc aaatcgctac  4800
aacatgccct tcaaggccca gattcagaag tgggtccaat atctgtccaa cagcaccgac  4860
atcatcgaat cctggatgac tgtccagaac ctctggatct acctggaagc ggtgtttgtc  4920
ggcggggata tcgcgaaaca gttgccaaag gaggcgaaaa ggttctcgaa cattgataaa  4980
tcctgggtga aaattatgac tcgcgcccac gaagtgccaa gcgtcgtcca atgctgtgtg  5040
ggggatgaaa ccctgggcca actgctgccc caccttctgg accagcttga gatctgtcag  5100
aaatccctga cgggctacct cgaaaagaaa agactttgct tccccaggtt cttctttgtc  5160
tcagacccgg ccctgctgga gatcctcgga caagcatcgg actcgcatac cattcaggca  5220
catctcctta acgtgttcga taatatcaag tccgtgaaat tccacgaaaa gatttacgac  5280
cggatcctta gcattagcag ccaggaagga gaaactatcg agcttgacaa accagtgatg  5340
gctgaaggaa atgtcgaggt ctggttgaat tcccttcttg aagagtcgca gagctccctc  5400
catcttgtca ttcggcaagc cgcagcgaat attcaggaga cggggtttca acttaccgag  5460
tttctttcga gcttccccgc tcaagtcggt ttgttgggca ttcagatgat ttggacgagg  5520
gactcggagg aggccctccg caatgctaag ttcgataaaa aaatcatgca aaaaaccaac  5580
```

-continued

```
caggcattcc ttgagcttct taacactctt atcgatgtca ccacccggga cttgtcctcc  5640
acggagaggg tcaagtacga aacgcttatc actatccacg tgcaccaacg ggacatcttt  5700
gatgacttgt gccatatgca tatcaaatcg ccaatggatt tcgagtggct gaaacagtgc  5760
cggttctact tcaacgaaga ttccgataaa atgatgattc acattaccga tgtcgcattc  5820
atttaccaaa atgagttcct cggatgtact gatcggcttg tcattacgcc cctgactgac  5880
aggtgttaca tcactctggc gcaagctctg ggtatgtcga tgggggcgc tccggcaggc  5940
cccgcgggta ccgggaagac cgaaactacg aaggatatgg gcagatgctt gggcaaatac  6000
gtggtcgtgt ttaactgttc agatcagatg gacttccggg ggctgggtcg catctttaag  6060
gggttggcac agtcaggctc ctggggatgt ttcgatgaat tcaatcggat cgacttgccg  6120
gtcttgagcg tggcagcgca acagatttca atcatcctta cctgtaagaa ggagcataag  6180
aagtcgttta ttttcacgga cggggacaac gtcaccatga acccagagtt tggattgttc  6240
ctcactatga atccggggta cgcaggccgc caagagctcc cagagaatct caaaattaat  6300
tttagatcag tggctatgat ggtcccggac agacagatca tcattcgggt gaaactcgcc  6360
agctgcggct tcatcgacaa cgtggtgttg gcgcggaaat ttttcacgct ctataaactc  6420
tgcgaagaac agctttcaaa acaggtgcac tatgatttg gcctccggaa cattctctcc  6480
gtcctgagaa ctctcggagc ggcgaaaagg gcaaatccta tggataccga gtcgacgatt  6540
gtgatgaggg tcctgagaga tatgaacctt tcaaaactga tcgacgagga cgaaccactg  6600
tttctttcgt tgatcgagga tttgtttccg aacatccttc tggacaaggc tggttacccg  6660
gagcttgaag ctgcgatttc acggcaagtc gaagaggctg gattgattaa ccacccgcca  6720
tggaagctga aagtcatcca attgtttgag actcaaagag tccgccatgg catgatgact  6780
cttggtccta gcggcgcggg gaagacgacg tgtatccaca ctttgatgag ggcaatgacg  6840
gattgcggta aacctcacag agaaatgagg atgaatccaa aggctattac cgcaccgcag  6900
atgttcggaa ggttggacgt ggcgacgaat gactggactg acggcatttt ctcaacgttg  6960
tggcgcaaga ccttgagagc caaaaaagga gaacatatct ggattatcct cgacggcccc  7020
gtggatgcca tctggattga gaatcttaac tcggtgctcg atgataataa gaccctgacc  7080
ctggctaacg gagataggat cccgatggcc cctaattgca aaatcatctt tgaaccgcat  7140
aacattgata atgcatcacc agcgaccgtc tccaggaatg gtatggtgtt catgagctca  7200
agcattctgg attggtcgcc cattcttgag ggattcctca aaaaaagatc acctcaggag  7260
gcagagattt tgagacaact gtatacggaa tccttcccgg atctgtatag attttgtatc  7320
caaaatctcg agtataaaat ggaggtcctt gaggctttcg tcattacgca aagcatcaat  7380
atgctgcagg gtctgatccc tttgaaagaa caggggggag aggtgtcaca agctcacctg  7440
ggaagactct tcgtgttcgc gttgctctgg agcgcaggcg cagcgctcga gctggatgga  7500
aggaggaggc tcgaattgtg gctgcggagc cgccccacgg gcactttgga actgccgccc  7560
ccggccggtc cgggcgacac cgcattcgac tactacgtgg cgccagatgg tacgtggact  7620
cactggaata cgagaaccca agaatatctt tatccatcgg ataccacgcc tgagtatggt  7680
agcattctgg tccctaatgt cgataatgtc agaacggact tcctcatcca aactattgcc  7740
aaacagggta aagccgtcct cttgatcggt gaacagggta ccgcaaagac cgtcattatc  7800
aaagggttca tgtcaaaata tgacccggag tgtcatatga tcaagagcct caacttctca  7860
tcagccacca ctccgctgat gttccaaagg actatcgagt cgtatgtcga caagaggatg  7920
ggcacgacgt atggcctcc tgccggcaag aagatgaccg tctttattga tgacgtgaat  7980
atgccgatta ttaacgaatg gggagatcag gtcactaatg aaatcgtccg ccaactgatg  8040
gagcagaacg ggttctataa tctggagaag cccggcgaat ttacttcaat tgtggatatt  8100
cagttcttgg cagctatgat ccatccaggc ggaggccgga acgacatccc ccaacggctg  8160
aagagacagt ttagcatctt taactgcacg ttgccctcag aggcatcagt ggataagatc  8220
tttggagtga tcggagtggg tcactactgt acccagcggg gtttctcgga ggaggtccgc  8280
gacagcgtca ctaagctggt gcccttgacg agacggctct ggcagatgac gaagattaag  8340
atgctgccaa ctcccgcgaa gttccactac gtgtttaatc tgcgggactt gagccgcgtg  8400
tggcagggga tgctcaacac cacgtcagag gtcatcaaag agccgaacga cctgctcaag  8460
ttgtggaaac acgaatgcaa acgggtgatt gcggatcgct ttacggtctc ctccgatgtc  8520
acctggttcg ataaggcctt ggtgtcactt gtcgaagagg agttcggcga ggaaaaaaag  8580
cttctcgtcg actgcggaat tgatacgtat tttgtggact tcctgaggga tgccccccgaa  8640
gcggcaggag agacttccga ggaagcagat gcggaaaccc ccaaaattta tgaaccgatc  8700
gagtcatttt cacacttgaa ggagcgcctg aacatgttcc tccaactcta taatgaatcg  8760
atccgcggtg caggaatgga catggtgttc tttgctgatg ctatggtcca tctggtcaaa  8820
atttcaagag tgattagaac tccgcagggc aatgcgctcc tcgtcggagt gggggggatcc  8880
gggaagcaat cgctcacccg gctggcctcg ttcatcgcgg ggtatgtgtc gttccaaatt  8940
actctcacca ggagctacaa taccagcaac cttatggagg acctcaaggt gctctacagg  9000
actgctggcc agcagggtaa gggcattacc tttattttta ccgataatga aattaaagac  9060
gaatcctttt tggagtacat gaacaatgtc ctttcgtcag gtgaagtgtc aaacctcttc  9120
gcaagggatg aaattgacga gatcaacagc gacctggcta gcgtgatgaa aaaagaattt  9180
ccgcggtgtt tgccaaccaa tgaaaacttg catgactact tcatgtcacg ggtccgccaa  9240
aacttgcaca tcgtcctctg tttttcgcca gtgggtgaga agtttcggaa cagggcactt  9300
aagttcccgg cactcatctc cggctgtact atcgactggt tctcgaggtg gcctaaagat  9360
gcattggtgg cagtgagcga gcacttcttg acgtcctacg atattgactg ttcgttggaa  9420
attaagaaag aggtggtcca gtgtatgggg tcctttcagg atggagtcgc agaaaaatgc  9480
gtcgactatt tccagagatt caggagatca acgcatgtca ctccgaagtc atatttgagc  9540
tttattcaag gctacaagtt tatttacggg gaaaagcatg tcgaggtcag aacccttgca  9600
aatagaatga ataccggctt ggagaaactc aaagaagcgt cggaatcagt ggcggcattg  9660
tcaaaggagc tcgaagcaaa ggaaaaggaa ttgcaggtgg ctaacgacaa agcggacatg  9720
gtgctgaaag aagtgaccat gaaagcccaa gctgcagaga aagtcaaagc tgaagtgcag  9780
aaggtgaagg accgcgcaca ggctatcgtc gattcgatct cgaaggataa ggctattgcc  9840
gaagagaaac ttgaggccgc caagcccgct cttgaagagg cggaagctgc attgcagacc  9900
attagaccct ccgacattgc aacggtcagg actctgggca ggccccctca cttgattatg  9960
agaatcatgg actgcgtgct ccttctgttc caaagaaagg tgtccgccgt gaagatcgat  10020
cttgagaagt catgcacgat gccgtcctgg caggaatcgc ttaagcttat gacggcaggt  10080
aactttctcc aaaatctcca gcaatttccc aaggatacca ttaacgaaga ggtcatcgaa  10140
ttcttgtcac cctactttga aatgcccgat tacaacattg agacggctaa acgggtctgc  10200
gggaatgtcg ccggactgtg tagctggact aaggccatgg caagcttctt ctccatcaac  10260
aaagaagtcc tgcctctgaa agcaaatctg gtggtccaag agaatagaca tcttctggct  10320
```

-continued

```
atgcaggact tgcaaaaagc ccaggcggag ttggacgata aacaagcaga gttggacgtg  10380
gtgcaggccg agtacgaaca ggctatgacc gagaagcaaa cgctcctcga ggatgcagag  10440
cgctgtaggc ataaaatgca gacggcatcc accctcatct cagggctggc tggggaaaag  10500
gagaggtgga ccgaacagtc acaagaattt gccgcccaga ctaagagact tgtgggagat  10560
gtcctgctcg caacggcctt cctgtcgtat agcggtccat ttaatcagga atttcgcgat  10620
ctcttgctta acgattggag aaaagaaatg aaggccagaa aaatcccgtt cggtaaaaac  10680
cttaatttgt cggagatgct gatcgacgcg cctactattt cagaatggaa tctgcaaggg  10740
ctgccaaatg acgacttgtc catccaaaac ggaattatcg tgactaaggc ttcgcggtat  10800
ccactcctca ttgatccgca gactcaaggt aaaatttgga tcaagaataa ggaatcgcgg  10860
aacgagcttc agatcacttc actcaaccac aaatatttcc gcaaccacct ggaggattcc  10920
ttgagccttg gaagaccgtt gctcatcgaa gatgtcggcg aagaacttga tccggccttg  10980
gacaacgtcc tggaaaggaa cttcatcaaa actggctcga cttttaaagt gaaggtgggc  11040
gacaaggaag tcgatgtcct ggatggattt aggctttaca ttacgactaa attgccgaat  11100
ccagcataca ccccggaaat ttcggcgagg accagcatca ttgactttac ggtgactatg  11160
aagggattgg aagaccagct cctcggcagg gtgattttga cggaaaaaca ggagctggaa  11220
aaagaaagga cgcacctcat ggaggatgtg accgccaata aacgccggat gaaggagctc  11280
gaggataatc tcctttatcg cctcacgagc actcaaggat ccttggtcga ggacgagtcc  11340
cttattgtcg tgcttagcaa cactaagaga acggcggagg aggtcactca gaaactcgaa  11400
attagcgcag aaacggaggt gcaaatcaac tcagctaggg aggaatatcg gccagtcgca  11460
actagaggct ccattctcta tttcctcatc accgaaatgc gcctcgtcaa tgagatgtac  11520
caaacttcac tgcgccaatt cctgggtctt tttgatctgt ccctcgcaag atcggtgaaa  11580
tcccccatta ccagcaagcg gattgcgaac attatcgaac atatgacgta tgaggtctac  11640
aagtatgccg ccagggggct ttacgaagag cacaagttcc tctttacgtt gttgttgact  11700
cttaagattg acattcagcg gaaccgcgtg aaacatgagg agtttctcac tctgatcaaa  11760
ggagggggcaa gccttgactt gaaggcatgc ccccccaaac catcgaaatg gattcttgat  11820
atcacctggc tcaacttggt cgagctgtca aagctccggc aattctcgga cgtccttgac  11880
caaatttcga ggaacgagaa gatgtggaag atctggttcg ataaagagaa tcccgaagag  11940
gagcctttgc ccaacgccta tgataaatca ttggactgct ttcgccggct ccttctcatc  12000
agaagctggt gtccagacag aacgattgcc caggcgcgga agtatatcgt cgatagcatg  12060
ggggaaaaat acgccgaggg tgtcattctt gaccttgaaa aacttggga ggaatccgat  12120
ccgcggactc ctttgatttg tttgctgtcc atgggctccg atcccactga tagcatcatt  12180
gcacttggta agaggcttaa aattgaaacg cgctacgtga gcatgggaca gggccaggag  12240
gtccatgctc ggaaacttct gcagcaaacg atggccaacg gtggttgggc cctttttgcag  12300
aattgccact tgggtctcga ttttatggat gaacttatgg acatcattat cgagaccgaa  12360
cttgtccacg acgcatttcg gctctggatg acgactgaag cgcataaaca gtttccgatc  12420
accttgctcc agatgtcgat taaattcgcg aacgaccctc cgcaagggct tagagcgggt  12480
ctcaaaagga cctactcggg ggtgtcacag gatcttcttg acgtctcctc cggcagccag  12540
tggaaaccaa tgctgtacgc tgtggcattc ttgcactcca cggtgcagga aaggcggaag  12600
ttcggagctt tgggctggaa tatcccgtac gaattcaacc aggccgattt taatgcaacg  12660
gtgcaattta tccagaatca tctcgatgac atggatgtga aaaagggggt ctcatggacc  12720
accattagat atatgatcgg ggaaatccaa tacggtggta gggtcactga tgattatgat  12780
aagagacttc tgaatacgtt cgcaaaggtc tggttctcag agaatatgtt tggtcctgat  12840
ttctcgtttt atcagggcta taacatccct aagtgcagca ccgtggataa ctatctccaa  12900
tatatccaat ccctccctgc ttatgattca ccagaagtct ttggcttgca tcctaatgca  12960
gatattacgt atcagtcaaa actggcgaag gacgtcttgg acactatcct gggtattcag  13020
ccgaaagata cgagcggggg tggagacgaa accagagagg cagtcgtggc gaggctggct  13080
gacgacatgc tggagaagct gcctcccgac tacgtcccct ttgaggtgaa agaaagactg  13140
cagaagatgg gccccttcca acctatgaac atcttcttga gacaagaaat cgacaggatg  13200
caaagagtgc tgagcctcgt gcgctccacc ctgactgaat tgaagctcgc aatcgatgga  13260
acgatcatca tgtcggaaaa cttgcgggac gcacttgact gtatgttcga cgccaggatc  13320
ccagcgtggt ggaaaaaagc atcatggatc tcatcgactc tgggtttctg gtttaccgaa  13380
ctgatcgaaa ggaattcgca gtttacgtcc tgggtgttta acggacggcc acattgcttc  13440
tggatgaccg gctttttttaa ccctcagggt tttcttacgg ctatgcgcca agaaatcacc  13500
cgggcaaaca agggttgggc acttgacaac atggtcttgt gtaacgaggt gactaagtgg  13560
atgaaggatg acatctcagc tccgccgact gagggggtct acgtgtatgg tctttatctg  13620
gagggcgcag gttgggataa acgcaacatg aagctgatcg agtcgaaacc aaaagtcttg  13680
ttcgagctca tgcccgtcat tagaatctac gccgagaaca atacgcttcg cgaccctaga  13740
ttctatagct gcccgattta taaaaaaccg gtgcggacgg acttgaatta tatcgcggca  13800
gtcgatctgc ggacggcgca gacccctgag cattgggtgc tgcggggagt ggctcttctg  13860
tgcgatgtca agtag                                                  13875
```

```
SEQ ID NO: 12          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 12
atgtttcgca tcgggaggcg gcagctctgg aagcactccg tgacgcgcgt gctgacgcag  60
cgccttaaag gcgaaaagga agcgaagcgg gcccttctgg acgctcggca taactacttg  120
tttgccattg tggcttcctg tcttgatctg aacaagacgg aggtcgagga tgcaatcctt  180
gaaggcaatc aaattgaaag aattgaccag ttgttcgcag tgggcggtct caggcatctt  240
atgttttact atcaagacgt cgaggaggcg gaaacgggcc aattggggag ccttgggggga  300
gtcaatctgg tgagcgggaa aatcaagaag ccgaaagtct ttgtgacgga gggaaacgac  360
gtggcgctta ccggtgtgtg cgtgttcttt attagaaccg acccatcgaa ggccatcacg  420
cccgacaaca ttcatcagga ggtgagcttc aacatgttgg atgcagcaga tgggggactg  480
ttgaactcgg tgagaagact cttgtccgac atttttatcc cggctttgcg ggcaactagc  540
cacggttggg gtgaattgga agggctccag gacgctgcaa atatccgcca agagtttctt  600
```

-continued

```
agctcccttg aaggttttgt gaatgtcttg agcggagcgc aggagtccct taaggaaaaa  660
gtcaatctga gaaaatgtga tattttggaa ctgaaaacgc tgaaggaacc gactgattac  720
ctgaccttgg cgaataatcc agaaacgttg gggaagatcg aagactgcat gaaagtgtgg  780
attaagcaga ccgagcaagt cttggcagaa aacaaccagt tgctcaagga ggctgacgac  840
gtggggcccc gggccgagct cgagcattgg aagaagcggt tgagcaagtt taactatttg  900
ctcgaacagt tgaaatcgcc tgacgtcaag gcggtgctcg cagtcttggc agctgcgaag  960
tcaaagttgc tgaaaacttg gcgcgagatg gacatccgca ttactgacgc taccaatgaa  1020
gcaaaagaca acgtgaaata tctgtatact ctcgagaaat gttgtgaccc tttgtattcg  1080
tcggaccccc tttcgatgat ggatgcaatc ccgacgttga tcaacgctat caagatgatt  1140
tattccattt cacactacta caatacgtcg gagaagatca cctccctgtt tgtcaaggtg  1200
acgaatcaga tcatttcggc gtgtaaagca tatatcacta acaacggcac ggcatccatt  1260
tggaaccagc ctcaggatgt cgtcgaagag aagatcttgt ccgctatcaa gctgaagcaa  1320
gagtatcaac tgtgtttca caagactaaa cagaagctca agcaaaaccc aaatgcgaag  1380
cagtttgatt tttcagaaat gtacatcttc gggaagttcg agaccttcca caggcggttg  1440
gctaaaatta tcgatatctt cacgacgctt aagacgtata gcgtccttca ggattcgact  1500
atcgaaggac ttgaagatat ggcgacgaag taccaaggga tcgtcgcaac gatcaagaag  1560
aaagagtata actttctcga tcagagaaag atggactttg atcaagacta tgaagagttc  1620
tgcaaacaaa ccaatgatct tcataacgaa ctgcggaaat tcatggatgt cacctttgcg  1680
aagatccaaa acaccaacca agccctcaga atgctcaaga aatttgaaag gcttaatatt  1740
ccaaatctcg gcattgatga taagtaccaa cttatcctcg aaaattacgg agccgacatc  1800
gacatgatta gcaagcttta caccaaacag aaatatgatc ccccattggc gagaaaccag  1860
ccccccattg caggtaaaat tttgtgggcc cgccagctct ttcatagaat tcagcagccg  1920
atgcagctgt ttcaacagca tcccgcagtg ctttccacgg cagaggccaa gccaatcatc  1980
cgctcgtata atagaatggc aaaggtgctt ctggaattcg aggtcctttt ccatcgggcc  2040
tggttgcggc agattgagga aatccatgtg ggccttgaag cgtcactgct tgtcaaagcc  2100
ccgggtactg gtgagctgtt tgtcaacttt gatccccaaa tcttgatttt gttccgggaa  2160
acggaatgca tggcccagat gggtctcgag gtctccccat tggccacgtc gctctttcaa  2220
aagcgggacc ggtacaaaag gaatttttcg aatatgaaaa tgatgctcgc tgaataccaa  2280
cgcgtcaaat cgaagatccc agctgctatt gaacaactca ttgtcccaca ccttgctaaa  2340
gtcgatgagg ccctgcagcc tggtcttgcc gctttgacgt ggactagcct taacattgaa  2400
gcatatcttg aaaatacgtt cgcaaagatc aaagaccttg agctcctgct cgaccgggtg  2460
aatgatctga tcgagttccg gatcgatgca atcttggaag aaatgtcgtc caccccactc  2520
tgtcaacttc cacaggagga acccctgacc tgtgaagaat tcttgcagat gaccaaagat  2580
ctttgcgtca acggtgctca gatcttgcac tttaagagca gcctggtcga ggaggcggtc  2640
aatgagctcg tcaatatgtt gcttgacgtc gaagtgttgt cggaagagga aagcgagaaa  2700
atttccaacg aaaattcagt caactacaaa aatgaaagct cggctaagag ggaggaaggc  2760
aatttcgata cgctgaccag ctccattaac gcgcgcgcta acgccctgct tctcaccacc  2820
gtcacccgga agaagaaaga gactgaaatg ctgggagaag aggctcggga gcttctcagc  2880
cactttaatc accaaaatat ggacgcgctc ttgaaggtca cccggaatac cctcgaggcg  2940
atccggaaga ggatccactc atcccacact attaattttc gcgattccaa cagcgctagc  3000
aacatgaaac agaattccct gccgattttt cgggctagcg tgactcttgc cattccaaac  3060
attgtgatgg ctccagcatt ggaagatgtg caacaaacgc ttaacaaggc ggtcgagtgt  3120
atcattagcg tgccaaaggg ggtcaggcaa tggagctccg agttgttgag caagaagaag  3180
attcaagagc ggaagatggc ggcactccaa tccaacgagg attcggattc agatgtcgag  3240
atgggtgaaa atgaactgca agatactctg gaaatcgcaa gcgtgaatct gccaattcct  3300
gtccaaacca agaattatta taaaaacgtc tcggagaaca aagaaatcgt caagctcgtg  3360
tcggtcctct caactatcat taatagcact aaaaaagaag tcattaccag catggactgt  3420
tttaaacggt ataatcatat ctggcagaaa ggaaaggaag aggcaatcaa gacgtttatc  3480
acccagagcc ccttgctctc agaattcgaa tcacagattc tctacttcca gaatcttgaa  3540
caagaaatca atgctgagcc agagtatgtg tgcgtggggt ccatcgcttt gtatacggcc  3600
gatctgaaat ttgcgttgac cgcagaaacg aaggcttgga tggtggtcat tggccgccat  3660
tgcaacaaaa agtatcggtc agaaatggaa aacatcttca tgctgattga agagtttaac  3720
aagaagttga atcggcctat taaagatctc gatgatattc gcattgctat ggctgctctg  3780
aaggagatta gggaagaaca aatttccatc gactttcaag tcggtcctat cgaagaaagc  3840
tacgctctcc tcaacaggta tggtctcctc attgctaggg aagaaatcga taaagtcgat  3900
acgttgcact atgcgtggga gaagttgctc gcccgggccg gcgaggtcca aaataaactt  3960
gtgtccttgc aaccctcgtt caagaaggag ctgatctcag cagtggaggt cttcttgcaa  4020
gactgccatc aattctactt ggattatgat ctgaatggac ctatggcaag cggcctcaag  4080
ccccaagagg cgtcagaccg cctgatcatg ttccaaaatc aatttgataa catttacaga  4140
aagtatatta cgtacaccgg cggagaggaa ctgtttgggc tcccagcaac gcaatatcct  4200
caactcctgg aaattaaaaa gcagcttaat cttcttcaga agatttacac tttgtacaac  4260
tcagtcatcg agaccgtgaa ttcatattat gatatccttt ggtcggaagt gaatatcgag  4320
aagatcaata atgaactcct tgaattccag aatcgctgta ggaaattgcc cagagcactg  4380
aaagattggc aagccttctt ggacctcaaa aagatcattg acgacttctc cgagtgttgt  4440
ccacttctcg agtacatggc ctcgaaggct atgatggaac gccattggga gcggatcacc  4500
acgctcacgg gacactcgct tgacgtcgga aatgagtcct tcaaattgag gaatattatg  4560
gaggcgcccc tgcttaagta taaggaggag attgaggaca tctgtatttc ggctgtgaag  4620
gaaagggaca ttgaacagaa attgaagcag gtgattaatg aatgggacaa taaaaccttt  4680
accttcggtt cctttaaaac tcgcggagag cttctgttgc ggggagacag cacttcggaa  4740
attatcgcca acatggaaga ttcacttatg ctcctggggt cgctgctctc gaatagatat  4800
aatatgccct tcaaagccca aattcagaaa tgggtgcagt atttgagcaa ctcgactgac  4860
atcattgaat cctggatgac tgtgcagaac ttgtggattt acttggaggc agtcttcgtg  4920
ggaggcgata tcgcaaaaca acttccgaag gaagctaaaa gattctccaa tatcgacaaa  4980
tcctgggtga aaatcatgac tcgggcacat gaagtcccat cggtcgtgca atgctgtgtc  5040
ggtgacgaaa ctcttgggca actgctgccg cacctgttgg atcagctcga gatctgtcaa  5100
aagtcattga cgggatacct ggaaaagaag cgcctgtgtt ttcctcgctt cttctttgtg  5160
tccgaccccg cgctgttgga gatcttgggc caggcttccg actcgcacac tattcaggcc  5220
catctcctta atgtgttcga caatattaaa tccgtgaaat ttcatgaaaa gatttatgat  5280
cgcattctgt cgatctcctc acaggaagga gagacgattg aacttgacaa gcctgtcatg  5340
```

```
gccgaaggga atgtcgaggt ctggttgaat tccctcttgg aagagtcgca gagctcgttg  5400
cacctcgtca ttaggcaggc cgcagctaac atccaagaga ccggatttca gcttacggaa  5460
ttcctttcga gctttccggc tcaagtcggt ctgctcggca tccagatgat ttggacgcgg  5520
gacagcgaag aggccctcag aaacgcgaaa tttgacaaaa aaatcatgca gaagactaat  5580
caggcatttt tggagttgct gaatacgctg attgacgtga ctacgaggga tttgtcaagc  5640
acggagcgcg tgaagtatga gactttgatc actatccatg tgcaccaaag agatattttc  5700
gacgacttgt gccatatgca tattaaaagc ccgatggact ttgagtggct gaaacaatgt  5760
agattttact tcaatgagga ctcagacaag atgatgattc acatcaccga cgtcgcgttt  5820
atctaccaaa acgaattttt ggggtgcact gatagactcg tgattacgcc cctcactgat  5880
aggtgttata tcaccttggc ccaggcgctt ggtatgagca tgggcggggc gccagcgggc  5940
ccggcaggaa ccggtaaaac ggaaactact aaagatatgg ggcgctgtct gggcaagtat  6000
gtcgtggtct tcaattgtag cgatcagatg gattttcggg gcctcggacg cattttttaag  6060
ggccttgccc aatccggctc ctggggatgt tttgacgagt tcaatcggat tgacttgccg  6120
gtcttgtccg tcgccgccca acaaatctcc atcatcctga cttgcaagaa agagcacaag  6180
aagtcgttca tctttaccga cggtgacaat gtgactatga atcctgagtt tggtctcttt  6240
ctcacgatga atccgggata tgcgggaagg caggaactgc ctgaaaatct caaaatcaat  6300
ttcaggtcag tggctatgat ggtgcccgat cgccaaatca tcattcgcgt caaactggcc  6360
tcgtgcggat ttatcgataa tgtcgtgctg gcgaggaaat ttttcactct ctacaaactc  6420
tgtgaagaac aacttagcaa acaggtccac tacgatttcg gactccggaa catccttagc  6480
gtcttgagaa ccctcggggc tgccaaacgg gcgaacccaa tggatactga gagcaccatt  6540
gtcatgagag tgttgagaga tatgaacctc tccaagctga tcgatgaaga tgaacccctt  6600
ttcctgagct tgatcgaaga tctctttccc aatatcctgc ttgacaaagc gggttatccc  6660
gaactcgaag ctgctattag caggcaggtg gaggaagcag gactcatcaa ccatcctccg  6720
tggaaactga aagtcattca gctgttcgaa acccaaaggg tgcggcatgg tatgatgacg  6780
ctggggcctt ccggtgccgg gaaaacgacc tgcatcccata ctcttatgag agccatgacg  6840
gattgcggca aacctcatcg cgaaatgagg atgaatccga aagcgattac cgccccacag  6900
atgtttggac ggttggatgt ggcgacgaac gactggactg acgggatttt ctcgacgttg  6960
tggcggaaga cgcttcgggc gaaaaagggg gagcatattt ggatcattct cgatggtccc  7020
gtggatgcca tttggatcga aaatttgaac tccgtgctcg acgataataa gactcttacg  7080
ttggcaaatg gtgacagaat tccgatggca ccaaactgca agattatctt cgaaccacac  7140
aatatcgaca atgcgtcccc cgccaccgtc tcccgcaacg ggatggtctt tatgtcatcg  7200
agcattttgg actggtcgcc aattctcgaa gggttcctga aaaaacgctc gccgcaggag  7260
gcggaaattc tgaggcaact ctatacggaa tcattcccag atctctatcg cttctgcatc  7320
caaaacctgg aatataaaat ggaagtcctc gaggcttttg tcattacgca atccattaac  7380
atgctccagg ggctcattcc attgaaagag caaggaggag aggtgagcca agcacacctg  7440
ggcaggcttt ttgtgttcgc actcttgtgg tcggcggggg ccgctctgga acttgatggg  7500
agacgcaggc tggaattgtg gcttcggtcg cggccaaccg gtacgttgga actcccacct  7560
cccgcaggcc caggggacac cgcttttgat tattatgtcg ccccagatgg cacctggacc  7620
cactggaaca ccagaacgca agaataccttt tatccgtcgg acaccactcc agagtatggg  7680
tccatccttg tgccgaacgt cgataatgtg agaacggatt ttcttatcca gaccattgcc  7740
aagcaaggaa aagcggtcct tctgatcgga gaacaaggga ccgctaaaac tgtgatcatc  7800
aaaggtttta tgtcgaagta tgatcccgaa tgtcacatga tcaaatcatt gaattttagc  7860
agcgcgacga ccccacttat gttccaaaga acgattgagt catatgtgga taaaagaatg  7920
ggtacgacct atgggccccc agcgggtaaa aagatgaccg tctttattga tgacgtcaat  7980
atgccgatta ttaatgagtg gggcgaccag gtcacgaacg agattgtccg gcagctcatg  8040
gagcaaaacg gcttctacaa tctcgaaaaa cccggagagt tcacgtcaat tgtggatatt  8100
cagttcctgg cagccatgat ccacccaggt gggggtagaa atgatatccc ccaaaggttg  8160
aagagacaat tttcgatttt taattgcacc ctccccagcg aagcctccgt ggataaaatt  8220
ttcggcgtca ttggagtggg gcactattgc acccaaagag gtttttccga agaagtccgc  8280
gattcggtca cgaaactcgt gcctctcacg cgccggcttt ggcagatgac taaaattaag  8340
atgctcccca cgccagctaa attccactac gtcttcaact tgagggacct gtcccgcgtg  8400
tggcagggca tgctcaacac tacctcggag gtgatcaaag agcccaatga tttgctgaaa  8460
ctctggaaac acgagtgcaa gagggtgatc gctgatcgct tcactgtctc gagcgacgtc  8520
acttggtttg acaaggcgct tgtcagcctg gtggaagagg aatttggtga agaaaaaaag  8580
ctcttggtcg actgtgggat cgatacttac tttgtcgatt ttctgaggga tgcgcccgaa  8640
gcggcggggg agacctccga agaagctgat gccgagactc cgaaaatcta cgagccgatt  8700
gaatcctttt cacatctcaa agagagactt aacatgttct tgcaactgta taacgaatca  8760
atccgggggg ccggaatgga catggtgttc ttcgctgacg caatggtcca tctggtcaaa  8820
atctcgcgcg tgattcgcac ccctcaaggg aatgctcttc tggtgggtgt gggagggtcc  8880
ggcaagcaaa gcctgacccg gcttgcctcc tttatcgccg gctacgtctc gtttcaaatt  8940
acgcttacgc gctcctataa cacgtcaaac cttatggaag atctcaaagt gttgtacaga  9000
actgctggac aacagggaaa gggaatcact tttatcttca ccgacaacga aatcaaggat  9060
gagagctttc tcgagtatat gaacaatgtg cttagcagcg gagaggtctc aaatttgttt  9120
gcgagagacg aaatcgatga gattaatagc gatctggcaa gcgtcatgaa aaaggagttt  9180
cctcggtgtt tgccgactaa tgaaaatttg cacgattatt tcatgtcacg cgtgcggcag  9240
aacctgcaca tcgtcctgtg cttctcacct gtgggtgaaa agtttaggaa ccgggcactc  9300
aagtttccgg cactgatcag cggctgtact attgattggt ttagccgctg gccaaaggat  9360
gccttggtgg cggtctcaga gcattttctc acctcctacg atattgattg cagcctcgag  9420
attaagaaag aagtcgtcca atgcatgggt tcgttccaag acggggtcgc cgaaaagtgt  9480
gtcgactatt tccagagatt caggcggagc actcatgtca ctccgaagtc ctatttgtcg  9540
ttcatccagg gatacaaatt tatttacgga gaaaagcatg tggaggtgag aactttggca  9600
aataggatga acacggggct tgagaaattg aaggaggcta gcgaatcagt ggccgcactc  9660
tcaaaagagt tggaagctaa ggagaaggag ttgcaggtgg ctaatgataa ggctgatatg  9720
gtccttaaag aggtcacgat gaaggcgcaa gccgcagaaa aagtcaaagc ggaagtgcaa  9780
aaagtgaaag atcgggctca ggctattgtc gacagcatct ccaaggataa agccattgcc  9840
gaggagaagc tcgaagctgc taagcctgct cttgaggaag ctgaggcagc actccagacc  9900
atcaggccgt ccgacatcgc aaccgtgagg acgctgggaa ggcctccgca ccttatcatg  9960
agaatcatgg attgcgtcct gctgctcttc caacggaaag tctccgcggt caagattgat  10020
ttggagaaat cgtgtaccat gccctcatgg caggaatcct tgaagttgat gaccgcaggc  10080
```

-continued

```
aactttctgc aaaacctgca gcaatttcca aaggacacca tcaacgaaga ggtcatcgag  10140
ttcctcagcc cctattttga gatgccggac tataatatcg aaacggcaaa acgcgtgtgt  10200
ggcaacgtcg caggcttgtg ctcctggacc aaagctatgg cttcgttctt ctcaattaac  10260
aaagaggtgc tgccgttgaa agcaaacctc gtggtgcagg agaatagaca tcttctggca  10320
atgcaggact tgcaaaaagc tcaagctgag ctggatgata agcaagcaga gcttgatgtg  10380
gtccaggctg agtacgagca ggctatgact gaaaagcaaa cgcttctgga ggacgcagaa  10440
cgctgcagac acaagatgca gactgcttcc accttgattt cagggctggc tggagagaaa  10500
gaacggtgga cggaacagtc acaagagttt gccgcacaaa ctaaaaggtt ggtcggtgac  10560
gtcttgcttg cgaccgcgtt tctttcgtac tcagggccat tcaaccaaga gtttcgggat  10620
ttgctgctca atgattggag gaaggaaatg aaagcgcgca agattccatt cggaaagaat  10680
ctcaacctct cggagatgct tatcgacgcc ccgaccattt cagagtggaa cctccaaggg  10740
ctgccgaatg atgatctctc catccagaac gggatcattg tcacgaaagc ctcacgctac  10800
cctctgctca tcgatccgca gactcagggg aagatctgga ttaagaataa ggagtcgagg  10860
aacgaactgc agatcactag cttgaaccac aaatacttta gaaaccacct tgaggattca  10920
ctcagcctcg gtaggccgct gctcattgag gatgtgggcg aggaactgga cccagccctt  10980
gataacgtcc tggagcggaa cttcatcaaa accgggtcga cgtttaaagt gaaggtcggc  11040
gacaaagagg tcgacgtgct ggatggattc aggctttaca tcactacgaa actgcctaac  11100
ccagcgtaca ctccggagat ttccgcccgg acctcgatta tcgacttcac cgtcaccatg  11160
aaagggcttg aggaccagct ccttggacgc gtgatcctca ctgaaaaaca agaactcgaa  11220
aaggaacgga cccacctgat ggaggatgtc accgccaata aaagaaggat gaaagaactt  11280
gaagataatc ttctttatcg cctcacgagc actcagggct cgttggtgga agatgaatcc  11340
cttatcgtcg tcttgtcgaa caccaaacgc actgcggaag aggtcaccca gaagctggaa  11400
atttcggcag aaacggaggt ccaaattaat tccgcaaggg aggagtacag gccggtggcg  11460
acccgcgggt cgattcttta ttttctcatt acggagatga ggttggtcaa cgaaatgtat  11520
caaacgtccc tcaggcagtt tcttggcttg ttcgacctgt cacttgctcg ctcggtgaag  11580
tcgccgatta cgtcgaagag aatcgcaaat atcattgagc atatgaccta tgaggtctat  11640
aaatatgccg cccggggcct gtatgaggaa cataaatttt tgtttaccct gttgcttacg  11700
ttgaaaatcg acatccaacg gaacagggtc aaacacgagg aatttttgac gctgatcaag  11760
ggtggtgcct ccctggatct gaaggcctgc ccccccaagc ctagcaaatg gattcttgat  11820
atcacttggc tcaacctggt cgagctgtca aaattgcgcc agttttcgga tgtgctcgac  11880
cagatctcaa ggaacgaaaa gatgtggaag atctggttcg ataaagagaa cccggaggag  11940
gaaccactgc ctaatgctta tgacaaatca ctggactgtt ttcggagatt gcttctgatc  12000
cggtcctggt gcccggatcg cactatcgcc caggcaagaa agtatatcgt cgattcgatg  12060
ggagagaaat atgcagaagg tgtgatcctc gatcttgaaa agacgtggga agagtcagat  12120
cctcgcactc ctcttatttg cctcctttcg atgggatcag acccaacgga cagcattatt  12180
gcgctgggca agcggttgaa aatcgaaacg cggtatgtgt caatgggtca ggggcaggaa  12240
gtgcatgcac gcaaacttct ccaacaaact atggccaatg ggggctgggc gttgctgcaa  12300
aactgccacc ttggcttgga ctttatggac gaacttatgg atattattat tgagaccgaa  12360
ctggtccatg atgctttcag attgtggatg actacggagg ctcacaagca atttccgatc  12420
actttgctcc aaatgtcgat caaatttgcc aatgaccccc ctcaaggact gcgcgccgga  12480
ttgaaaagaa cttactccgg ggtgtcgcag gatttgcttg acgtctcaag cgggtcccag  12540
tggaagccca tgctttatgc tgtggccttc ttgcattcaa ctgtccaaga acgccggaag  12600
ttcggtgcac ttggctggaa cattccctat gaattcaacc aggctgattt caatgccacg  12660
gtccagttca tccaaaacca cctggatgat atggatgtca agaagggtgt ctcctggact  12720
actatccggt acatgatcgg tgaaattcaa tatggcggta gggtcacgga cgactacgat  12780
aaaaggctct tgaatacttt cgcgaaggtc tggttctcgg aaaacatgtt tggtccagac  12840
tttagctttt accagggata caacatccct aaatgtagca cggtggacaa ttatttgcag  12900
tacattcaaa gccttcctgc ttatgactcg ccggaggtct tcggtttgca tccaaacgcg  12960
gacattacgt atcagtcgaa acttgcaaaa gatgtgctcg acacgatcct ggggattcag  13020
ccgaaagata cgagcggcgg aggggacgaa actcgggaag ccgtcgtggc taggctggcg  13080
gatgacatgt tggaaaagct ccccccgac tatgtgcctt tcgaagtcaa agagaggctt  13140
caaaagatgg ggccgttcca acctatgaac attttccttc ggcaggagat cgatcgcatg  13200
caacgcgtcc tgagccttgt ccgcagcacc ctcactgaac tcaagctggc cattgatggg  13260
accatcatta tgtccgaaaa cctgcgcgat gcgcttgact gcatgtttga cgcgcgcatt  13320
ccagcttggt ggaagaaggc ctcctggatc tcatccactt tgggtttctg gtttaccgag  13380
ctgattgaac gcaactcgca attcacttcg tgggtcttca atgggcgccc gcactgtttc  13440
tggatgaccg gtttttttaa tcctcaaggt ttcttactg ctatgcgcca agagatcacc  13500
agggccaata aggggtgggc cctcgacaat atggtcctct gcaatgaagt cactaagtgg  13560
atgaaggacg atatctcagc acccccaacg gagggtgtct atgtctacgg cttgtacctg  13620
gaaggtgcgg gatgggacaa aaggaacatg aaacttatcg aatccaagcc caaggtgctt  13680
tttgagttga tgccggtgat ccggatttat gcggaaaata acactctgag agaccctagg  13740
ttctactcat gcccaattta caaaaaaccg gtccgcacgg acttgaacta cattgcggcg  13800
gtggacctcc gcaccgccca aaccccggaa cattgggtcc tcagaggcgt cgccctgctt  13860
tgcgacgtga agtag                                                  13875
```

```
SEQ ID NO: 13          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 13
atgtttcgga ttgggaggag gcaactctgg aaacacagcg tgaccagagt gcttacccag  60
cggctgaagg gagagaaaga agccaaacgc gctttgttgg atgctaggca caactatctc  120
tttgccattg tggcctcgtg cctcgatttg aacaaaactg aagtggagga cgccattctg  180
gaaggcaacc aaattgaaag aattgatcaa ctctttgctg tgggcggttt gagacacctc  240
atgttttatt accaggatgt ggaagaggcc gaaactggac aactgggatc gcttggtggt  300
gtcaatcttg tctccggaaa gatcaaaaag ccaaaagtgt tcgtgacgga aggaaacgat  360
```

-continued

```
gtcgccctga ctggggtgtg tgtgttcttt attagaaccg acccctccaa agcgatcacc  420
cccgataaca ttcatcagga ggtgtccttt aatatgcttg atgctgccga cggtggtctc  480
ttgaacagcg tgagacggtt gctttcagat atcttcatcc ctgcattgag ggcgacttcc  540
catggttggg gtgaattgga aggcttgcaa gacgctgcca atatccgcca ggagtttttg  600
tcgtccttgg aaggatttgt caacgtcctt agcggagcgc aagagtcgct taaggagaag  660
gtcaatttgc gcaaatgcga tatccttgag ctcaaaactc tcaaggaacc cacggattac  720
ttgaccttgg caaataaccc cgaaaccttg ggaagattg aggactgcat gaaggtgtgg  780
atcaaacaga cggagcaagt cctcgccgaa aataatcagt tgcttaagga ggctgacgat  840
gtcggcccca gggccgaact tgagcattgg aagaagcggc tctcgaaatt taactatttg  900
ctcgagcaac ttaagtcccc tgacgtcaaa gctgtgctgg cagtgcttgc cgcggccaag  960
tcaaaactgc tcaaaacgtg gagagaaatg gatattagaa tcactgacgc cacgaacgag  1020
gccaaagaca atgtgaaata cttgtacact cttgagaagt gctgcgatcc actgtactcg  1080
tcggatccgt tgagcatgat ggatgcgatc cccactctca tcaatgctat taaaatgatc  1140
tatagcattt cccattacta caacacgtcc gaaaagatca cgtccttgtt tgtgaaagtc  1200
accaatcaga ttatctcagc ttgtaaagca tacattacta ataatgggac tgcgtcaatc  1260
tggaatcagc cacaggacgt ggtggaggaa aagattcttt cggcgatcaa acttaagcaa  1320
gagtaccagc tctgcttcca taaaaccaag caaaagctta agcaaaatcc caatgccaag  1380
caatttgact tttcagagat gtacattttc ggtaagttcg agactttcca ccggcggctc  1440
gctaagatta tcgatatttt cactaccctt aaaacttaca gcgtcctcca agattccacg  1500
atcgaaggac tcgaggacat ggccaccaag taccagggta ttgtggcaac tatcaaaaaa  1560
aaagaatata acttttttgga tcagagaaaa atggattttg atcaagatta tgaggagttc  1620
tgtaaacaga ctaacgacct ccacaatgaa ctccggaaat ttatggacgt cacctttgcc  1680
aagatccaga acacgaacca agctttgcgg atgcttaaga aatttgaaag acttaacatt  1740
ccaaacctcg gcatcgacga taaataccag ctcatccttg aaaattatgg ggcggatatt  1800
gatatgatta gcaaattgta cactaagcag aagtacgacc cgcctttggc acggaaccaa  1860
cccccctatcg cgggcaagat cctttgggcc aggcagttgt ttcatcgcat ccagcagcct  1920
atgcagcttt ttcaacaaca tccggcagtc ctgtcaaccg ccgaagcgaa gcctattatt  1980
aggagctata accgcatggc caaagtgctg ctcgaatttg aggtcttgtt tcacagagca  2040
tggcttagac agattgagga aatccatgtc ggccttgaag catccctgct ggtcaaagct  2100
ccaggcacgg gcgaactttt cgtcaatttt gacccccaaa tcctcattct gttcagagag  2160
acggagtgta tggcacaaat ggggttggag gtgtcccccct tggcaacgtc cctttttcag  2220
aaacgggacc gctacaagag gaattttagc aacatgaaga tgatgcttgc ggagtaccag  2280
cgggtgaagt ccaaaatccc agctgcaatc gaacaactga tcgtgcccca ccttgccaag  2340
gtcgacgagg ccctgcaacc aggcctcgcc gcgttgactt ggacctcgct gaatatcgaa  2400
gcctatttgg aaaatacttt tgcgaagatc aaagaccttg agctgttgct tgacagggtc  2460
aacgacttga tcgaattccg gattgatgcc atccttgagg aaatgagcag cacccccctc  2520
tgtcaattgc ctcaagagga gcctttgacg tgcgaggaat tcctgcaaat gacgaaggat  2580
ctttgcgtga acggggcaca aatccttcac ttcaaatcat ccttggtcga ggaggccgtc  2640
aacgaactcg tcaatatgct tctcgatgtg gaggtcctta gcgaagaaga gagcgagaaa  2700
atttccaatg aaaactccgt gaattacaaa aatgagagct ccgcaaaaag ggaggagggg  2760
aacttcgaca ctctgacctc atccatcaac gcaagagcaa atgcattgct gcttactacg  2820
gtgactcgca aaaagaaaga gaccgagatg cttggtgagg aggccagaga actcttgtca  2880
cactttaatc atcagaacat ggacgccctt ctcaaggtga ccaggaatac cttggaagcg  2940
atcagaaaga gaatccacag cagccatacc attaacttta gggattcgaa ttcagcctcc  3000
aatatgaagc agaattcgtt gcctatcttc cgggcgtcag tgacccttgc cattccaaac  3060
attgtgatgg cccctgcact cgaagacgtc caacaaacgc ttaacaaagc ggtcgaatgt  3120
atcatttcgg tgccgaaggg agtgcggcaa tggtcatccg aactgttgtc gaaaaagaag  3180
attcaggaaa gaaagatggc cgctctgcaa agcaatgagg attcagattc agatgtcgag  3240
atgggagaaa atgagctcca ggatactctg gagattgctt cggtgaactt gcccatcccc  3300
gtgcaaacga aaaattacta caaaaatgtc tcggagaaca aagagatcgt caaacttgtg  3360
tcggtcctct ccacgattat caacagcacc aaaaaggaag tcattacgtc aatggattgc  3420
tttaaaagat ataaccatat ttggcagaag ggcaaggagg aagctatcaa gacctttatt  3480
acccaatccc ctctcctcag cgagttcgaa agccagattc tctatttcca aaacttggaa  3540
caagagatta acgccgagcc agaatacgtc tgtgtggggt cgatcgcgct gtacacggcg  3600
gacctcaaat ttgcacttac ggcggagacg aaggcctgga tggtcgtcat cggtaggcat  3660
tgtaacaaga aatacagaag cgagatggaa aatatcttca tgcttattga agaattcaat  3720
aagaaactga acaggcctat caaagatctt gatgatatca gaatcgcgat ggctgccctg  3780
aaagaaattc gggaggaaca aatttcgatc gattttcagg tgggtcctat cgaagaaagc  3840
tatgctttgt tgaatagata tgggctcctg atcgcacggg aagaaattga caaagtcgat  3900
actctgcatt acgcctggga aaagcttctc gcgagagccg gggaagtcca gaacaaactt  3960
gtctcccttc agcctagctt taagaaagag ctgatcagcg ctgtggaagt gtttcttcaa  4020
gattgccatc aattctacct cgactacgat ctcaacggtc caatggcctc cggtttgaag  4080
ccccaagagg cctccgacag acttatcatg ttccaaaacc agtttgataa tatctacaga  4140
aaatatatta cgtacacggg tggcgaggaa ctgttcggtc tcccagcaac ccaatacccct  4200
cagctgcttg agattaaaaa acaactgaat ttgttgcaga agatttacac gctctataac  4260
tcggtgatcg aaacggtcaa cagctattac gatattctct ggtcagaagt gaatatcgag  4320
aagatcaata atgaattgct cgaatttcag aatcggtgta gaaaactgcc cagggcactc  4380
aaagactggc aagccttcct tgatttgaag aaaattattg atgacttcag cgaatgctgt  4440
cccttctcg agtacatggc ctcgaaggcc atgatggaga ggcactggga acgcattacc  4500
actctgactg gccacagcct cgatgtgggt aatgagtcat tcaaattgag aaacatcatg  4560
gaggctcccc ttctgaaata taaggaggag atcgaggata tttgtatttc ggctgtgaag  4620
gagcgcgata ttgagcagaa attgaagcag gtgattaatg aatgggataa caagaccttc  4680
acgtttggtt ccttcaaaac cagaggcgag ctgcttctgc ggggcgactc aacgagcgag  4740
attatcgcaa acatggaaga ttccttgatg ctgttggggt cactgctttc aaatcgctat  4800
aatatgccgt ttaaggcaca aattcagaaa tgggtgcagt atctttccaa ttccaccgat  4860
attattgaat cgtggatgac tgtccaaaac ttgtggatct accttgaagc cgtgttcgtc  4920
ggtggggata ttgctaagca gttgccaaaa gaagctaaac gcttttccaa tatcgataaa  4980
agctgggtga agatcatgac tagagcacat gaggtgcctt ccgtggtgca gtgttgtgtc  5040
ggcgatgaaa cgcttggaca gcttctcccc caccttctcg accaactgga aatctgccaa  5100
```

-continued

```
aaatccttga ccgggtatct tgaaaagaaa agactttgct ttccaagatt ctttttcgtc  5160
tcagatcctg cgcttttgga aatcctgggc caggccagcg attcccatac gattcaagca  5220
cacctcctca atgtgttcga taatatcaaa tcagtcaagt ttcatgagaa aatttacgat  5280
cgcatcctgt caatctcctc ccaagaaggt gagaccatcg agttggataa acctgtcatg  5340
gcggagggga acgtggaagt gtggttgaac tccttgttgg aagaatccca atcatccctg  5400
caccttgtga ttcgccaggc ggcggctaat atccaggaaa cggggttcca gctcaccgag  5460
tttctcagct cattccctgc tcaggtcggg ctgctcggca ttcagatgat ttggacgcgg  5520
gactcggagg aagccctcag aaatgcgaag tttgacaaaa aaatcatgca aaagaccaat  5580
caagcctttc ttgaactgct gaatacccctc atcgatgtga ctaccaggga tctgtcgtcg  5640
accgaacggg tcaaatacga gacgcttatt actatccacg tccaccaaag ggatatcttc  5700
gatgatctct gtcacatgca tatcaaatca ccaatggact ttgaatggct gaagcagtgt  5760
cgcttttact ttaacgagga ttcagacaag atgatgattc acattaccga tgtggcattt  5820
atttatcaaa atgaattcct gggttgcacg gatcgcctgg tgattacgcc actcacggat  5880
cggtgttata tcacgctcgc acaggcattg ggaatgtcaa tggggggggc cccggcaggg  5940
ccagctggaa cgggtaaaac cgaaacgact aaggatatgg gtcggtgtct tggaaagtac  6000
gtggtcgtgt tcaattgcag cgatcaaatg gacttccggg gattgggaag aatttttcaag  6060
ggattggccc aatccggatc ctgggggtgt tttgacgaat tcaatagaat tgatcttccg  6120
gtcctgtcag tggccgcgca gcagattagc atcatcctta cttgcaaaaa agaacacaag  6180
aagagcttca tttttacgga cggagataac gtgactatga atccggagtt cgggctcttc  6240
ctgaccatga atccgggcta cgcgggcagg caggagctgc ctgagaatct caaaattaac  6300
tttcggtcag tggctatgat ggtccctgat cgccagatta ttatccgcgt caaacttgcg  6360
tcgtgcggtt ttatcgacaa tgtcgtgttg gcaaggaaat tctttactct ttataagctc  6420
tgtgaggaac aactctccaa gcaagtgcac tacgacttcg ggctccggaa tattctttcc  6480
gtccttcgga cgctcggcgc cgcaaaaagg gctaacccca tggacacgga atccacgatc  6540
gtcatgaggg tgctgcgcga catgaacctg tcgaagctca tcgacgaaga cgagccgctg  6600
tttttgagcc tcatcgaaga cctctttcct aacatccttc ttgacaaggc cgggtaccct  6660
gagcttgaag ccgctatttc gcggcaagtg gaggaggcgg ggcttatcaa tcatccgccc  6720
tggaagctta aggtcatcca attgtttgag acgcagaggg tccgccatgg aatgatgacg  6780
ctgggcccaa gcggtgccgg gaagactacc tgcatccaca ccctcatgag agcgatgacg  6840
gactgcggga agccccacag agagatgaga atgaacccta aggcaattac tgcaccccaa  6900
atgttcggcc gcctggacgt ggctacgaat gattggaccg acggaatctt ctcgaccctc  6960
tggaggaaaa cgctcagagc gaagaaggga gagcatatct ggattatcct cgacgggcct  7020
gtcgacgcaa tttggattga aaacttgaat tcagtcttgg acgataacaa gacgctgacc  7080
ttggcgaacg gcgatcggat ccctatggct cccaactgca aaatcatctt cgaaccccat  7140
aatatcgaca atgcgtcccc ggctacggtg tcgaggaacg gtatggtctt catgagctca  7200
tccatcctgg attggtcccc gattctggaa gggtttctca aaaagcggtc cccgcaagaa  7260
gcagaaattt tgagacaact ttatactgag agctttcccg acttgtatcg cttttgtatc  7320
caaaacttgg agtataagat ggaggtcttg gaggcatttg tcatcactca gtccatcaac  7380
atgctccagg ggctcattcc gctgaaagag caaggaggtg aggtgtcgca ggcacatctg  7440
ggaaggcttt tcgtgtttgc cctgctgtgg agcgcaggag ctgccctgga gttggacggt  7500
cggagaagac tggagctctg gctgcgctca agaccgacgg gcaccctgga acttccgcct  7560
ccagccgggc cgggcgacac tgcgttcgat tactacgtcg ctccggatgg aacttggacg  7620
cactggaata ctcgcactca agagtatctc tatccttcag ataccactcc ggaatacggc  7680
tcaattctcg tgccgaacgt cgacaatgtc aggaccgatt tccttatcca aaccattgct  7740
aagcaaggga aagccgtcct gcttattggc gagcaaggta ctgctaagac tgtcatcatt  7800
aaagggttca tgtcgaaata tgaccctgaa tgccacatga ttaaaagcct caatttcagc  7860
tcggccacta cgccgcttat gttccaacgc actatcgagt cgtacgtcga caagagaatg  7920
ggtaccactt atggtccacc ggcaggaaaa aaaatgactg tgtttattga tgacgtgaac  7980
atgcccatca ttaacgaatg gggtgatcag gtgacgaacg agattgtgcg gcaactcatg  8040
gagcaaaacg gcttttataa tttggaaaag ccaggcgagt ttacctcaat cgtggacatc  8100
cagttcctcg cagcgatgat tcaccccggg ggcgggcgca atgacatccc acagaggctg  8160
aagagacagt tttcaatttt caattgcacg ctgccctcgg aagcaagcgt cgacaaaatt  8220
tttggtgtca tcggagtggg tcactactgc actcaacgcg gcttctccga agaagtgaga  8280
gattcagtca ctaagctggt cccactgact cggcggcttt ggcagatgac gaaaattaaa  8340
atgctgccta ctcccgcgaa attccactac gtctttaatt tgagggatct ttcccgggtc  8400
tggcaaggta tgctcaatac cacttcggag gtcatcaagg agcccaacga tctcttgaaa  8460
ttgtggaagc atgaatgcaa gagagtcatc gccgaccggt tcacggtgag cagcgacgtg  8520
acttggttcg acaaagcgct tgtctcattg gtggaggagg aatttggcga agagaagaag  8580
ttgttggtgg actgtggaat cgatacttac ttcgtggatt ttcttcgcga tgcaccggaa  8640
gctgcgggag aaacgtcgga agaagcagac gccgaaacgc ctaaaatcta cgaaccaatt  8700
gagtcatttt cccaccttaa agaacggctg aatatgtttc tgcaacttta caacgaatca  8760
attcgcggtg cagggatgga catggtcttc tttgccgacg caatggtcca tctcgtgaaa  8820
atttcgagag tgattaggac gcctcagggt aatgcactcc ttgtcggggt gggcggctcc  8880
ggaaaacaat cattgacgcg gcttgcttca tttattgcag ggtacgtctc atttcagatt  8940
acgcttacca gatcgtataa cacctccaat ctcatggagg accttaaagt gttgtatcgg  9000
actgctgggc agcaggggaa ggggattacc ttcattttca ctgataatga aattaaagat  9060
gaaagctttc tggaatatat gaataatgtg ctttcatcgg gggaggtctc aaatcttttc  9120
gccagggatg aaattgacga aatcaacagc gaccttgcct ccgtgatgaa gaaagaattc  9180
cctcggtgcc tccctactaa cgagaatctc cacgattatt tcatgtccag agtgcgccaa  9240
aatctccata tcgtcctgtg tttttcgcca gtcggtgaaa agtttagaaa tagagctctt  9300
aaatttcccg cactcatcag cggctgtacg attgattggt tttcacgctg gcccaaagac  9360
gcgcttgtcg ccgtgtccga gcacttcctg actagctacg acattgactg ctcactggag  9420
attaaaaaag aagtggtcca atgtatgggt tcgtttcaag atggagtggc cgaaaaaatgc  9480
gtggattact tccagagatt cagacggtcc acgcacgtga cgccgaaatc atacctgtca  9540
tttatccagg ggtacaagtt tatttacggg gaaaagcatg tggaggtccg cacgcttgct  9600
aacaggatga atacgggcct ggagaagctt aaagaagctt ccgaatcggt cgcggcactg  9660
tcaaaggagc ttgaagccaa agagaaggag ctccaagtcg cgaatgataa agctgacatg  9720
gtcctgaagg aggtcacgat gaaggctcaa gcggcagaaa aggtgaaggc cgaggtgcag  9780
aaagtcaagg atcgcgcaca ggctatcgtc gattcaattt caaaggataa agctatcgcg  9840
```

```
gaagaaaagc tggaagctgc aaagccggcc cttgaagagg cggaggccgc tctgcaaact  9900
attcgcccgt ccgatatcgc tacggtgagg actctcggac gcccaccaca tctcatcatg  9960
agaattatgg attgcgtgct gcttcttttc cagagaaaag tcagcgcagt caagatcgat  10020
ctggagaaat catgtactat gccgtcatgg caggagagcc tgaagctgat gacggcagga  10080
aacttcttgc aaaacttgca acagtttccg aaagacacca tcaacgagga agtgattgag  10140
ttcttgtcgc cttactttga gatgccagat tacaatattg agaccgcaaa aagagtctgt  10200
ggcaacgtgg ccgggctttg tagctggact aaagcaatgg cctccttttt ctccatcaac  10260
aaagaggtcc tgcctcttaa ggcgaacctg gtggtgcagg agaataggca tcttctggca  10320
atgcaagacc tccaaaaggc ccaggctgag ttggatgaca agcaggccga actggacgtc  10380
gtccaggctg aatatgaaca ggcaatgacg gagaaacaaa ctctcctgga agatgccgaa  10440
cggtgcaggc ataagatgca aactgcttcc actcttatca gcggattggc gggcgaaaag  10500
gagagatgga cggagcaatc acaagaattc gcggctcaga ccaagcggct ggtcggtgac  10560
gtcctcctcg ccaccgcctt cttgtcgtac tcgggaccct tcaaccagga atttagagat  10620
cttcttttga atgactggag aaaggaaatg aaggctagaa aaatcccatt tggcaagaac  10680
ctcaacctct cggagatgct gattgacgct cccactattt ccgaatggaa ccttcaaggt  10740
ctgccaaacg atgacctcag cattcagaat ggaattattg tgactaaggc atcaaggtat  10800
ccattgctta ttgacccgca gacgcaaggc aaaatttgga tcaaaaataa ggagtccaga  10860
aacgagctgc agattactag ccttaatcac aaatacttta gaaaccattt ggaggactcc  10920
ttgtcactgg ggcgcccgtt gcttatcgag gacgtggggg aggagctgga cccggcgctg  10980
gacaacgtcc ttgaaaggaa tttcatcaag actggaagca cgtttaaagt caaggtcggg  11040
gataaggagg tggatgtcct ggatggattt cggctctata ttacgactaa actccccaac  11100
ccggcgtata ctccggagat ctcagcgcgc acgtcgatca ttgacttcac tgtcactatg  11160
aaaggtcttg aggatcagct tctgggaagg gtgatcctta ctgaaaagca agagctggag  11220
aaagagagga cgcatcttat ggaggatgtg actgcgaata aaaggcggat gaaagagctc  11280
gaagataacc tgttgtaccg cctgacgagc acccagggat cattggtgga agatgaatca  11340
ctgatcgtgg tcctgtcaaa caccaaaagg accgcagagg aggtgaccca aaagctggag  11400
atttcggctg agaccgaagt ccaaattaac tcggccagag aagaatacag gcctgtcgct  11460
actcggggaa gcattctgta ttttcttatt accgagatgc gccttgtgaa tgagatgtat  11520
caaacttcac tgaggcaatt tctcggactc ttcgatctgt cgcttgcgag atcagtgaaa  11580
tcccctatta cttcaaaacg gattgctaat attattgagc acatgacgta tgaagtctac  11640
aaatacgctg caagaggctt gtacgaggag cacaagtttc tgttcactct cctcttgacg  11700
cttaagattg acatccagcg gaacagagtg aagcatgagg agtttctgac gcttattaag  11760
ggaggtgctt cactggacct gaaagcatgt cctccgaagc cttccaagtg gattctggac  11820
atcacgtggc ttaatctggt ggagctctca aaactcagac aattttcaga cgtgttggat  11880
caaatttcaa ggaacgagaa aatgtggaag atttggttcg acaaagaaaa cccggaagag  11940
gagccattgc cgaacgctta tgacaaatcc ctggactgtt tcagaaggct gttgctcatt  12000
cggagctggt gtcctgatcg caccatcgca caggcgagaa aatatatcgt ggactcaatg  12060
ggtgagaagt acgcagaggg ggtcatcctg gatttggaaa agacttggga ggaatcagat  12120
ccgcgcactc ccctcatttg cctcctgtcc atgggaagcg atcccactga ttcgatcatt  12180
gcgcttggca aacggcttaa gattgaaacg aggtatgtct cgatgggtca aggacaggag  12240
gtccacgcta ggaaattgct tcagcaaacg atggccaatg gtgggtgggc gcttctccag  12300
aactgccatc tcggtcttga cttcatggac gaactgatgg atatcattat tgaaaccgag  12360
ttggtccatg acgcttttag gctgtggatg actaccgagg cccataaaca gttcccaatt  12420
acgttgctcc aaatgtccat taagtttgcg aacgaccctc cgcaaggttt gcgcgcgggc  12480
cttaaacgga cttactccgg agtcagccag gacttgctgg acgtcagcag cggatcacaa  12540
tggaagccca tgctctatgc agtggccttt ttgcacagca ctgtccagga gagaaggaag  12600
tttggagcgc tggggtggaa tatcccctat gaattcaacc aagcggactt taacgctacg  12660
gtccagttca tccagaacca ccttgatgac atggatgtca agaaaggcgt ctcgtggacg  12720
acgatcaggt acatgatcgg ggaaattcag tacggcggta gggtcaccga cgattacgac  12780
aaaaggctct tgaatacttt tgccaaagtg tggttttcag agaacatgtt cgggccggac  12840
ttctcctttt accaaggtta taatatcccc aagtgctcga ccgtcgacaa ttatcttcaa  12900
tacatccagt cgctgccagc atacgattcg ccagaggtct tcggtctgca tcctaacgcg  12960
gacatcacgt accaatccaa gttggcgaaa gatgtcttgg atactatttt gggtatccag  13020
cctaaagaca cctcgggggg gggcgatgaa accagggagg cagtggtcgc gaggctcgca  13080
gatgatatgc ttgagaagct gccacccgat tacgtgccct tcgaggtgaa ggagaggctc  13140
caaaaaatgg gaccattcca gccgatgaat attttcttgc gccaggagat cgacaggatg  13200
cagcgcgtgc tgtcactcgt ccgcagcact cttaccgagc tgaagcttgc catcgatggc  13260
acgattatta tgtcagagaa ccttagagac gcgctcgact gcatgtttga cgcaagaatt  13320
cccgcttggt ggaagaaggc atcatggatt tcctcgacgt tgggcttttg gttcacggag  13380
cttattgaac ggaattccca gttcacttcc tgggtgttca atggcagacc acactgtttt  13440
tggatgaccg gcttcttcaa cccgcagggg tttctgacgg cgatgaggca ggaaattact  13500
cgggctaata agggttgggc tcttgacaac atggtgctct gcaacgaagt gactaagtgg  13560
atgaaggacg atatttcggc ccctcctact gaaggggtgt atgtctatgg actttacttg  13620
gaaggggcag gttgggataa gaggaatatg aagcttatcg aatcaaaacc aaaagtgctc  13680
tttgagttga tgcctgtgat cagaatctat gcagaaaaca atactctcag ggatcccaga  13740
ttctactcct gtcctatcta taagaaaccc gtccgcacgg acttgaacta tatcgccgcg  13800
gtcgatctcc gcactgctca gactcccgag cactgggtcc ttcgcggggt cgcgctcctt  13860
tgtgacgtga agtag                                                   13875
```

```
SEQ ID NO: 14          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 14
atgttccgga tcggccggag gcaactgtgg aagcattcag tcaccagagt ccttacccaa  60
cgcctcaagg gagagaaaga ggccaaacgc gcgctgctgg acgctcgcca taattacctc  120
```

-continued

```
tttgcgattg tcgcctcatg cttggatctc aacaagactg aagtcgaaga cgccatcctt  180
gaaggcaacc aaatcgaacg gatcgatcag cttttcgccg tcgggggtct ccggcacctt  240
atgttttact accaggacgt ggaagaagct gaaacgggac agctggggtc acttggtggg  300
gtgaacctgg tgtccgggaa aattaagaag ccgaaggtgt ttgtcaccga gggcaatgac  360
gtggccctta ccggagtgtg cgtgttcttt atcagaacgg acccatcaaa agcaattact  420
ccggataaca tccatcaaga ggtcagcttc aacatgcttg atgcggcaga tggtggtttg  480
cttaattcag tccgccggtt gctttcggac atcttcattc ctgcccttcg cgcaacctcc  540
cacggttggg gagaacttga ggggttgcag gacgccgcta acattcgcca agaatttctt  600
tcaagcctcg aaggcttcgt gaatgtgctg tcgggggcac aggagtcgct caaagagaaa  660
gtcaatctga gaaaatgtga cattctcgag ctcaagactc tcaaggaacc cactgattat  720
ttgacgctcg cgaataatcc agaaaccctc gggaaaatcg aggactgtat gaaagtgtgg  780
attaaacaaa cggagcaagt gctcgcagaa aataatcaac tcctcaagga ggcggatgac  840
gtcggccctc gcgcggagct tgaacattgg aaaaagaggc tttcgaagtt taattatctg  900
ctcgaacagc ttaagtcacc ggatgtgaag gcagtgctgg cggtgcttgc agctgcaaag  960
tcgaaattgc tcaagacttg gcgggagatg gacatcagga tcactgacgc aacgaatgag  1020
gcgaaggata acgtgaagta cctgtatacc ttggaaaagt gctgtgatcc tctttatagc  1080
tccgaccctc tctcgatgat ggatgctatc ccaaccctca ttaatgccat taagatgatt  1140
tattcgattt cgcattatta taatacctcg gaaaaaatta cctcgttgtt cgtgaaggtc  1200
acgaatcaga ttatttcagc atgcaaagct tacattacca ataatggtac cgcttcgatc  1260
tggaatcagc cgcaagatgt ggtggaggag aaaattttga gcgcaatcaa gttgaaacag  1320
gaataccagt tgtgcttcca caagactaag caaaagttga agcaaaaccc aaacgctaaa  1380
caatttgatt ttagcgaaat gtatattttc gggaagtttg aaacctttca taggagactc  1440
gcgaagatta tcgacatttt cactacgctt aagacttatt cggtgttgca ggactccact  1500
attgagggat tggaggatat ggctactaag taccagggta ttgtcgccac gattaaaaag  1560
aaggaataca actttctgga ccaacgcaaa atggactttg accaagacta tgaagagttc  1620
tgcaagcaga ccaatgacct tcataatgaa ttgagaaagt tcatggacgt cactttcgcg  1680
aaaatccaga acaccaatca ggcccttagg atgctcaaaa aattcgagag acttaacatt  1740
cccaatctcg gaatcgacga caaatatcag ctcattctcg agaattatgg cgctgacatc  1800
gacatgatct caaaactgta caccaaacaa aagtatgatc cacctctggc taggaaccag  1860
cctccaatcg cggggaagat cctttgggcc cggcagcttt tccataggat ccagcagcct  1920
atgcaacttt tccagcagca tccagctgtg ttgtccacgg cggaggccaa accgattatc  1980
cgctcctata atcggatggc aaaggtcttg ctcgagttcg aagtgctctt ccaccgcgca  2040
tggcttcggc aaatcgagga gattcacgtg ggtctcgaag ctagcctttt ggtcaaggct  2100
cctggcacgg gggagctttt tgtcaatttt gatcctcaaa ttttgattct gttcagggaa  2160
actgaatgta tggcgcagat gggcttggag gtgtcaccct tggcgacgag cctctttcag  2220
aagagggaca ggtataagcg caatttctcc aatatgaaaa tgatgctggc tgagtaccag  2280
cgggtcaaat caaagatccc cgctgccatt gaacaactta ttgtgccaca tctcgcaaaa  2340
gtggacgaag ccctccaacc cggactcgcc gcgctcactt ggacttcgct gaacatcgag  2400
gcctacttgg aaaatacctt cgctaagatc aaagacctgg aattgttgct tgacagagtc  2460
aacgatctga ttgagttccg gattgacgct atcttggaag agatgtcgtc gacgccgctt  2520
tgtcagttgc cccaggagga gccattgact tgtgaagagt tccttcaaat gacgaaggac  2580
ttgtgcgtga acggtgccca aatcctccac ttcaagtcgt cattggtcga agaggctgtg  2640
aatgaactcg tgaatatgtt gcttgatgtc gaggtgctga gcgaggaaga atccgagaaa  2700
atttcgaatg agaattccgt caattataaa aatgaatcca gcgccaaacg ggaggagggg  2760
aactttgaca ctctgacgtc gtcgattaac gcacgcgcaa atgccctgtt gctgactacg  2820
gtgacgcgca agaaaaagga aaccgagatg ttgggcgagg aggccagaga actccttagc  2880
catttcaacc atcaaaatat ggatgctctc ctcaaagtga cccggaacac cctcgaggct  2940
atcagaaagc ggattcactc ctcgcacacc attaatttcc gggactcgaa ctcagcgagc  3000
aatatgaaac aaaactcact gccaatcttt cgcgcaagcg tgactctcgc aatcccaaat  3060
atcgtgatgg cccccgcctt ggaggatgtc cagcagacgc tgaataaggc tgtggagtgc  3120
atcatctcgg tgccaaaagg agtccgccag tggtccagcg agctcttgtc gaagaaaaaa  3180
atccaagagc gcaagatggc cgcccttcaa tccaacgagg atagcgattc agacgtcgag  3240
atgggcgaga acgagttgca agacaccttg gagattgcat ccgtgaatct cccaattcca  3300
gtccagacta agaactacta taaaaatgtg tccgaaaata aagaaatcgt caaactcgtg  3360
agcgtgctta gcaccattat caattccact aaaaaagagg tgattacgtc aatggactgt  3420
ttcaaacggt acaatcatat ttggcagaag ggcaaggaag aggctattaa aacgttcatt  3480
acgcagagcc cgctcctctc agaattcgaa tcccagattt tgtatttcca aaatttggag  3540
caggagatca atgcggagcc tgaatatgtg tgcgtgggat ccattgctct ttatactgcg  3600
gatctgaagt tcgctctgac ggctgaaact aaggcgtgga tggtggtcat tggcagacat  3660
tgcaataaaa agtataggtc cgaaatggaa aatatcttca tgctgatcga agagtttaat  3720
aagaaactca atcggccgat taaggatctg gatgatatcc gcattgccat ggcagccttg  3780
aaagagatca gagaagagca gatctcgatc gatttccagg tcgggcccat tgaggagagc  3840
tacgctctgc tgaatcgcta cggtcttctg attgcgcggg aggaaatcga caaggtggat  3900
actctccatt acgcatggga aaaacttttg gcacgcgccg gggaagtcca gaataaattg  3960
gtgtcgctgc agccttcgtt caaaaaaagag ttgatttccg ccgtggaagt ctttttgcag  4020
gattgccatc agttctatct ggactacgac ctcaacggac ctatggcttc gggccttaaa  4080
ccccaggaag cgtccgaccg gctgatcatg ttccagaatc agtttgataa tatctatagg  4140
aaatacatta cgtacacggg tggggaggag ctgttcggac tgccagcaac ccaatacccct  4200
caattgttgg agattaagaa gcagttgaat ttgctccaga agatctacac gctgtataac  4260
tcggtcattg aaactgtcaa ttcgtactat gacatcttgt ggtcagaagt caacatcgag  4320
aagatcaata acgaattgct cgaattccaa aatcgctgta ggaagttgcc aagggctctg  4380
aaggattggc aagccttcct ggatcttaag aaaattattg acgacttttc agaatgttgc  4440
ccactcctgg aatacatggc gagcaaagct atgatggaaa ggcactggga gcgcattacg  4500
actttgaccg ggcactcact tgatgtcggc aatgaatcgt ttaaactgcg gaatattatg  4560
gaggcaccgt tgttgaagta caaagaggaa attgaagata tctgtatcag cgcggtcaaa  4620
gaacgcgata tcgaacagaa actcaaacaa gtgattaatg agtgggacaa taagacgttt  4680
acgtttgggt cattcaagac tcggggagaa ctgctcttga ggggagactc cacttccgag  4740
atcattgcca acatggaaga ttccttgatg ttgcttggat ccttgctctc gaatcgctat  4800
aacatgccgt tcaaagccca gatccaaaag tgggtccagt atctctcgaa cagcaccgac  4860
```

```
atcatcgaat cgtggatgac ggtccaaaat ttgtggattt acctggaagc cgtcttcgtg  4920
ggcggcgata tcgcaaagca gttgcctaaa gaggcaaaaa gattttccaa tatcgacaaa  4980
agctgggtca aaattatgac cagagcacac gaagtgcctt ccgtggtcca gtgttgcgtg  5040
ggcgacgaaa cgcttggtca actgctcccg caccttttgg atcaactcga gatctgtcag  5100
aaatccctga ccggttatct tgagaaaaaa agactttgct ttcctagatt ctttttcgtc  5160
tcggacccgg cactgctgga gatcctcggt caggcgtcgg actcccacac tattcaagcc  5220
caccttctca acgtcttcga caatatcaaa tcggtcaaat tccatgagaa gatctacgat  5280
agaatcctgt cgatctcgtc acaagaaggc gaaactattg aactcgataa gcctgtgatg  5340
gcagaaggga acgtcgaagt ctggttgaat agcctcctgg aggagtcaca gtcgagcttg  5400
catcttgtca ttcggcaagc cgctgctaat attcaggaga ctggtttcca acttaccgag  5460
tttttgtcgt cctttccagc tcaggtgggc ctcctgggca ttcagatgat ttggacgagg  5520
gatagcgaag aagcccttcg caacgcaaag ttcgacaaga aaattatgca aaagaccaac  5580
caagcttttc tggaactcct caatactctg attgacgtga ccacgcggga tctcagctcc  5640
accgaaagag tcaagtacga gacgctcatt accatccacg tccatcaaag ggatattttc  5700
gacgacctct gccatatgca catcaaatcg cctatggatt tcgagtggtt gaaacagtgc  5760
cggttttact tcaacgagga ctccgacaaa atgatgattc atattaccga tgtggcattc  5820
atctatcaaa acgagtttct tggttgtacc gacagactcg tcattacccc tttgacggat  5880
aggtgctaca tcacccttgc acaagctctc ggaatgagca tgggaggtgc gcccgccggc  5940
ccggcgggaa ctggcaagac cgaaaccact aaggacatgg gcagatgtct gggcaagtat  6000
gtggtggtgt tcaactgttc cgaccaaatg gactttaggg gcctgggacg catcttcaaa  6060
ggactggcgc agagcggatc atggggctgc tttgacgagt ttaaccgcat cgatctcccg  6120
gtgctctccg tggccgccca gcagatttcg attattctca cctgtaagaa ggaacacaag  6180
aagtcattca ttttcacgga tggtgataat gtcacgatga accccgaatt tgggctgttt  6240
ctcactatga atccagggta tgctggcaga caagaactgc cagagaacct taaaattaat  6300
tttcggtccg tcgcgatgat ggtgcccgac cgccaaatta ttatccgggt gaaactggcg  6360
tcatgtggct tcattgataa cgtcgtcttg gcgcggaaat tttttactct ttataagctt  6420
tgtgaagaac agctctccaa gcaggtgcac tacgacttcg gtctgcggaa tatcctcagc  6480
gtcttgcgca cgcttggcgc cgcgaagagg gctaatccca tggatactga aagcactatc  6540
gtgatgcgcg tccttcgcga catgaacctg tcaaagttga tcgatgaaga cgaaccactg  6600
tttctgtcgc tgatcgaaga cttgtttccc aatatcctcc tcgacaaggc gggttatcct  6660
gaattggagg cagcgatttc ccggcaagtg gaggaagcgg gcctgatcaa ccatcctccg  6720
tggaagctga aggtgattca gcttttcgag actcaacggg tgcggcatgg gatgatgacg  6780
cttggtccgt ccggggctgg taaaactact tgtattcaca ccctgatgag agccatgacc  6840
gattgcggta aacctcaccg cgagatgagg atgaatccaa aggccattac ggcacctcag  6900
atgtttgggc gcctggacgt ggccaccaac gattggaccg acggaatttt ttcgaccctg  6960
tggcgcaaaa ctcttagagc caagaaagga gagcatattt ggatcattct ggacggtcca  7020
gtcgatgcta tttggatcga aaacctgaac tcggtcttgg acgacaataa gacgctcacg  7080
cttgctaacg gagaccgcat ccctatggcg cccaattgca aaattatttt cgagccacac  7140
aacatcgata acgcatcacc tgccactgtc agccggaatg gcatggtctt tatgtcgagc  7200
tcgattctgg actggagccc gatcctggaa ggatttctca aaaagcgcag cccgcaagaa  7260
gcagagattc ttaggcaact ctacaccgaa agcttccccg acttgtacag gttttgcatt  7320
cagaatcttg aatacaagat ggaggtcctt gaggccttcg tcatcacgca gtcaattaac  7380
atgcttcagg gcctgatccc actcaaagaa cagggcggag aggtgtcaca ggcacacctc  7440
gggagattgt ttgtgtttgc tcttctttgg tcagcgggcg cggcacttga actggatggg  7500
cgccgccgcc ttgagctctg gctgcggtcg agacctaccg gaactcttga actgccgcct  7560
cctgctggtc ctggagacac ggcatttgac tactatgtgg ccccagacgg cacttggact  7620
cattggaaca ccagaactca agaatatctt tacccatccg atactacgcc agagtatggg  7680
agcatccttg tgcctaacgt cgacaatgtc cgcacggatt tccttattca aactattgcg  7740
aaacagggga aggccgtcct gcttatcgga gagcaaggga ctgccaagac tgtcatcatc  7800
aaggggttta tgagcaaata tgacccagag tgccatatga tcaagtcatt gaatttttca  7860
tccgccacta cgcctctcat gtttcaacgc accatcgaat cctacgtcga caaaagaatg  7920
ggaactactt atgggccccc tgccgggaag aaaatgactg tgttcatcga tgacgtgaac  7980
atgcccatta ttaatgagtg gggagatcag gtcaccaatg aaattgtcag acagcttatg  8040
gaacagaatg gattctataa tctcgaaaag ccaggggaat ttacctccat tgtcgacatt  8100
caattcctcg cagccatgat ccatccagga ggtgggagga acgatattcc gcaacgcctt  8160
aagcggcagt tctccatttt caattgcacc ctcccctccg aggctagcgt cgataaaatt  8220
tttggggtca tcggtgtcgg gcactactgc actcaaaggg gcttttcgga agaggtgaga  8280
gattcagtca cgaaactggt gccgttgact agacgcttgt ggcagatgac caaaatcaaa  8340
atgcttccaa ctcccgctaa attccactac gtgtttaatt tgcgggacct ttcgcgcgtg  8400
tggcagggta tgctgaacac tacctccgag gtcatcaaag aacccaacga tttgctgaag  8460
ctctggaaac atgaatgcaa acgcgtcatt gctgatagat tcacggtcag ctccgatgtc  8520
acctggttcg ataaagcgct ggtcagcctg gtcgaggaag agtttgggga agagaagaag  8580
ttgttggtcg attgtggtat tgacacctat tttgtcgatt ttctcagaga cgcgcctgaa  8640
gctgcgggtg agacctccga ggaggctgat gctgaaactc ccaaaattta tgaaccgatc  8700
gagtccttct cccatttgaa ggaacggctg aacatgttcc tgcagctcta taatgagagc  8760
atccgcggtg ccggaatgga catggtcttt ttcgcagatg ctatggtgca cttggtgaaa  8820
atttcaagag tcattaggac gccccagggt aatgcattgc tggtcggggt gggtggatcc  8880
ggtaagcaat ccctgacccg ccttgcatca tttatcgcgg ggtacgtgtc attccagatc  8940
actcttacga gaagctataa tacgagcaat cttatggagg acttgaaagt gttgtatagg  9000
acggccggtc agcagggcaa gggtatcacg ttcatcttca ccgataatga gatcaaagat  9060
gagtccttct tggagtacat gaataacgtg ctcagcagcg gtgaggtgtc gaaccttttc  9120
gcaagagacg aaatcgatga aattaactcc gatctggcgt ccgtcatgaa aaaggaattt  9180
ccaaggtgcc tcccgacgaa cgagaatctc cacgactatt tcatgagcag agtccggcag  9240
aacctgcaca ttgtgttgtg cttctcaccg gtgggcgaaa agtttaggaa ccgcgcgctt  9300
aaattccccg ctctcatttc aggttgcact atcgattggt tctcaaggtg gccgaaggat  9360
gcactggtcg cagtgtcgga acactttctc acttcatatg atatcgattg ctcccttgaa  9420
atcaagaaag aggtggtgca gtgtatggga tcattccagg acggtgtggc ggagaaatgt  9480
gtcgactact ttcaaagatt cagaagaagc acgcacgtga cccctaaatc atacctctca  9540
tttattcagg gatacaagtt tatctacggc gaaaaacatg tcgaggtccg gactttggcg  9600
```

-continued

```
aaccgcatga acactggttt ggaaaagttg aaagaagcgt cagaatcggt cgctgcactg  9660
tcaaaggaac ttgaagcgaa ggagaaagaa ttgcaggtcg cgaacgacaa ggccgatatg  9720
gtcttgaagg aagtcaccat gaaggcacaa gctgccgaaa aggtgaaggc cgaagtgcaa  9780
aaagtcaaag atcgggcaca agccattgtg gattcaattt cgaaagacaa ggcgattgct  9840
gaagaaaagt tggaggcggc gaagccagcc ctggaagagg ctgaggcggc gcttcaaacc  9900
attaggcctt cagatattgc cacggtcaga accctgggca ggccgcctca ccttattatg  9960
agaattatgg attgcgtcct tcttttgttc cagcgcaaag tctcagctgt caagattgac  10020
ctcgagaaat cgtgtactat gccttcatgg caggaatcgc ttaagcttat gacggctggt  10080
aatttccttc aaaatctcca gcagttcccg aaggatacta tcaatgagga agtgattgag  10140
ttcctctcac cgtacttcga gatgcccgac tataacattg agacggcaaa gagagtgtgc  10200
ggaaacgtcg ccggactgtg ttcgtggacg aaggcaatgg cctcgttctt ttcaatcaat  10260
aaagaagtgt tgcctctgaa ggcaaacctc gtggtgcagg aaaacaggca tcttctcgct  10320
atgcaggatc ttcaaaaagc acaagctgag ctcgatgaca aacaggctga actcgatgtg  10380
gtgcaagccg agtatgagca agcaatgact gaaaaacaaa cgctccttga ggacgcggaa  10440
aggtgtagac acaagatgca aactgcatca actttgattt cggggcttgc cggagaaaaa  10500
gagagatgga ccgagcaatc acaagagttc gccgctcaaa cgaagaggtt ggtcggtgac  10560
gtcttgctcg caaccgcctt cctgtcctat tcaggtccat ttaaccaaga gtttcgggat  10620
ctcttgttga acgactggcg caaggaaatg aaggcccgca aaatcccatt cggtaagaat  10680
cttaatctga gcgagatgct tatcgacgcg cctaccatta gcgaatggaa tcttcagggt  10740
cttccaaatg acgatctgtc gattcagaat gggatcattg tgacgaaagc gagccgctat  10800
ccgctgctta tcgacccaca gactcagggt aaaatctgga tcaagaacaa ggaaagccgg  10860
aacgaactcc aaatcactag ccttaatcat aagtactttc ggaaccattt ggaggattca  10920
ctgtccttgg ggcggccact gttgattgag gatgtgggtg aagagctcga tccggcgctc  10980
gataacgtcc tggaaaggaa tttcattaaa accgggagca ccttcaaggt gaaagtcgga  11040
gacaaggagg tggacgtctt ggatggattc cggctctaca ttacgactaa gctcccaaac  11100
cctgcttata ctcccgagat ctcggcccgc acgagcatca ttgatttcac ggtcacgatg  11160
aaaggtctcg aggaccagtt gttggggagg gtcattctca cggagaagca agagcttgaa  11220
aaggaaagaa cgcatctcat ggaggatgtg accgccaata agcggcggat gaaggagctg  11280
gaagacaacc tgttgtatcg gctgacgagc acccagggca gcctggtgga agacgaaagc  11340
cttatcgtcg tgctgagcaa cactaagagg actgctgaag aagtcactca gaaacttgaa  11400
atctcagctg aaacggaggt gcaaatcaat tccgcgcggg aagagtaccg cccggtcgct  11460
acgagaggtt cgattcttta tttcttgatt accgagatgc gcctggtgaa cgagatgtac  11520
caaacctccc ttcgccagtt tcttggactc ttcgacttga gcctcgcaag atcggtcaag  11580
agccccatca ctagcaaaag aattgctaat attatcgagc acatgactta tgaagtctac  11640
aagtatgcag caagaggcct gtatgaagaa cataagtttc tgtttacgtt gttgctgacc  11700
ctgaaaattg acattcagag aaatagagtc aagcatgagg agttcctcac gcttattaaa  11760
ggtggagcct cacttgactt gaaagcttgt cctccaaagc cctcaaaatg gattctcgac  11820
attacctggc tcaatcttgt ggagctttcc aaactcagac agttttcaga cgtccttgac  11880
cagatctcgc ggaatgaaaa gatgtggaag atttggttcg acaaggaaaa tcctgaagaa  11940
gaaccacttc ctaatgccta tgacaaatcc ctcgactgtt ttagaagatt gctgcttatt  12000
cggagctggt gtcctgatcg caccattgct caggcaagga aatatatcgt ggactccatg  12060
ggggaaaagt acgcagaagg ggtgattctt gatctggaga agacctggga ggaatcagat  12120
cctcggacgc cccttatttg cctgttgtcg atggggagcg atcccactga ctccattatc  12180
gcacttggca agagattgaa gattgaaacc agatatgtga gcatgggtca aggtcaagaa  12240
gtgcacgcca ggaagttgtt gcaacagacg atggccaatg gagggtgggc actccttcaa  12300
aattgccacc tcggcttgga cttcatggac gaacttatgg acattatcat cgaaaccgag  12360
ctggtccacg atgcgttcag attgtggatg acgactgaag cacacaaaca gttcccaatc  12420
acgctgcttc aaatgtcgat caagtttgcg aatgatccac cacaaggact tcgggccgga  12480
ttgaagcgga cttattcggg cgtctcacag gatctcctcg acgtgtcgtc agggagccaa  12540
tggaagccga tgctttatgc ggtggcgttc ctgcatagca ccgtgcaaga gaggagaaaa  12600
ttcggcgccc ttggatggaa tatcccttac gagtttaacc aggctgattt caatgccacc  12660
gtgcaattta ttcaaaacca cttggacgac atggatgtga agaaaggggt ctcgtggact  12720
acgattcggt acatgattgg agaaatccag tacggaggaa gggtcactga cgattatgac  12780
aagcggctgc ttaacacttt tgccaaagtc tggttctcgg aaaatatgtt tgggcccgat  12840
ttctcatttt accagggcta taatatcccg aagtgctcga ccgtcgataa ctatctccaa  12900
tacatccaat cgttgccagc ctatgacagc ccagaggtgt ttggtcttca cccaaacgct  12960
gatattacct accagtccaa actcgctaag gacgtgctcg acaccatcct gggtatccag  13020
ccaaaagata cgtcaggagg gggggacgaa acccgcgagg cagtggtggc tcgcctcgct  13080
gatgatatgc ttgaaaagtt gccaccagat tatgtgcctt tcgaggtcaa agaaagattg  13140
caaaagatgg gcccgttcca accaatgaac atcttcctca gacaggaaat cgacaggatg  13200
caacgggtgc tctcgttggt cagaagcacg cttacggagt tgaagttggc aatcgacggg  13260
acgatcatta tgtcagaaaa ccttagagac gccttggatt gtatgttcga cgctcgcatt  13320
ccggcttggt ggaaaaaagc gtcatggatt agctcaacgc tcgggttttg gtttacggag  13380
cttattgaaa ggaattcaca gtttacttcc tgggtgttca atggtcggcc acattgcttt  13440
tggatgacgg gtttctttaa ccctcaagga ttcttgactg cgatgaggca ggagatcact  13500
cgggcaaata agggttgggc gctggataat atggtccttt gcaacgaagt gactaaatgg  13560
atgaaagacg acattagcgc accgcctact gaaggtgtct acgtctacgg cttgtacttg  13620
gagggagcag gttgggacaa aaggaatatg aaactgatcg agtccaaacc gaaggtcctc  13680
tttgaactga tgccggtgat tcggatttac gctgagaata atacgctccg ggacccaaga  13740
ttttatagct gcccgattta caaaaaacct gtcaggacgg atctgaacta cattgcagca  13800
gtggatctca gaaccgctca aacgccagag cattgggtgc tgcgcggggt cgcattgttg  13860
tgtgatgtga aatag                                                    13875
```

```
SEQ ID NO: 15          moltype = DNA  length = 13875
FEATURE                Location/Qualifiers
misc_feature           1..13875
                       note = Synthetic polynucleotide
source                 1..13875
                       mol_type = other DNA
```

-continued organism = synthetic construct
SEQUENCE: 15
atgtttcgga ttggtcggcg ccagctttgg aagcactccg tgactagggt cctgacccag 60
agattgaagg gagaaaagga agcgaaacgc gccttgctcg atgcgcgcca caattatctc 120
tttgccattg tggcctcatg cctcgatttg aacaagaccg aggtcgagga cgctatcctg 180
gaaggtaacc aaattgagag aattgaccaa ttgttcgccg tgggcggact tcggcacctg 240
atgttctact accaggatgt cgaagaggcc gaaacgggtc agcttggtag cctgggcgga 300
gtgaaccttg tctcagggaa aattaagaaa cccaaagtct ttgtgactga aggaaatgac 360
gtggcattga ctggggtgtg tgtctttttt atccggactg atccgtccaa ggctatcact 420
cctgacaaca ttcaccagga ggtctcattc aatatgctgg acgctgctga cggcggtctt 480
cttaactcag tcaggcgcct cctgtccgat atcttcattc ctgccctgag ggcaacgagc 540
cacggatggg gcgaacttga ggggttgcaa gacgcagcaa atatcaggca ggaatttctg 600
tcaagcttgg agggtttcgt gaacgtcttg tcaggagccc aagagtccct caaagaaaaa 660
gtgaatctcc ggaaatgcga tatcctggag ctgaagacgc tcaaggagcc cactgactat 720
ttgactttgg caaataatcc agagacgctt ggaaaaatcg aggattgtat gaaagtctgg 780
attaagcaga cggagcaagt ccttgccgaa aataaccaac tgctgaaaga ggcagacgat 840
gtgggtccca gagctgaact cgaacactgg aagaaacgcc tgtcgaagtt taactacctt 900
ctggaacagc ttaagtcgcc ggatgtcaaa gcggtgctcg cagtcctcgc ggccgcgaag 960
tccaagcttt tgaaaacctg gagggagatg gacatccgca tcacggatgc tactaatgag 1020
gccaaagaca acgtgaagta tttgtatact cttgaaaagt gctgcgaccc tttgtactcg 1080
tcggacccgc tgtcaatgat ggacgctatc cccacgttga ttaatgcgat taagatgatc 1140
tactccattt cgcattacta caatacgtcc gagaagatta cctcactgtt cgtcaaagtg 1200
acgaaccaga tcatttcagc gtgtaaagcg tacattacca acaacggcac cgctagcatt 1260
tggaatcaac cccaagacgt ggtggaggag aagatccttt ccgcgatcaa gcttaagcag 1320
gagtatcaat tgtgctttca caaaactaaa caaaagctta agcagaatcc taacgccaag 1380
cagttcgatt tttcagaaat gtacatcttc ggaaagtttg aaacgttcca cagacgcctc 1440
gccaaaatca ttgatatctt tacgaccctc aagacctata gcgtgctgca ggattcgacg 1500
atcgagggc ttgaggatat ggctactaag taccaaggaa tcgtcgctac tattaaaaag 1560
aaggaatata actttctcga ccaacgcaaa atggacttcg atcaggacta cgaggaattc 1620
tgtaaacaga ctaatgatct gcataatgaa cttagaaagt ttatggacgt cactttcgct 1680
aaaattcaaa acactaatca agcactcaga atgctgaaaa aatttgaacg gttgaatatc 1740
ccaaatctgg gcattgatga taaatatcaa cttatcctcg agaactatgg ggcagacatc 1800
gacatgatct ccaagttgta tactaagcaa aaatacgacc ccccccttgc tcgcaaccaa 1860
cccccaattg caggaaaaat cctgtgggcc aggcagctct tccaccggat ccaacagcca 1920
atgcagctct ttcagcaaca tcccgctgtg cttagcaccg cagaagccaa acctatcatc 1980
aggtcataca accgcatggc taaggtgctg ctggaatttg aagtcctttt ccatcgggct 2040
tggcttagac aaatcgagga gattcacgtc ggactcgaag cctcccttct ggtgaaagca 2100
ccgggaacgg gggagctgtt cgtgaatttt gatccccaaa ttttgatctt gttccgggaa 2160
acggagtgca tggctcaaat gggtcttgaa gtctcaccac tcgctaccag cctctttcag 2220
aagagagata gatacaaacg gaacttttcc aacatgaaaa tgatgctcgc ggagtatcaa 2280
agggtgaaga gcaaaatccc tgccgcaatt gaacagttga tcgtcccgca cctggccaag 2340
gtggacgaag ccctccagcc cggacttgca gctttgacgt ggacgtcact taatattgag 2400
gcgtatctgg aaaatacgtt cgcgaagatc aaggacctgg agctcttgct cgatcgggtc 2460
aatgatctca tcgaatttag gattgatgca atcctcgagg agatgtccag cactcctctt 2520
tgtcaacttc ctcaggagga gcccttgact tgcgaggagt ttctgcagat gacgaaagat 2580
ctctgtgtca acggtgcaca aatcttgcac tttaagagca gccttgtgga agaagcagtc 2640
aatgagcttg tcaatatgtt gcttgacgtg gaagtcctct ccgaggaaga gagcgagaag 2700
atttccaacg aaaactccgt caattacaag aatgaatcaa gcgctaaacg cgaggaaggg 2760
aatttcgaca ctctcacgtc atcgatcaac gctcgggcca acgctcttct cctgaccact 2820
gtcacgagaa agaagaaaga aacggagatg ctgggagaag aggccagaga attgctttcg 2880
cactttaatc accaaaatat ggatgccctg ctcaaggtca ccaggaacac cctggaggcc 2940
attagaaaac ggattcacag ctcacatacc atcaacttta gggattccaa tagcgcttcg 3000
aatatgaagc agaactcatt gccaatcttc cgcgcttccg tgaccctggc gattcctaac 3060
attgtgatgg ccccggcatt ggaagacgtg cagcagactc tgaataaggc cgtcgaatgt 3120
atcatttcgg tccctaaagg ggtgcgccag tggtcgtcag aactcctgag caagaaaaag 3180
atccaggaga gaaaaatggc ggccttgcaa tcgaatgagg attcggattc agatgtcgaa 3240
atgggtgaga atgaactcca agacacgctt gagatcgcct cggtcaatct cccaatccct 3300
gtccaaacta aaaactacta taagaacgtc tccgaaaaca aggaaattgt gaaattggtg 3360
tcggtcttga gcactatcat taactcaacg aaaaaagagg tcatcaccag catggattgc 3420
tttaaaagat ataatcatat ttggcagaag ggtaaggaag aggccatcaa gacctttatt 3480
acccaatcac ctctgctctc ggaattcgag tcgcaaatcc tgtacttcca aaatctggag 3540
caagagatta atgctgagcc agaatatgtc tgcgtcggca gcattgcgct gtataccgct 3600
gatctgaagt ttgcattgac ggcggaaact aaagcttgga tggtcgtgat tgggcgccat 3660
tgtaacaaaa aatataggtc ggaaatggaa aacatcttca tgttgatcga ggagtttaat 3720
aagaagctca ataggcccat caaagacctg gacgatatta ggattgccat ggcagccctc 3780
aaggaaatta gagaggaaca aatctcaatt gacttccagg tcggacccat tgaagagtca 3840
tatgcgctgc ttaatcgcta cggattgttg attgcccggg aagagatcga taaagtggac 3900
actcttcatt acgcatggga gaaactcctc gctagggccg gtgaagtgca gaataagctt 3960
gtcagcctcc aacccagctt caaaaaagaa ctgatctccg cagtcgaggt cttcttgcag 4020
gattgccacc agttttactt ggattatgat ctgaatggtc ccatggcatc cggcttgaag 4080
cctcaggaag ccagcgatcg cctcattatg ttccagaacc agtttgataa tatttacaga 4140
aagtacatta cctataccgg aggcgaagag ctttttggct tgcctgctac ccaatatccg 4200
cagttgctcg aaattaaaaa gcagctcaat ctgcttcaga aaatttacac cttgtataac 4260
tcagtgattg aaacggtgaa ctcgtactac gatattctct ggagcgaggt gaatattgag 4320
aaaatcaaca acgaactcct tgaattccaa aaccggtgta gaaagctgcc cagggcgctg 4380
aaagattggc aggccttctt ggacctgaag aaaattattg atgacttctc agaatgctgc 4440
cccctcttgg agtatatggc atcaaaagcc atgatggaaa gacattggga acgcattacg 4500
acgcttacgg gacactccct tgacgtgggc aatgaatcct tcaagcttcg gaacatcatg 4560
gaagctccct tgttgaagta caaagaagag atcgaagata tctgcatttc agccgtcaaa 4620

-continued

```
gaaagggaca tcgagcagaa gcttaaacag gtgattaacg aatgggacaa caaaacgttt  4680
actttcggga gcttcaagac caggggcgag ctgcttcttc gcggtgactc aacttcagag  4740
attatcgcaa atatggaaga cagccttatg cttctcgggt cactcctctc gaatcggtat  4800
aacatgccct ttaaagccca aattcaaaag tgggtccaat acctttccaa ctcgactgat  4860
attattgagt cctggatgac cgtccaaaac ttgtggattt acctcgaagc cgtcttcgtc  4920
ggtggagaca tcgccaagca actccccaag gaggccaaga ggttctcaaa cattgataag  4980
tcctgggtca aaatcatgac tcgggcacac gaggtcccgt cagtggtcca gtgctgtgtc  5040
ggcgacgaaa ctcttgggca gctccttccg caccttctcg atcaattgga gatttgtcaa  5100
aaatccttga ctggctacct tgaaaagaaa cggttgtgtt ttccacgctt tttctttgtc  5160
agcgatcctg cgttgctgga aatcttgggt caggcgtcgg actcgcacac cattcaggca  5220
cacctgctta atgtctttga taatattaaa agcgtgaaat tccatgagaa gatctatgac  5280
agaatttga gcatttcgtc acaagaaggt gagactattg aactcgataa accagtcatg  5340
gctgaaggta acgtcgaggt ctggcttaat tcactcttgg aagagtcgca gtccagcttg  5400
cacctggtca ttagacaagc ggcggcaaac attcaagaga ctggttttca acttaccgag  5460
tttttgtcct ccttccccgc tcaagtgggt ctgttgggga ttcagatgat ttggactagg  5520
gatagcgaag aggcgcttcg gaatgcgaaa tttgataaaa aaatcatgca gaaaactaac  5580
caagcgtttc tcgaacttct taataccctg atcgacgtca cgaccagaga cctgagctcg  5640
actgaaagag tcaagtacga aaccctgatt acgattcacg tccaccagag ggatatcttt  5700
gatgacttgt gccacatgca tatcaaatca ccgatggatt ttgaatggct caagcagtgc  5760
agattctatt tcaatgagga tagcgataaa atgatgatcc atatcactga cgtggcgttc  5820
atctatcaga acgagtttct tggctgcact gatagactgg tcatcactcc tctgactgat  5880
cgctgttaca ttacccttgc ccaagccctt ggtatgtcca tgggcggtgc tccagctggg  5940
cccgcgggca cgggaaagac cgaaactacg aaggacatgg gcaggtgtct gggaaagtat  6000
gtcgtcgtgt tcaattgctc cgatcagatg gacttccggg gcctcggcag aatttttaag  6060
ggcctggctc agtcgggttc atgggggtgc ttcgacgaat tcaatcggat tgacttgcca  6120
gtgttgtcag tggcggcgca acagattagc attattttga cgtgtaaaaa agagcacaag  6180
aaatcgttta tcttcactga cggcgataac gtcacgatga atcccgaatt tggcttgttc  6240
ttgactatga atcccgggta cgcaggtcgc caggaacttc cggaaaatct taaaattaat  6300
tttaggagcg tcgcgatgat ggtgccagat cgccagatca ttatccgggt caaattggcc  6360
tcgtgtggat tcattgataa cgtggtgctg gcgagaaaat tttttaccct ttataaattg  6420
tgcgaggaac agctctcgaa gcaggtgcac tacgacttcg gactccgcaa tattctttca  6480
gtcttgagaa ctctgggtgc agctaaaagg gcaaacccga tggacacgga aagcactatt  6540
gtcatgaggg tgcttcggga tatgaacctt tccaaattga ttgacgaaga cgaacctttg  6600
tttctcagcc tgattgaaga tctcttcccg aatattctcc tggacaaggc cggctaccct  6660
gaattggagg cagccatttc ccggcaggtc gaagaagccg gcttgatcaa ccatcctcca  6720
tggaagctca aagtgatcca gctcttcgag actcaacggg tgcggcacgg tatgatgacg  6780
cttggtccgt cgggtgccgg taaaaccact tgcatccaca ctctcatgag ggcgatgact  6840
gactgtggca aaccgcaccg cgaaatgcgc atgaatccga aagcgattac tgctccccaa  6900
atgttcggac ggttggatgt cgcgactaac gactggaccg atggcatctt ctcgacgttg  6960
tggcgcaaaa cgctgcgcgc caaaaagggc gagcacattt ggatcattct tgacggtcct  7020
gtggacgcga tttggattga gaatctgaat tccgtgcttg atgacaacaa aaccttgacc  7080
cttgccaacg gtgataggat ccccatggcc ccgaattgca aaattatttt cgaacctcac  7140
aatattgata atgcgtcacc cgctacggtc tcccgcaacg gcatggtctt tatgagctcg  7200
tcaatcctgg attggtcacc tatcctcgaa ggattcttga agaagcgctc cccccaagag  7260
gcagagattc tccggcaact ctataccgaa agcttccccg acctgtatcg cttttgtatt  7320
cagaacttgg agtacaaaat ggaagtcctt gaggcctttg tcattacgca atcgattaac  7380
atgcttcaag gccttattcc tttgaaagag caaggaggag aggtgtccca agcacatctg  7440
gggaggttgt ttgtgtttgc gcttctttgg tcagcgggcg ccgcgttgga actggacggc  7500
cgcagacggc tcgagttgtg gctccgctcg agacctactg gtacgttgga actcccgcct  7560
cccgcaggtc ctggggacac cgcgtttgat tattacgtgg ctcccgacgg tacctggact  7620
cactggaaca ctaggaccca agagtacctc tacccttcag acacgacccc tgaatacggg  7680
tcgattcttg tgcccaatgt cgacaatgtc aggaccgact ttctcatcca gacgattgca  7740
aaacagggta aagcagtcct gctgatcggg gaacagggca cggcaaaaac tgtgatcatt  7800
aagggtttca tgtccaagta tgatccagag tgtcacatga ttaagtcatt gaacttttca  7860
tcggcgacta cgccgctcat gttccaaaga acgatcgagt cgtacgtgga caaacgcatg  7920
ggaaccactt atggcccacc agccgggaaa aagatgactg tgtttattga cgacgtgaat  7980
atgcctatta ttaatgagtg gggcgatcag gtcaccaacg aaattgtgag gcaacttatg  8040
gagcagaatg ggttttataa cctcgaaaag ccaggggaat tcacttccat cgtcgacatc  8100
caattcctcg ctgccatgat tcatccaggg ggaggtagaa acgatatccc ccagcggctg  8160
aaacggcaat tttcaatctt taattgcacg ctgcccagcg aggcctcagt ggacaagatc  8220
tttggggtca ttggggtcgg acactactgc acgcaacgcg gattttcaga agaagtccgg  8280
gactcggtga ccaagctcgt cccgcttacc cgccggcttt ggcaaatgac caaaatcaag  8340
atgcttccaa cccccgcaaa gtttcactac gtcttcaatc ttcgcgatct ttcacgggtg  8400
tggcaaggga tgctgaacac tacgtcggag gtgattaagg agcccaacga cttgctcaaa  8460
ttgtggaaac atgaatgtaa gcgggtgatt gcagacaggt ttactgtgtc cagcgacgtc  8520
acgtggttcg ataaggctct cgtctccctg gtcgaagaag agttcggcga ggaaaaaaaa  8580
ctgcttgtcg attgcgggat tgatacctat ttcgtggact tcctgcggga tgccccagag  8640
gcggcgggag agacttccga agaggctgac gcggagaccc ctaagatcta tgaacctatc  8700
gaaagctttt cacacctcaa ggaacgcttg aacatgtttc tccaactgta caatgaatcg  8760
attagaggcg ccggcatgga catggtgttc ttcgccgacg cgatggtcca tctcgtgaaa  8820
atctcgcggg tcattcgcac ccctcaaggt aacgcgcttt tggtcggtgt cggcggcagc  8880
ggaaagcaga gcttgacccg cttggcttcc tttatcgcgg ggtatgtctc gtttcaaatc  8940
acgctgacca gatcgtataa tacttccaat ttgatggaag accttaaagt cctttataga  9000
actgcagggc aacaaggcaa gggtatcact tttatcttca ccgacaacga aattaaggac  9060
gaatccttcc tggaatatat gaataatgtg ctttcgagcg gggaggtgag caatcttttt  9120
gcccgcgacg aaatcgatga aatcaatagc gaccttgcga gcgtcatgaa gaaggagttc  9180
ccaagatgtt tgcctacgaa cgaaaacctt catgactact tcatgtcacg ggtgaggcag  9240
aacttgcata tcgtcctgtg tttttccccg gtgggtgaga agtttcgcaa tcgcgcactg  9300
aaatttccgg cattgattag cggctgcacg atcgactggt tctcgcggtg gcctaaagac  9360
```

```
gcattggtgg cggtgagcga gcattttctg acctcatatg acatcgactg ttccctggaa  9420
attaaaaaag aagtcgtcca atgcatggga agcttccagg acggtgtcgc cgagaagtgc  9480
gtggattact tccagcggtt tcgccgctcg actcatgtca ctccaaaaag ctacttgtcc  9540
ttcattcaag gatataagtt tatctatggt gagaaacacg tggaggtgag gacccttgcc  9600
aatcgcatga acactggcct ggaaaaactg aaggaagcaa gcgagtccgt ggctgcgttg  9660
tcgaaagaac tcgaggcgaa agaaaaagaa ctccaagtcg ctaatgataa agcggacatg  9720
gtgctcaaag aggtgacgat gaaggctcaa gcagcagaga aagtcaaggc ggaggtccaa  9780
aaagtgaagg accgcgccca ggcgatcgtc gattcgattt ccaaagataa ggctatcgcc  9840
gaagaaaaat tggaggccgc gaagcctgct cttgaagagg ctgaagcagc acttcaaacc  9900
attagaccct cggacattgc cacggtgcgg actctgggca gacctccgca ccttatcatg  9960
agaatcatgg attgcgtctt gctgttgttc caaagaaaag tctccgcagt caaaatcgat  10020
ctcgaaaaat cgtgtacgat gccgtcctgg caggagtccc tcaaactgat gaccgcgggt  10080
aacttccttc aaaatctgca gcaattccct aaagacacta tcaacgagga agtgatcgaa  10140
ttcctgtcgc cgtactttga aatgcctgat tacaatatcg agaccgctaa aagagtgtgc  10200
gggaacgtgg ccggtctctg cagctggacc aaggcgatgg cttcgttctt ctcgattaat  10260
aaggaggtgc ttcccctcaa agccaacctc gtcgtccagg agaacaggca tctgctggcc  10320
atgcaagatc tccaaaaagc ccaagcagaa ttggatgaca agcaggcaga gcttgacgtc  10380
gtccaagccg agtacgagca agcaatgacg gaaaagcaaa ctcttctcga agacgcggaa  10440
aggtgtcggc acaaaatgca aaccgcttcc actcttatct cagggttggc aggagaaaag  10500
gaacgctgga ccgaacaaag ccaagaattt gcggctcaaa cgaagagatt ggtcggcgat  10560
gtgttgctcg caaccgcgtt tctgtcgtat tccggcccct ttaatcagga gtttcgcgat  10620
ttgctcctca atgattggcg gaaagagatg aaggcaagga agatcccgtt cggcaagaac  10680
ctgaatctct cggagatgct catcgacgct cctactatct cggagtggaa tctccaagga  10740
ctgcctaacg atgacctctc cattcaaaat gggattattg tcacgaaggc gagccgctac  10800
ccccttctga tcgatcccca gactcaaggg aagatctgga tcaagaacaa agaatcgcgc  10860
aatgagctcc aaattacttc cctcaaccat aagtactttc gcaaccacct cgaagactcg  10920
ctttcattgg gcaggccact cttgatcgaa gatgtgggag aagaactgga ccctgccctt  10980
gataacgtgc tggaacgcaa cttcattaag acgggatcaa ctttcaaagt gaaagtgggt  11040
gataaggaag tggatgtgct cgacggattc agactttaca ttactacgaa gctccctaat  11100
ccagcctaca cgcctgagat ctccgctcgg acttcaatca tcgatttcac ggtgacgatg  11160
aagggccttg aggaccaact gttgggcaga gtcattctca ccgagaaaca ggaactcgaa  11220
aaggagcgga cgcatcttat ggaggacgtg acggccaata agcgccggat gaaggaattg  11280
gaagataact tgctctacag gctcactagc acgcagggta gcctcgtgga ggacgaaagc  11340
ctgattgtgg tcctcagcaa cacgaaaagg acggccgagg aggtgaccca aaagttggaa  11400
atttcagctg aaacggaggt gcagatcaat tcagcaaggg aagagtatag gcctgtggcg  11460
acgagggggt caatcttgta tttcctgatt acggaaatgc gccttgtcaa cgaaatgtac  11520
cagacgtcat tgcgccaatt tctcgggctt tttgacctgt cgctcgctag gtcggtcaaa  11580
tcccctatca cgtccaaacg cattgcaaac attattgaac atatgacgta cgaggtgtac  11640
aagtatgcag cacggggact gtacgaggaa cacaaattcc ttttcaccct tctgctcacc  11700
ttgaagattg acattcagag gaatagagtc aaacacgagg agttcctcac tctcatcaaa  11760
ggtggggcgt cgctcgactt gaaggcttgt ccgcctaaac catccaagtg gattctggat  11820
attacgtggc tcaatctcgt cgaattgtca aaattgagac aattttcaga tgtgctcgat  11880
cagatttccc gcaacgagaa gatgtggaaa atctggttcg ataaagagaa tcccgaggag  11940
gagcccctte caaatgcgta tgacaaatcg ctggactgct ttcggaggtt gctcctgatt  12000
cgctcgtggt gtccagatag aaccatcgcc caggcgcgga agtatattgt ggattcgatg  12060
ggtgaaaaat acgctgaagg agtcattttg gatctggaaa agacgtggga agagtcggac  12120
ccacgcaccc cgctcatctg cctccttagc atgggctcgg acccaactga ttcgattatt  12180
gccttgggga aaaggctcaa aattgaaacc aggtacgtca gcatgggtca gggtcaagag  12240
gtgcacgctc ggaaactgtt gcaacagacc atggcaaacg gcggatgggc tctgctccag  12300
aactgccacc tcgggttgga cttcatggac gaactgatgg acattatcat cgaaaccgaa  12360
ctggtgcacg atgcttttcg cctctggatg acgaccgagg cccataagca atttcccatc  12420
acgctcctcc aaatgagcat taaatttgcg aatgatccgc cacaggggct gagagctggt  12480
ttgaagcgga cttatagcgg agtcagccag gatctgttgg atgtctccag cggaagccag  12540
tggaagccca tgttgtatgc agtggccttt ttgcattcaa ctgtccagga gaggcggaag  12600
ttcggcgccc tcgggtggaa catcccgtat gaatttaacc aggcggattt caacgcgact  12660
gtgcagttta ttcagaacca tctggatgat atggatgtca aaaagggagt gtcctggacg  12720
accatcaggt atatgattgg tgagatccaa tatggtggga gggtcacgga cgattatgac  12780
aagaggcttc tcaacacctt tgcgaaagtg tggttttccg aaaacatgtt cggccctgac  12840
tttagctttt accagggtta caatatcccc aaatgtagca ccgtggacaa ttacctgcaa  12900
tacattcaga gccttcccgc atacgacagc ccggaggtgt tcggtttgca tccgaatgca  12960
gatattacgt atcaatccaa gctcgcaaaa gacgtcttgg acacgatcct cggaattcaa  13020
cctaaagaca cgtccggcgg cggcgatgaa acccgcgaag ccgtcgtcgc gcggcttgcg  13080
gacgatatgt tggagaaatt gccacccgat tacgtccctt ttgaagtcaa ggaaaggctt  13140
cagaagatgg gcccttttca acccatgaat atcttcctta ggcaggaaat tgaccgcatg  13200
cagagggtgt tgtcgctcgt ccggtcgacg cttaccgagt tgaagcttgc gatcgatggg  13260
accatcatta tgtccgaaaa tctcagagac gctctcgact gtatgttcga tgccaggatc  13320
ccagcttggt ggaaaaaggc gagctggatc agctccactt tgggcttttg gttcacggag  13380
ctcattgaga gaaactcgca gtttacttcg tgggtgttca acggcagacc acactgtttt  13440
tggatgactg gattctttaa tccccagggc tttttgactg ctatgaggca ggaaattact  13500
cgggctaaca aaggttgggc attggataac atggtgcttt gtaacgaagt cacgaagtgg  13560
atgaaggacg acatctcggc cccccccact gagggggtgt acgtgtacgg gttgtacctg  13620
gaaggcgcgg gctgggacaa aagaaacatg aagctcattg aatcaaagcc caaggtcctt  13680
ttcgaactca tgcctgtcat tcgcatctat gccgagaata acactctcag agatcctagg  13740
ttctattcgt gtccgatcta caaaaagccc gtgagaaccg atcttaatta cattgctgca  13800
gtggacttga gaacggctca aactcccgaa cactgggtcc tgagaggcgt ggcactcttg  13860
tgcgatgtca aatag                                                  13875
```

SEQ ID NO: 16 moltype = DNA length = 13875
FEATURE Location/Qualifiers

-continued

```
misc_feature            1..13875
                        note = Synthetic polynucleotide
source                  1..13875
                        mol_type = other DNA
                        organism = synthetic construct
SEQUENCE: 16
atgttcagaa ttgggcggcg gcaactttgg aagcatagcg taacacgggt gctgactcag  60
agactgaaag gagaaaagga ggcgaaaagg gccttgctgg acgcccgcca taactacctc  120
ttcgcgattg tggcctcatg cctggacctg aataagactg aagtcgagga cgctatcctc  180
gagggcaacc aaatagagcg catcgaccaa ttgttcgccg tgggtggact tcggcacctg  240
atgttctact accaagacgt ggaagaagcg gaaaccgggc agctgggatc actggggggc  300
gtgaacctcg tgagcggaaa gatcaagaag cccaaggtgt tcgtcaccga aggcaacgat  360
gtggcgctca ccggggtgtg cgtgtttttc attcgcactg acccatcaaa ggccattact  420
cccgataaca tccatcaaga ggtgtccttc aacatgctgg acgctgccga tggaggactg  480
ctcaacagcg tgcgccggct cctctcggac attttcatcc ccgccctgag agctaccagc  540
catggatggg gggaactcga gggactacag gacgcggcaa acattcgcca agaattcctg  600
tcctcattgg agggcttcgt gaacgtgctc agcggagctc aggaaagcct caaagaaaaa  660
gtcaacctcc gcaagtgcga catcctagag ctcaaaacgc tgaaggagcc cacagactac  720
ctcactctcg ccaataaccc agaaaccctc ggaaagatcg aggactgcat gaaggtctgg  780
attaagcaaa cagaacaagt cctggcggag aacaaccagc tccttaagga ggcggacgac  840
gtcggcccga gggcggagtt agaacactgg aagaaacgcc tcagcaagtt taattacctc  900
ctggagcaat tgaagtcccc tgacgtgaag gccgtgctcg cagtgttggc agcggccaaa  960
tcgaagctgc tgaaaacttg gcgggagatg gacattagaa ttactgacgc gactaacgag  1020
gccaaggata acgtcaaata cttgtacacc ctcgagaagt gttgcgaccc gttgtatagc  1080
tcagacccac tgagcatgat ggacgccatc cccacccctca ttaacgccat taagatgatt  1140
tactcaatct cccattacta caacacctca gagaagatta cttcactctt cgtgaaggtg  1200
accaaccaaa ttatctcggc ctgcaaggct tacattacta ataacgggac agcttccatc  1260
tggaaccagc cgcaagatgt cgtggaagag aagatcctgt cggccatcaa acttaaacag  1320
gagtaccaac tctgctttca caaaaccaag cagaagctga agcaaaatcc gaacgccaag  1380
caattcgact tctccgaaat gtacatcttc ggaaagttcg aaaccttcca ccggagactg  1440
gccaagatca ttgacatttt cactactctt aagacctaca gcgtgctcca ggacagcact  1500
atcgagggac tggaggacat ggcaacgaag taccaaggca tcgtcgccac cattaaaaaa  1560
aaggaataca acttcctgga tcagcggaag atggacttcg atcaggatta tgaggagttc  1620
tgcaaacaga ccaacgacct ccacaacgaa ctgcgcaagt ttatggacgt gaccttcgca  1680
aagatccaaa acacgaacca ggcgctgcgg atgctcaaga agttcgagag attgaacatc  1740
ccgaatctcg gcatcgacga taagtaccaa ctcatcctgg aaaactacgg ggccgacatc  1800
gacatgatct ccaagctgta tactaagcag aagtacgacc cgccactggc gagaaaccag  1860
ccccccattg ccggcaagat cctctgggcc cgacagcttt tccaccgaat ccagcaaccc  1920
atgcagcttt tccagcaaca ccccgccgtg ctctcaaccg ccgaggccaa gcccatcatt  1980
aggagctaca acagaatggc gaaggtcctg ctcgaattcg aagtcttgtt ccaccgcgca  2040
tggttgcgcc agatcgagga aatacacgtg ggactggaag cgtcgctgct cgtgaaggca  2100
cctgggaccg gagaactgtt cgtcaacttc gacccgcaaa tcctgatcct gttccgcgaa  2160
actgaatgca tggctcagat gggattggaa gtcagccccc tggcgacttc cctcttccaa  2220
aagagagata gatacaaacg gaacttctcc aacatgaaga tgatgctggc ggaataccag  2280
cgcgtgaaat ccaagattcc ggccgctatc gagcagctca tcgtgcctca ccttgccaag  2340
gtcgacgaag cactgcagcc tggcctggcc gctctcactt ggaccagcct caacatcgag  2400
gcctacttgg aaaacacctt cgccaagatc aaggacctcg aactcctcct cgaccgggtg  2460
aacgacttga tcgagtttag gattgatgcc attctggagg agatgagctc cactccgctg  2520
tgtcaactgc cacaggagga accccctcaca tgcgaggaat tcctgcaaat gactaaggac  2580
ctgtgcgtca acggggccca aatcctgcac ttcaaatcct ccctggtcga ggaggcagtc  2640
aacgagctcg tgaacatgct cctggatgtg gaagtgctgt ccgaggagga gtccgagaag  2700
atctccaacg aaaatagcgt gaactataag aacgaatcca gcgccaagcg ggaagagggg  2760
aatttcgata ccctgacttc cagcatcaac gccagggcca acgccctctt actaactacc  2820
gtgactagaa agaagaaaga aaccgaaatg ctgggcgagg aggcacgcga actcctgtcc  2880
cactttaacc atcagaacat ggacgccctt cttaaggtca cccggaacac tttggaggcg  2940
attcgcaaga gaatccacag cagccacacc attaacttcc gcgacagcaa ctcggcatcc  3000
aacatgaagc agaattcact gccgatcttc agggccagcg tgactttggc tatcccgaat  3060
attgtcatgg cgcctgctct ggaggacgtc cagcaaaccc tgaacaaggc cgtcgagtgc  3120
atcatcagcg tgccgaaggg tgtccggcag tggtccagcg aattgttgtc taaaaagaag  3180
attcaagaga ggaagatggc tgcgctccaa tccaatgaag atagcgacag cgacgtggag  3240
atgggcgaga acgaactgca ggacaccctc gagatcgcgt ccgtcaacct tcctatcccg  3300
gtccagacca agaactacta caagaatgtc tcggaaaaca aggagatcgt gaagctcgtg  3360
tcggtcctgt ccaccattat caactccaca aagaaggagg tcattacttc catggactgc  3420
ttcaagaggt ataaccacat ttggcaaaag gggaaggaag aggccatcaa gacctttatc  3480
acccagtcgc cactcttgag cgagtttgag tcacagattc tgtacttcca gaacctggaa  3540
caggagatta atgctgaacc agagtacgtg tgcgtgggct ccattgcgct gtatactgcg  3600
gacctcaagt tcgcgttgac tgcagagact aaggcctgga tggtggtcat tggcagacac  3660
tgcaacaaga agtacaggag cgaaatggag aacattttca tgttgatcga agagttcaac  3720
aagaagctca accggccaat caaggacctc gatgatattc gcattgccat ggcggccctc  3780
aaggaaatcc gggaggagca gatctccatc gacttccagg tcggccctat tgaagagagc  3840
tacgcactgc tcaaccgcta tggactgtta atcgcccggg aagaaattga taaggtggat  3900
accctgcatt acgcttggga aaagttgctg gcccgggcag gagaggtgca gaacaagctc  3960
gtcagcctcc aaccctcctt caaaaaggaa ttgatcagcg cggtggaggt ctttctccaa  4020
gactgccacc agttctactt ggattatgat ctgaacggcc ccatggctag cggcctgaag  4080
cctcaagagg cctcagaccg gctgatcatg tttcagaacc aattcgataa catctaccgg  4140
aagtacatta cctatactgg cggagaggag ttgtttggat tgccggcaac ccagtaccct  4200
cagctcctgg agatcaagaa gcagctgaac ttgctgcaga agatctacac cctctacaac  4260
tccgtcatag agactgtgaa ctcctactac gacattcttt ggagcgaagt aaacatcgaa  4320
aagatcaata acgagctctt ggaatttcag aaccgatgca ggaagctgcc ccgggccctg  4380
```

-continued aaagactggc aggctttctt ggaccttaag aagattattg atgacttctc agaatgctgc 4440
cccctcctgg agtacatggc ctccaaggcc atgatggaac gccactggga gcggatcact 4500
accctgacgg gacacagcct ggatgtcggc aacgagagct tcaaactgag aaacatcatg 4560
gaagcgccac tcctgaagta caaggaagag attgaggata tttgcatttc cgccgtgaaa 4620
gaaagggaca ttgaacagaa acttaagcaa gtcatcaacg agtgggacaa caaaaccttc 4680
acgttcggct ccttcaaaac ccgcggcgag ctcctcctga ggggagactc aaccagcgaa 4740
atcatcgcca acatggagga tagcctgatg ctcctgggat cgctgctgtc gaacagatat 4800
aacatgccct tcaaggccca gattcagaag tgggtgcagt acctctccaa ctccaccgac 4860
atcatcgagt cctggatgac tgtgcagaac ttgtggatct acctcgaggc cgtgttcgtc 4920
ggaggggata tcgcaaaaca acttcctaag gaagccaaga ggttcagcaa tattgacaag 4980
agctgggtga agatcatgac ccgggcacac gaagtgcctt cggtggtgca atgttgcgtg 5040
ggggatgaaa ccctcggaca gttgctgcct cacctccttg accaactcga gatttgtcaa 5100
aagtccctga ctggatacct cgagaagaaa cgcttgtgct tcccaaggtt tttcttcgtg 5160
tccgatcctg ccctcttgga aatcctgggt caggcctccg actcacacac catccaagcc 5220
cacctcctta acgtctttga taacattaag agcgtcaagt tccatgagaa aatctacgac 5280
cggatcctct ccatttcgtc ccaagaggga gaaacgattg agctggataa gccagtgatg 5340
gccgaaggaa atgtcgaggt gtggctcaac agcctgctgg aagagtcaca aagctccctt 5400
catcttgtga tccggcaggc agccgccaat atccaggaaa ccggattcca actcaccgag 5460
ttcctcagct ccttccccgc acaagtggga ctgctgggca ttcaaatgat ctggacgcgg 5520
gactccgagg aagccctgag gaacgcaaag ttcgacaaga agatcatgca aaaaaccaac 5580
caggctttcc tcgaacttct caacaccctg atcgatgtga ccactagaga tctctcctcg 5640
acggaacggg tgaaatacga aaccctcatc accatccacg tgcaccagcg ggatattttc 5700
gacgacctct gccacatgca tattaagagc ccaatggatt ttgaatggtt gaaacagtgc 5760
cggtttttact tcaacgagga cagcgacaag atgatgatcc atatcaccga cgtcgccttc 5820
atctaccaga acgaattcct gggatgcacc gataggctgg tgattacccc gctgactgac 5880
cggtgctaca ttacgctggc ccaggccctg ggaatgtcga tgggcggcgc ccctgccgga 5940
ccggctggca ccggcaagac cgaaaccacc aaggatatgg gacggtgtct cggaaagtac 6000
gtggtggtgt ttaactgctc ggaccagatg gacttccgcg gacttggaag gatttttcaaa 6060
ggcctcgccc aaagcggttc atggggatgc ttcgacgagt tcaaccgcat tgatttgccg 6120
gtgctgtccg tcgcagcgca gcaaatttcg atcatcctga cctgtaaaaa ggaacacaaa 6180
aagtcgttca tttttaccga cggagacaac gtcacaatga acccggagtt cgggttgttc 6240
ctgactatga accctgggta cgccgggcgc caggaactcc ctgaaaacct gaaaattaac 6300
ttccgctcag tggcaatgat ggtgcctgac agacagatca ttattcgggt gaagctggcg 6360
agctgcggct tcatcgataa cgtggtgctg gcgcggaagt tttcacact gtacaaactt 6420
tgcgaggagc agctctccaa acaggtgcac tacgatttcg gactgagaaa tatcctgagc 6480
gtgctcagga ccctgggggc cgctaagcgc gcgaacccca tggatactga atccaccatt 6540
gtgatgaggg tgctgagaga catgaacctg tccaagctca tcgacgagga tgaacccctg 6600
ttcctgtccc tgattgaaga tctgttccca aacatcctcc tggacaaggc gggataccccc 6660
gagctggaag cagccatttc cagacaagtg gaggaggccg gactcatcaa ccacccaccc 6720
tggaagctca aggtcatcca gctgttcgaa acgcagagag tgcgacacgg catgatgaca 6780
ctggggccgt caggggcagg aaagaccacg tgcatccaca ccttgatgcg ggcgatgacc 6840
gactgcggga agccgcaccg ggagatgcgc atgaacccga aggcgattac tgcccctcaa 6900
atgttcggac ggctcgacgt ggccactaac gactggaccg acggcatttt ctcgacattg 6960
tggcgcaaga ccctaagagc caagaaggga gagcatatct ggatcatcct ggatggtcca 7020
gtggatgcga tttggatcga gaaccttaac tccgtgctgg acgacaacaa gaccctgaca 7080
ctggctaacg gcgaccggat ccctatggcg cccaactgca aaatcatctt cgagcctcac 7140
aacattgaca acgcctcgcc cgccaccgtg tcgcggaacg gcatggtgtt catgtcgtcg 7200
tccatcctgg actggtcccc cattctcgaa ggcttcctga agaagcgcag ccctcaagaa 7260
gccgagatac tccggcaact ctacaccgag tcgttccccg atctttaccg gttctgtatc 7320
cagaacttgg agtacaaaat ggaagtcctt gaggccttcg tgatcaccca gtcgatcaac 7380
atgctgcagg gactcatccc cctgaaagaa cagggaggtg aagtatccca ggctcacctg 7440
ggccgcctgt tcgtgtttgc gttgctttgg agcgcggggg ctgcgctcga gctggacggg 7500
cgacgccgcc tggagctctg gctccgcagt aggccgaccg gaaccctgga actcccgccc 7560
ccggccggcc ctggagacac cgccttcgac tactacgtgg cccccgacgg gacctggact 7620
cactggaaca cgagaaccca agaatacctg taccccctccg acaccactcc ggaatacgga 7680
agcatccttg tgccgaacgt ggacaacgtg cgcactgact tcctaattca gaccatcgcc 7740
aaacagggga aggcagtgct gcttattgga gaacaaggta ccgcaaagac cgtgatcatc 7800
aagggattca tgtccaagta cgatcctgag tgtcacatga tcaagtcact taacttctcc 7860
agcgctacta cccctctgat gttccagaga accatcgaaa gctacgtcga caagcgcatg 7920
ggaaccacgt acggtccccc ggccggaaag aagatgaccg tattcatcga cgacgtgaac 7980
atgccgatca ttaacgaatg gggggatcag gtcaccaacg aaatcgtgcg gcaattaatg 8040
gagcagaacg gattctacaa cctggaaaag cccggagagt tcacttcaat cgtggacatt 8100
cagttcctgg ccgccatgat ccacccggc ggaggaagaa acgacatccc gcagagactc 8160
aaaagacaat tctcaatctt caactgcacc ctgccgtccg aggcctcagt cgataagatt 8220
ttcggagtga tcggagtggg ccactactgc acgcagaggg gtttcagcga ggaggtccgc 8280
gactccgtga ccaaattggt cccactcact cgaaggctgt ggcagatgac caagattaag 8340
atgctcccca ctcctgccaa gtttcattac gtgtttaacc ttcgggactt gtcccgggtc 8400
tggcagggaa tgctgaatac gacctccgaa gtgattaagg aaccaaatga cctcctgaag 8460
ctctggaaac acgaatgcaa gagggtgatc gcggatagat tcacggtgtc ctccgacgtg 8520
acctggttcg acaaggccct cgtgtccttg gtggaagaag agttcggtga agagaagaag 8580
ctcctggtgg actgcggaat cgacacctac tttgtcgact tcttgagaga tgccccggag 8640
gctgcgggag aaacctcaga agaggccgat gcggagactc cgaagattta cgaacccatc 8700
gaatccttca gccacttgaa ggaaaggctc aacatgttcc tgcagctcta caacgaaagc 8760
atccggggag ctgggatgga catggtgttc ttcgccgacg ccatggtgca ccttgtcaag 8820
atctcccggg tcattcgaac gccccaggga aacgcattgc tcgtgggtgt cggaggatcc 8880
ggaaaacagt ccctgacgag gctggcgtcc ttcattgcgg ggtacgtgag cttccaaatt 8940
actctcaccc gctcctacaa tacttccaac cttatggagg acttgaaggt cttgtaccgc 9000
accgccggac aacagggaaa ggggatcacc ttcatcttca ccgacaacga aatcaaggac 9060
gagagcttcc tggagtacat gaacaacgtc ctttcgtccg gagaagtgtc caacctcttc 9120

-continued

```
gcacgcgatg aaatcgacga gattaactcc gacttggcca gcgtcatgaa aaaagaattc  9180
cctcgctgtc tccccaccaa cgagaacctc catgattact ttatgagccg ggtccgccaa  9240
aacttgcaca ttgtgctgtg cttctcgccc gtgggggaga aatttcggaa ccgggcgctg  9300
aagttccccg cgctgattag cggatgtact atcgactggt tctcgagatg gcccaaagac  9360
gccctggtcg ccgtgagcga acacttcctg acttcgtatg atatcgactg cagcctcgaa  9420
attaagaagg aagtggtgca gtgcatgggg tcatttcagg atggagtggc cgagaagtgc  9480
gtcgactact tccagagatt ccggcggtca actcatgtga cgcccaaaag ctacctttcg  9540
ttcatccagg gttacaagtt catatacggg gaaaagcacg tcgaagtgcg gaccctggcc  9600
aaccgcatga acaccggcct tgagaagttg aaagaggcct cggaatccgt ggcggcgctc  9660
agcaaggaac tggaggccaa agagaaggaa ctccaagtcg cgaatgataa agcagacatg  9720
gtgctgaagg aagtgacgat gaaagcccag gccgccgaga aggtcaaggc cgaggtccag  9780
aaagtgaagg accgcgctca agcaatcgtg gattcgattt ccaaggacaa agcaatcgca  9840
gaggagaagc tggaggccgc aaagcccgcg ctcgaagagg ctgaagcggc actgcagact  9900
atccggccgt ccgacattgc caccgtgaga accctgggcc gcccccccaca cctcatcatg  9960
cgcatcatgg actgcgtcct cttgctcttt caacggaagg tgtccgccgt caagatcgac  10020
cttgagaaat catgcaccat gccatcgtgg caggagtccc tgaaactcat gacagccggc  10080
aacttcctgc agaatctgca acagttcccc aaagacacca tcaacgaaga agtgatcgag  10140
ttcttgtccc cgtacttcga aatgcctgat tataacattg aaaccgccaa gcgcgtgtgc  10200
ggaaatgtcg cgggcctgtg ctcctggact aaggccatgg cctccttctt tagcattaac  10260
aaggaagtgc tcccactgaa ggccaacctc gtggtgcagg aaaatcgcca cttgctggcc  10320
atgcaggatc tccagaaggc tcaagcggag ctggacgata aacaggccga acttgacgtg  10380
gtgcaggcgg agtacgagca ggctatgacg gaaaagcaga ccttgctgga agatgcagaa  10440
agatgcaggc acaagatgca gaccgcctcc acccttattt ccggcctggc cggcgaaaag  10500
gaacggtgga ccgagcagtc ccaggaattc gcagctcaga ccaagaggct cgtgggcgat  10560
gtgctgctgg ccactgcctt cttgagctac tcaggcccct ttaaccagga atttcgggac  10620
ctcctgctga acgattggag gaaggaaatg aaggcgcgga agatcccatt cgggaagaac  10680
ttgaacctct ccgaaatgct catcgacgct cccaccatta gcgagtggaa cctccaggga  10740
ctgcccaacg acgaccttag cattcaaaac gggatcatcg tgaccaaggc ctcgcgctac  10800
cccctcctta tcgacccaca aactcaagga aagatttgga ttaagaacaa ggagtcacgc  10860
aacgagctgc agatcacctc cctgaaccat aagtacttca gaaaccatct cgaggattcc  10920
ctgagcctgg gcagacccct tctgatcgag gacgtgggcg aggagctcga tccggccctg  10980
gacaacgtcc tggagagaaa cttcatcaag actggatcca ccttcaaggt caaggtcggc  11040
gataaggaag tcgatgtcct ggatggcttc aggctgtata tcaccaccaa attgcctaac  11100
cccgcataca ccccggaaat ctcagcgcgc acctcgatca ttgactttac tgtcaccatg  11160
aaaggactgg aggatcaact gctgggcaga gtcattctca ccgaaaagca agagctcgaa  11220
aaggaacgca cccatctcat ggaggacgtg accgcgaaca agcggcggat gaaagagctt  11280
gaggataact tgctgtaccg cctgacctcg actcaggggt ccctcgtcga agatgagtcc  11340
ctgatcgtcg tcctgagcaa tactaagagg accgccgagg aagtaaccca gaagctcgag  11400
atcagcgcgg aaaccgaagt gcagatcaac agcgcaagag aagaatatag acccgtagct  11460
acgaggggga gcattctgta cttcctcatc acggagatga gacttgtcaa cgaaatgtac  11520
cagacctcat tgcggcaatt cctcggactg ttcgacctgt ccctcgctcg gtccgtcaag  11580
tcccctatca cttcaaagcg cattgcgaac attatcgagc acatgaccta cgaagtgtac  11640
aagtacgcgg ccaggggggtt gtatgaggag cacaagtttc tcttcaccct cctgctgacc  11700
ttgaagatcg acattcaaag gaatcgcgtg aagcatgaag aattcctgac cctcatcaaa  11760
ggcggcgctt ccctcgatct gaaggcttgc ccaccgaaac cgagcaaatg gatcctggac  11820
atcacgtggc tgaaccttgt cgaacttagc aagctgcggc aattctccga cgtcctggac  11880
cagatctccc ggaacgagaa aatgtggaag atctggttcg acaaagaaaa ccccgaggag  11940
gagcctctgc ccaacgcgta tgacaaaagc ctggactgct tccggcggct cctcctcatt  12000
cgctcgtggt gtcccgaccg gaccattgca caggcccgca agtacatcgt ggactccatg  12060
ggggagaagt acgctgaggg cgtgatcctt gacctggaga aaacttggga ggaaagcgac  12120
ccgaggacgc ctctgatttg cctgctttca atgggaagcg acccgaccga tagcatcatc  12180
gcgctgggaa agaggcttaa gattgaaact cgctacgtca gcatggggca aggccaggaa  12240
gtgcacgccc ggaagctgct ccagcagacc atggccaacg gaggctgggc gctgctgcag  12300
aactgccacc ttggactgga cttcatggac gaactcatgg acatcattat cgagactgaa  12360
cttgtccacg acgccttcag actgtggatg actaccgagg cccataagca gttccccatc  12420
acactcctcc agatgagcat caaattcgcc aacgatcctc cacagggcct gcgcgccgga  12480
ttgaaaagga cgtactcagg ggtgtcccag gacctcctgg acgtgtcctc cggctcccaa  12540
tggaagccaa tgctctacgc agtggcattc ctgcacagca ctgtgcagga gaggcggaag  12600
tttggagccc tgggatggaa cattccatac gagttcaacc aggccgactt caacgcgact  12660
gtgcaattca tccagaacca cctggacgat atggatgtga aaaagggggt gtcctggacg  12720
accattcgct acatgatcgg ggagatccag tacgggggaa gagtgaccga tgattacgac  12780
aagaggctcc tgaacacttt cgctaaggtc tggttctccg aaaacatgtt cggccccgac  12840
ttctcgttct accaggggta taacattcca aagtgctcga cggtggataa ctacctccag  12900
tacatccagt cgctgccggc ctacgattcc cccgaggtgt tcggcctcca ccccaacgcc  12960
gacattacct accagagcaa gctggctaaa gacgtgctgg acaccatact ggggatccaa  13020
ccgaaggata cctccggagg aggggacgaa acccgcgaag cagtggtggc acgccttgcc  13080
gacgacatgc tggaaaaact gccccctgac tacgtcccct ttgaggtcaa ggaacgcctc  13140
cagaagatgg gacctttcca gccaatgaac attttcttgc gacaagagat cgaccggatg  13200
cagcgcgtcc tctccctcgt gcgctcaacc ctcaccgagc tcaagctggc aatcgacggt  13260
accattatca tgtcggaaaa cctccgggac gcactggact gcatgttcga tgcgcggatc  13320
ccagcgtggt ggaagaaagc ctcctggatt tcgtcgaccc tggggttctg gttcaccgag  13380
ctgattgaaa ggaactccca attcacctcc tgggtcttta acggcagacc gcactgcttc  13440
tggatgaccg gctttttttaa cccccaggga tttctcaccg ccatgcgcca agagatcacc  13500
agggcgaaca agggctgggc gttggataac atggtgctgt gcaacgaagt gactaagtgg  13560
atgaaagatg acatttcagc cccgccaacc gaaggcgtct acgtctacgg gctctacttg  13620
gaaggggccg gatgggacaa gagaaatatg aaactcattg agtccaagcc gaaggtgctg  13680
ttcgagctga tgccagtgat ccgcatctac gctgaaaata acactctccg ggatcccagg  13740
ttctactcgt gcccaattta caagaagccc gtgcggaccg acctgaacta catcgccgcc  13800
gtcgaccttc gcactgccca gactccggag cactgggtgc tgcggggagt cgccctgctt  13860
```

```
tgcgacgtga agtag                                              13875

SEQ ID NO: 17          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 17
atgtttagga ttggaaggag acaattgtgg aaacacagcg tgaccagggt gctcactcaa  60
cgccttaaag gggagaagga ggctaaacgg gcgctgctcg acgctaggca taactacctc  120
ttcgccatcg tggcatcctg ccttgatctt aacaagacgg aagtggagga cgctattctt  180
gagggcaacc aaatcgagag aatcgaccag ctgttcgccg tgggaggcct gcgccacctt  240
atgttctact atcaggacgt ggaggaggcc gagactggac agctggggtc tttgggagga  300
gtcaatttgg tcagcggcaa aatcaagaag ccaaaagtgt ttgtcacgga aggcaatgac  360
gtcgcgctga ctggggtctg cgtgttcttc atccggaccg acccctctaa ggccatcacc  420
ccagataaca ttcaccagga ggtgtctttc aacatgctgg acgccgcaga tggaggcctg  480
ctgaactccg tgaggaggct cctcagcgac atcttcattc ccgccctgcg cgccacctcg  540
catggatggg gagaactgga ggggcttcaa gacgccgcga acattcggca agaattcctg  600
tcctccctgg aaggattcgt gaacgtgctg agcggcgcac aggaatccct caaggagaaa  660
gtcaacttga gaaagtgcga catcctcgaa ctcaagactt tgaaggagcc taccgattac  720
ctcaccctcg cgaacaaccc tgaaaccttg ggaaagatcg aagattgtat gaaggtctgg  780
attaagcaga ctgaacaggt gctggctgag aacaaccaac tgctgaagga ggccgacgat  840
gtcgggccgc gggcggaact cgaacattgg aaaaagagac tctccaagtt taattacctc  900
ctggaacagc ttaaatcccc ggatgtgaag gcggtgctgg cagtcctggc ggccgccaag  960
tccaagctgc tcaagacttg gcgcgagatg gacatccgca ttaccgatgc caccaacgag  1020
gcaaaggaca acgtgaaata tctgtacacc ctcgagaagt gctgcgaccc tttgtactca  1080
agcgatccac tctcaatgat ggacgccatt ccgactttga ttaacgccat taagatgatt  1140
tactccattt cgcattacta caatacctcg gaaaagatca cttcgttgtt cgtgaaggtg  1200
accaaccaga tcattagcgc ctgcaaggca tacatcacaa ataacggaac cgcctccatt  1260
tggaaccaac cgcaggacgt ggtggaggaa aagattttgt cagcaatcaa gttgaagcag  1320
gagtaccagc tctgtttcca taagactaag cagaagttga agcagaatcc caatgccaag  1380
caattcgact tctccgaaat gtacatcttc ggcaagtttg agactttcca ccggcggctg  1440
gcaaagatca ttgatatctt caccacgctt aagacctaca gcgtcctcca ggattcgact  1500
atcgaagggt tggaagatat ggcgaccaag tatcaaggaa ttgtcgctac catcaagaag  1560
aaggagtaca acttcctcga ccagagaaaa atggacttcg atcaggacta cgaggagttc  1620
tgtaagcaaa ccaacgatct gcataacgag cttcggaagt tcatggacgt cacgtttgcc  1680
aagattcaga ataccaacca agccctgagg atgcttaaga agtttgaacg gctcaacatt  1740
cccaacctcg gcatcgacga caagtaccaa ctcattctcg aaaattatgg ggcagacatt  1800
gatatgatca gcaagctgta caccaagcag aagtacgacc ctccactagc caggaatcag  1860
cctcctatcg ccggcaagat cctgtgggcg agacaactct tccacagaat tcagcagcca  1920
atgcaactgt tccagcagca tcccgcggtg ctgtcgactg cggaagccaa gcctatcatc  1980
cgctcctaca ataggatggc caaggtcctg ctggagttcg aagtgctgtt ccatagagct  2040
tggctccgcc agatcgaaga aattcacgtc ggccttgaag catccctcct ggtcaaggcc  2100
cccggcaccg gtgaactctt cgtcaacttc gaccctcaga tcctcatcct gtttagagag  2160
actgagtgca tggcccagat gggactcgaa gtttcgccgc ttgccactag cttatttcaa  2220
aagcgggatc ggtataagcg gaacttctcc aacatgaaga tgatgctggc cgagtatcaa  2280
cgggtgaaat ccaagattcc cgcggcgatt gaacagctca ttgtgccgca cctcgccaaa  2340
gtggatgagg ccttgcagcc gggacttgca gcactgacct ggacttcgct caacattgaa  2400
gcctacttgg agaacacttt cgccaagatc aaagacctgg aactgttgct cgatagggtg  2460
aacgacctca ttgagttccg gatcgacgcc atcctcgaag aaatgtccag cactcccctg  2520
tgtcaactcc cccaagagga acccctcact tgcgaagaat ttctgcagat gacgaaggat  2580
ctttgcgtca acggggcaca gattctgcac ttcaagtcat cacttgtgga agaggccgtg  2640
aacgaacttg ttaacatgtt gcttgacgtc gaggtcttga gcgaggagga atccgagaaa  2700
atctccaatg aaaactcggt gaactataag aacgagtcct ccgccaagag ggaagaggga  2760
aacttcgaca ccctgacctc gtccatcaac gccagggcca atgccctgtt gctgactact  2820
gtgaccagaa agaagaagga gactgaaatg ctgggggagg aagcaaggga gctcctcagc  2880
cacttcaacc atcaaaacat ggacgccctg ctcaaggtga ccaggaatac ccttgaggcc  2940
attcggaagc ggattcactc gagccacacc attaacttcc gcgatagcaa ctcagccagc  3000
aacatgaagc agaacagtct ccccatcttc agagcctccg tgactctggc cattccgaac  3060
attgtcatgg cccccgcttt ggaggatgtc cagcagactc ttaacaaggc cgtggagtgc  3120
atcatttccg tacccaaggg cgtgcgccaa tggtctagcg aactcctgtc caagaagaag  3180
attcaggaac gcaagatggc cgccctccag agtaatgaag atagcgactc cgatgtggaa  3240
atgggggaaa acgaactcca ggatactctt gagatcgcct cggtgaactt gccgattccc  3300
gtccagacta agaactacta caagaacgtc agcgaaaaca aagaaatcgt gaagctcgtg  3360
tcggtgctga gcacgatcat taacagcact aagaaggaag tgattactag tatggactgc  3420
ttcaagcggt ataaccacat ttggcagaag ggcaaggaag aggctattaa gaccttcatc  3480
acccaatccc ccctgctgag cgagttcgag tcccagatct tgtacttcca gaacctcgaa  3540
caagaaatta atgccgagcc cgagtacgtc tgcgtgggct ccatcgcgct gtacaccgcc  3600
gatctgaagt ttgccctgac cgccgagact aaggcctgga tggtcgtgat cggcagacac  3660
tgcaacaaga agtaccgctc ggagatggaa aacattttta tgcttattga agagttcaac  3720
aagaaattga accgccctat caaggatctc gacgacattc gaatagctat ggccgccctg  3780
aaggaaatcc gggaagaaca gatctcaatt gacttccagg tcgggcccat cgaagaaagc  3840
tacgcactcc ttaatcgcta cggactactc attgccaggg aagagatcga caaggtcgac  3900
accctccatt acgcatggga gaagctgctc gctcgcgctg gcgaagtgca gaacaaactc  3960
gtcagcctgc agccgagctt taagaaggaa ctgatctccg ccgtggaagt gtttctgcaa  4020
gactgccacc aattctacct tgattacgac ctcaatggtc caatggcctc gggcctgaag  4080
ccccaagagg cctcggaccg gctgatcatg ttccaaaacc agttcgacaa catctaccgg  4140
```

-continued

```
aagtacatta cctacactgg tggcgaagaa cttttcggcc tgccagctac ccagtatccg  4200
cagctcctgg agatcaagaa gcaactgaac ttgttacaaa agatctacac tctctacaat  4260
agcgtcattg aaaccgtcaa ctcctactac gacatcctgt ggagcgaagt gaatattgaa  4320
aaaattaata acgagctgct tgagttccag aacagatgcc gcaagctccc gcgggcactc  4380
aaggactggc aagcattctt ggacctcaag aaaattatcg acgatttcag cgagtgctgc  4440
ccgctcctgg agtacatggc ctccaaggcg atgatggaac gccattggga gcggatcact  4500
accctgacgg ggcacagcct ggacgtgggc aacgagagct ttaagctccg gaacattatg  4560
gaagccccgt tgctgaagta taaggaagag atcgaggata tttgcatcag cgccgtgaag  4620
gaaagggaca tcgagcagaa actaaagcaa gtgatcaacg agtgggacaa caagacgttc  4680
acgttcggct cgttcaagac tagaggagaa ctcctcctga gaggagactc cacttccgaa  4740
atcatcgcga acatggagga tagccttatg cttctcggct ccctacttag caacagatac  4800
aacatgccgt tcaaggcgca gatccaaaag tgggtgcaat acctgagcaa ctccaccgat  4860
attattgaat cctggatgac cgtgcagaac ttgtggatct acctcgaagc cgtgttcgtg  4920
ggtggagaca ttgccaagca actgcccaaa gaggcgaagc ggttttccaa cattgacaag  4980
agctgggtga agattatgac cagggcccac gaagtgccga gcgtggtgca gtgctgtgtc  5040
ggtgacgaga ctctcggcca gctgctccct catctcctgg atcagctgga gatttgtcag  5100
aagtcgttga ccggatacct tgaaaagaaa aggctctgct tcccgcgctt cttcttcgtg  5160
agcgaccccg cgctgttgga gattttgggt caagcgtccg attcccacac catccaagcc  5220
cacctcctca acgtctttga taacattaag tcagtgaagt tccatgagaa gatctacgac  5280
agaattctta gcatctcgtc ccaggagggc gagacaatcg agctggacaa gccggtgatg  5340
gccgagggta acgtcgaggt ctggcttaac tcgttgctgg aagagagcca gtcaagcctg  5400
cacttggtca ttcgccaagc cgcggccaac atccaggaga ctggattcca gctcaccgag  5460
ttcctgagca gcttcccggc tcaagtcgga ctcctgggca tccaaatgat ttggacgaga  5520
gactctgagg aggcgttgcg caacgccaag tttgacaaga aaattatgca aaagacaaac  5580
caggccttcc ttgaattgct aaacaccctt attgacgtga ccaccagaga tctcagctcg  5640
actgagcgcg tgaagtacga aaccctgatc actatccacg tgcaccagag agacatcttc  5700
gacgacttgt gtcacatgca tattaagtcg ccgatggact tcgaatggct caagcagtgt  5760
agattctact tcaacgagga ctcggataaa atgatgattc atattactga tgtggcgttt  5820
atctaccaaa acgaattctt gggctgcact gataggttgg tgatcactcc cctgactgac  5880
agatgctata tcaccctggc ccaggcgttg ggaatgtcaa tgggaggcgc ccctgccgga  5940
ccggctggca ctggaaagac cgaaacgact aaggatatgg ggagatgctt gggaaaatac  6000
gtcgtagtgt tcaactgctc cgaccagatg gacttccgcg gcctgggcag aatttttaag  6060
ggcctcgccc agtcagggtc gtgggggtgc ttcgacgagt tcaatagaat tgacttgccc  6120
gtcctgtcgg tggccgccca gcaaattagc atcatattga cgtgcaagaa ggaacataag  6180
aaatccttca tctttaccga cggggacaat gtcactatga atccagagtt cggtcttttc  6240
ctaaccatga acccaggcta cgctggcaga caggagctgc ctgagaactt gaagatcaat  6300
ttcagaagcg tggcgatgat ggtccccgac cgacaaatca ttatacgcgt caaactggcc  6360
tcgtgtggct tcatcgacaa cgtcgtcctg gcccggaagt tttcaccct ctacaagctc  6420
tgtgaggagc agctcagcaa acaagtgcat tacgatttcg ggcttcggaa catcctgagc  6480
gtcctccgga ccctcggagc cgccaagaga gccaacccaa tggacaccga gtcaaccatt  6540
gtgatgcgcg tcttgcgaga tatgaacttg tccaagctca tcgacgagga cgagcccctc  6600
ttcctgagcc tgattgagga cctgttccct aacatcctcc tggataaggc cggctaccct  6660
gaactggagg cggccattag cagacaggtg gaggaggcgg ggctgatcaa ccatccccct  6720
tggaagctca aggtcatcca gttgttcgag actcagcgcg tgcggcacgg catgatgacc  6780
ctgggaccgt ccggcgcagg caaaactacg tgcattcaca ccctcatgcg ggcgatgacc  6840
gactgtggca agccccacag agaaatgaga atgaatccca aagccattac tgctccccaa  6900
atgtttggcc ggctggacgt ggccaccaat gactggacgg acggaatctt tagcaccttg  6960
tggcggaaaa ccctgagagc taagaagggc gaacacattt ggatcattct cgacggccct  7020
gtggacgcga tttggattga aaatctgaat agcgtgctgg atgacaataa gactctcacg  7080
cttgccaacg gtgatcggat tcccatggcc ccgaattgta agattatttt cgagcctcat  7140
aacatcgata acgcttcgcc tgcgactgtc tcaagaaatg gcatggtgtt tatgtcctct  7200
tccattctgg actggtcccc gattctcgag ggcttcctga agaaaaggtc accacaagag  7260
gctgaaattt tgaggcaact gtacactgag tccttcccag acctgtaccg gttttgcatc  7320
cagaacctcg agtacaaaat ggaagtcttg gaagccttcg tcattactca gtcaatcaac  7380
atgctccagg ggctcatccc cctcaaggag cagggggggag aggtcagcca ggcgcacctc  7440
ggacggctgt tcgtgttcgc actcctgtgg agcgcggggg ctgcactgga actggatggg  7500
aggaggcggt tggagttgtg gctgagaagc agaccgacgg gtaccctgga actacccccc  7560
cccgcgggtc cgggagacac cgccttcgat tactacgtcg cgcccgatgg cacttggacc  7620
cattggaaca ctcgcaccca agagtatttg taccccttccg atactacgcc tgaatacggc  7680
agcatcctcg tgcctaacgt ggacaacgtc cggacagact tccttatcca aaccattgcc  7740
aaacagggca aggccgtgct cttgattggg gagcaaggca ctgccaagac ggtgatcatt  7800
aagggcttca tgtcgaagta cgacccagaa tgccatatga tcaaatcact gaacttcagc  7860
agcgccacta ccccactcat gttccaacgc acaattgagt cgtacgtcga taaaagaatg  7920
ggcaccacct acggacctcc ggccggaaaa aaaatgaccg tgtttatcga cgatgtgaat  7980
atgcctatta tcaacgagtg gggtgaccaa gtgaccaacg aaatcgtgcg ccagcttatg  8040
gaacagaacg gattttacaa cctggagaag cctggggagt ttacctctat cgtggacatc  8100
caattcctgg ccgcaatgat tcacccggga ggaggtcgga acgacatccc gcagcgactg  8160
aagcggcaat tctcgatctt caactgtact ctcccgtcgg aggcgtcagt ggacaagatc  8220
tttggagtca tcggggtggg ccattactgt acccagaggg gtttcagcga agaggtgcgc  8280
gattccgtga ccaagctggt gcccccttacc agacgcctgt ggcaaatgac caagatcaaa  8340
atgcttccca ctcccgcgaa gttccactac gtgtttaacc tccgcgatct gtcccgggtc  8400
tggcagggca tgttgaacac taccagtgaa gtcatcaagg agccgaacga cttgctcaag  8460
ctgtggaagc acgaatgcaa gcgcgtcatc gccgaccggt ttacggtgtc ctccgacgtg  8520
acctggttcg acaaagcgtt ggtgtcattg gtcgaagagg aattcggtga ggaaaaaaag  8580
ctcctggtgg attgtgggat tgacacttac tttgtcgatt ttctccgcga cgcccctgaa  8640
gcggccggtg aaaccagcga ggaagccgac gccgaaaccc cgaagatcta cgagccgatt  8700
gaatcgttca gccatctcaa agagcggctc aacatgttcc tccagctgta caacgaatca  8760
atcaggggcg ctggaatgga catggtgttc ttcgccgatg ccatggtcca ccttgtcaag  8820
atctcgcgcg tgatccggac ccctcaagga aacgccctct tggtcggtgt cggagggtca  8880
```

```
ggaaagcaga gcctgacccg gctcgcgtcg ttcattgccg gttacgtgag ctttcaaatt  8940
actctcaccc ggtcgtataa cacctcgaac ttgatggagg acctgaaggt cctctatcgc  9000
accgccgggc agcaaggcaa aggaatcacc ttcatcttca ccgacaacga aattaaggat  9060
gaatcatttc tggaatacat gaacaatgtc ctgagcagcg gagaagtgtc caacttgttc  9120
gctcgcgatg agatcgatga aattaactcc gacctggcct ccgtgatgaa gaaggagttc  9180
cctaggtgcc tgccgaccaa cgaaaacctc catgactact tcatgtccag ggtccggcaa  9240
aatctgcata ttgtgctgtg tttctcaccc gtgggggaaa aatttcgcaa tcgcgcgctg  9300
aagttccccg cactgatcag cggctgcacc atcgactggt tctcccggtg gccgaaggat  9360
gccctggtgg cagtcagcga acacttcctg actagctacg atattgactg tagcctcgaa  9420
attaagaagg aggtggtcca atgcatgggg tcattccagg atggtgtcgc agaaaaatgc  9480
gtggattatt tccaaaggtt ccggagaagc acccatgtga cgccgaagtc gtacttgtcg  9540
ttcattcagg gctacaaatt catctatggc gaaaaacacg tcgaagtgcg gaccctggct  9600
aacagaatga acaccggcct ggaaaaactg aaggaagcta gcgaaagcgt ggccgcgctc  9660
agcaaggaac ttgaagcgaa ggaaaaagaa ctgcaagtgg ctaacgacaa agcggacatg  9720
gtgttgaaag aggtgaccat gaaggcccag gcagcagaga aggtgaaggc cgaggtgcaa  9780
aaggtcaaag accgggccca ggccattgtg gactcgatct ccaaggataa ggctatcgct  9840
gaggagaagt tggaagcggc taagccagcc ctggaagagg ccgaggccgc cctgcaaacc  9900
atcaggccgt ccgacatcgc gaccgtgcgc accttgggca gaccgcccca cctcatcatg  9960
cggatcatgg actgtgtact cctcctgttc cagcgcaagg tgtccgcagt caagatcgat  10020
ctggaaaagt catgcacgat gcccagctgg caggaaagtc ttaaactcat gactgccggt  10080
aacttcctgc aaaaccttca acaatttccc aaggacacca ttaacgaaga agtcatcgaa  10140
ttcctgtcgc cgtacttcga aatgcctgac tacaatattg agactgccaa acgcgtgtgc  10200
ggaaacgtcg ccggactttg ctcctggacg aaggccatgg catccttctt cagcattaac  10260
aaggaggtcc tgccgctgaa ggcgaacctc gtggtccagg aaaaccgcca ccttctggcc  10320
atgcaagatc tccaaaaagc acaagccgaa ctggacgaca agcaggcgga acttgacgtg  10380
gtccaggccg agtacgagca agcaatgacc gagaagcaga ctttgctgga ggacgcagaa  10440
cgctgccggc acaagatgca gacggcgtca acgttgatct cgggcctcgc cggagaaaag  10500
gaaagatgga ccgagcagag ccaagaattc gcagcgcaga ctaagagact tgtcggagat  10560
gttctcctgg ccaccgcctt tctgtcctac agcgggccat tcaaccagga attcagagat  10620
ctgctgctga acgactggcg caaggaaatg aaggctcgca agattccgtt cgggaagaat  10680
ctcaatctct cggaaatgct tatcgacgca ccaaccatct ctgaatggaa tctgcaaggc  10740
ctgccgaacg acgaccttag catccagaac ggaatcatcg tgactaaggc ctccaggtac  10800
cccctcctga tcgaccccca gactcaggga aagatctgga ttaagaacaa ggaatcgcgg  10860
aacgaactcc agatcacctc actcaaccac aagtacttcc gcaaccatct cgaggattca  10920
ctcagcctgg gtcggcccct gcttattgag gacgtcggag aggagctgga tcctgccctc  10980
gacaacgtcc tcgagagaaa cttcatcaag acgggatcaa ccttcaaggt gaaggtcgga  11040
gacaaggaag tcgacgtgct ggatggattc aggctctaca tcaccactaa gctccccaac  11100
cccgcctaca ctccggagat ttcggcccgc acctccatca tcgactttac cgtcaccatg  11160
aagggactcg aagatcagct cctcgggaga gtgatcctga cagaaaagca ggaactggaa  11220
aaagaaagaa cgcatctgat ggaggatgtg actgcgaata agcggagaat gaaggaactc  11280
gaagataact tgctgtatag acttacgagc acccaagggt ccctggtcga ggacgagtca  11340
ttgatcgtgg tgctgtccaa caccaagcgc accgccgagg aggtgacgca gaagctcgaa  11400
atctcggcgg aaacggaagt ccagattaat tcggctcgcg aggaatatcg cccggtcgca  11460
actcggggat cgatcctgta cttcctgatc actgaaatgc ggctcgtcaa cgaaatgtac  11520
cagacatcgc tgcggcaatt cctgggactt tttgacctga gcctggcccg gtccgtcaag  11580
tcgccgatca cctcaaagag aattgcgaac atcattgaac acatgaccta cgaagtgtac  11640
aagtacgccg cccgtggatt gtacgaggag cacaaattcc tgtttacctt gctgcttacc  11700
cttaagatag acatccagag gaacagagtg aagcacgaag agttccttac gctgattaag  11760
ggcggagcct cactcgactt gaaggcatgc cccccgaagc catcaaagtg gattctcgac  11820
atcacctggc tgaacctggt ggagctctcc aagctccggc agttctcgga cgtcctggac  11880
caaatatcga gaaacgaaaa aatgtggaag atttggtttg acaaggaaaa cccggaagag  11940
gagcccottc ccaatgccta tgacaagtcg ctggactgct ttcggcgcct cctcctgatt  12000
aggtcctggt gccctgatag gactattgcc caggccagaa agtacattgt ggactcaatg  12060
ggagagaagt acgccgaagg agtcatcctt gacctcgaaa agacttggga ggaatcagac  12120
cctcgcaccc cgctgatttg tctcctttcg atgggctcgg atcctacaga tagcatcatc  12180
gccctgggaa agcgcctcaa gatcgaaact cggtacgtgt ccatgggaca aggtcaggaa  12240
gtccatgccc ggaagctgct tcaacagact atggcgaacg gtggatgggc cctgcttcag  12300
aactgccacc ttgggctcga tttcatggac gaattgatgg acattattat cgaaacggag  12360
ctggtgcacg acgcttttag actctggatg accactgagg cccataagca attcccccatt  12420
acgctgctcc aaatgtctat caaattcgcc aatgatcccc cgcaaggtct gcgggctggt  12480
cttaaaagga cgtactccgg agtgtcccag gacttgctgg atgtctccag cgggtcgcag  12540
tggaaaccaa tgctttacgc cgtcgccttc cttcactcga ccgtgcagga acgccggaag  12600
ttcggcgccc ttggctggaa cattccctac gaattcaatc aagccgactt caatgccact  12660
gtgcaattca tccagaacca cttagacgat atggacgtca aaaagggagt gagctggacc  12720
accatccgct acatgattgg tgaaatccag tacggcggac gggtcacgga cgattatgac  12780
aaacggctcc tcaacacctt cgcgaaagtg tggttcagcg agaacatgtt cggtccggac  12840
ttctccttct accaaggcta taatattcca aagtgctcga ctgtggataa ctacctccag  12900
tacattcaga gccttcctgc atatgactcc cctgaagtgt tcggattgca tccgaacgcc  12960
gatattactt accagagcaa gctggcaaag gacgtgctgg acaccattct gggcatccag  13020
cccaaggata cgagcggagg aggagatgaa acccgcgaag ccgtcgtcgc acgcttggca  13080
gacgacatgc tggagaaact gcctcccgac tacgtgccgt ttgaggtgaa ggaacggctg  13140
cagaaaatgg gaccatttca gccgatgaat attttcctgc ggcaggaaat cgaccggatg  13200
caacgcgtgc tttccctcgt ccgcagcacc ctgaccgagc tgaaacttgc tatcgatgga  13260
accattatca tgagcgagaa cttgcgcgac gccttagact gtatgttcga tgcgagaatc  13320
ccggcgtggt ggaagaaagc cagttggatc tcgtcgacac tggggttctg gttcaccgag  13380
cttatcgaaa ggaactccca attcacgtcc tgggtgttca acggtagacc gcattgcttc  13440
tggatgactg gattcttcaa cccgcagggc ttcctgaccg ccatgcggca ggagatcacc  13500
agagccaaca aggatgggc tttggacaac atggtgctct gcaacgaagt cacaaagtgg  13560
atgaaggacg atatctccgc cccgcctacg gagggcgtat acgtctacgg gctctacttg  13620
```

-continued

```
gaaggagccg gatgggacaa gagaaatatg aagctgatcg aaagcaagcc gaaggtgcta  13680
ttcgaactga tgccagtgat ccgcatttac gccgagaaca acacacttcg cgatccgcga  13740
ttctacagct gccctatcta caaaaagccc gtgaggactg acctgaacta tatcgcagca  13800
gtggaccttc gcaccgccca aaccccgaa cactgggtgt tgagggggt ggcgctgctc  13860
tgcgacgtga agtag                                                 13875

SEQ ID NO: 18          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 18
atgttccgga tcggacggcg ccaactttgg aagcattccg tcacccgcgt gctgactcag  60
cgcctcaagg gtgaaaaaga ggccaaaagg gccctgctcg atgctagaca taactactta  120
tttgccattg tcgcatcctg cctggatctg aataagaccg aagtcgagga cgcgattctg  180
gaagggaacc aaatcgagcg gatcgaccaa ctcttcgccg tgggtgggct gcgccatctc  240
atgttctact accaggatgt ggaagaagca gaaaccggcc aattgggatc actgggaggt  300
gtcaatctcg tatccggcaa gattaagaaa cctaaggtgt tcgtgactga gggaaacgac  360
gtcgcgctta cgggcgtctg cgtctttttc attcggaccg atccttcgaa ggccatcacc  420
ccggacaaca tccaccaaga agtgtccttc aacatgcttg acgcagccga cggcgggctt  480
ttaaacagcg tcagacggct cctgagcgac attttcattc ctgccctgcg ggccactagc  540
cacggctggg gagaattgga gggacttcag gacgctgcta atattagaca agaattcctc  600
tcctcgttgg aaggattcgt gaacgtgcta agcggcgccc aggaaagcct gaaagagaag  660
gtcaacttga ggaagtgcga catcctcgaa ttgaaaacac tgaaggagcc tactgattac  720
ctgacactgg caaacaatcc tgagactctc gggaaaatcg aggattgtat gaaggtctgg  780
atcaagcaga ccgagcaagt gctcgccgaa aacaatcaac tcctcaagga ggcggatgac  840
gtgggtccta gggcagaatt ggagcattgg aaaaaaagac tctccaagtt caactacttg  900
ctcgaacagc tgaaatcgcc tgacgtgaag gccgtccttg ccgtgctggc cgctgccaag  960
agcaaactcc tgaaaacttg gcgggaaatg gacattcgga tcactgatgc caccaacgag  1020
gctaaggaca atgtgaagta cttgtacaca ctcgagaagt gttgcgaccc gctgtattcg  1080
agcgatccac tcagcatgat ggacgcgatc ccgaccctca ttaacgcaat taagatgatc  1140
tactcgataa gccattatta caacacctct gaaaagatca cctccctttt cgtgaaggtg  1200
acgaaccaga ttatttcagc ctgcaaggct tacattacta acaacggcac tgcctccatc  1260
tggaatcagc ctcaggacgt cgtggaggag aaaatcctgt ccgcgatcaa gctgaagcaa  1320
gaataccagc tgtgcttcca caagaccaag caaaagctca aacagaaccc caatgctaaa  1380
caattcgact tttcggagat gtacatcttc ggaaagtttg aaaccttcca tcggaggctc  1440
gcgaagatta tcgacatctt caccacctc aagacttaca gcgtgctcca ggatagcact  1500
atcgaaggcc tagaagatat ggctaccaaa taccaaggaa ttgtggcaac catcaagaag  1560
aaggaataca acttcctgga ccagcgcaaa atggatttcg atcaggatta tgaggagttt  1620
tgtaagcaga ccaacgatct gcataatgaa ctgaggaagt tcatggacgt gacgttcgct  1680
aagatccaaa atactaatca agccctgagg atgctgaaga agtttgaacg cctgaacatc  1740
cccaacctcg gaatcgacga taaataccaa ctcatcctcg aaaactacgg agcagatatc  1800
gacatgatct ccaagttgta cacgaagcag aagtatgacc ctcctctcgc ccggaaccag  1860
cctccgattg cgggaaagat cctttgggcc cgccagctct ttcaccggat ccagcagcca  1920
atgcagctct ttcagcaaca tcctgcggtc cttagcaccg ccgaagccaa acctattatc  1980
agatcataca accgcatggc caaagtgttg ttggagttcg aggtcctgtt ccatcgcgcc  2040
tggctgaggc agatcgaaga gatccacgtc ggcctcgagg cgtccctgct tgtcaaggcc  2100
ccgggtactg ggaactcttt cgtgaatttt gacccccaga tcttgatcct tttccgcgag  2160
acagagtgca tggcgcaaat gggactggaa gtctcgccgt tggccacttc gttgttccag  2220
aagcgggata ggtacaagcg aaacttcagc aacatgaaga tgatgctggc agaataccaa  2280
cgtgtgaagt cgaaaattcc cgccgcaatc gaacagctca tcgtgcccca cttggctaaa  2340
gtggacgagg ccctgcagcc gggactcgct gcgctgacct ggaccagcct caacattgaa  2400
gcctacctcg agaacacctt cgctaagatc aaggatctcg agctcctcct cgatagagtc  2460
aacgacctga ttgaattcag gattgacgca attctggagg aaatgagctc aactcccctc  2520
tgtcagctcc cccaagaaga accgctgact tgcgaagaat ttctccagat gaccaaagac  2580
ctgtgcgtca atggggcgca gatcctccac tttaagagtt cactcgtcga ggaggccgtg  2640
aacgaactcg tgaacatgct gctggatgtg gaagtgctgt cggaggaaga gtcggagaag  2700
atttccaacg aaaacagcgt gaattacaaa aacgagtcat cagcaaagcg cgaagagggg  2760
aacttcgata ccctgaccag cagcatcaac gccagggcca acgctttgct cctcacgacc  2820
gtgacccgaa agaagaaaga aaccgagatg ctcggagagg aagcgcggga attgctgtcg  2880
cacttcaacc accagaacat ggacgcactc cttaaagtga ctcggaacac tttggaggcg  2940
atccggaaga ggatccattc ctcccatacc atcaacttca gggacagcaa cagcgcgtcg  3000
aacatgaagc agaactcact cccaatttc agagcgtcgg tgacacttgc cattccgaac  3060
atcgtcatgg ctcccgcact ggaggatgtc caacagaccc tgaacaaggc agtggagtgt  3120
atcatttcgg tccccaaagg ggtgcggcag tggagctccg aacttctttc caaaaaaaag  3180
atccaagaac ggaagatggc ggccctccaa tccaacgaag attcggactc agacgtcgaa  3240
atgggtgaaa acgaattgca agacactctg gaaattgcca gcgtgaatct ccctatcccc  3300
gtccaaacta agaattacta caagaacgtg agcgagaaca aggagattgt gaagctggtg  3360
tccgtcttga gcactatcat caattcgacc aagaaggagg tgatcaccag tatggattgc  3420
ttcaagcgct acaaccatat ctggcaaaag ggaaaggagg aggccatcaa gaccttcatc  3480
acccaaagcc ctcttctctc cgaattcgaa tcgcagatcc tctatttcca aaacttggaa  3540
caggaaatca acgccgagcc tgagtacgtg tgcgtggggt caatcgccct gtatactgcg  3600
gacctgaaat tcgcgctgac tgccgaaact aaggcctgga tggtggtcat tggccggcac  3660
tgcaacaaaa aataccgcag cgagatggag aacatcttca tgctcatcga ggaattcaac  3720
aagaagctga acagaccgat caaggacctc gatgatatca ggattgccat ggcggccctt  3780
aaggaaatcc gggaggaaca aattagcatc gatttccagg tcggcccaat cgaggaatcc  3840
tacgccttgc tgaaccgcta tggcctgctg attgcacggg aagagatcga caaggtggac  3900
```

-continued

```
accccttcatt atgcgtggga gaagctgctt gcgcgggcgg gagaagtcca aaacaagctg  3960
gtgtccctgc agccttcctt caaaaaggag ctgatctcag ccgtggaagt gttcttgcaa  4020
gattgtcatc aattctacct cgactacgac ttgaatggac ccatggcatc aggcctgaaa  4080
ccacaggagg cgtcagaccg gctgatcatg ttccagaacc aattcgacaa catttacagg  4140
aagtatatca cgtacactgg aggagaggaa ttgttcggcc ttcctgccac tcagtacccg  4200
caactgctgg aaattaagaa gcaacttaac ctcctccaga agatctatac tctctacaat  4260
tcagtgattg agactgtgaa ctcgtactac gacattctgt ggtcagaggt gaacatcgaa  4320
aagatcaata acgagttgct ggaatttcag aaccgctgca gaaagctccc tagagccctc  4380
aaagactggc aggccttctt ggacctgaag aaaattatcg acgacttctc cgaatgctgc  4440
ccgctgcttg agtacatggc ctccaaagcg atgatggaac gccattggga acggatcacg  4500
actttgactg gacacagcct ggatgtgggg aacgaatcct ttaaactgag gaacatcatg  4560
gaagctccgc tgctcaaata taaagaagaa atcgaggaca tttgcatcag cgccgtcaag  4620
gaaagggaca ttgaacagaa gctgaaacag gtcatcaacg agtgggacaa taagactttc  4680
accttcggca gcttcaagac tcggggcgaa ctcctcctga gaggagattc gacgagcgag  4740
attattgcga acatggagga ttcgctgatg ctccttggaa gcctcctctc gaatagatac  4800
aacatgccgt ttaaggcaca gatccaaaag tgggtccagt acctctcgaa ctccaccgac  4860
attatcgagt cctggatgac cgtgcaaaac ctctggatct atctcgaagc agtattcgtc  4920
gggggggata tcgccaaaca actgcctaaa gaggccaaga gattctccaa catcgataag  4980
tcgtgggtga aaattatgac tcgggcacat gaggtgccca gcgtggtcca atgctgcgtc  5040
ggtgacgaaa ctctcggtca actgcttcca cacttgctgg accaactgga gatttgccag  5100
aagtcactca ctggatatct cgaaaagaag cggctctgtt tcccccgctt ctttttcgtg  5160
agcgaccctg ccttgttgga aatcttgggg caggcctccg actcgcacac catccaggcc  5220
cacctcctga acgtctttga caacatcaag tccgtgaagt ttcatgagaa gatctacgac  5280
cgcatcctga gcatttcgtc acaggaaggt gaaactatcg aactggataa acctgtcatg  5340
gcggaaggga acgtggaagt gtggctgaac agcctgctgg aggagtcaca gagctcgctc  5400
cacctggtca ttcggcaggc cgccgcgaat atccaagaga ctggattcca gctgacggag  5460
ttcctgagca gcttcccggc ccaagtgggc ctgctgggaa ttcaaatgat ctggacccgg  5520
gacagcgaag aggccctgag aaacgctaag ttcgacaaaa aaatcatgca gaaaacgaac  5580
caggccttcc tggaattgct gaacaccctc attgacgtca ccactcgcga ccttagctcc  5640
accgagaggg tgaaatacga aactctgatt accatccacg tgcatcaacg cgatattttc  5700
gacgacctct gccacatgca cattaagtcg ccgatggatt tcgagtggct gaagcagtgt  5760
agattctact ttaacgagga ttcggacaag atgatgatcc acatcaccga tgtcgccttt  5820
atctaccaga atgagttcct gggatgcacc gacagactcg tgatcacccc actgaccgac  5880
agatgctaca tcacccttgc gcaggctctg ggcatgtcga tgggtggggc cccggcgggc  5940
cctgcaggca ccggcaagac ggaaaccacc aaggatatgg gaaggtgcct tgggaagtac  6000
gtggtcgtgt tcaactgctc agaccagatg gacttccgcg ggctgggacg cattttcaag  6060
ggcctggccc agtcgggctc gtggggttgc ttcgacgagt tcaacaggat cgacttgccg  6120
gtcctgtccg tggctgcaca gcagatttcg attatcctca cttgcaagaa ggagcacaag  6180
aagtccttca ttttcaccga cggagacaac gtcaccatga atccggaatt cggccttttc  6240
ctgactatga accctgggta cgcgggaagg caggaactgc cagaaaacct caagattaat  6300
tttcgcagcg tggctatgat ggtgccggac cggcaaatca ttattagagt gaagctcgca  6360
tcgtgcggat tcatcgacaa cgtcgtgctc gcaagaaagt tcttcactct gtacaagctg  6420
tgcgaggaac agcttagcaa acaggtgcac tacgattttg gcctccggaa cattctctca  6480
gtgctccgga ccctgggagc cgcgaagagg gccaacccca tggacaccga atcaaccatt  6540
gtgatgcggg tcctgagaga catgaacttg tccaagctca tcgacgagga cgaacccctg  6600
ttcttgagct tgatcgagga cctgttccct aacatcctcc tggataaagc aggctacccg  6660
gaattggaag ccgccattag cagacaagtg gaggaagccg gattgattaa tcatccaccg  6720
tggaagctga aagtcatcca gttattcgaa acccaacgcg tgcgccatgg aatgatgacc  6780
ctcggccctt ccggagccgg caaaaccacg tgcatccaca ccctcatgcg cgccatgact  6840
gactgtggca agccacaccg ggaaatgagg atgaacccga aagctattac cgcgccacag  6900
atgttcggac gcctggacgt ggccactaac gattggacgg atgggatctt ctcgaccctt  6960
tggcgcaaaa ctctgcgcgc caagaaggga gaacacatct ggatcattct tgacggacct  7020
gtggacgcca tttggattga aaatctgaac tcggtgcttg acgacaacaa gactctcacc  7080
ttggcaaatg gcgaccgaat tcctatggcc ccgaactgca agattatttt cgagcctcac  7140
aatattgata acgcttcgcc agcgactgtc tcccgcaacg ggatggtgtt catgtcaagc  7200
tcgatcctgg attggagccc aatcctcgag ggctttttaa aaaagcggtc gcctcaggaa  7260
gcggaaatcc ttcggcagct ttacaccgag tcgttcccgg atctctaccg cttctgcatt  7320
cagaacctcg aatacaagat ggaagtgctc gaagccttcg tgatcacaca gtccattaac  7380
atgctgcagg gcctgatccc cctgaaggag caaggaggag aagtgtccca ggcccatctg  7440
ggtagacttt tcgtgttcgc gctcctgtgg tccgccggtg ccgcgctcga acttgacggc  7500
cgaaggcggc tggaactgtg gctgaggtcg aggccgaccg gaactttgga gctgcctcca  7560
cccgccggac ctggcgacac tgcctttgac tactacgtcg cccctgacgg aacctggacc  7620
cactggaaca ccaggactca ggagtacctc taccccttccg acacgactcc cgagtacggg  7680
tcaattttgg tgccgaacgt ggataacgtg cggacagact ttctgatcca gactatcgcg  7740
aagcagggaa aggcagtcct gctgatcggc gaacaaggaa cggcaaagac ggtcattatt  7800
aagggcttca tgagcaagta cgaccctgag tgccatatga tcaagtcact gaatttctcc  7860
agcgcgacga ccccccttat gtttcaaaga accattgagt cgtacgtcga caagagaatg  7920
ggcactacgt atgggcctcc cgccggaaaa aagatgaccg tgttcatcga cgatgtgaac  7980
atgccgatta tcaacgaatg gggggaccaa gtcacgaacg agatcgtgag gcagcttatg  8040
gaacagaacg gtttctacaa tcttgagaag ccgggagagt tcacttccat cgtcgatatt  8100
cagttcctgg ccgccatgat ccacccagga ggaggccgga atgatatccc tcagcgcctg  8160
aaaaggcagt tctcgatctt taattgcacc ttgccgtcag aagcctcggt ggacaagatc  8220
ttcggcgtga tcggcgtggg gcattactgc actcagcgcg gcttctcgga ggaggtccgg  8280
gactcggtca ccaagctggt gccactgacc cgcaggctct ggcaaatgac caagattaag  8340
atgctgccta cccccgccaa gttccattat gtgttcaacc tcagggacct ctcacgggtg  8400
tggcaaggaa tgctgaatac tacttccgaa gtgatcaaag agcctaacga ccttttgaag  8460
ttgtggaagc acgagtgcaa gcgcgtcatt gccgaccggt tcaccgtgtc ctcagacgtg  8520
acttggttcg acaaggccct cgtgtccctg gtcgaagagg agtttggaga agaaaaaaag  8580
ctccttgtgg actgcggtat cgatacctac ttcgtggact ttcttcggga cgcaccggaa  8640
```

-continued

```
gcagccggag aaactagcga agaagctgac gccgaaactc cgaagatcta tgagcctatc  8700
gagagctttt cgcacctgaa ggaacggctg aacatgttcc tccagcttta taatgagagc  8760
attcgcggtg ccgggatgga tatggtgttc ttcgccgacg cgatggtgca ccttgtgaag  8820
atttcacggg tcattcggac cccacaagga aacgcgctgc tggtcggtgt cgggggatcc  8880
gggaaacagt cactgacgag attggcgagc ttcattgccg gatacgtgag cttccagatc  8940
acgctgacca ggtcctacaa taccagcaac ttgatggagg atttgaaggt gctgtaccgc  9000
accgcgggcc aacaaggaaa ggggattact ttcatttca ctgacaacga aatcaaggac  9060
gaatcgttcc tggaatacat gaataacgtc ctctcgagcg gggaagtgtc caacctgttc  9120
gccagggatg agattgacga gatcaatagc gaccttgcaa gcgtcatgaa gaaggaattc  9180
cctcgctgcc tccccacaaa cgaaaacctc cacgattact tcatgagccg ggtcagacag  9240
aacctccata ttgtgctgtg cttctcacct gtgggtgaaa agtttcggaa ccgcgcactg  9300
aaattccccg cactgatctc ggggtgcacc atcgactggt ttcccggtg gcctaaggac  9360
gccctggtcg ccgtgtccga gcacttcctc actagctatg atatagattg cagcttggaa  9420
atcaagaagg aggtagtcca gtgcatggga tcgttccaag atggcgtcgc ggaaaagtgc  9480
gtggattact tccagaggtt tcggagatcg acccacgtga ccccgaagtc atacctgagc  9540
tttattcaag gttataagtt tatttacggc gaaaagcacg tcgaagtccg caccctcgcc  9600
aaccgaatga acaccgggct ggaaaagctc aaggaagcct cagaatccgt ggccgcactg  9660
agcaaggaac tcgaggctaa agaaaaagag ttgcaagtgg ccaacgacaa agcggacatg  9720
gtgcttaaag aagtgaccat gaaggcccaa gcagcggaaa aggtgaaggc cgaagtgcag  9780
aaggtcaagg acagggcgca agcaatcgtg gactcgatca gcaaagacaa ggctattgcg  9840
gaggagaagc tcgaggccgc caagcctgca ctggaggaag cagaagccgc tctccagacc  9900
atcagaccta gcgacatcgc caccgtgcgg actcttggcc ggcctcccca cttgattatg  9960
cgcatcatgg actgcgtgct gctgctcttt cagcggaagg tgtcggcggt gaagatcgac  10020
ttggaaaagt cgtgtactat gccttcgtgg caagaatcac tcaaactcat gaccgcaggc  10080
aacttcctac agaacctcca acaattccca aaggatacca tcaacgaaga agtcattgaa  10140
ttcctctctc cgtatttcga aatgcccgat tacaacattg aaacggccaa acgcgtgtgc  10200
ggcaacgtgg cgggactgtg ctcatggact aaggcgatgg cgtccttctt ctcgattaac  10260
aaggaagtgc ttccacttaa ggcgaacctg gtggtccagg agaatcgaca cctcctggcg  10320
atgcaggacc ttcagaaggc ccaggccgaa cttgacgaca agcaggcaga actggacgtg  10380
gtgcaggccg aatacgagca ggctatgact gagaagcaaa cgctgctgga ggatgccgag  10440
cggtgccggc ataaaatgca gaccgcctcg acccttattt ccggactcgc tggagagaag  10500
gaacgctgga ctgaacagag ccaggaattt gccgcgcaaa ccaagagact tgtgggcgac  10560
gtcctgctcg caactgcctt cctgtcctac tccggcccat tcaatcagga attccgcgac  10620
ctgttgctta atgactggcg gaaagagatg aaagcccgca agatcccttt cgggaagaac  10680
cttaacctct ccgagatgct gatcgacgca ccgaccatta gcgaatggaa cctccaagga  10740
ttgccaaatg acgatctaag tatccagaac gggatcatcg tgacgaaggc ctccaggtac  10800
cctcttctga tcgatccgca gacccaagga aagatctgga tcaagaataa ggagagcaga  10860
aatgaactgc agataacctc actcaatcac aagtacttta ggaaccacct tgaggattca  10920
ctgagcttgg gacggccgct gttgatcgag gatgtggggg aggaactgga tccagcgttg  10980
gataacgtcc tggagcgcaa cttcatcaag accggatcga ccttcaaggt gaaggttggc  11040
gataaggaag tggacgtgct ggacgggttt agactctaca taaccactaa gctccccaac  11100
cctgcctaca cgcctgaaat ttccgccaga acctcaatta tcgacttcac cgtcactatg  11160
aagggactcg aggaccagtt gctgggtcgc gtcatcctga ctgaaaagca ggaactggag  11220
aaggaacgga ctcatctcat ggaggatgtg accgccaata agcgccggat gaaggaattg  11280
gaagataact tgctgtatag acttacttcc acccaaggct ccctcgtgga ggacgaaagc  11340
ctcattgtgg tcctgtccaa tactaagcgc actgccgaag aagtcactca aaagctggaa  11400
atttcagcgg agactgaggt gcagatcaac tcggccagag aggaataccg gcccgtggct  11460
actcgcggga gcatcctgta cttcctcatt actgagatgc gcctggtgaa cgagatgtat  11520
cagacctccc tccgacaatt ccttggtctt ttcgacttga gccttgctcg ctcggtcaag  11580
agccccatta ctagcaaacg catcgcgaac atcatcgagc acatgactta cgaagtgtac  11640
aagtacgcgg ctagaggact gtacgaggag cacaagttcc ttttcacact cctcctcacc  11700
ctcaagatcg atattcaacg gaacagagtc aagcacgaag aattcctgac tctcatcaag  11760
ggaggagcct cgctcgatct caaggcctgc cctccgaagc catccaagtg gatcttggat  11820
attacctggc tgaacctcgt ggagcttagc aaactgcggc aattcagcga cgtgctggac  11880
cagatttcca gaaacgaaaa gatgtggaag atttggtttg acaaggagaa ccccgaggaa  11940
gaaccattgc cgaatgccta tgataaaagc ctggactgct ttaggcggct gctcctgatc  12000
agatcatggt gccctgatcg taccatcgcc caagcgcgca agtatatcgt cgactccatg  12060
ggtgaaaagt acgctgaggg ggtgatcctc gacctggaaa agacgtggga agagagcgac  12120
ccacgcaccc cgctcatttg cctcttaagc atgggatccg accccaccga tagcattatt  12180
gctctgggca aaaggctcaa aatcgaaacg cggtacgtga gcatggggca gggtcaggag  12240
gtgcacgccc ggaagctgct ccagcaaact atggcgaacg gcggatgggc gcttcttcag  12300
aactgccatc tcggcctcga cttcatggat gagctgatgg atattattat tgaaaccgag  12360
ctggtccacg acgcattcag gctctggatg accaccgagg cccacaaaca attcccccatc  12420
acgctgttgc agatgtccat caagttcgct aacgatcccc ctcaaggact tagggctggg  12480
ctcaagcgga cgtattcagg agtctcacag gatctccttg atgtgtcaag cggctcacaa  12540
tggaaaccca tgctctacgc tgtggctttc cttcactcca cggtgcagga acggcgcaag  12600
ttcggagcct tggggtggaa tatcccctac gaattcaacc aagcggactt caacgctacc  12660
gtgcaattca tccaaaatca tcttgacgac atggatgtga agaagggagt gagctggacc  12720
accattagat acatgattgg cgagatccag tacgggggggc gcgtgaccga cgactatgac  12780
aaacggctct tgaacacgtt cgcaaaagtg tggtttagcg agaacatgtt cggcccagac  12840
ttctctttct accaaggtta caatatcccg aagtgctcca ccgtcgataa ctacctccag  12900
tacatccaaa gccttcccgc ctacgactcg cccgaggtgt tcggtctgca tccgaacgcg  12960
gacatcacct accaatccaa actggctaag gacgtccttg atacgattct gggtattcag  13020
ccaaaagaca cgagcggagg aggggacgaa accagagaag ccgtggtcgc ccgcttggct  13080
gacgacatgc tggaaaaact tccgccggac tacgtgccgt ttgaagtgaa agaacgcttg  13140
cagaagatgg gtccctttca accaatgaac atattcttga gacaagagat tgatagaatg  13200
cagcgggtgc tgagcttggt gcggtcgacc ctcacagaac ttaaactggc gattgacggg  13260
acgatcatta tgagcgagaa tctgcgcgac gccttggact gcatgtttga tgctcggatc  13320
cccgcgtggt ggaagaaggc ttcttggatc tcgagcacgc tcgggttttg gtttaccgaa  13380
```

-continued

```
ctcatcgagc ggaattcgca gttcacttca tgggtcttta acgggcgacc ccactgcttc  13440
tggatgacgg gcttcttcaa cccgcaaggt tttctcaccg ccatgcggca ggagatcact  13500
agagccaaca aaggctgggc gttggacaat atggtcctgt gcaacgaagt gaccaagtgg  13560
atgaaggacg acatctccgc gccccccacc gagggcgttt atgtctacgg actttacttg  13620
gaaggtgccg gatgggacaa gcggaacatg aagctcatcg agagcaaacc gaaggtgctg  13680
tttgagctca tgcccgtgat ccgcatctat gccgaaaata acacattgag agatccccgc  13740
ttctactcgt gccccatcta taagaagcct gtcagaaccg acttgaacta cattgccgcc  13800
gtcgacctga gaacggccca gactcccgag cattgggtcc tgaggggagt ggcgctgctg  13860
tgcgatgtga agtag                                                  13875
```

```
SEQ ID NO: 19          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 19
atgtttagaa ttggcaggcg ccagctgtgg aagcactcag tgacccgggt gctaacgcag  60
cggcttaagg gcgagaagga ggcgaagcgg gccttgctgg acgccaggca caactacctc  120
ttcgcgattg tggcgtcgtg ccttgacctg aacaaaaccg aggtcgagga cgcgattttg  180
gaagggaacc agatcgaaag gatcgaccaa ttgtttgccg tcggaggtct gcggcacctg  240
atgttctact accaggatgt ggaggaggcc gaaaccggcc agctaggctc cctcggagga  300
gtgaacctgg tgtcgggaaa aatcaagaag cccaaggtgt tcgtcaccga aggcaatgat  360
gtcgctctga ccggcgtgtg cgtgttcttc attcggaccg acccctcaaa agcaatcacc  420
ccggacaata tccaccagga ggtttccttc aacatgctcg acgcggctga cggtggactg  480
cttaacagcg tccggaggct cctctcggac attttcattc ccgccctgcg ggctactagc  540
catggctggg gagaactgga ggggcttcag gacgccgcta atattagaca ggaattcctg  600
tcctcgctgg agggattcgt gaacgtcctg tcgggcgccc aggaaagtct caaagaaaag  660
gtcaacctca gaaagtgcga catcttggaa ctgaaaacgc ttaaagaacc gaccgattac  720
ctgaccctgg ctaacaaccc ggaaaccctg ggcaagatcg aagattgcat gaaagtgtgg  780
atcaagcaaa cagaacaggt cctggctgaa aacaaccagc tgctgaagga agccgatgat  840
gtggggccca gagccgaact ggagcactgg aagaagaggt taagcaagtt caactacctt  900
ctggaacagc ttaaatcccc ggatgtgaag gccgtgctgg ccgtgctggc cgccgccaag  960
agcaagctcc tcaagacttg gagagagatg gacatccgga tcacggacgc tacgaacgaa  1020
gccaaggata atgtcaagta cctttacacc ttggagaagt gctgcgaccc actgtacagc  1080
agcgatcctc tgagcatgat ggatgctatc ccgaccctta tcaacgcgat caagatgatt  1140
tacagcatca gccactatta caacacaagc gaaaaaatta cttcactgtt cgtgaaggtc  1200
actaaccaga ttatttccgc ttgtaaggcc tacatcacta acaacggaac tgccagcatc  1260
tggaaccagc cacaggacgt ggtggaggag aagatcctga gcgccatcaa gctgaaacaa  1320
gagtatcagc tgtgctttca caagacgaaa cagaagctga aacagaaccc aaacgctaag  1380
cagttcgatt tctcagaaat gtacatcttc ggcaagttcg aaaccttcca caggcgcctc  1440
gccaagatta ttgacatctt cactaccctt aaaacgtaca gcgtcctcca agactccacc  1500
attgaagggc tggaggatat ggccaccaag taccagggga tcgtggccac catcaagaag  1560
aaggaataca acttccttga ccaacggaag atggacttcg accaggacta tgaggagttc  1620
tgcaaacaaa ccaacgattt gcacaatgaa ctcaggaagt tcatggatgt gacctttgcc  1680
aagatccaga atactaacca ggccctgcgc atgctgaaga agttcgaacg gctgaatatt  1740
ccgaacttgg ggatcgacga caagtaccaa ctcatcctgg aaaactacgg cgctgacatt  1800
gacatgatct cgaaactcta caccaagcag aaatacgacc caccgctggc tcggaaccag  1860
ccgcctatcg cgggaaagat cctgtgggcg agacagctgt tccataggat tcagcagcca  1920
atgcagcttt tccagcagca tccggccgtg ctcagcaccg ccgaggcgaa acctatcatt  1980
cggtcataca acaggatggc caaagtgttg ctggaattcg aagtgctgtt ccaccgggcg  2040
tggctccggc agatcgagga gatccacgtc gggctagagg cctccctcct cgtgaaggct  2100
cccggaaccg gggagctgtt cgtcaacttt gaccctcaaa tcttgatcct tttccgggag  2160
actgaatgca tggcccagat gggattggag gtgtcaccat tggctacttc gctctttcaa  2220
aagcgggacc gctacaaaag gaatttcagc aacatgaaga tgatgctcgc agaataccag  2280
cgcgtcaagt ccaagatccc tgccgccatc gaacagctca tcgtcccgca ccttgccaaa  2340
gtggacgaag cgcttcagcc cggactggcg gctctgacgt ggactagcct taacatcgaa  2400
gcgtatttag agaacacctt cgccaagatc aaggacctgg agctgctctt ggatagggtg  2460
aacgacctga tcgagttcag aatcgacgct atactggagg aaatgagctc aacgccgctg  2520
tgccagctcc ctcaggaaga acccttgact tgtgaagaat tcctgcagat gactaaggac  2580
ttgtgcgtga acggtgcgca gattctgcat tttaagtcat ccttggtgga ggaggcggtg  2640
aacgagcttg tcaacatgct cctggacgtg gaggtgctgt cagaggagga atcggaaaaa  2700
atctccaacg aaaacagcgt caactacaag aacgaatcga gtgccaagcg ggaagagggt  2760
aacttcgaca ccctcacctc gagcattaac gcgcgggcga acgccctcct tctcaccact  2820
gtgacgcgga agaagaagga gactgaaatg cttggcgagg aagccagaga actcctgtcc  2880
cattttaatc atcaaaatat ggatgcactg ctcaaggtca ctcgcaacac tctcgaggcc  2940
atccgcaaac gaatccacag ctcacacact atcaacttcc gggattccaa ctccgcaagc  3000
aacatgaagc agaactcact gccgattttt cgggcttcag tcactctggc gatcccgaat  3060
attgtgatgg ccccggccct ggaagatgtc cagcaaaccc tcaacaaggc ggtggaatgt  3120
atcatctcag tgcctaaggg tgtgaggcaa tggagcagcg agcttctctc caagaagaag  3180
atccaggagc gcaagatggc ggctctccag agcaacgaag attcggactc cgacgtggag  3240
atgggcgaaa acgaactgca agacacgctg gaaattgcat cagtgaacct cccaattcct  3300
gtgcaaacta aaaactacta taaaaacgtc agcgaaaata aggagatcgt caagctggtc  3360
agcgtcctgt cgaccattat taactccacg aagaaagaag tgataaccag catggactgc  3420
tttaagcgct acaaccacat ttggcagaag ggaaaggagg aagccattaa gactttcatt  3480
acccagtccc cgctcttgag cgagttcgag tcccagatcc tgtacttcca gaacctcgag  3540
caggagatta acgctgagcc cgaatacgtc tgcgtgggta gcattgcgct gtatactgcc  3600
gatctcaagt ttgccctcac ggctgaaact aaggcctgga tggtcgtgat cgggaggcat  3660
```

-continued

```
tgtaacaaga agtaccgctc cgaaatggaa aacattttca tgcttatcga agagttcaac  3720
aagaaactca atcggcccat caaggatttg gacgatatcc ggattgcgat ggccgcgctc  3780
aaggagatcc gagaggaaca gatctcgatt gacttccagg tcgggcctat cgaggagagc  3840
tacgccctgc tgaacagata tggactcctc attgctcggg aagaaattga caaggtggac  3900
actctgcatt atgcctggga gaaactgctg gcccgcgcag gggaggtcca gaacaaactg  3960
gtcagcctcc aacctagctt caagaaagag ctgatctccg cagtggaggt gtttctgcag  4020
gactgccatc aattctacct tgattacgac ctcaacggcc cgatggccag cggactcaaa  4080
cctcaagagg catccgaccg gctcatcatg ttccagaacc aattcgacaa catctaccgg  4140
aagtatatca cttataccgg cggagaagaa ctgttcggat tgccggcgac tcagtacccc  4200
caacttctcg aaatcaagaa gcaattgaac ctcctgcaaa agatttacac gctttacaac  4260
agcgtgatcg aaacggtgaa ctcctactac gacatccttt ggtccgaagt gaacatcgaa  4320
aaaatcaaca atgaactgct ggaattccag aacagatgcc gcaagttgcc acgcgctctg  4380
aaggattggc aggccttctt ggacctgaag aagattatcg acgattttag cgaatgctgc  4440
cccttgctgg aatacatggc tagcaaggcc atgatggaga gacattggga gcgcatcacg  4500
accctcactg gccacagcct tgacgtgggc aatgagtcgt tcaagctgag aaacattatg  4560
gaagcaccgc tgctcaagta caaggaagag atcgaagata tttgcattag cgcggtcaag  4620
gaacgggaca ttgagcagaa acttaaacag gtcatcaacg agtgggacaa taagactttt  4680
acctttggat cctttaagac ccggggcgag ctccttctga gaggcgactc gactagcgag  4740
atcatcgcaa atatggagga ttccctgatg ctcctgggat cactcctgag caacagatat  4800
aatatgccct ttaaggctca aatccagaag tgggtgcaat acctgtccaa cagcaccgac  4860
attatcgaga gctggatgac cgtccagaac ttgtggatct acctggaagc ggtgttcgtc  4920
ggcggtgata ttgccaagca gctccctaag gaggctaaaa ggttctccaa cattgacaag  4980
agctgggtga agatcatgac tagagcccat gaagtcccga gtgtggtcca atgctgtgtg  5040
ggggacgaga ctctggggca gctgctaccc cacctcctgg accagcttga gatctgtcaa  5100
aagagcctga cgggctacct ggagaagaaa cgcctgtgct ttccgaggtt cttcttcgtg  5160
agcgacccgg ccctgctgga aattctcgga caagcgagcg actcccatac catccaggca  5220
catctgctta acgtgttcga taacatcaag agcgtgaagt tccacgagaa gatctacgac  5280
cggatcctga gcatctcatc gcaggaagga gagactatag agcttgacaa accagtgatg  5340
gccgaaggaa atgtggaggt gtggttgaac tccctgctcg aagagagcca gagctccctg  5400
cacctcgtca ttcgccaggc cgcggcgaat attcaggaaa ccgggttcca acttaccgag  5460
ttcttgtcca gctttcccgc gcaagtcgga ctcttgggta ttcaaatgat ttggaccaga  5520
gattccgaag aggccctccg caacgccaag ttcgacaaaa agatcatgca aaaaactaac  5580
caagcattcc tggagctgct taacaccctt atcgatgtga ccaccaggga tctcagctcc  5640
actgagcggg tcaaatacga aacgttgatt actatccacg tgcaccaacg cgacatcttc  5700
gacgacttgt gccacatgca catcaagagc ccgatggatt tcgagtggct caaacagtgc  5760
cggttctact tcaacgagga ttccgacaaa atgatgattc acattaccga tgtggctttc  5820
atttaccaaa acgaattcct gggctgtact gaccggctgg tgatcacgcc gctgaccgac  5880
cgctgctaca tcactctggc acaggctctg ggaatgtcga tgggaggagc tcctgcgggc  5940
ccagcgggaa ctggcaaaac cgaaaccacg aaggatatgg ggcggtgtct ggggaagtac  6000
gtcgtggtgt ttaactgctc agaccagatg gactttaggg gactgggtcg gatctttaag  6060
ggactggccc agtcaggctc ctgggggtgt ttcgatgaat tcaatcggat cgacttgccg  6120
gtgctgtccg tggccgcgca gcaaatttcc atcatcctta cctgtaagaa ggagcacaag  6180
aagtccttca tctttaccga cggggacaac gtgaccatga acccagagtt cggactcttc  6240
ctcactatga atcccgggta cgccggccgc caagagctcc cagagaatct gaagattaat  6300
tttcgctcag tggccatgat ggtcccggat agacaaatca tcatccgggt gaagttggcg  6360
tcctgcggct tcatcgacaa cgtggtgttg gccagaaaat tcttcacgct ctataagttg  6420
tgtgaagaac agctctcaaa acaggtgcac tacgacttcg gacttaggaa catcctcagc  6480
gtgttgagaa ctctcggagc ggcgaagcgc gcaaacccca tggataccga gtcgactatc  6540
gtgatgagag tgctgagaga catgaacctt tcaaagctga ttgacgagga cgaaccgctg  6600
ttcctttcct tgatcgagga cctcttcccg aacatcctcc tcgataaggc cggttacccc  6660
gagctcgaag ccgcgatttc acggcaagtt gaagaggctg gactcattaa ccacccacca  6720
tggaagctca aggtcatcca gctgttcgag actcagagag tgcggcatgg aatgatgaca  6780
cttggtccta gcggcgcggg aaagactacg tgtatccaca ccttgatgcg ggcgatgacc  6840
gattgcggca agccgcacag ggaaatgcgg atgaacccga aggcgatcac cgcaccccaa  6900
atgttcggac ggctcgacgt ggcgaccaac gactggaccg acggcatttt ttcgaccttg  6960
tggcgcaaga ccctgcgggc caagaaagga gaacacatct ggattatcct ggatggcccg  7020
gtggatgcga tctggattga aaaccttaac tcagtgctcg acgacaataa gaccctgacc  7080
ctggctaacg gcgataggat cccgatggct cctaactgca aaatcatctt cgagccgcat  7140
aacattgata atgcatcacc agccaccgtg tcccgcaatg gtatggtgtt catgagctcc  7200
agcatcctgg attggtcgcc cattcttgag ggattcctca agaagcgctc accacaggag  7260
gccgagattt tgaggcagct gtataccgaa tcatttccgg atctctacag attttgtatc  7320
cagaacctcg agtacaagat ggaggtcctt gaagccttcg tcatcaccca aagcattaac  7380
atgctgcagg gacttatccc cttgaaggaa cagggcggag aggtgtcaca ggctcacctg  7440
ggaaggctgt tcgtgtttgc cttgttgtgg tccgccggcg cggccctcga gctggatggc  7500
aggaggcggc tcgagttgtg gctgcggagc cgccccaccg ggactttgga actgccgccc  7560
ccggcgggtc cgggcgacac cgctttcgac tactacgtcg cgccggacgg aacttggact  7620
cactggaata ccagaaccca agaatacctt tatccatcgg atactacccc tgaatatggt  7680
agcatcctcg tccctaacgt ggacaacgtc cgaacggact tcctcatcca aactatcgcc  7740
aagcagggca aggcagtcct gctgatcggc gaacaaggca ctgccaagac cgtcattatc  7800
aaaggcttta tgagcaaata cgatccggag tgccatatga tcaagagcct gaacttctcc  7860
tccgcgacaa ctccgctgat gttccaaaga actattgagt cgtacgtgga taagcgcatg  7920
ggaaccactt acgggccgcc ggccggaaag aagatgaccg tgttcattga tgacgtgaac  7980
atgccgatca tcaacgaatg gggcgaccag gtcactaacg aaatcgtgag acaactgatg  8040
gagcagaacg gattctacaa cctggagaag cccggagagt ttacctccat cgtggatatc  8100
cagttcctgg ccgccatgat ccatccgggc ggagggcgga acgacatccc acaaagactg  8160
aagagacagt tctccatctt taattgcacc ttgccctcgg aggcctcagt ggataagatt  8220
tttggagtga ttggcgtggg ccactactgc acccagcggg gtttcagcga ggaggtcagg  8280
gatagcgtga ccaagctcgt gcccttgacc agacggctgt ggcagatgac gaagattaag  8340
atgctgccca ccccggcgaa gttccactac gtgttcaatc tgagggactt gtcccgcgtg  8400
```

-continued

```
tggcagggaa tgctgaacac cacgagcgaa gtgatcaagg agccgaacga cttgctcaaa  8460
ttgtggaaac acgaatgcaa aagagtgatt gcggaccgct tcaccgtgag ctccgacgtg  8520
acctggttcg acaaggctct cgtgtccctg gtggaagagg agttcggcga agaaaaaaag  8580
ctcctggtgg attgcggcat cgatacgtac ttcgtggact tcctgagaga tgcacccgag  8640
gccgcaggag aaacttccga ggaagcagac gccgaaaccc ccaaaattta cgagcccatc  8700
gagtcctttt cacacctgaa ggaacgcctg aacatgttcc tccagctcta caacgaatcg  8760
atccgcggcg caggaatgga catggtgttc ttcgcggacg ccatggtgca tctcgtgaag  8820
atctccagag tgatcagaac tccccagggc aacgctctgc tggtcggagt gggggggatcg  8880
gggaagcaat cgctcaccag actggccagc ttcatcgcgg gctacgttag cttccaaatc  8940
accctcacca ggagctacaa tacctcgaac ctgatggagg atctgaaggt cctctacagg  9000
actgcgggac agcaggggaa gggtattacc ttcatcttta ccgataacga gataaaggat  9060
gagagttttc tcgagtacat gaacaatgtg ctgtcgtcgg gggaagtgtc aaacctcttc  9120
gcccgcgatg aaatcgacga gatcaacagc gacttagcta gcgtgatgaa aaaggagttt  9180
ccgagatgct tgccgaccaa tgagaacttg catgactact ttatgtcaag ggtccgccaa  9240
aacctccaca tcgtgctttg tttctcgcca gtgggagaga agttccgcaa ccgcgcactt  9300
aaattccccg ccctgatctc cggttgtacc attgactggt tctcccgctg gcctaaagat  9360
gcactcgtgg cagtctcgga gcacttcctg acttcgtacg atattgactg ctccttggag  9420
attaagaaag aggtcgtcca gtgtatgggg agcttccagg acggagtcgc cgaaaaatgc  9480
gtggactact ttcagagatt caggcggagc acccatgtca cccccaagtc atacctcagc  9540
tttatccaag gctacaagtt catctacggc gaaaagcatg tcgaggtccg caccctggca  9600
aacagaatga ataccggtct ggagaagctc aaggaagcgt cggagtcagt ggctgccttg  9660
tcaaaggaac tcgaagccaa ggaaaaggaa ttacaggtgg cgaacgacaa ggccgacatg  9720
gtgctgaaag aagtgactat gaaggcccag gcggcggaga aggtgaaggc cgaagtgcag  9780
aaggtcaagg accgcgccca agctatcgtg gactcgatct cgaaggacaa ggcgattgct  9840
gaggagaagc tcgaagccgc caagccggct ctggaggaag ccgaagcggc attgcaaacc  9900
attagacctt cagacatcgc tacggtcagg actctgggaa ggccccccca tttgatcatg  9960
cggatcatgg actgcgtgct cctcctgttc caaagaaaag tgagcgccgt gaagatcgat  10020
cttgagaaat cctgcacgat gccctcatgg caggagtcgc tcaagctcat gacggccggt  10080
aacttcctgc aaaacctcca gcagtttcct aaggatacaa tcaacgaaga ggtgattgaa  10140
ttcctcagcc cgtactttga gatgcccgac tacaacatcg aaactgcgaa acgcgtgtgc  10200
gggaacgtgg ccggactgtg tagctggacc aaggccatgg cctccttctt ctccatcaac  10260
aaggaagtgc tgcctctaaa ggcaaacttg gtcgtgcagg aaaaccggca ccttctcgca  10320
atgcaggacc ttcagaaggc acaagcggag ctggacgaca agcaggctga gctggacgtg  10380
gtccaggctg agtacgagca ggcgatgact gagaagcaaa cgctactgga ggacgcagag  10440
cgctgtagac ataaaatgca gaccgcatcc accctgatct ccgggctcgc cggcgaaaag  10500
gagaggtgga ctgaacagtc acaagaattt gctgctcaaa caaagcgcct ggtcggtgat  10560
gtcctgcttg ccactgcctt cctgagctac agcggtcctt ttaaccaaga gttccgcgac  10620
ctcctcctca atgactggag aaaggaaatg aaggctcgga agatcccgtt cggcaagaac  10680
ctcaatctta gcgagatgct cattgacgca cctactatca gcgaatggaa cttgcaagga  10740
ctgccgaacg acgacctgtc cattcaaaac ggaatcatcg tcaccaaggc ttcgcggtat  10800
ccactcctca ttgacccgca gactcagggc aagatatgga ttaaaaacaa ggaaagccgc  10860
aatgaactgc aaattacctc cctgaaccac aagtacttcc gcaaccacct cgaggacagc  10920
ctcagccttg ggcgcccatt gctcatcgag gacgtcggcg aggaactgga tccggccctg  10980
gacaacgtcc tggaaagaaa cttcatcaag accggctcga catttaaagt caaggtgggc  11040
gacaaggaag tggacgtgct ggatggcttt agactctaca ttaccaccaa attaccgaac  11100
ccggcctaca ccccagaaat ttcggcgcgg acctccatca ttgactttac tgtgactatg  11160
aagggcctgg aggaccagct cctcggccgg gtgatcctga ctgaaaaaca agagctcgaa  11220
aaggaaagga ctcacctcat ggaggacgtg acggcgaaca aaagacggat gaaggaattg  11280
gaggataatc tcctgtatag actcactagc actcaagggt ccctggtcga agatgagtcc  11340
cttattgtgg tcctttcgaa tacaaaacgg accgcggaag aggtcactca gaaactcgag  11400
atctccgcgg aaactgaagt gcagatcaac agcgctcgag aggaatacag gccagtggca  11460
accaggggct ccatactcta cttcctcatc accgaaatgc gcctcgtcaa tgagatgtac  11520
caaacctcgc tgcggcaatt cttggggctt ttcgacctct cactcgcacg gtcggtgaaa  11580
tcgccgatta ctagcaagag aattgccaat atcatcgagc acatgaccta cgaggtgtac  11640
aagtacgcag ccaggggact gtacgaggaa cacaagttcc tgtttaccct tctcctgaca  11700
ctgaagattg acattcagag aaacagagtg aaacatgagg aatttctcac cctcatcaaa  11760
ggaggggcta gccttgattt gaaggcgtgc ccgccgaaac cttcgaagtg gatcctggat  11820
atcacctggc tcaacctggt ggagctgtca aagctgcggc agttttccga cgtgctggac  11880
caaatttcgc gcaacgagaa gatgtggaag atctggttcg acaaagagaa ccccgaagag  11940
gagccgctgc ccaacgctta tgacaagtca cttgactgct tccgccgcct cctgctcata  12000
cggagctggt gcccagaccg gaccattgcc caggcgcgaa agtacatcgt cgatagcatg  12060
ggggaaaagt acgcggaggg tgtgattctc gacctcgaga aacttggga ggaatcagac  12120
cctcgcaccc ccttgatttg cctcctgtcc atgggctccg atcccactga cagcatcatt  12180
gcactcggga agaggctgaa gatcgaaacg cgctacgtgt caatgggaca gggacaagaa  12240
gtccacgctc ggaagctcct ccagcaaacg atggcgaacg gtggttgggc cctgttgcag  12300
aattgccatc tggggctgga cttcatggat gaactcatgg acattattat cgaaacggaa  12360
ctggtccacg atgcctttag actttggatg acgactgaag cccataaaca attccctatc  12420
accctgcttc aaatgtcgat caagttcgcc aatgaccctc cgcaggggct ccgggccggc  12480
ctcaaaagga cttactccgg ggtgtcacag gaccttcttg acgtgtcctc cggaagccaa  12540
tggaagccaa tgctttacgc cgtcgcgttc ctccactcca cggtgcagga acggcggaag  12600
ttcggagctc tgggctggaa tattccgtac gaattcaacc aggcagattt caatgcaacc  12660
gtccagttca tccaaaacca tctcgatgat atggatgtga agaaaggagt gtcatggact  12720
accattagat acatgatcgg ggagatccag tacgggggac gagtgactga cgattacgat  12780
aagcgccttc tgaacacttt cgctaaggtc tggtttagcg aaaacatgtt tggtccagac  12840
ttctccttct accaagggta taacatcccg aagtgctcca ccgtggacaa ctacctccag  12900
tacattcagt cgctccccgc ttatgattca ccagaagtct ttggcttgca cccaaatgcc  12960
gatatcacct accaaagcaa actcgcgaag gacgtcctgg acaccatact ggggatccag  13020
ccgaaagata cctcgggggg cggcgatgag actcgcgaag cagtcgtggc gagactggcg  13080
gacgacatgc ttgaaaagct gcctcctgac tacgtgccat ttgaagtgaa agaaagattg  13140
```

-continued

```
cagaagatgg gccctttcca gcctatgaac attttcctga ggcaggagat tgaccgcatg  13200
caacgggtgc tcagcctcgt gcgatccacc ctcactgagt tgaagctcgc catcgatggg  13260
accatcatca tgagcgaaaa cttgcgggat gcactcgact gcatgttcga cgctaggatc  13320
ccagcgtggt ggaaaaaggc atcatggatt agctccaccc tgggcttctg gttcaccgaa  13380
ctcatcgaga ggaactccca gttcacctcc tgggtgttca acggacggcc tcattgcttt  13440
tggatgaccg gcttcttcaa cccccagggt tttctcacgg ccatgcgcca ggaaattacc  13500
cgggcaaaca aggggtgggc cctcgacaac atggtgcttt gtaacgaggt tactaagtgg  13560
atgaaggacg acatctcagc ccccccctacc gagggagtct acgtgtacgg cctgtacctg  13620
gagggcgcag gatgggataa acggaacatg aagctgatcg agtcgaagcc gaaagtcctg  13680
ttcgagctca tgcccgtcat tcgcatctac gccgagaaca acaccctgcg cgacccaaga  13740
ttctacagct gcccgattta caaaaagccc gtccggacgg acttgaacta tatcgcggcc  13800
gtcgatctgc ggactgcgca gacccctgag cactgggtgc tgcggggagt ggcgctgctc  13860
tgcgacgtca agtag                                                  13875

SEQ ID NO: 20           moltype = DNA  length = 13875
FEATURE                 Location/Qualifiers
misc_feature            1..13875
                        note = Synthetic polynucleotide
source                  1..13875
                        mol_type = other DNA
                        organism = synthetic construct
SEQUENCE: 20
atgttccgga tcggacgcag gcagctctgg aaacatagcg tcacgagagt gctgacccag  60
cgcctcaagg gggagaagga agcgaagcgg gccctgctcg acgccagaca caattacttg  120
ttcgccattg tcgcctcctg cctggatctg aacaagactg aggtcgaaga tgccatcctc  180
gagggaaacc aaatcgaaag aattgaccaa ttattcgccg tgggcgggtt gcgccatttg  240
atgttctact accaagacgt tgaggaggca gagactggac agcttggttc cttgggtgga  300
gtgaacttag tgtcggggaa gatcaagaag ccgaaagtgt tcgtgactga aggcaacgat  360
gtggctctga ctggagtgtg cgtgttcttt attcgcactg acccctctaa ggccattacg  420
ccggacaaca ttcatcagga ggtgtcattc aacatgctgg acgccgcgga tggcggcctg  480
ctcaacagcg tgcgccggct gctttccgac attttcattc ctgcattgag agcgacttcg  540
catggttggg gtgaactgga agggctgcaa gacgctgcca acatccgaca ggaattcctg  600
agctccctgg aaggtttcgt gaacgtcctc agcggcgccc aggaaagcct caaggaaaag  660
gtcaacctga gaaagtgtga catcctggaa ctgaaaacgc tgaaggagcc cacagattac  720
cttaccttgg ccaataaccc ggaaaccctc gggaagatcg aggactgcat gaaggtctgg  780
atcaagcaga ctgaacaagt gctcgcagag aacaaccaac tcctgaagga agccgacgac  840
gtcgggcctc gggcagagct cgagcactgg aagaagcggc tgagcaagtt caactacctc  900
ctggaacagt tgaagtcgcc ggacgtgaag gcggtgctcg ccgtgttggc cgccgccaag  960
agcaagctgc tcaaaacttg gcgggagatg gacattagga tcaccgacgc caccaacgaa  1020
gcaaaggaca atgtgaagta cttatacacc ctcgagaagt gctgcgatcc gctctactcg  1080
tcggaccccc tgtcgatgat ggatgctatc ccgacgctca tcaacgcaat caagatgata  1140
tattccatca gccactacta caatacgagc gagaagatta cttccctgtt cgtgaaggtt  1200
accaaccaga ttatctccgc gtgcaaggcc tacattacca acaacggaac tgccagtatc  1260
tggaatcaac ctcaagacgt ggtcgaagag aagatactct cggctatcaa gctgaagcag  1320
gaataccaac tgtgctttca caagaccaag caaaagctga agcagaaccc aaacgccaaa  1380
cagttcgatt tcagcgagat gtacatcttc gggaagttcg agacttttca ccgccggctg  1440
gccaagatca tcgacatctt caccaccctc aagacgtact ccgtgctgca agactcgact  1500
atcgagggat tggaggatat ggccacgaag tatcaaggca ttgtggcaac catcaagaag  1560
aaagaataca actttctcga ccagagaaag atggatttcg accaagatta tgaagagttc  1620
tgcaagcaaa ccaatgacct tcataacgaa ctccggaagt tcatggatgt caccttcgcg  1680
aagatccaga acacgaacca agcactgaga atgctcaaga agttcgaacg ccttaacatt  1740
ccaaacctcg ggattgatga caagtaccaa cttatcctgg agaattacgg tgccgacatc  1800
gacatgatct ccaaattgta caccaaacaa aagtacgatc ctccactggc gcgcaaccaa  1860
ccccccatcg ccggaaagat cctgtgggca agacaattat tccacagaat ccagcagccg  1920
atgcaactgt ttcagcagca tcccgctgtc cttagcacgg cggaagccaa gcctatcatc  1980
agatcgtata atcgcatggc aaaggtgctg ctggaattcg aggtcctctt ccaccgggcg  2040
tggctgaggc agattgagga gattcacgtg ggacttgagg cgagcctgct tgtcaaagct  2100
ccgggcaccg gagagctgtt cgtgaatttc gacccacaaa tcttgatcct gttccgggaa  2160
actgagtgca tggcccagat gggcctcgag gtgtcaccac tggccacgtc attgttccaa  2220
aagcgggaca gatacaagcg caatttttcg aacatgaaaa tgatgctggc cgaataccaa  2280
cgggtgaaat ccaagattcc cgctgccatt gaacaactca tcgtgcctca tcttgcgaaa  2340
gtcgatgagg ccctgcaacc gggactggcg gcgctgactt ggacttccct taacattgag  2400
gcatacctcg agaacacctt cgcaaagatt aaagacctag agctcctcct cgaccgcgtg  2460
aacgacctta tcgagttccg gatcgatgcc atcctggaag agatgtcgtc cactccactt  2520
tgccaacttc cccaggagga accgttgact tgtgaagaat tcttgcagat gaccaaagac  2580
ctttgcgtca acggcgccca gatcctgcac tttaagtcta gcctggtgga ggaagcggtg  2640
aacgagctcg tcaacatgct tctcgacgtg gaagtgctgt cggaagagga atccgagaaa  2700
atctccaacg aaaatagcgt gaactacaaa aatgagtcat cagccaagag ggaagagggt  2760
aacttcgata cgctgactag cagcattaac gccagggcaa acgccctgct cctgaccacc  2820
gtgactcgga agaagaaaga gactgagatg ctgggagaag aagctcggga gcttctgagc  2880
cacttcaacc accaaaacat ggatgccctg cttaaggtga cccggaacac actggaggcg  2940
atccggaagc ggatccactc gagccatacc attaattttc gggattcgaa cagcgcctcg  3000
aacatgaagc aaaattccct gccgattttt agagcgagcg tcaccctggc catccccaac  3060
atcgtgatgg cgcccgcatt ggaggacgtg cagcagaccc ttaacaaggc ggtggagtgt  3120
atcattagcg tccctaaggg cgtccgccaa tggagctcag agttgctctc gaagaagaaa  3180
atccaggagc ggaagatggc ggctctccag tccaacgagg actccgattc ggacgtggag  3240
atgggtgaaa atgagttgca agacactctc gagatcgcct ccgtcaatct gccgattccc  3300
gtccaaacca agaactacta caaaaacgtg agcgagaaca aagagatcgt gaagctcgtc  3360
agcgtgctca gcactatcat taactcaacg aagaaagaag tgatcactag catggactgc  3420
```

-continued

```
tttaagcggt acaaccatat ctggcagaaa ggcaaggaag aagccatcaa gaccttcatc  3480
acccaatccc ccttgttgtc ggaattcgag tcacagattt tgtacttcca gaatctcgag  3540
caggagatca atgcggagcc agaatacgtg tgcgtggggt ccattgcgct atacaccgcc  3600
gaccttaaat tcgcgctgac ggccgaaacc aaggcctgga tggttgtgat cggccgccat  3660
tgtaacaaga agtacaggag cgaaatggag aatatcttca tgctgatcga agagttcaac  3720
aagaagttga accggcccat taaggacctg gatgatattc gcattgccat ggccgccctt  3780
aaggagatcc gcgaagaaca gatctccatc gactttcagg tcggccctat cgaagagagc  3840
tacgccctcc tgaaccgcta cgggctcctc attgccaggg aagaaattga caaggtcgat  3900
acccttcact acgcatggga gaagttgctg gcgcgcgccg gagaggtcca aaacaagttg  3960
gtgtccctgc aaccctcctt caagaaggaa ctgatttcgg cagtcgaggt gttcttgcaa  4020
gactgccatc aattttacct ggactacgac ctgaatggac ccatggcgtc cggcctcaag  4080
ccccaagagg cctcagacag actgatcatg tttcagaacc aattcgacaa catctaccgg  4140
aagtatatca cgtataccgg tggagaagaa ctgttcggac tcccggccac gcaataccCg  4200
cagctcctcg agattaagaa gcagcttaac cttcttcaga agatttacac gctgtacaat  4260
agcgtcatcg agactgtgaa ttcctattat gacatccttt ggagcgaagt caatatcgag  4320
aaaatcaaca acgaactcct cgagttccag aacaggtgcc ggaaattgcc ccgcgccctg  4380
aaggactggc aggcgttctt ggatctgaaa aagattattg acgacttctc cgaatgctgt  4440
cctttgctcg agtacatggc ctctaaggct atgatggagc gacattggga acgcatcacc  4500
accctcaccg gacacagcct cgacgtcggc aatgagtcct tcaagttgag aaatattatg  4560
gaggcgcctc tgctgaagta caaagaagag atcgaggaca tttgcatttc ggcggtcaag  4620
gagagggaca ttgaacagaa gctcaagcaa gtcatcaatg agtgggataa taagaccttc  4680
acatttggga gctttaagac ccgcggcgag ctactcctgc gcggcgactc gaccagcgaa  4740
atcattgcca acatggaaga ttcactcatg ctgctgggtt ccttgctctc gaacagatat  4800
aacatgccct tcaaagcgca gatacagaag tgggtgcagt acctgtctaa tagcaccgac  4860
attatcgaat cctggatgac tgtgcagaac ctctggattt acctggaggc cgtgttcgtc  4920
ggcggagaca tcgcgaagca actgccgaag gaggctaaaa gattctccaa tatcgataag  4980
tcgtgggtga aaatcatgac gcgcgcacac gaggtcccat cagtggtgca gtgctgtgtc  5040
ggtgacgaga ctttgggtca actgctgccg cacctcctcg accagctcga gatttgccaa  5100
aagtccttga cgggatacct ggaaaagaag cggctttgct tcccccgctt cttcttcgtg  5160
tccgaccccg cgctgctcga gatcctgggc caggctagcg actcacacac cattcaggcg  5220
catctcctga acgtgttcga caacattaag tcagtgaagt tccacgaaaa aatttacgac  5280
cgcatcctga gcatcagctc gcaggagggg gagactattg aactcgacaa gcccgtcatg  5340
gccgaggggga acgtggaggt gtggttgaac tcactcctgg aggaaagcca atcctcgctc  5400
cacctcgtga ttcgccaggc cgcagcgaac atccaggaga ctggatttca gctcaccgag  5460
ttcctctcga gctttcctgc acaagtcggc ctgcttggca ttcagatgat ttggacccgc  5520
gacagcgaag aggccctgag aaacgccaag ttcgacaaga agatcatgca aaagactaat  5580
caggcattct tggaactgct gaacactctg atcgatgtca ccactcggga tctgtcgagc  5640
actgagcgcg tgaagtacga gactttgatt accattcatg tgcaccagcg ggacatcttc  5700
gacgacctgt gccatatgca tattaaaagc ccgatggatt ttgagtggct gaagcaatgc  5760
agattctact tcaatgagga ctcagacaag atgatgattc atatcaccga cgtggccttt  5820
atctaccaaa acgaattcct gggttgtact gataggttag tgatcactcc gctcaccgac  5880
aggtgctata tcaccctggc acaggccctg ggaatgtcga tgggaggggc ccccgccggc  5940
ccggccggaa ccgggaaaac tgaaactact aaagatatgg ggcggtgcct tgggaagtac  6000
gtcgtggtgt tcaattgcag cgatcaaatg gatttccggg gacttggacg cattttcaag  6060
ggtctggcgc aaagcggcag ctggggatgc ttcgacgaat tcaaccggat cgacttgccc  6120
gtgctctccg tcgcagccca acaaatctcc atcatcctga cttgcaagaa ggagcacaag  6180
aagtcgttca tcttcaccga cggagacaat gtcactatga acccagagtt tggcctattc  6240
ctgacgatga acccgggcta tgccggcagg caggagctgc ctgagaatct gaagatcaac  6300
ttccggagcg tggctatgat ggtgcctgat cgccaaatca ttatccgcgt gaaactggcc  6360
tcgtgtggat tcatcgacaa tgtggtgttg gctaggaagt tttcactct ctacaagctc  6420
tgtgaagaac agctcagcaa acaggtccat tacgacttcg gcctccggaa cattcttagc  6480
gtgctccgga ctcttggagc cgccaagcgg gcgaacccga tggacaccga gtccaccatt  6540
gtgatgaggg tgttgcggga tatgaacctc tccaaactga tcgacgaaga tgaacctttg  6600
ttcctgagcc tcatcgagga tctgtttcct aacatcctgc tcgacaaagc cggatatccc  6660
gaactcgaag ccgctatcag ccgccaggtg gaggaagcgg ggctcatcaa ccatcctccg  6720
tggaagctca aggtcattca gctgtttgaa acgcagagag tgcggcacgg catgatgacc  6780
ctgggaccga gcggtgccgg aaaaacgact tgcatccaca ccctcatgag agccatgacc  6840
gattgtggca agccgcaccg ggaaatgcgg atgaacccaa aagcgattac ggccccccag  6900
atgtttggac ggttggatgt ggcaaccaac gactggactg atgggatttt ctcaactctg  6960
tggcgcaaga cgctgcgcgc gaaaaagggg gaacacattt ggatcattct tgacggtccg  7020
gtggacgcca tttggattga aaatttgaac agcgtgctgg atgataacaa gacgctgact  7080
ttggccaacg gagacagaat ccccatggcc ccaaactgca agatcatctt cgaacctcac  7140
aacatcgaca atgcctcgcc cgcgaccgtg agccgcaacg gaatggtctt tatgagtagc  7200
agcattttgg actggagccc tatcctcgag ggattcctga agaagcgctc accgcaggag  7260
gcggagatcc tgaggcagct ttacactgaa agtttccccg atctctaccg cttctgcatc  7320
cagaaccttg aatacaagat ggaggtgctc gaggccttcg tcatcaccca gtccatcaac  7380
atgctccaag ggctcatccc gctgaaggag caaggcggag aggtgtcaca agcgcacctc  7440
ggcagactgt ttgtgtttgc cctgttgtgg agcgccggag cagctttgga gcttgatggg  7500
cggcggcgcc tggaattgtg gctgcgctcc cggcctaccg ggactttgga actcccacct  7560
cccgccggcc ccggcgacac agcgttcgat tattacgtgg cccccgacgg cacctggacc  7620
cactggaaca cccgcactca agaatacctg tacccttcgg acaccactcc agagtatgga  7680
tccattcttg tgcctaacgt ggacaatgtc cggacggact ttttaatcca gaccattgct  7740
aagcagggaa aggcggtgct gctcattgga gagcaaggga cagcaaagac cgtgatcatc  7800
aaggggttca tgtcgaagta tgacccggaa tgccatatga taaagtcact gaatttcagc  7860
agcgctacaa ccccactcat gttccaaaga accatcgagt catacgtcga caagagaatg  7920
ggcactactt acggcccacc ggccggaaag aagatgaccg tgttcatcga tgatgtgaac  7980
atgccaatca ttaacgagtg gggcgaccag gtcaccaacg agattgtccg gcagctcatg  8040
gagcaaaacg gcttctacaa cctggagaag cccggagagt ttacctcaat cgtggatatt  8100
cagttccttg cagcgatgat ccacccgggc ggaggtcgca atgacatccc ccagaggctt  8160
```

-continued

```
aaaagacagt tctcgatttt taactgcacc ttacccagcg aagcgtcggt ggataagatc  8220
ttcggagtca tcggcgtggg gcactattgc acccagagag gcttttccga ggaagtccgg  8280
gactccgtca cgaagctcgt gcctttgacc cgccgcctgt ggcagatgac caaaattaag  8340
atgctcccta cgccggctaa atttcactac gtgttcaacc tacgggacct gtcccgggtg  8400
tggcaaggca tgctgaacac aaccagcgaa gtcatcaaag agccgaacga cttgctcaag  8460
ctctggaaac acgaatgcaa gcgcgtgatc gcggaccggt ttaccgtcag cagcgacgtg  8520
acctggttcg acaaggcgct cgtgtcgttg gtcgaagagg agtttgggga agaaaaaaag  8580
ctccttgtgg actgtggcat cgacacctac ttcgtggatt tcctgcggga tgccccagag  8640
gcggcgggag aaaccagcga agaagccgac gcagaaactc caaagattta cgagccgatt  8700
gaatcgtttt cgcacctcaa agaacgcctc aacatgttcc tccagcttta taacgaatcc  8760
atccggggag cgggcatgga tatggtgttc ttcgctgacg caatggtcca ccttgtgaag  8820
atctcgcgcg tcatccgcac cccacagggg aacgccctct tggtgggggt cggaggctcc  8880
ggaaagcaaa gcctgacccg gcttgcctcc ttcattgccg gctacgtcag ttttcaaatc  8940
acgctgaccc gctcctataa caccagcaac cttatggaag atctcaaagt cttgtaccgg  9000
accgctggcc agcagggcaa gggtatcacc ttcatcttca ctgacaatga gattaaagat  9060
gagagttttc tcgaatacat gaacaatgtg ctgtcaagcg gcgaagtctc caacctttt  9120
gcgcgggatg agattgatga aattaactcg gacctggcaa gcgtgatgaa gaaggagttc  9180
ccgaggtgct tgccgaccaa cgaaaacttg cacgactact tcatgagccg cgtgagacag  9240
aacttgcata tcgtgctgtg cttctcgccg gtcggagaga agttccggaa ccgcgcgctc  9300
aagtttcctg cactgatctc gggctgcacc attgattggt tctcacgctg gccaaaggac  9360
gccctggtgg ctgtctccga gcacttcctc acctcctacg atattgactg cagcctcgag  9420
attaaaaagg aggtggtgca gtgcatgggt agcttccaag acggggtcgc cgaaaagtgc  9480
gtggactatt ttcaacggtt caggcggagc actcacgtca ctccgaagtc ctacttgtcg  9540
ttcatccagg gctacaagtt tatctacggc gaaaagcacg tggaggtcag aactctcgcc  9600
aataggatga acaccgggct ggagaagtta aaggaggcct cggaaagcgt ggccgccctc  9660
tcaaaggagc tggaagctaa ggagaaggag ctgcaagtcg ctaacgataa ggccgacatg  9720
gtgctgaagg aggtcaccat gaaggcccag gcggccgaaa aagtgaaggc cgaagtgcaa  9780
aaagtcaaag acagagcgca ggctatcgtc gacagcatct cgaaggataa ggccattgcc  9840
gaggagaagc tcgaggctgc aaagcctgcc ctggaggaag cggaagcagc actgcagacc  9900
atcagacctt ccgatatcgc caccgtcagg accctgggaa ggcctcctca cctcatcatg  9960
cggatcatgg attgcgtcct gttgcttttc caacggaagg tgtccgccgt caagatcgac  10020
ttggagaagt cgtgcaccat gccatcatgg caggagtcac tgaagctcat gactgcagga  10080
aactttctcc agaaccttca gcaattccca aaggatacca tcaacgaaga ggtgatcgag  10140
ttcttgtcgc cgtatttcga aatgccggat tacaatatcg aaactgcaaa acgcgtgtgc  10200
ggtaacgtgg caggcttgtg ctcctggacc aaggccatgg ctagcttttt ctcgattaac  10260
aaggaagtac tgccactcaa ggcaaacttg gtggtgcagg aaaatagaca tcttctcgcg  10320
atgcaggatc tgcaaaaggc tcaagccgag ctggatgata agcaggccga actggatgtc  10380
gtgcaggccg aatacgagca ggccatgact gaaaagcaaa cgctgctgga ggacgcggaa  10440
cgctgcagac acaagatgca gacagcttcc accttgattt cgggcctcgc tggagagaaa  10500
gagagatgga cggagcagag ccaggagttt gccgcgcaaa ctaaacgcct ggtgggcgac  10560
gtgctgctgg ccacagcgtt ccttagctac agcggcccat ttaaccagga attccgggac  10620
ttgctcctga atgactggag gaaagaaatg aaggcgcgca agattccttt cggcaagaac  10680
ctgaacttgt ccgagatgct tatcgacgcc ccgaccattt cagagtggaa tctgcaaggg  10740
ctccccaatg acgatctgag catccagaac ggcatcattg tgacaaaggc ctcgcgctac  10800
ccgctgctca tcgatccgca gactcaaggg aagatctgga ttaagaataa ggagagccgg  10860
aacgaactgc agatcaccag cttgaaccac aagtacttta gaaaccacct ggaggattca  10920
ctgagcctgg gccgccctct gctcatcgaa gatgtcggag aggaactgga tccggccctt  10980
gacaacgtcc tggagcggaa ctttatcaaa actgggtcga ctttcaaggt caaggtcggc  11040
gacaaagagg tcgacgtgct ggacgggttc aggctttaca tcaccactaa actccccaat  11100
cctgcctaca ctcctgagat ctccgcccgc acctcgatta tcgacttcac agtgaccatg  11160
aaagggcttg aggaccagct ccttggacgc gtgatcctga ctgaaaagca agaactggaa  11220
aaggaacgga cccacttgat ggaggacgtc accgccaaca aaagacgcat gaaggaattg  11280
gaagataatc tcctgtatag acttaccagc actcagggta gtctggtgga agatgaatcc  11340
ctcatcgtcg tgttgtccaa caccaagcgc actgcggaag aagtcaccca gaagctggaa  11400
atttcggcag aaaccgaggt tcagattaac tcggcaaggg aagaataccg gcctgtggcc  11460
acccggggtt ccattctcta cttcctcatc accgaaatga ggctggtcaa tgaaatgtac  11520
cagacctcac tccgccagtt cctgggactg ttcgatctga gcctggcccg ctcggtgaag  11580
tcgcctatca cgtcaaagag gatcgcaaac atcatcgagc acatgaccta tgaggtctac  11640
aaatacgccg cccggggcct ttacgaggaa cataagtttt tgttcacgct cttgcttact  11700
ctcaagattg acatccagcg gaaccgggtc aaacacgagg aattcctgac cctgatcaag  11760
ggtggtgcct ccttggatct gaaggcatgc cctcctaagc ctagcaagtg gattcttgac  11820
atcacttggc tgaacctggt ggagctgagc aaactgaggc agttttcgga cgtgctcgac  11880
cagatttcaa ggaacgaaaa gatgtggaag atctggttcg acaaagagaa cccggaggaa  11940
gaaccgctgc ctaacgccta tgacaagtca ctggactgtt tccggagatt gctgctgatc  12000
aggtcctggt gcccggatag aaccattgcg caggccagga agtacattgt ggattcgatg  12060
ggagaaaaat acgccgaggg agtgatcctc gatctggaaa agacctggga agagagcgat  12120
cctcgcaccc ctctgatttg cctcctttcg atgggaagcg acccgactga tagcatcatt  12180
gcactgggga aacgcttgaa aatcgaaact cgatatgtgt caatgggaca gggacaggaa  12240
gtgcacgcaa gaaagctctt gcagcagact atggccaacg ggggatgggc gctcctccag  12300
aactgccact tgggactgga cttcatggat gaactcatgg atattatcat tgagactgaa  12360
ctcgtgcatg acgctttcag attgtggatg actacggagg cccacaagca gttccctatc  12420
acccttttac aaatgtccat caaattcgcc aacgaccccc cccagggcct gcgggccggg  12480
ttgaaacgaa cttactccgg agtgtcgcag gacctactgg acgtcagctc cggctcacag  12540
tggaagccaa tgctgtatgc cgtggccttc ttgcactcca ctgtgcagga gcgcagaaag  12600
ttcggtgcct tgggctggaa cattccctac gaatttaacc aagccgactt caacgccacc  12660
gtgcagttca tccagaacca cctggacgat atggacgtca agaagggtgt cagctggact  12720
accatcaggt acatgattgg tgaaattcaa tacggcggac gcgtgacgga cgactacgac  12780
aagaggctcc tcaacacctt cgctaaggtc tggttctcgg aaaacatgtt tggaccagac  12840
ttttcattct accaaggata caatatcccg aagtgctcga cggtggataa ctacttgcag  12900
```

```
tatattcaaa gccttcctgc ctacgattcg ccagaagtgt ttgggttgca tcctaacgcg  12960
gatattacct accagtcgaa acttgcaaag gatgtgctcg acacgatcct gggcattcaa  13020
ccgaaagaca ccagcggggg aggcgacgag actcgggagg cggtggtggc tcgcctggcg  13080
gacgacatgc tggaaaagct cccgcccgat tacgtgccgt ttgaagtcaa agagcgcctt  13140
caaaaaatgg gacccttcca gcctatgaac attttcctaa gacaggagat cgacagaatg  13200
caacgggtcc tgagccttgt gcgcagcact ctcactgagc tcaagttggc gatcgacggg  13260
accatcatta tgtcggaaaa ccttagagat gcgctcgact gcatgttcga tgcgagaatt  13320
ccagcttggt ggaagaaggc ctcatggata tcatccaccc tcgggttctg gtttactgag  13380
ctgattgaac ggaactccca gttcacgtcg tgggtgttca acggaaggcc gcactgcttc  13440
tggatgacag ggttctttaa tccgcaaggt ttccttactg cgatgcgcca agagattacc  13500
cgcgcgaaca aggggtgggc gctggacaat atggtgctct gcaacgaagt gaccaagtgg  13560
atgaaggacg acatatcggc ccccctacc gagggcgtct acgtgtacgg attgtacctg  13620
gaaggggcgg gctgggacaa gcgaaacatg aaattaatcg aatcgaagcc caaggtgctt  13680
tttgaactga tgcccgtgat ccggatttat gctgaaaata acactctgcg cgacccgcgc  13740
ttttactcat gcccaattta caaaaagccg gtcagaacgg acctcaacta catcgccgct  13800
gtggacctca gaacggccca gacccccgag cactgggtgc tgagaggtgt cgcgctgctt  13860
tgcgacgtga agtag                                                   13875

SEQ ID NO: 21          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 21
atgtttcgca ttggtaggcg gcagctctgg aagcactcgg tgactagagt gctgactcaa  60
cgcctcaagg gcgagaagga agcaaagcgc gctctgctgg atgctcggca caactacctc  120
ttcgcgatag tcgccagctg cctcgacctg aataagaccg aagtcgagga cgccatcctg  180
gagggcaacc aaatcgaaag aattgatcaa ctgttcgccg tgggcggact gagacacctg  240
atgttctatt accaggatgt ggaagaggcg gagactggac aactaggatc gctcggtggt  300
gtcaacctcg tcagcggaaa gatcaagaag cccaaagtgt tcgtgaccga aggaaacgat  360
gtggccctga ctggggtgtg cgtgttcttt attagaaccg acccttcgaa ggcgatcact  420
cccgacaaca ttcaccagga ggtgtccttt aacatgcttg acgccgcaga tggaggcctg  480
ctgaactcag tcagaaggct gctttcagac atttttatcc ctgccctgag agccacttct  540
catggttggg gagaattgga aggcttgcaa gacgctgcca atattcgcca agaattcttg  600
tcctcattgg aaggattcgt gaacgtgctc agtggagccc aggaaagcct gaaagaaaag  660
gtcaacttgc gaaagtgcga catcctcgag ctcaaaaccc tgaaggagcc cactgattac  720
ctcaccttag ccaacaatcc cgaaaccttg ggcaaaatcg aggactgcat gaaggtctgg  780
atcaaacaga cggagcaagt cctcgccgaa aacaaccaat tgctgaagga ggctgacgat  840
gtgggcccta gggccgaact cgagcattgg aagaagagac tgtcgaaatt taactacttg  900
ctggaacagc ttaagagccc tgacgtcaag gctgtgctgg cggtgctggc cgcagccaag  960
tccaagttac tcaaaacgtg gagagagatg gatataagaa tcaccgacgc cacgaacgag  1020
gctaaggaca acgtgaagta cttgtatact ctcgagaagt gctgcgatcc cctgtactct  1080
tccgacccctt tgagcatgat ggacgcgatc ccgaccctga tcaacgcgat taagatgatc  1140
tatagcatct cccactacta caacacttcc gaaaagatta cgtccctctt cgtcaaggtg  1200
accaaccaga ttatttccgc ctgtaaggcg tatattacta acaacggaac cgcctcgatc  1260
tggaaccagc cgcaggacgt cgtggaagag aagatcctga gcgccatcaa gttgaagcag  1320
gaataccaac tgtgcttcca taagaccaaa cagaagctca agcaaaatcc aaatgccaaa  1380
caattcgact tctccgaaat gtacattttc ggcaagttcg aaactttcca ccggaggctc  1440
gcgaagatta tcgacatttt cactaccctt aaaacctaca gcgtgcttca agattctacc  1500
atcgaaggac tcgaggacat ggccacgaag taccagggta ttgtggcaac catcaagaag  1560
aaagaatata acttcctgga ccagcgcaaa atggattttg accaggatta tgaggagttc  1620
tgcaaacaga ctaacgacct ccacaatgaa ctcagaaagt ttatggacgt gaccttcgcc  1680
aagatccaga acacgaacca agccctgagg atgcttaaga agttcgaacg cttgaacatt  1740
ccgaacctcg gcatcgatga caaataccaa ctcatcttgg aaaattacgg cgcggatatt  1800
gatatgatct caaagttgta cactaagcag aagtacgatc cgccgctggc ccggaaccaa  1860
ccgcctatcg cgggcaagat cctgtgggcc cggcagttgt ttcaccggat tcagcagccg  1920
atgcagcttt ttcaacaaca tcccgcggtg ctctcgaccg ctgaagctaa gcctattatt  1980
cggagctaca accgcatggc taaggtgctg ctggagtttg aggtcttgtt ccatcgggca  2040
tggctcagac agatcgagga aatccacgtc ggactggagg cttccctgct cgtcaaagcg  2100
ccaggcacgg gcgaactttt cgtgaatttc gatccgcaaa tcctgattct gttccgcgaa  2160
acggagtgca tggcgcaaat gggattggaa gtgtcgcccc ttgccacttc cctgttccaa  2220
aagcgcgacc gctacaagcg gaatttcagc aatatgaaga tgatgctcgc cgaataccag  2280
cgggtgaaaa gcaagatccc agccgccatc gagcaactca tcgtgcctca cctcgccaag  2340
gtcgacgagg ccctgcaacc gggtttggcc gcactgactt ggacctcgtt aaacatcgaa  2400
gcctacttgg aaaacacttt cgcgaagatc aaggatcttg aacttctgct ggaccgcgtg  2460
aacgacctaa tcgagttccg gatcgatgcc atcctggaag agatgagttc caccccctc  2520
tgccagttgc cacaagaaga acctctgaca tgcgaagaat tcctccaaat gactaaggac  2580
ttgtgcgtca acggggcaca gatccttcac ttcaaatcct ccctggtcga ggaggccgtg  2640
aacgagctag tgaacatgct ccttgatgtg gaggtcctca gcgaggaaga gtccgaaaag  2700
atcagcaacg aaaactccgt gaactacaaa aacgagagca gcgctaaaag ggaggaggga  2760
aatttcgaca ccctgacttc ctccatcaac gcgagagcga atgcactcct cctgactact  2820
gtgacaagga agaagaaaga gactgaaatg ctcggcgagg aggccagaga actgttgtcg  2880
cacttcaacc accagaacat ggacgccctg ctcaaggtga cccgaaacac cctggaagcg  2940
atcagaaaga gaatccacag cagccacacc attaacttta gggacagcaa ctcagcctca  3000
aatatgaagc agaattcact gcccatcttc cgcgcgtcag tgaccctggc catcccgaac  3060
atcgtcatgg cgcccgcatt ggaggacgtg cagcagactc tgaacaaggc cgtcgagtgt  3120
attattagcg ttcccaaggg agtgcggcag tggagctccg aactgttgtc gaaaaagaag  3180
```

-continued

```
atccaggaac gcaagatggc cgccctgcaa tctaacgaag attcggactc agacgtggag  3240
atgggagaga acgaattgca ggatactctg gagattgctt cggtgaactt gcccatcccg  3300
gtgcagacga aaaattacta caagaatgtc agcgagaaca aagagattgt taagctcgtg  3360
tcggtgctct caaccatcat caactcaact aaaaaggaag tcattaccag catggattgc  3420
ttcaaacggt ataaccacat ttggcagaag gggaaggaag aggccattaa gaccttcata  3480
acccaatcac cgctcctgtc cgagtttgag tcgcagatcc tgtactttca aaacttggaa  3540
caggaaatca acgccgaacc cgaatacgtc tgcgtgggta gcatcgccct gtatactgcg  3600
gacctcaagt tcgcgcttac tgctgaaacc aaggcatgga tggtggtcat cggtaggcat  3660
tgtaacaaga agtaccgcag cgagatggaa aatatcttca tgctgattga agaattcaac  3720
aaaaaactga acagacctat caaagacctg gacgatatta gaatcgccat ggcggccctg  3780
aaggagattc gggaggaaca gatttccatc gacttccaag tgggccctat cgaagagagc  3840
tacgccttat tgaacagata tggattgttg atcgcacggg aagagatcga caaagtcgac  3900
actttgcact acgcatggga aaagctgctc gcccgagccg gggaggtcca gaacaaactt  3960
gtgtcgcttc agccctcctt caagaaggag ctgatcagcg cggtggaagt gttcctccaa  4020
gattgccatc aattctacct ggactacgat ttggaacggac ctatggctag cggcctgaag  4080
ccccaggagg cgtccgacag acttatcatg tttcagaacc agtttgacaa catttacaga  4140
aagtacatta cctacactgg tggcgaagaa ctcttcggac ttccggccac ccagtacccc  4200
cagctccttg agatcaagaa gcaactgaac ttgctgcaga agatctacac tctgtataat  4260
tccgtgattg aaacggtgaa ctcctactac gacattctct ggagcgaggt gaacatcgaa  4320
aagatcaaca acgaattgct cgaatttcaa aacagatgcc ggaagctgcc cagggcactc  4380
aaggactggc aagcgttcct cgacttgaaa aaaattattg atgatttctc ggagtgctgc  4440
ccgctgctcg aatacatggc aagcaaggcg atgatggagc ggcactggga acggattacc  4500
accctgactg gacactcgct cgatgtggga aatgagtcct ttaagctgcg gaacatcatg  4560
gaagcccctc ttctgaagta taaggaggaa atcgaggata tttgcatctc cgctgtcaag  4620
gagcgcgata tcgagcagaa gctcaagcaa gtcattaatg aatgggataa caagaccttc  4680
acttttggct ccttcaagac tcgcggcgaa ctgcttcttc ggggcgactc aacgagcgaa  4740
attatcgcga acatggagga ttcactgatg ctcctgggat cgctgctctc aaacaggtat  4800
aacatgccct ttaaggctca gatccagaag tgggtgcagt acctgtcaaa ttccactgac  4860
ataattgaat cgtggatgac cgtgcaaaac ctttggatct acctggaggc cgtgttcgtg  4920
ggtggcgata ttgctaagca actccctaaa gaagctaaaa ggttcagcaa catcgataag  4980
agctgggtca agatcatgac cagagcccat gaagtgcctt cggtggtgca gtgctgcgtg  5040
ggcgatgaaa cgctgggaca gctcctgcct cacctcctgg accaattgga gatttgtcag  5100
aagtcgctga ctgggtacct tgaaaagaaa agactttgct tcccacgctt cttctttgtc  5160
tccgacccgg cgcttcttga gattctggga caggccagcg actcccatac catccaagcc  5220
cacttgctca acgtgttcga taacattaaa tcagtgaagt tccatgagaa aatttacgac  5280
cgaatcctgt cgatctccag ccaggagggc gaaaccatcg agttggataa acccgtgatg  5340
gccgaaggaa acgtggaagt gtggttgaac tccttgctgg aagagagcca gagctccctc  5400
cacctggtga tccgccaggc ggcggccaac attcaggaaa cggggttcca gctcaccgag  5460
tttctgagct cgttccctgc ccaggtggga ctcctgggca tccaaatgat ctggacccgg  5520
gattcggagg aagccctgag aaatgcgaaa tttgacaaga agattatgca aaagactaac  5580
caggcctttc ttgaattgct gaatactctg atcgacgtga ccacccggga cctttcgtcc  5640
acggaaaggg ttaagtacga aactttaatt actatccacg ttcaccaaag ggacattttc  5700
gatgatctct gtcacatgca catcaagagc ccaatggact ttgagtggct gaagcaatgc  5760
cggtttttact tcaacgaaga tagcgacaag atgatgatcc acatcaccga tgtcgcgttt  5820
atctaccaaa acgaattcct gggttgcact gaccgcctcg tgatcacccc gctgaccgat  5880
aggtgttaca tcaccctggc acaagcattg gggatgtcca tggggggagc tccagccggg  5940
cctgccggca ccggcaaaac cgaaacgaca aaggacatgg ggagatgcct tgggaagtac  6000
gtggtggtgt tcaattgcag cgaccaaatg gacttccgcg ggctgggacg gatcttcaag  6060
ggtctggctc aaagcggaag ctgggggtgc ttcgatgaat tcaatagaat tgacctccct  6120
gtgctgtcgg tggccgcgca gcagatcagc atcatcctta cttgcaagaa ggagcacaag  6180
aagtcattca ttttcactga cggagataac gtgactatga acccggaatt cggcctgttc  6240
ttaaccatga accccggcta cgcgggccgg caggagctgc cagaaaacct gaaaatcaac  6300
tttcggagtg tcgctatgat ggtcccggac agacagatca tcatcagagt gaaactcgcg  6360
tcgtgcggtt tcatcgataa cgtcgtgctg gcccgcaaat tcttcaccct ctacaagttg  6420
tgcgaagaac agctctccaa gcaagtgcac tacgacttcg gactgcgcaa cattcttagc  6480
gtgcttcgca cgctcggagc cgcaaagaga gcgaaccccta tggacacgga atccaccatc  6540
gtcatgcggg tgctgcgcga catgaacctg tccaagctca tcgacgaaga tgagccgctc  6600
tttttgtccc tgatcgagga cctgttccct aacatccttc ttgacaaggc cggctaccct  6660
gagcttgaag ccgccatttc cagacaggtg gaagaagccg gccttattaa tcatccccca  6720
tggaaactca aagtgatcca gctctttgag actcaaaggg tccggcacgg gatgatgaca  6780
ctcggaccta gcggtgccgg caagactact tgtatccaca ccctcatgcg cgccatgacc  6840
gactgtggaa aaccccacag agagatgaga atgaacccta aggccatcac tgcaccgcag  6900
atgttcggcc ggctggacgt ggccacgaat gactggactg acggcatctt cagcaccctc  6960
tggaggaaaa ccttgagagc gaagaaggc gaacacattt ggatcatcct cgatgggcct  7020
gtggatgcga tttggattga gaacctcaat agcgtcctcg atgacaacaa gaccctgacc  7080
ctcgccaacg ggaccggat ccccatggcc cccaactgca agatcatctt cgagccgcat  7140
aacattgaca atgctagccc ggccacggtg tcccggaacg ggatggtctt tatgagctca  7200
tccatcctgg attggtcccc tatcctcgaa gggttcctca agaagcggtc ccctcaggaa  7260
gccgaaatcc tgcggcagct ctacacggag agcttcccgg acttgtaccg gttctgcatt  7320
cagaacttgg aatacaagat ggaagtcttg gaggccttcg tcattaccca gagcatcaac  7380
atgctgcagg ggctcattcc actcaaggaa cagggcggag aggtgtcgca ggcccatctc  7440
gggaggcttt tcgtattcgc actgctgtgg tctgcaggag ctgccctgga actggacggc  7500
cgcaggaggc tggagctctg gctgcgctca cggcccacgg gcacccttga actgcctccc  7560
cccgcgggtc cgggagatac cgccttcgac tactacgtcg ctccggacgg cacatggacg  7620
cactggaata cccgcactca ggagtatctc taccccttccg acactactcc ggaatacggc  7680
agcatcctcg tgccgaacgt ggacaacgtg agaacggact tccttatcca aactattgct  7740
aagcaaggaa aagccgtctt gcttatcggc gagcaaggca ccgcaaagac cgtgatcatc  7800
aaggggttta tgagcaagta cgacccagaa tgccacatga tcaaaagcct caactttagc  7860
tccgccacca ctccactgat gtttcagcgc actattgagt cgtacgtcga caagcgcatg  7920
```

-continued

```
ggaaccactt acggtccacc ggccggaaag aagatgactg tgtttattga cgatgtgaac  7980
atgcccatca tcaacgaatg gggcgatcaa gtgactaacg agattgtgcg ccagctgatg  8040
gaacaaaacg gattctacaa cctggaaaag ccgggcgaat tcacctcgat tgtcgacatc  8100
caattcctgg cagccatgat tcatcccgga ggcggaagaa acgacattcc tcagaggctc  8160
aagcggcaat tctccatttt caattgcacc ctgccgtcgg aagcctccgt ggacaaaatt  8220
ttcggcgtca ttggagtggg gcactactgc acccagcggg gcttcagcga agaagtgaga  8280
gattccgtca ccaagctggt gccactcacc agacggcttt ggcaaatgac caagatcaaa  8340
atgctgccta ccccggccaa atttcactac gtctttaacc tccgggatct cagccgggtg  8400
tggcagggaa tgctcaatac tacttccgag gtgatcaagg aacccaatga cctcctgaaa  8460
ctgtggaagc acgaatgcaa gcgcgtgatt gctgaccgct ttaccgtgag cagcgacgtg  8520
acgtggtttg acaaagcgct cgtgtcactc gtcgaggaag aatttggcga ggagaagaag  8580
ttgttggtgg actgtggaat tgatacctac ttcgtggatt tccttcggga cgcccctgaa  8640
gcggccggag aaacttccga agaagcagat gccgaaaccc caaagattta cgaaccgatt  8700
gagtcgtttt cacacctcaa agaacgcctc aacatgttcc ttcagctgta caacgagtca  8760
atccggggtg ccggaatgga catggtgttt ttcgcggacg ccatggtaca cctcgtgaag  8820
atctcgcgcg tgattagaac gccacagggg aacgccctgc tggtcggtgt ggggggtagc  8880
ggaaagcagt cattgacccg gctggcctcg ttcattgcgg gatacgtgtc attccagata  8940
acccttacca gatcgtacaa cacctccaac ctgatggagg acctgaaggt gctgtatcgc  9000
actgccgggc agcaagggaa aggaataact ttcattttca ctgacaatga gattaaggat  9060
gagagcttcc ttgaatacat gaacaacgtc ctttcatccg gggaagtcag caaccttttc  9120
gcccgcgacg agatcgacga gattaacagc gatcttgcgt ccgtcatgaa gaaggaattc  9180
cctagatgct tgccgaccaa cgaaaaccta cacgattact tcatgtcaag agtgcgccaa  9240
aacctccaca tcgtgctgtg tttcagcccg gtgggcgaga agttcagaaa cagggctttg  9300
aaattccccg cactgatttc cggttgtacg attgattggt tctcacgctg gccgaaggac  9360
gccctggtgg ccgtcagcga gcacttcctg accagctacg acattgactg cagcctcgag  9420
atcaagaagg aggtggtcca gtgtatgggc tccttccaag atggagtggc cgaaaagtgc  9480
gtggactact tccagagatt cagacgctcc actcacgtga ctcccaaatc ctacttgtcc  9540
ttcatccaag gttataagtt catttacggc gaaaagcatg tcgaggtccg gactctggcc  9600
aaccggatga acaccggact ggagaagctg aaagaagcca gcgagtcggt ggccgctctc  9660
tcaaaggaac tggaggccaa ggagaaggag ctccaggtgg cgaacgacaa ggcggacatg  9720
gtcctgaagg aggtgaccat gaaggcccag gccgctgaga aagtgaaggc ggaggtgcag  9780
aaggtcaaag atagggcgca ggccatcgtc gattccatca gcaaggacaa ggccattgcg  9840
gaagagaagc tggaggctgc aaagccggcg cttgaagaag ccgaggccgc gctgcaaacc  9900
attcgcccca gcgacatcgc caccgtgagg actctgggac gacccccaca ccttatcatg  9960
cggatcatgg attgcgtgct cctcctgttc cagcgcaaag tgtcggcagt caagatcgac  10020
ctggagaaat catgcactat gccttcatgg caggagtcct tgaagctgat gacggcaggc  10080
aacttcctgc aaaacttgca gcagtttccg aaggatacca tcaacgaaga agtgatcgag  10140
ttcctttcgc cgtactttga gatgcccgat tacaacattg aaaccgcaaa gagggtctgc  10200
ggcaacgtgg cagggctgtg cagctggacc aaggcaatgg cctcgttctt ctcgattaac  10260
aaggaagtgc tgccgctgaa ggcgaacctg gtcgtacagg agaacaggca ccttctggcc  10320
atgcaagacc tccaaaaggc acaagccgaa ttggacgaca agcaggccga gctcgatgta  10380
gtccaggctg aatacgaaca ggccatgacc gagaaacaga ctctgctgga agatgccgag  10440
cggtgccgcc acaagatgca gaccgcttcg accctcatta gcgggctggc cggcgaaaag  10500
gagaggtgga ccgaacagtc acaagaattc gccgcccaga cgaaacgcct ggtcggcgac  10560
gtcctcctcg ccaccgcctt cctgagctac agcgggcctt tcaaccagga attcagagat  10620
ctccttctga acgactggcg gaaggaaatg aaggccagaa agatcccgtt cggcaagaac  10680
ctgaacctct cggagatgct gattgacgct ccgacaattt cagagtggaa ccttcagggt  10740
ctgccaaatg atgacctgag cattcaaaat ggcatcatcg tgaccaaggc atccaggtac  10800
cctctcctta ttgatcccca aacccagggg aagatctgga tcaagaacaa agagtccaga  10860
aacgaactgc agattaccag cctcaaccat aaatactttc gcaatcacct ggaagattcc  10920
ctgagcctcg ggaggcccct gctcatcgag gatgtgggag aggaactgga ccccgcgctc  10980
gataacgtgc tggagcgcaa tttcatcaag accggaagca ccttcaaagt caaggtcggc  11040
gataaggagg tggatgtcct ggatggtttc cggctctaca ttactacgaa actcccgaac  11100
cctgcctata cgccggaaat ctcagcccga accagcatca tcgacttcac tgtgactatg  11160
aaaggcctgg aggaccagct cctcggacgc gtgatcctga cggagaagca agagctggag  11220
aaggagagga ctcatctcat ggaggatgtc accgcgaaca aaagacggat gaaggagctg  11280
gaggacaacc tgttgtacag gctgacgtca actcagggat cactggtgga agatgagtcc  11340
ctcatcgtcg ttctgtccaa caccaagcgg accgccgagg aagtcaccca gaagctcgag  11400
attagcgctg aaaccgaagt ccagattaac tccgccagag aggaataccg gcccgtggct  11460
actcggggct ctatcctgta cttcctcatc accgagatgc gcttggtcaa cgaaatgtac  11520
cagacttccc ttcggcaatt cctgggactg ttcgatttga gcctcgccag atccgtgaag  11580
tcgcccatca cttcaaagag gattgcgaac atcatcgaac acatgactta cgaggtgtac  11640
aagtacgccg cacgaggcct gtacgaagaa cacaagttcc tgttcacttt actgttgacg  11700
cttaagatcg acatccagcg gaacagagtg aagcacgagg agttcctcac gcttattaag  11760
ggcggtgctt ccctggacct gaaggcctgt cctcccaagc ctagcaagtg gatcctggat  11820
atcacgtggc tgaacttggt ggagctctcc aaacttagac agttctccga cgtcttggac  11880
cagatttcaa ggaatgagaa aatgtggaag atctggttcg acaaggagaa cccggaagag  11940
gagcccttgc cgaacgctta cgacaagtcc ctggactgtt tcaggagact gttgctcatt  12000
cggtcctggt gtccggatag gaccatcgcc caggcccgca agtacatcgt ggatagcatg  12060
ggtgaaaagt acgctgaagg cgtcattctt gacctggaaa agacttggga ggaaagcgac  12120
ccgcgcaccc cactgatttg cctcctctcg atgggaagcg atcctacgga ctccatcatt  12180
gcccttggta aaagacttaa gatcgagact cgctatgtct cgatgggcca ggggcaggag  12240
gtccacgccc ggaagttgct tcagcagact atggccaatg gaggttgggc gctgctccag  12300
aactgccatc tgggtttgga cttcatggac gaattaatgg atatcatcat tgaaaccgaa  12360
ctggtgcatg acgctttccg gctgtggatg accaccgaag cccataagca atttccaatt  12420
accctcctcc aaatgagcat caagtttgcc aacgacccac cacaaggttt gcgcgcgggc  12480
cttaagcgga cttactccgg agtcagccag gacttgctcg acgtcagcag cggatcacag  12540
tggaagccca tgctctacgc agtggccttt ttgcacagca ctgtgcagga gagaaggaag  12600
tttggagcgc tggggtggaa tattccgtac gaattcaacc aagcggactt taatgctacg  12660
```

```
gtccagttca tccagaacca ccttgacgat atggacgtca aaaagggcgt gtcgtggacg  12720
acgatcaggt acatgatcgg ggaaatccag tacggcggaa gagtcactga cgattacgac  12780
aagaggctcc tgaacacttt tgccaaagtg tggttttcag agaacatgtt cgggccggac  12840
ttctccttct accaaggata caatatcccc aaatgcagca ccgtggacaa ctacttgcaa  12900
tacatccaga gcctgccagc atacgactcc ccagaagtct ttggactgca cccgaacgcc  12960
gacattacct accagagcaa gttggcgaag gacgtcttgg acactattct tggtatccag  13020
ccgaaagaca cctcgggggg gggggacgaa accagagagg cagtggtcgc gcggctcgct  13080
gacgacatgc tggaaaagct gcccccggat tacgtcccgt tcgaggtcaa ggagaggctg  13140
cagaagatgg gaccattcca gcctatgaat attttcctga ggcaggagat cgaccggatg  13200
cagcgcgtcc tgtcactcgt gcgcagcact ctcaccgagt tgaaactggc aatcgatggc  13260
acgattatca tgtcggaaaa ccttcgcgat gcactggact gcatgtttga cgccagaatt  13320
cccgcttggt ggaagaaggc ttcatggata agctccacct tgggattctg gttcacagag  13380
ctcattgaac gcaacagcca gttcacttcc tgggtgttca atggcagacc ccactgcttc  13440
tggatgaccg gattcttcaa cccccagggg ttcctgaccg ctatgcggca ggagattact  13500
cgggcgaata agggatgggc cctggacaac atggtgctct gcaacgaagt gaccaaatgg  13560
atgaaggatg atattagcgc gccgccgact gagggagtgt acgtctacgg actttacttg  13620
gagggcgcgg ggtgggataa aaggaacatg aagttgatcg agtcaaaacc caaggtgctc  13680
tttgaattga tgccggtgat ccgcatctac gccgaaaaca acactctcag agatcccaga  13740
ttctactcgt gtcctattta caagaagccc gtccgcaccg acttgaacta tatcgccgcg  13800
gtcgatttga gaactgccca gactcccgag cactgggtgc ttcggggagt cgcgctgctt  13860
tgcgatgtga agtag                                                   13875

SEQ ID NO: 22          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 22
atgttccgca tcggccgccg ccagctctgg aagcatagcg tgactagagt ccttacccaa  60
cgcctgaagg gtgaaaaaga ggccaagcgc gccctgctgg acgcccggca taattacctg  120
tttgccattg tcgcctcatg cctggacctg aataagactg aggtcgagga tgccatcctt  180
gaagggaacc aaatcgagag aatcgatcaa ctcttcgccg tgggggggct gcggcatctc  240
atgttctact accaggacgt ggaagaagca gaaaccggcc agcttggctc ccttggtggg  300
gtgaacctcg tgtcggggaa gatcaaaaag cctaaggtgt tcgtgaccga gggcaacgac  360
gtggcgctta ccggagtgtg cgtgttcttc ataaggacgg atccatcaaa ggccattacc  420
cctgataaca ttcatcaaga ggtcagcttc aacatgctcg atgccgcgga tggaggtttg  480
ctgaatagcg tgcgcagatt gctctcagac attttcatcc ctgcgctccg cgccacctcc  540
cacggttggg gagaacttga ggggctccag gatgccgcca acattagaca ggaattcctg  600
agcagcctgg aaggattcgt gaacgtgctg tccggggcac aagagagcct caaagaaaag  660
gtcaatttga gaaaatgcga catcctcgaa ctcaagactc tgaaggaacc gactgattat  720
ctgactctcg cgaataaccc agaaaccctc ggaaagatcg aggactgcat gaaggtctgg  780
attaaacaaa cggagcaagt gctggctgag aataaccagc ttctcaagga agccgatgac  840
gtcggcccga gagcagagct tgaacattgg aagaagagac tttccaagtt caactacctc  900
ctcgaacagc tgaagtcccc ggacgtcaag gccgtgctcg ccgtgctggc cgctgccaag  960
agcaagctgc tcaagacttg gcgggaaatg gacatcagga tcaccgacgc aacgaacgag  1020
gccaaagata acgtcaagta cctttatacc ttggagaagt gctgtgatcc gctttactcg  1080
agcgaccctc tgtcgatgat ggacgccatc ccaactctga ttaacgccat taagatgatt  1140
tatagcatca gccactacta caatacctcc gaaaaaatca cctcgttgtt cgtgaaggtc  1200
accaatcaga ttatttccgc ttgcaaggcg tacattacca ataacggtac cgcgagcatc  1260
tggaaccagc cgcaggacgt ggtggaagaa aaaattctga gcgcaattaa gctgaaacaa  1320
gagtaccagt tgtgctttca caagaccaag cagaagttga agcagaaccc aaacgccaag  1380
cagtttgatt tttccgaaat gtacattttc gggaagtttg agactttcca ccggagactc  1440
gcgaagatta ttgacatttt caccaccctt aagacttaca gcgtgctaca ggactcgacc  1500
attgaggggc tcgaggatat ggccaccaag taccagggaa ttgtggccac aattaagaag  1560
aaggaataca acttcctcga ccagcgcaag atggacttcg accaagacta cgaggagttt  1620
tgcaagcaga ctaatgacct tcataatgag ctgcggaagt tcatggatgt gaccttcgcg  1680
aaaatccaga acaccaacca ggccctgcgg atgctcaaga aattcgaacg cctgaacatt  1740
cctaacctcg ggatcgacga caaataccaa ctcattttgg agaactatgg ggcggatatc  1800
gatatgatct ccaaactcta caccaaacag aagtacgacc cgcccttggc tcggaaccag  1860
ccacccatcg cgggaaagat cctgtgggcc cgccaacttt tccatcgcat ccagcagcct  1920
atgcagctgt tccagcagca tcccgccgtg ctctccacgg ccgaagcaaa gccgattatt  1980
cgctcctata accggatggc caaagtgctg ctcgagttcg aagtgctgtt ccatcgcgca  2040
tggctccggc agatcgagga gattcacgtg ggcctcgaag ctagcttgct cgtgaaggct  2100
cctggcactg gagaactttt cgtgaacttt gaccctcaaa tcctgatcct gttcagggag  2160
actgagtgca tggcgcagat gggcttggag gtgtcaccct tggccacgag cctgtttcag  2220
aagagagaca ggtacaagcg caacttttcc aacatgaaga tgatgctggc cgaataccag  2280
cgcgtgaaat ccaagatacc ggcggccatc gaacaactta ttgtgcccca cctcgcaaag  2340
gtggacgagg cgcttcaacc cggactcgcc gcgctcacat ggacgtcgct gaacatcgag  2400
gcctacttgg agaacacctt tgccaagatc aaggacctgg aactgttgct agatcgcgtg  2460
aacgacctga ttgaattccg gattgatgct attttggaag agatgtcgtc gaccccgctg  2520
tgtcagctgc cccaggagga gcctctcact tgcgaagagt tcttacaaat gacgaaggac  2580
ttgtgcgtga acggtgccca aatcctgcac ttcaagtcct cgctcgtcga ggaggccgtg  2640
aacgagctcg tgaatatgct tcttgatgtc gaggtgctga gcgaggaaga atcagagaaa  2700
atttcgaatg agaatagcgt caattacaag aacgagagta gcgcgaagcg cgaggagggg  2760
aattttgaca ctcttacctc ctccatcaac gcccgggcaa atgcactcct tctgactacc  2820
gtgacccgga agaagaagga aaccgagatg ctgggagaag aagcaagaga gctccttagc  2880
cacttcaacc accagaacat ggacgcgctc ctgaaagtga cccggaacac cctggaggct  2940
```

-continued

```
atccggaagc ggatccatag cagccacacc attaatttcc gcgacagcaa cagcgcaagc  3000
aacatgaagc agaactcact gccaatcttc cgcgcctccg tgactctcgc cattccaaac  3060
atcgtgatgg ctcctgcctt ggaggatgtc cagcaaaccc tgaataaggc cgtggaatgc  3120
atcatctccg tgccgaaggg agtcaggcag tggtcgtcag agctcctgtc aaaaaagaag  3180
atccaagagc ggaagatggc cgccctgcaa tccaacgaag atagcgattc ggacgtggag  3240
atgggagaga acgagttgca ggataccctc gagatcgcct ccgtgaatct gccaatccca  3300
gtgcagacta agaattatta caagaacgtg agcgaaaaca aagaaattgt caaactcgtg  3360
agcgtcctga gcaccattat caattccact aagaaggaag tcatcaccag catggactgc  3420
ttcaagaggt acaaccatat ttggcagaag ggaaaggaag aggcgattaa gaccttcatc  3480
actcaatccc ccctcctcag cgagttcgaa tcgcagattc tgtacttcca aaacttggag  3540
caggaaatta acgccgagcc tgaatacgtg tgcgtgggct ccatcgccct gtacaccgcg  3600
gatctcaagt tcgcgctcac cgcagaaacc aaggcgtgga tggtggtgat cgggagacac  3660
tgcaacaaaa agtaccggtc cgaaatggaa aacatcttca tgctgattga ggaattcaac  3720
aagaaactga accggccgat aaaggacctc gacgacatca ggatagccat ggcagccttg  3780
aaggaaatcc gcgaggagca gatcagcatt gacttccagg tcggaccgat tgaggagtcc  3840
tacgccctgc tgaatagata cggtctgcta atcgccagag aagagatcga caaggtggac  3900
accttgcact acgcttggga aaagctcctt gcccgggccg gggaagtgca gaacaagctg  3960
gtcagcttac agccatcctt taaaaaggaa ttgatctccg ccgtggaagt gttcttgcaa  4020
gattgccacc agttctacct ggactacgac ctcaacggac cgatggctag cggccttaag  4080
ccacaggagg catcagaccg gctgatcatg tttcagaacc aattcgacaa catctacaga  4140
aagtacatta cctacaccgg gggcgaggaa ttgttcggcc tgccggcaac ccaataccc  4200
cagcttctcg agattaagaa acaattgaac ttgctccaga agatctacac gctctataac  4260
tccgtgatcg agactgtgaa ctcgtactat gacattctct ggtcagaggt caacatcgaa  4320
aagattaata acgaactgct ggaatttcaa aatcggtgca ggaagctccc tagggctctg  4380
aaggattggc aggccttcct ggaccttaag aagatcattg acgacttctc ggaatgctgc  4440
ccactcctgg agtatatggc tagcaaggct atgatggaga ggcattggga gcgcatcacc  4500
actttgactg gccacagcct tgacgtgggc aatgaatcct tcaaactgcg caacatcatg  4560
gaggcaccat tgttgaaata caaggaagaa atcgaagata tctgcatcag cgccgtcaag  4620
gaacgcgata tcgaacagaa gctcaaacag gtcattaacg agtgggacaa caagacgttc  4680
accttcggga gcttcaagac taggggagaa ctgctgttga gaggagactc cacttcggag  4740
atcattgcca acatggaaga tagcctcatg ttgctgggct ccttgctctc gaaccgctat  4800
aacatgccat tcaaggcaca aatccagaag tgggtccaat acctctccaa tagcacagac  4860
atcatcgaat cgtggatgac cgtccaaaac ctgtggatct acctggaagc cgtgttcgtg  4920
ggcggagata ttgcgaagca gttgcctaag gaggcaaaaa gattcagcaa tatcgacaag  4980
tcgtgggtga agatcatgac cagagcccac gaggttcctt ccgtggtgca gtgctgcgtc  5040
ggagatgaga ctctgggcca gctcctcccg caccttctgg atcaactgga aatctgccaa  5100
aagtccctga ctggctacct ggaaaaaaaa agactgtgct ttcctcggtt cttcttcgtg  5160
tccgaccccg ctctgctgga aatcctcgga caggcgtccg actcccacac tatccaggcc  5220
caccttctca acgtgttcga taatatcaag tcggtcaaat tccatgagaa gatctacgac  5280
agaatcctgt ccatctcgtc acaagagggc gagactatcg agcttgataa gccagtcatg  5340
gccgaaggca acgtcgaagt ctggctcaat tcactcctgg aagaatcaca gtcgtccttg  5400
catctggtca ttcgccaagc cgccgctaac attcaggaga ctggtttcca acttactgag  5460
ttcttgtcgt cattccccgc ccaagtgggc ctgctgggca ttcagatgat ttggacgagg  5520
gattccgaag aggcccttcg caatgcaaaa ttcgacaaga aaattatgca gaaaaccaat  5580
caagccttcc tggaacttct gaacactttg attgatgtga ctactcggga tctcagctcc  5640
accgaaagag tcaaatacga gactctcatc accatccacg tgcatcaacg cgacattttc  5700
gacgacttgt gccacatgca tatcaaatcc ccgatggatt tcgagtggct gaagcagtgt  5760
cgcttttact tcaacgaaga ttccgacaaa atgatgattc acatcaccga tgtggccttt  5820
atttaccaaa acgaattctt gggctgtact gaccggctgg tgattactcc tttgactgat  5880
cgctgctaca ttacccttgc ccaggctctg ggaatgtcca tgggaggggc gcctgccggc  5940
ccggccggaa ctggaaagac cgaaaccacg aaggacatgg gtcggtgcct gggcaagtac  6000
gtggtggtgt tcaactgcag cgaccaaatg gactttcggg gactgggaag aatcttcaag  6060
ggactcgccc agtcggggtc atggggctgc tttgacgaat tcaacaggat tgacctcccg  6120
gtcctgtccg tcgccgccca acaaatttca atcattctca cctgtaagaa agaacataag  6180
aagtcattca tcttcaccga cggagacaac gtgaccatga accctgaatt tggactgttc  6240
ctcaccatga acccgggata tgcgggccgg caggagctgc cagagaacct taagattaat  6300
ttccggtccg tcgcgatgat ggtgccggac cggcaaatta tcatccgggt aaagctggct  6360
tcatgcgggt tcatcgataa cgtcgtcctc gcccggaaat ttttcaccct ttataagctg  6420
tgcgaagaac agctttcgaa acaggtgcat tacgattttg gtctgcggaa catcctgagc  6480
gtcctccgga ctctgggagc cgcgaagagg gctaatccga tggacactga gtccactatc  6540
gtcatgagag tcctgcgcga catgaacctt tccaagctca tcgacgagga tgagcctctc  6600
ttcctgagcc tgatcgagga cctgttcccc aacatcctgc tcgacaaggc gggatatcct  6660
gaactggagg cggccatcag cagacaggtc gaggaggccg gcctaatcaa ccaccctccc  6720
tggaagctca aggtgatcca gctgtttgag acacaacggg tgcggcatgg aatgatgacc  6780
ctggggccgt ccggggctgg aaaaactact tgtatccata ctctcatgcg cgccatgacc  6840
gattgtggaa aacctcaccg cgagatgaga atgaatccca aggcgattac tgccccccag  6900
atgtttgggc ggctggacgt cgccactaac gactggacgg acggaatttt ctccaccctc  6960
tggcgcaaaa cactgagagc caagaaggga gagcatatct ggatcattct ggacggtcca  7020
gtcgatgcga tttggatcga gaacctgaac tccgtcttgg acgataacaa gacgctcacc  7080
ctggctaacg gcgatagaat cccaatggcc ccaaattgta agatcatctt cgagccacac  7140
aacattgata acgcgtcacc ggccaccgtc agccggaacg gaatggtgtt tatgagcagc  7200
tcgattcttg actggagccc gatcctcgaa ggtttcctca aaaagagatc cccccaggag  7260
gcagagattc tcaggcagct ctacaccgag tcattcccgg atctgtacag gttctgcatt  7320
cagaatctgg aatacaagat ggaagtcctt gaagccttcg tgatcaccca atcgattaac  7380
atgcttcagg ggctgatccc actcaaagaa caagggggag aggtgtctca ggcgcacctg  7440
ggccgcttgt tcgtgtttgc tttgctttgg agcgcgggcg ccgcccttga actggatggc  7500
cgcaggcgcc tcgagctctg gctgagaagc agacctacgg gaacccttga actccctccc  7560
cccgctggcc ccggagatac cgccttcgac tactacgtgg ccccggacgg gacttggact  7620
cattggaaca ccagaactca agagtacctt tatccgtccg atactactcc ggagtacgga  7680
```

-continued tccatcctgg tccctaacgt ggacaacgtg cgaaccgact tcctgattca gacaatcgcc 7740
aagcagggaa aggcggtgct gcttatcgga gaacaaggaa cagccaagac tgtcatcatc 7800
aagggattta tgagcaagta tgatcctgag tgccacatga tcaagagctt gaacttctcg 7860
tcggccacta ctcccctcat gttccaaaga accatcgagt cctacgtgga caaaagaatg 7920
ggaaccacgt acgggccccc tgccgggaag aagatgaccg tctttatcga tgacgtgaac 7980
atgcccatca tcaacgagtg ggtgatcaa gtcaccaacg aaatcgtgcg gcagctcatg 8040
gaacagaacg gattctacaa cctggaaaag ccaggggaat tcacctccat cgtggatatt 8100
cagttcctgg ccgccatgat ccatccaggc ggaggccgca atgacattcc gcaacgcctg 8160
aagcggcagt tctcaatctt caattgcacc ctcccgtcgg aagctagcgt ggataagatt 8220
tttggtgtca tcggagtcgg acactactgc acccaacgag gctttagcga agaggtcaga 8280
gatagcgtca cgaaactcgt gccgttgact cgccgccttt ggcagatgac caagatcaag 8340
atgctaccca cccccgctaa gttccactac gttttcaatt tgcgggactt gagccgggtg 8400
tggcagggaa tgctgaacac cacctcggaa gtcatcaaag aacctaacga cttgctgaag 8460
ctctggaagc acgaatgcaa gcgcgtgatc gccgaccgct tcactgtgag cagcgacgtg 8520
acgtggtttg ataaggctct ggtcagcctg gtcgaggagg agttcgggga agagaagaag 8580
ctcctggtcg actgtggcat cgacacgtat ttcgtggact ttctcagaga tgcgcccgaa 8640
gccgcgggcg aaacctcgga agaagcagac gctgagactc ccaagatcta cgagccgatt 8700
gagagcttca gccacttgaa ggagagactt aacatgtttc tgcagctcta caacgaaagc 8760
attcggggcg ctgggatgga catggtgttt ttcgctgacg ccatggttca cttagtgaaa 8820
atctcccgcg taattaggac cccgcagggt aatgccctgc ttgtaggcgt gggcggatcc 8880
ggaaagcagt cactgacccg gcttgcatca ttcatcgcgg gctacgtgag cttccagatc 8940
actcttacta gatcatataa cacgtccaat ctcatggagg acctgaaagt gctgtatagg 9000
accgcgggcc agcaggggaa gggtatcacc ttcattttta ccgacaacga aatcaaagat 9060
gagtccttct tggagtacat gaacaacgtg ctctccagcg gcgaagtgag caacctttc 9120
gcccgcgatg agatcgatga aattaactcc gacctggcct cagtgatgaa gaaggaattt 9180
ccgcgctgcc tccctacgaa cgaaaatctg cacgattact tcatgtcaag agtccggcag 9240
aatctccaca tcgtgctgtg cttttcaccg gtgggagaga agtttcgcaa ccgcgcactg 9300
aagttcccgg ccctgatttc gggatgcacg attgattggt tctcgcggtg gcctaaagat 9360
gccctcgtgg cggtgtccga gcacttcctt acttcctacg acatcgattg ctccctggag 9420
atcaagaaag aggtggtgca gtgtatgggt tcattccagg acggggtcgc agagaagtgc 9480
gtggactact ttcagagatt cagacgctcc actcacgtca ctccgaaatc ctacctgagc 9540
ttcatccagg gatacaagtt tatatacggc gaaaagcacg tcgaagtgag aacactcgcc 9600
aacaggatga acactggttt ggaaaagctc aaggaggcgt ccgaatcggt ggccgcactg 9660
tcaaaggagc tcgaagcgaa ggagaaagaa ctccaggtcg cgaacgacaa ggccgacatg 9720
gtgttgaagg aagtaaccat gaaggcccag gccgccgaga aggtgaaggc cgaagtgcaa 9780
aaggtcaagg atagggcaca agccatcgtc gactcaattt cgaaggacaa ggcaatcgcc 9840
gaagaaaagt tggaggccgc gaagccggcc ctcgaagaag cggaggcggc gctgcagacc 9900
atcaggcctt cagatatcgc tacggtccgc accctgggtc gccctcctca cctcattatg 9960
agaatcatgg actgcgtgct gcttttgttc cagcgcaaag tctcagcagt gaagatcgat 10020
ctcgaaaagt catgcaccat gccatcatgg caggagagcc tgaagctaat gaccgctgga 10080
aatttccttc aaaatctgca gcaattccca aaggacacta ttaacgaaga agtgatcgaa 10140
ttcctctcgc cttacttcga gatgcccgac tacaacatcg aaaccgccaa aagagtgtgc 10200
ggcaacgtcg ccgggctttg ctcctggacg aaggcaatgg ccagcttctt ctcaatcaac 10260
aaagaggtgc tgcccttgaa ggccaacttg gtggtccagg aaaacaggca ccttctcgcc 10320
atgcaagatc tccaaaaggc ccaagccgag ctcgatgaca agcaggccga gctggatgtg 10380
gtgcaggcgg agtacgagca ggcgatgaca gaaaagcaga cgttgcttga ggacgccgag 10440
agatgccggc acaaaatgca gaccgcctcc accctgatct cggggctggc aggcgaaaaa 10500
gaaagatgga ccgagcaatc gcaggagttt gccgctcaaa ccaagaggtt ggtgggcgac 10560
gtgttgttgg caaccgcatt cctgagctac agcggaccat tcaaccaaga gttccgcgac 10620
ctgttgctga acgactggag aaaggagatg aaggcccgca agatcccatt cggcaagaac 10680
cttaatctca gcgaaatgct gattgatgcc cctacaattt ccgagtggaa tctgcaggga 10740
cttccaaacg acgacctgag catccaaaat ggcatcatcg tgaccaaggc ttcacggtac 10800
cccctcctca tcgacccgca gactcaagga aagatttgga tcaagaataa ggaaagccgg 10860
aacgagctgc agatcacttc ccttaaccac aagtacttta gaaaccacct cgaggactcc 10920
ctttccttgg gtcggccgct cctcattgag gacgtgggcg aggaattaga cccagccctc 10980
gacaacgtgc tggaaagaaa cttcattaag accggatcca cctttaaggt gaaagtcgga 11040
gataaggaag tcgacgtcct ggacggcttc agactctaca ttacgactaa gctcccaaac 11100
cctgcctata ccccggagat ctccgcgcgc actagcatta ttgacttcac cgtcacgatg 11160
aagggactgg aggaccagct gctggggagg gtgatcctga cggaaaagca ggaactcgag 11220
aaggagcgga cgcatttgat ggaggacgtg actgcgaaca agcggcgcat gaaggagctg 11280
gaggataacc tgttgtaccg gctgaccagc acccagggct cactggtcga ggacgaaagc 11340
cttatcgtgg tgctgtcgaa cactaagcgg actgccgagg aggtcactca gaagctggag 11400
atctccgctg agacagaagt ccagattaac tccgcccgcg aagagtacag gcctgtcgcc 11460
actagaggat ccatcctgta cttcttgatt accgaaatga gactcgtcaa cgagatgtac 11520
caaacctccc tgagacaatt cctgggcctg ttcgacctga gcctggcccg gtcggtaaag 11580
tcccctatca ccagcaagcg catcgctaat atcattgagc acatgaccta tgaggtgtac 11640
aagtacgccg cccgggggct ctacgaagaa cataagttcc tgtttaccct tctgctcacc 11700
cttaagatcg acattcagcg gaaccgcgtg aagcacgagg aattcctgac ccttatcaag 11760
ggaggagcct cactcgactt gaaagcgtgt cccccaaagc cctcgaagtg gatactggac 11820
attacctggc tgaaccttgt ggagctctcc aaactccggc aattttcaga cgtcttggat 11880
caaatttcaa ggaacgaaaa aatgtggaag atctggttcg acaaggaaaa tccggaggaa 11940
gaaccactgc cgaacgccta cgacaagagc ctcgactgct ttcggcggct gctgctcatt 12000
agaagctggt gcccggatcg gaccatcgcg caggccagga agtatatagt ggattcgatg 12060
ggggagaagt acgcggaagg cgtgattctc gatcttgaaa agacgtggga ggaatcggat 12120
cccaggacgc ccctcatttg cctgctgtcg atgggcagcg atcccacaga ctccatcatt 12180
gcactgggca agcggctcaa gattgaaact agatacgtgt cgatgggtca gggtcaagag 12240
gtgcacgcca gaaagttgct tcaacaaacc atggcaaacg gaggttgggc cctgcttcaa 12300
aattgccacc tgggactgga tttcatggac gaactcatgg atattattat cgaaaccgag 12360
ctggtccacg acgccttcag actgtggatg accaccgagg cccacaagca gtttccgatc 12420

```
acgctgctgc aaatgtcgat caagttcgcg aatgatccgc cgcaaggact ccgggccgga  12480
ttgaagagga cctactcggg agtctcacag gacctcctcg acgtttcgag cggctcacaa  12540
tggaagccca tgctgtacgc ggtcgctttc ctgcacagca ccgtgcaaga acggcggaag  12600
ttcggcgcgc ttgggtggaa tatcccgtac gaattcaacc aagccgactt taacgccacc  12660
gtgcagttta tccagaacca cctcgatgat atggatgtca aaaagggagt ctcgtggacc  12720
accattcggt acatgattgg agaaattcag tacgggggac gcgtcaccga tgattacgac  12780
aagaggcttc tcaacacctt cgccaaagtg tggttctcgg aaaatatgtt tggaccggac  12840
ttctcgtttt accagggtta caacatcccg aaatgctcaa ccgtcgataa ctacctccaa  12900
tacatccaat cgctgcccgc gtatgactcg ccagaggtct ttggactgca tcctaacgcc  12960
gatattacct accagtccaa actggcgaag gacgtcctcg ataccatcct cgggatccaa  13020
ccaaaggaca cgagcggagg aggcgacgaa acccgcgagg cagtggtggc tcgcctggcc  13080
gatgatatgc ttgaaaagct gcccccagac tatgtgccgt tcgaggtcaa ggaaagattg  13140
caaaagatgg gacccttcca accgatgaac atcttcctga gacaggagat cgacaggatg  13200
cagcgcgtgc tatcgctggt cagatcgacg ctgaccgagc tgaaattggc aattgacgga  13260
acgattatca tgagcgaaaa ccttcgggac gcccttgatt gcatgttcga cgccagaatt  13320
ccggcttggt ggaaaaaagc gtcatggatt agctcaaccc tcgggttttg gttcacggag  13380
ctcattgaga ggaactccca gttcacttca tgggtgttta atggacggcc tcattgcttc  13440
tggatgactg gattctttaa tcctcaaggt ttcctgactg cgatgcggca ggagattact  13500
cgggccaata agggttgggc cctggataac atggtgttgt gcaacgaagt gactaaatgg  13560
atgaaggatg acatcagcgc accgcccacg gaaggcgtgt acgtctacgg attgtatctc  13620
gaaggagcgg gttgggacaa aaggaacatg aagctgatcg agtccaaacc aaaagtgctc  13680
tttgagctga tgcccgtgat ccggatctac gcagagaaca acaccctgcg ggatccccgc  13740
ttttattcat gcccgattta caagaagccc gtgaggaccg acctcaacta catcgcagcc  13800
gtggatttgc gcaccgccca aaccccggag cactgggtgc tgagggggggt cgcattgttg  13860
tgcgatgtga aatag                                                    13875
```

```
SEQ ID NO: 23          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 23
atgttccgga ttgggaggag acagctttgg aagcactcag tcactagggt gctgacccaa  60
agactgaagg gcgaaaagga agcgaagaga gctttgctcg atgcgcgcca caattacctc  120
ttcgcgattg tggcctcatg cctggatctc aacaaaaccg aggtcgagga cgcgatcctc  180
gagggtaacc aaatcgaacg catcgaccag ttgtttgccg tgggtggact gcggcacttg  240
atgttctact accaggatgt cgaagaggct gaaacgggcc agctgggttc actcggagga  300
gtgaatcttg tcagcgggaa gatcaaaaag ccgaaagtgt tcgtcaccga aggtaacgat  360
gtagccctga ccggagtgtg tgtgttcttt atccggaccg atccgtccaa ggcgatcact  420
cctgataata ttcaccagga ggtgtcgttc aacatgctgg acgctgctga cggaggactg  480
cttaacagcg tcaggagact cctgtccgac atcttcattc ctgccctgcg ggcaaccagc  540
cacggatggg gagagctcga gggattgcag gacgcggcaa acattaggca ggaattcctg  600
agctccttgg agggcttcgt gaacgtcctt agcggagccc aagagtcctt gaaggaaaaa  660
gtgaacttgc ggaaatgcga tatcctggag ctcaagactc tcaaggagcc gaccgattat  720
ctgacgctgg ccaataatcc agagactctc ggcaagatcg aggattgtat gaaggtctgg  780
attaagcaga ctgagcaagt gctcgctgaa aataaccaac tgctgaagga agcggatgat  840
gtgggaccgc gcgctgaact ggaacactgg aagaaacgcc tgtcgaagtt taactacctc  900
ctggaacagc tcaagagccc ggatgtgaag gcagtgctcg cagtgttggc ggccgcgaag  960
tcaaagctcc ttaagacttg gcgggagatg gacatccgga tcactgatgc gaccaacgaa  1020
gccaaagaca acgtgaaata cttgtacact ctggaaaagt gctgcgaccc attgtactcc  1080
agcgacccgc tgtcaatgat ggacgctatc cccacgttga ttaacgcgat taagatgatc  1140
tactcaatca gccactacta caacacctcc gaaaagatta cctcactctt cgtcaaagtg  1200
acgaaccaga tcatctcagc gtgcaaggcg tacattacta acaacggcac cgccagcatt  1260
tggaatcaac ctcaagacgt cgtggaggag aagatcttga gcgccatcaa gctgaagcag  1320
gagtaccaac tatgctttca caaaaccaag caaaagctca agcagaaccc taacgccaag  1380
caattcgact tctccgaaat gtacatcttc ggcaagtttg aaactttcca caggcgcctc  1440
gccaaaatca tcgacatctt caccaccctc aaaacttaca gcgtgctgca ggattccact  1500
atcgagggac ttgaagatat ggctaccaag taccaaggaa tcgtggccac cattaagaag  1560
aaggaataca attttctgga ccaacgcaaa atggacttcg accaggatta cgaggagttc  1620
tgcaagcaga ctaacgatct gcacaatgag ctccggaagt tcatggacgt gactttcgca  1680
aagatccaaa acaccaacca agccctccgc atgctgaaga aattcgaaag actcaatatc  1740
cctaacctgg gcattgacga taaataccaa cttatcctcg agaactatgg cgcggatatc  1800
gacatgatct cgaaactgta cactaagcag aaatacgacc cgccccttgc tcgcaatcag  1860
cccccgattg ccggaaagat cctgtgggcc cggcagctct ttcacagaat tcaacagcca  1920
atgcagctct ttcagcaaca tcccgccgtg ctttccaccg cggaggctaa gcctatcatc  1980
cggtcctaca accggatggc taaggtcctc cttgagttcg aagtcctgtt ccaccgggcc  2040
tggcttagac aaatcgaaga gattcacgtg ggactcgaag ctagcttgct cgtaaaagca  2100
ccgggaacgg gggagctttt cgtcaacttt gacccccaaa tcctgatcct gttccgcgaa  2160
accgagtgca tggctcaaat gggacttgag gtgtccccac tcgcgactag cctctttcag  2220
aagagagaca gatacaagcg caacttctcc aacatgaaaa tgatgctggc tgagtatcaa  2280
cgcgtgaagt cgaaaattcc agccgccatt gaacagctga ttgtgcctca cctggccaaa  2340
gtggatgaag ccctgcagcc cggtctggcc gctttgacgt ggaccagcct caacatcgaa  2400
gcgtacttag agaacacttt cgccaagatc aaggatctcg aactcctcct ggaccgagtc  2460
aatgacctca tcgaattcag gatcgatgcc attttggaag agatgtccag cactcccctt  2520
tgccagcttc cccaggagga gccgcttact tgcgaggagt tcctccagat gactaaggat  2580
ctctgcgtga acggtgctca aatcctgcac tttaagtcct ccctggtgga agaagccgtc  2640
aatgagctgg tgaacatgtt gcttgacgtg gaggtcctgt cggaggaaga gagcgagaag  2700
```

-continued

```
atttccaacg aaaacagcgt caattacaag aacgagagta gcgccaaacg cgaggaagga  2760
aacttcgaca ctctgacatc ctcaatcaac gcccgcgcta atgctctcct cctgaccact  2820
gtcacgagaa agaagaagga aaccgagatg ctcggggagg aggctagaga gctcctgagc  2880
cactttaacc accaaaacat ggacgcgctg cttaaggtga cccgcaacac cctcgaggcg  2940
atcagaaagc ggatccactc gtcacacacc attaactttc gagactccaa ttccgcatcg  3000
aacatgaagc aaaattcact accgatcttc agagcctcgg tgactttggc aattcccaac  3060
atcgtcatgg ctcctgcact cgaggatgtc cagcaaaccc tcaataaggc cgtcgagtgt  3120
atcatcagcg tgccgaaggg agtgcgccag tggtcgtcag aactcctcag caagaaaaag  3180
atccaggaaa gaaagatggc cgcgctccag tctaacgaag atagcgactc cgacgtggaa  3240
atgggagaga acgagctgca agacactctg gaaatcgcca gcgtcaatct ccctatcccc  3300
gtccagacca agaactacta taagaacgtc agcgaaaaca aggaaatcgt gaagttggtg  3360
tccgtcttgt ccacgatcat caactcgacc aaaaaggagg tgatcaccag catggattgc  3420
tttaagagat acaaccacat ttggcagaag ggcaaggagg aggctatcaa gaccttcatt  3480
acccagtccc cactgttgtc ggaattcgaa tcgcagatcc tgtacttcca gaatctggaa  3540
caggagatta atgccgagcc cgagtacgtc tgcgtcggca gcatcgcgct gtacaccgcc  3600
gatttgaagt tcgccttgac tgccgagact aaggcctgga tggtggtgat tggccgccat  3660
tgcaacaaga agtataggag cgaaatggaa aatattttca tgttgatcga ggaattcaat  3720
aagaagctga atagaccaat caaggacctc gacgacatta ggattgccat ggcagccctg  3780
aaggaaattc gcgaggaaca aatcagcatt gacttccagg tcggcccaat cgaagaaagc  3840
tacgccctgc ttaaccgcta cggactgctc attgcccgcg aagagatcga caaagtggac  3900
acgttacatt acgcttggga gaaactcctg gctcgcgccg gagaggtgca aaacaagctg  3960
gtcagcctcc aacccagctt caagaaggag ctgatctccg ccgtcgaggt gttcttgcag  4020
gattgccacc aattttacct ggattacgac ctgaacggac cgatggcgtc cggcctcaag  4080
ccgcaagagg ctagcgacag gctgatcatg tttcagaacc aattcgacaa catttacaga  4140
aagtacatca cttacaccgg aggcgaggag cttttcggcc tgcccgccac tcagtaccca  4200
caattgctgg agatcaagaa gcagctcaat ctgctgcaga aaatttacac cttgtacaac  4260
tcagtgattg aaactgtgaa cagctactac gacatcctgt ggagcgaggt caacattgaa  4320
aagatcaata atgaactgct ggagttccag aaccggtgcc gcaagctgcc tagggcgctg  4380
aaggactggc aggcgttcct ggacctgaag aagattatcg acgatttctc agaatgctgc  4440
ccactgctcg agtacatggc ctcgaaggcc atgatggaac ggcactggga gcgcatcacg  4500
actttgactg gacatagcct tgacgtgggc aatgagtcct tcaagctgcg gaacatcatg  4560
gaagctccct tgctcaagta caaggaagaa atcgaagata tctgcatctc cgccgtgaag  4620
gaacgcgaca tcgaacagaa actgaaacag gtcatcaacg aatgggacaa caagactttt  4680
actttcggga gcttcaagac caggggcgag ctccttcttc ggggtgactc aacctcagag  4740
attatcgcca atatggaaga tagcctcatg cttctcggaa gcctcctgtc caaccgctat  4800
aacatgccct ttaaggccca aatccaaaag tgggtccaat acttatctaa cagcaccgat  4860
attatcgaat cgtggatgac cgtgcagaac ctttggattt acctggaggc cgtgttcgtc  4920
ggcggagata ttgccaagca actgcccaag gaggccaagc gcttctcaaa catcgacaag  4980
tcctgggtca aaatcatgac tcgggcccac gaagtcccct cagtggtcca gtgctgtgtc  5040
ggcgacgaaa ccttggggca gctcctgccg caccttctcg accagttgga gatttgtcaa  5100
aagtccttga ccggctacct tgaaaaaaag aggttgtgct tcccacgctt tttctttgtg  5160
agcgaccccg cgctcctcga gatcctgggt caggcgagcg actcccacac catccaggcg  5220
cacctcctga acgtgttcga caacattaag agcgtcaaat tccatgaaaa gatctacgac  5280
agaatcctga gcatctccag ccaagagggt gaaaccatcg aactcgacaa gccagtgatg  5340
gctgagggaa acgtcgaggt ctggctgaat tcattgctgg aagaatcgca gagcagcttg  5400
cacctcgtga tccgccaggc cgcggcgaac attcaggaga ctggctttca gttgaccgag  5460
tttttgagct ccttccccgc gcaagtgggc ctgctgggga tccagatgat ttggactagg  5520
gattccgaag aggcgctgag aaatgccaag tttgacaaaa aaattatgca gaaaaccaac  5580
caggcctttc tcgagcttct gaacactttg atcgacgtca ctacacgcga tctgagctcg  5640
actgagcgcg tcaagtatga aaccctgatt accatccacg tccatcaacg ggatattttc  5700
gatgacctct gccacatgca tatcaaatca ccgatggatt ttgaatggct caaacagtgc  5760
cgcttctact tcaatgaaga tagcgacaag atgatgattc atatcaccga tgtggccttc  5820
atctaccaga acgaattcct tggctgcact gacagactgg tcatcactcc tctgaccgat  5880
agatgctata ttacccttgc ccaggcctta ggaatgtcga tgggcggtgc tccagccggg  5940
cccgcgggca ccggaaagac agagactacg aaggatatgg gaaggtgcct gggcaagtac  6000
gtcgtcgtgt tcaattgcag cgaccagatg gatttccggg gcctgggccg catttttcaag  6060
ggccttgcgc agtcgggatc gtgggggtgc ttcgatgaat tcaatcggat cgacttgcca  6120
gtgttgagcg tcgcggccca acagatttca atcatactaa cctgtaaaaa ggagcacaag  6180
aaatccttca ttttcacgga cggggacaac gtgacgatga acccagaatt tggcctcttc  6240
ctcactatga atccagggta cgccggtcgg caggaacttc ccgaaaatct gaaaattaac  6300
ttcaggagcg tcgccatgat ggtcccagat cggcaaatca tcattagggt caaactggct  6360
tcgtgcggat tcattgataa cgtggtgctg gccagaaagt tcttcaccct ttacaaattg  6420
tgcgaggaac agctctcgaa gcaagtgcac tacgactttg gcctcagaaa catcctaagc  6480
gtgctgcgca ctctgggggc agccaaaaga gccaacccaa tggacaccga gagcactatt  6540
gtgatgaggg tccttcgcga catgaacctc tcaaaactta tcgacgagga cgagccgcta  6600
ttcctcagcc tgatcgaaga tctgttcccc aacatcctgc tggacaaggc gggctaccct  6660
gaactggagg ccgccatttc ccgccaagtc gaagaggccg gcttgattaa ccatcctccc  6720
tggaagctca aggtgatcca gttattcgag actcagcgcg tacggcacgg gatgatgacg  6780
ctgggtccgt cgggtgccgg aaagactact tgtatccaca ccctcatgag ggctatgacc  6840
gattgtggaa aaccccaccg ggaaatgcgc atgaacccga aggcgattac ggctccgcag  6900
atgtttggac gcctggatgt cgccactaac gactggaccg atgggatttt ctccacgctg  6960
tggagaaaaa ccttgcgcgc caaaaagggc gaacacattt ggatcattct tgacggaccg  7020
gtggacgcga tctggatcga aaatctgaat tccgtcctgg acgataacaa aactctcacc  7080
ctggctaacg gtgatcggat ccctatggcg ccgaattgta aaattatctt cgaacctcat  7140
aacattgaca atgctagccc cgcaacggtc agccgcaatg gcatggtgtt tatgtcatcg  7200
tccatcctgg attggtcacc gatcctcgag ggattcctca agaagcgctc ccctcaagag  7260
gccgaaattc tccggcagct ctacaccgag tcgttcccag atttgtacag gttctgtatt  7320
cagaacctgg aatacaagat ggaagtgttg gaagcattcg tgatcacgca gtcgatcaac  7380
atgctgcaag gtctgattcc tttgaaggag cagggcggcg aggtgtccca agcgcacctg  7440
```

-continued

```
ggacggttgt tcgtatttgc cttgctgtgg tccgccgggg ccgccctgga actggacggg  7500
cgccgccgcc tggagctctg gctccggtcc agacctaccg gaacgttgga actgcccccc  7560
ccggccggtc ccggggacac cgcctttgac tactacgtgg ctcccgacgg cacttggact  7620
cattggaaca cccggactca agagtacctg tacccttcag acacaactcc cgagtacggt  7680
tcaatccttg tgccaaacgt cgacaacgtg cgcaccgact ttctcattca gaccattgcc  7740
aagcaaggaa aggcagtcct gctcatcgga gagcagggca cggccaagac cgtgatcatc  7800
aagggattca tgagcaagta tgaccctgag tgtcatatga tcaagtcact gaacttttcg  7860
agcgctacta caccgctcat gttccagcgg actatcgaaa gctacgtgga caaaagaatg  7920
ggaaccactt acggaccgcc agccggaaag aagatgaccg tgttcattga cgatgtgaac  7980
atgcccatta tcaacgaatg gggcgaccag gtcaccaacg aaatcgtgag gcaattgatg  8040
gagcagaacg gattttataa cctcgaaaag ccaggcgaat tcacctccat cgtggatatc  8100
cagttcctgg ccgcaatgat ccatcccggc ggcggtagaa acgacatccc gcaacgcctg  8160
aagcggcaat tctcaatttt caattgtact ctcccctccg aggcctccgt ggacaagatc  8220
tttggagtca ttggggtggg ccactactgc acccagagag gcttttccga ggaagtccgg  8280
gactcggtca ccaagctggt gccgcttacc cgcaggctct ggcaaatgac caaaatcaag  8340
atgcttccta ccccggccaa gtttcactac gtgttcaacc tccgcgatct gtcacgcgtg  8400
tggcagggga tgctcaacac cacttccgag gtcatcaagg aaccgaacga cctcctgaaa  8460
ctgtggaaac atgaatgcaa aagagtcatt gctgaccgct tcaccgtgag tagcgacgtc  8520
acatggttcg acaaggcact ggtcagcctg gtcgaagagg agttcggcga ggaaaaaaaa  8580
ctgcttgtgg actgtgggat cgatacttat ttcgtggatt tcctgaggga tgccccagag  8640
gcggccggcg aaacatccga agaagcagac gccgaaaccc ctaagatcta cgagcccatt  8700
gaatcctttt cccacttaaa ggaacgcctg aacatgttcc tgcagctgta caatgaaagc  8760
attcgcggcg ccgggatgga catggttttc ttcgccgatg ccatggtgca cctcgtgaag  8820
ataagccggg tcattagaac ccctcaaggg aacgccctgt tggtcggtgt cggcggctcg  8880
gggaagcaga gcttgactcg gctcgccagc tttatcgccg ggtatgtctc atttcaaatc  8940
accctgaccc gctcctacaa cactagcaac ctgatggagg acctgaaggt gctgtacaga  9000
actgccgggc agcagggcaa gggtatcacg tttattttca ccgataacga aattaaggat  9060
gagagctttc tcgaatacat gaacaacgtg ctgagttccg gggaggtgtc caaccttttt  9120
gcaagggacg aaatcgatga gatcaactcc gacttggcca gcgtgatgaa gaaggaattc  9180
ccaagatgcc tcccaactaa cgaaaatctc cacgactatt tcatgtcaag agtccgacaa  9240
aacttgcaca tcgtgctgtg ctttagtcct gtgggagaga agttccggaa ccgggctctg  9300
aagtttcccg ccctgattag cggatgcacc attgactggt tctcccggtg gcccaaagat  9360
gcgctggttg ctgtgtcgga acacttcctg acctcgtacg atattgactg ttccctggaa  9420
atcaagaagg aagtcgtcca atgcatggga agtttccagg acggtgtcgc cgaaaagtgc  9480
gtggattact ttcaaaggtt ccgccgcagt actcatgtca cccccaaaag ctacctgtca  9540
ttcattcagg ggtacaaatt catctacgga gagaaacacg tggaggtgcg gactctggcc  9600
aatcgcatga acaccgggct ggagaagctc aaggaagcga gcgagagcgt ggccgccttg  9660
tccaaggaac tcgaggccaa ggaaaaagag ctccaggtag ccaatgacaa ggccgatatg  9720
gtgctgaagg aggtcaccat gaaagcacag gcagcagaga aagtcaaggc ggaagtccaa  9780
aaggtgaagg accgggccca ggccatcgtc gactcgatct ccaaggataa ggccattgcc  9840
gaggaaaaat tagaggcggc gaagccggct ctcgaggaag cggaagctgc cctgcaaacc  9900
atcagaccct ccgacatcgc caccgtgagg actctgggcc gccctccgca tcttatcatg  9960
cggatcatgg actgcgtcct gctcctgttc cagcgaaagg tgtccgccgt gaagatcgat  10020
ctcgagaagt cgtgtaccat gccctcgtgg caggaatcgc tcaaattgat gacggccgga  10080
aacttcctgc aaaatctgca gcagttccct aaagacacta tcaacgagga agtgatcgaa  10140
ttcctctcgc cgtacttcga gatgccggac tacaacatcg aaaccgctaa acgggtctgc  10200
ggcaacgtcg ccggtctttg ctcctggacc aaggcgatgg cctccttctt ctcgattaac  10260
aaggaggtgc tgcctctcaa ggccaacctc gtcgtgcaag aaaacagaca cctactagcg  10320
atgcaagacc ttcagaaggc acaggccgag ctggacgaca agcaagcaga actggacgtc  10380
gtgcaggccg agtacgagca agccatgacc gagaagcaga ctctgctaga ggacgccgag  10440
cgctgtcggc acaaaatgca aaccgcgtcc acccttattt cgggattggc aggagaaaag  10500
gaacggtgga ctgaacagag ccaagaattt gccgcgcaaa ccaagagact tgtgggcgac  10560
gtgctcctgg ccactgcctt cctgagctat tccggacctt tcaatcagga attccgcgac  10620
ctcctgctga atgactggcg gaaggagatg aaggcacgca agatcccttt cggaaagaac  10680
ttgaacctct ccgagatgct tatcgacgcg cctaccattt ccgaatggaa cctccaggga  10740
ctgccgaatg acgatctcag cattcaaaac gggatcatcg tgacgaaggc cagccgctac  10800
cccctgctca tcgaccccca gactcagggg aagatttgga tcaagaacaa ggaaagccgg  10860
aacgaactcc aaattaccag ccttaaccac aagtactttc gcaaccacct cgaggacagc  10920
ctttccttgg gcagaccttt actgatcgag gatgtgggag aggaactgga ccctgccctt  10980
gataacgtac tggaaagaaa ctttatcaag actggctcta ctttcaaagt gaaagtgggt  11040
gacaaggaag tggatgtgct ggacgggttc cggctgtaca tcaccaccaa gctccccaat  11100
ccagcctaca cccctgaaat ctccgcccgg actagcatca ttgatttcac cgtgactatg  11160
aagggccttg aggaccaact gctgggcaga gtcattctga ccgagaaaca ggaactggaa  11220
aaggaaagga cgcatcttat ggaggacgtc actgcgaaca agcggcggat gaaggagttg  11280
gaagataact tgctctaccg gctgaccagc acccagggaa gcctcgtgga ggatgaatca  11340
ctcatcgtgg tcctcagcaa caccaagagg actgcagagg aagtgaccca gaagttggaa  11400
attagcgcag aaacggaggt gcagatcaat agtgctcggg aggaatacag gcccgtcgcg  11460
accaggggga gcatcctgta cttcctgatt actgaaatgc gcctggtcaa tgaaatgtac  11520
cagacgtccc tgcgccaatt cctggggctt tttgacttgt ccctcgctag gtcggtgaag  11580
tcccctatca cgtccaaaag aattgcaaac attattgaac acatgacgta cgaagtctac  11640
aagtatgcag ccagaggtct gtacgaggaa cacaagttcc ttttcaccct tctgctgacc  11700
ctgaagattg atatccagcg caatagggtg aaacatgaag agttcctcac cctgatcaaa  11760
ggtggcgctt ccctcgattt gaaggcatgt ccgcctaagc cttcaaagtg gatcctggat  11820
attacgtggc tcaatctcgt ggaactgtcc aagttgcgac agtttagtga cgtgctggac  11880
cagatttccc gcaatgaaaa gatgtggaag atctggttcg ataaggaaaa ccccgaagag  11940
gagccgctgc ccaacgccta cgacaagtcg ctggattgct ttcggaggtt actcctgatt  12000
agatcgtggt gcccggatcg caccatcgct caggccagga agtacatagt ggactcgatg  12060
ggggaaaaat acgccgaagg agtcattttg gacctcgaaa agacttggga ggagtccgac  12120
cctcgcactc cgctgatctg cctgcttagc atgggctcgg accctactga ttcgatcatt  12180
```

-continued

```
gccttgggga agcgcctcaa gatcgaaacc agatacgtgt cgatgggcca aggtcaagag  12240
gtgcacgcgc ggaaactcct ccagcagacc atggcgaacg gcggctgggc gctgctgcag  12300
aactgccacc tcgggctgga cttcatggac gagctgatgg acatcattat cgaaaccgag  12360
ctggtgcacg acgcgttccg cctttggatg accaccgagg cccataagca atttcccatc  12420
acactcctcc aaatgtccat caagtttgcc aacgaccctc cgcagggtct gcgggctggt  12480
ctgaagagga cttattccgg agtcagccag gacctcctag atgtcagcag cggatcccaa  12540
tggaagccaa tgttgtacgc cgtggccttt ttgcactcca ccgtccagga aaggaggaag  12600
ttcggagcct tagggtggaa tatcccgtac gaattcaacc aggccgattt caatgctact  12660
gtccagttca tccagaatca tctggacgat atggacgtaa agaagggagt gtcgtggacg  12720
acgattcgct acatgattgg tgagattcag tacgggggc gggtcactga cgactatgat  12780
aagaggcttc tcaatacctt tgcgaaggtc tggttctccg aaaacatgtt cggcccccgat  12840
ttctccttct accaaggtta caatatcccg aagtgctcga ccgtggacaa ctacctccag  12900
tacattcaga gccttcctgc ctacgactcc ccggaagtgt tcggcctgca ccctaacgcg  12960
gacattacgt atcaaagcaa gctggccaaa gacgtgctgg acactattct cggaatccag  13020
cctaaggaca catcgggagg aggcgatgaa acccgcgaag ccgtggtggc gcggctggcg  13080
gatgacatgt tggagaagtt gccaccggac tacgtgccat tcgaagtgaa agaaaggctg  13140
caaaagatgg gaccgtttca acccatgaac attttcctta gacaggaaat tgatagaatg  13200
caaagggtcc tgtcgctcgt tagatccacg ctgaccgagt taaagctggc tatcgacggc  13260
accattatca tgagcgagaa tctccgggac gctctcgact gcatgttcga tgcaaggatt  13320
ccggcttggt ggaagaaggc gagctggatt agctccactt tgggcttttg gttcactgaa  13380
ctcattgaac ggaactccca gtttacttcg tgggtcttta acggtaggcc acactgcttt  13440
tggatgactg gattctttaa cccccagggc ttccttaccg ctatgcggca ggagattacc  13500
agagccaaca agggttgggc actggacaac atggtgcttt gtaacgaagt gaccaagtgg  13560
atgaaggacg atattagcgc tcccccgacc gaaggggtct acgtctacgg actctacctg  13620
gaagggggccg gttgggacaa aagaaacatg aagctcattg agtctaagcc caaggtcctc  13680
ttcgaactca tgccagtcat tcgcatttac gccgaaaata acactctccg cgatcctcgg  13740
ttctactcat gcccgatcta caagaagccc gtgagaactg acttgaatta catcgctgcc  13800
gtggacctca gaacggccca gacccccgaa cactgggtcc tgagaggggt ggcactgctg  13860
tgcgatgtca agtag                                                   13875

SEQ ID NO: 24          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 24
atgttcagaa tcggaaggag acaactatgg aagcacagcg tgacgcgggt acttacccaa  60
cgtctaaagg gggagaagga ggcgaagcgg gcactgctag acgcgcgtca taattacctc  120
tttgcaatag ttgccagctg cctcgacctc aacaagacgg aggtagagga cgccatatta  180
gagggcaacc agattgagcg gatcgatcag ctatttgccg tgggcgggct ccggcatcta  240
atgtttttact accaggacgt cgaggaagct gagaccgggc aactgggatc cctgggaggc  300
gtcaacctcg tctccggcaa gataaaaaag cctaaggttt tcgttacaga gggcaacgac  360
gtagcgctga ctggtgtatg cgtcttcttc atacggacag accccagcaa ggcgattacg  420
ccagacaaca tccaccagga ggtctcgttt aacatgctcg acgccgccga tggcgggctg  480
ctgaactcgg tgcgccggct gctctcggat atctttatcc ccgcgcttcg ggcgacgagc  540
cacgggtggg gtgagctgga aggcctacag gacgcggcca atattcgtca ggagttccta  600
tccagcctgg aaggttttgt taacgtgctg tccggcgccc aggagtcgct taaggagaag  660
gtgaacttac gaaagtgtga tatattagag ctgaaaaccc tgaaggaacc tacagactat  720
ctcaccctcg caaacaaccc cgaaaccctc ggcaaaattg aagattgcat gaaggtgtgg  780
attaagcaga cggaacaagt cctggcagag aacaaccaac tcttgaagga ggccgacgac  840
gtgggcccgc gcgctgagct ggagcactgg aagaagaggc tcagcaagtt taactatctt  900
cttgagcagc tgaagagccc ggacgttaag gcggtactag cggtcctcgc ggctgcgaag  960
tcgaagctgc tcaagacctg gcgtgagatg gacatacgca tcacggacgc aaccaacgaa  1020
gctaaggaca acgttaagta tttgtatacc ctcgagaagt gctgcgaccc cctctactca  1080
tctgatccgc tcagtatgat ggatgccatc cccacgctaa ttaacgccat taagatgatc  1140
tactcgatat cgcactatta caacacgtct gaaaaaatca ccagcctctt cgtaaaagtg  1200
actaaccaaa tcattagcgc ctgcaaggct tacatcacta acaacggcac cgccagtata  1260
tggaaccagc cccaggacgt cgtggaggag aagatcctat cggccataaa gctgaagcag  1320
gagtatcagc tgtgcttcca caaaaccaag cagaaactca agcagaaccc aaatgctaag  1380
cagttcgact tttctgagat gtatattttc gggaagtttg aaacatttca tcgccgcctg  1440
gccaaaatca tcgacatatt caccactctg aagacctact cagtcctaca agacagcact  1500
atagaagggc tagaggatat ggccacaaag taccagggca tcgtggccac tatcaaaaag  1560
aaggagtaca acttcttaga ccagcgtaaa atggatttcg accaggacta tgaagaattc  1620
tgcaaacaaa cgaatgattt gcacaacgag cttcggaaat tcatggatgt gacttttgcc  1680
aaaatacaga ataccaacca agctcttagg atgttaaaga aatttgaaag gctcaatatt  1740
cctaatttgg gcattgatga caaataccag ttgatactcg aaaattatgg agcagatatt  1800
gatatgatct ctaaactgta cacaaaacaa aaatatgatc ccccgctagc tagaaatcaa  1860
cctccgattg ctggtaagat actctgggcc agacagctct ttcaccgcat ccagcagccc  1920
atgcagctgt ttcagcagca ccctgcggtg ctgtccaccg ccgaagcgaa acccattatt  1980
cgatcttata accgcatggc caaggttctg ttagagtttg aagttttgtt ccaccgtgcc  2040
tggttacgtc agatcgagga gatccatgtg ggactggagg cctctctcct agtcaaggcc  2100
cccggcacag gcgaactctt tgtcaatttt gatccccaga ttctaatact cttccgggaa  2160
accgagtgca tggcccagat gggcttagag gttagtcctc tggctacttc tctgttccag  2220
aagagagacc gctataaacg gaatttcagc aatatgaaga tgatgctcgc tgaatatcag  2280
agggtcaagt ccaaaatccc cgctgcgatc gagcagctga tagtgccaca cctggccaaa  2340
gtagatgagg ccctacaacc aggactggcc gcgctgacgt ggacctctct gaatatcgaa  2400
gcgtatttgg agaacacctt tgccaagatt aaggacctgg agcttttact ggacagagtg  2460
```

-continued

```
aacgatctca ttgaattccg catagacgcg attttagagg agatgtcttc cacgccacta  2520
tgccagcttc ctcaggagga gcctttaaca tgtgaagagt tccttcagat gactaaggac  2580
ctctgcgtga atggcgctca gatactacat ttcaagtcta gcttggtcga ggaggcagtg  2640
aacgaattgg ttaacatgtt actggatgta gaagtcctta gcgaggagga atccgaaaag  2700
atcagcaacg aaaattcggt gaactataag aacgaatcta gcgccaagcg ggaggagggc  2760
aactttgata cactcacttc ttccatcaat gcgagggcta atgctctctt gttgacgacc  2820
gttaccagaa aaaaaaagga gactgagatg cttggggaag aggcaaggga gttgctgtcc  2880
cacttcaacc atcagaatat ggacgccctc ttaaaggtta cccgaaacac gttagaggca  2940
attaggaagc gtattcactc aagccacacg ataaacttcc gcgactcaaa ctcagcatca  3000
aatatgaagc aaaactcctt gccgatcttc agagccagcg tcaccctggc catacctaac  3060
atcgttatgg caccggcact tgaggacgta caacaaacct tgaacaaagc agtagagtgc  3120
atcatcagcg tccctaaagg agttcgccaa tggtccagtg aactgctatc caagaagaag  3180
atccaggagc gtaaaatggc tgcgttacag agtaacgaag attcggactc tgacgttgaa  3240
atgggtgaaa acgagctcca agacacactg gagattgcga gcgttaacct gcctataccc  3300
gtccagacca agaactacta caaaaacgtg tccgaaaaca aggagatcgt caagctcgtt  3360
tctgtgctca gcaccataat aaattcgact aagaaagaag ttataacttc catggattgt  3420
ttcaaacggt ataaccacat ctggcagaaa ggcaaggaag aagctatcaa gacatttatt  3480
acccagagcc cactactaag cgagttcgag tctcagatcc tctacttcca gaatcttgag  3540
caggagatca acgctgagcc cgaatatgtg tgcgtcggct cgatagccct gtacacggct  3600
gatctgaaat ttgcgctgac cgctgagacg aaggcttgga tggtggtgat tggccgacac  3660
tgcaacaaga agtaccggtc tgaaatggag aacatcttta tgctaatcga ggaatttaac  3720
aaaaagctga accgtcccat taaggatctg gacgacatca ggattgccat ggcggcccta  3780
aaggaaatta gagaggagca gatatccatt gattttcagg ttggccccat cgaagaatca  3840
tatgcccttc tgaatcgata cggtctatta atcgcccgag aggaaataga taaggtggac  3900
acacttcatt atgcatggga gaaactctta gcgcgggccg gcgaagtgca gaataagctc  3960
gtatcgctgc agccatcatt taagaaggag ctcatcagtg ctgtcgaggt ctttctgcag  4020
gactgccacc agttctatct ggattatgac ctgaacggtc cgatggcgag tggtctgaag  4080
ccccaagagg cttcagaccg gcttatcatg ttccaaaatc agttcgacaa tatttaccga  4140
aagtatatca cctatacagg gggtgaagaa ttgtttggtc tcccagccac ccagtatcca  4200
caattattgg aaataaagaa gcagctgaac cttcttcaaa aaatctacac tctctataat  4260
tcggtaattg aaactgttaa ttcctactac gatattctct ggagcgaggt caacattgag  4320
aaaattaata acgaactctt ggagttccaa aacagatgcc gcaagttgcc gagagcgctg  4380
aaggactggc aggcttttct cgaccttaag aaaataatcg atgatttcag tgaatgctgt  4440
cctctcttag aatacatggc gagtaaggct atgatggaga gacactggga gaggattacg  4500
actctgacgg ggcattcttt ggacgttggc aacgagtcct tcaagctgcg taatataatg  4560
gaggctccac ttctcaagta caaagaggaa atagaagaca tctgtatatc tgctgtcaaa  4620
gagcgcgaca tagaacagaa actaaagcag gtaattaacg aatgggacaa taaaacgttt  4680
acatttggca gtttcaagac acgtggagaa ttattgcttc gaggcgactc cacctcggaa  4740
attatcgcta acatggagga ctctctcatg ttactcggct cgctgttatc gaaccggtat  4800
aatatgccat tcaaagcaca gatccagaag tgggtgcagt atctatctaa tagtacggat  4860
ataatagaga gctggatgac cgtccagaat ctctggatct acctggaggc ggtgtttgtg  4920
ggaggtgata tagcgaagca gcttccaaag gaggccaaaa gattctccaa cattgacaaa  4980
tcctgggtca agattatgac tcgggcccac gaagtgccct ccgtggtgca gtgctgcgtc  5040
ggggacgaaa ccttgggcca gctgttgccc cacctgttgg atcaattgga aatctgccaa  5100
aagagcctga ctggctacct agagaaaaag cgtctgtgct ttccccggtt cttcttcgtt  5160
tctgaccctg cactactcga aatcttgggt caggcctctg attctcacac aattcaggct  5220
catttgttaa atgtgtttga caacatcaaa agtgtgaaat ttcatgaaaa gatttatgac  5280
aggatcttgt ccatttcatc ccaagaggga gaaaccattg agcttgataa gcctgtgatg  5340
gcagagggaa acgtggaggt ctggcttaac agtctcctgg aagagtccca gtcctcactg  5400
cacctggtca tccgccaggc ggcggctaat atccaggaga caggattcca gctcacggaa  5460
ttccttagtt cgtttccggc gcaagtgggg ctcctcggca ttcagatgat ctggacgaga  5520
gattcggagg aagccctccg caacgccaag tttgacaaga agattatgca gaaaactaac  5580
caagccttcc tagagctcct caacactctg atcgatgtca caactcgtga tctatcgtct  5640
accgagcggg tcaagtatga gacactgatt accatacacg ttcaccagcg tgatatattc  5700
gatgatctat gccacatgca cataaagagt cccatggact tcgaatggct aaaacagtgc  5760
aggttctact ttaatgaaga ctcggataag atgatgatcc atatcacaga tgtagcgttt  5820
atttaccaaa acgagttcct tggctgcaca gacaggttag tcataactcc gttaactgat  5880
cgctgctaca ttacactcgc ccaagcgctt ggaatgtcca tgggtggagc cccccgcaggg  5940
ccggcgggga caggtaagac cgaaacaact aaagatatgg gccgttgcct cgggaagtat  6000
gtagtagttt ttaactgctc agaccaaatg gatttccgag ggctgggccg tatctttaaa  6060
gggctggcgc aatccggttc ctggggctgt tttgacgagt tcaatcgtat tgatttaccg  6120
gtgctaagtg ttgccgcaca gcaaattagt ataattttga catgtaagaa agaacacaag  6180
aaaagtttta tatttactga cggcgacaac gtcactatga atcctgaatt cgggcttttc  6240
ttgactatga acccagggta tgctggccgt caagaacttc ctgaaaatct gaaaatcaac  6300
tttcgatcgg tggctatgat ggtaccggac cgccagatca tcatccgggt aaaactggcc  6360
tcgtgtggct tcatcgacaa cgtcgtactt gctcgaaagt tcttcaccct ttacaagcta  6420
tgtgaggagc agttatcgaa acaagttcat tacgactttg ggctccggaa tatcttgtcc  6480
gtcttacgca cactcggagc ggctaaacgt gcaaatccca tggacactga gagtacgatt  6540
gtgatgcgag tgttaaggga tatgaatctc tcaaaattaa tagacgagga cgagcctctt  6600
tttctcagcc ttatagagga tctgttccca aacatcctcc tggacaaggc tggatatccc  6660
gagttggaag cggcgattag caggcaggtg gaggaggccg gattgattaa tcacccgccc  6720
tggaaactga aagtcatcca gctgttcgag actcagcggg tccgacacgg tatgatgact  6780
ttaggcccat ctggcgcggg gaaaaccacc tgcatccaca ccctgatgag ggctatgacc  6840
gattgtggga agcctcaccg tgagatgcgg atgaacccga aggcgatcac agcgccccaa  6900
atgtttgggc gtctggatgt ggcgacaaat gactggaccg atggaatctt ttccacactc  6960
tggaggaaga ccctgcgcgc aaaaaaagga gagcacatct ggatcattct cgatggcccc  7020
gttgacgcta tttggatcga aaacttaaac agcgtgctcg acgacaacaa gaccctgaca  7080
ttggcaaatg gtgaccggat tcctatggct cccaattgca aaatcatttt tgaacctcac  7140
aacatcgaca acgccagtcc ggctacggtg tcccgcaacg gtatggtttt catgagcagt  7200
```

-continued

```
tccatactgg attggagtcc gatattggaa ggatttctca agaaacgcag tccccaggag  7260
gcggaaattc tgcggcaact gtatacggaa agtttcctg acctgtaccg tttctgtatt  7320
caaaatctcg agtataagat ggaggtgttg gaggccttcg tcatcacaca gtccattaac  7380
atgcttcagg gcttgatccc cttgaaggag caaggagggg aagtcagcca ggcacatcta  7440
gggcggcttt tcgttttcgc ccttctctgg tccgcgggtg ctgctctcga gctagacggt  7500
cgccggcgct tggagttgtg gctgaggtct cgcccgaccg ggacactcga gctgccgccg  7560
ccagccggac ccggggacac ggcattcgac tactacgttg ctccggacgg cacctggacc  7620
cactggaaca cccgtacgca ggagtatctc tatcccagcg atacaactcc tgagtatggt  7680
agcatactcg ttccgaacgt agacaacgtc agaaccgact ttctgatcca gaccattgct  7740
aagcagggca aggcagtcct attgatcgga gagcaaggga ccgcgaaaac cgtgattatc  7800
aagggcttca tgagtaaata tgacccagag tgtcatatga ttaagtccct caacttcagt  7860
tctgctacca caccactcat gtttcagcgt actatcgaat cctacgtgga caagcggatg  7920
ggcaccacct acgggccgcc tgccgggaag aagatgacgg tatttataga cgacgttaac  7980
atgcccatca tcaacgagtg gggagatcaa gtgacaaacg aaatcgttcg gcaacttatg  8040
gaacaaaacg ggttctataa cctcgagaag ccgggcgagt tcacctcaat agtagacatt  8100
caatttctgg cagctatgat ccatcccgga ggaggacgga acgacattcc ccagcggctc  8160
aagcgccaat tcagcatctt caactgcacg ctgccaagtg aagcatcggt agacaaaatc  8220
ttcggcgtca tcggggtggg tcactactgc acccagcgcg gcttttcaga ggaagtccga  8280
gattctgtta ctaaactggt tcctttgact agaaggctgt ggcagatgac caaaattaag  8340
atgcttccta ctccagctaa attccactac gtgttcaatc tgcgagactt atccagggta  8400
tggcaaggta tgcttaatac cacctctgag gtaattaaag aaccgaacga tctgctgaaa  8460
ctgtggaagc acgaatgtaa gagagttatt gcagataggt ttactgtttc gtcagatgtt  8520
acctggttcg ataaagccct ggtgtctttg gtcgaagaag agtttgggga agagaagaag  8580
ctactcgtcg attgcgggat cgacacttac tttgtggact tcttaagaga cgcccctgag  8640
gctgccggcg aaacatcgga agaggcagac gctgagactc ctaagatcta tgagccgatc  8700
gagagcttta gccacctcaa ggaacgtctg aatatgtttt tacaattgta taatgagagc  8760
attcgtggtg ctgggatgga tatggtgttc ttcgcggatg caatggtgca tctggtaaag  8820
atttctcggg tgattcgcac gccacaggga aacgcgctac tggtcggggt gggtgggtca  8880
ggaaagcaat cgttaactcg tttggcatcc tttatcgcgg gatatgtgag ttttcaaatc  8940
accctgacaa ggtcctataa tacatccaac ctgatggagg atcttaaagt tctctacagg  9000
acggcgggac aacagggcaa aggaataacc ttcatcttca cagataacga aattaaagac  9060
gaatcattct tggagtatat gaacaacgtc ttatcaagcg gcgaagtttc gaacctcttc  9120
gcgcgggacg aaatcgatga gatcaactct gatctcgctt ctgtcatgaa gaaagaattc  9180
ccccggtgtt tgccgacgaa tgagaacttg catgactatt tcatgtcccg tgtgcggcag  9240
aatttgcaca ttgtgctttg cttttcaccg gtgggggaga agttccgaaa tagagctttg  9300
aagttccctg ctttgatttc tgggtgcact attgactggt ttcccgttgg gcccaaggac  9360
gctctggtcg ccgtgtccga gcacttttta accagctatg atatcgactg cagcctcgaa  9420
attaagaagg aagtagttca gtgtatgggc tctttccaag acggtgtggc agagaagtgc  9480
gtcgactatt tccagaggtt tcgccgatct actcatgtca cacctaagag ctacttgtcc  9540
ttcatacagg ggtacaagtt tatatatggg gagaaacacg ttgaagtaag gactctggca  9600
aaccgtatga atactggctt agagaagctc aaggaggcct cagaaagtgt ggctgctctc  9660
tcaaaggagc ttgaagctaa ggagaaggaa ctccaagttg cgaacgataa agcggatatg  9720
gttctaaaag aagtgactat gaaagcacaa gcggctgaaa aggttaaggc ggaggtacag  9780
aaggtgaagg atcgcgccca ggcaatagtc gattccattt ccaaagacaa ggccatcgcg  9840
gaagaaaagc tagaagccgc caagccggcc ttagaagagg cagaggctgc cttgcaaacc  9900
ataagaccga gtgacatcgc gacggtacga acccttggtc gtcctcctca tttgattatg  9960
aggattatgg actgtgtcct gcttttattt caacgtaaag tatctgcagt taagattgat  10020
ttggaaaaat cctgtaccat gccctcatgg caggaatccc tgaaattgat gaccgcgggc  10080
aatttccttc aaaatctaca acaattcccc aaggacacca ttaacgaaga ggtcatagaa  10140
tttttatctc catattttga gatgccagat tacaatattg aaacagcgaa gcgcgtctgt  10200
ggtaacgtag caggtctctg ttcgtggacc aaagctatgg cctccttctt tagtatcaat  10260
aaagaggtac ttccactgaa agccaacctg gtggtacagg agaaccggca tctgcttgct  10320
atgcaggatc ttcagaaggc ccaggccgaa ttagacgaca aacaggctga gcttgacgtt  10380
gtgcaagcag aatacgaaca agctatgact gaaaagcaga ctttattaga ggacgctgaa  10440
cgctgcagac ataagatgca gactgcaagc accctcatat ccgggttggc tggagaaaaa  10500
gaacggtgga cagagcagtc gcaagaattc gctgctcaaa ccaaaaggtt ggttggagac  10560
gttctactcg cgacagcttt tctctcctat tctggtcctt tcaaccagga attccgggac  10620
cttttgctga atgactggag aaaagaaatg aaggctcgca aaataccatt tggtaagaat  10680
ttgaacttgt ctgaaatgct tattgacgca cccactatat cagagtggaa tcttcaggga  10740
cttccaaatg acgatctgtc catccaaaac ggaattattg taaccaaggc gagtcgctac  10800
cctctgctca ttgacccgca gacacagggc aagatctgga ttaaaaataa ggaaagcagg  10860
aacgaactcc agatcacaag tctcaaccac aagtacttcc gtaaccacct cgaagatagt  10920
ctgtccctgg gacggccgtt gctaatcgag gacgttggag aagagctgga ccccgcatta  10980
gacaacgtcc ttgaaagaaa ttttatcaag acaggatcaa cttttaaagt taaagtagga  11040
gataaagaag tggatgtgtt agatggcttc cgcctatata tcacaactaa actcccgaat  11100
cccgcctata ctccagagat cagcgctaga actagcatca tagatttcac tgtaactatg  11160
aaggggttag aagatcaatt attaggacgc gtgatcctga cggagaaaca ggaattggaa  11220
aaagagcgta cacacctcat ggaagacgtg acagctaaca aacgacggat gaaggaactg  11280
gaggacaatt tactgtatcg gttgacatca acacagggct cccttgttga ggacgagagt  11340
ctgatcgtgg tcctgtctaa cacaaagagg actgctgaag aagtaactca gaaattggag  11400
atttctgccg aaactgaagt tcagattaac tccgctagag aagagtatcg tccagtcgct  11460
actcggggct ctatcctata cttcctcata actgagatgc gcttggtcaa tgaaatgtac  11520
cagacttcac tccggcaatt cctgggcttg tttgacttgt cgctggcaag atcagtaaaa  11580
tctccaatta ccagcaagag aatcgcaaac atcattgagc acatgacgta cgaggtgtat  11640
aaatacgcgg cgaggggtct ttatgaagag cataagttcc tcttcaccct actattaacg  11700
ttgaagatag atattcagag gaaccgggtg aagcacgagg agtttctaac tctaataaaa  11760
ggaggagcta gtttagattt gaaagcctgt ccaccgaaac cttctaagtg gattttagac  11820
ataacatggc tgaatttagt ggagttgtcc aagttacgtc agttcagtga cgtattggat  11880
cagatatcca ggaacgagaa gatgtggaag atctggttcg ataaagagaa tccggaggag  11940
```

```
gagcccttgc caaatgctta tgataaatca ctagactgct tcaggaggtt gttgctcatc  12000
cgctcctggt gccccgaccg cactattgcc caagctagga aatacattgt ggactccatg  12060
ggggagaagt atgccgaggg agtcatactc gacctggaaa agacttggga agagtcagat  12120
ccgaggacgc ccctcatttg tcttctttcc atgggttctg atcccacgga ctctattata  12180
gcactcggga aaagactaaa gatcgagaca cgctatgtta gcatgggaca ggggcaagag  12240
gtccatgccc gcaaactact acagcaaact atggctaatg gaggttgggc tctgttacag  12300
aactgtcact taggcctgga ttttatggac gaattgatgg acataataat tgagacggag  12360
ctagtccacg acgcatttcg cttatggatg acgactgaag cacacaagca gtttccgatt  12420
accctgttgc agatgtccat caagttcgca aatgaccctc ctcagggcct tagggcaggt  12480
ctcaaaagga cctacagcgg cgtttcccag gatttacttg acgtcagctc cggatcccag  12540
tggaagccca tgctctacgc tgtggctttc cttcacagca cagttcaaga aaggcggaag  12600
tttggtgcgc taggctggaa catcccctac gagttcaacc aagctgattt taatgcaaca  12660
gtacagttta ttcaaaatca tctggatgac atggatgtta aaaaaggtgt gtcatggact  12720
acaataaggt acatgattgg ggagattcag tacggaggac gggtaactga tgattatgac  12780
aagcggctac tgaacacatt cgctaaagtg tggttttctg agaatatgtt cggtccagat  12840
ttcagcttct accaaggtta caatataccc aagtgctcca cggtcgacaa ctaccttcag  12900
tacatccaga gcttgcccgc gtacgacagc ccggaagtct tcggactcca ccccaacgcc  12960
gacatcacgt accagagcaa gctggccaag gacgtgcttg acaccattct cggcatccag  13020
ccgaaggaca cgtccggcgg gggggacgag acgcgggagg ccgtcgtcgc gcgcttggca  13080
gatgacatgc tggagaagct cccccccgat tacgtcccgt ttgaggtcaa ggaaaggctc  13140
cagaagatgg gcccgttcca gcccatgaac atcttcctcc gccaggagat cgaccggatg  13200
cagcgcgtgc ttagcctggt gcgctcaacg ctgaccgagc tgaagctggc catcgacggg  13260
acgatcatta tgtcggagaa cctccgggac gcgctggact gcatgttcga cgcgcgtatc  13320
ccggcctggt ggaagaaggc gtcgtggatc tccagcaccc tggggttctg gttcacggag  13380
ctgatcgagc gcaactcgca attcacctcc tgggtgttca acgggcggcc ccactgcttc  13440
tggatgacgg gcttctttaa cccgcagggc ttcctgacgg ctatgcggca ggaaatcacc  13500
cgggcgaaca agggttgggc gctcgacaat atggtgctct gcaacgaggt cacgaagtgg  13560
atgaaggacg acatctcggc gcctcccacc gaaggggtct acgtctatgg cctgtacctc  13620
gagggggcgg gctgggacaa gcgtaacatg aagctgatcg agtcgaagcc caaggtcctg  13680
ttcgagctga tgcccgtcat ccgcatctac gcagaaaaca acacgctgcg cgacccgcgg  13740
ttctactcgt gccccatcta caagaagccg gtgcggacgg acctcaacta catcgccgcc  13800
gtcgacctcc gcaccgcgca gacccccgag cactgggtgc tgcggggggt cgcactgctc  13860
tgcgacgtca agtag                                                   13875
```

```
SEQ ID NO: 25          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 25
atgttcagaa tcggaaggag acaactatgg aagcacagcg tgacgcgggt acttacccaa  60
cgtctaaagg ggagaagga ggcgaagcgg gcactgctag acgcgcgtca taattacctc  120
tttgcaatag ttgccagctg cctcgacttg aacaagacgg aggtagagga cgccatatta  180
gagggcaacc agattgaacg gatcgatcag ctatttgccg tgggcgggct ccggcatcta  240
atgtttttact accaggacgt cgaggaagct gagaccggcc aactgggatc cctgggaggc  300
gtcaacctcg tctccggcaa gataaaaaag cctaaggttt tcgttacaga gggcaacgac  360
gtagcgctga ctggtgtatg cgtcttcttc atacggacag acccctcaaa ggcaattacg  420
ccagacaaca tccaccagga ggtctcgttt aacatgctcg acgccgccga tggcgggctg  480
ctgaactcgg tgcgccggct gctctcggat atctttatcc ccgcgcttcg ggcgacgagc  540
cacgggtggg gtgagctgga aggcctacag gacgcggcca atattcgtca ggagttccta  600
tccagcctgg aaggttttgt taacgtgtta tccggcgccc aggagtcgct taaggagaag  660
gtgaacttac gaaagtgtga tatattagag ctgaaaaccc tgaaggaacc tacagactat  720
ctcaccctcg caaacaaccc cgaaacactc ggcaaaattg aagattgcat gaaggtgtgg  780
attaagcaga cggaacaagt cctggcagag aacaaccaac tcttgaagga ggccgacgac  840
gtgggcccgc gcgctgagct ggagcactgg aagaagaggc tcagcaagtt taactatctt  900
cttgagcagc tgaagagccc ggacgttaag gcggtactag cggtcctcgc ggctgcgaag  960
tcgaagctcc tcaagacctg gcgtgagatg gacatacgca tcacggacgc gaccaacgaa  1020
gctaaggaca acgttaagta tttgtatacc ctcgagaagt gctgcgaccc cctctactca  1080
tctgatccgc tcagtatgat ggatgccatc cccacgttga ttaacgccat taaaatgatc  1140
tactcgatat cgcactatta caacacgtct gaaaaaatca ccagcctctt cgtaaaagtg  1200
actaaccaaa tcattagcgc ctgcaaggct tacatcacta acaacggcac cgccagtata  1260
tggaaccagc cccaggacgt cgtggaggag aagatcctat cggccataaa gctgaagcag  1320
gagtatcagc tgtgcttcca caaaaccaag cagaaactca agcagaaccc aaatgctaag  1380
cagttcgact tctctgagat gtacatttc gggaagtttg aaacatttca tcgccgcctg  1440
gccaaaatca tcgacatatt caccactctg aagacctact cagtcctaca agatagcact  1500
atagaagggc tagaggatat ggccacaaag taccagggca tcgtggccac tatcaaaaag  1560
aaggagtaca acttcttaga ccagcgtaaa atggatttcg accaggacta tgaagaattc  1620
tgcaaacaaa cgaatgattt gcacaacgag cttcggaaat tcatggatgt gacttttgcc  1680
aaaatacaga ataccaacca agctcttagg atgttaaaga aatttgaaag gctcaatatt  1740
cctaatttgg gcattgatga caaataccag ttgatactcg aaaattatgg agcagatatt  1800
gatatgatct ctaaactgta cacaaaacaa aaatatgatc ccccgctagc tagaaatcaa  1860
cctccgattg ccggtaagat actctgggcc agacagctct ttcaccgcat ccagcagccc  1920
atgcagctgt ttcagcagca ccctgcggtg ctgtccaccg ccgaagcgaa acccattatt  1980
cgatcttata accgcatggc caaggttctg ttagagtttg aagttttgtt ccaccgtgcc  2040
tggttacgtc agatcgagga gatccatgtg ggactggagg cctctctcct agtcaaggcc  2100
cccggcacag gcgaactctt tgtcaatttt gatccccaga ttctaatact cttccgggaa  2160
accgagtgca tggcccagat gggcttagag gttagtcctc tggctacttc tctgttccag  2220
```

-continued

```
aagagagacc gctataaacg gaatttcagc aatatgaaga tgatgctcgc tgaatatcag  2280
agggtcaagt ccaaaatccc cgctgcgatc gagcagctga tagtgccaca cctggccaaa  2340
gtagatgagg ccctacaacc aggactggcc gcgctgactt ggacctctct gaatatcgaa  2400
gcgtatttgg agaacacctt tgcaaagatt aaggacctgg agcttttact ggacagagtg  2460
aacgatctca ttgaattccg catagacgcg attttagagg agatgtcttc cacgccacta  2520
tgccagcttc ctcaggagga gcctttaaca tgtgaagagt tccttcagat gactaaggac  2580
ctctgcgtga atggcgctca gatactacat ttcaagtcta gcttggtcga ggaggcagtg  2640
aacgaattgg ttaacatgtt actggatgta gaagtcctta gcgaggagga atccgaaaag  2700
atcagcaacg aaaattcggt gaactataag aacgaatcta gcgccaagcg ggaggagggc  2760
aactttgata cactcacttc ttccatcaat gcgagggcta atgctctctt gttgacgacc  2820
gttaccagaa aaaaaaagga gactgagatg cttggggaag aggcacgtga gttgctgtcc  2880
cacttcaacc atcagaatat ggacgccctc ttaaaggtta cccgaaacac gctagaggca  2940
attaggaagc gtattcactc aagccacacg ataaacttcc gcgactcaaa ctcagcatca  3000
aatatgaagc aaaactcctt gccgatcttc agagccagcg tcaccctggc catacctaac  3060
atcgttatgg caccggcact tgaggacgta caacaaacct tgaacaaagc agtcgagtgc  3120
atcatcagcg tccctaaagg agttcgccaa tggtccagtg aactgctatc caagaagaag  3180
atccaggagc gtaaaatggc tgcgttacag agtaacgaag attcggacag cgacgttgaa  3240
atgggtgaaa acgagctcca agacacactg gagattgcga gcgttaacct gcctataccc  3300
gtccagacca agaactacta caaaaacgtg tccgaaaaca aggagatcgt caagctcgtt  3360
tctgtgctca gcaccataat aaattcgact aagaaagaag ttataacttc catggattgt  3420
ttcaaacggt ataaccacat ctggcagaaa ggtaaggaag aagctatcaa gacatttatt  3480
acccagagcc cactactaag cgagttcgag tctcagatcc tctacttcca gaatttagag  3540
caggagatca acgctgagcc cgaatatgtg tgcgtcggct cgatagccct gtacacggct  3600
gatctgaaat ttgcgctgac cgctgagacg aaggcttgga tggtggtgat tggccgacac  3660
tgcaacaaga agtaccggtc tgaaatggag aacatcttta tgctaatcga ggaatttaac  3720
aaaaagctga accgtcccat taaggatctg gacgacatca ggattgccat ggcggcccta  3780
aaggaaatta gagaggagca gatatccatt gattttcagg ttggccccat cgaagaatca  3840
tatgcccttc tgaatcgata cggtctatta atcgcccgag aggaaataga taaggtggac  3900
acacttcatt atgcatggga gaaactctta gcgcgggccg gcgaagtgca gaataagctc  3960
gtatcgctgc agccatcatt taagaaggag ctcatcagtg ctgtcgaggt ctttctgcag  4020
gactgccacc agttctatct ggattatgac ctgaacggtc cgatggcgag tggtctgaag  4080
ccccaagagg cttcagaccg gcttatcatg ttccaaaatc agttcgacaa tatttaccga  4140
aagtatatca cctatacagg gggtgaagaa ttgtttggtc tcccagccac ccagtatcca  4200
caattattgg aaataaagaa gcagttgaac cttctccaaa aaatctacac tctctataat  4260
tcggtaattg aaactgttaa ttcctactac gatattctct ggagcgaggt caacattgag  4320
aaaattaata acgaactctt ggagttccaa aacagatgcc gcaagttgcc gagagcgctg  4380
aaggactggc aggcttttct cgaccttaag aaaataatcg atgatttcag tgaatgctgt  4440
cctctcttag aatacatggc gagtaaggct atgatggaga gacactggga gaggattacg  4500
actctgacgg ggcattcttt ggacgttggc aacgagtcct tcaagctgcg taatataatg  4560
gaggctccac ttctcaagta caaagaggaa atagaagata tctgtatatc tgctgtcaaa  4620
gagcgcgaca tagaacagaa actaaagcag gtaattaacg aatgggacaa taaaacgttt  4680
acatttggca gtttcaagac acgtggagaa ttattgcttc gaggcgactc cacttcggaa  4740
attatcgcta acatggagga ctctctcatg ttactcggct cgctgttatc gaaccggtat  4800
aatatgccat tcaaagcaca gatccagaag tgggtgcagt atctatctaa tagtacggat  4860
ataatagaga gctggatgac cgtccagaat ctgtggatct acctggaggc ggtgttcgtg  4920
ggaggtgata tagcgaagca gcttccaaag gaggccaaaa gattctccaa cattgacaaa  4980
tcctgggtca agattatgac tcgggcccac gaagtgccct ccgtggtgca gtgctgcgtc  5040
ggggacgaaa ccttgggcca gctgttgccc cacctgttgg atcaattgga aatctgccaa  5100
aagagcctga ctggctacct agagaaaaag cgtctgtgct ttccccggtt cttcttcgtt  5160
tctgaccctg cactactcga aatcttgggt caggcctctg attcccacac aattcaggct  5220
catttgttaa atgtgtttga caacatcaaa agtgtgaaat ttcatgaaaa gatttatgac  5280
aggatcttgt ccatttcatc ccaagaggga gaaaccattg agcttgataa gcctgtgatg  5340
gcagagggaa acgtggaggt ctggcttaac agtctcctgg aagagtccca gtcctcactg  5400
cacctggtca tccgccaggc ggcggctaat atccaggaga caggattcca gctcacggaa  5460
ttccttagtt cgtttccggc gcaagtgggg ctcctcggca ttcagatgat ctggacgaga  5520
gattcggagg aagccctccg caacgccaag tttgacaaga agattatgca gaaaactaac  5580
caagccttcc tagagctcct caacactctg atcgatgtca caactcgtga tctatcgtct  5640
accgagcggg tcaagtatga gacactgatt accatacacg ttcaccagcg tgatatattc  5700
gatgatctat gccacatgca cataaagagt cccatggact tcgaatggct aaaacagtgc  5760
aggttctact ttaatgaaga ctcggataag atgatgatcc atatcacaga tgtagcgttt  5820
atttaccaaa acgagttcct tggctgcaca gacaggttag tcataactcc gttaactgat  5880
cgctgctaca ttacactcgc ccaagcgctt ggaatgtcca tgggtggagc cccgcaggg  5940
ccggcgggga caggtaagac cgaaacaact aaagatatgg gccgttgcct cggaaagtat  6000
gtagtagttt ttaactgctc agaccaaatg gatttccgag ggctggggcg tatctttaaa  6060
gggctggcgc aatccggttc ctggggctgt tttgacgagt tcaatcgtat tgatttaccg  6120
gtgctaagtg ttgccgcaca gcaaattagt ataattttga catgtaagaa agaacacaag  6180
aaaagtttta tatttaccga cggcgacaac gtcactatga atcctgaatt cgggcttttc  6240
ttgactatga acccagggta tgctggacgt caagaacttc ctgaaaatct gaaaatcaac  6300
tttcgatcgg tggctatgat ggtaccggac cgccagatca tcatccgggt aaaactggcc  6360
tcgtgtggct tcatcgacaa cgtcgtactt gctcgaaagt tcttcaccct ttacaagcta  6420
tgtgaggagc agttatcgaa acaagttcat tacgactttg ggctccggaa tatcttgtcc  6480
gtcttacgca cactcggagc ggctaaacgt gccaatccca tggacactga gagtacgatt  6540
gtgatgcgag tgttaaggga tatgaatctc tcaaaactga tagacgagga cgagcctctt  6600
tttctcagcc ttatagagga tctgttccca aacatcctcc tcgacaaggc tggatatccc  6660
gagttggaag cggcgattag caggcaggtg gaggaggccg gattgattaa tcacccgccc  6720
tggaaactga aagtcatcca gctgttcgag actcagcggg tccgacacgg tatgatgact  6780
ttaggcccat ctggcgcggg gaaaaccacc tgcatccaca ccctgatgag ggctatgacc  6840
gattgtggga agcctcaccg tgagatgcgg atgaacccga aggccatcac agcgccgcaa  6900
atgtttgggc gtctggatgt ggcgacaaat gactggaccg atggaatctt ttccacactc  6960
```

-continued tggaggaaga ccctgcgcgc aaaaaaagga gagcacatct ggatcattct cgatggcccc 7020
gttgacgcta tttggatcga aaacttaaac agcgtgctcg acgacaacaa gaccctgaca 7080
ttggcaaatg gtgaccggat tccaatggct cccaattgca aaatcatttt cgaacctcac 7140
aacatcgaca acgccagtcc ggctacggtg tcccgcaacg gtatggtttt catgagctca 7200
tccatactgg attggagtcc gatattagaa ggatttctca agaagcgcag tccccaggag 7260
gcggaaattc tgcggcaact gtatacggaa agttttcctg acctgtaccg tttctgtatt 7320
caaaatctcg agtataagat ggaggtgttg gaggccttcg tcatcacaca gtccattaac 7380
atgcttcagg gtttgatccc cttgaaggag caaggagggg aagtcagcca ggcacatcta 7440
gggcggcttt tcgttttcgc ccttctctgg tccgcgggtg ctgctctcga gctagacggt 7500
cgccggcgct tggagttgtg gctgaggtct cgcccgaccg ggacactcga gctgccgccg 7560
ccagccggac cgggggacac ggcattcgac tactacgttg ctccggacgg cacctggacc 7620
cactggaaca cccgtacgca ggagtacctc tatcccagcg atacaactcc tgagtatggt 7680
agcatactcg ttccgaacgt agacaacgtc cgtaccgact ttctgatcca gaccattgct 7740
aagcagggca aggcagtcct attgatcgga gagcaaggga ccgcgaaaac cgtgattatc 7800
aagggcttca tgagtaaata tgacccagag tgtcatatga ttaagtccct caacttcagt 7860
tctgctacca caccactcat gtttcagcgt actatcgaat cctacgtgga caagcggatg 7920
ggcaccacct acgggccgcc tgccgggaag aagatgacgg tatttataga cgacgttaac 7980
atgcccatca tcaacgagtg gggagatcaa gtgacaaacg aaatcgttcg gcaacttatg 8040
gaacaaaacg ggttctataa cctcgagaag ccgggcgagt tcacctcaat agtagacatt 8100
caatttctgg cagctatgat ccatcccgga ggagggcgga acgacattcc acagcggctc 8160
aagcgccaat tcagcatctt caactgcacg ctgccaagtg aagcatcggt agacaaaatc 8220
ttcggcgtca tcggggtggg tcactactgc acccagcgcg gcttttcaga ggaagtccga 8280
gattctgtta ctaaactggt tcctttgact agaaggctgt ggcagatgac caaaattaag 8340
atgcttccta ctccagctaa attccactac gtgttcaatc tgcgagactt atcgagggta 8400
tggcaaggta tgcttaatac cacctctgag gtaattaaag aaccgaacga tctgctgaaa 8460
ctgtggaagc acgaatgtaa gagagttatt gcagataggt ttactgtttc gtcagatgtt 8520
acctggttcg ataaagccct ggtttctttg gtcgaagaag agtttgggga agagaagaag 8580
ctactcgtcg attgcgggat cgacacttac tttgtggact tcttaagaga cgcccctgag 8640
gctgccggcg aaacatcgga agaggcagac gctgagactc ctaagatcta tgagccgatc 8700
gagagcttta gccacctcaa ggaacgtctg aatatgtttt tacaattgta taatgagagc 8760
attcgtggtg ctgggatgga tatggtgttc ttcgcggatg ccatggtgca tctggtaaag 8820
atttctcggg tgattcgcac gccacaggga aacgcgctac tggtcggggt gggtgggtca 8880
ggaaagcaat cgttaactcg tttggcatcc tttatcgcgg gatatgtgag ttttcaaatc 8940
accctgacaa ggtcctataa tacatccaac ctgatggagg atcttaaagt tctctacagg 9000
acggcgggac aacagggcaa aggtataacc ttcatcttca cagataacga aattaaagac 9060
gaatcattct tggagtatat gaacaacgtc ttatcaagcg gcgaagtttc gaacctcttc 9120
gctagggacg aaatcgatga gatcaactct gatctcgctt ctgtcatgaa gaaagaattc 9180
ccccggtgtt tgccgacgaa tgagaacttg catgactatt tcatgtcccg tgtgcggcag 9240
aatttgcaca ttgtgctttg cttttcaccg gtgggggaga agttccgaaa tagagctttg 9300
aagttccctg cgttgatttc tgggtgcact atcgactggt tttcccgttg gcccaaggac 9360
gctctggtcg ccgtgtccga gcacttttta accagctatg atatcgactg cagcctcgaa 9420
attaagaagg aagtagttca gtgtatgggc tctttccaag acggtgtggc agagaagtgc 9480
gtcgactatt tccagaggtt tcgccgatct actcatgtca cacctaagag ctacttgtcc 9540
ttcatacagg ggtacaagtt tatatatggg gagaaacacg ttgaagtaag gactctggca 9600
aaccgtatga atactggctt agagaagctc aaggaggcct cagaaagtgt ggctgctctc 9660
tcaaaggagc ttgaagctaa ggagaaggaa ctccaagttg cgaacgataa agcggatatg 9720
gttctaaaag aagtgactat gaaagcacaa gcggctgaaa aggttaaggc ggaggtacag 9780
aaggtgaagg atcgcgccca ggcaatagtc gattccattt ccaaagacaa ggccatcgcg 9840
gaagaaaagc tagaagccgc caagccggcc ttagaagagg cagaggctgc cttgcaaacc 9900
ataagaccga gtgacatcgc gacggtacgc acccttggtc gtcctcctca tttgattatg 9960
aggattatgg actgtgtcct gctcttgttc cagcggaagg tgagcgcggt gaaaatcgac 10020
ctagaaaaga gctgtacgat gccgagctgg caggagtccc tcaagctcat gaccgccggg 10080
aacttcttac agaacttgca gcagttcccg aaggacacca taaacgagga ggtgatcgag 10140
tttcttagcc cctactttga gatgcccgac tacaacatcg agaccgcgaa gcgcgtctgc 10200
gggaacgtgg ccggtctctg ctcgtggacc aaggctatgg cctccttctt ttcgataaat 10260
aaggaggtcc tgccgctcaa ggccaacctc gtcgtgcagg agaaccgtca cctactcgct 10320
atgcaggacc tccagaaggc gcaggcggag ttggacgaca aacaggccga gctggacgtc 10380
gtgcaagccg agtacgaaca ggctatgacg gagaagcaga cgctgctaga agacgcggag 10440
cggtgccggc ataaaatgca gacggcgagc acactgattt cgggcctagc aggggagaaa 10500
gagcggtgga cggagcagtc gcaagagttc gccgcccaaa ctaagcgact ggtgggcgac 10560
gtgctcctgg ctactgcttt tttgtcctat tcgggcccct tcaatcaaga gttccgggac 10620
ttgctactca acgactggcg taaggagatg aaggcccgca agatccccttc cgggaagaac 10680
ctgaacctca gtgaaatgct gatagacgcc cccactatct ctgagtggaa tctccagggg 10740
ctgcctaacg acgacctgag catacagaac gggatcatag tcaccaaggc gtcgcgctac 10800
cccctgctga tcgatccgca aacccagggg aagatctgga tcaagaacaa ggagtcccgg 10860
aacgagttgc aaatcacgtc cctcaatcac aagtactttc ggaaccacct agaggactcg 10920
ctgtcgttgg ggcgcccgct tctgattgag gacgttggcg aggagctgga tcctgcgctg 10980
gacaacgttc ttgagcgcaa cttcatcaag accgggtcca ccttcaaggt aaaggtggga 11040
gacaaggagg tcgacgtgct ggacggcttt cgcctatata tcaccacgaa gctgcctaac 11100
ccggcgtaca cgcccgagat cagtgcgcgt acgagcatca ttgacttcac cgtgactatg 11160
aaaggcctcg aagatcagct gctcggtcgc gtcattctca cggaaaagca ggagctggag 11220
aaggagcgaa cacacctgat ggaggacgtg acggccaaca agcggcgtat gaaagagcta 11280
gaggacaacc tgctgtaccg cttgacatca acccaggggt cgctggtcga ggacgaatcc 11340
ctgatcgtgg tgctgagtaa taccaaacgg acagcagaag aggtcacgca gaaactcgag 11400
atctcggcgg agaccgaggt gcagatcaac tccgcgcggg aagagtaccg cccggtggcc 11460
acccgcggga gcatcttgta cttcctgatc actgagatgc ggcttgtgaa tgagatgtac 11520
cagacaagcc tgcggcagtt ccttggcctg ttcgatcttt cgctggcccg gtccgtcaag 11580
tctccgatta cctccaagcg gatcgctaac ataattgaac acatgacgta cgaggtgtac 11640
aagtacgcgg cgcgaggcct ctacgaagag cacaagttcc tgttcacgct gctcctcacg 11700

-continued

```
ctcaagatcg acatccagcg caaccgcgtc aagcacgagg agtttctcac cctgataaag  11760
ggtggagcgt ccctggacct gaaggcctgt ccgccgaagc cgtcgaagtg gatcctggac  11820
ataacgtggc tcaaccttgt cgagctgtcc aagctccgtc agttctcgga cgtgctcgac  11880
cagatttcgc ggaacgagaa gatgtggaaa atttggttcg acaaggaaaa tccagaggag  11940
gagcccttgc ccaacgcgta tgacaagtcg ctcgactgct tccgtcgcct gctgctgatc  12000
cgcagctggt gccccgaccg gacgatcgcg caggcgagga agtacatcgt ggacagtatg  12060
ggtgagaaat atgcggaggg cgttattctg gatctggaga agacttggga ggagagcgac  12120
ccccgcaccc ccctgatctg cctgctgtct atggggtccg acccgaccga tagcatcatt  12180
gcgctgggga aacggctcaa gatcgagacc cggtacgtgt ccatgggtca ggggcaggag  12240
gtgcatgccc gcaagctcct gcagcagact atggcgaacg ggggttgggc gctcttacag  12300
aactgccatc tggggctcga cttcatggat gaactcatgg atatcatcat cgagacggaa  12360
ctcgtgcacg acgcattccg cctgtggatg accaccgagg cgcacaagca gttcccgatc  12420
acgttgctgc agatgtccat caagttcgcc aacgaccctc cgcagggcct ccgggcgggc  12480
ctgaagcgca cgtatagcgg cgtgtctcag gatctccttg atgtcagctc ggggagccag  12540
tggaagccga tgctctatgc cgtggcattt ctacactcga ccgtccagga gcggcgaaag  12600
tttggagcgc tggggtggaa cataccctac gagtttaacc aggccgactt caacgccacc  12660
gtacagttca tccagaacca tttggacgat atggatgtga agaagggggt gtcctggacg  12720
accatacggt acatgatcgg cgagatccag tatgggggcc gggtcacgga cgactacgac  12780
aagcggttgc tgaacacgtt cgcgaaggtc tggttcagcg agaatatgtt cgggcccgat  12840
ttttcctttt accagggcta caatataccc aagtgctcca cggtagacaa ctatcttcag  12900
tacatccaga gccttcccgc gtacgacagc ccggaagtct tcggactcca ccccaacgcc  12960
gacatcacgt accagagcaa gctggccaag gacgtgctcg acaccattct cggcatccag  13020
ccgaaggaca cgtccggcgg gggggacgag acgcgggagg ccgtcgtcgc gcgcttggca  13080
gatgacatgc tggagaagct ccccccccgat tacgtcccgt tcgaggtcaa ggaaaggctc  13140
cagaagatgg gcccgttcca gcccatgaac atcttcctcc gccaggagat cgaccggatg  13200
cagcgcgtgc ttagcctggt ccgctcaacg ctgacggagc tgaagctggc catcgacggg  13260
acgatcatta tgtcggagaa cctccgggac gcgctggact gcatgttcga cgcgcgtatc  13320
ccggcctggt ggaagaaggc gtcgtggatc tccagcaccc tggggttctg gttcacggag  13380
ctgatcgagc gcaactcgca attcacctcc tgggtcttca acgggcggcc ccactgcttc  13440
tggatgacgg gcttcttcaa cccgcagggc ttcctgacgg ctatgcggca ggaaatcacc  13500
cgggcgaaca agggttgggc gctcgacaat atggtgctct gcaacgaggt cacgaagtgg  13560
atgaaggacg acatctcggc gcctcccacc gaaggggtct acgtatacgg cctgtacctc  13620
gagggggcgg gctgggacaa gcgtaacatg aagctgatcg agtcgaagcc caaggtcctg  13680
ttcgagctga tgcccgtcat ccgcatctac gcagagaaca acacgctgcg cgacccgcgg  13740
ttctactcgt gccccatcta caagaagccg gtgcggacgg acctcaacta catcgccgcc  13800
gtcgacctcc gcaccgcgca gacccccgag cactgggtgc tgcggggggt cgcactgctc  13860
tgcgacgtca agtag                                                   13875
```

```
SEQ ID NO: 26           moltype = DNA  length = 13875
FEATURE                 Location/Qualifiers
misc_feature            1..13875
                        note = Synthetic polynucleotide
source                  1..13875
                        mol_type = other DNA
                        organism = synthetic construct
SEQUENCE: 26
atgttcagaa tcggaaggcg tcaactatgg aaacacagcg tcaccagagt actgactcaa  60
cggctcaaag gagaaaaaga ggcgaagcga gcgcttctcg acgcccgaca caattatcta  120
ttcgcgattg tagcatcgtg tcttgacctc aataagacgg aggtggaaga cgccatatta  180
gaaggaaacc agattgagcg gatcgaccaa ttgtttgcgg ttggtggact cagacattta  240
atgttttact atcaagacgt tgaagaagcg gaaactgggc aactcgggtc acttggtgga  300
gttaacctcg tcagcggtaa aattaaaaag ccaaaagtat ttgtcacaga gggaaacgac  360
gttgcactca caggtgtatg tgtattcttt attcggactg atccctcaaa agccataaca  420
ccagataata tacaccagga agtcagcttt aacatgctcg acgccgccga cggcgggctg  480
ctgaactcgg tgcgccggct gctctcggat atctttatcc ccgcgcttag agcgacgagc  540
cacgggtggg gtgagctgga aggcctacag gacgcggcca atatcaggca ggaattcctg  600
tcatccctgg aaggtttgt gaacgtgctc agcggcgcac aggagtcatt gaaagaaaag  660
gtgaacttgc ggaagtgtga cattctggaa ttaaagactt tgaaggagcc aaccgactat  720
ctcaccttgg cgaacaatcc ggagactcta gggaaaatag aggactgcat gaaggtgtgg  780
ataaaacaga ccgagcaagt tttagcagaa aataaccagc tgctgaagga ggcggacgac  840
gtaggccctc gggcggaact tgaacattgg aagaagcggc tgtctaagtt taattacctt  900
ttagaacagt taaaatctcc agatgtcaaa gcagtgcttg cagtcctcgc agctgcaaag  960
tccaaactgc tgaagacgtg gcgtgagatg gacatacgga taactgacgc gaccaatgaa  1020
gccaaggata acgttaagta cctatacacc ctagagaagt gttgtgatcc tctatattcc  1080
tctgatccgc tgtctatgat ggatgcaata cctacgttga tcaacgctat taagatgatt  1140
tacagtatct ctcactatta taatacaagc gaaaaaataa cttccttatt cgtaaaagtc  1200
acgaaccaaa ttatatcagc ctgtaaagca tatataacca ataacggcac ggcatctata  1260
tggaatcagc cccaagacgt ggttgaggaa aaaattctta gtgctataaa actaaagcaa  1320
gagtatcaat tgtgcttcca taagactaag cagaagctaa agcagaaccc aaacgctaag  1380
cagttcgact tctctgagat gtatattttt gggaagtttg aaaccttcca ccgacgtcta  1440
gccaaaatta tcgacatctt tacgacgtta aaaacttaca gcgtgctgca agattctacg  1500
atagaagggc tagaagatat ggccacaaag taccagggca tcgtggccac tatcaaaaag  1560
aaggagtaca acttcttaga ccagcgtaaa atggatttcg accaggacta tgaagaattc  1620
tgcaaacaaa cgaatgattt gcacaacgag cttcggaaat tcatggatgt gacttttgcc  1680
aaaatacaga acaccaacca agctcttagg atgttaaaaa aatttgaaag gctcaatatt  1740
cctaatttgg gcattgatga caaataccag ttgatactcg aaaattatgg agcagatatt  1800
gatatgatct ctaaactgta caccaaacaa aaatatgatc caccgctagc tagaaatcaa  1860
cctccgattg ctggtaagat actctgggcc agacaactct ttcaccgcat ccagcagccc  1920
atgcagctgt ttcagcagca ccctgcggtg ctttccaccg ccgaggcgaa acccattatt  1980
```

-continued

```
cgatcttata accgcatggc caaggttctg ttagagtttg aagttttgtt ccacagagcc  2040
tggttacgtc agatagagga gatccatgtg ggactggagg cctctctcct agtcaaggcc  2100
cccggcacag gcgaactctt tgtcaatttt gatccccaga ttctaatact cttccgggaa  2160
accgagtgca tggcccagat gggcttagag gtttcgcctc tggctacttc tctgttccag  2220
aaaagagacc gctataaacg gaatttcagc aatatgaaga tgatgctcgc tgaatatcag  2280
agggtcaagt ccaagatccc cgctgcgatc gagcagctga tagtgccaca cctggcaaaa  2340
gtagatgagg ccctacaacc aggactggct gcgctgacgt ggacctctct gaatatcgaa  2400
gcgtatcttg agaacacctt tgccaagatt aaagacctgg agcttttact ggacagagtg  2460
aacgatctca ttgaattccg catagacgcg attttagagg agatgtctag cacgccacta  2520
tgccagcttc ctcaggagga gcctttaact tgtgaagagt tccttcagat gactaaggat  2580
ctctgcgtga atggcgctca gatactacat ttcaagtcta gcttggtcga ggaggcagta  2640
aacgaattgg ttaacatgtt actggatgta gaagtcctta gcgaggagga aagcgaaaag  2700
atcagcaacg aaaattcggt gaactataag aacgaatcta gcgccaagcg ggaggagggc  2760
aactttgata cactcacttc ttccatcaat gcgagggcta atgctctctt gttgacgacg  2820
gttaccagga aaaaaaagga gactgagatg cttggtgaag aggcaaggga gctactgtcc  2880
cacttcaacc atcagaatat ggacgccctc ttaaaggtta cccgaaacac gttagaggca  2940
attaggaagc gtattcactc aagccacacg ataaacttcc gagactcaaa ctcagcatca  3000
aatatgaagc aaaactccct gccgatcttc agagccagcg tcaccctggc catacctaac  3060
atcgttatgg caccggcact tgaggacgta caacaaacct tgaacaaagc agtagagtgc  3120
atcatcagcg tccctaaagg agttcgccaa tggtccagtg aactgctatc caagaagaag  3180
atccaggagc gtaaaatggc tgcgttacag agtaacgaag attcggactc tgacgttgaa  3240
atgggtgaaa acgagctcca agacacactg gagattgcga gcgttaacct gcctatacca  3300
gtccagacca agaactacta caaaaacgtg tccgaaaaca aggagatcgt caagctcgtt  3360
tctgtgctca gcaccatcat aaattcgact aagaaagaag ttataacttc catggattgt  3420
ttcaaacggt ataaccacat ctggcagaaa ggcaaggagg aagctatcaa gacatttatt  3480
acccagagcc cactactaag cgagttcgag tctcagatcc tctacttcca gaatcttgag  3540
caggagatca acgctgagcc cgaatatgtg tgcgtcggct cgatagccct gtacacggct  3600
gatctgaaat ttgcgctgac cgctgagacg aaggcttgga tggtggtgat tggccgacac  3660
tgcaacaaga agtaccgatc tgaaatggag aacatcttta tgctaatcga ggaatttaac  3720
aaaaagctga accgtcccat taaagatctg gacgacatca ggattgccat ggcggcccta  3780
aaggaaatta gagaggagca gatatccatt gattttcagg ttggccccat cgaagaatca  3840
tatgcccttc tgaatcgata cggtctatta atcgccaggg aggaaataga taaggtggac  3900
acactacatt atgcatggga gaaactctta gcgcgggccg gcgaagtgca gaataagctc  3960
gtatcgttac aaccatcatt taagaaggag ctcatcagtg ctgtcgaggt ctttctgcag  4020
gactgccatc agttctatct ggattatgac ctgaacggtc cgatggcgag tggtctgaag  4080
ccccaagagg cttcagaccg gcttatcatg ttccaaaatc agtttgacaa tatttacagg  4140
aagtatatca cctatacagg gggtgaagaa ttgtttggtc tcccagccac ccagtatcca  4200
caattattgg aaataaagaa gcagctgaac cttcttcaaa aaatctacac tctctataat  4260
tcggtaattg aaactgttaa ttcctactac gatattctct ggagcgaggt caacattgag  4320
aaaattaata acgaactctt ggagtttcaa aaccgatgcc gcaagttgcc gagagcgctg  4380
aaggactggc aggcttttct cgaccttaag aaaataatcg atgatttcag tgaatgctgt  4440
cctctcttag aatacatggc gagtaaggct atgatggaga gacactggga gaggattacg  4500
actctgaccg gccattcttt ggacgttggc aacgagtcct tcaagctgcg taatataatg  4560
gaggctccac ttctcaagta caaagaggaa atagaagaca tctgtatatc tgctgtcaaa  4620
gagcgcgaca tagaacagaa actaaagcag gtaattaacg aatgggacaa taaaacgttt  4680
acatttggca gtttcaagac acgtggagaa ttattgcttc gtggcgactc cacctcggaa  4740
attatcgcta acatggagga ctctctcatg ttactcggct cgctgttatc gaaccggtat  4800
aatatgccat tcaaagcaca gatccaaaag tgggtgcagt atctatctaa tagtacggat  4860
attatagaga gctggatgac cgtccagaat ctctggatct acctggaggc ggtgtttgtg  4920
ggaggtgata ttgcgaagca gcttccaaag gaggccaaaa gattctccaa cattgacaag  4980
tcctgggtca agattatgac tcgggcccac gaagtgccgt ccgtggtgca atgctgcgtt  5040
ggggacgaaa ccttgggcca gctgttgccc cacctgttgg atcaattgga aatctgccaa  5100
aagagcctga ctggctacct agaaaaaaag cgtctgtgct ttccccggtt ctttttcgtt  5160
tctgaccctg cactcctcga aatcttgggt caggcctcag attctcacac aattcaggct  5220
catttgttaa atgtgtttga caacatcaaa agtgtgaagt ttcatgaaaa gatttatgac  5280
aggatcttgt ccatttcatc ccaagagggg gaaaccattg agcttgataa gcctgtgatg  5340
gcagagggaa acgtggaggt ctggcttaac agtctcctgg aagagtccca gtcctcactg  5400
cacctggtca tccgccaggc ggcggctaac atccaggaga caggattcca gctcacggaa  5460
ttcctttcct cgtttccggc gcaagtgggg ctcctcggca ttcagatgat ctggacgaga  5520
gattcggagg aagccctccg caacgccaag tttgacaaga agattatgca gaaaactaac  5580
caagccttcc tagagctcct caacaccctg atcgatgtca caacacgtga tctatcgtct  5640
accgagcggg tcaagtatga gacactgatt accattcacg tgcaccagcg tgatatattc  5700
gatgatctct gccacatgca cataaagagt cccatggact tcgaatggct aaaacagtgc  5760
aggttctact ttaatgaaga ctcggataag atgatgatcc atatcacaga tgtagcgttt  5820
atttaccaaa acgagttcct tggctgcaca gacaggttag tcataactcc gttaactgat  5880
cgctgctaca ttacactcgc ccaagcgctt ggaatgtcca tgggtggagc cccccgcaggg  5940
ccggcgggga ctggtaagac cgaaacaacg aaagatatgg gccgttgcct cgggaagtat  6000
gtagtagttt ttaactgttc agaccaaatg gatttccgag ggctgggccg tatctttaaa  6060
gggctggcgc aatccggttc ctggggctgt tttgacgagt tcaatcgtat tgatttaccg  6120
gtgctatcgg ttgccgcaca gcaaattagt ataattttga cttgtaagaa agaacacaag  6180
aaaagtttta tatttactga tggcgacaac gtcactatga atcctgaatt cgggcttttc  6240
ttgactatga acccagggta tgctggccgt caagaacttc ctgaaaatct gaagatcaac  6300
ttccgatcgg tggctatgat ggtaccggat cgccagatca ttatacgggt aaaactggcc  6360
tcgtgtggct tcatcgacaa cgtcgtactt gctagaaagt tcttcaccct ttataagcta  6420
tgtgaggagc agttatcgaa gcaagttcat tacgactttg ggctccggaa tatcttgtcc  6480
gtcttacgca cactcggagc ggctaaacgt gcaaatccca tggacactga gagtacgatt  6540
gtgatgcgag tgttaaggga tatgaatctc tcaaaattaa tagacgagga cgagcctctt  6600
tttctcagcc ttatagagga tctgtttcca aacatcctcc tggacaaggc gggatatccc  6660
gagttggaag cggccattag caggcaggtg gaggaggccg gattgattaa tcacccgccc  6720
```

-continued

```
tggaaactga aagtcatcca gctgttcgag actcagcggg tccgacacgg tatgatgact  6780
ttaggcccat ctggtgcggg caaaactacc tgcatccaca ccctgatgag ggctatgacc  6840
gattgtggga agcctcaccg tgagatgcgg atgaacccca aggcgatcac tgcgccccaa  6900
atgtttgggc gtctggatgt ggcgacaaat gactggaccg atggaatctt ttccacactc  6960
tggaggaaga ccctgcgcgc aaaaaaagga gagcacatct ggatcattct cgatggcccc  7020
gttgacgcta tttggatcga aaacttaaac agcgtgctcg acgacaacaa gaccctgaca  7080
ttggcaaatg gtgaccgaat tcctatggct cccaactgca aaatcatttt tgaacctcac  7140
aacatcgaca acgccagtcc ggctacggtg tcccgcaacg gtatggtttt catgagcagt  7200
tccatactgg attggagtcc gatattggaa ggatttctca agaaacgcag tccccaggag  7260
gcggaaattc tgagacaact gtatacggaa agttttcctg acctgtaccg cttctgtatt  7320
caaaatctcg agtataagat ggaggtgttg gaggccttcg tcatcacaca gtccattaac  7380
atgcttcagg ggttgatccc cttgaaggaa caaggagggg aagtcagcca ggcacatcta  7440
gggcggcttt tcgttttcgc cctgctatgg tccgcgggtg ctgctctcga gctagacggt  7500
cgccggcgct tggagttgtg gctgaggtct cgcccgaccg ggacactcga gctgccgccg  7560
ccagccggac ccggggacac tgcattcgac tactacgtag ctccggacgg cacctggacc  7620
cactggaaca cccgtacgca ggagtacctc tatcccagcg atacaactcc tgagtatgga  7680
agcatactcg ttccgaacgt agacaacgtc agaaccgact ttctgatcca gaccattgct  7740
aagcagggca aggcagtcct attgatcgga gagcaaggga ccgcgaaaac cgtgattatc  7800
aagggcttca tgtctaaata tgacccagag tgtcatatga ttaagtcgct caacttcagt  7860
tctgctacca caccactcat gtttcagcgt actatcgaat cctacgtgga caagcggatg  7920
ggcaccacct acgggccacc tgccgggaag aagatgacgg tatttataga cgacgttaac  7980
atgcccatca tcaacgagtg gggagatcaa gtgaccaacg agatcgttcg gcaacttatg  8040
gaacaaaacg ggttctataa cctcgagaaa ccgggcgagt tcacctcaat agtggacatt  8100
caatttctgg cagctatgat ccaccccgga ggaggacgga acgacattcc ccagcggctc  8160
aagcgccaat tcagcatctt caactgcacg ctgccaagtg aagcatcggt agacaaaatc  8220
ttcggcgtca tcggggtggg tcattactgc acccagcgcg gcttttcaga ggaagtccga  8280
gattctgtta ctaaactggt tcctttgact agaaggttat ggcagatgac caaaattaaa  8340
atgcttccta ctccagctaa attccactac gtgttcaatc tgcgagactt atccagggta  8400
tggcaaggta tgcttaatac cacctctgag gtaattaaag aaccgaacga tctgctgaaa  8460
ctgtggaagc acgaatgtaa gagagttatt gcagacaggt ttactgtatc gtcagatgtt  8520
acctggttcg ataaagcact ggtgtctttg gtggaagaag agtttgggga agagaagaag  8580
ctactcgtcg attgcgggat cgacacttac ttcgtggact tcttaagaga cgcccctgag  8640
gctgccggcg aaacatcgga agaggcagac gctgagactc ctaagatcta tgagccgatc  8700
gagagcttta gccacctcaa ggaacgtctg aatatgtttt tacaattgta taacgagagc  8760
attcgtggtg ctgggatgga tatggtgttc ttcgcggatg caatggtgca tctggttaag  8820
atttctcggg tgattcgcac gccacaggga aacgcgctac tggtcggggt gggtgggtca  8880
ggaaagcaat cgttgactcg tctcgcatcc tttatcgcgg gatatgtgag ttttcaaatc  8940
accctgacaa ggtcctataa tacatccaac ctgatggagg atcttaaagt tctctacagg  9000
acggcgggac aacaaggcaa aggaataacc ttcatcttca ctgataacga aattaaagac  9060
gaatcattct tggagtatat gaacaacgtc ttatcaagcg gcgaagtttc gaacctcttc  9120
gcgcgggacg aaatcgatga gatcaactct gatctcgctt ctgtcatgaa gaaagaattc  9180
ccacgctgtt tgccgacgaa tgagaacttg catgactatt tcatgtcccg tgtgcggcag  9240
aatttgcaca ttgtgctttg cttttcaccg gtgggggaga agttccgaaa tagagctttg  9300
aagttccctg ctttgatttc tgggtgtact attgactggt tttcccgttg gcccaaggac  9360
gctctggtcg ccgtgtccga gcacttttta accagctatg atatcgactg cagcctcgaa  9420
attaagaagg aagtagttca gtgtatgggc tctttccaag acggtgtggc agagaagtgc  9480
gtcgactatt tccagaggtt tcgccgatct actcatgtca cacctaagag ctacttgtcc  9540
ttcatacagg ggtacaagtt tatatatggg gagaaacacg ttgaagtaag gactctggca  9600
aaccgtatga atactggctt agagaagctc aaggaggcct cagaaagtgt ggctgctctc  9660
tcaaaggagc ttgaagctaa ggagaaggaa ctccaagttg cgaacgataa agcggatatg  9720
gttctaaaag aagttactat gaaagcacaa gcggctgaaa aggttaaggc ggaggtacag  9780
aaggtgaagg atcgcgccca ggcaatagtc gatagcattt ccaaggacaa ggcgatcgcg  9840
gaagagaagc tcgaggccgc gaagcctgcg ctggaggagg ccgaggccgc gctgcagacc  9900
atccgcccct ccgacatcgc gacggttcgc acgttggggc ggccacctca ccttatcatg  9960
cgcattatgg actgcgttct gctcttgttc cagcggaagg tgagcgcggt gaaaatcgac  10020
ctggaaaaga gctgtaccat gccgagctgg caggagtccc tcaagctcat gacggccggg  10080
aacttcttac aaaacctgca gcagttcccg aaggacacca taaacgagga ggtgatcgag  10140
tttcttagcc cctactttga gatgcccgac tacaacatcg agaccgcgaa gcgcgtatgc  10200
gggaacgtgg ccggtctctg ctcgtggacc aaggctatgg cgtccttctt ttcgataaat  10260
aaggaggtct tgccgctcaa ggccaacctc gtcgtgcagg agaaccgtca cctactcgct  10320
atgcaggacc tccagaaagc gcaggcggag ttggacgaca aacaggccga gctggacgtc  10380
gtgcaagccg agtacgaaca ggctatgacg gagaagcaga cgctgctaga agacgcggag  10440
cggtgccggc ataaaatgca gacggcgagc acactgatta gtggcctagc aggggagaaa  10500
gagcggtgga cggagcagtc gcaagagttc gccgcccaaa ctaagcgact ggtgggcgac  10560
gtgctcctgg ctactgcttt tttgtcctat tcgggcccct tcaatcaaga gttccgggac  10620
ttgctactca acgactggcg taaggagatg aaggcccgca agatcccctt cgggaagaac  10680
ctgaacctca gtgaaatgct gatcgacgcc cccactatct ctgagtggaa tctccagggg  10740
ctgcccaacg acgacctgtc gatacaaaac ggaataatag tcaccaaggc gtcgcgctac  10800
cccctgctga tcgatccgca aacccagggg aagatctgga tcaagaacaa ggagtcccgg  10860
aacgagttgc aaatcacgtc cctcaatcac aagtactttc ggaaccacct cgaggactcg  10920
ctgtcgttgg ggcgcccgct tctgatcgag gacgttggcg aggagctgga tcctgcgctg  10980
gacaacgttc ttgagcgcaa cttcatcaag accgggtcca ccttcaaggt aaaggtggga  11040
gataaggagg tcgacgtgct ggacggcttt cgcctatata tcaccacgaa gctgcctaac  11100
ccggcgtaca cgcccgagat cagtgcgcgt acgagcatca ttgacttcac cgtgactatg  11160
aaaggcctcg aagatcagct gctcggtcgc gtgattctca cggaaaagca ggagctggag  11220
aaggagcgaa cacacctgat ggaggacgtg acggccaaca agcggcgtat gaaagagcta  11280
gaggacaacc tgctgtaccg ccttacgtca acccaggggt cgctggtcga ggacgaatcc  11340
ctgatcgtgg tgctgagtaa taccaagcgg acagctgagg aggtcacgca gaaactcgag  11400
atctcggccg agaccgaggt gcagatcaac agcgcgcggg aggagtaccg cccggtggcc  11460
```

-continued

```
acccgcggga gcatcttgta cttcctgatc actgagatgc gccttgtgaa tgagatgtac  11520
cagacaagcc tgcggcagtt ccttggcctg ttcgatcttt cgctggcccg gtccgtcaag  11580
tctccgatta cctccaagcg gatcgctaac ataattgaac acatgacgta cgaggtgtac  11640
aagtacgcgg cgcggggcct ctacgaagag cacaagttcc tgttcacgct cctcctcacg  11700
ctcaagatcg acatccagcg caaccgcgtc aagcacgagg agtttctcac cctgataaag  11760
gggggagcgt ccttagacct gaaggcctgt ccgccgaagc cgtcgaagtg gatcctggac  11820
ataacgtggc tcaacctcgt cgagctgtcc aagctccgtc agttctcgga cgtgctcgac  11880
cagatttcgc ggaacgagaa gatgtggaaa atatggttcg acaaggagaa tccagaggag  11940
gagcccttgc ccaatgcgta tgacaagtcg ctcgactgct tccgtcgcct gctgctgatc  12000
cgcagctggt gccccgaccg gacgatcgcg caggcgagga agtacatcgt tgacagtatg  12060
ggtgagaaat acgcggaggg cgttattctg gatctggaga agacttggga ggagagcgac  12120
ccccgcaccc ccctgatttg ccttctgtct atggggtccg acccgaccga tagcatcatt  12180
gcgctgggga aacggctcaa gatcgagacc cggtacgtgt ctatgggaca ggggcaggag  12240
gtgcatgccc gcaagctcct gcagcagact atggcgaacg gggggttgggc gctcttacag  12300
aactgccatc tggggctcga cttcatggat gaactgatgg acatcatcat cgagacggaa  12360
ctcgtgcacg acgcattccg cctgtggatg accaccgagg cgcacaagca gttcccgatc  12420
acgttgctgc agatgtccat caagttcgcc aacgaccctc cgcagggcct ccgggcgggc  12480
ctgaagcgca cgtattcggg cgtgtctcaa gatctcctag atgtcagctc ggggtcccag  12540
tggaagccga tgctctatgc cgtggcattt ctacactcga ccgtccagga gcggcgaaag  12600
tttggagcgc tggggtggaa cataccctac gagtttaacc aggccgactt caacgccacc  12660
gtacagttca tccagaacca tttggacgat atggatgtta agaagggggt gtcctggacg  12720
accatacggt atatgattgg cgagatccag tatgggggc gggtcacgga cgactacgac  12780
aagcggttac tgaacacgtt cgcgaaggtc tggttctccg agaatatgtt cgggcccgat  12840
ttttcctttt accagggcta taatataccc aagtgctcca cggtcgacaa ctaccttcag  12900
tacatccaga gcctacccgc gtacgacagc ccggaagtct tcggactcca ccccaacgcc  12960
gacatcacgt accagagcaa gctggccaag gacgtgctcg acaccatact cggcatccag  13020
ccgaaggaca cgtccggcgg gggggacgag acgcgggagg ccgtcgtcgc gcgcttggca  13080
gatgacatgc tggagaagct cccccccgat tacgtcccgt tcgaggtcaa ggaaaggctc  13140
cagaagatgg gcccgttcca gcccatgaac atcttcctcc gccaggagat cgaccggatg  13200
cagcgcgtgc ttagcctggt gcgctcaacg ctgacggagc tgaagctggc catcgacggg  13260
acgatcatta tgtcggagaa cctccgggac gcgctggact gcatgttcga cgcgcgtatc  13320
ccggcctggt ggaagaaggc gtcgtggatc tccagcaccc tggggttctg gttcacggag  13380
ctgatcgagc gtaattctca atttacatct tgggtgttta atggtcgtcc ccattgtttt  13440
tggatgactg gttttttaa tccacaagga tttttaactg ctatgagaca ggaaataact  13500
cgtgcgaata agggttgggc attagataat atggttttgt gtaatgaagt aactaagtgg  13560
atgaaagacg atataagtgc accacctact gaaggtgttt atgtatatgg tttatattta  13620
gaaggagctg gatgggataa acgtaatatg aaattaatag aatcgaaacc aaaagtttta  13680
tttgaactga tgccagttat tagaatttat gcagaaaata atacattaag agatcctaga  13740
ttttatagtt gtccgattta taaaaaacct gtaagaacag atttaaatta tatagcagcc  13800
gtcgatctta gaactgctca aacaccagaa cattgggtat taagaggagt agctttactt  13860
tgtgatgtta aatag                                                   13875
```

```
SEQ ID NO: 27          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 27
atgttcagaa taggcagacg acagttatgg aaacacagtg tgactagggt tctaacacag  60
agactaaaag gagagaaaga ggcaaaaaga gcgctactcg atgcaagaca taactatcta  120
ttcgctattg tggcgtcgtg tttagattta aataaaactg aagtagagga cgccattctc  180
gagggaaatc aaatagaacg catcgaccaa ttattcgcgg ttggaggact tagacatttg  240
atgttttact atcaagacgt tgaagaagcg gaaactgggc aactcgggtc actaggtgga  300
gttaatttag tctcaggtaa gatcaaaaag ccaaaagtat ttgtaacaga aggaaacgac  360
gttgcactaa caggtgtttg cgtgtttttt attagaactg atccgtctaa agccataaca  420
cccgacaaca tccatcagga agtttcgttt aacatgctgg atgcggccga cggaggacta  480
ctgaattcag tgcgtcgcct gctatctgac attttcattc ctgctttgcg tgcgaccagt  540
cacgggtggg gggagttaga aggactccag gacgccgcga atatccggca ggaattcctg  600
tccagcctgg aaggttttgt taacgtcctg tccggcgccc aggagagcct taaggagaag  660
gtgaacttac gaaagtgcga catactcgag ctcaaaaccc tgaaggaacc tacagactac  720
ctcaccctcg caaacaaccc cgaaaccctc ggcaaaattg aagattgcat gaaggtttgg  780
attaagcaga cggaacaagt cctggccgag aacaaccaac tcctaaagga ggccgacgac  840
gtgggcccgc gcgctgagct ggagcactgg aagaagaggc tcagcaagtt taactatctt  900
cttgagcagc tgaagagccc ggacgttaag gcggtactag ccgtcctcgc ggctgcgaag  960
tcgaaactgc tcaagacctg gcgtgagatg gatatacgca ttacggacgc aaccaacgaa  1020
gctaaggaca acgttaagta cttgtatacc ctcgagaagt gctgcgaccc actctactca  1080
tctgacccgc tcagtatgat ggatgccatc cccacgctaa ttaacgcaat taagatgatc  1140
tactcgatat cgcactatta caacacgtct gaaaaaataa ccagcctctt cgtaaaagtg  1200
accaaccaga tcatttcagc ctgtaaggct tacatcacaa acaacggcac cgcctccata  1260
tggaaccagc cccaggacgt cgtggaagag aagatcctat cggccataaa gctgaagcag  1320
gagtaccagc tgtgcttcca caaaaccaag cagaaactca agcagaaccc caatgctaag  1380
cagttcgact tctctgagat gtatattttc gggaagtttg aaaccttcca ccgccgcctg  1440
gcgaagatca tcgacatatt cacaactctg aagacctaca gtgttctaca agacagcact  1500
atagagggtc tcgaggatat ggccactaag taccagggca ttgtcgcaac tatcaagaag  1560
aaagaatata atttcctcga tcagcgtaag atggacttcg accaggacta cgaagaattc  1620
tgcaagcaga cgaatgattt gcataacgaa ctccggaagt tcatggacgt aacgtttgcc  1680
aagattcaaa acacaaatca ggcgttgcgg atgctaaaga agttcgagcg tctgaacatc  1740
```

-continued

```
cctaatctag ggattgacga caagtaccaa cttatactgg aaaactacgg ggctgacatc  1800
gatatgatct ccaagctata taccaagcaa aagtatgacc cgccgttagc tcggaatcag  1860
cccccgatcg ccgggaagat cctgtgggca cggcagcttt ttcaccgcat tcagcagcct  1920
atgcagctgt tccagcagca cccggcggtt ctctccaccg ccgaggctaa gccaattata  1980
cgtagctaca accgcatggc gaaagtcctg ctcgagtttg aggtcttgtt ccaccgagcg  2040
tggcttcggc agatcgaaga gatccacgtc gggctcgagg cctcgctcct ggttaaggcg  2100
ccggggaccg gtgagctgtt cgtaaacttc gacccgcaaa tactaatcct gttccgtgaa  2160
accgagtgca tggcccagat gggcctcgag gtctcacctt tggccacgag cctgttccag  2220
aagcgcgacc gctacaagcg gaacttctct aacatgaaga tgatgcttgc cgagtaccag  2280
agggttaagt cgaagatccc tgctgccatc gagcagctca tcgtgccaca tctggccaag  2340
gttgacgagg cactccaacc gggcttggcg gccctgacgt ggacctccct aaacattgag  2400
gcctacttgg aaaatacttt cgcgaagatt aaggatctcg aattactact ggatcgtgtg  2460
aatgacctca tagaattccg gatagacgcg atcctagagg agatgtcgag caccccccctc  2520
tgtcagctcc cgcaggagga gccgctcaca tgcgaggaat ttctccagat gactaaggac  2580
ctctgcgtta acggggccca gatactccat ttcaagtcgt ccctcgttga ggaggcggtg  2640
aatgaactgg ttaatatgct cttggatgtg gaagtgctct cggaggaaga atccgagaag  2700
attagcaacg agaatagcgt gaactacaag aacgagagct cagcaaaacg ggaggagggg  2760
aattttgata cgctgacttc ctccatcaac gcgcgggcca acgctctctt gctgacaaca  2820
gtaacgcgca aaaagaagga gactgagatg ctaggagagg aggcgcgcga gctgctgtcc  2880
catttcaacc accaaaatat ggatgcgctt ctcaaagtca cccggaatac cctcgaggcg  2940
atacgcaagc gcatccattc gagccatacg ataaacttca gggacagcaa ctccgcgtca  3000
aatatgaagc agaactcgtt gccgatattc cgggcctcgg tgacgctggc gatcccgaac  3060
attgtgatgg caccggccct cgaggacgta cagcagaccc ttaacaaggc ggtggagtgc  3120
atcatctccg ttcccaaggg cgtccgccag tggtcctcgg agctgctcag caagaaaaag  3180
attcaggagc gtaaaatggc ggcccttcaa tcgaacgaag actccgactc tgacgttgag  3240
atgggagaga acgagctaca ggatacctta gaaatcgcct ccgtgaacct ccctatcccg  3300
gtgcagacga aaaactacta caagaacgtc agcgaaaaca aggaaatcgt aaagctggtg  3360
agcgtcctga gtaccatcat taacagcaca aagaaggaag tgataacctc gatggactgc  3420
tttaagcgct acaaccacat ttggcagaaa ggcaaggagg aggctataaa aacgttcatc  3480
acgcagagcc ccctgctctc ggagttcgag tcacaaatcc tctacttcca aaatctggag  3540
caggagatca acgctgagcc ggaatatgtg tgcgtcggct cgatagccct gtacacggct  3600
gatctgaaat ttgcgctgac cgctgagacg aaggcttgga tggtggtgat tggccgacac  3660
tgcaacaaga agtaccggtc tgaaatggag aacatcttta tgctaatcga ggaatttaac  3720
aaaaagctga accgtcccat taaggatctg gacgacatcc gaattgccat ggcggcccta  3780
aaggaaatta gagaggagca gatatccatt gactttcagg ttggccccat cgaagaatca  3840
tatgcccttc tgaatcgata cggtctatta atcgcccgag aggaaataga taaggtggac  3900
acacttcatt atgcatggga gaaactctta gcgcgggccg gcgaagtgca gaataagctc  3960
gtatcgctgc aaccatcatt taagaaggag ctcatcagtg ctgtcgaagt ctttctgcag  4020
gactgccacc agttctatct ggattatgac ctgaacggtc cgatggcgag tggtctgaag  4080
ccccaagagg cttcagaccg gcttattatg ttccaaaatc agtttgataa tatttaccgg  4140
aagtatatca cctatacagg gggtgaagaa ttgtttggtc tcccagccac ccagtaccca  4200
caattattgg aaataaagaa gcagctgaac cttcttcaaa aaatctacac tctctataat  4260
tcggtaattg aaactgttaa ttcctactac gatattctct ggagcgaggt caacattgag  4320
aaaattaaca acgaactctt ggagtttcaa aacagatgcc gcaagttgcc cagagcgctg  4380
aaggactggc aggcttttct cgaccttaaa aaaataatcg atgatttcag tgaatgctgt  4440
cctctcttag aatacatggc ctcaaaggct atgatggaga gacactggga gaggattacg  4500
actctcacgg ggcattcttt ggacgttggc aacgagtcct tcaagctgcg taatataatg  4560
gaggctccac ttctcaagta caaagaggaa atagaagaca tctgtatatc tgctgtcaaa  4620
gagcgcgata tagaacagaa actaaagcag gtaattaacg aatgggacaa taaaacgttt  4680
acatttggca gtttcaagac acgtggagaa ttattgcttc gtggcgactc cacctcggaa  4740
attatagcta acatggagga ctctctcatg ttactcggct cgctgttatc gaaccggtat  4800
aatatgccat tcaaagcaca gattcagaag tgggtgcagt atctatctaa tagtacggat  4860
attatagaga gctggatgac cgtccagaat ctctggatct acctggaggc ggtgtttgtg  4920
ggtggtgata ttgcgaagca gcttccaaag gaggccaaaa gattctccaa cattgacaaa  4980
tcctgggtca agattatgac tcgggcccac gaagtgccct ccgtggtgca gtgctgcgtt  5040
ggcgacgaaa ccttgggcca gctgttgccc cacctgttgg atcaattgga aatctgccaa  5100
aagagcctga ctggctacct agaaaaaaag cgtctgtgct ttccccggtt ctttttcgtt  5160
tctgaccctg cactactcga aatcttgggt caggcctcag attctcacac aattcaggct  5220
catttgttaa atgtgtttga caacatcaaa agtgtgaaat ttcatgaaaa gatttatgac  5280
aggatcttgt ccatttcatc ccaagagggg gaaaccattg agcttgataa gcctgtgatg  5340
gcagagggaa acgtggaggt ctggttaaac agtctcctgg aagagtccca gtcctcactg  5400
cacctggtaa tccgccaggc ggcggctaat atccaggaga caggattcca gctcacggaa  5460
ttccttagtt cgtttccggc gcaagtgggg ctcctcggca ttcagatgat ctggacgaga  5520
gattcggagg aagccctcag aaacgccaag tttgacaaga agattatgca gaaaactaac  5580
caagccttcc tagagctcct caacaccctg atcgatgtca caacacgtga tctatcgtct  5640
accgagcggg tcaagtatga gacactgatt accatacacg tgcaccagcg tgatatattc  5700
gatgatctct gccacatgca cataaagagt cccatggact tcgaatggct aaaacagtgc  5760
cgcttctact ttaatgaaga ctcggataag atgatgatcc atatcacaga tgtagcgttt  5820
atttaccaaa acgagttcct tggctgcaca gacaggttag tcataactcc gttaactgat  5880
cgctgctaca ttacactcgc ccaagcgctt ggaatgtcca tgggtggagc ccccgcaggg  5940
ccggcgggga ctggtaagac cgaaacaact aaagatatgg gccgttgcct cgggaagtat  6000
gtggtagttt ttaactgctc agaccaaatg gatttccgag ggctgggccg tatctttaaa  6060
gggctggcgc aatcaggttc ctggggctgt tttgacgagt tcaatcgtat tgatttaccg  6120
gtgctaagtg ttgccgcaca gcaaattagt ataattctaa cttgtaagaa agaacacaag  6180
aaaagtttta tatttactga tggcgacaac gtcactatga atcctgaatt cgggcttttc  6240
ttgactatga acccagggta tgctggccgt caagaacttc ctgaaaatct gaagatcaac  6300
tttcgatcgg tggctatgat ggtaccggat cgccagatca ttatccgagt aaaactggct  6360
tcgtgtggct tcatcgacaa cgtcgtactt gctcgaaagt tcttcaccct ttacaagcta  6420
tgtgaggagc agttatcgaa acaagttcat tacgactttg ggctccggaa tatcttgtcc  6480
```

-continued

```
gtcctccgca cactcggagc ggctaaacgt gcaaatccca tggacactga gagtacgatt  6540
gtgatgcgag tgttaaggga tatgaatctc tcaaaattaa tcgacgagga cgagcctctt  6600
tttttaagcc ttatagagga tctgttccca aacatcctcc tggacaaggc gggatatccc  6660
gagttggaag cggccattag caggcaggtg gaggaggccg gattgattaa tcacccgccc  6720
tggaaactga aagtcatcca gctgttcgag actcagcggg tccgacacgg tatgatgact  6780
ttaggcccat ctggcgcggg caaaaccacc tgcatccaca ccctgatgag ggctatgacc  6840
gattgtggga agcctcaccg tgagatgcgg atgaacccga aggcgatcac tgcgccccaa  6900
atgtttgggc gtctggatgt ggcgacaaat gactggaccg atggaatctt tagcacactc  6960
tggaggaaga ccctgcgcgc caaaaaagga gagcacatct ggatcattct cgatggcccc  7020
gttgacgcta tttggatcga aaacttaaac agcgtgctcg acgacaacaa gaccctgaca  7080
ttggcaaatg gtgaccggat tcctatggct cccaattgca aaatcatttt tgaacctcac  7140
aacatcgaca acgccagtcc ggctacggtg tcccgcaacg gtatggtttt catgagcagt  7200
tccatactgg attggagtcc gatattggaa ggatttctca agaaacgcag tccccaggag  7260
gcggaaattc tgcggcaact gtatacggaa agtttttcctg acctgtaccg cttctgtatt  7320
caaaatctcg agtataagat ggaggtgttg gaggccttcg tcatcacaca gtccattaac  7380
atgcttcagg gcttgatccc cttgaaggag caaggagggg aagtcagcca ggcacatcta  7440
gggcggcttt tcgttttcgc ccttctctgg tccgcgggtg ctgctctcga gctagacgga  7500
cgccggcgct tggagttgtg gctgaggtct cgcccgaccg ggacactcga gctcccgccg  7560
ccagccggac ccggggacac tgcattcgac tactacgtag ctccggacgg cacctggacc  7620
cactggaaca cccgtacgca ggagtatctc tatcccagcg atacaactcc tgagtatggt  7680
agcatactcg ttccgaacgt agacaacgtc agaaccgact ttctgatcca gaccattgct  7740
aagcagggca aggcagtcct acttatcgga gagcaaggga ccgcgaaaac cgtgattatc  7800
aagggcttca tgagtaaata tgacccagag tgtcatatga ttaaatccct caacttctcc  7860
tctgctacca caccactcat gtttcagcgc actatcgaat cctacgtgga caagcggatg  7920
ggcaccacct acggaccgcc tgccgggaag aagatgacgg tatttataga cgacgttaac  7980
atgcccatca tcaacgagtg gggagatcaa gtgaccaacg aaatcgttcg gcaacttatg  8040
gaacaaaacg ggttctataa cctcgagaag ccgggcgagt tcacctcaat agtagacatt  8100
caatttctgg cagctatgat ccacccccgga ggaggacgga acgacattcc ccagcggctc  8160
aagcgccaat tcagcatctt caactgcacg ctgccaagtg aagcatcggt tgacaaaatc  8220
ttcggcgtca tcggggtggg tcactactgc acccagcgcg gcttttcaga ggaagtccga  8280
gattctgtta ctaaactggt tcctttgact agaaggctgt ggcagatgac caaaattaaa  8340
atgcttccta ctccagctaa attccactac gtgttcaatc tgcgagactt atccagggta  8400
tggcaaggta tgcttaatac cacctctgag gtaattaaag aaccgaacga tctgctgaaa  8460
ctgtggaagc acgaatgtaa gagagttatt gcagataggt ttactgtatc gtcagatgtt  8520
acctggttcg ataaagcact ggtgtctttg gtcgaagaag agtttgggga agagaagaag  8580
ctactcgtcg attgcgggat agacacttac tttgtggact tcttaagaga cgcccctgag  8640
gctgccggcg aaacatcgga agaggcagac gctgagactc ctaagatcta tgagccgatc  8700
gagagcttta gccacctcaa ggagcgtctg aatatgtttt tacaattgta taacgagagc  8760
attcgtggtg ctgggatgga tatggtgttc ttcgccgatg caatggtgca tctggttaag  8820
attagccggg tgattcgcac gccacaggga aacgcgctac tggtcggggt gggtgggtca  8880
ggaaagcaat cgttaactcg tttggcatcc tttatcgcgg gatatgtgag ttttcaaatc  8940
accctgacga ggtcctataa tacatccaac ctgatggagg atcttaaagt tttgtacagg  9000
acggcgggac aacagggcaa aggaataacc ttcatcttca cagataacga aattaaagac  9060
gaatcattct tggagtatat gaacaacgtc ttatcaagcg gcgaagtttc gaacctcttc  9120
gcgcgggacg aaatcgatga gatcaactct gatctcgctt ctgtcatgaa gaaagaattc  9180
cccccgctgtt tgccgacgaa tgagaacttg catgactatt tcatgtcccg tgtgcggcag  9240
aatttgcaca ttgtgctatg tttttcaccg gtgggggaga agttccgaaa tagagctttg  9300
aagttccctg ctttgatttc tgggtgtact attgactggt tttcccgttg gcccaaggac  9360
gctctggtcg ccgtgtccga gcacttttta accagctatg atatcgactg cagcctcgaa  9420
attaagaagg aagtagttca gtgtatgggc tctttccaag acggtgtggc agagaagtgc  9480
gtcgactatt tccagaggtt tcgccgatct actcatgtca cacctaagag ctacttgtcc  9540
ttcatacagg ggtacaagtt tatatatggg gagaaacacg ttgaagtaag gactctggca  9600
aaccgtatga atactggctt agagaagctc aaggaggcct cagaatccgt ggctgctctc  9660
tcaaaggagc ttgaagctaa ggagaaggaa ctccaagttg ctaacgataa agcggatatg  9720
gttctaaagg aagtcactat gaaagcacaa gcggctgaaa aggttaaggc ggaggtacag  9780
aaggtgaagg atcgcgccca ggcaatagtc gattccattt ccaaagacaa ggccatcgcg  9840
gaagaaaagc tagaagcggc gaagccggcc ttagaagagg cagaggctgc cttgcaaacc  9900
ataagaccca gtgacatcgc cacggtacga acccttggtc gtcctcctca tttgattatg  9960
aggattatgg actgtgtcct gcttttattt caacgtaaag tatctgcagt taagattgat  10020
ttggaaaaat cctgtaccat gccctcatgg caggaatccc tgaaattgat gaccgcgggc  10080
aatttccttc aaaatttgca acaattcccc aaggacacca ttaacgaaga ggtcatagaa  10140
tttttatctc catattttga gatgccagac tacaatattg aaacagcgaa gcgcgtctgt  10200
ggtaacgttg caggtctctg ttcgtggacc aaagctatgg cctccttctt tagtatcaat  10260
aaagaggtac taccactgaa agccaacctg gtggtacagg agaaccggca tctgcttgct  10320
atgcaggatc ttcagaaggc ccaggccgaa ttagacgaca agcaggctga gcttgacgtt  10380
gtgcaagcag aatacgaaca agctatgaca gaaaagcaga ctttattaga agacgctgaa  10440
cgctgcagac ataagatgca gactgcaagc accctcatat ccggtttggc tggagaaaaa  10500
gagcggtgga cagagcagtc gcaagaattc gctgctcaaa ccaaaaggtt ggttggagac  10560
gttctactcg cgacagcgtt tctctcctat tctggtcctt tcaaccagga attccgggac  10620
cttttgctga atgactggag aaaagaaatg aaggctcgca aaataccatt tggaaagaat  10680
ttgaacttgt ctgaaatgct tattgacgca cccactatat cagagtggaa tcttcaggga  10740
cttccaaatg acgatctgtc catccaaaac ggaattattg taaccaaggc gagccgctac  10800
cctctgctaa ttgacccgca gacacagggc aagatctgga ttaaaaataa ggaaagcagg  10860
aacgagctcc agatcactag tctcaaccac aagtacttcc gtaaccacct cgaagatagt  10920
ctgtccctgg gacggccgtt gctaatcgag gacgtcggag aagagctgga ccccgcatta  10980
gacaacgttc ttgaaagaaa ttttatcaag acaggatcaa ctttcaaagt taaagtagga  11040
gataaagaag tggatgtgtt agatggcttc cgcctatata tcacgactaa actcccgaat  11100
cccgcctata ctccagagat cagcgctaga actagcatca tagatttcac tgtaactatg  11160
aaggggttag aagatcaatt attaggacgc gtcatcctga cggagaaaca ggaacttgaa  11220
```

-continued

```
aaagagcgta cacacctcat ggaagacgtg acagctaaca aacgtcggat gaaggaactg  11280
gaggacaatt tactgtatcg gttgacatca acacagggct cccttgttga ggacgagagt  11340
ctgatcgtgg tcctgtctaa cacaaagagg actgctgaag aagtcactca gaaattggag  11400
atttctgccg aaactgaagt tcagattaac tccgctagag aagagtatcg tccagtcgct  11460
actcggggct ctatcctata cttcctcata actgagatgc gcttggtcaa tgagatgtac  11520
cagacttcac tccggcaatt cctgggcttg tttgacttgt cgctggcaag atcagtaaaa  11580
tctccaatta ccagcaagag aatcgcaaac atcattgagc acatgacgta cgaggtgtat  11640
aaatacgcgg cgaggggtct ttatgaagag cataagttcc tcttcaccct actattaacg  11700
ttgaagatag atattcagag gaaccgggtg aagcacgagg agtttctaac tctaataaaa  11760
ggaggagctt ctttagatct taaagcctgt ccaccgaaac cttctaagtg gattttagac  11820
ataacatggc tgaatttagt ggagttgtcc aagttacgtc agttcagtga cgttttggat  11880
cagatatcta ggaacgagaa gatgtggaag atctggttcg ataaagagaa tccggaggag  11940
gagcccttgc caaatgctta tgataaaagc ctagactgct tcaggaggct tttgctcatc  12000
cgctcctggt gccccgaccg cactattgcc caagctagga aatacattgt ggactccatg  12060
ggggagaagt atgccgaagg agtcatactc gacttggaga agacttggga agagtcagat  12120
ccgaggacgc ccctcatttg tcttctttcc atgggttctg atcccacgga ctctattata  12180
gcactcggga aaagactaaa gatcgagaca cgctatgtta gcatgggaca ggggcaagag  12240
gtccatgccc gcaaactact acagcagact atggctaatg gaggttgggc tctgttacag  12300
aactgtcact taggccttga ttttatggac gaattgatgg acatcataat tgagacggag  12360
ctagttcacg acgcatttcg cttatggatg acgactgaag cacacaagca gtttccgata  12420
accctgttgc agatgtccat caagttcgcc aacgaccctc cccagggcct tagggcaggt  12480
ctcaaaagga cctacagcgg cgtttcccag gatttacttg acgtctccag cggatcccag  12540
tggaagccca tgttgtacgc cgtggctttc cttcacagca cagttcagga aaggcggaag  12600
tttggtgcgc taggctggaa catcccctac gagttcaacc aggctgactt taatgcaaca  12660
gtacagttta ttcaaaatca tctggatgac atggatgtca aaaaaggtgt gtcatggact  12720
acaataaggt acatgattgg ggagatacag tacggaggcc gggtaactga tgattatgat  12780
aaaagattgt taaacacttt tgctaaagtt tggtttagtg aaaatatgtt tggacctgat  12840
tttagttttt atcaaggtta taatatacct aagtgctcaa ctgtagataa ttatttacaa  12900
tatattcaaa gtttacctgc atatgatagt cctgaagttt ttggtttgca tcctaatgca  12960
gatataacat accaatcaaa attagcaaaa gacgtcttag atacaatact tggtatccag  13020
cctaaggaca ccagtggggg cggtgacgag actcgcgagg ctgtggtggc ccggctcgct  13080
gatgacatgc tagagaaact tcccccggac tacgtcccct ttgaggtcaa agagcggctg  13140
cagaaaatgg ggcccttcca gcccatgaac atattcttgc gccaggagat agaccgtatg  13200
caacgagtcc tgagcctggt ccgctcgact ctaaccgagc tcaagctggc catcgatggg  13260
acgatcatta tgtctgagaa tttgagggac gcgctcgatt gcatgtttga cgccaggatc  13320
ccagcctggt ggaaaaaagc tagttggatc tcatctaccc tggggttctg gttcacagag  13380
ttgatagagc gcaactcgca attcacctcc tgggtgttca acgggcggcc ccactgcttc  13440
tggatgacgg gcttcttcaa cccgcagggc ttcctgacgg ctatgcggca ggaaatcacc  13500
cgggcgaaca agggttgggc gctcgacaat atggtgctct gcaacgaggt cacgaagtgg  13560
atgaaggacg acatctcggc gcctcccacc gaaggggtct acgtatacgg cctgtacctc  13620
gagggggcgg gctgggacaa gcgtaacatg aagctgatcg agtcgaagcc caaggtgctg  13680
ttcgagctga tgcccgtcat ccggatctac gcagagaaca acacgctgcg cgacccgcgg  13740
ttctactcgt gccccatcta caagaagccg gtgcggacgg acctcaacta catcgccgcc  13800
gtcgacctcc gcaccgcgca gacccccgag cactgggtgc tgcggggggt cgcattgctc  13860
tgcgacgtca agtag                                                   13875
```

```
SEQ ID NO: 28           moltype = DNA  length = 13875
FEATURE                 Location/Qualifiers
misc_feature            1..13875
                        note = Synthetic polynucleotide
source                  1..13875
                        mol_type = other DNA
                        organism = synthetic construct
SEQUENCE: 28
atgttcagaa taggcagacg acagttatgg aaacacagtg tgactagggt tctaacacag  60
agactaaaag gagagaaaga ggcaaaaaga gcgctactcg atgcaagaca taactatcta  120
ttcgctattg tggcgtcgtg tttagattta aataaaactg aagtagagga cgccattctc  180
gagggaaatc aaatagaacg catcgaccaa ttattcgcgg ttggaggact tagacatttg  240
atgttttact atcaagacgt tgaagaagcg gaaactgggc aactcgggtc actaggtgga  300
gttaatttag tctcaggtaa gatcaaaaag ccaaaagtat ttgtaacaga aggaaacgac  360
gttgcactaa caggtgtttg cgtgtttttt attagaactg atccgtctaa agccataaca  420
cccgacaaca tccatcagga agtttcgttt aacatgctgg atgcggccga cggaggacta  480
ctgaattcag tgcgtcgcct gctatctgac attttcattc ctgctttgcg tgcgaccagt  540
cacgggtggg gggagttaga aggactccag gacgccgcga atatccggca ggaattcctg  600
tccagcctgg aaggttttgt taacgtcctg tccggcgccc aggagagcct taaggagaag  660
gtgaacttac gaaagtgcga catactcgag ctcaaaaccc tgaaggaacc tacagactac  720
ctcaccctcg caaacaaccc cgaaaccctc ggcaaaattg aagattgcat gaaggtttgg  780
attaagcaga cggaacaagt cctggccgag aacaaccaac tcctaaagga ggccgacgac  840
gtgggcccgc gcgctgagct ggagcactgg aagaagaggc tcagcaagtt taactatctt  900
cttgagcagc tgaagagccc ggacgttaag gcggtactag ccgtcctcgc ggctgcgaag  960
tcgaaactgc tcaagacctg gcgtgagatg gatatacgca ttacggacgc aaccaacgaa  1020
gctaaggaca acgttaagta cttgtatacc ctcgagaagt gctgcgaccc actctactca  1080
tctgacccgc tcagtatgat ggatgccatc cccacgctaa ttaacgcaat taagatgatc  1140
tactcgatat cgcactatta caacacgtct gaaaaaataa ccagcctctt cgtaaaagtg  1200
accaaccaga tcatttcagc ctgtaaggct tacatcacaa acaacggcac cgcctccata  1260
tggaaccagc cccaggacgt cgtggaagag aagatcctat cggccataaa gctgaagcag  1320
gagtaccagc tgtgcttcca caaaaccaag cagaaactca agcagaaccc caatgctaag  1380
cagttcgact tctctgagat gtatattttc gggaagtttg aaaccttcca ccgccgcctg  1440
gcgaagatca tcgacatatt cacaactctg aagacctaca gtgttctaca agacagcact  1500
```

-continued

```
atagagggtc tcgaggatat ggccactaag taccagggca ttgtcgcaac tatcaagaag  1560
aaagaatata atttcctcga tcagcgtaag atggacttcg accaggacta cgaagaattc  1620
tgcaagcaga cgaatgattt gcataacgaa ctccggaagt tcatggacgt aacgtttgcc  1680
aagattcaaa acacaaatca ggcgttgcgg atgctaaaga agttcgagcg tctgaacatc  1740
cctaatctag ggattgacga caagtaccaa cttatactgg aaaactacgg ggctgacatc  1800
gatatgatct ccaagctata taccaagcaa aagtatgacc cgccgttagc tcggaatcag  1860
cccccgatcg ccgggaagat cctgtgggca cggcagcttt ttcaccgcat tcagcagcct  1920
atgcagctgt tccagcagca cccggcggtt ctctccaccg ccgaggctaa gccaattata  1980
cgtagctaca accgcatggc gaaagtcctg ctcgagtttg aggtcttgtt ccaccgagcg  2040
tggcttcggc agatcgaaga gatccacgtc gggctcgagg cctcgctcct ggttaaggcg  2100
ccggggaccg gtgagctgtt cgtaaacttc gacccgcaaa tactaatcct gttccgtgaa  2160
accgagtgca tggcccagat gggcctcgag gtctcacctt tggccacgag cctgttccag  2220
aagcgcgacc gctacaagcg gaacttctct aacatgaaga tgatgcttgc cgagtaccag  2280
agggttaagt cgaagatccc tgctgccatc gagcagctca tcgtgccaca tctggccaag  2340
gttgacgagg cactccaacc gggcttggcg gccctgacgt ggacctccct aaacattgag  2400
gcctacttgg aaaatacttt cgcgaagatt aaggatctcg aattactact ggatcgtgtg  2460
aatgacctca tagaattccg gatagacgcg atcctagagg agatgtcgag cacccccctc  2520
tgtcagctcc cgcaggagga gccgctcaca tgcgaggaat ttctccagat gactaaggac  2580
ctctgcgtta acggggccca gatactccat ttcaagtcgt ccctcgttga ggaggcggtg  2640
aatgaactgg ttaatatgct cttggatgtg gaagtgctct cggaggaaga atccgagaag  2700
attagcaacg agaatagcgt gaactacaag aacgagagct cagcaaaacg ggaggagggg  2760
aattttgata cgctgacttc ctccatcaac gcgcgggcca acgctctctt gctgacaaca  2820
gtaacgcgca aaaagaagga gactgagatg ctaggagagg aggcgcgcga gctgctgtcc  2880
catttcaacc accaaaatat ggatgcgctt ctcaaagtca cccggaatac cctcgaggcg  2940
atacgcaagc gcatccattc gagccatacg ataaacttca gggacagcaa ctccgcgtca  3000
aatatgaagc agaactcgtt gccgatattc cgggcctcgg tgacgctggc gatcccgaac  3060
attgtgatgg caccggccct cgaggacgta cagcagaccc ttaacaaggc ggtggagtgc  3120
atcatctccg ttcccaaggg cgtccgccag tggtcctcgg agctgctcag caagaaaaag  3180
attcaggagc gtaaaatggc ggcccttcaa tcgaacgaag actccgactc tgacgttgag  3240
atgggagaga acgagctaca ggatacctta gaaatcgcct ccgtgaacct ccctatcccg  3300
gtgcagacga aaaactacta caagaacgtc agcgaaaaca aggaaatcgt aaagctggtg  3360
agcgtcctga gtaccatcat taacagcaca aagaaggaag tgataacctc gatggactgc  3420
tttaagcgct acaaccacat ttggcagaaa ggcaaggagg aggctataaa aacgttcatc  3480
acgcagagcc ccctgctctc ggagttcgag tcacaaatcc tctacttcca aaatctggag  3540
caggagatca acgctgagcc ggaatatgtg tgcgtcggct cgatagccct gtacacggct  3600
gatctgaaat ttgcgctgac cgctgagacg aaggcttgga tggtggtgat tggccgacac  3660
tgcaacaaga agtaccggtc tgaaatggag aacatcttta tgctaatcga ggaatttaac  3720
aaaaagctga accgtcccat taaggatctg gacgacatcc gaattgccat ggcggcccta  3780
aaggaaatta gagaggagca gatatccatt gactttcagg ttggccccat cgaagaatca  3840
tatgcccttc tgaatcgata cggtctatta atcgcccgag aggaaataga taaggtggac  3900
acacttcatt atgcatggga gaaactctta gcgcgggccg gcgaagtgca gaataagctc  3960
gtatcgctgc aaccatcatt taagaaggag ctcatcagtg ctgtcgaagt ctttctgcag  4020
gactgccacc agttctatct ggattatgac ctgaacggtc cgatggcgag tggtctgaag  4080
ccccaagagg cttcagaccg gcttattatg ttccaaaatc agtttgataa tatttaccgg  4140
aagtatatca cctatacagg gggtgaagaa ttgtttggtc tcccagccac ccagtaccca  4200
caattattgg aaataaagaa gcagctgaac cttcttcaaa aaatctacac tctctataat  4260
tcggtaattg aaactgttaa ttcctactac gatattctct ggagcgaggt caacattgag  4320
aaaattaaca acgaactctt ggagtttcaa aacagatgcc gcaagttgcc cagagcgctg  4380
aaggactggc aggcttttct cgaccttaaa aaaataatcg atgatttcag tgaatgctgt  4440
cctctcttag aatacatggc ctcaaaggct atgatggaga gacactggga gaggattacg  4500
actctcacgg ggcattcttt ggacgttggc aacgagtcct tcaagctgcg taatataatg  4560
gaggctccac ttctcaagta caaagaggaa atagaagaca tctgtatatc tgctgtcaaa  4620
gagcgcgata tagaacagaa actaaagcag gtaattaacg aatgggacaa taaaacgttt  4680
acatttggca gtttcaagac acgtggagaa ttattgcttc gtggcgactc cacctcggaa  4740
attatagcta acatggagga ctctctcatg ttactcggct cgctgttatc gaaccggtat  4800
aatatgccat tcaaagcaca gattcagaag tgggtgcagt atctatctaa tagtacggat  4860
attatagaga gctggatgac cgtccagaat ctctggatct acctggaggc ggtgtttgtg  4920
ggtggtgata ttgcgaagca gcttccaaag gaggccaaaa gattctccaa cattgacaaa  4980
tcctgggtca agattatgac tcgggcccac gaagtgccct ccgtggtgca gtgctgcgtt  5040
ggcgacgaaa ccttgggcca gctgttgccc cacctgttgg atcaattgga aatctgccaa  5100
aagagcctga ctggctacct agaaaaaaag cgtctgtgct ttccccggtt ctttttcgtt  5160
tctgaccctg cactactcga aatcttgggt caggcctcag attctcacac aattcaggct  5220
catttgttaa atgtgtttga caacatcaaa agtgtgaaat ttcatgaaaa gatttatgac  5280
aggatcttgt ccatttcatc ccaagagggg gaaaccattg agcttgataa gcctgtgatg  5340
gcagagggaa acgtggaggt ctggttaaac agtctcctgg aagagtccca gtcctcactg  5400
cacctggtaa tccgccaggc ggcggctaat atccaggaga caggattcca gctcacggaa  5460
ttccttagtt cgtttccggc gcaagtgggg ctcctcggca ttcagatgat ctggacgaga  5520
gattcggagg aagccctcag aaacgccaag tttgacaaga agattatgca gaaaactaac  5580
caagccttcc tagagctcct caacaccctg atcgatgtca caacacgtga tctatcgtct  5640
accgagcggg tcaagtatga gacactgatt accatacacg tgcaccagcg tgatatattc  5700
gatgatctct gccacatgca cataaagagt cccatggact tcgaatggct aaaacagtgc  5760
cgcttctact ttaatgaaga ctcggataag atgatgatcc atatcacaga tgtagcgttt  5820
atttaccaaa acgagttcct tggctgcaca gacaggttag tcataactcc gttaactgat  5880
cgctgctaca ttacactcgc ccaagcgctt ggaatgtcca tgggtggagc cccccgcaggg  5940
ccggcgggga ctggtaagac cgaaacaact aaagatatgg gccgttgcct cgggaagtat  6000
gtggtagttt ttaactgctc agaccaaatg gatttccgag ggctgggccg tatctttaaa  6060
gggctggcgc aatcaggttc ctggggctgt tttgacgagt tcaatcgtat tgatttaccg  6120
gtgctaagtg ttgccgcaca gcaaattagt ataattctaa cttgtaagaa agaacacaag  6180
aaaagtttta tatttactga tggcgacaac gtcactatga atcctgaatt cgggcttttc  6240
```

-continued

```
ttgactatga acccagggta tgctggccgt caagaacttc ctgaaaatct gaagatcaac  6300
tttcgatcgg tggctatgat ggtaccggat cgccagatca ttatccgagt aaaactggct  6360
tcgtgtggct tcatcgacaa cgtcgtactt gctcgaaagt tcttcaccct ttacaagcta  6420
tgtgaggagc agttatcgaa acaagttcat tacgactttg ggctccggaa tatcttgtcc  6480
gtcctccgca cactcggagc ggctaaacgt gcaaatccca tggacactga gagtacgatt  6540
gtgatgcgag tgttaaggga tatgaatctc tcaaaattaa tcgacgagga cgagcctctt  6600
tttttaagcc ttatagagga tctgttccca aacatcctcc tggacaaggc gggatatccc  6660
gagttggaag cggccattag caggcaggtg gaggaggccg gattgattaa tcacccgccc  6720
tggaaactga aagtcatcca gctgttcgag actcagcggg tccgacacgg tatgatgact  6780
ttaggcccat ctggcgcggg caaaaccacc tgcatccaca ccctgatgag ggctatgacc  6840
gattgtggga agcctcaccg tgagatgcgg atgaacccga aggcgatcac tgcgccccaa  6900
atgtttgggc gtctggatgt ggcgacaaat gactggaccg atggaatctt tagcacactc  6960
tggaggaaga ccctgcgcgc caaaaaagga gagcacatct ggatcattct cgatggcccc  7020
gttgacgcta tttggatcga aaacttaaac agcgtgctcg acgacaacaa gaccctgaca  7080
ttggcaaatg gtgaccggat tcctatggct cccaattgca aaatcatttt tgaacctcac  7140
aacatcgaca acgccagtcc ggctacggtg tcccgcaacg gtatggtttt catgagcagt  7200
tccatactgg attggagtcc gatattggaa ggatttctca agaaacgcag tccccaggag  7260
gcggaaattc tgcggcaact gtatacggaa agttttcctg acctgtaccg cttctgtatt  7320
caaaatctcg agtataagat ggaggtgttg gaggccttcg tcatcacaca gtccattaac  7380
atgcttcagg gcttgatccc cttgaaggag caaggagggg aagtcagcca ggcacatcta  7440
gggcggcttt tcgttttcgc ccttctctgg tccgcgggtg ctgctctcga gctagacgga  7500
cgccggcgct tggagttgtg gctgaggtct cgcccgaccg ggacactcga gctcccgccg  7560
ccagccggac ccggggacac tgcattcgac tactacgtag ctccggacgg cacctggacc  7620
cactggaaca cccgtacgca ggagtatctc tatcccagcg atacaactcc tgagtatggt  7680
agcatactcg ttccgaacgt agacaacgtc agaaccgact ttctgatcca gaccattgct  7740
aagcagggca aggcagtcct acttatcgga gagcaaggga ccgcgaaaac cgtgattatc  7800
aagggcttca tgagtaaata tgacccagag tgtcatatga ttaaatccct caacttctcc  7860
tctgctacca caccactcat gtttcagcgc actatcgaat cctacgtgga caagcggatg  7920
ggcaccacct acggaccgcc tgccgggaag aagatgacgg tatttataga cgacgttaac  7980
atgcccatca tcaacgagtg gggagatcaa gtgaccaacg aaatcgttcg gcaacttatg  8040
gaacaaaacg ggttctataa cctcgagaag ccgggcgagt tcacctcaat agtagacatt  8100
caatttctgg cagctatgat ccacccccgga ggaggacgga acgacattcc ccagcggctc  8160
aagcgccaat tcagcatctt caactgcacg ctgccaagtg aagcatcggt tgacaaaatc  8220
ttcggcgtca tcggggtggg tcactactgc acccagcgcg gcttttcaga ggaagtccga  8280
gattctgtta ctaaactggt tcctttgact agaaggctgt ggcagatgac caaaattaaa  8340
atgcttccta ctccagctaa attccactac gtgttcaatc tgcgagactt atccagggta  8400
tggcaaggta tgcttaatac cacctctgag gtaattaaag aaccgaacga tctgctgaaa  8460
ctgtggaagc acgaatgtaa gagagttatt gcagataggt ttactgtatc gtcagatgtt  8520
acctggttcg ataaagcact ggtgtctttg gtcgaagaag agtttgggga agagaagaag  8580
ctactcgtcg attgcgggat agacacttac tttgtggact tcttaagaga cgcccctgag  8640
gctgccggcg aaacatcgga agaggcagac gctgagactc ctaagatcta tgagccgatc  8700
gagagcttta gccacctcaa ggagcgtctg aatatgtttt tacaattgta taacgagagc  8760
attcgtggtg ctgggatgga tatggtgttc ttcgccgatg caatggtgca tctggttaag  8820
attagccggg tgattcgcac gccacaggga aacgcgctac tggtcggggt gggtgggtca  8880
ggaaagcaat cgttaactcg tttggcatcc tttatcgcgg gatatgtgag ttttcaaatc  8940
accctgacga ggtcctataa tacatccaac ctgatggagg atcttaaagt tttgtacagg  9000
acggcgggac aacagggcaa aggaataacc ttcatcttca cagataacga aattaaagac  9060
gaatcattct tggagtatat gaacaacgtc ttatcaagcg gcgaagtttc gaacctcttc  9120
gcgcgggacg aaatcgatga gatcaactct gatctcgctt ctgtcatgaa gaaagaattc  9180
ccccgctgtt tgccgacgaa tgagaacttg catgactatt tcatgtcccg tgtgcggcag  9240
aatttgcaca ttgtgctatg tttttcaccg gtgggggaga agttccgaaa tagagctttg  9300
aagttccctg ctttgatttc tgggtgtact attgactggt tttcccgttg gcccaaggac  9360
gctctggtcg ccgtgtccga gcactttta accagctatg atatcgactg cagcctcgaa  9420
attaagaagg aagtagttca gtgtatgggc tctttccaag acggtgtggc agagaagtgc  9480
gtcgactatt tccagaggtt tcgccgatct actcatgtca cacctaagag ctacttgtcc  9540
ttcatacagg ggtacaagtt tatatatggg gagaaacacg ttgaagtaag gactctggca  9600
aaccgtatga atactggctt agagaagctc aaggaggcct cagaatccgt ggctgctctc  9660
tcaaaggagc ttgaagctaa ggagaaggaa ctccaagttg ctaacgataa agcggatatg  9720
gttctaaagg aagtcactat gaaagcacaa gcggctgaaa aggttaaggc ggaggtacag  9780
aaggtgaagg atcgcgccca ggcaatagtc gattccattt ccaaagacaa ggccatcgcg  9840
gaagaaaagc tagaagcggc gaagccggcc ttagaagagg cagaggctgc cttgcaaacc  9900
ataagaccca gtgacatcgc cacggtacga acccttggtc gtcctcctca tttgattatg  9960
aggattatgg actgtgtcct gcttttattt caacgtaaag tatctgcagt taagattgat  10020
ttggaaaaat cctgtaccat gccctcatgg caggaatccc tgaaattgat gaccgcgggc  10080
aatttccttc aaaatttgca acaattcccc aaggacacca ttaacgaaga ggtcatagaa  10140
tttttatctc catattttga gatgccagac tacaatattg aaacagcgaa gcgcgtctgt  10200
ggtaacgttg caggtctctg ttcgtggacc aaagctatgg cctccttctt tagtatcaat  10260
aaagaggtac taccactgaa agccaacctg gtggtacagg agaaccggca tctgcttgct  10320
atgcaggatc ttcagaaggc ccaggccgaa ttagacgaca agcaggctga gcttgacgtt  10380
gtgcaagcag aatacgaaca agctatgaca gaaaagcaga ctttattaga agacgctgaa  10440
cgctgcagac ataagatgca gactgcaagc accctcatat ccggtttggc tggagaaaaa  10500
gagcggtgga cagagcagtc gcaagaattc gctgctcaaa ccaaaaggtt ggttggagac  10560
gttctactcg cgacagcgtt tctctcctat tctggtcctt tcaaccagga attccgggac  10620
cttttgctga atgactggag aaaagaaatg aaggctcgca aaataccatt tggaaagaat  10680
ttgaacttgt ctgaaatgct tattgacgca cccactatat cagagtggaa tcttcaggga  10740
cttccaaatg acgatctgtc catccaaaac ggaattattg taaccaaggc gagccgctac  10800
cctctgctaa ttgacccgca gacacagggc aagatctgga ttaaaaataa ggaaagcagg  10860
aacgagctcc agatcactag tctcaaccac aagtacttcc gtaaccacct cgaagatagt  10920
ctgtccctgg gacggccgtt gctaatcgag gacgtcggag aagagctgga ccccgcatta  10980
```

```
gacaacgttc ttgaaagaaa ttttatcaag acaggatcaa ctttcaaagt taaagtagga  11040
gataaagaag tggatgtgtt agatggcttc cgcctatata tcacgactaa actcccgaat  11100
cccgcctata ctccagagat cagcgctaga actagcatca tagatttcac tgtaactatg  11160
aaggggttag aagatcaatt attaggacgc gtcatcctga cggagaaaca ggaacttgaa  11220
aaagagcgta cacacctcat ggaagacgtg acagctaaca aacgtcggat gaaggaactg  11280
gaggacaatt tactgtatcg gttgacatca acacagggct cccttgttga ggacgagagt  11340
ctgatcgtgg tcctgtctaa cacaaagagg actgctgaag aagtcactca gaaattggag  11400
atttctgccg aaactgaagt tcagattaac tccgctagag aagagtatcg tccagtcgct  11460
actcggggct ctatcctata cttcctcata actgagatgc gcttggtcaa tgagatgtac  11520
cagacttcac tccggcaatt cctgggcttg tttgacttgt cgctggcaag atcagtaaaa  11580
tctccaatta ccagcaagag aatcgcaaac atcattgagc acatgacgta cgaggtgtat  11640
aaatacgcgg cgaggggtct ttatgaagag cataagttcc tcttcaccct actattaacg  11700
ttgaagatag atattcagag gaaccgggtg aagcacgagg agtttctaac tctaataaaa  11760
ggaggagctt ctttagatct taaagcctgt ccaccgaaac cttctaagtg gattttagac  11820
ataacatggc tgaatttagt ggagttgtcc aagttacgtc agttcagtga cgttttggat  11880
cagatatcta ggaacgagaa gatgtggaag atctggttcg ataaagagaa tccggaggag  11940
gagcccttgc caaatgctta tgataaaagc ctagactgct tcaggaggct tttgctcatc  12000
cgctcctggt gccccgaccg cactattgcc caagctagga aatacattgt ggactccatg  12060
ggggagaagt atgccgaagg agtcatactc gacttggaga agacttggga agagtcagat  12120
ccgaggacgc ccctcatttg tcttctttcc atgggttctg atcccacgga ctctattata  12180
gcactcggga aaagactaaa gatcgagaca cgctatgtta gcatgggaca ggggcaagag  12240
gtccatgccc gcaaactact acagcagact atggctaatg gaggttgggc tctgttacag  12300
aactgtcact taggccttga ttttatggac gaattgatgg acatcataat tgagacggag  12360
ctagttcacg acgcatttcg cttatggatg acgactgaag cacacaagca gtttccgata  12420
accctgttgc agatgtccat caagttcgcc aacgaccctc cccagggcct tagggcaggt  12480
ctcaaaagga cctacagcgg cgtttcccag gatttacttg acgtctccag cggatcccag  12540
tggaagccca tgttgtacgc cgtggctttc cttcacagca cagttcagga aaggcggaag  12600
tttggtgcgc taggctggaa catcccctac gagttcaacc aggctgactt taatgcaaca  12660
gtacagttta ttcaaaatca tctggatgac atggatgtca aaaaaggtgt gtcatggact  12720
acaataaggt acatgattgg ggagatacag tacggaggcc gggtaactga tgattatgat  12780
aaaagattgt taaacacttt tgctaaagtt tggtttagtg aaaatatgtt tggacctgat  12840
tttagttttt atcaaggtta taatatacct aagtgctcaa ctgtagataa ttatttacaa  12900
tatattcaaa gtttacctgc atatgatagt cctgaagttt ttggtttgca tcctaatgca  12960
gatataacat accaatcaaa attagcaaaa gacgtcttag atacaatact tggtatccag  13020
cctaaggaca ccagtggggg cggtgacgag actcgcgagg ctgtggtggc ccggctcgct  13080
gatgacatgc tagagaaact tcccccggac tacgtcccct ttgaggtcaa agagcggctg  13140
cagaaaatgg ggcccttcca gcccatgaac atattcttgc gccaggagat agaccgtatg  13200
caacgagtcc tgagcctggt ccgctcgact ctaaccgagc tcaagctggc catcgatggg  13260
acgatcatta tgtctgagaa tttgagggac gcgctcgatt gcatgtttga cgccaggatc  13320
ccagcctggt ggaaaaaagc tagttggatc tcatctaccc tggggttctg gttcacagag  13380
ttgatagagc gcaactcgca attcacctcc tgggtgttca acgggcggcc ccactgcttc  13440
tggatgacgg gcttcttcaa cccgcagggc ttcctgacgg ctatgcggca ggaaatcacc  13500
cgggcgaaca agggttgggc gctcgacaat atggtgctct gcaacgaggt cacgaagtgg  13560
atgaaggacg acatctcggc gcctcccacc gaaggggtct acgtatacgg cctgtacctc  13620
gagggggcgg gctgggacaa gcgtaacatg aagctgatcg agtcgaagcc caaggtgctg  13680
ttcgagctga tgcccgtcat ccggatctac gcagagaaca acacgctgcg cgacccgcgg  13740
ttctactcgt gccccatcta caagaagccg gtgcggacgg acctcaacta catcgccgcc  13800
gtcgacctcc gcaccgcgca gacccccgag cactgggtgc tgcggggggt cgcattgctc  13860
tgcgacgtca agtag                                                   13875
```

```
SEQ ID NO: 29           moltype = DNA  length = 13875
FEATURE                 Location/Qualifiers
misc_feature            1..13875
                        note = Synthetic polynucleotide
source                  1..13875
                        mol_type = other DNA
                        organism = synthetic construct
SEQUENCE: 29
atgttcagaa tcgggcggcg acaattatgg aaacactcag tcactagagt tctaacacaa  60
aggttaaaag gagaaaaaga agcaaaaaga gcgctattgg acgcaagaca taattatttg  120
ttcgcgatag tcgcatcgtg tttagattta aataaaactg aagtagaaga cgctattttg  180
gaaggaaatc aaatcgaacg gatcgaccaa ttattcgcgg ttggaggact ccgtcattta  240
atgttttact accaagacgt ggaggaagcg gaaactgggc aactcgggtc acttgggga  300
gttaacttag tctcaggtaa aattaagaag ccaaaagtat ttgtaacaga aggaaacgac  360
gttgcactaa caggtgtttg cgtatttttt attcgaactg atccgtcaaa agccattaca  420
ccagataata ttcatcagga ggtttcattt aacatgctag atgctgctga tggaggttta  480
ctaaattccg tacgtaggtt gctaagcgat attttcattc ctgccctaag agcaacttct  540
cacggatggg gtgagttaga aggtttacaa gacgctgcaa acatacgtca agaattcctt  600
tcaagtcttg agggatttgt caatgtgctc tcaggagccc aagaatcact aaaggagaaa  660
gtaaatttga gaaagtgtga tattcttgaa ttgaaaacct taaaagaacc taccgattat  720
ctaacgcttg caaataatcc tgagacatta ggtaaaatcg aggattgtat gaaagtgtgg  780
atcaaacaga ctgaacaagt cttagcagaa aataaccagt tattaaaaga agcggatgac  840
gttggaccgc gagcagaact agaacactgg aagaagaggc taagtaaatt taattatctt  900
cttgaacaac tgaagtctcc agatgttaag gcggttctcg cggtgttagc agctgcaaaa  960
tcaaaactcc ttaaaacgtg gcgtgaaatg gatataagga ttactgatgc aactaacgaa  1020
gcaaaagata acgtaaaata tttgtatacg ctcgaaaagt gttgtgatcc tttatattca  1080
tcagatccac ttagtatgat ggacgctata cctacattaa ttaacgctat taaaatgatt  1140
tatagtatct ctcattatta taatacaagc gaaaaaataa cttccttatt cgtaaaagtc  1200
acgaaccaga ttatatcagc gtgtaaagca tatataacta acaacggtac tgcatctata  1260
```

-continued

```
tggaatcagc cccaagacgt ggttgaggaa aaaattttga gtgctataaa attaaaacaa  1320
gaatatcaat tgtgctttca taaaactaaa caaaaactga agcaaaatcc aaatgcaaaa  1380
caatttgact tttctgaaat gtatatattc ggtaaattcg aaacgtttca ccgtcgatta  1440
gccaaaatta tcgacatctt tacgacgtta aaaacttaca gcgtgctaca agattctacg  1500
atagaagggc tagaggatat ggccacaaag taccagggca tcgtggccac tatcaagaag  1560
aaggagtaca acttcttaga ccagcgtaaa atggatttcg accaggacta tgaagaattc  1620
tgcaaacaaa cgaatgatct gcacaacgag ctgcggaaat tcatggatgt gacttttgcc  1680
aaaatacaga ataccaacca agctcttagg atgttaaaga aatttgaaag gctcaacatt  1740
cctaatttgg gcattgatga caaataccag ttgatactcg aaaattatgg agcagatatt  1800
gatatgatct ctaaactata cacaaaacaa aaatatgatc ctccgttagc tagaaatcaa  1860
ccgccgattg ctggtaagat actctgggcc agacaactct ttcaccgcat ccagcagccc  1920
atgcagctgt ttcagcagca ccctgcggtg ctctccaccg ccgaggcgaa acccattatt  1980
cgatcttata accgcatggc caaggttctg ttagagtttg aagttttgtt ccaccgtgcc  2040
tggttacgtc agatcgagga gatccatgtg ggactggagg cctctctcct agtcaaggcc  2100
cccggcaccg gcgaactctt tgtcaatttt gatccccaga ttctaatact cttccgggaa  2160
accgagtgca tggcccagat gggtttagag gttagtcctc tggctacttc actgttccag  2220
aagagggacc gctataaacg gaatttcagc aatatgaaga tgatgctcgc tgagtatcag  2280
agggtcaagt ccaaaatccc cgctgcgatc gagcagctga tcgtgccaca cctggccaaa  2340
gtagatgagg ccctacaacc aggactggct gcgctgacgt ggacctctct gaatatcgaa  2400
gcgtatcttg aaaacacctt tgccaagatt aaagacctgg agcttttact ggacagagtg  2460
aacgacctca ttgaattccg catagacgcg attttagagg agatgtcttc cacgccacta  2520
tgtcagcttc ctcaggagga gcctctcaca tgtgaagagt tccttcagat gactaaggat  2580
ctctgcgtga atggcgctca gatactacat ttcaaatcta gcttggtcga ggaggcagtg  2640
aacgaattgg ttaacatgtt actggatgta gaagtcctta gcgaggagga atccgaaaag  2700
atcagcaacg aaaattcggt gaactataag aacgaatctt ctgccaagcg ggaggagggc  2760
aactttgata cactcacatc ttccatcaat gcgcgcgcta atgcactctt gttgacgacg  2820
gttaccagga aaaagaagga gactgagatg cttggggaag aggcaaggga gttactgtcc  2880
cacttcaacc atcagaatat ggacgccttg ttaaaggtta cccgaaacac gttagaggca  2940
attcgtaagc gtattcactc aagccacacg ataaacttcc gagactcaaa ctcagcatca  3000
aatatgaagc aaaactcctt gccgatcttc agagccagcg tcaccctggc catacctaac  3060
atcgttatgg caccggcact tgaggacgta caacaaacct tgaacaaagc agtagagtgc  3120
atcatcagcg tccctaaagg agttcgccaa tggtccagtg aactgctatc caagaagaag  3180
atccaggagc gtaaaatggc tgcgttacag agtaacgaag attcggactc tgacgttgaa  3240
atgggtgaaa acgagctcca agacacactg gagattgcga gcgttaacct gcctataccc  3300
gtccagacca agaactacta caaaaacgtg tccgaaaaca aggagatcgt caagctcgtt  3360
tctgtgctca gcaccatcat aaattcgact aagaaagaag ttataacttc catggattgt  3420
ttcaaacggt ataaccacat ctggcagaaa ggcaaggagg aagctatcaa gacatttatt  3480
acccagtccc cactactaag cgagttcgag tctcagatcc tttacttcca gaatcttgag  3540
caggagatca acgcggagcc cgaatatgtg tgcgtcggct cgatagccct gtacacggct  3600
gatctgaaat ttgcgctgac cgcggagacg aaggcttgga tggtggtgat tggccgacac  3660
tgcaacaaga agtaccggtc tgaaatggag aacatcttta tgctaatcga ggaatttaac  3720
aaaaagctga accgtcccat taaggatctg gacgacatca ggattgccat ggcggcccta  3780
aaggaaatta gagaggagca gatatccatt gattttcagg ttggccccat cgaagaatca  3840
tatgcccttc tgaatcgata cggtctatta atcgcccgag aggaaataga taaggtggac  3900
acacttcatt acgcatggga gaaactctta gcgcgggccg gcgaagtgca gaataagctc  3960
gtatcgctgc aaccatcatt taagaaggag ctcatcagtg ctgtcgaggt ctttctgcag  4020
gactgccacc agttctatct ggattatgac ttaaacggtc cgatggcgag tggtctgaag  4080
ccccaagagg cttcagaccg gcttatcatg ttccaaaatc agtttgacaa tatttaccga  4140
aagtatatca cctatacagg gggtgaagaa ttgtttggtc tcccagccac ccagtatcca  4200
caattattgg aaataaaaaa gcagctgaac cttttacaaa aaatctacac tctctataat  4260
tcggtaattg aaactgttaa ttcctactac gatattctct ggagcgaggt caacattgag  4320
aaaattaata acgaactctt ggagtttcaa aacagatgcc gcaagttgcc gagagcgctg  4380
aaggactggc aggcttttct cgaccttaag aaaataatcg atgatttcag tgaatgctgt  4440
cctctcttag aatacatggc gagtaaggct atgatggaga gacactggga gaggattacg  4500
actctgacgg ggcattcttt agacgttggc aacgagtcct tcaagctgcg taatataatg  4560
gaggctccac ttctcaaata caaagaggaa atagaagaca tctgtatctc tgctgtcaaa  4620
gagcgcgaca tagaacagaa actaaagcag gtcattaacg aatgggacaa taaaacgttt  4680
acatttggca gtttcaagac acgtggagaa ttattgcttc gtggcgactc cacctcggaa  4740
attatcgcta acatggagga ctctctcatg ttactcggct cgctgttatc gaaccggtat  4800
aatatgccat tcaaagcaca gatccagaag tgggtgcagt atctatctaa tagcacggat  4860
attatagaga gctggatgac cgtccaaaat ctctggatct acctggaggc ggtgtttgtg  4920
ggaggtgata ttgcgaagca gcttccaaag gaggccaaaa gattctccaa catcgacaag  4980
tcctgggtca agattatgac tcgggcccac gaagtgccct ccgtggtgca gtgctgcgtt  5040
ggggacgaaa ccttgggcca gctgttgccc cacctgttgg atcaattgga aatctgccaa  5100
aagagcctga cgggctacct agaaaaaaag cgtctgtgct ttccccggtt ctttttcgtt  5160
tctgaccctg cactactcga aatcttgggt caggcctcag attctcacac aattcaggct  5220
catttgttaa atgtgtttga caatatcaaa agtgtgaaat ttcatgaaaa gatttatgac  5280
aggatcttgt ccatttcatc ccaagagggg gaaaccattg agcttgataa gcctgtgatg  5340
gcagagggaa acgtggaggt ctggcttaac agtctcctgg aagagtccca gtcctcactg  5400
cacctggtca tccgccaggc ggcggctaat atccaggaga caggattcca gctcacggaa  5460
ttccttagtt cgtttccggc gcaagtgggg ctcctcggaa ttcagatgat ctggacgaga  5520
gattcggagg aagccctccg caacgccaag tttgacaaga agattatgca gaaaactaac  5580
caagccttcc tagagctcct caacaccctg atcgatgtca caacacgtga tctatcgtct  5640
accgagcggg tcaagtatga gacactgatt accatacacg tgcaccagcg tgatatattc  5700
gacgatctct gccacatgca cataaagagt cccatggact tcgaatggct aaaacagtgc  5760
aggttctact ttaacgaaga ctcggataag atgatgatcc atatcacaga tgtagcgttt  5820
atttaccaaa acgagttcct tggctgcaca gacaggttag tcataactcc gttaactgat  5880
cgctgctaca ttacactcgc ccaagcgctt ggaatgtcca tgggtggagc ccccgcaggg  5940
ccggcgggga ctggtaagac cgaaacaact aaagatatgg gccgttgcct cgggaagtat  6000
```

-continued

```
gtagtagttt ttaactgctc agaccaaatg gatttccgag ggctgggccg tatctttaaa  6060
gggctggcgc aatccggttc ctggggctgt tttgacgagt tcaatcgtat tgatttaccg  6120
gtgctaagtg ttgccgcaca gcaaattagt ataatattga cttgtaagaa agaacacaag  6180
aaaagtttta tatttactga tggcgacaac gtcactatga atcctgaatt cgggcttttc  6240
ttgactatga acccagggta tgctggccgt caagaacttc ctgaaaatct gaagatcaac  6300
tttcgatcgg tggctatgat ggtaccggat cgccagatca ttatccgggt aaaactggcg  6360
tcgtgtggct tcatcgacaa cgtggtactt gctcgaaagt tcttcaccct ttacaagcta  6420
tgtgaggagc agttatcgaa acaagttcat tacgactttg ggctccggaa tatcttgtcc  6480
gtcttacgca cactcggagc ggctaaacgt gcaaatccca tggacactga gagtacgatt  6540
gtgatgaggg tgttaaggga tatgaatctc tcaaaattaa tagacgagga cgagcctctt  6600
tttctctccc ttatagagga tctgttccca aacattctcc tggacaaggc gggatatccc  6660
gagttggaag cggcgatcag caggcaggtg gaggaggccg gattgattaa tcacccgccc  6720
tggaaactga aagtcatcca gctgttcgag actcagcggg tccgacacgg tatgatgact  6780
ttaggcccct ctggcgcggg gaaaaccacc tgcatccaca ccctgatgag ggctatgacc  6840
gattgtggga agcctcaccg tgagatgcgg atgaacccga aggcgatcac agcgccccaa  6900
atgtttgggc gtctggatgt ggcgacaaat gactggaccg atggaatctt ttccacactc  6960
tggaggaaga ccctgcgcgc aaaaaaagga gagcacatct ggatcattct cgatggcccc  7020
gttgacgcta tttggatcga aaacttaaac agcgtgctcg acgacaacaa gaccctgaca  7080
ttggcaaatg gtgaccggat tcctatggct cccaattgca aaatcatttt tgaacctcac  7140
aacatcgaca acgccagtcc ggctacggtg tcccgcaacg gtatggtttt catgagcagt  7200
tccatactgg attggagtcc gatattggaa ggatttctca agaaacgcag tccccaggag  7260
gcggaaattc tgcggcaact gtatacggaa agtttccctg acctgtaccg cttctgtatt  7320
caaaatctcg agtataagat ggaggtgttg gaggccttcg tcatcacaca gtccattaac  7380
atgcttcagg gcttgatccc cttgaaggag caaggagggg aagtcagcca ggcacatcta  7440
gggcggcttt tcgttttcgc ccttctctgg tccgcgggtg ctgctctcga gctagacggt  7500
cgccggcgct tggagttgtg gctgaggtct cgcccgaccg ggacactcga gctgccgccg  7560
ccagccggac ccggcgacac tgcattcgac tactacgtag ctccggacgg cacctggacc  7620
cactggaaca cccgtacgca ggagtatctc tatcccagcg atacaactcc tgagtatggt  7680
agcatactcg ttccgaacgt agacaacgtc agaaccgact ttctgatcca gaccattgct  7740
aagcagggca aggcagtcct attgatcgga gagcaaggga ccgcgaaaac cgtgattatc  7800
aagggcttca tgagtaaata tgacccagag tgtcatatga ttaagtccct taacttcagt  7860
tctgctacca caccactcat gtttcagcgt actatcgaat cctacgtgga caagcggatg  7920
ggcaccacct acgggccgcc tgccgggaag aagatgacgg tatttataga cgacgttaac  7980
atgcccatca tcaacgagtg ggagatcaa gtgaccaacg aaatcgttcg gcaacttatg  8040
gaacaaaacg ggttctataa cctcgagaag ccgggcgagt tcacctcaat agtagacatt  8100
caatttctgg cagctatgat ccaccccgga ggaggacgga acgacattcc ccagcggctc  8160
aagcgccaat tcagcatctt caactgcacg ctgccaagtg aagcatcggt agacaaaatc  8220
ttcggcgtca tcggggtggg tcactactgc acccagcgcg gcttttcaga ggaagtccga  8280
gattctgtta ctaaactggt tcctttgact agaaggctgt ggcagatgac caaaattaaa  8340
atgcttccta ctccagctaa attccactac gtgttcaatc tgcgagactt atccagggta  8400
tggcaaggta tgcttaatac cacctctgag gtaattaaag aaccgaacga tctgctgaaa  8460
ctgtggaagc acgaatgtaa gagagttata gcagataggt ttactgtatc gtcagatgtt  8520
acctggttcg ataaagcact ggtgtctttg gtcgaagaag agtttgggga agagaagaag  8580
ctactcgtcg attgcgggat cgacacttac tttgtggact tcttaagaga cgcccctgag  8640
gctgccggcg aaacatcgga agaggcagac gctgagactc ctaagatcta tgagccgatc  8700
gagagcttta gccacctcaa ggagcgtctg aatatgtttt tacaattgta taacgagagc  8760
attcgtggtg ctgggatgga tatggtgttc ttcgcggatg caatggtgca tctggttaag  8820
atttctcggg tcattcgcac gccacaggga aacgcgctac tggtcggggt gggtgggtca  8880
ggaaagcaat cgttaactcg tttggcatcc tttatcgcgg gatatgtgag ttttcaaatc  8940
acactgacaa ggtcctataa tacatccaac ctgatggagg atcttaaagt tctttacagg  9000
acggcgggac aacagggcaa aggaataacc ttcatcttca cagataacga aattaaagac  9060
gaatcattct tggagtatat gaacaacgtc ttatcaagcg gcgaagtttc gaacctcttt  9120
gcgcgggacg aaatcgatga gatcaactct gatctcgctt ctgtcatgaa gaaagaattc  9180
ccccgctgtt tgccgacgaa cgagaacttg catgactatt tcatgtcccg tgtgcggcag  9240
aatttgcaca ttgtgctttg cttttcaccg gtgggcgaga agttccgaaa tagagctttg  9300
aagttccctg ctttgatttc tgggtgtact attgactggt tttcccgttg gcccaaggac  9360
gctctggtcg ccgtgtccga gcacttttta accagctatg atatcgactg cagcctcgaa  9420
attaagaagg aagtagttca gtgtatgggc tctttccaag acggtgtggc agagaagtgc  9480
gtcgactatt tccagaggtt tcgccgatct actcatgtca cacctaagag ctacttgtcc  9540
ttcatacagg ggtacaagtt tatatacggg gagaaacacg ttgaagtaag gactctggcg  9600
aaccgtatga atactggctt agagaagctc aaggaggcct cagaaagtgt ggctgctctc  9660
tcaaaggaac ttgaagctaa ggagaaggaa ctccaagttg cgaacgataa agcggatatg  9720
gttctaaaag aagtcactat gaaagcacaa gcggctgaaa aggttaaggc ggaggtacag  9780
aaggtgaaag atcgcgccca ggcaatagtc gattccattt ccaaagacaa ggccatcgcg  9840
gaagaaaagc tagaagccgc caagccggcc ttagaagagg cagaggctgc cttgcaaacc  9900
ataagaccga gcgacatcgc gacggtacga acccttggtc gtcctcctca tttgattatg  9960
aggattatgg actgtgtcct gcttttattt caacgtaaag tatctgcagt taagattgat  10020
ttggagaaat cctgtaccat gccctcatgg caggaatccc tgaaattgat gaccgcgggc  10080
aatttccttc aaaatctaca acaattcccc aaggacacca ttaacgaaga ggtcatagaa  10140
tttttatctc catattttga gatgccagat tacaatatag aaacagcgaa gcgcgtctgt  10200
ggaaacgttg caggtctctg ttcgtggacc aaagctatgg cctccttctt tagtatcaat  10260
aaagaggtac taccactgaa agccaacctg gtggtacagg agaaccggca tctgcttgct  10320
atgcaggatc ttcagaaggc ccaggccgaa ttagacgaca agcaggctga gcttgacgtt  10380
gtgcaagcag aatatgaaca agctatgact gaaaagcaga ctttattaga ggacgctgaa  10440
cgctgcagac ataagatgca gactgcaagc accctcatat ccgggttggc tggagaaaaa  10500
gagcggtgga cagagcagtc gcaagaattc gctgctcaaa ccaaaaggtt ggttggagac  10560
gttctactcg cgacagcttt cctctcctat tctggtcctt tcaaccagga attccgggac  10620
cttttgctga atgactggag aaaagaaatg aaggctcgca agataccatt tggtaagaat  10680
ttgaacttgt ctgaaatgct tattgacgca cccactatat cagagtggaa tcttcaggga  10740
```

```
cttccaaatg acgatctgtc catccaaaac ggaattattg taaccaaggc gagtcgctac  10800
cctctgctca ttgacccgca gacacagggc aagatctgga ttaaaaataa ggaaagcagg  10860
aacgaattgc agatcactag tctcaaccac aagtacttcc gtaaccacct cgaagatagt  10920
ctgtccctgg gaaggccgct tctgatcgag gacgttggcg aggagctgga tcctgcgctg  10980
gacaacgttc ttgagcgcaa cttcatcaag accgggtcca ccttcaaggt aaaggtggga  11040
gacaaggagg tggacgtgct ggacggcttt cgcctatata tcaccacgaa gctgcctaac  11100
ccggcgtaca cgcccgagat cagtgcgcgt acgagcatca ttgacttcac cgtgactatg  11160
aaaggcctcg aagatcagct gctcggtcgc gtcattctca cggaaaagca ggagctggag  11220
aaggagcgaa cgcacctgat ggaggacgtg acggccaaca agcggcgtat gaaagagcta  11280
gaggacaacc tgctgtaccg cctcacgtca acccaggggt cgctggtcga ggacgaatcc  11340
ctgatcgtgg tgctgagtaa taccaagcgg acagcagagg aggtcacgca gaaactcgag  11400
atctcggcgg agaccgaggt gcagatcaac agcgcgcggg aggagtacag gccggtggcc  11460
acccgcggga gcatcttata cttcctgatc actgagatgc gccttgtgaa tgagatgtac  11520
cagacaagcc tgcggcagtt ccttggcctg ttcgatcttt cgctggcccg gtccgtcaag  11580
tctccgatta cctccaagcg gatcgctaac ataattgaac acatgacgta cgaggtgtac  11640
aagtacgcgg cgaggggcct ctacgaagag cacaagttcc tgttcacgct gctcctcacg  11700
ctcaagatcg acatccagcg caaccgcgtc aagcacgagg agtttctcac cctgataaag  11760
gggggagcgt ccctggacct gaaggcctgt ccgccgaagc cgtcgaagtg gatcctggac  11820
ataacgtggc tcaacctcgt cgagctgtcc aagctccgtc agttttcgga cgtgctcgac  11880
cagatttcgc ggaacgagaa gatgtggaaa atatggttcg acaaggagaa tccagaggag  11940
gagcccttgc ccaacgcgta tgacaagtcg ctcgactgct tccgtcgcct gctgctgatc  12000
cgcagctggt gccccgaccg gacgatcgcg caggcgagga agtacatcgt tgacagtatg  12060
ggtgagaaat acgcggaggg cgttattctg gatctggaga agacttggga ggagagcgac  12120
ccccgcaccc ccctgatctg ccttctgtct atggggtccg acccgaccga tagcatcatt  12180
gctctgggga agcggctcaa gatcgagacc cggtacgtgt ccatgggaca ggggcaggag  12240
gtgcatgccc gcaagctcct gcagcagact atggcgaacg gggggttgggc gctcttacag  12300
aactgccatc tggggctcga cttcatggat gaactcatgg acatcatcat cgagacggaa  12360
ctcgtgcacg acgcattccg cctgtggatg accaccgagg cgcacaagca gttcccgatc  12420
acgttgctgc agatgtccat caagttcgcc aacgaccctc cgcagggcct ccgggcgggc  12480
ctgaagcgca cgtatagcgg cgtgtctcag gatctccttg atgtcagctc ggggagccag  12540
tggaagccga tgctctatgc cgtggcattt ctacactcga ccgtccagga gcggcgaaag  12600
tttggagcgc tggggtggaa cataccctac gagtttaacc aggccgactt caacgccacc  12660
gtgcagttca tccagaacca tttggacgat atggatgtga agaaggggggt gtcctggacg  12720
accatacggt atatgatcgg cgagatccag tatgggggggc gggtcacgga cgactacgac  12780
aagcggttgc tgaacacgtt cgcgaaggtc tggttcagcg agaatatgtt cgggcccgat  12840
ttttcctttt accagggcta caatataccc aagtgctcca cggtcgacaa ctaccttcag  12900
tacatccaga gcttgcccgc atacgacagc ccggaagtct tcggactcca ccccaacgcc  12960
gacatcacgt accagagcaa gctggccaag gacgtgctcg acaccattct cggcatccag  13020
ccgaaggaca cgtccggcgg gggggacgag acgcgggagg ccgtcgtcgc gcgcttggca  13080
gatgacatgc tggagaagct cccccccgat tacgtcccgt tcgaggtcaa ggaaaggctc  13140
cagaagatgg gcccgttcca gcccatgaac atcttcctcc gccaggagat cgaccggatg  13200
cagcgcgtgc ttagcctggt gcgctcaacg ctgacggagc tgaagctggc catcgacggg  13260
acgatcatta tgtcggagaa cctccgggac gcgctggact gcatgttcga cgcgcgtatc  13320
ccggcctggt ggaagaaggc gtcgtggatc tccagcaccc tggggttctg gttcacggag  13380
ctgatcgagc gcaactcgca attcacctcc tgggtgttca acgggcggcc ccactgcttc  13440
tggatgacgg gcttcttcaa cccgcagggc ttcctgacgg ctatgcggca ggaaatcacc  13500
cgggcgaaca agggttgggc gctcgacaat atggtgctct gcaatgaggt cacgaagtgg  13560
atgaaggacg acatctcggc gcctcccact gaaggggtct acgtctacgg cctgtacctc  13620
gagggggcgg gctgggacaa gcgtaacatg aagctgatcg agtcgaagcc caaggtcctg  13680
ttcgagctga tgcccgtcat ccgcatctac gccgagaaca acacgctgcg cgacccgcgg  13740
ttctactcgt gccccatcta caagaagccg gtgcggacgg acctcaacta catcgccgcc  13800
gtcgacctcc gcaccgcgca gacccccgag cactgggtgc tgcggggggt cgcactgctc  13860
tgcgacgtca agtag                                                   13875
```

```
SEQ ID NO: 30           moltype = DNA  length = 13875
FEATURE                 Location/Qualifiers
misc_feature            1..13875
                        note = Synthetic polynucleotide
source                  1..13875
                        mol_type = other DNA
                        organism = synthetic construct
SEQUENCE: 30
```

```
atgttcagaa taggaaggag acaactatgg aagcacagcg tgacgcgggt acttacccaa  60
cgtctaaagg gggagaagga ggcgaagcgg gcactgctag acgcgcgtca taattacctc  120
tttgcaatag ttgccagctg cctcgacctc aacaagacgg aggtagagga cgccatatta  180
gagggcaacc agattgagcg gatcgatcag ctatttgccg tgggcgggct ccggcatcta  240
atgttttact accaggacgt cgaggaagct gagaccgggc aactgggatc cctgggaggc  300
gtcaacctcg tctccggcaa gataaaaaag cctaaggttt tcgttacaga gggcaacgac  360
gtagcgctga ctggtgtatg cgtcttcttc atccggacag accccagcaa ggcaattacg  420
ccagacaaca tccaccagga ggtctcgttt aacatgctcg acgctgccga tggcgggctg  480
ctgaactcgg tgcgccggct gctctcggat atctttatcc ccgcgcttcg ggcgacgagc  540
cacgggtggg gtgagctgga aggcctacag gacgcggcca atattcgtca ggagttccta  600
tccagcctgg aaggttttgt taacgtgctg tccggcgccc aggagtcgct taaggagaag  660
gtgaacttac gaaagtgtga tatattagag ctgaaaaccc tgaaggaacc tacagactat  720
ctcaccctcg caaacaaccc cgaaaccctc ggcaaaattg aagattgcat gaaggtgtgg  780
attaagcaga cggaacaagt cctggcagag aacaaccaac tcttgaagga ggccgacgac  840
gtgggcccgc gcgctgagct ggagcactgg aagaagaggc tcagcaagtt taactatctt  900
cttgagcagc tgaagagccc ggacgttaag gcggtactag cggtcctcgc ggctgcgaag  960
tcgaagctgc tcaagacctg gcgtgagatg gacatacgca tcacggacgc aaccaacgaa  1020
```

-continued

```
gctaaggaca acgttaagta tttgtatacc ctcgagaagt gctgcgaccc cctctactca  1080
tctgatccgc tcagtatgat ggatgccatc cccacgctaa ttaacgccat taagatgatc  1140
tactcgatat cgcactatta caacacgtct gaaaaaatca ccagcctctt cgtaaaagtg  1200
actaaccaaa tcatcagcgc ctgcaaggct tacatcacta acaacggcac cgccagtata  1260
tggaaccagc cccaggacgt cgtggaggag aagatcctat cggccataaa gctgaagcag  1320
gagtatcagc tgtgcttcca caaaacaaag cagaaactca agcagaaccc aaatgctaag  1380
cagttcgact tttctgagat gtacattttc gggaagtttg aaacatttca tcgccgcctg  1440
gccaaaatca tcgacatatt caccactctg aagacctact cagtcctaca agacagcact  1500
atagaagggc tagaggatat ggccacaaag taccagggca tcgtggccac tatcaaaaag  1560
aaggagtaca acttcttaga ccagcgtaaa atggatttcg accaggacta tgaagaattc  1620
tgcaaacaaa cgaatgattt gcacaacgag cttcggaaat tcatggatgt gacttttgcc  1680
aaaatacaga ataccaacca agctcttagg atgttaaaga aatttgaaag gcttaatatt  1740
cctaatttgg gcattgatga caaataccag ttgatactcg aaaattatgg agcagatatt  1800
gatatgatct ctaagctgta cacaaaacaa aaatatgatc cccgctagc tagaaatcaa  1860
cctccgattg ctggtaagat actctgggcc agacagctct ttcaccgcat ccagcagccc  1920
atgcagctgt ttcagcagca ccctgcggtg ctgtccaccg ccgaagcgaa acccattatt  1980
cgatcttata accgcatggc caaggttctg ttagagtttg aagttttgtt ccaccgtgcc  2040
tggttacgtc agatcgagga gatccatgtg ggactggagg cctctctcct agtcaaggcc  2100
cccggcacag gcgaactctt tgtcaatttt gatccccaga ttctaatact cttccgggaa  2160
accgagtgca tggcccagat gggcttagag gttagtcctc tggctacttc tctgttccag  2220
aagagagacc gctataaacg gaatttcagc aatatgaaga tgatgctcgc tgaatatcag  2280
agggtcaagt ccaaaatccc cgctgcgatc gagcagctga tagtgccaca cctggccaaa  2340
gtagatgagg ccctacaacc aggactggcc gcgctgacgt ggacctctct gaatatcgaa  2400
gcgtatttgg agaacacctt tgccaagatc aaggacctgg agcttttact ggacagagtg  2460
aacgatctca ttgaattccg catagacgcg attttagagg agatgtcttc cacgccacta  2520
tgccagcttc ctcaggagga gccgttaaca tgtgaagagt tcctgcagat gactaaggac  2580
ctctgcgtga atggcgctca gatactacat ttcaagtcta gcttggtcga ggaggcagtg  2640
aacgaattgg ttaacatgtt actggatgta gaagtccttt ccgaggagga atccgaaaag  2700
atcagcaacg aaaattcggt gaactataag aacgaatcta gcgccaagcg ggaggagggc  2760
aactttgata cactcacttc ttccatcaat gcgagggcta atgctctctt gttgacaacc  2820
gttaccagaa aaaaaaagga gactgagatg cttggggaag aggcaaggga gttgctgtcc  2880
cacttcaacc atcagaatat ggacgccctc ttaaaggtta cccgaaacac gttagaggca  2940
attaggaagc gtattcactc aagccacacg ataaacttca gagactcaaa ctctgcatca  3000
aatatgaagc aaaactcctt gccgatcttc agagccagcg tcaccctggc catacctaac  3060
atcgttatgg caccggcact tgaggacgta caacaaacct tgaacaaagc agtagagtgc  3120
atcatcagcg tccctaaagg agttcgccaa tggtccagtg aactgctatc caagaagaag  3180
atccaggagc gtaaaatggc tgcgttacag agtaacgaag attcggactc tgacgttgaa  3240
atgggtgaaa acgaactcca agacacactg gagattgcga gcgttaacct gcctataccc  3300
gtccagacca agaactacta caaaaacgta tccgaaaaca aggagatcgt caagctcgtt  3360
tctgtgctca gcaccataat aaattcgact aagaaagagg ttataacttc catggattgt  3420
ttcaaacggt ataaccacat ctggcagaaa ggcaaggaag aagctatcaa gacatttatt  3480
acccagagcc cactactaag cgagttcgag tctcagatcc tctacttcca gaatcttgag  3540
caggagatca acgctgagcc cgaatatgtg tgcgtcggct cgatagccct gtacacggct  3600
gatctgaaat ttgccctgac cgctgagact aaggcttgga tggtggtgat tggccgacac  3660
tgcaacaaga agtaccggtc tgaaatggag aacatcttta tgctaatcga ggaatttaac  3720
aaaaagctga accgtcccat taaggatctg gacgacatca ggattgccat ggcggcccta  3780
aaggaaatta gagaggagca gatatccatt gattttcagg ttggccccat cgaagaatca  3840
tatgcccttc tgaatcgata cggtctatta atcgcccgag aggaaataga taaggtggac  3900
acacttcatt atgcatggga gaaactctta gcgcgggccg gcgaagtgca gaataagctc  3960
gtatcgctgc agccatcatt taagaaggag ctcatcagtg ctgtcgaggt ctttctgcag  4020
gactgccacc agttctatct ggattatgac ctgaacggtc cgatggcgag tggtctgaag  4080
ccccaagagg cttcagaccg gcttatcatg ttccaaaatc agttcgacaa tatttaccga  4140
aagtatatca cctatacagg gggtgaagaa ttgtttggtc tcccagccac ccagtatcca  4200
caattattgg aaataaagaa gcagctgaac cttcttcaaa aaatctacac tctctataat  4260
tcggtaattg aaactgttaa ttcctactac gatattctct ggagcgaggt caacattgag  4320
aaaattaata acgaactctt ggagttccaa aacagatgcc gcaagctgcc gagagcgctg  4380
aaggactggc aggcttttct cgaccttaag aaaataatcg atgatttcag tgaatgctgt  4440
cctctcttag aatacatggc gagtaaggct atgatggaga gacactggga gaggattacg  4500
actctgacgg ggcattcttt ggacgttggc aacgagtcct tcaagctgcg taatataatg  4560
gaggctccac ttctcaagta caaagaggaa atagaagaca tctgtatatc tgctgtcaaa  4620
gagcgcgaca tagaacagaa actaaagcag gtaattaacg agtgggacaa taaaacgttt  4680
acatttggca gtttcaagac acgtggagaa ttattgcttc gaggtgactc cacctcggaa  4740
attatcgcta acatggagga ctctctcatg ttactcggct cgctgttatc gaaccggtat  4800
aatatgccat tcaaagcaca gatccagaag tgggtgcagt atctatctaa tagtacggat  4860
attatagaga gctggatgac cgtccagaat ctctggatct acctggaggc ggtgtttgtg  4920
ggaggtgata tagcgaagca gcttccaaag gaggccaaaa gattctccaa cattgacaaa  4980
tcctgggtca agattatgac tcgggcccac gaagtgccct ccgttgtgca gtgctgcgtc  5040
ggggacgaaa ccttgggcca gctgttgccc cacctgttgg atcaattgga aatctgccaa  5100
aagagcctga ctggctacct agagaaaaag cgtctgtgct ttccccggtt cttcttcgtt  5160
tctgaccctg cactactcga aatcttgggt caggcctctg attctcacac aattcaggct  5220
catttgttaa atgtgtttga caacatcaaa agtgtgaaat ttcatgaaaa gatttatgac  5280
aggatcttgt ccatttcatc ccaagaggga gaaaccattg agcttgataa gcctgtgatg  5340
gcagagggaa acgtggaagt ctggcttaac agtctcctgg aagagtccca gtcctcactg  5400
cacctggtca tccgccaggc ggcggctaat atccaggaga caggattcca gctcacggaa  5460
ttccttagtt cgtttccggc gcaagtgggg ctcctcggca ttcagatgat ctggacgaga  5520
gattcggagg aagccctccg caacgccaag tttgacaaga agattatgca gaaaactaac  5580
caagccttcc tagagctcct caacactctg atcgatgtca caactcgtga tctatcgtct  5640
accgagcggg tcaagtatga gacactcatt accatacacg ttcaccaacg tgatatattc  5700
gatgatctat gccacatgca cataaagagt cccatggact tcgaatggct aaaacagtgc  5760
```

-continued

```
aggttctact ttaatgaaga ctctgataaa atgatgatac acatcacaga tgttgctttt  5820
atctatcaaa acgaattttt aggttgtacc gacagactag taatcactcc attgacagat  5880
agatgttata ttacacttgc tcaggctcta ggtatgagta tgggtggagc accagcgggt  5940
ccggcaggaa caggtaaaac agaaacgaca aaggatatgg gacgttgttt aggtaaatat  6000
gtagtcgtat ttaactgttc tgaccaaatg gattttcgtg gtcttggtag aatttttaaa  6060
ggtttagctc aatcaggttc ttggggttgt tttgacgaat ttaatcggat agatttgcct  6120
gttttatctg tcgcggctca acaaatctcc ataattttaa cttgtaaaaa agaacataaa  6180
aaaagtttca tttttaccga tggtgataac gttacgatga accctgaatt tggtttgttc  6240
ttaactatga atccaggata cgccggccgt caagagttac ctgaaaattt gaaaataaac  6300
tttagatcag tggctatgat ggttcctgat cgccagatta ttatccgagt caaattagca  6360
agttgtggat ttattgataa cgttgtttta gcaagaaagt tttttacact atacaaatta  6420
tgtgaggaac aattgtctaa acaagtacat tacgattttg gtctaagaaa tatattatca  6480
gtattgcgaa cattaggagc agctaagaga gcaaatccaa tggatactga atcaactatt  6540
gtaatgcgcg ttttaagaga tatgaattta tcaaagttaa ttgatgaaga cgaacctctt  6600
tttctcagcc ttatagagga tctgtttcca aacattctcc tggacaaggc gggatatccc  6660
gagttggaag cggccattag caggcaggtg gaggaggccg gattgattaa tcacccgccc  6720
tggaaactga aagtcatcca gctgttcgag actcagcggg tccgacacgg tatgatgact  6780
ttaggcccat ctggcgcggg caaaaccacc tgcatccaca cccttatgag ggctatgacc  6840
gactgtggga agcctcaccg tgagatgcgg atgaacccga aggcgatcac tgcgccccaa  6900
atgtttgggc gtctggatgt ggcgacaaat gactggaccg atgggatctt ttccacactc  6960
tggaggaaga ccctgcgcgc caaaaaagga gagcacatct ggatcattct cgatggcccc  7020
gttgacgcta tttggatcga aaacttaaac agcgtgctcg acgacaacaa gaccctgaca  7080
ttggcaaatg gtgaccggat tcctatggct cctaattgca aaataatttt tgaacctcac  7140
aacatcgaca acgccagtcc ggctacggtg tcccgcaacg gtatggtttt catgagcagt  7200
tccatactgg attggagtcc gatattggaa ggatttctca agaaacgcag tccccaggag  7260
gcggaaattc tgcggcaact gtatacggaa agttttcctg acctgtaccg cttctgcatt  7320
caaaatctcg agtataagat ggaggtgttg gaggccttcg tcatcacaca gtccattaac  7380
atgcttcagg gcttgatccc cttgaaggag caaggggggg aagtcagcca ggcacatcta  7440
gggcggcttt ttgttttcgc cctgctctgg tccgcgggtg ctgctctcga gctagacggt  7500
cgccggcgct tggagttgtg gctgaggtct cgcccgaccg ggacactcga gctgccgccg  7560
ccagccggac ccggggacac tgcattcgac tactacgtag ctccggacgg cacctggacc  7620
cactggaaca cccggacgca ggagtatctc tatcccagcg atacaactcc tgagtatggt  7680
agcatactcg ttccgaacgt agacaacgtc agaaccgact ttctgatcca gaccattgct  7740
aagcaaggca aggcagtcct attgatcgga gagcaaggga ccgcgaaaac cgtgattatc  7800
aagggcttca tgagtaaata tgacccagag tgtcatatga ttaagtcact caacttcagt  7860
tctgctacca caccactcat gtttcagcgt actatcgaat cctacgtgga caagcggatg  7920
ggcaccacct acgggccgcc tgccgggaag aagatgacgg tatttataga cgacgttaac  7980
atgcccatca tcaacgagtg gggagatcaa gtgaccaacg aaatcgttcg gcaacttatg  8040
gaacaaaacg ggttctacaa cctcgagaag ccgggcgagt tcacctcaat agtagacatt  8100
caatttctgg cagctatgat ccaccccgga ggaggacgaa acgacattcc ccagcggctg  8160
aagcgccaat tcagcatctt caactgcacg ctgccaagcg aagcatcggt agacaaaatc  8220
ttcggcgtca tcggggtggg tcactactgc acccagcgcg gcttttcaga ggaagtccga  8280
gattctgtta ctaaactggt tcctttgact agaaggctgt ggcagatgac caaaattaaa  8340
atgcttccta ctccagctaa attccactac gtgttcaatc tgcgagactt atccagggta  8400
tggcaaggta tgcttaatac cacctctgag gtaattaaag aaccgaacga tctgctgaaa  8460
ctgtggaagc acgaatgtaa gagagtcatt gcagataggt ttactgtatc gtcagatgta  8520
acctggttcg ataaagcact ggtgtctttg gtcgaagaag agtttgggga agagaagaag  8580
ctactcgtcg attgcgggat cgacacttac tttgtagact tcttaagaga cgcccctgag  8640
gctgccggtg aaacatcgga agaggcagac gctgagactc ctaagatcta tgagccgatc  8700
gagagcttta gccacctcaa ggagcgtctg aatatgtttt tacaactcta taacgagagc  8760
attcgtggtg ctgggatgga tatggtgttc ttcgcggatg caatggtgca tctggtcaag  8820
atctctcggg tgattcgcac gccacaggga aacgcgctac tggtcggggt gggtgggtca  8880
ggaaagcaat cgttaactcg tttggcatcc tttatcgcgg gatatgtgtc atttcaaatc  8940
accctgacaa ggtcctataa tacatccaac ctgatggagg atcttaaagt tctctacagg  9000
acggcgggac aacagggcaa aggaataacc ttcatcttca cagataacga aattaaagac  9060
gaatcattct tggagtatat gaacaacgtc ttatcaagcg gcgaagtttc gaacctcttc  9120
gcgcgggacg aaatagatga gatcaactct gatctcgctt ctgtcatgaa gaaagaattc  9180
cccgcgctgtt tgccgacgaa tgagaacttg catgactatt tcatgtcccg tgtgcggcag  9240
aatttgcaca ttgtgctttg cttttcaccg gtgggggaga agttccgaaa tagagctttg  9300
aagttccctg ctttgattag cgggtgtact attgactggt tttcccgttg gcccaaggac  9360
gctctggtcg ccgtgtccga gcacttttta acctcttatg atatcgactg cagcctcgaa  9420
attaagaaag aagtagttca gtgtatgggc tctttccaag acggtgtggc agagaagtgc  9480
gtcgactatt tccagaggtt tcgccgatct actcatgtca cacctaagag ctacttgtcc  9540
ttcatacagg ggtacaagtt catatatggg gagaaacacg ttgaagtaag gactctggca  9600
aaccgtatga atactggctt agagaagctc aaggaggcct cagaaagtgt ggctgctctc  9660
tcaaaggagc ttgaagctaa ggagaaggaa ctccaagttg cgaacgataa agcggatatg  9720
gttctaaaag aagtcactat gaaagcacaa gcggctgaaa aggttaaggc ggaggtacag  9780
aaggttaagg atcgcgccca ggcaatagtc gattccattt ccaaagacaa ggccatcgcg  9840
gaagaaaagc tagaagccgc caagcctgcc ttagaagagg cagaggctgc cttgcaaacc  9900
ataagaccga gtgacatcgc gacggtacga acccttggtc gtcctcctca tttgattatg  9960
aggattatgg actgtgtcct gcttttattt caacgtaaag tatctgcagt taagattgat  10020
ttggaaaaat cctgtaccat gccctcatgg caggagtccc tgaaattgat gaccgcgggc  10080
aatttccttc aaaatctaca acaattcccc aaggacacca ttaacgaaga ggtcatagaa  10140
tttttatctc catattttga gatgccagat tacaatattg aaactgcgaa gcgcgtctgt  10200
ggtaacgttg caggtctctg ttcgtggacc aaagctatgg cctccttctt tagtatcaat  10260
aaagaggtac taccactgaa agccaacctg gtggtacagg agaaccggca tttgcttgct  10320
atgcaggatc ttcagaaggc acaggccgaa ttagacgaca agcaggctga gcttgacgtt  10380
gtgcaagcag aatacgaaca agctatgact gaaaagcaga ctttattaga ggacgctgaa  10440
cgctgcagac ataagatgca gactgcaagc accctcatat ccgggttggc tggagaaaaa  10500
```

```
gagcggtgga cagagcagtc gcaagaattt gctgctcaaa ccaaaaggtt ggttggagac  10560
gtgctactcg cgacagcttt tctctcctat tctggtcctt tcaaccagga attccgggac  10620
cttttgctga atgactggag aaaagaaatg aaggctcgca aaataccatt tggtaagaat  10680
ttgaacttgt ctgaaatgct tattgacgca cccactatat cagagtggaa tcttcaggga  10740
cttccgaatg acgacctgtc tatccaaaac ggaattattg taaccaaggc gagtcgctac  10800
cctctgctca ttgacccgca gacacagggc aagatctgga ttaaaaataa ggaaagcagg  10860
aacgaactcc agatcactag tctcaaccac aagtacttcc gtaaccacct cgaagatagt  10920
ctgtccctgg gacggccatt gctaatcgag gacgtcggag aagagctgga ccccgcatta  10980
gacaacgtcc ttgaaagaaa tttcatcaag acaggatcaa ctttcaaagt taaagtagga  11040
gataaagaag tggatgtgtt agatggcttc cgcctatata tcacaactaa actcccgaat  11100
cccgcctata ctccagagat cagcgctaga actagcatca tagatttcac tgtaactatg  11160
aaggggttag aagatcaatt attaggacgc gtgatcctga cggagaaaca ggaattggaa  11220
aaagagcgta cacatctcat ggaagacgtg acagctaaca aacgtcgaat gaaggaactg  11280
gaggacaatt tactgtatcg gttgacatca acacagggct cccttgttga ggacgagagt  11340
ctgatcgtgg tcctgtctaa cacaaagagg actgctgaag aagtaactca gaaattggag  11400
atttctgccg aaactgaagt tcagattaac tccgctagag aagagtatcg tccagtcgct  11460
actcggggct cgatcctata cttcctcata actgagatgc gcttggtcaa tgagatgtat  11520
cagacttcac tccggcaatt cctgggcttg tttgacttgt cgctggcaag atcagtgaaa  11580
tctccaatta ccagcaagag aatcgcaaac atcattgagc acatgacgta cgaggtgtat  11640
aaatacgcgg caaggggact ttacgaagag cataagttcc tcttcaccct actattaacg  11700
ttgaagatag atattcagag gaaccgggtg aagcacgagg agtttctaac tctaataaaa  11760
ggaggagctt ctttggattt gaaagcctgt ccaccgaaac cttctaagtg gattttagac  11820
ataacatggc tgaatctcgt ggagttgtcc aagctccgtc agttcagtga cgttttggat  11880
cagatatcca ggaacgagaa gatgtggaag atctggttcg ataaagagaa tccggaggaa  11940
gagcccttgc caaatgctta tgataaaagc ctagactgct tcaggaggct tttgctcatc  12000
cgctcctggt gccccgaccg cactattgcc caggctagga aatacattgt ggactccatg  12060
ggggagaagt atgccgaagg agtcatactc gacttggaga agacttggga agagtcagat  12120
ccgaggacgc ccctcatttg tcttctttcc atgggttctg atcccacgga ctctattata  12180
gcactcggga aaagactaaa gatcgagaca cgctatgtta gcatgggaca ggggcaagag  12240
gtccatgccc gcaaactact acagcagact atggctaatg gaggttgggc tctgttacag  12300
aactgtcact taggcttaga ttttatggac gaattgatgg acatcataat tgagacggag  12360
ctagtccacg acgcatttcg cttatggatg acgactgaag cacacaagca gtttccgata  12420
accctgttgc agatgtccat caagttcgcc aatgaccctc cccagggcct tagggcaggt  12480
ctcaaaagga cctacagcgg cgtttcccag gatttacttg acgtctcctc cggatcccag  12540
tggaagccca tgttgtacgc tgtggctttc cttcacagca cagttcagga aaggcggaag  12600
tttggtgcgc taggctggaa catcccctac gagttcaacc aggctgactt taatgcaaca  12660
gtacagttta ttcaaaatca tctggatgac atggatgtta aaaaaggtgt gtcatggact  12720
acaataaggt acatgattgg ggagatacag tacggaggcc gggtaactga tgattatgac  12780
aagcggctac tgaacacttt cgctaaagtg tggttttctg agaatatgtt cggtccagat  12840
ttcagcttct accaaggtta taacattcca aagtgctcca cagtcgacaa ctacctccaa  12900
tatattcaaa gtttacctgc atatgatagt cctgaagttt ttggtttgca tcctaatgca  12960
gatataacat atcaaagtaa attagcaaaa gacgtcttag atacaatact aggaatccaa  13020
ccaaaagata catccggtgg gggagacgaa actcgagaag ccgttgttgc aagattagca  13080
gatgatatgt tagaaaaatt acctcctgac tatgtacctt ttgaagttaa agaacgtttg  13140
caaaaaatgg gaccttttca accaatgaat atctttctaa ggcaggagat tgatcgaatg  13200
caaagggttt tatccttagt acgatctact ttaacagaac ttaaactagc tatagatggt  13260
actataatta tgagtgaaaa tttaagagac gcattagatt gtatgtttga tgcaaggatt  13320
ccagcttggt ggaaaaaagc atcttggata tcatcaacat tgggattttg gtttactgaa  13380
ttgatagaac gtaattctca atttacaagt tgggtattta atggtcgtcc acattgtttt  13440
tggatgactg gtttttttaa tccacaagga tttttaactg ccatgagaca ggaaataact  13500
agagcaaata agggttgggc attagataat atggttttgt gtaatgaagt aactaagtgg  13560
atgaaagacg atataagtgc accaccaact gagggtgttt atgtatatgg tttatattta  13620
gaaggagctg gatgggataa acgtaatatg aaattaatag aatcgaaacc aaaagtttta  13680
tttgaattaa tgccagttat cagaatttat gcagagaata atacattaag agatcctaga  13740
ttttatagtt gtccaattta taaaaaacct gtcagaacag atcttaatta tatagcagcc  13800
gtcgatctta gaactgctca aacaccagaa cattgggtat taagaggagt agctttactt  13860
tgtgatgtta aatag                                                  13875
```

```
SEQ ID NO: 31          moltype = DNA  length = 13875
FEATURE                Location/Qualifiers
misc_feature           1..13875
                       note = Synthetic polynucleotide
source                 1..13875
                       mol_type = other DNA
                       organism = synthetic construct
SEQUENCE: 31
atgttcagaa tcggaaggcg gcaattatgg aagcattcag taactagagt cttgacacag  60
aggctcaaag gtgaaaaaga ggcaaagcgt gcgctattgg atgcacggca taattacttg  120
ttcgcgatag tagcaagttg tttagatcta aacaaaactg aagtagaaga cgccattctc  180
gaaggaaatc aaattgagcg gattgaccaa ttattcgctg ttggaggcct cagacattta  240
atgttttact atcaagacgt tgaagaagcg gaaactgggc aactcgggtc actaggtggc  300
gttaatttag tctcaggtaa aattaaaaag ccaaaagtat ttgttactga gggcaacgac  360
gtggccctaa ctggagtatg tgtgtttttt attcggaccg acccgagtaa ggccattacg  420
ccagacaata ttcatcaaga ggtatcattt aacatgctag atgctgctga tggtggactt  480
ctgaatagcg tgcgtcgcct gctatctgac attttcattc ctgctttacg cgcgaccagt  540
cacgggtggg gggagcttga aggcctccag gacgccgcca atatcaggca ggaattcctg  600
tcctccttag aaggttttgt gaatgttctc agcggtgccc aggagtcact aaaagaaaag  660
gtgaacttgc ggaagtgtga cattcttgaa ttaaagactc tgaaggagcc aaccgattac  720
ctcacgttag ctaacaaccc ggagactcta ggcaaaatcg aggactgcat gaaggtgtgg  780
```

-continued

```
atcaaacaga ctgagcaagt tttagcagaa aacaaccagc tccttaagga agcggatgac  840
gtaggccctc gggcggaact tgaacattgg aagaagcggt tgtctaagtt taattatctt  900
cttgaacagc ttaaatctcc tgatgtcaaa gcagtgcttg cagtcctcgc tgcagcaaag  960
tccaagctgc ttaagacctg gcgtgaaatg gacataagga taactgacgc taccaatgaa  1020
gctaaggata acgttaagta cctatacaca ctagagaagt gttgtgatcc tttatactcc  1080
tctgatccac tgtctatgat ggatgcaata cctacgctaa tcaacgctat taagatgatt  1140
tatagtatct ctcactatta taacacatct gagaaaatta cttccctttt cgtgaaagtt  1200
acgaaccaga ttattagcgc ctgcaaggct tacataacca ataacggtac agcgagcata  1260
tggaatcagc cacaggacgt cgttgaagag aagattttgt ccgccatcaa attgaaacag  1320
gagtaccagc tgtgcttcca taaaacaaag cagaagctga agcagaaccc aaacgctaag  1380
cagttcgact tctctgagat gtatattttt gggaaattg aaaccttcca ccgacgtcta  1440
gccaaaatta tcgacatctt tacgacgtta aaaacttaca gcgtgctgca agattctacg  1500
atagaagggc tagaggatat ggccacaaag taccagggca tcgtggccac tatcaaaaag  1560
aaggagtaca acttcttaga ccagcgtaaa atggatttcg accaagacta tgaagaattc  1620
tgcaaacaaa cgaatgattt gcacaacgag cttcggaaat tcatggatgt gacttttgcc  1680
aaaatacaga ataccaacca agctcttagg atgttgaaga aatttgaaag gttgaatatt  1740
cctaatttgg gcattgatga caaataccag ttgatactcg aaaattatgg agcagatatt  1800
gatatgatct ctaaactgta cacaaaacaa aaatatgatc ccccgctagc tagaaatcaa  1860
cctccgattg ctggtaagat actctgggcc agacaactct ttcaccgcat ccagcagccc  1920
atgcagctgt ttcagcagca ccctgcggtg ctctccaccg ccgaggcgaa acccattatt  1980
cgatcttata accgcatggc caaggttctg ttagagtttg aagttttgtt ccaccgtgcc  2040
tggttacgtc agatcgagga gatccatgtg ggactggagg cctctctcct agtcaaggcc  2100
cccggcacag gcgaactctt tgtcaatttt gatccccaga ttttaatact cttccgggag  2160
accgagtgca tggcccagat gggcttagag gttagtcctc tggctacttc tctgttccag  2220
aagagagacc gctataaacg gaatttcagc aatatgaaga tgatgctcgc tgaatatcag  2280
agggtcaagt ccaaaatccc cgctgcgatc gagcagctga tagtgccaca cctggccaaa  2340
gtagatgagg ccctacaacc aggactggcc gcgctgacgt ggacctctct gaatatcgaa  2400
gcgtatttgg agaacacgtt tgccaagatt aaggacctgg agcttttact ggacagagtg  2460
aacgatctca ttgaattccg catagacgcg attttagagg agatgtcttc cacgccacta  2520
tgccagcttc ctcaggagga gcctttaaca tgtgaagagt tccttcagat gactaaggac  2580
ctctgcgtga atggcgctca gatactacat ttcaagtcta gcttggtcga ggaggcagtg  2640
aacgaattgg ttaacatgtt actggatgta gaagtcctta gcgaggagga atccgaaaag  2700
atcagcaacg aaaattcggt gaactataag aacgaatcta gcgccaagcg ggaggagggg  2760
aactttgata ctctcacttc ttccatcaat gcgagggcta atgctctctt gttgacgacc  2820
gttaccagaa aaaaaaagga gactgagatg cttggggaag aggcaaggga gttgctgtcc  2880
catttcaacc atcagaatat ggacgccctc ttaaaggtta cccgaaacac gttagaagcc  2940
attaggaagc gtattcactc aagccacacg ataaatttcc gcgactcaaa ctcagcatca  3000
aatatgaagc aaaactcctt gccgatcttc agagccagcg tcaccctggc catacctaac  3060
atcgttatgg caccggcact tgaggacgta caacaaacct tgaacaaagc agtagagtgc  3120
atcatcagtg tccctaaagg agttcgccaa tggtccagtg aactgctatc caagaagaag  3180
atccaggagc gtaaaatggc tgcgttacag agtaacgaag attcggactc tgacgttgaa  3240
atgggtgaaa acgagctcca agacacactg gagattgcga gcgttaacct gcctatacct  3300
gtccagacca agaactacta caaaaacgtg tcggaaaaca aggagattgt caagctcgtt  3360
tctgtgctca gcaccataat aaattcaact aagaaagaag ttataacttc catggattgt  3420
ttcaaacggt ataaccacat ctggcagaaa ggcaaggaag aagctatcaa aacatttatt  3480
acccagagcc cactactaag cgaattcgag tctcagatcc tctacttcca gaatcttgag  3540
caggagatca acgctgagcc cgaatatgtg tgcgtcggct cgatagccct gtacacggct  3600
gatctgaaat ttgcgctgac cgctgagaca aaggcttgga tggtggtgat tggccgacac  3660
tgcaacaaga agtaccggtc tgaaatggag aacattttta tgctaatcga ggaatttaac  3720
aaaaagctga accgtcccat taaggatctg gacgacatca ggattgccat ggcggcccta  3780
aaggaaatta gagaggagca gatatccatt gattttcagg taggccccat cgaagaatca  3840
tatgcccttc tgaatcgata cggtctatta atcgcccgag aggaaataga taaggtggac  3900
acacttcatt atgcatggga gaaactctta gcgcgggccg gcgaagtgca gaataagctc  3960
gtatcgctgc agccatcatt taagaaggag ctcatcagtg ctgtcgaggt ctttctgcag  4020
gactgccacc agttctatct ggattatgac ctgaacggtc cgatggcgag tggtctgaag  4080
ccccaagagg cttcagaccg gcttatcatg ttccaaaatc agttcgacaa tatttacagg  4140
aagtatatca cctatacagg gggtgaagaa ttgttcggtc tcccagccac ccagtatcca  4200
caattattgg aaataaagaa gcagttaaac cttcttcaaa aaatctacac tctctataat  4260
tcggtaatag aaactgttaa ttcctactac gatattctct ggagcgaggt caatattgag  4320
aaaattaata acgaactctt ggagttccaa aacagatgcc gcaagttgcc gagagcgctg  4380
aaggactggc aggcttttct cgaccttaag aaaataatcg atgatttcag tgaatgctgt  4440
cctctcttag aatacatggc gagtaaggct atgatggaga gacactggga gaggattacg  4500
actctgacgg ggcattcttt ggacgttggc aacgagtcct tcaagctgcg taatataatg  4560
gaggctccac ttctcaagta caaagaggag atagaggaca tctgtatatc tgctgtcaaa  4620
gagcgcgaca tagaacagaa actaaagcag gtaattaacg aatgggacaa caaaacgttt  4680
acatttggca gtttcaagac acgtggagaa ttattgcttc gaggcgactc cacctcggaa  4740
attatcgcta acatggagga ctctctcatg ttacttggct cgctgttatc gaaccggtat  4800
aatatgccat tcaaagcaca gatccagaag tgggtgcagt atctatctaa tagtacggat  4860
ataatagaga gctggatgac cgtccagaat ctctggatct acttggaggc ggtgtttgtg  4920
ggaggtgata tagcgaagca gcttcccaag gaggccaaaa gattctccaa cattgacaaa  4980
tcctgggtca agattatgac tcgggcccac gaagtgccct ccgtggtgca gtgctgcgta  5040
ggggacgaaa ccttgggcca gctgttgccc cacctgttgg atcaactcga aatctgccaa  5100
aagtctctga ctggctacct agagaaaaag cgtctgtgct ttccccggtt cttcttcgtt  5160
tctgatcctg cactactcga aatcttgggt caggcctctg attctcacac aattcaggct  5220
catttgttaa atgtgtttga caacatcaaa agtgtgaaat ttcatgaaaa gatttatgac  5280
aggatcttgt ccatttcatc ccaagaggga gaaaccattg agcttgataa gcctgtgatg  5340
gcagagggaa acgtggaggt ctggcttaac agtctcttgg aagagtccca gtcctcactg  5400
cacctggtca tccgccaggc ggcggctaat atccaggaga caggattcca gctcacggaa  5460
ttccttagtt cgtttccggc gcaagtgggg ctcctcggca ttcagatgat ctggacgaga  5520
```

-continued

```
gattcggagg aagccctccg caacgccaag tttgacaaga agattatgca gaaaactaac  5580
caagccttcc tagagctcct caacactctg atcgatgtca caactcgtga cctatcgtct  5640
accgagcggg tcaagtatga gacactgatt acaatccacg ttcaccagcg tgatatattc  5700
gatgatctat gccacatgca cataaaaagt cccatggact tcgaatggct aaaacagtgc  5760
aggttctact ttaatgaaga cagtgataag atgatgatcc atatcacaga tgtagcgttt  5820
atttaccaaa acgagttcct tggctgtaca gacaggttag tcataactcc gttaactgat  5880
cgctgctaca ttacactcgc ccaagcgctt ggaatgtcca tgggtggagc cccgcaggg  5940
ccggcgggga caggtaagac cgaaacaact aaagatatgg gccgttgcct cgggaagtat  6000
gttgtagtat ttaactgctc agaccaaatg gatttccgag ggctgggccg tatctttaaa  6060
gggctggcgc aatccggttc ctggggctgt tttgacgagt tcaatcgtat tgatttaccg  6120
gtgctaagtg ttgccgcaca gcaaattagt ataattttga catgtaagaa agaacacaag  6180
aaaagtttta tatttactga cggcgacaac gtcactatga atcctgaatt cgggcttttc  6240
ttgactatga acccagggta cgctggccgt caagaacttc ctgaaaatct gaaaatcaac  6300
tttcgatcgg tggctatgat ggtaccggac cgccagatca tcatccgggt aaaactggcc  6360
tcgtgtggct tcatcgacaa cgtcgtactt gctcgaaagt tcttcaccct ttacaagcta  6420
tgtgaggagc agttatcgaa acaagttcat tacgactttg ggctccggaa tatcttgtcc  6480
gtcttacgca cactcggagc ggctaaacgt gcaaatccca tggacactga gagtacgatt  6540
gtgatgcgag tgttaaggga tatgaatctc tcgaagttaa tagacgagga cgagcctctt  6600
tttctcagcc ttatagagga tctgttccca aacatcctcc tggacaaggc tggatatccc  6660
gagttggaag cggcgattag caggcaggtg gaggaggccg gattgattaa tcacccgccc  6720
tggaaactga aagtcatcca gctgttcgag actcagcggg tccgacacgg tatgatgact  6780
ttaggcccat ctggcgcggg gaaaaccacc tgcatccaca ccctgatgag ggctatgacc  6840
gattgtggga agcctcaccg tgagatgcgg atgaacccga aggcgatcac agcgccccaa  6900
atgtttgggc gtctggatgt ggcgacaaat gactggaccg atggaatctt ttccacactc  6960
tggaggaaga ccctgcgcgc aaaaaaagga gagcacatct ggatcattct cgatggcccc  7020
gttgacgcta tttggatcga aaacttaaac agcgtgctcg acgacaacaa gaccctgaca  7080
ttggcaaatg gtgaccggat tcctatggct cccaattgca aaatcatttt tgaacctcac  7140
aacatcgaca acgccagtcc ggctacggtg tcccgcaacg gtatggtttt catgagcagt  7200
tccatactgg attggagtcc gatattggaa ggatttctca agaaacgcag tccccaggag  7260
gcggaaattc tgcggcaact gtatacggaa agtttttcctg acctgtaccg cttctgtatt  7320
caaaatctcg agtataagat ggaggtgttg gaggccttcg tcatcacaca gtccattaac  7380
atgcttcagg gcttgatccc cttgaaggag caaggagggg aagtcagcca ggcacatcta  7440
gggcggcttt tcgttttcgc ccttctctgg tccgcgggtg ctgctctcga gctagacggt  7500
cgccggcgct tggagttgtg gctgaggtct cgcccgaccg ggacactcga gctgccgccg  7560
ccagcgggac ccggggacac tgcattcgac tactacgtag ctccggacgg cacctggacc  7620
cactggaaca cccgtacgca ggagtatctc tatcccagcg atacaactcc tgagtatggt  7680
agcatactcg ttccgaacgt agacaacgtc agaaccgact ttctgatcca gaccattgct  7740
aagcagggca aggcagtcct attgatcgga gagcaaggga ccgcgaaaac cgtgattatc  7800
aagggcttca tgagtaaata tgacccagag tgtcatatga ttaagtccct caacttcagt  7860
tctgctacca caccactcat gtttcagcgt actatcgaat cctacgtgga caagcggatg  7920
ggcaccacct acgggccgcc tgccgggaag aagatgacgg tatttataga cgacgttaac  7980
atgcccatca tcaacgagtg ggagatcaa gtgaccaacg aaatcgttcg gcaacttatg  8040
gaacaaaacg ggttctataa cctcgagaag ccgggcgagt tcacctcaat agtagacatt  8100
caatttctgg cagctatgat ccacccccgga ggaggacgga acgacattcc ccagcggctc  8160
aagcgccaat tcagcatctt caactgcacg ctgccaagtg aagcatcggt agacaaaatc  8220
ttcggcgtca tcggggtggg tcactactgc acccagcgcg gcttttcaga ggaagtccga  8280
gattcagtta ctaaactggt tcctttgact agaaggctgt ggcagatgac caaaattaaa  8340
atgcttccta ctccagctaa attccactac gtgttcaatc tgcgagactt atccagggta  8400
tggcaaggta tgcttaatac cacctctgag gtaattaaag aaccgaacga tctgctgaaa  8460
ctgtggaagc acgaatgtaa gagagttatt gcagataggt ttactgtatc gtcagatgtt  8520
acctggttcg ataaagcact ggtgtctttg gtcgaagaag agtttgggga agagaagaag  8580
ctactcgtcg attgcgggat cgacacttac tttgtggact tcttaagaga cgcccctgag  8640
gctgccggcg aaacatcgga agaggcagac gctgagactc ctaagatcta tgagccgatc  8700
gagagcttta gccacctcaa ggagcgtctg aatatgtttt tacaattgta taacgagagc  8760
attcgtggtg ctgggatgga tatggtgttc ttcgcggatg caatggtgca tctggttaag  8820
atttctcggg tgattcgcac gccacaggga aacgcgctac tggtcggggt gggtgggtca  8880
ggaaagcaat cgttaactcg tttggcatcc tttatcgcgg gatatgtgag ttttcaaatc  8940
accctgacaa ggtcctataa tacatccaac ctgatggagg atcttaaagt tctctacagg  9000
acggcgggac aacagggcaa aggaataacc ttcatcttca cagataacga aattaaagac  9060
gaatcattct tggagtatat gaacaacgtc ttatcaagcg gcgaagtttc gaacctcttc  9120
gcgcgggacg aaatcgatga gatcaactct gatctcgctt ctgtcatgaa gaaagaattc  9180
ccccgctgtt tgccgacgaa tgagaacttg catgactatt tcatgtcccg tgtgcggcag  9240
aatttgcaca ttgtgctttg cttttcaccg gtggggggaga agttccgaaa tagagctttg  9300
aagttccctg ctttgatttc tgggtgtact attgactggt tttcccgttg gcccaaggac  9360
gctctggtcg ccgtgtccga gcacttttta accagctatg atatcgactg cagcctcgaa  9420
attaagaagg aagtagttca gtgtatgggc tctttccaag acggtgtggc agagaagtgc  9480
gtcgactatt tccagaggtt tcgccgatct actcatgtca cacctaagag ctacttgtcc  9540
ttcatacagg ggtacaagtt tatatatggg gagaaacacg ttgaagtaag gactctggca  9600
aaccgtatga atactggctt agagaagctc aaggaggcct cagaaagtgt ggctgctctc  9660
tcaaaggagc ttgaagctaa ggagaaggaa ctccaagttg cgaacgataa agcggatatg  9720
gttctaaaag aagtcactat gaaagcacaa gcggctgaaa aggttaaggc ggaggtacag  9780
aaggtgaagg atcgcgccca ggcaatagtc gattccattt ccaaagacaa ggccatcgcg  9840
gaagaaaagc tagaagccgc caagccggcc ttagaagagg cagaggctgc cttgcaaacc  9900
ataagaccga gtgacatcgc gacggtacga acccttggtc gtcctcctca tttgattatg  9960
aggattatgg actgtgtcct gcttttattt caacgtaaag tatctgcagt taagattgat  10020
ttggaaaaat cctgtaccat gccctcatgg caggaatccc tgaaattgat gaccgcgggc  10080
aatttccttc aaaatctaca acaattcccc aaggacacca ttaacgaaga ggtcatagaa  10140
tttttatctc catatttga gatgccagat tacaatattg aaacagcgaa gcgcgtctgt  10200
ggtaacgttg caggtctctg ttcgtggacc aaagctatgg cctccttctt tagtatcaat  10260
```

-continued

```
aaagaggtac taccactgaa agccaacctg gtggtacagg agaaccggca tctgcttgct  10320
atgcaggatc ttcagaaggc ccaggccgaa ttagacgaca agcaggctga gcttgacgtt  10380
gtgcaagcag aatacgaaca agctatgact gaaaagcaga ctttattaga ggacgctgaa  10440
cgctgcagac ataagatgca gactgcaagc accctcatat ccgggttggc tggagaaaaa  10500
gagcggtgga cagagcagtc gcaagaattc gctgctcaaa ccaaaaggtt ggttggagac  10560
gttctactcg cgacagcttt tctctcctat tctggtcctt tcaaccagga attccgggac  10620
cttttgctga atgactggag aaaagaaatg aaggctcgca aaataccatt tggtaagaat  10680
ttgaacttgt ctgaaatgct tattgacgca cccactatat cagagtggaa tcttcaggga  10740
cttccaaatg acgatctgtc catccaaaac ggaattattg taaccaaggc gagtcgctac  10800
cctctgctca ttgacccgca gacacagggc aagatctgga ttaaaaataa ggaaagcagg  10860
aacgaactcc agatcactag tctcaaccac aagtacttcc gtaaccacct cgaagatagt  10920
ctgtccctgg gacggccgtt gctaatcgag gacgtcggag aagagctgga ccccgcatta  10980
gacaacgttc ttgaaagaaa ttttatcaag acaggatcaa ctttcaaagt taaagtagga  11040
gataaagaag tggatgtgtt agatggcttc cgcctatata tcacaactaa actcccgaat  11100
cccgcctata ctccagagat cagcgctaga actagcatca tagatttcac tgtaactatg  11160
aaggggttag aagatcaatt attaggacgc gtgatcctga cggagaaaca ggaattggaa  11220
aaagagcgta cacacctcat ggaagacgtg acagctaaca aacgtcggat gaaggaactg  11280
gaagacaatt tactgtatcg gttgacatca acacagggct cccttgttga ggacgagagt  11340
ctgatcgtgg tcctgtctaa cacaaagagg actgctgaag aagtaactca gaaattggag  11400
atttctgccg aaactgaagt tcagattaac tccgctagag aagagtatcg tccagtcgct  11460
actcggggct ctatcctata cttcctcata actgagatgc gcttggtcaa tgagatgtac  11520
cagacttcac tccggcaatt cctgggcttg tttgacttgt cgctggcaag atcagtaaaa  11580
tctccaatta ccagcaagag aatcgcaaac atcattgagc acatgacgta cgaggtgtat  11640
aaatacgcgg cgaggggtct ttatgaagag cataagttcc tcttcaccct actattaacg  11700
ttgaagatag atattcagag gaaccgggtg aagcacgagg agtttctaac tctaataaaa  11760
ggaggagctt ctttagattt gaaagcctgt ccaccgaaac cttctaagtg gattttagac  11820
ataacatggc tgaatttagt ggagttgtcc aagttacgtc agttcagtga cgttttggat  11880
cagatatcca ggaacgagaa gatgtggaag atctggttcg ataaagagaa tccggaggag  11940
gagcccttgc caaatgctta tgataaaagc ctagactgct tcaggaggct tttgctcatc  12000
cgctcctggt gccccgaccg cactattgcc caagctagga aatacattgt ggactccatg  12060
ggggagaagt atgccgaagg agtcatactc gacttggaga agacttggga agagtcagat  12120
ccgaggacgc ccctcatttg tcttctttcc atgggttctg atcccacgga ctctattata  12180
gcactcggga aaagactaaa gatcgagaca cgctatgtta gcatgggaca ggggcaagag  12240
gtccatgccc gcaaactact acagcagact atggctaatg gaggttgggc tctgttacag  12300
aactgtcact taggccttga ttttatggac gaattgatgg acatcataat tgagacggag  12360
ctagtccacg acgcatttcg cttatggatg acgactgaag cacacaagca gtttccgata  12420
accctgttgc agatgtccat caagttcgcc aatgaccctc cccagggcct tagggcaggt  12480
ctcaaaagga cctacagcgg cgtttcccag gatttacttg acgtctcctc cggatcccag  12540
tggaagccca tgttgtacgc tgtggctttc cttcacagca cagttcagga aaggcggaag  12600
tttggtgcgc taggctggaa catcccctac gagttcaacc aggctgactt taatgcaaca  12660
gtacagttta ttcaaaatca tctggatgac atggatgtta aaaaaggtgt gtcatggact  12720
acaataaggt acatgattgg ggagatacag tacggaggcc gggtaactga tgattatgac  12780
aagcggctac tgaacacttt cgctaaagtg tggttttctg agaatatgtt cggtccagat  12840
ttcagcttct accaaggtta taacattcca aagtgctcca cagtcgacaa ctacctccag  12900
tacatccaat cgttaccagc atacgacagc ccggaagttt ttggcctgca cccaaacgcg  12960
gacatcactt atcagtcgaa gctggcaaag gacgtgctcg acaccatcct tggtatacag  13020
cctaaggaca ccagtggggg cggtgacgag actcgcgagg ctgtggtggc ccggctcgct  13080
gatgacatgc tagagaaact tcccccggac tacgtcccct ttgaggtcaa agagcggctg  13140
cagaaaatgg ggcccttcca gcccatgaac atattcttgc gccaggagat agaccgtatg  13200
caacgggtcc tgagcctggt ccgctcgact ctaaccgagc tcaagctggc catcgatggg  13260
acgattatta tgtctgagaa tttgagggac gcgctcgatt gcatgtttga tgccaggatc  13320
ccagcctggt ggaaaaaagc tagttggatc tcatctactc tggggttttg gtttacagag  13380
ttgatagaac ggaacagcca gtttacttct tgggtattca atggtaggcc tcactgtttt  13440
tggatgacag gcttctttaa cccccagggt ttcctcactg cgatgagaca agagattacg  13500
cgagccaata agggctgggc actagataac atggtcctgt gtaatgaagt gaccaaatgg  13560
atgaaagacg acatatcagc gccccccacc gagggtgtgt acgtatatgg cctctatttg  13620
gaaggggctg gatgggacaa gcgtaacatg aaactgatag aatccaagcc taaggtcctc  13680
tttgagctaa tgccggttat acgaatctac gccgagaaca atacattgag agatccaaga  13740
ttttattctt gtcccatata caagaagcct gtccgtacag atttgaatta cattgctgcc  13800
gtcgacctgc gcaccgcaca aactcccgag cactgggtgc tgcgggggt cgcactgctc  13860
tgcgacgtca agtag                                                   13875
```

COMPOSITION AND METHODS FOR TREATMENT OF PRIMARY CILIARY DYSKINESIA

CROSS-REFERENCE TO RELATED APPLICATIONS

This application is a continuation of United States Application Ser. No. 16/736,417, filed Jan. 7, 2020, now allowed, which claims benefit of, and priority to, U.S. Provisional Patent Application Ser. No. 62/789,414 filed on Jan. 7, 2019, the contents of which are incorporated herein in its entirety.

INCORPORATION-BY-REFERENCE OF SEQUENCE LISTING

The contents of the xml file named "MRT-2060US2 SL" which was created on Dec. 6, 2022 and is 396 KB in size, are hereby incorporated by reference in its entirety.

BACKGROUND

Primary ciliary dyskinesia (PCD) is an auto recessive disorder characterized by abnormal cilia and flagella that are found in the linings of the airway, the reproductive system, and other organs and tissues. PCD occurs in approximately 1 in 16,000. Symptoms are present as early as at birth, with breathing problems, and the affected individuals develop frequent respiratory tract infections beginning in early childhood. People with PCD also have year-round nasal congestion and chronic cough. Chronic respiratory tract infections can result in condition called bronchiectasis, which damages the passages, called bronchi, and can cause life-threatening breathing problems. Some individuals with PCD also have infertility, recurrent ear infections, abnormally placed organs within their chest and abdomen.

Mutations in the DNAH1 or DNAH5 genes account for about a third of all cases of primary ciliary dyskinesia. The DNAH5 gene encodes dynein axonemal heavy chain 5, which forms the inner structure of cilia. With an absent or abnormal dynein axonemal heavy chain 5, defective cilia cannot produce the force and movement needed to eliminate fluid, bacteria, and particles from the lungs. The movement of cilia also helps establish the left-right axis during embryonic development and propel the sperm cells forward to the female egg cell.

There is currently no cure for PCD. Current standard of care includes aggressive measures to enhance clearance of mucus and with antibiotic therapy for bacterial infections of the airways. Routine immunizations are administered to prevent respiratory infections and other secondary complications. For some patients, lobectomy, lung transplantation, and sinus surgery are considered. Gene therapy has been studied to address the urgent need for new, more effective treatments of PCD. However, due to the large size of DNAH5 conventional gene therapy methods remain challenging.

SUMMARY OF THE INVENTION

The present invention provides, among other things, methods and compositions for use in the treatment of primary ciliary dyskinesia (PCD). The present invention is based, in part, on the surprising discovery that DNAH5 mRNA, which is approximately 14 kb in length, can be successfully encapsulated in a liposome and effectively delivered to target tissues in vivo.

In some aspects, the present invention provides a method of delivery of a 10 kb or greater mRNA encoding for a protein or peptide in vivo comprising administering to a subject in need of delivery a 10 kb or greater mRNA encoding a protein or peptide. In some embodiments, the 10 kb or greater mRNA is encapsulated in a liposome. In some embodiments, the 10 kb or greater mRNA is 11 kb or greater in length. In some embodiments, the 10 kb or greater mRNA is 12 kb or greater in length. In some embodiments, the 10 kb or greater mRNA is 13 kb or greater in length. In some embodiments, the 10 kb or greater mRNA is 14 kb or greater in length.

In some aspects, the present invention provides a method of delivery of human axonemal dynein heavy chain 5 (DNAH5) in vivo comprising administering to a subject in need of delivery an mRNA encoding a human DNAH5 protein. In some embodiments, the DNAH5 mRNA is encapsulated in a liposome.

In some aspects, the present invention provides a method of treating primary ciliary dyskinesia (PCD) comprising administering to a subject in need of treatment an mRNA encoding human axonemal dynein heavy chain 5 (DNAH5) at an effective dose and an administration interval such that at least one symptom or feature of PCD is reduced in intensity, severity, or frequency or has delayed in onset.

In some embodiments, the DNAH5 mRNA is encapsulated in a liposome.

In some embodiments, the liposome comprises one or more cationic lipids, one or more non-cationic lipids and one or more PEG-modified lipids.

In some embodiments, the one or more cationic lipids are selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, DLinSSDMA, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), ccBene, ML7 and combinations thereof.

In some embodiments, the cationic lipid is ICE.

In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)) or combinations thereof. In some embodiments, the non-cationic lipid is DOPE.

In some embodiments, the one or more PEG-modified lipids comprise a poly(ethylene) glycol chain of up to 5 kDa in length covalently attached to a lipid with alkyl chain(s) of C6-C20 length.

In some embodiments, the cationic lipid constitutes about 30-60% of the liposome by molar ratio.

In some embodiments, the cationic lipid constitutes about 30%, 40%, 50%, or 60% of the liposome by molar ratio.

In some embodiments, the liposome comprises ICE, DOPE and DMG-PEG2K.

In some embodiments, the liposome has a size of about 80 nm to 200 nm, optionally wherein the liposome has a size of about 100 nm or less than 100 nm.

In some embodiments, the DNAH5 mRNA is codon optimized.

In some embodiments, the DNAH5 mRNA comprises one or more modified nucleotides.

In some embodiments, the one or more modified nucleotides are selected from pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and/or 2-thiocytidine.

In some embodiments, the mRNA is unmodified.

In some embodiments, the mRNA comprises a 5'-untranslated region (5'-UTR) that has a sequence set forth in SEQ ID NO: 2 or SEQ ID NO: 3.

In some embodiments, the mRNA comprises a 3'-untranslated region (3'-UTR) that has a sequence set forth in SEQ ID NO: 4 or SEQ ID NO: 5.

In some embodiments, the mRNA comprises a coding sequence at least 70%, 75%, 80%, 85%, 90%, or 95% identical to any one of SEQ ID NO: 6 to SEQ ID NO: 31. In some embodiments, the mRNA comprises a coding sequence at least 70% identical to any one of SEQ ID NO: 6 to SEQ ID NO: 31. In some embodiments, the mRNA comprises a coding sequence at least 80% identical to any one of SEQ ID NO: 6 to SEQ ID NO: 31. In some embodiments, the mRNA comprises a coding sequence at least 90% identical to any one of SEQ ID NO: 6 to SEQ ID NO: 31. In some embodiments, the mRNA comprises a coding sequence at least 95% identical to any one of SEQ ID NO: 6 to SEQ ID NO: 31. In some embodiments, the mRNA comprises a coding sequence at least 96%, at least 97%, at least 98%, or at least 99% identical to SEQ ID NO: 6 to SEQ ID NO: 31. In some embodiments, the mRNA comprises a coding sequence set forth in SEQ ID NO: 6 to SEQ ID NO: 31.

In some embodiments, the mRNA comprises a coding sequence at least 70%, 75%, 80%, 85%, 90%, or 95% identical to SEQ ID NO: 6. In some embodiments, the mRNA comprises a coding sequence at least 70% identical to SEQ ID NO: 6. In some embodiments, the mRNA comprises a coding sequence at least 80% identical to SEQ ID NO: 6. In some embodiments, the mRNA comprises a coding sequence at least 90% identical to SEQ ID NO: 6. In some embodiments, the mRNA comprises a coding sequence at least 95% identical to SEQ ID NO: 6. In some embodiments, the mRNA comprises a coding sequence at least 96%, at least 97%, at least 98%, or at least 99% identical to SEQ ID NO: 6. In some embodiments, the mRNA comprises a coding sequence set forth in SEQ ID NO: 6.

In some embodiments, the mRNA comprises a coding sequence at least 70%, 75%, 80%, 85%, 90%, or 95% identical to SEQ ID NO: 7. In some embodiments, the mRNA comprises a coding sequence at least 70% identical to SEQ ID NO: 7. In some embodiments, the mRNA comprises a coding sequence at least 80% identical to SEQ ID NO: 7. In some embodiments, the mRNA comprises a coding sequence at least 90% identical to SEQ ID NO: 7. In some embodiments, the mRNA comprises a coding sequence at least 95% identical to SEQ ID NO: 7. In some embodiments, the mRNA comprises a coding sequence at least 96%, at least 97%, at least 98%, or at least 99% identical to SEQ ID NO: 7. In some embodiments, the mRNA comprises a coding sequence set forth in SEQ ID NO: 7.

In some embodiments, the mRNA comprises a coding sequence at least 70%, 75%, 80%, 85%, 90%, or 95% identical to SEQ ID NO: 8. In some embodiments, the mRNA comprises a coding sequence at least 70% identical to SEQ ID NO: 8. In some embodiments, the mRNA comprises a coding sequence at least 80% identical to SEQ ID NO: 8. In some embodiments, the mRNA comprises a coding sequence at least 90% identical to SEQ ID NO: 8. In some embodiments, the mRNA comprises a coding sequence at least 95% identical to SEQ ID NO: 8. In some embodiments, the mRNA comprises a coding sequence at least 96%, at least 97%, at least 98%, or at least 99% identical to SEQ ID NO: 8. In some embodiments, the mRNA comprises a coding sequence set forth in SEQ ID NO: 8.

In some embodiments, the mRNA comprises a coding sequence at least 70%, 75%, 80%, 85%, 90%, or 95% identical to SEQ ID NO: 9. In some embodiments, the mRNA comprises a coding sequence at least 70% identical to SEQ ID NO: 9. In some embodiments, the mRNA comprises a coding sequence at least 80% identical to SEQ ID NO: 9. In some embodiments, the mRNA comprises a coding sequence at least 90% identical to SEQ ID NO: 9. In some embodiments, the mRNA comprises a coding sequence at least 95% identical to SEQ ID NO: 9. In some embodiments, the mRNA comprises a coding sequence at least 96%, at least 97%, at least 98%, or at least 99% identical to SEQ ID NO: 9. In some embodiments, the mRNA comprises a coding sequence set forth in SEQ ID NO: 9.

In some embodiments, the mRNA comprises a coding sequence at least 70%, 75%, 80%, 85%, 90%, or 95% identical to SEQ ID NO: 10. In some embodiments, the mRNA comprises a coding sequence at least 70% identical to SEQ ID NO: 10. In some embodiments, the mRNA comprises a coding sequence at least 80% identical to SEQ ID NO: 10. In some embodiments, the mRNA comprises a coding sequence at least 90% identical to SEQ ID NO: 10. In some embodiments, the mRNA comprises a coding sequence at least 95% identical to SEQ ID NO: 10. In some embodiments, the mRNA comprises a coding sequence at least 96%, at least 97%, at least 98%, or at least 99% identical to SEQ ID NO: 10. In some embodiments, the mRNA comprises a coding sequence set forth in SEQ ID NO: 10.

In some embodiments, the mRNA comprises a coding sequence at least 70%, 75%, 80%, 85%, 90%, or 95% identical to SEQ ID NO: 11. In some embodiments, the mRNA comprises a coding sequence at least 70% identical to SEQ ID NO: 11. In some embodiments, the mRNA comprises a coding sequence at least 80% identical to SEQ ID NO: 11. In some embodiments, the mRNA comprises a coding sequence at least 90% identical to SEQ ID NO: 11. In some embodiments, the mRNA comprises a coding sequence at least 95% identical to SEQ ID NO: 11. In some embodiments, the mRNA comprises a coding sequence at least 96%, at least 97%, at least 98%, or at least 99% identical to SEQ ID NO: 11. In some embodiments, the mRNA comprises a coding sequence set forth in SEQ ID NO: 11.

In some embodiments, the mRNA comprises a coding sequence at least 70%, 75%, 80%, 85%, 90%, or 95% identical to SEQ ID NO: 12. In some embodiments, the mRNA comprises a coding sequence at least 70% identical to SEQ ID NO: 12. In some embodiments, the mRNA comprises a coding sequence at least 80% identical to SEQ ID NO: 12. In some embodiments, the mRNA comprises a coding sequence at least 90% identical to SEQ ID NO: 12. In some embodiments, the mRNA comprises a coding sequence at least 95% identical to SEQ ID NO: 12. In some embodiments, the mRNA comprises a coding sequence at least 96%, at least 97%, at least 98%, or at least 99% identical to SEQ ID NO: 12. In some embodiments, the mRNA comprises a coding sequence set forth in SEQ ID NO: 12.

In some embodiments, the mRNA comprises a coding sequence at least 70%, 75%, 80%, 85%, 90%, or 95% identical to SEQ ID NO: 13. In some embodiments, the mRNA comprises a coding sequence at least 70% identical to SEQ ID NO: 13. In some embodiments, the mRNA comprises a coding sequence at least 80% identical to SEQ ID NO: 13. In some embodiments, the mRNA comprises a coding sequence at least 90% identical to SEQ ID NO: 13. In some embodiments, the mRNA comprises a coding sequence at least 95% identical to SEQ ID NO: 13. In some embodiments, the mRNA comprises a coding sequence at least 96%, at least 97%, at least 98%, or at least 99% identical to SEQ ID NO: 13. In some embodiments, the mRNA comprises a coding sequence set forth in SEQ ID NO: 13.

In some embodiments, the mRNA comprises a coding sequence at least 70%, 75%, 80%, 85%, 90%, or 95% identical to SEQ ID NO: 14. In some embodiments, the mRNA comprises a coding sequence at least 70% identical to SEQ ID NO: 14. In some embodiments, the mRNA comprises a coding sequence at least 80% identical to SEQ ID NO: 14. In some embodiments, the mRNA comprises a coding sequence at least 90% identical to SEQ ID NO: 14. In some embodiments, the mRNA comprises a coding sequence at least 95% identical to SEQ ID NO: 14. In some embodiments, the mRNA comprises a coding sequence at least 96%, at least 97%, at least 98%, or at least 99% identical to SEQ ID NO: 14. In some embodiments, the mRNA comprises a coding sequence set forth in SEQ ID NO: 14.

In some embodiments, the mRNA comprises a coding sequence at least 70%, 75%, 80%, 85%, 90%, or 95% identical to SEQ ID NO: 15. In some embodiments, the mRNA comprises a coding sequence at least 70% identical to SEQ ID NO: 15. In some embodiments, the mRNA comprises a coding sequence at least 80% identical to SEQ ID NO: 15. In some embodiments, the mRNA comprises a coding sequence at least 90% identical to SEQ ID NO: 15. In some embodiments, the mRNA comprises a coding sequence at least 95% identical to SEQ ID NO: 15. In some embodiments, the mRNA comprises a coding sequence at least 96%, at least 97%, at least 98%, or at least 99% identical to SEQ ID NO: 15. In some embodiments, the mRNA comprises a coding sequence set forth in SEQ ID NO: 15.

In some embodiments, the mRNA comprises a coding sequence at least 70%, 75%, 80%, 85%, 90%, or 95% identical to SEQ ID NO: 16. In some embodiments, the mRNA comprises a coding sequence at least 70% identical to SEQ ID NO: 16. In some embodiments, the mRNA comprises a coding sequence at least 80% identical to SEQ ID NO: 16. In some embodiments, the mRNA comprises a coding sequence at least 90% identical to SEQ ID NO: 16. In some embodiments, the mRNA comprises a coding sequence at least 95% identical to SEQ ID NO: 16. In some embodiments, the mRNA comprises a coding sequence at least 96%, at least 97%, at least 98%, or at least 99% identical to SEQ ID NO: 16. In some embodiments, the mRNA comprises a coding sequence set forth in SEQ ID NO: 16.

In some embodiments, the mRNA comprises a coding sequence at least 70%, 75%, 80%, 85%, 90%, or 95% identical to SEQ ID NO: 17. In some embodiments, the mRNA comprises a coding sequence at least 70% identical to SEQ ID NO: 17. In some embodiments, the mRNA comprises a coding sequence at least 80% identical to SEQ ID NO: 17. In some embodiments, the mRNA comprises a coding sequence at least 90% identical to SEQ ID NO: 17. In some embodiments, the mRNA comprises a coding sequence at least 95% identical to SEQ ID NO: 17. In some embodiments, the mRNA comprises a coding sequence at least 96%, at least 97%, at least 98%, or at least 99% identical to SEQ ID NO: 17. In some embodiments, the mRNA comprises a coding sequence set forth in SEQ ID NO: 17.

In some embodiments, the mRNA comprises a coding sequence at least 70%, 75%, 80%, 85%, 90%, or 95% identical to SEQ ID NO: 18. In some embodiments, the mRNA comprises a coding sequence at least 70% identical to SEQ ID NO: 18. In some embodiments, the mRNA comprises a coding sequence at least 80% identical to SEQ ID NO: 18. In some embodiments, the mRNA comprises a coding sequence at least 90% identical to SEQ ID NO: 18. In some embodiments, the mRNA comprises a coding sequence at least 95% identical to SEQ ID NO: 18. In some embodiments, the mRNA comprises a coding sequence at least 96%, at least 97%, at least 98%, or at least 99% identical to SEQ ID NO: 18. In some embodiments, the mRNA comprises a coding sequence set forth in SEQ ID NO: 18.

In some embodiments, the mRNA comprises a coding sequence at least 70%, 75%, 80%, 85%, 90%, or 95% identical to SEQ ID NO: 19. In some embodiments, the mRNA comprises a coding sequence at least 70% identical to SEQ ID NO: 19. In some embodiments, the mRNA comprises a coding sequence at least 80% identical to SEQ ID NO: 19. In some embodiments, the mRNA comprises a coding sequence at least 90% identical to SEQ ID NO: 19. In some embodiments, the mRNA comprises a coding sequence at least 95% identical to SEQ ID NO: 19. In some embodiments, the mRNA comprises a coding sequence at least 96%, at least 97%, at least 98%, or at least 99% identical to SEQ ID NO: 19. In some embodiments, the mRNA comprises a coding sequence set forth in SEQ ID NO: 19.

In some embodiments, the mRNA comprises a coding sequence at least 70%, 75%, 80%, 85%, 90%, or 95% identical to SEQ ID NO: 20. In some embodiments, the mRNA comprises a coding sequence at least 70% identical to SEQ ID NO: 20. In some embodiments, the mRNA comprises a coding sequence at least 80% identical to SEQ ID NO: 20. In some embodiments, the mRNA comprises a coding sequence at least 90% identical to SEQ ID NO: 20. In some embodiments, the mRNA comprises a coding sequence at least 95% identical to SEQ ID NO: 20. In some embodiments, the mRNA comprises a coding sequence at least 96%, at least 97%, at least 98%, or at least 99% identical to SEQ ID NO: 20. In some embodiments, the mRNA comprises a coding sequence set forth in SEQ ID NO: 20.

In some embodiments, the mRNA comprises a coding sequence at least 70%, 75%, 80%, 85%, 90%, or 95% identical to SEQ ID NO: 21. In some embodiments, the mRNA comprises a coding sequence at least 70% identical to SEQ ID NO: 21. In some embodiments, the mRNA comprises a coding sequence at least 80% identical to SEQ ID NO: 21. In some embodiments, the mRNA comprises a coding sequence at least 90% identical to SEQ ID NO: 21. In some embodiments, the mRNA comprises a coding sequence at least 95% identical to SEQ ID NO: 21. In some embodiments, the mRNA comprises a coding sequence at least 96%, at least 97%, at least 98%, or at least 99% identical to SEQ ID NO: 21. In some embodiments, the mRNA comprises a coding sequence set forth in SEQ ID NO: 21.

In some embodiments, the mRNA comprises a coding sequence at least 70%, 75%, 80%, 85%, 90%, or 95% identical to SEQ ID NO: 22. In some embodiments, the mRNA comprises a coding sequence at least 70% identical to SEQ ID NO: 22. In some embodiments, the mRNA comprises a coding sequence at least 80% identical to SEQ ID NO: 22. In some embodiments, the mRNA comprises a coding sequence at least 90% identical to SEQ ID NO: 22. In some embodiments, the mRNA comprises a coding sequence at least 95% identical to SEQ ID NO: 22. In some embodiments, the mRNA comprises a coding sequence at least 96%, at least 97%, at least 98%, or at least 99% identical to SEQ ID NO: 22. In some embodiments, the mRNA comprises a coding sequence set forth in SEQ ID NO: 22.

In some embodiments, the mRNA comprises a coding sequence at least 70%, 75%, 80%, 85%, 90%, or 95% identical to SEQ ID NO: 23. In some embodiments, the mRNA comprises a coding sequence at least 70% identical to SEQ ID NO: 23. In some embodiments, the mRNA comprises a coding sequence at least 80% identical to SEQ ID NO: 23. In some embodiments, the mRNA comprises a coding sequence at least 90% identical to SEQ ID NO: 23. In some embodiments, the mRNA comprises a coding sequence at least 95% identical to SEQ ID NO: 23. In some embodiments, the mRNA comprises a coding sequence at least 96%, at least 97%, at least 98%, or at least 99% identical to SEQ ID NO: 23. In some embodiments, the mRNA comprises a coding sequence set forth in SEQ ID NO: 23.

In some embodiments, the mRNA comprises a coding sequence at least 70%, 75%, 80%, 85%, 90%, or 95% identical to SEQ ID NO: 24. In some embodiments, the mRNA comprises a coding sequence at least 70% identical to SEQ ID NO: 24. In some embodiments, the mRNA comprises a coding sequence at least 80% identical to SEQ ID NO: 24. In some embodiments, the mRNA comprises a coding sequence at least 90% identical to SEQ ID NO: 24. In some embodiments, the mRNA comprises a coding sequence at least 95% identical to SEQ ID NO: 24. In some embodiments, the mRNA comprises a coding sequence at least 96%, at least 97%, at least 98%, or at least 99% identical to SEQ ID NO: 24. In some embodiments, the mRNA comprises a coding sequence set forth in SEQ ID NO: 24.

In some embodiments, the mRNA comprises a coding sequence at least 70%, 75%, 80%, 85%, 90%, or 95% identical to SEQ ID NO: 25. In some embodiments, the mRNA comprises a coding sequence at least 70% identical to SEQ ID NO: 25. In some embodiments, the mRNA comprises a coding sequence at least 80% identical to SEQ ID NO: 25. In some embodiments, the mRNA comprises a coding sequence at least 90% identical to SEQ ID NO: 25. In some embodiments, the mRNA comprises a coding sequence at least 95% identical to SEQ ID NO: 25. In some embodiments, the mRNA comprises a coding sequence at least 96%, at least 97%, at least 98%, or at least 99% identical to SEQ ID NO: 25. In some embodiments, the mRNA comprises a coding sequence set forth in SEQ ID NO: 25.

In some embodiments, the mRNA comprises a coding sequence at least 70%, 75%, 80%, 85%, 90%, or 95% identical to SEQ ID NO: 26. In some embodiments, the mRNA comprises a coding sequence at least 70% identical to SEQ ID NO: 26. In some embodiments, the mRNA comprises a coding sequence at least 80% identical to SEQ ID NO: 26. In some embodiments, the mRNA comprises a coding sequence at least 90% identical to SEQ ID NO: 26. In some embodiments, the mRNA comprises a coding sequence at least 95% identical to SEQ ID NO: 26. In some embodiments, the mRNA comprises a coding sequence at least 96%, at least 97%, at least 98%, or at least 99% identical to SEQ ID NO: 26. In some embodiments, the mRNA comprises a coding sequence set forth in SEQ ID NO: 26.

In some embodiments, the mRNA comprises a coding sequence at least 70%, 75%, 80%, 85%, 90%, or 95% identical to SEQ ID NO: 27. In some embodiments, the mRNA comprises a coding sequence at least 70% identical to SEQ ID NO: 27. In some embodiments, the mRNA comprises a coding sequence at least 80% identical to SEQ ID NO: 27. In some embodiments, the mRNA comprises a coding sequence at least 90% identical to SEQ ID NO: 27. In some embodiments, the mRNA comprises a coding sequence at least 95% identical to SEQ ID NO: 27. In some embodiments, the mRNA comprises a coding sequence at least 96%, at least 97%, at least 98%, or at least 99% identical to SEQ ID NO: 27. In some embodiments, the mRNA comprises a coding sequence set forth in SEQ ID NO: 27.

In some embodiments, the mRNA comprises a coding sequence at least 70%, 75%, 80%, 85%, 90%, or 95% identical to SEQ ID NO: 28. In some embodiments, the mRNA comprises a coding sequence at least 70% identical to SEQ ID NO: 28. In some embodiments, the mRNA comprises a coding sequence at least 80% identical to SEQ ID NO: 28. In some embodiments, the mRNA comprises a coding sequence at least 90% identical to SEQ ID NO: 28. In some embodiments, the mRNA comprises a coding sequence at least 95% identical to SEQ ID NO: 28. In some embodiments, the mRNA comprises a coding sequence at least 96%, at least 97%, at least 98%, or at least 99% identical to SEQ ID NO: 28. In some embodiments, the mRNA comprises a coding sequence set forth in SEQ ID NO: 28.

In some embodiments, the mRNA comprises a coding sequence at least 70%, 75%, 80%, 85%, 90%, or 95% identical to SEQ ID NO: 29. In some embodiments, the mRNA comprises a coding sequence at least 70% identical to SEQ ID NO: 29. In some embodiments, the mRNA comprises a coding sequence at least 80% identical to SEQ ID NO: 29. In some embodiments, the mRNA comprises a coding sequence at least 90% identical to SEQ ID NO: 29. In some embodiments, the mRNA comprises a coding sequence at least 95% identical to SEQ ID NO: 29. In some embodiments, the mRNA comprises a coding sequence at least 96%, at least 97%, at least 98%, or at least 99% identical to SEQ ID NO: 29. In some embodiments, the mRNA comprises a coding sequence set forth in SEQ ID NO: 29.

In some embodiments, the mRNA comprises a coding sequence at least 70%, 75%, 80%, 85%, 90%, or 95% identical to SEQ ID NO: 30. In some embodiments, the mRNA comprises a coding sequence at least 70% identical to SEQ ID NO: 30. In some embodiments, the mRNA comprises a coding sequence at least 80% identical to SEQ ID NO: 30. In some embodiments, the mRNA comprises a coding sequence at least 90% identical to SEQ ID NO: 30. In some embodiments, the mRNA comprises a coding sequence at least 95% identical to SEQ ID NO: 30. In some embodiments, the mRNA comprises a coding sequence at least 96%, at least 97%, at least 98%, or at least 99% identical to SEQ ID NO: 30. In some embodiments, the mRNA comprises a coding sequence set forth in SEQ ID NO: 30.

In some embodiments, the mRNA comprises a coding sequence at least 70%, 75%, 80%, 85%, 90%, or 95% identical to SEQ ID NO: 31. In some embodiments, the mRNA comprises a coding sequence at least 70% identical to SEQ ID NO: 31. In some embodiments, the mRNA comprises a coding sequence at least 80% identical to SEQ ID NO: 31. In some embodiments, the mRNA comprises a coding sequence at least 90% identical to SEQ ID NO: 31. In some embodiments, the mRNA comprises a coding sequence at least 95% identical to SEQ ID NO: 31. In some embodiments, the mRNA comprises a coding sequence at least 96%, at least 97%, at least 98%, or at least 99% identical to SEQ ID NO: 31. In some embodiments, the mRNA comprises a coding sequence set forth in SEQ ID NO: 31.

In some embodiments, administering the mRNA to the subject is performed by intratracheal, intranasal, intravenous, intramuscular or subcutaneous delivery.

In some embodiments, administering the mRNA to the subject is performed by intratracheal delivery.

In some embodiments, administering the mRNA to the subject is performed by intranasal delivery.

In some embodiments, administering the mRNA to the subject is performed by aerosol delivery.

In some embodiments, administering the mRNA to the subject is performed by nebulized delivery.

In some embodiments, administering the mRNA to the subject is performed by dry powder inhalation.

In some embodiments, the composition is administered once a week.

In some embodiments, the composition is administered once every two weeks.

In some embodiments, the composition is administered twice a month.

In some embodiments, the composition is administered once a month.

In some embodiments, the administering the mRNA results in DNAH5 protein expression detectable in one or more internal organs selected from lung, heart, liver, spleen, kidney, brain, stomach, intestines, ovary and testis.

In some embodiments, the administering the mRNA results in DNAH5 protein expression detectable in the lung.

In some embodiments, the administering the mRNA results in DNAH5 protein expression detectable in the lung epithelium.

In some aspects, the invention provides a composition for use in the treatment of primary ciliary dyskinesia (PCD), the composition comprising an mRNA encoding human axonemal dynein heavy chain 5 (DNAH5) encapsulated in a liposome, wherein the liposome comprises one or more cationic lipids, one or more non-cationic lipids and one or more PEG-modified lipids.

In some embodiments, the mRNA comprises a DNAH5 coding sequence at least 70%, 75%, 80%, 85%, 90%, or 95% identical to any one of SEQ ID NO: 6 to SEQ ID NO: 31.

In some embodiments, mRNA comprises a coding sequence at least 70%, at least 80%, at least 90%, at least 95% or at least 98% identical to SEQ ID NO: 6. In some embodiments, mRNA comprises a coding sequence at least 70%, at least 80%, at least 90%, at least 95% or at least 98% identical to SEQ ID NO: 7.

In some embodiments, the mRNA comprises a coding sequence set forth in SEQ ID NO: 6. In some embodiments, the mRNA comprises a coding sequence set forth in SEQ ID NO: 7.

In some embodiments, the mRNA has a 5'-untranslated region (5'-UTR) that has a sequence set forth in SEQ ID NO: 2 or SEQ ID NO: 3, and a 3'-untranslated region (3'-UTR) that has a sequence set forth in SEQ ID NO: 4 or SEQ ID NO: 5.

In some embodiments, wherein the mRNA has one or more modified nucleotides.

In some embodiments, the modified one or more nucleotides is selected from pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and/or 2-thiocytidine.

In some embodiments, the mRNA is unmodified.

In some embodiments, the liposome is 100 nm in diameter or less.

In some embodiments, the invention provides a pharmaceutical composition comprising the composition described above and a suitable excipient.

In some aspects, the present invention provides a method of delivery of a mRNA encoding for a protein or peptide in vivo comprising administering to a subject in need of delivery a mRNA encoding a protein or peptide and having a 5'-untranslated region (5'-UTR) that has a sequence at least 70%, 75%, 80%, 85%, 90%, or 95% identical to SEQ ID NO: 2 and that is not SEQ ID NO: 3. In some embodiments, the mRNA comprises a 5'-untranslated region (5'-UTR) that has a sequence at least 70% identical to SEQ ID NO: 2 that is not SEQ ID NO: 3. In some embodiments, the mRNA comprises a 5'-untranslated region (5'-UTR) that has a sequence at least 75% identical to SEQ ID NO: 2 that is not SEQ ID NO: 3. In some embodiments, the mRNA comprises a 5'-untranslated region (5'-UTR) that has a sequence at least 80% identical to SEQ ID NO: 2 that is not SEQ ID NO: 3. In some embodiments, the mRNA comprises a 5'-untranslated region (5'-UTR) that has a sequence at least 85% identical to SEQ ID NO: 2 that is not SEQ ID NO: 3. In some embodiments, the mRNA comprises a 5'-untranslated region (5'-UTR) that has a sequence at least 90% identical to SEQ ID NO: 2 that is not SEQ ID NO: 3. In some embodiments, the mRNA comprises a 5'-untranslated region (5'-UTR) that has a sequence at least 95% identical to SEQ ID NO: 2 that is not SEQ ID NO: 3. In some embodiments, the mRNA comprises a 5'-untranslated region (5'-UTR) that is at least 96%, at least 97%, at least 98%, or at least 99% identical to SEQ ID NO: 2 that is not SEQ ID NO: 3. In some embodiments, the mRNA comprises a 5'-untranslated region (5'-UTR) set forth in SEQ ID NO: 2. Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only, not for limitation.

FIG. 1B (left) shows data from Group 1 mice who were administered MRT-1 hDNA5 mRNA; FIG. 1B (right) shows data from Group 2 mice who were administered MRT-1 hDNA5-GFP mRNA.

FIG. 2A depicts representative IHC data for hDNA-5 protein staining in MRT-1 hDNA5 mRNA treated mice compared to saline-treated control (Group 1, left); and IHC data for GFP protein staining in MRT-1 hDNA5-GFP mRNA treated mice compared to saline-treated control (Group 2, right). FIG. 2B shows detailed localization of the respective hDNA5 mRNA derived protein in epithelial tissue of the airways in Group 1 (upper panel) and Group 2 (lower panel) mice.

DEFINITIONS

Figure 1A:
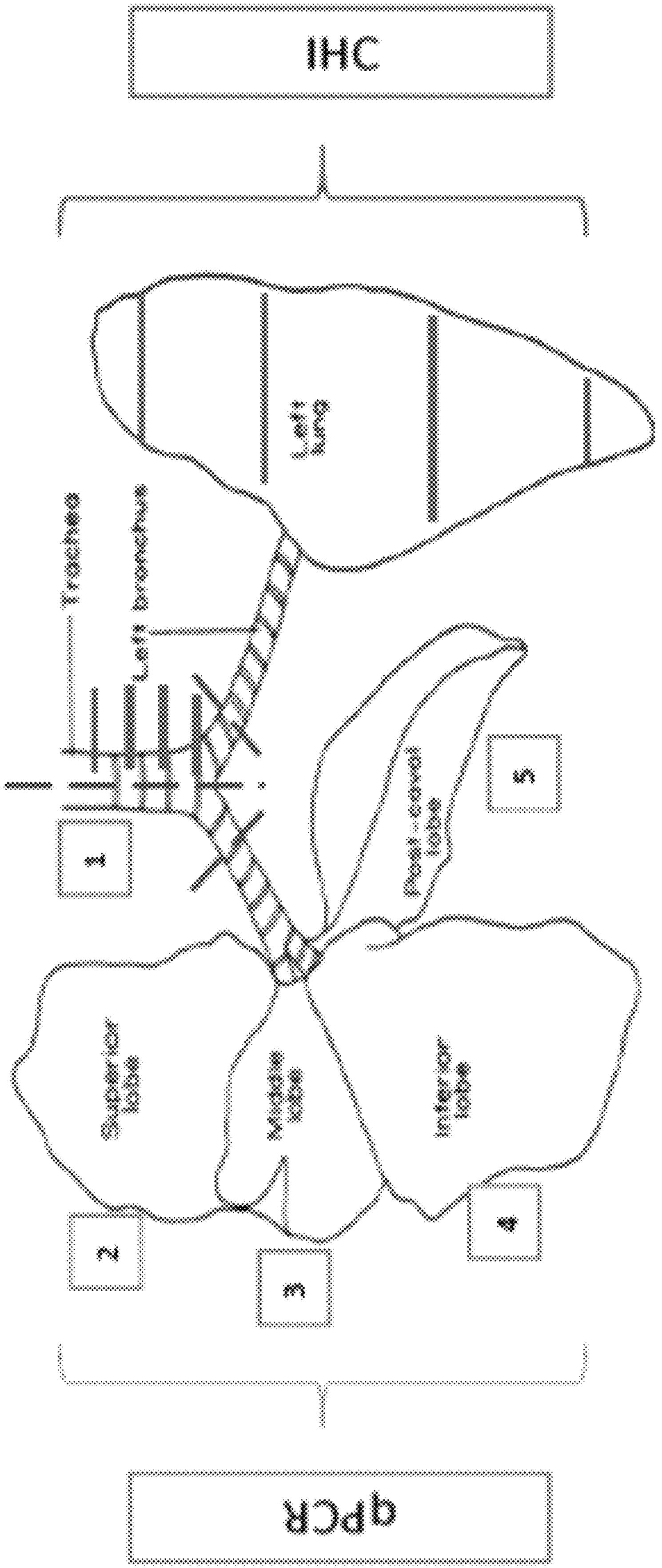
FIG. 1A is a schematic diagram that shows the dissection and usage of various parts of mouse trachea and lungs for quantitative PCR analysis (qPCR) and immunohistochemistry (IHC) analysis, 24 hours after mRNA administration.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("C1-15 alkyl"). In some embodiments, an alkyl group has 1 to 3 carbon atoms ("C1-3 alkyl"). Examples of C1-3 alkyl groups include methyl (C1), ethyl (C2), n-propyl (C3), and isopropyl (C3). In some embodiments, an alkyl group has 8 to 12 carbon atoms ("C8-12 alkyl"). Examples of C8-12 alkyl groups include, without limitation, n-octyl (C8), n-nonyl (C9), n-decyl (C10), n-undecyl (C11), n-dodecyl (C12) and the like. The prefix "n-" (normal) refers to unbranched alkyl groups. For example, n-C8 alkyl refers to $(CH_2)_7CH_3$, n-C10 alkyl refers to $(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Typically, the term "approximately" or "about" refers to a range of values that within 10%, or more typically 1%, of the stated reference value.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Codon-optimized: As used herein, the term describes a nucleic acid in which one or more of the nucleotides present in a naturally occurring nucleic acid sequence (also referred to as 'wild-type' sequence) has been substituted with an alternative nucleotide to optimize protein expression without changing the amino acid sequence of the polypeptide encoded by the naturally occurring nucleic acid sequence. For example, the codon AAA may be altered to become AAG without changing the identity of the encoded amino acid (lysine). In some embodiments, the nucleic acids of the invention are codon optimized to increase protein expression of the protein encoded by the nucleic acid. For the purpose of this application, nucleobase thymidine (T) and uracil (U) are used interchangeably in narration of mRNA sequences.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Dosing interval: As used herein dosing interval in the context of a method for treating a disease is the frequency of administering a therapeutic composition in a subject (mammal) in need thereof, for example an mRNA composition, at an effective dose of the mRNA, such that one or more symptoms associated with the disease is reduced; or one or more biomarkers associated with the disease is reduced, at least for the period of the dosing interval. Dosing frequency and dosing interval may be used interchangeably in the current disclosure.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Effective dose: As used herein, an effective dose is a dose of the mRNA in the pharmaceutical composition which when administered to the subject in need thereof, hereby a mammalian subject, according to the methods of the invention, is effective to bring about an expected outcome in the subject, for example reduce a symptom associated with the disease.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polyribonucleotide that encodes at least one polypeptide. mRNA may contain one or more coding and non-coding regions. mRNA can be purified from natural sources, produced using recombinant expression systems and optionally purified, in vitro transcribed, chemically synthesized, etc. An mRNA sequence is presented in the 5' to 3' direction unless otherwise indicated. Typically, the mRNA of the present invention is synthesized from adenosine, guanosine, cytidine and uridine nucleotides that bear no modifications. Such mRNA is referred to herein as mRNA with unmodified nucleotides or 'unmodified mRNA' for short. Typically, this means that the mRNA of the present invention does not comprise any of the following nucleoside analogs: 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine. An mRNA suitable for practising the claimed invention commonly does not comprise nucleosides comprising chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4 alkyl)4 salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Various aspects of the invention are described in detail in the following sections. The use of sections is not meant to limit the invention. Each section can apply to any aspect of the invention. In this application, the use of "or" means "and/or" unless stated otherwise.

DETAILED DESCRIPTION

Primary Ciliary Dyskinesia (PCD)

Primary ciliary dyskinesia (PCD) is an autosomal recessive disorder characterized by abnormal cilia and flagella that are found in the linings of the airway, the reproductive system, and other organs and tissues. Mutations in the DNAH5 gene, which encodes the dynein axonemal heavy chain 5 protein that forms the inner structure of cilia, cause PCD. Over 80 different mutations in the DNAH5 gene have been identified in patients with PCD.

Mutations in the DNAH5 gene result in an absent or abnormal dynein axonemal heavy chain 5, which is required for the proper functioning of cilia. Without a normal version of dynein axonemal heavy chain 5, defective cilia cannot produce the force and movement needed to eliminate fluid, bacteria, and particles from the lungs, to establish the left-right axis during embryonic development, and to propel the sperm cells. PCD can lead to chronic respiratory tract infections, bronchiectasis, year-round nasal congestion, abnormally placed organs within their chest and abdomen, and infertility.

Polyribonucleotides of the disclosure can be used, for example, to treat a subject having or at risk of having primary ciliary dyskinesia or any other condition associated with a defect or malfunction of a gene whose function is linked to cilia maintenance and function. Non limiting examples of genes that have been associated with primary ciliary dyskinesia include: armadillo repeat containing 4 (ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), cyclin O (CCNO), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH1 1), dynein axonemal heavy chain 5 (DNAH5), dynein axonemal heavy chain 6 (DNAH6), dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), growth arrest specific 8 (GAS8), axonemal central pair apparatus protein (HYDIN), leucine rich repeat containing 6 (LRRC6), ME/M23 family member 8 (NME8), oral-facial-digital syndrome 1 (OFD1), retinitis pigmentosa GTPase regulator (RPGR), radial spoke head 1 homolog (*Chlamydomonas*) (RSPH1), radial spoke head 4 homolog A (*Chlamydomonas*) (RSPH4A), radial spoke head 9 homolog (*Chlamydomonas*) (RSPH9), sperm associated antigen 1 (SPAG1), and zinc finger MY D-type containing 10 (ZMYND10).

Dynein Axonemal Heavy Chain 5 (DNAH5) Gene and Protein Sequence

In some embodiments, the present invention provides methods and compositions for delivering mRNA encoding to a subject for the treatment of PCD. A suitable DNAH5 mRNA encodes any full length, fragment or portion of a DNAH5 protein which can be substituted for naturally-occurring DNAH5 protein activity and/or reduce the intensity, severity, and/or frequency of one or more symptoms associated with PCD.

In some embodiments, a suitable mRNA sequence is an mRNA sequence encoding a human DNAH5 protein. The naturally-occurring human DNAH5 mRNA coding sequence and the corresponding amino acid sequence are shown in Table 1:

The naturally-occurring human DNAH5 mRNA coding sequence and the corresponding amino acid sequence are shown in Table 1:

TABLE 1

| Human DNAH5 Amino Acid Sequence | |
|---|---|
| Human | (SEQ ID NO: 1) |
| DNAH5 | MFRIGRRQLWKHSVTRVLTQRLKGEKEAKRALLDARHNYLFAIVASCLDL |
| Protein | NKTEVEDAILEGNQIERIDQLFAVGGLRHLMFYYQDVEEAETGQLGSLGGV |
| Sequence | NLVSGKIKKPKVFVTEGNDVALTGVCVFFIRTDPSKAITPDNIHQEVSFNML |
| | DAADGGLLNSVRRLLSDIFIPALRATSHGWGELEGLQDAANIRQEFLSSLEG |
| | FVNVLSGAQESLKEKVNLRKCDILELKTLKEPTDYLTLANNPETLGKIEDCM |
| | KVWIKQTEQVLAENNQLLKEADDVGPRAELEHWKKRLSKFNYLLEQLKSP |
| | DVKAVLAVLAAAKSKLLKTWREMDIRITDATNEAKDNVKYLYTLEKCCDP |
| | LYSSDPLSMMDAIPTLINAIKMIYSISHYYNTSEKITSLFVKVTNQIISACKAYI |
| | TNNGTASIWNQPQDVVEEKILSAIKLKQEYQLCFHKTKQKLKQNPNAKQFD |
| | FSEMYIFGKFETFHRRLAKIIDIFTTLKTYSVLQDSTIEGLEDMATKYQGIVAT |
| | IKKKEYNFLDQRKMDFDQDYEEFCKQTNDLHNELRKFMDVTFAKIQNTNQ |
| | ALRMLKKFERLNIPNLGIDDKYQLILENYGADIDMISKLYTKQKYDPPLARN |
| | QPPIAGKILWARQLFHRIQQPMQLFQQHPAVLSTAEAKPIIRSYNRMAKVLL |
| | EFEVLFHRAWLRQIEEIHVGLEASLLVKAPGTGELFVNFDPQILILFRETECM |
| | AQMGLEVSPLATSLFQKRDRYKRNFSNMKMMLAEYQRVKSKIPAAIEQLIV |
| | PHLAKVDEALQPGLAALTWTSLNIEAYLENTFAKIKDLELLLDRVNDLIEFRI |
| | DAILEEMSSTPLCQLPQEEPLTCEEFLQMTKDLCVNGAQILHFKSSLVEEAV |
| | NELVNMLLDVEVLSEEESEKISNENSVNYKNESSAKREEGNFDTLTSSINAR |
| | ANALLLTTVTRKKKETEMLGEEARELLSHFNHQNMDALLKVTRNTLEAIRK |
| | RIHSSHTINFRDSNSASNMKQNSLPIFRASVTLAIPNIVMAPALEDVQQTLNK |
| | AVECIISVPKGVRQWSSELLSKKKIQERKMAALQSNEDSDSDVEMGENELQ |
| | DTLEIASVNLPIPVQTKNYYKNVSENKEIVKLVSVLSTIINSTKKEVITSMDCF |
| | KRYNHIWQKGKEEAIKTFITQSPLLSEFESQILYFQNLEQEINAEPEYVCVGSI |
| | ALYTADLKFALTAETKAWMVVIGRHCNKKYRSEMENIFMLIEEFNKKLNRP |
| | IKDLDDIRIAMAALKEIREEQISIDFQVGPIEESYALLNRYGLLIAREEIDKVDT |
| | LHYAWEKLLARAGEVQNKLVSLQPSFKKELISAVEVFLQDCHQFYLDYDLN |
| | GPMASGLKPQEASDRLIMFQNQFDNIYRKYITYTGGEELFGLPATQYPQLLE |
| | IKKQLNLLQKIYTLYNSVIETVNSYYDILWSEVNIEKINNELLEFQNRCRKLP |
| | RALKDWQAFLDLKKIIDDFSECCPLLEYMASKAMMERHWERITTLTGHSLD |
| | VGNESFKLRNIMEAPLLKYKEEIEDICISAVKERDIEQKLKQVINEWDNKTFT |
| | FGSFKTRGELLLRGDSTSEIIANMEDSLMLLGSLLSNRYNMPFKAQIQKWVQ |
| | YLSNSTDIIESWMTVQNLWIYLEAVFVGGDIAKQLPKEAKRFSNIDKSWVKI |
| | MTRAHEVPSVVQCCVGDETLGQLLPHLLDQLEICQKSLTGYLEKKRLCFPR |
| | FFFVSDPALLEILGQASDSHTIQAHLLNVFDNIKSVKFHEKIYDRILSISSQEGE |
| | TIELDKPVMAEGNVEVWLNSLLEESQSSLHLVIRQAAANIQETGFQLTEFLSS |
| | FPAQVGLLGIQMIWTRDSEEALRNAKFDKKIMQKTNQAFLELLNTLIDVTTR |
| | DLSSTERVKYETLITIHVHQRDIFDDLCHMHIKSPMDFEWLKQCRFYFNEDS |
| | DKMMIHITDVAFIYQNEFLGCTDRLVITPLTDRCYITLAQALGMSMGGAPA |
| | GPAGTGKTETTKDMGRCLGKYVVVFNCSDQMDFRGLGRIFKGLAQSGSWG |
| | CFDEFNRIDLPVLSVAAQQISIILTCKKEHKKSFIFTDGDNVTMNPEFGLFLT |
| | MNPGYAGRQELPENLKINFRSVAMMVPDRQIIIRVKLASCGFIDNVVLARKF |
| | FTLYKLCEEQLSKQVHYDFGLRNILSVLRTLGAAKRANPMDTESTIVMRVL |

TABLE 1-continued

| Human DNAH5 Amino Acid Sequence |
|---|
| RDMNLSKLIDEDEPLFLSLIEDLFPNILLDKAGYPELEAAISRQVEEAGLINHP<br>PWKLKVIQLFETQRVRHGMMTLGPSGAGKTTCIHTLMRAMTDCGKPHREM<br>RMNPKAITAPQMFGRLDVATNDWTDGIFSTLWRKTLRAKKGEHIWIILDGP<br>VDAIWIENLNSVLDDNKTLTLANGDRIPMAPNCKIIFEPHNIDNASPATVSRN<br>GMVFMSSSILDWSPILEGFLKKRSPQEAEILRQLYTESFPDLYRFCIQNLEYK<br>MEVLEAFVITQSINMLQGLIPLKEQGGEVSQAHLGRLFVFALLWSAGAALEL<br>DGRRRLELWLRSRPTGTLELPPPAGPGDTAFDYYVAPDGTWTHWNTRTQE<br>YLYPSDTTPEYGSILVPNVDNVRTDFLIQTIAKQGKAVLLIGEQGTAKTVIIK<br>GFMSKYDPECHMIKSLNFSSATTPLMFQRTIESYVDKRMGTTYGPPAGKKM<br>TVFIDDVNMPIINEWGDQVTNEIVRQLMEQNGFYNLEKPGEFTSIVDIQFLA<br>AMIHPGGGRNDIPQRLKRQFSIFNCTLPSEASVDKIFGVIGVGHYCTQRGFSE<br>EVRDSVTKLVPLTRRLWQMTKIKMLPTPAKFHYVFNLRDLSRVWQGMLNT<br>TSEVIKEPNDLLKLWKHECKRVIADRFTVSSDVTWFDKALVSLVEEEFGEEK<br>KLLVDCGIDTYFVDFLRDAPEAAGETSEEADAETPKIYEPIESFSHLKERLNM<br>FLQLYNESIRGAGMDMVFFADAMVHLVKISRVIRTPQGNALLVGVGGSGK<br>QSLTRLASFIAGYVSFQITLTRSYNTSNLMEDLKVLYRTAGQQGKGITFIFTD<br>NEIKDESFLEYMNNVLSSGEVSNLFARDEIDEINSDLASVMKKEFPRCLPTNE<br>NLHDYFMSRVRQNLHIVLCFSPVGEKFRNRALKFPALISGCTIDWFSRWPKD<br>ALVAVSEHFLTSYDIDCSLEIKKEVVQCMGSFQDGVAEKCVDYFQRFRRST<br>HVTPKSYLSFIQGYKFIYGEKHVEVRTLANRMNTGLEKLKEASESVAALSKE<br>LEAKEKELQVANDKADMVLKEVTMKAQAAEKVKAEVQKVKDRAQAIVD<br>SISKDKAIAEEKLEAAKPALEEAEAALQTIRPSDIATVRTLGRPPHLIMRIMD<br>CVLLLFQRKVSAVKIDLEKSCTMPSWQESLKLMTAGNFLQNLQQFPKDTIN<br>EEVIEFLSPYFEMPDYNIETAKRVCGNVAGLCSWTKAMASFFSINKEVLPLK<br>ANLVVQENRHLLAMQDLQKAQAELDDKQAELDVVQAEYEQAMTEKQTLL<br>EDAERCRHKMQTASTLISGLAGEKERWTEQSQEFAAQTKRLVGDVLLATAF<br>LSYSGPFNQEFRDLLLNDWRKEMKARKIPFGKNLNLSEMLIDAPTISEWNLQ<br>GLPNDDLSIQNGIIVTKASRYPLLIDPQTQGKIWIKNKESRNELQITSLNHKYF<br>RNHLEDSLSLGRPLLIEDVGEELDPALDNVLERNFIKTGSTFKVKVGDKEVD<br>VLDGFRLYITTKLPNPAYTPEISARTSIIDFTVTMKGLEDQLLGRVILTEKQEL<br>EKERTHLMEDVTANKRRMKELEDNLLYRLTSTQGSLVEDESLIVVLSNTKR<br>TAEEVTQKLEISAETEVQINSAREEYRPVATRGSILYFLITEMRLVNEMYQTS<br>LRQFLGLFDLSLARSVKSPITSKRIANIIEHMTYEVYKYAARGLYEEHKFLFT<br>LLLTLKIDIQRNRVKHEEFLTLIKGGASLDLKACPPKPSKWILDITWLNLVEL<br>SKLRQFSDVLDQISRNEKMWKIWFDKENPEEEPLPNAYDKSLDCFRRLLLIR<br>SWCPDRTIAQARKYIVDSMGEKYAEGVILDLEKTWEESDPRTPLICLLSMGS<br>DPTDSIIALGKRLKIETRYVSMGQGQEVHARKLLQQTMANGGWALLQNCH<br>LGLDFMDELMDIIIETELVHDAFRLWMTTEAHKQFPITLLQMSIKFANDPPQ<br>GLRAGLKRTYSGVSQDLLDVSSGSQWKPMLYAVAFLHSTVQERRKFGALG<br>WNIPYEFNQADFNATVQFIQNHLDDMDVKKGVSWTTIRYMIGEIQYGGRVT<br>DDYDKRLLNTFAKVWFSENMFGPDFSFYQGYNIPKCSTVDNYLQYIQSLPA<br>YDSPEVFGLHPNADITYQSKLAKDVLDTILGIQPKDTSGGGDETREAVVARL<br>ADDMLEKLPPDYVPFEVKERLQKMGPFQPMNIFLRQEIDRMQRVLSLVRST<br>LTELKLAIDGTIIMSENLRDALDCMFDARIPAWWKKASWISSTLGFWFTELI<br>ERNSQFTSWVFNGRPHCFWMTGFFNPQGFLTAMRQEITRANKGWALDNM<br>VLCNEVTKWMKDDISAPPTEGVYVYGLYLEGAGWDKRNMKLIESKPKVLF<br>ELMPVIRIYAENNTLRDPRFYSCPIYKKPVRTDLNYIAAVDLRTAQTPEHWV<br>LRGVALLCDVK |

In some embodiments, a suitable mRNA is a wild-type human DNAH5 mRNA of sequence. In some embodiments, a suitable therapeutic candidate mRNA is a codon-optimized hDNAH5 sequence that can encodes a DNAH5 amino acid sequence shown in Table 1 as SEQ ID NO: 1 or an amino acid sequence at least 70%, 75%, 80%, 85%, 90%, 95%, 96%, 97%, 98%, or 99% identical to SEQ ID NO: 1. In some embodiments, an mRNA according to the present invention encodes a DNAH5 protein with an amino acid sequence that is identical to SEQ ID NO: 1.

Codon Optimization

According to an increasing amount of research, mRNAs contain numerous layers of information that overlap the amino acid code. Traditionally, codon optimization has been used to remove rare codons which were thought to be rate-limiting for protein expression. While fast growing bacteria and yeast both exhibit strong codon bias in highly expressed genes, higher eukaryotes exhibit much less codon bias, making it more difficult to discern codons that may be rate-limiting. In addition, it has been found that codon bias per se does not necessarily yield high expression but requires other features.

For example, rare codons have been implicated in slowing translation and forming pause sites, which may be required for correct protein folding. Therefore, variations in codon usage may provide a mechanism to fine-tune the temporal pattern of elongation and thus increase the time available for a protein to take on its correct confirmation. Codon optimization can interfere with this fine-tuning mechanism, resulting in less efficient protein translation or an increased amount of incorrectly folded proteins. Similarly, codon optimization may disrupt the normal patterns of cognate and wobble tRNA usage, thereby affecting protein structure and function because wobble-dependent slowing of elongation may likewise have been selected as a mechanism for achieving correct protein folding.

Despite these obstacles, the inventors have arrived at a codon-optimized hDNAH5 sequence that improves expression of the DNAH5 protein at least threefold over the coding sequence of the wild type gene. The increase in expression is not limited to cell cultures of mammalian cells but was also observed in vivo in a mouse model. It is expected that the observed improvement in expression of the codon-optimised DNAH5 coding sequence will result in an improved, more cost-effective mRNA replacement therapy for patients suffering from PCD, because it does not require the use of modified nucleotides for the preparation of the mRNA and allows treatment with a reduced dose and/or at extended dosing intervals.

Exemplary Codon Optimized DNAH5 mRNA Sequences

The sequences that follow recite select, exemplary codon-optimized DNAH5 mRNA sequences.

In some embodiments, a suitable mRNA may be a codon-optimized sequence, as shown in SEQ ID NO: 6.

In some embodiments, a suitable mRNA may be a codon-optimized sequence, as shown in SEQ ID NO: 7.

In some embodiments, a suitable mRNA may be a codon-optimized sequence, as shown in SEQ ID NO: 8.

In some embodiments, a suitable mRNA may be a codon-optimized sequence, as shown in SEQ ID NO: 9.

In some embodiments, a suitable mRNA may be a codon-optimized sequence, as shown in SEQ ID NO: 10.

In some embodiments, a suitable mRNA may be a codon-optimized sequence, as shown in SEQ ID NO: 11.

In some embodiments, a suitable mRNA may be a codon-optimized sequence, as shown in SEQ ID NO: 12.

In some embodiments, a suitable mRNA may be a codon-optimized sequence, as shown in SEQ ID NO: 13.

In some embodiments, a suitable mRNA may be a codon-optimized sequence, as shown in SEQ ID NO: 14.

In some embodiments, a suitable mRNA may be a codon-optimized sequence, as shown in SEQ ID NO: 15.

In some embodiments, a suitable mRNA may be a codon-optimized sequence, as shown in SEQ ID NO: 16.

In some embodiments, a suitable mRNA may be a codon-optimized sequence, as shown in SEQ ID NO: 17.

In some embodiments, a suitable mRNA may be a codon-optimized sequence, as shown in SEQ ID NO: 18.

In some embodiments, a suitable mRNA may be a codon-optimized sequence, as shown in SEQ ID NO: 19.

In some embodiments, a suitable mRNA may be a codon-optimized sequence, as shown in SEQ ID NO: 20.

In some embodiments, a suitable mRNA may be a codon-optimized sequence, as shown in SEQ ID NO: 21.

In some embodiments, a suitable mRNA may be a codon-optimized sequence, as shown in SEQ ID NO: 22.

In some embodiments, a suitable mRNA may be a codon-optimized sequence, as shown in SEQ ID NO: 23.

In some embodiments, a suitable mRNA may be a codon-optimized sequence, as shown in SEQ ID NO: 24.

In some embodiments, a suitable mRNA may be a codon-optimized sequence, as shown in SEQ ID NO: 25.

In some embodiments, a suitable mRNA may be a codon-optimized sequence, as shown in SEQ ID NO: 26.

In some embodiments, a suitable mRNA may be a codon-optimized sequence, as shown in SEQ ID NO: 27.

In some embodiments, a suitable mRNA may be a codon-optimized sequence, as shown in SEQ ID NO: 28.

In some embodiments, a suitable mRNA may be a codon-optimized sequence, as shown in SEQ ID NO: 29.

In some embodiments, a suitable mRNA may be a codon-optimized sequence, as shown in SEQ ID NO: 30.

In some embodiments, a suitable mRNA may be a codon-optimized sequence, as shown in SEQ ID NO: 31.

In some embodiments, a suitable mRNA sequence may be an mRNA sequence a homolog or an analog of human DNAH5 protein. For example, a homolog or an analog of human DNAH5 protein may be a modified human DNAH5 protein containing one or more amino acid substitutions, deletions, and/or insertions as compared to a wild-type or naturally-occurring human DNAH5 protein while retaining substantial DNAH5 protein activity. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more homologous to SEQ ID NO: 1. In some embodiments, an mRNA suitable for the present invention encodes a protein substantially identical to human DNAH5 protein. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more identical to SEQ ID NO: 1. Typically, an mRNA according to the present invention encodes a DNAH5 protein with an amino acid sequence that is identical to SEQ ID NO: 1.

In some embodiments, an mRNA suitable for the present invention encodes a fragment or a portion of human DNAH5 protein. In some embodiments, an mRNA suitable for the present invention encodes a fragment or a portion of human DNAH5 protein, wherein the fragment or portion of the protein still maintains DNAH5 activity similar to that of the wild-type protein.

In some embodiments, a suitable mRNA encodes a fusion protein comprising a full length, fragment or portion of a DNAH5 protein fused to another protein (e.g., an N or C terminal fusion). In some embodiments, the protein fused to the mRNA encoding a full length, fragment or portion of a DNAH5 protein encodes a signal or a cellular targeting sequence.

In some embodiments, an mRNA suitable for the present invention comprises a nucleotide sequence at least 85%, 90%, 91%, 92%, 93%, 94%, 95%, 96%, 97%, 98%, 99% or more identical to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31. More typically, an mRNA in accordance with the present invention comprises a nucleotide sequence at least 95% identical to SEQ ID NO: 6. Preferably, an mRNA according to the present invention comprises a nucleotide sequence at least 99% identical to SEQ ID NO: 7. For example, an mRNA according to the present invention comprises the nucleotide sequence of SEQ ID NO: 6 or SEQ ID NO: 7.

Messenger RNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Typically, the mRNA according to the present invention is synthesized as unmodified mRNA. Accordingly, the mRNAs of the invention are synthesized from naturally occurring nucleotides including purines (adenine (A), guanine (G)) or pyrimidines (cytosine (C), uracil (U)).

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., DNAH5-encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

In some embodiments, mRNAs (e.g., DNAH5-encoding mRNAs) include a 3' poly(A) tail structure. A poly-A tail on the 3' terminus of mRNA typically includes about 10 to 800 adenosine nucleotides (e.g., about 300 to 500 adenosine nucleotides, about 300 to 800 adenosine nucleotides, about 10 to 500 adenosine nucleotides, about 10 to 300 adenosine nucleotides, about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). Typically, a poly-A tail in an mRNA in accordance with the invention is about 300 to about 800 adenosine nucleotides long. More commonly, the poly-A tail is about 300 adenosine nucleotides long. In some embodiments, the poly(A) tail structure comprises at least 85%, 90%, 95% or 100% adenosine.

In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the mRNA further comprises a 5' untranslated region (5' UTR) comprising a nucleotide sequence and positioned between the 5' cap structure and coding sequence, and/or a 3' untranslated region (3' UTR) comprising a nucleotide sequence and positioned between the coding sequence and the poly(A) tail structure. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Modified mRNA mRNAs according to the present invention are typically synthesized as unmodified mRNAs. In some embodiments, it may be advantageous to synthesize an mRNA encoding a codon-optimized DNAH5 coding sequence of the present invention with one or more modified nucleotides. Typically, mRNAs are modified to enhance their stability or reduce their immunogenic properties, in particular when administered to a subject as naked mRNAs or in complexed form. Therefore, providing an mRNA encoding a codon-optimized DNAH5 coding sequence of the present invention may have synergistic effects, resulting in sustained in vivo function that exceeds that observed with unmodified mRNAs.

Modifications of mRNA can include, for example, modifications of the nucleotides of the RNA. A modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs of the present invention may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs of the present invention may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs of the present invention may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of m7G(5')ppp(5')N, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is m7G(5')ppp(5')G, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form m7G(5')ppp(5')G ("m7GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH3.

Additional cap analogs include, but are not limited to, a chemical structures selected from the group consisting of m7GpppG, m7GpppA, m7GpppC; unmethylated cap analogs (e.g., GpppG); dimethylated cap analog (e.g., m2,7GpppG), trimethylated cap analog (e.g., m2,2, 7GpppG), dimethylated symmetrical cap analogs (e.g., m7Gpppm7G), or anti reverse cap analogs (e.g., ARCA; m7,2'OmeGpppG, m72'dGpppG, m7,3'OmeGpppG, m7,3'dGpppG and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("m7G") linked via a triphosphate bridge to the 5'-end of the first transcribed nucleotide, resulting in m7G (5')ppp(5')N, where N is any nucleoside. A preferred embodiment of a m7G cap utilized in embodiments of the invention is m7G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m7G cap analogs are known in the art, many of which are commercially available. These include the m7GpppG described above, as well as the ARCA 3'-OCH3 and 2'-OCH3 cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly-A tail is thought to stabilize natural messengers and synthetic sense RNA. Therefore, in certain embodiments a long poly-A tail can be added to an mRNA molecule thus rendering the RNA more stable. Poly-A tails can be added using a variety of art-recognized techniques. For example, long poly-A tails can be added to synthetic or in vitro transcribed RNA using poly A polymerase (Yokoe, et al. Nature Biotechnology. 1996; 14: 1252-1256). A transcription vector can also encode long poly-A tails. In addition, poly-A tails can be added by transcription directly from PCR products. Poly-A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly-A tail can be at least about 10, 50, 100, 200, 300, 400 or 500 nucleotides in length. In some embodiments, a poly-A tail on the 3' terminus of mRNA typically includes about 10 to 800 adenosine nucleotides (e.g., about 300 to 500 adenosine nucleotides, about 300 to 800 adenosine nucleotides, about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). Typically, a poly-A tail in an mRNA in accordance with the invention is about 300 to about 800 adenosine nucleotides long. More commonly, the poly-A tail is about 300 adenosine nucleotides long.

In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' untranslated region (UTR). In some embodiments, mRNAs include a 3' untranslated region. In some embodiments, mRNAs include both a 5' untranslated region and a 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and 5' untranslated region sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

In certain embodiments, the codon-optimized DNAH5 mRNA includes a coding region having a codon-optimized coding region flanked by 5' and 3' untranslated regions as represented as X and Y, respectively (vide infra)

X-Coding Region-Y where the coding region sequence is SEQ ID NO: 6, or a sequence 70%, 75%, 80%, 85%, 90%, 91%, 92%, 93%, 94%, 95%, 96%, 97%, 98%, 99% or more identical to SEQ ID NO: 6; or SEQ ID NO: 7 or a sequence 70%, 75%, 80%, 85%, 90%, 91%, 92%, 93%, 94%, 95%, 96%, 97%, 98%, 99% or more identical to SEQ ID NO: 7; SEQ ID NO: 8 or a sequence 70%, 75%, 80%, 85%, 90%, 91%, 92%, 93%, 94%, 95%, 96%, 97%, 98%, 99% or more identical to SEQ ID NO: 8; SEQ ID NO: 9 or a sequence 70%, 75%, 80%, 85%, 90%, 91%, 92%, 93%, 94%, 95%, 96%, 97%, 98%, 99% or more identical to SEQ ID NO: 9; SEQ ID NO: 10 or a sequence 70%, 75%, 80%, 85%, 90%, 91%, 92%, 93%, 94%, 95%, 96%, 97%, 98%, 99% or more identical to SEQ ID NO: 10; SEQ ID NO: 11 or a sequence 70%, 75%, 80%, 85%, 90%, 91%, 92%, 93%, 94%, 95%, 96%, 97%, 98%, 99% or more identical to SEQ ID NO: 11; SEQ ID NO: 12 or a sequence 70%, 75%, 80%, 85%, 90%, 91%, 92%, 93%, 94%, 95%, 96%, 97%, 98%, 99% or more identical to SEQ ID NO: 12; SEQ ID NO: 13 or a sequence 70%, 75%, 80%, 85%, 90%, 91%, 92%, 93%, 94%, 95%, 96%, 97%, 98%, 99% or more identical to SEQ ID NO: 13; SEQ ID NO: 14 or a sequence 70%, 75%, 80%, 85%, 90%, 91%, 92%, 93%, 94%, 95%, 96%, 97%, 98%, 99% or more identical to SEQ ID NO: 14; SEQ ID NO: 15 or a sequence 70%, 75%, 80%, 85%, 90%, 91%, 92%, 93%, 94%, 95%, 96%, 97%, 98%, 99% or more identical to SEQ ID NO: 15; SEQ ID NO: 16 or a sequence 70%, 75%, 80%, 85%, 90%, 91%, 92%, 93%, 94%, 95%, 96%, 97%, 98%, 99% or more identical to SEQ ID NO: 16; SEQ ID NO: 17 or a sequence 70%, 75%, 80%, 85%, 90%, 91%, 92%, 93%, 94%, 95%, 96%, 97%, 98%, 99% or more identical to SEQ ID NO: 17; SEQ ID NO: 18 or a sequence 70%, 75%, 80%, 85%, 90%, 91%, 92%, 93%, 94%, 95%, 96%, 97%, 98%, 99% or more identical to SEQ ID NO: 18; SEQ ID NO: 19 or a sequence 70%, 75%, 80%, 85%, 90%, 91%, 92%, 93%, 94%, 95%, 96%, 97%, 98%, 99% or more identical to SEQ ID NO: 19; SEQ ID NO: 20 or a sequence 70%, 75%, 80%, 85%, 90%, 91%, 92%, 93%, 94%, 95%, 96%, 97%, 98%, 99% or more identical to SEQ ID NO: 20; SEQ ID NO: 21 or a sequence 70%, 75%, 80%, 85%, 90%, 91%, 92%, 93%, 94%, 95%, 96%, 97%, 98%, 99% or more identical to SEQ ID NO: 21; SEQ ID NO: 22 or a sequence 70%, 75%, 80%, 85%, 90%, 91%, 92%, 93%, 94%, 95%, 96%, 97%, 98%, 99% or more identical to SEQ ID NO: 22; SEQ ID NO: 23 or a sequence 70%, 75%, 80%, 85%, 90%, 91%, 92%, 93%, 94%, 95%, 96%, 97%, 98%, 99% or more identical to SEQ ID NO: 23; SEQ ID NO: 24 or a sequence 70%, 75%, 80%, 85%, 90%, 91%, 92%, 93%, 94%, 95%, 96%, 97%, 98%, 99% or more identical to SEQ ID NO: 24; SEQ ID NO: 25 or a sequence 70%, 75%, 80%, 85%, 90%, 91%, 92%, 93%, 94%, 95%, 96%, 97%, 98%, 99% or more identical to SEQ ID NO: 25; SEQ ID NO: 26 or a sequence 70%, 75%, 80%, 85%, 90%, 91%, 92%, 93%, 94%, 95%, 96%, 97%, 98%, 99% or more identical to SEQ ID NO: 26; SEQ ID NO: 27 or a sequence 70%, 75%, 80%, 85%, 90%, 91%, 92%, 93%, 94%, 95%, 96%, 97%, 98%, 99% or more identical to SEQ ID NO: 27; SEQ ID NO: 28 or a sequence 70%, 75%, 80%, 85%, 90%, 91%, 92%, 93%, 94%, 95%, 96%, 97%, 98%, 99% or more identical to SEQ ID NO: 28; SEQ ID NO: 29 or a sequence 70%, 75%, 80%, 85%, 90%, 91%, 92%, 93%, 94%, 95%, 96%, 97%, 98%, 99% or more identical to SEQ ID NO: 29; SEQ ID NO: 30 or a sequence 70%, 75%, 80%, 85%, 90%, 91%, 92%, 93%, 94%, 95%, 96%, 97%, 98%, 99% or more identical to SEQ ID NO: 30; SEQ ID NO: 31 or a sequence 70%, 75%, 80%, 85%, 90%, 91%, 92%, 93%, 94%, 95%, 96%, 97%, 98%, 99% or more identical to SEQ ID NO: 31; and where X (5' UTR Sequence) is AGACAGAUCGCCUGGAGACGCCAUCCACGCU-GUUUUGACCUCCAUAGAAGACACC GGGACCGAUCCAGCCUCCGCGGCCGG-GAACGGUGCAUUGGAACGCGGAUUCCCCG UGCCAAGAGUGACUCACCGUCCUUGACACG [SEQ ID NO.: 2] or a sequence 70%, 75%, 80%, 85%, 90%, 91%, 92%, 93%, 94%, 95%, 96%, 97%, 98%, 99% or more identical to SEQ ID NO: 2, or GGACAGAUCGCCUGGAGACGCCAUCCACGCU-GUUUUGACCUCCAUAGAAGACACC GGGACCGAUCCAGCCUCCGCGGCCGG-GAACGGUGCAUUGGAACGCGGAUUCCCCG UGCCAAGAGUGACUCACCGUCCUUGACACG (SEQ ID NO: 3) or a sequence 70%, 75%, 80%, 85%, 90%, 91%, 92%, 93%, 94%, 95%, 96%, 97%, 98%, 99% or more identical to SEQ ID NO: 3; and where Y (3' UTR Sequence) is

CGGGUGGCAUCCCUGUGACCCCUCCCCAGUGC-CUCUCCUGGCCCUGGAAGUUGCC

ACUCCAGUGCCCACCAGCCUUGUCC-UAAUAAAAUUAAGUUGCAUCAAGCU (SEQ ID NO: 4) or a sequence 70%, 75%, 80%, 85%, 90%, 91%, 92%, 93%, 94%, 95%, 96%, 97%, 98%, 99% or more identical to SEQ ID NO: 4, or GGGUGGCAUCCCUGUGACCCCUCCCCAGUGC-CUCUCCUGGCCCUGGAAGUUGCCA CUCCAGUGCCCACCAGCCUUGUCC-UAAUAAAAUUAAGUUGCAUCAAAGCU (SEQ ID NO: 5) or a sequence 70%, 75%, 80%, 85%, 90%, 91%, 92%, 93%, 94%, 95%, 96%, 97%, 98%, 99% or more identical to SEQ ID NO: 5.

In Vitro Transcription

In certain embodiments of the invention, a codon-optimized human dynein axonemal heavy chain 5 messenger RNA (DNAH5 mRNA) is synthesized by in vitro transcription from a plasmid DNA template encoding the gene, which is followed by the addition of a 5' cap structure (Fechter, P.; Brownlee, G. G. "Recognition of mRNA cap structures by viral and cellular proteins" J. Gen. Virology 2005, 86, 1239-1249) and a 3' poly(A) tail of approximately 100, 200, 250, 300, 400, 500 or 800 nucleotides in length as determined by gel electrophoresis.

Delivery Vehicles

According to the present invention, mRNA encoding a DNAH5 protein (e.g., a full length, fragment or portion of a DNAH5 protein) as described herein may be delivered as naked RNA (unpackaged) or via delivery vehicles. As used herein, the terms "delivery vehicle," "transfer vehicle," "nanoparticle" or grammatical equivalent, are used interchangeably.

In some embodiments, mRNAs encoding a DNAH5 protein may be delivered via a single delivery vehicle. In some embodiments, mRNAs encoding a DNAH5 protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

Liposomes

In some embodiments, a suitable delivery vehicle is a liposome. As used herein, liposomes are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, liposome typically serves to transport a desired mRNA to a target cell or tissue. A typical liposome in accordance with the invention comprises one or more cationic lipids, one or more non-cationic lipids, one or more cholesterol-based lipids and one or more PEG-modified lipids.

Cationic Lipids

As used herein, the phrase "cationic lipids" refers to any of a number of lipid species that have a net positive charge at a selected pH, such as physiological pH.

Several cationic lipids have been described in the literature, many of which are commercially available. Suitable cationic lipids for use in the compositions and methods of the invention include the cationic lipids as described in International Patent Publication WO 2010/144740, which is incorporated herein by reference.

In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

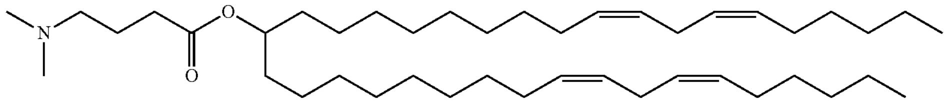 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

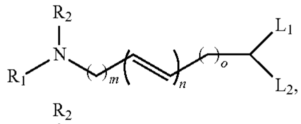

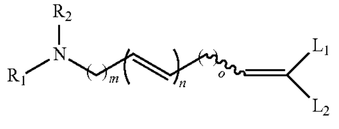

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

(HGT-5000)

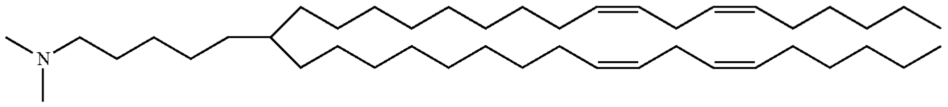

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

(HGT-5001)

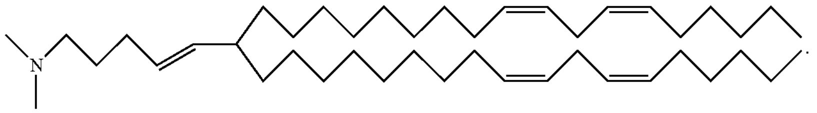

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

(HGT-5002)

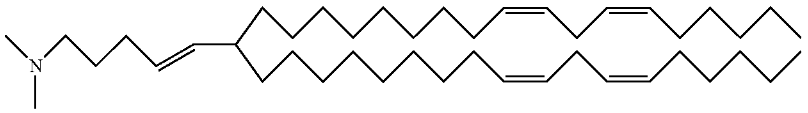

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

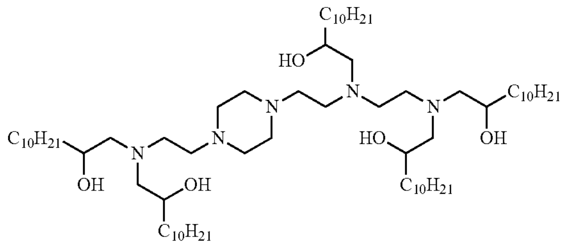

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

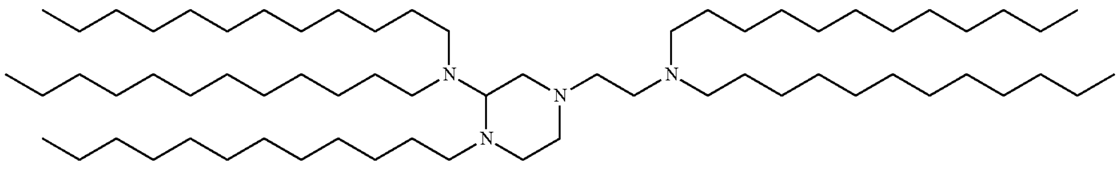 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

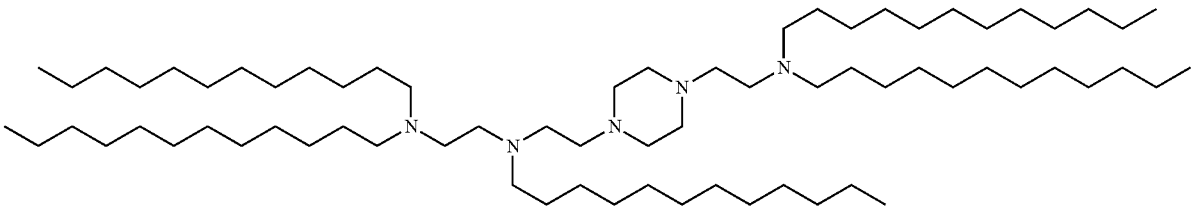 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

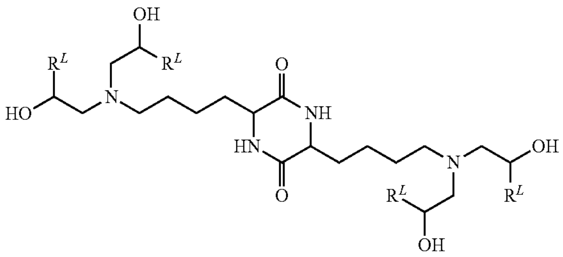

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

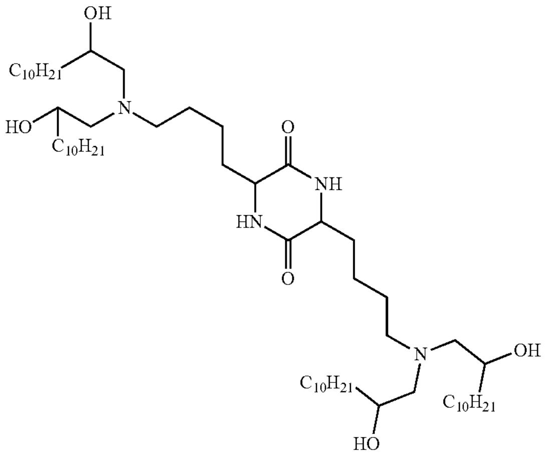

and pharmaceutically acceptable salts thereof. In certain embodiments, the compositions and methods of the present invention include a cationic lipid having a compound structure of:

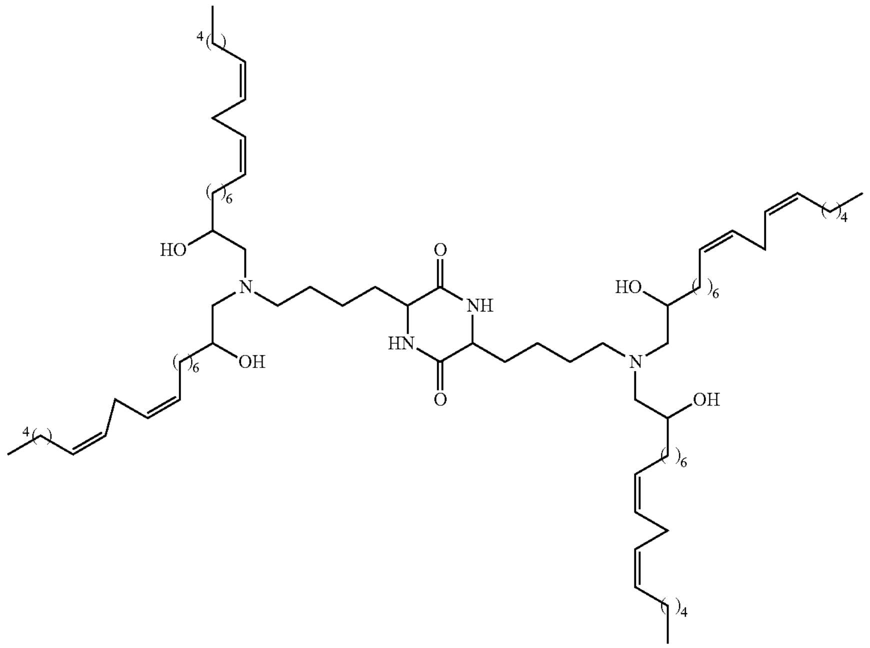

and pharmaceutically acceptable salts thereof. In certain embodiments, the compositions and methods of the present invention include a cationic lipid having a compound structure of:

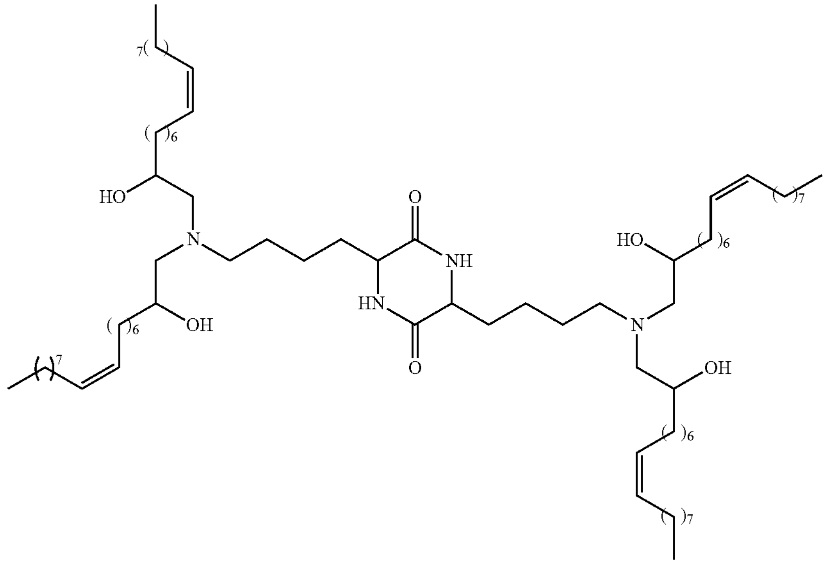

and pharmaceutically acceptable salts thereof. In certain embodiments, the compositions and methods of the present invention include a cationic lipid having a compound structure of:

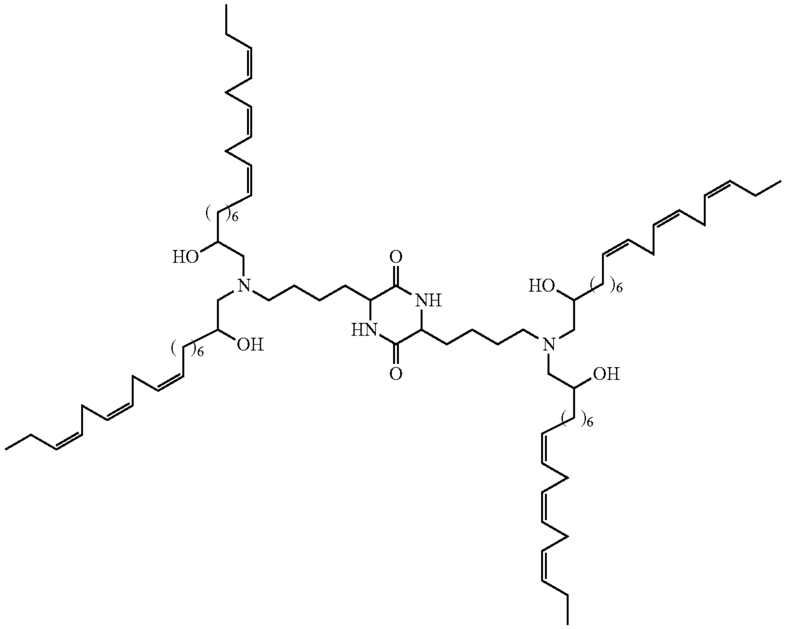

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

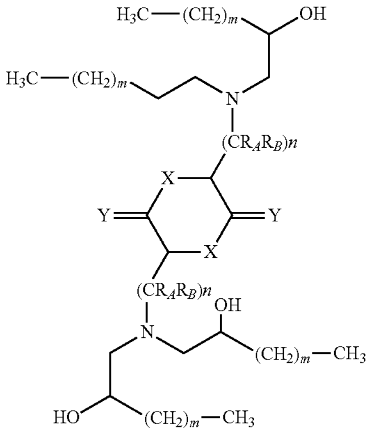

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

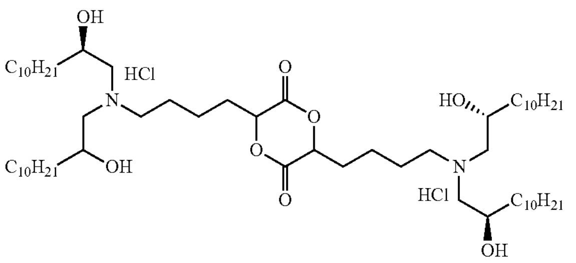

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

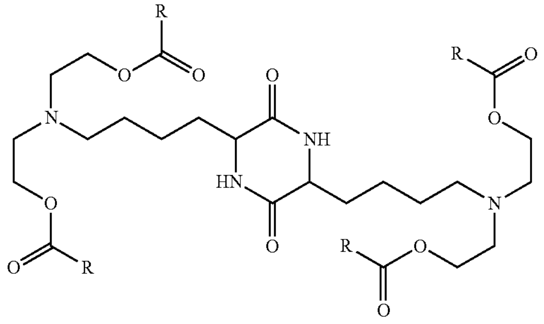

R = 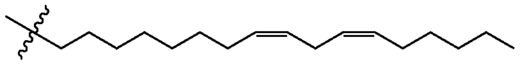

or a pharmaceutically acceptable salt thereof. In some embodiments, the compositions and methods of the present invention include a cationic lipid having the compound structure:

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

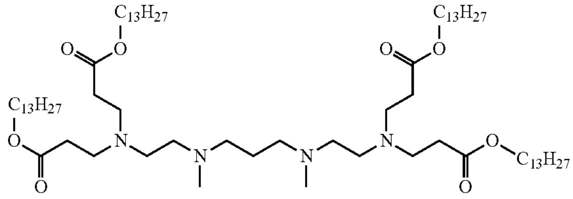

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

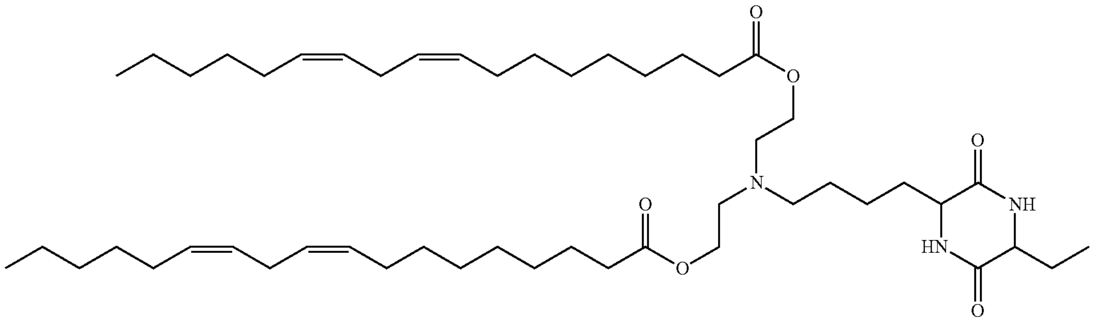 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

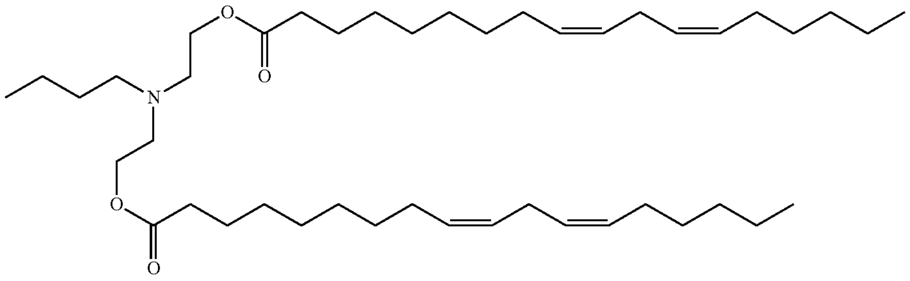 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

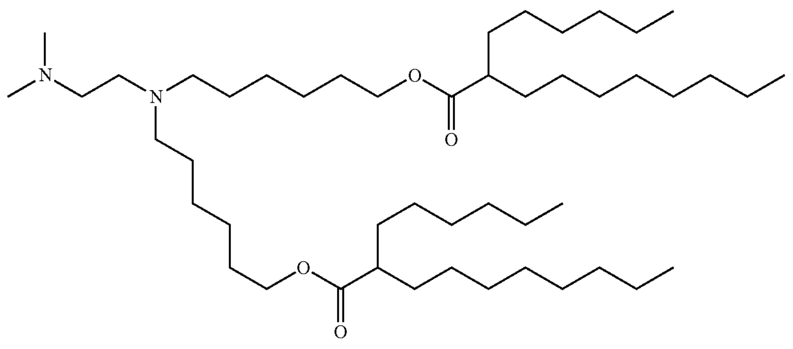 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

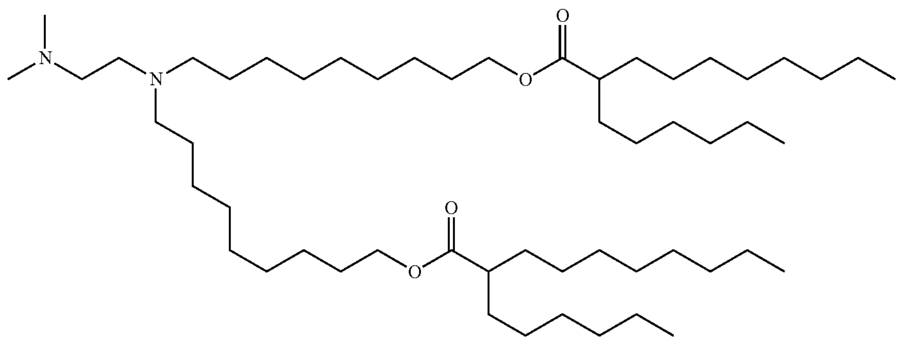 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

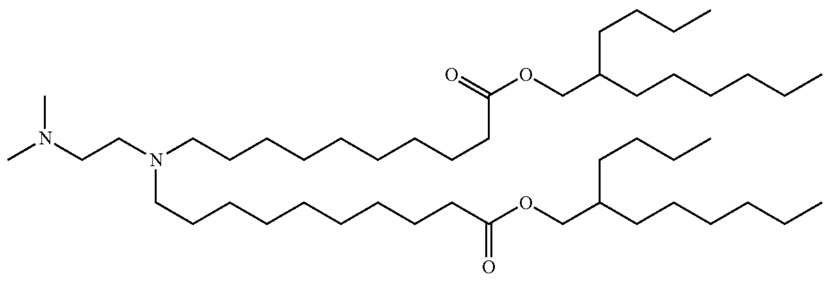 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

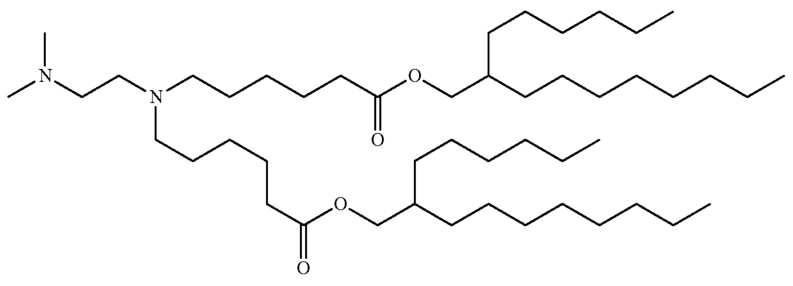 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

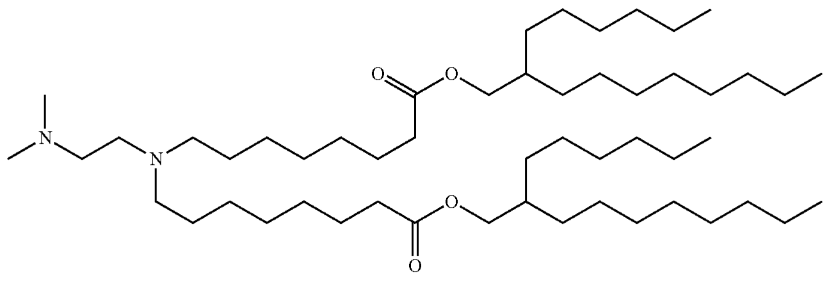 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

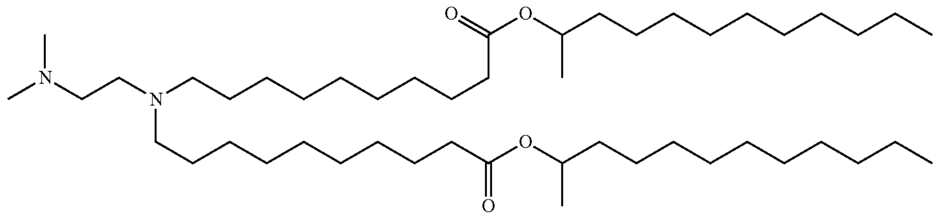 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

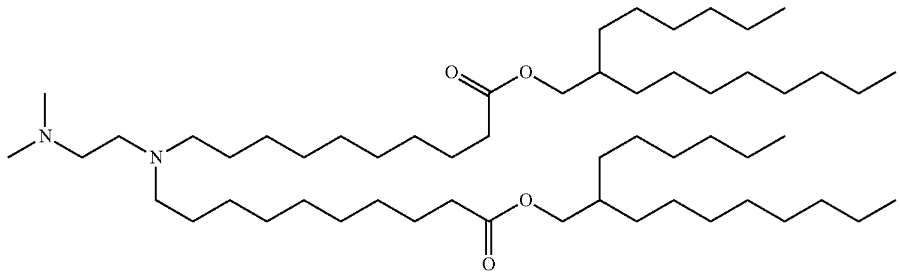 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

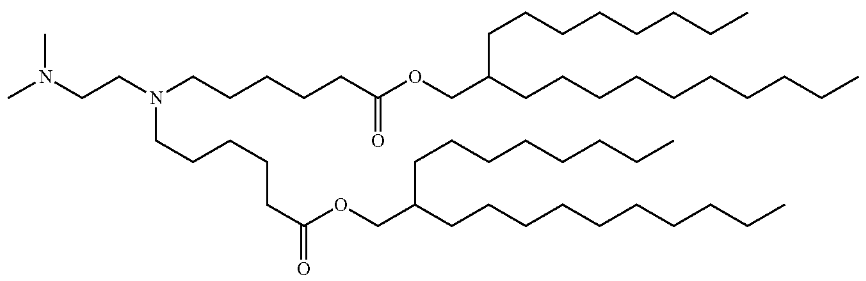 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

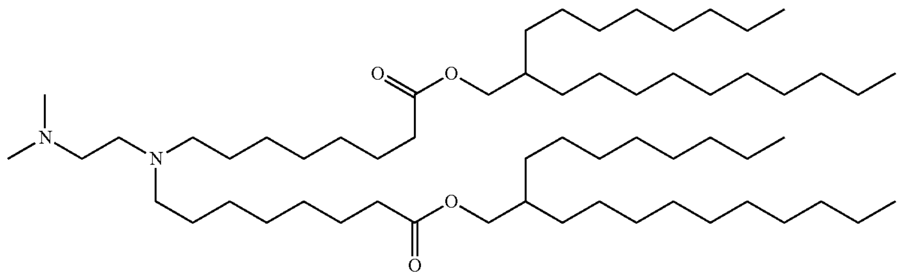 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

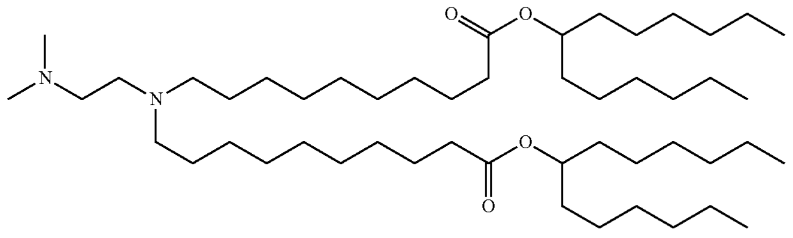 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

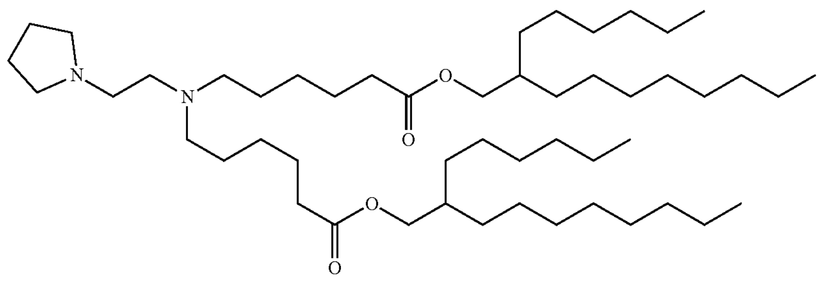 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

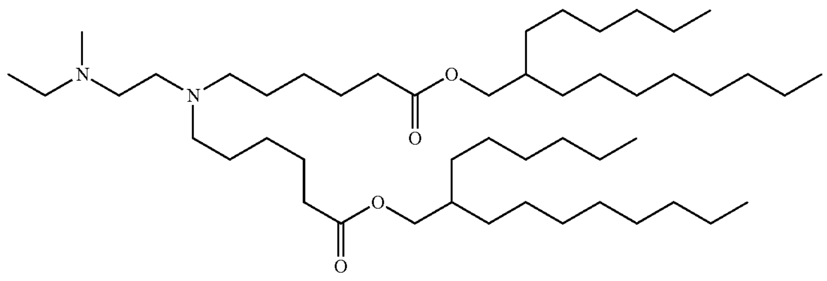 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

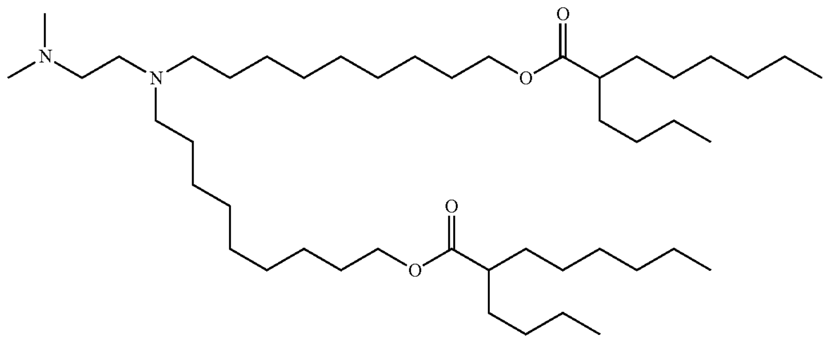 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

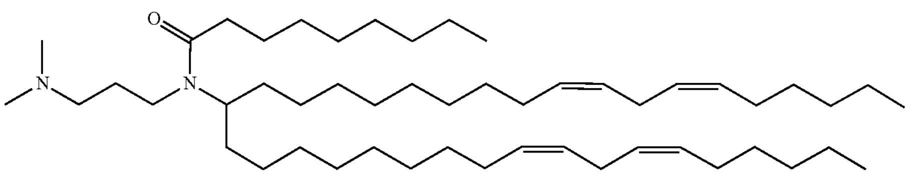 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

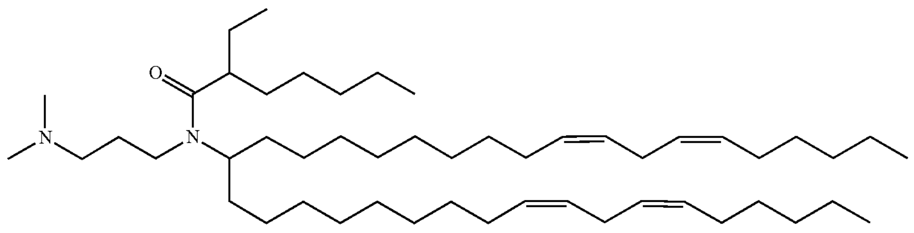 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

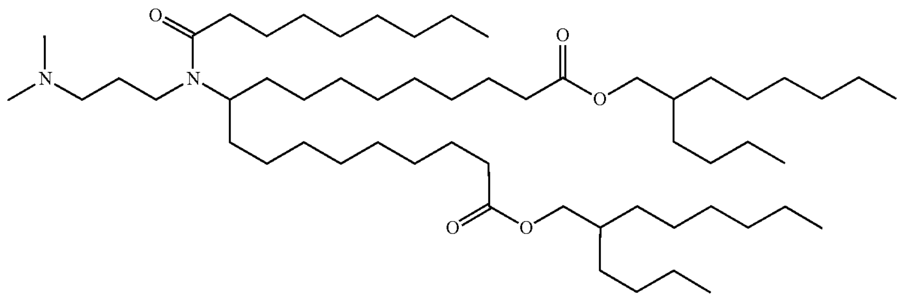 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

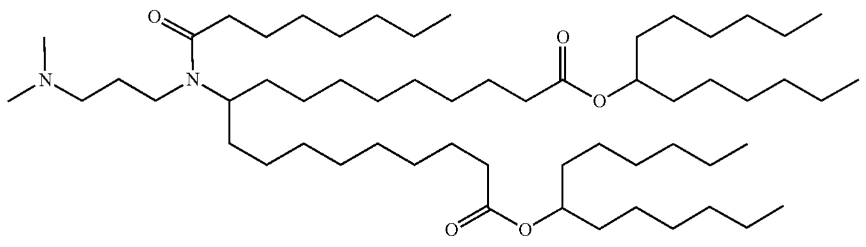 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

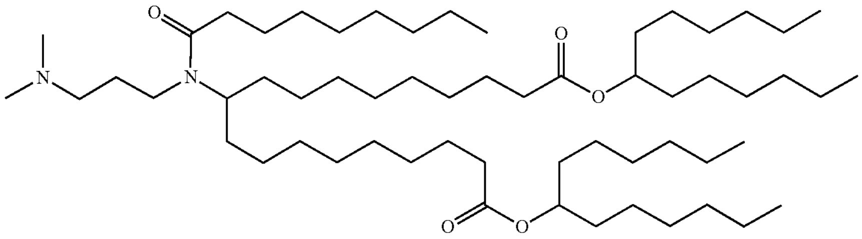 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

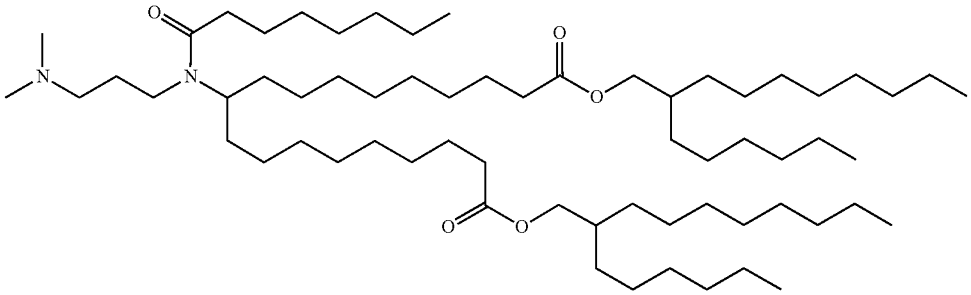 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

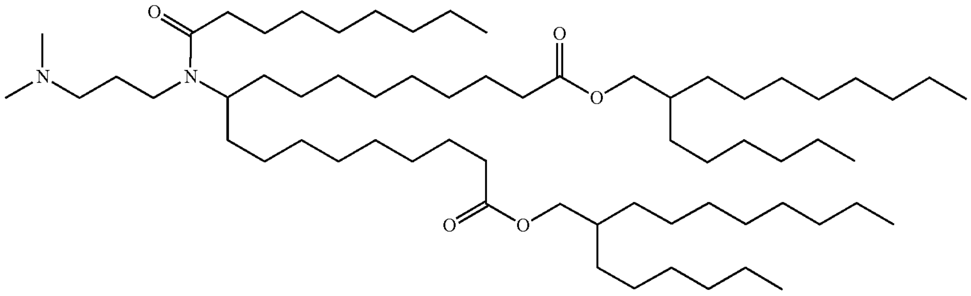 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

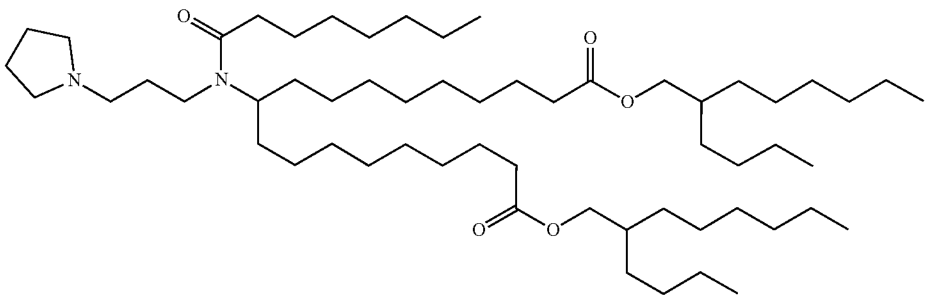 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

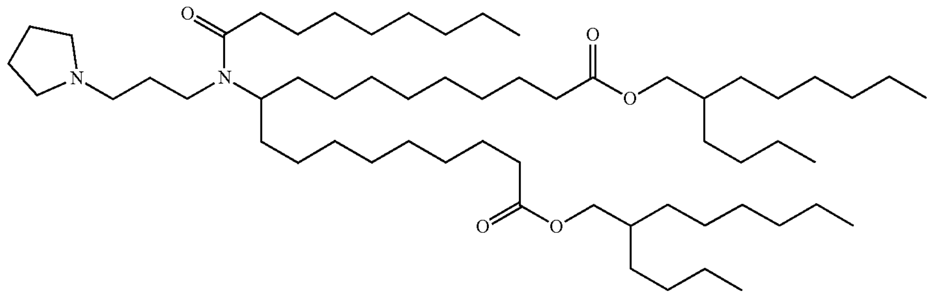 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

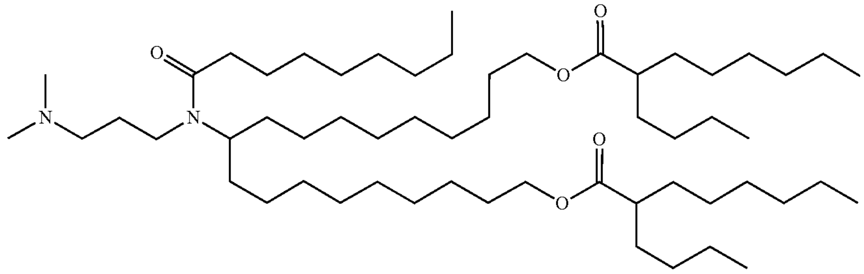 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

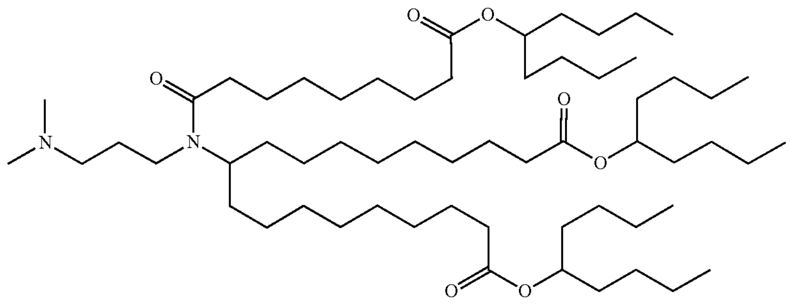 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

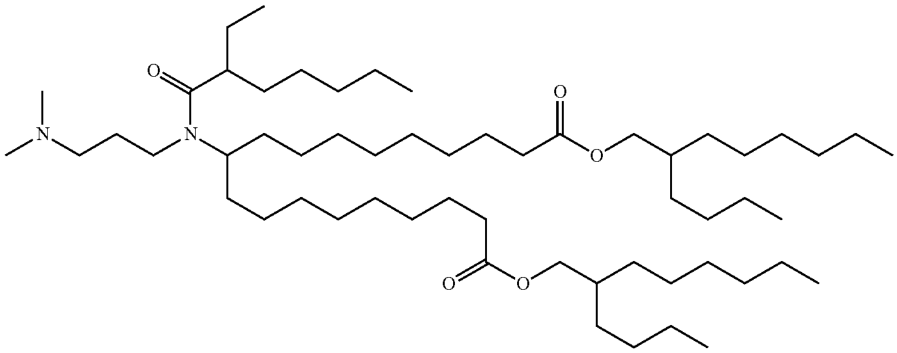 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

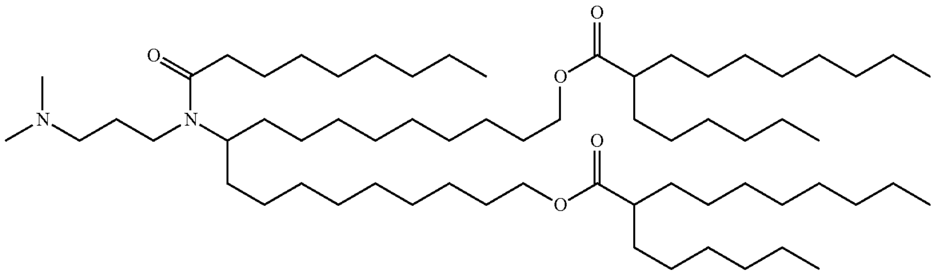 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

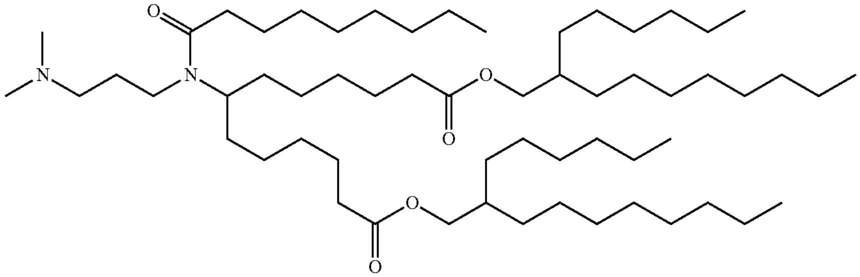 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

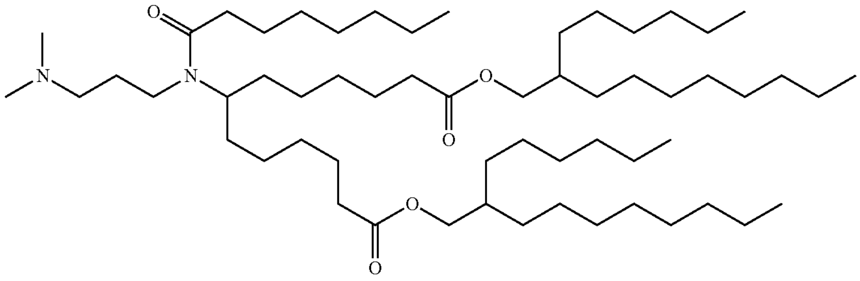 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

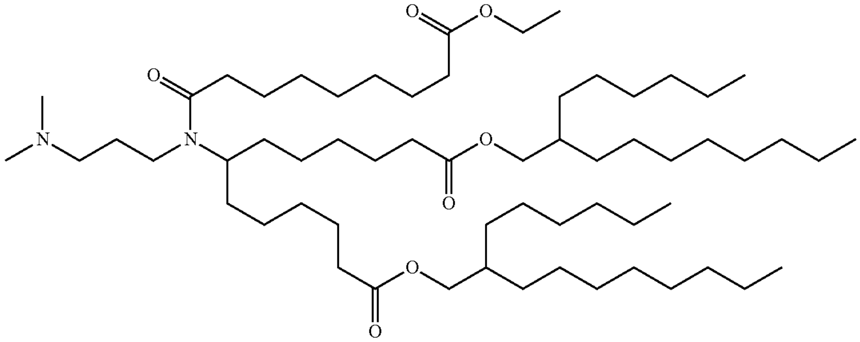 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

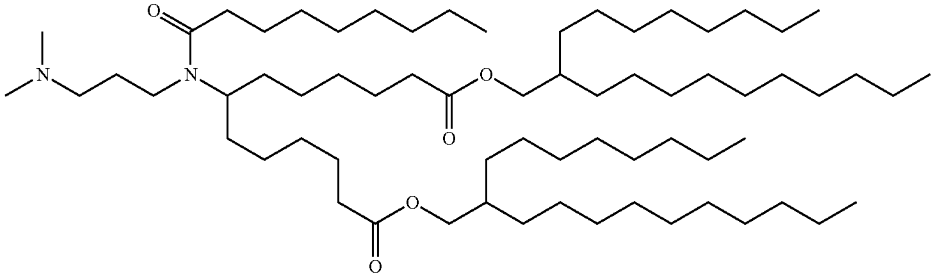 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

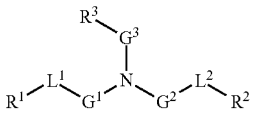

or a pharmaceutically acceptable salt thereof, wherein one of $L^1$ or $L^2$ is —O(C═O)—, —(C═O)O—, —C(═O)—, —O—, —S(O)$_x$, —S—S—, —C(═O)S—, —SC(═O)—, —NR$^a$C(═O)—, —C(═O)NR$^a$—, NR$^a$C(═O)NR$^a$—, —OC(═O)NR$^a$—, or —NR$^a$C(═O)O—; and the other of $L^1$ or $L^2$ is —O(C═O)—, —(C═O)O—, —C(═O)—, —O—, —S(O)$_x$, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)OR$^4$, —OC(═O)R$^4$ or —NR$^5$ C(═O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

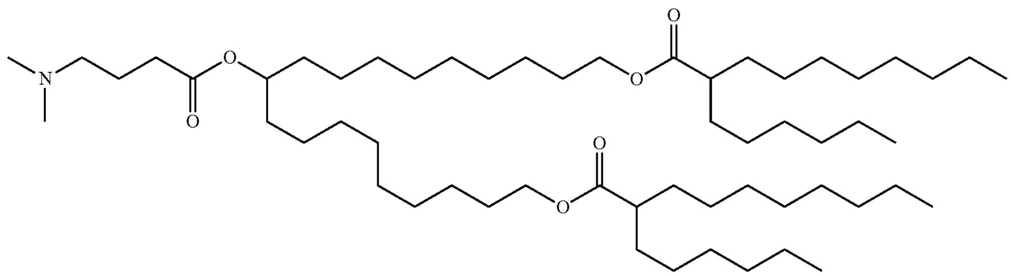 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

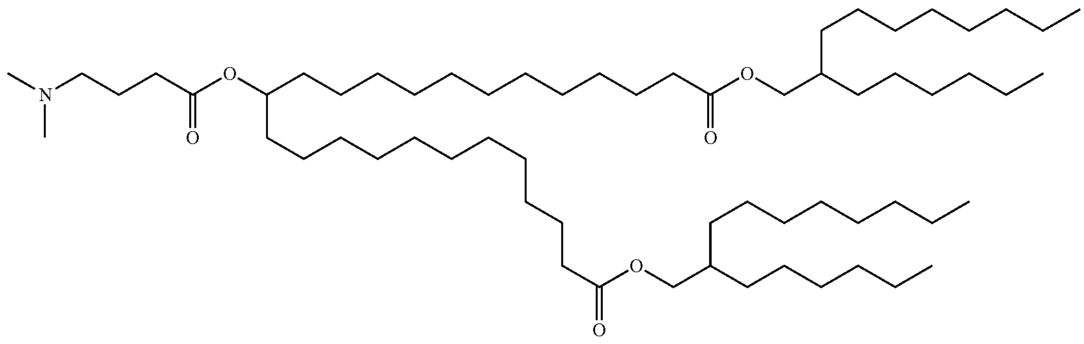 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

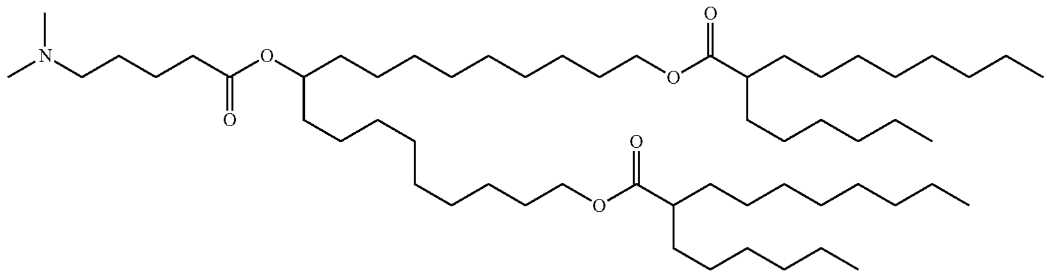 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

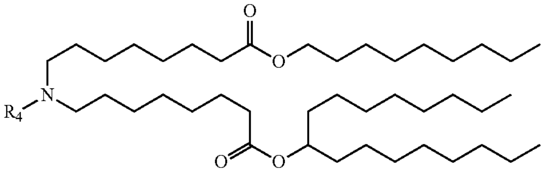

,

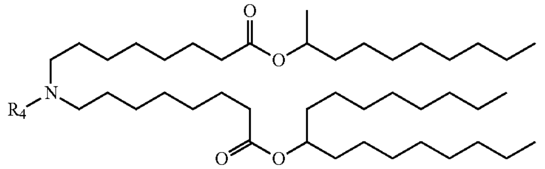

,

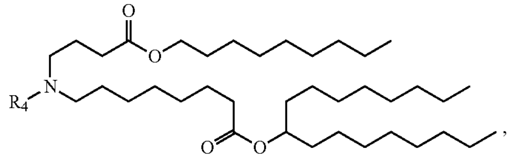

, and

-continued

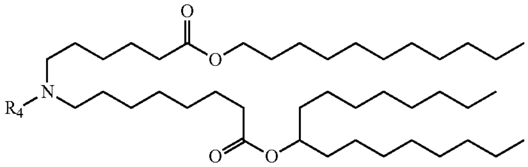

, and pharmaceutically acceptable salts thereof. For any one of these four formulas, $R_4$ is independently selected from $—(CH_2)_nQ$ and $—(CH_2)_nCHQR$; Q is selected from the group consisting of —OR, —OH, $—O(CH_2)_nN(R)_2$, —OC(O)R, $—CX_3$, —CN, —N(R)C(O)R, —N(H)C(O)R, $—N(R)S(O)_2R$, $—N(H)S(O)_2R$, $—N(R)C(O)N(R)_2$, $—N(H)C(O)N(R)_2$, —N(H)C(O)N(H)(R), $—N(R)C(S)N(R)_2$, $—N(H)C(S)N(R)_2$, —N(H)C(S)N(H)(R), and a heterocycle; and n is 1, 2, or 3. In certain embodiments, the compositions and methods of the present invention include a cationic lipid having a compound structure of:

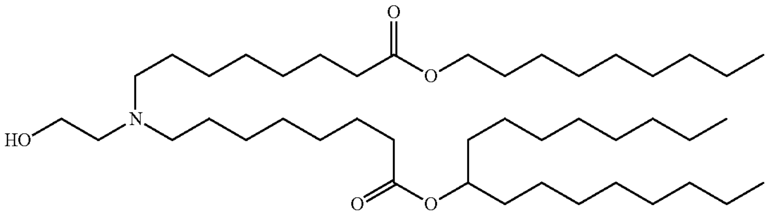 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

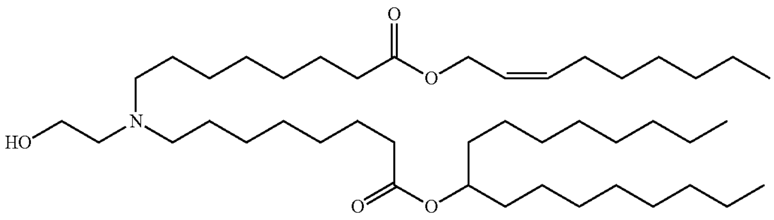 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

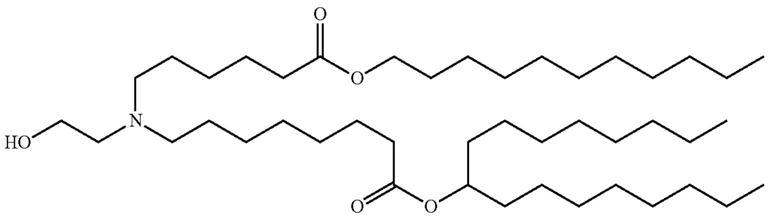 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

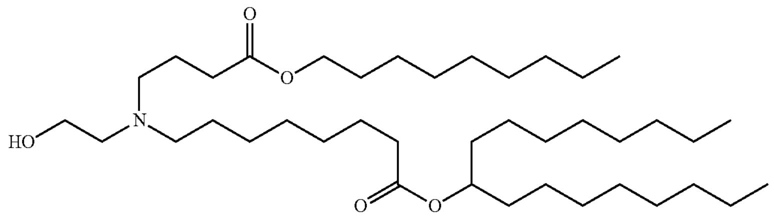 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

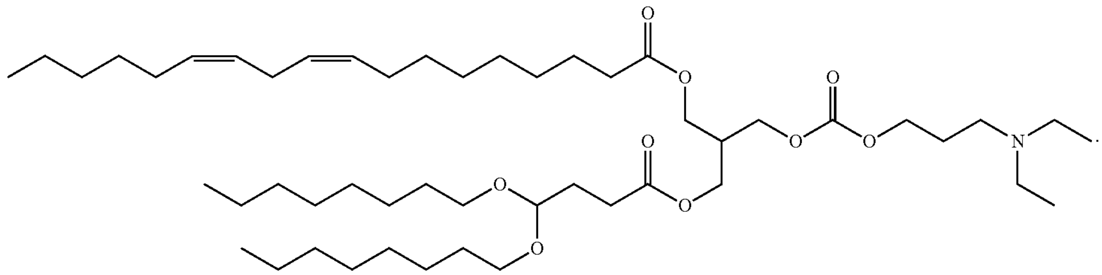 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

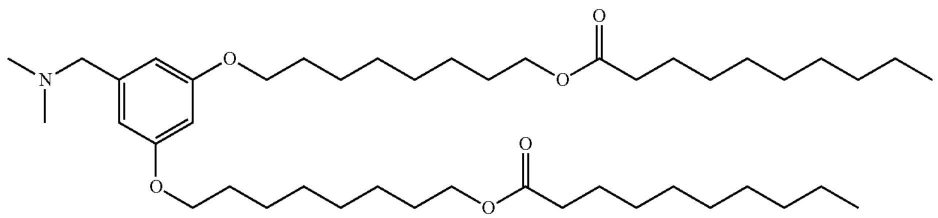 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

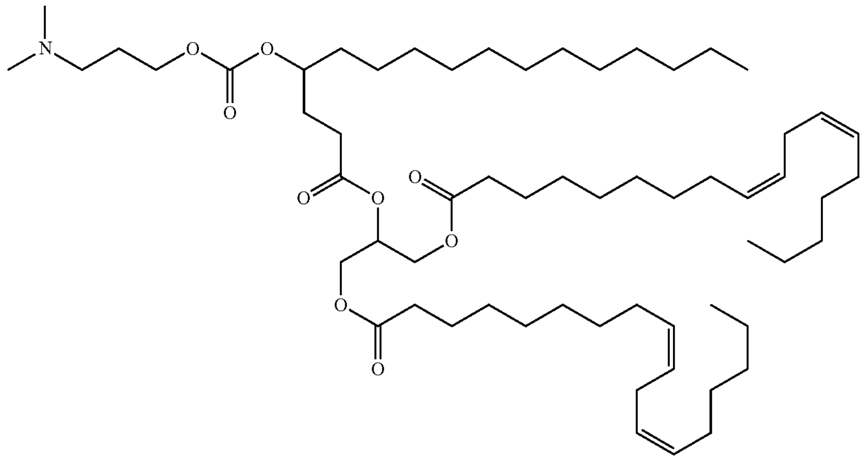 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

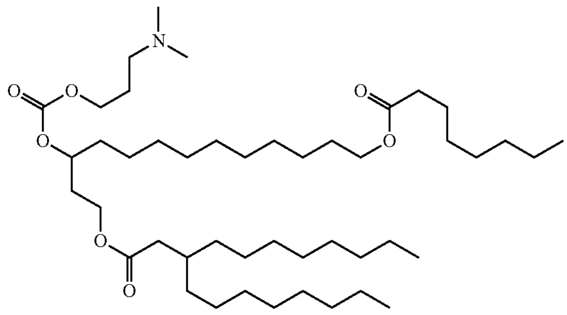 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

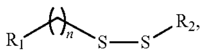

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

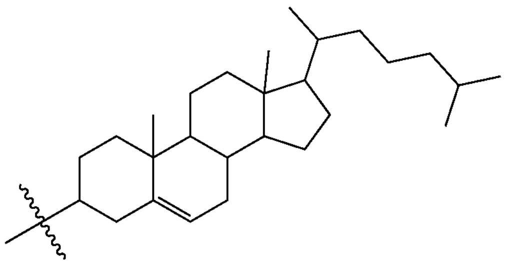

and

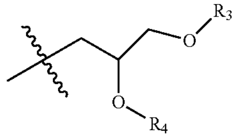

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

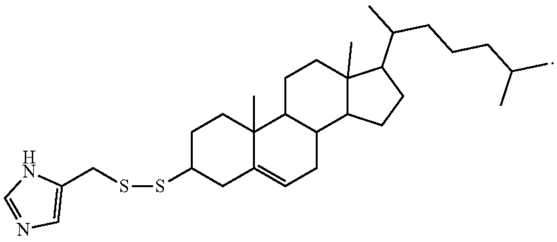

and pharmaceutically acceptable salts thereof. In certain embodiments, the compositions and methods of the present invention include a cationic lipid, "HGT4002", having a compound structure of:

(HGT4002)

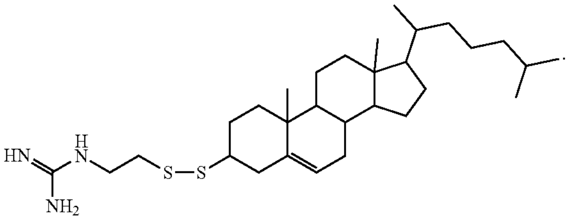

and pharmaceutically acceptable salts thereof. In certain embodiments, the compositions and methods of the present invention include a cationic lipid, “HGT4003”, having a compound structure of:

(HGT4003)

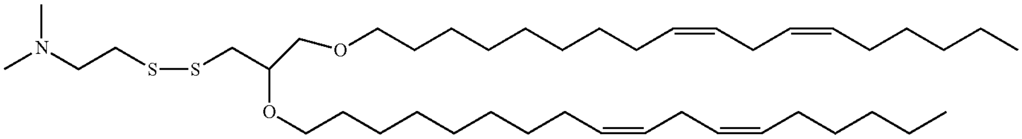

and pharmaceutically acceptable salts thereof. In certain embodiments, the compositions and methods of the present invention include a cationic lipid, “HGT4004”, having a compound structure of:

(HGT4004)

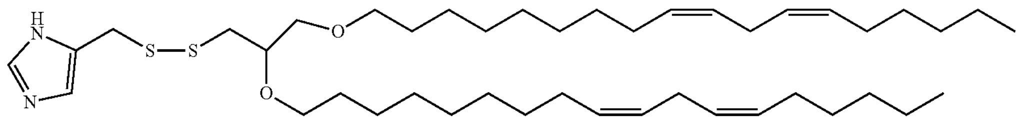

and pharmaceutically acceptable salts thereof. In certain embodiments, the compositions and methods of the present invention include a cationic lipid “HGT4005”, having a compound structure of:

(HGT4005)

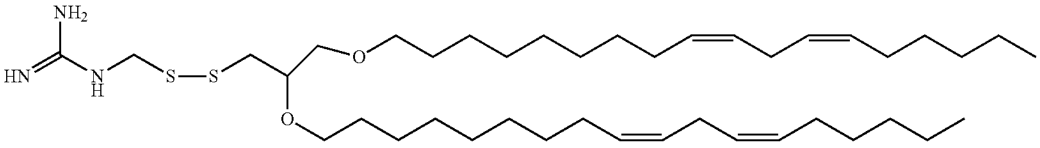

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'), (I')

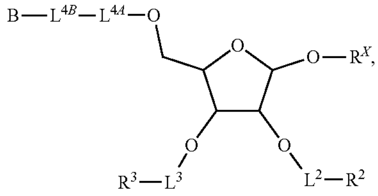

wherein:

$R^X$ is independently —H, $-L^1-R^1$, or $-L^{5A}-L^{5B}-B'$;

each of $L^1$, $L^2$, and $L^3$ is independently a covalent bond, —C(O)—, —C(O)O—, —C(O)S—, or —C(O)$NR^L$—;

each $L^{4A}$ and $L^{5A}$ is independently —C(O)—, —C(O)O—, or —C(O)$NR^L$—; each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is $NR^4R^5$ or a 5- to 10-membered nitrogen-containing heteroaryl;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; and each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of:

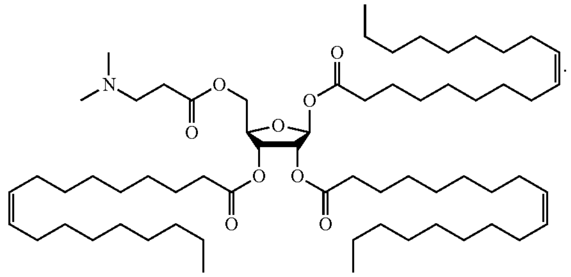

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido)ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy]octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)-N,N-dimethyl-2,2-di((9Z,12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by the following structure:

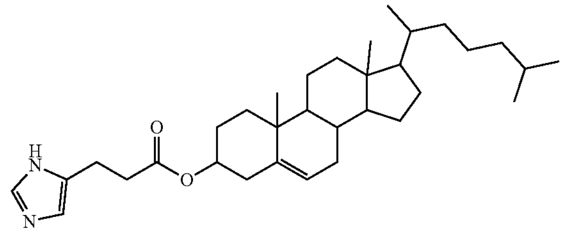

(ICE)

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the liposome may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 2 kDa, up to 3 kDa, up to 4 kDa or 5 kDa in length covalently attached to a lipid with alkyl chain(s) of C6-C20 length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). In some embodiments, a PEG-modified or PEGylated lipid is PEGylated cholesterol or PEG-2K. In some embodiments, particularly useful exchangeable lipids are PEG-ceramides having shorter acyl chains (e.g., C14 or C18).

In some embodiments, particularly useful exchangeable lipids are PEG-ceramides having shorter acyl chains (e.g., C14 or C18). The PEG-modified phospholipid and derivitized lipids of the present invention may comprise a molar ratio from about 0% to about 15%, about 0.5% to about 15%, about 1% to about 15%, about 4% to about 10%, or about 2% of the total lipid present in the liposome. PEG-modified phospholipid and derivatized lipids may constitute at least about 5%, 10%, 20%, 30%, 40%, 50%, 60%, or 70% of the total lipids in a suitable lipid solution by weight or by molar. In some embodiments, PEGylated lipid lipid(s) constitute(s) about 30-50% (e.g., about 30-45%, about 30-40%, about 35-50%, about 35-45%, or about 35-40%) of the total lipids in a suitable lipid solution by weight or by molar.

According to various embodiments, the selection of cationic lipids, non-cationic lipids and/or PEG-modified lipids which comprise the liposome, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly.

Liposome Formulations

A suitable liposome for the present invention may include one or more of any of the cationic lipids, non-cationic lipids, cholesterol lipids, PEGylated lipids and/or polymers described herein at various ratios. Typically, a liposome in accordance with the present invention comprises a cationic lipid, a non-cationic lipid, a cholesterol lipid and a PEGylated lipid. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K or ICE, DOPE and DMG-PEG2K. Additional combinations of lipids are described in the art, e.g., U.S. Ser. No. 62/420,421 (filed on Nov. 10, 2016), U.S. Ser. No. 62/421,021 (filed on Nov. 11, 2016), U.S. Ser. No. 62/464,327 (filed on Feb. 27, 2017), and PCT Application entitled "Novel ICE-based Lipid Nanoparticle Formulation for Delivery of mRNA," filed on Nov. 10, 2017, the disclosures of which are included here in their full scope by reference.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEGylated lipid(s) may be between about 30-60:25-35:20-30:1-15, respectively. In some embodiments, the ratio of cationic lipid(s) to non-cationic lipid(s) to cholesterol-based lipid(s) to PEGylated lipid(s) is approximately 40:30:20:10, respectively. In some embodiments, the ratio of cationic lipid(s) to non-cationic lipid(s) to cholesterol-based lipid(s) to PEGylated lipid(s) is approximately 40:30:25:5, respectively. In some embodiments, the ratio of cationic lipid(s) to non-cationic lipid(s) to cholesterol-based lipid(s) to PEGylated lipid(s) is approximately 40:32:25:3, respectively. In some embodiments, the ratio of cationic lipid(s) to non-cationic lipid(s) to cholesterol-based lipid(s) to PEGylated lipid(s) is approximately 50:25:20:5.

Formation of Liposomes

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase then may be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more liposomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. In a typical embodiment, the mRNA of the invention is encapsulated in a liposome using the methods described in WO 2018/089801 (the teachings of which are incorporated herein by reference in their entirety). Briefly, the mRNA is encapsulated by mixing of a solution comprising pre-formed liposomes with mRNA such that liposomes encapsulating mRNA are formed.

Typically, the liposome-incorporated nucleic acids are completely located in the interior space of the liposome within the bilayer membrane of the liposome, although as discussed above, some of the mRNA (e.g., no more than 10% of total mRNA in the liposome composition) may also be associated with the exterior surface of the liposome membrane. The incorporation of a nucleic acid into liposomes is also referred to herein as "encapsulation". Typically, the purpose of incorporating an mRNA into a liposome is to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). Liposomes with a size of 80-200 nm are particularly suitable for some application. In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Liposome Formulations for DNAH5 mRNA Delivery and Expression

This section provides exemplary liposome formulations for effective delivery and expression of DNAH5 mRNA in vivo.

Lipid Materials

The formulations described herein include a multi-component lipid mixture of varying ratios employing one or more cationic lipids, helper lipids (e.g., non-cationic lipids and/or cholesterol-based lipids) and PEGylated lipids designed to encapsulate mRNA encoding DNAH5 protein. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), cKK-E12 (3,6-bis(4-(bis(2-hydroxydodecyl)amino)butyl)piperazine-2,5-dione), HGT5000, HGT5001, HGT4003, ICE, OF-02, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of C6-C20 length.

Exemplary Formulation Protocols

A. cKK-E12

Aliquots of 50 mg/mL ethanolic solutions of cKK-E12, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution was injected rapidly into the aqueous mRNA solution and shaken to yield a final suspension in 20% ethanol. The resulting liposome suspension was filtered, diafiltrated with 1×PBS (pH 7.4), concentrated and stored at 2-8° C. The final concentration, Zave, Dv(50) and Dv(90) of the DNAH5 encapsulated mRNA were determined.

B. C12-200

Aliquots of 50 mg/mL ethanolic solutions of C12-200, DOPE, cholesterol and DMG-PEG2K are mixed and diluted with ethanol to 3 mL final volume. Separately, an aqueous buffered solution (10 mM citrate/150 mM NaCl, pH 4.5) of DNAH5mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

C. HGT4003

Aliquots of 50 mg/mL ethanolic solutions of HGT4003, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

D. ICE

Aliquots of 50 mg/mL ethanolic solutions of ICE, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

E. HGT5001

Aliquots of 50 mg/mL ethanolic solutions of HGT5001, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

F. HGT5000

Aliquots of 50 mg/mL ethanolic solutions of HGT5000, DOPE, cholesterol and DMG-PEG2K are mixed and diluted with ethanol to 3 mL final volume. Separately, an aqueous buffered solution (10 mM citrate/150 mM NaCl, pH 4.5) of DNAH5T mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

G. DLinKC2DMA

Aliquots of 50 mg/mL ethanolic solutions of DLinKC2DMA, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

H. DODAP

Aliquots of 50 mg/mL ethanolic solutions of DODAP, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

I. DODMA

Aliquots of 50 mg/mL ethanolic solutions of DODMA, DOPE, cholesterol and DMG-PEG2K are mixed and diluted with ethanol to 3 mL final volume. Separately, an aqueous buffered solution (10 mM citrate/150 mM NaCl, pH 4.5) of DNAH5 mRNA is prepared from a 1 mg/mL stock. The lipid solution is injected rapidly into the aqueous mRNA solution and shaken to yield a final suspension in 20% ethanol. The resulting liposome suspension is filtered, diafiltrated with 1×PBS (pH 7.4), concentrated and stored at 2-8° C. The final concentration, Zave, Dv(50) and Dv(90) of the DNAH5 encapsulated mRNA are determined.

Clinical or therapeutic candidate mRNA formulations are selected from the exemplary codon-optimized mRNA sequences having a 5'-cap and a 3'-poly A tail, which is formulated in a suitable lipid combination as described above. Clinically relevant mRNA candidates are characterized by efficient delivery and uptake by in vivo tissue, high level of expression and sustained protein production, without detectable adverse effects in the subject to whom the therapeutic is administered, either caused by the pharmacologically active ingredient or by the lipids in the liposome, or by any excipients used in the formulation. In general, high efficiency with low dose administration is favorable for the selection process of a relevant candidate therapeutic.

Pharmaceutical Compositions

The present invention provides compositions for use in the treatment of primary ciliary dyskinesia (PCD). The compositions of the present invention are for use in the manufacture of a medicament for the treatment of primary ciliary dyskinesia (PCD).

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject, the mammal, (e.g., treating, modulating, curing, preventing and/or ameliorating PCD). For example, a therapeutically effective amount may be an amount sufficient to achieve a desired therapeutic and/or prophylactic effect. Generally, the amount of a therapeutic agent (e.g., mRNA encoding aDNAH5 protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, an effective therapeutic dose of the pharmaceutical composition comprising an mRNA encoding dynein axonemal heavy chain 5 protein is administered to the mammal at a dosing interval sufficient to reduce for the period of the dosing interval or longer the level of at least one symptom or biomarker associated with PCD in the mammal relative to its state prior to the treatment.

In some embodiments the mammal is a human. A suitable therapeutic dose that may be applicable for a human being can be derived based on animal studies. A basic guideline for deriving a human equivalent dose from studies performed in animals can be obtained from the U.S> Food and Drug Administration (FDA) website at https://www.fda.gov/downloads/drugs/guidances/ucm078932.pdf, entitled, "Guidance for Industry Estimating the Maximum Safe Starting Dose in Initial Clinical Trials for Therapeutics in Adult Healthy Volunteers." Based on the guidelines for allometric scaling, a suitable dose of, for example, 0.6 mg/kg in a mouse, would relate to a human equivalent dose of 0.0048 mg/kg. Thus, considering the derived human equivalent dose, a projected human therapeutic dose can be derived based on studies in other animals.

In some embodiments, the dosing interval is once every 15 days or longer, or once every 20 days or longer, or once every 21 days, or once every 22 days, or once every 23 days, or once every 24 days, or once every 25 days, once every 26 days, or once every 27 days, or once every 28 days, or once every 29 days or longer, or once every 30 days or longer, or once every 31 days or longer. In some embodiments, the dosing interval is once every 40, 45 or 50 days or 60 days, or any number of days in between. In some embodiments, the dosing interval is once every 80, 90 or 120 days or 150 days, or any number of days in between.

In some embodiments, the therapeutic low dose is administered at a dosing interval of once every 2 weeks or longer, which is sufficient to reduce the level of at least one symptom or biomarker associated with PCD in the mammal relative to the state prior to the treatment. In some embodiments, the therapeutic low dose is administered at a dosing interval of once every 3 weeks or longer, which is sufficient to reduce the level of at least one symptom or biomarker associated with PCD in the mammal relative to the state prior to the treatment. In some embodiments, the dosing interval is once every 4 weeks or longer. In some embodiments, the dosing interval is once every 5 weeks or longer. In some embodiments, the dosing interval is once every 6 weeks or longer. In some embodiments, the dosing interval is once every 8 weeks or longer. In some embodiments, the dosing interval is once every 12 or 15 or 18 weeks or longer.

In some embodiments, the dosing interval is once a month. In some embodiments, the dosing interval is once in every two months. In some embodiments, the dosing interval is once every three months, or once every four months or once every five months or once every six months or anywhere in between.

In some embodiments, administering the provided composition results in an increased dynein axonemal heavy chain 5 mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased DNAH5 mRNA expression level by at least about 10%, 20%, 30%, 40%, 50%, 60%, 70%, 80%, 90%, or 95% as compared to the baseline level immediately before treatment. In some embodiments, administering the provided composition results in an increased DNAH5 mRNA expression level as compared to a DNAH5 mRNA expression level in subjects who are not treated According to the present invention, a therapeutically effective dose of the provided composition, when administered regularly, results in an increased DNAH5 protein expression or activity level in a subject as compared to a baseline DNAH5 protein expression or activity level before treatment. Typically, the DNAH5 protein expression or activity level is measured in a biological sample obtained from the subject such as blood, plasma or serum, urine, or solid tissue extracts. In some embodiments, the administering of a composition of the invention results in DNAH5 expression detectable in the liver. In some embodiments, administering the provided composition results in an increased DNAH5 protein expression or activity level in a biological sample (e.g., plasma/serum or urine) by at least about 10%, 20%, 30%, 40%, 50%, 60%, 70%, 80%, 90%, or 95% as compared to a baseline level before treatment. In some embodiments, administering the provided composition results in an increased DNAH5 protein expression or activity level in a biological sample (e.g., plasma/serum or urine) by at least about 10%, 20%, 30%, 40%, 50%, 60%, 70%, 80%, 90%, or 95% as compared to a baseline level before treatment for at least 24 hours, at least 48 hours, at least 72 hours, at least 3 days, at least 4 days, at least 5 days, at least 6 days, at least 7 days, at least 8 days, at least 9 days, at least 10 days, at least 11 days, at least 12 days, at least 13 days, at least 14 days, or at least 15 days.

In some embodiments, the therapeutic dose is sufficient to achieve at least some stabilization, improvement or elimination of symptoms and other indicators, such as biomarkers, are selected as appropriate measures of disease progress, disease regression or improvement by those of skill in the art.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

In some embodiments, the therapeutically effective dose comprising the mRNA encoding dynein axonemal heavy chain protein is administered to the subject by intramuscular administration.

In some embodiments, the therapeutically effective dose comprising the mRNA encoding dynein axonemal heavy chain protein is administered to the subject by subcutaneous administration.

In particular embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Most commonly, the therapeutically effective dose comprising the mRNA encoding dynein axonemal heavy chain protein is administered to the subject by intravenous administration.

Alternatively or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In particular embodiments, DNAH5 encoding mRNA is administered intravenously, wherein intravenous administration is associated with delivery of the mRNA to hepatocytes.

In some embodiments, the therapeutically effective dose comprising the mRNA encoding dynein axonemal heavy chain protein is administered for suitable delivery to the mammal's liver. In some embodiments, the therapeutically effective dose comprising the mRNA encoding dynein axonemal heavy chain protein is administered for suitable expression in hepatocytes of the administered mammal.

Provided methods of the present invention contemplate single as well as multiple administrations of a therapeutically effective amount of the therapeutic agents (e.g., mRNA encoding a DNAH5 protein) described herein. Therapeutic agents can be administered at regular intervals, depending on the nature, severity and extent of the subject's condition (e.g., PCD). In some embodiments, a therapeutically effective amount of the therapeutic agents (e.g., mRNA encoding a DNAH5 protein) of the present invention may be administered intrathecally periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily or every other day. In some embodiments, the compositions of the present invention are administered to a subject twice a week, once a week, once every 7 days, once every 10 days, once every 14 days, once every 28 days, once every 30 days, once every two weeks, once every three weeks, once every four weeks, once a month, twice a month, once every six weeks, once every eight weeks, once every other month, once every three months, once every four months, once every six months, once every eight months, once every nine months or annually.

In a preferred embodiment, the compositions of the present invention are administered to a subject once a week, once every two weeks or once a month. In a more preferred embodiment, the compositions of the present invention are administered to a subject once every two weeks or once every month. In the most preferred embodiment, the compositions of the present invention are administered to a subject once every month.

In some embodiments the mRNA is administered concurrently with an additional therapy.

Also contemplated are compositions and liposomes which are formulated for depot administration (e.g., intramuscularly, subcutaneously, intravitreally) to either deliver or release an mRNA over extended periods of time. Preferably, the extended-release means employed are combined with modifications made to the mRNA to enhance stability.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts. According to the present invention, a therapeutically effective dose of the provided composition, when administered regularly, results in at least one symptom or feature of PCD is reduced in intensity, severity, or frequency or has delayed onset.

Also contemplated herein are lyophilized pharmaceutical compositions comprising one or more of the liposomes disclosed herein and related methods for the use of such compositions as disclosed for example, in International Patent Application PCT/US12/41663, filed Jun. 8, 2012, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

In some embodiments, the pharmaceutical composition comprises a lyophilized liposomal delivery vehicle that comprises a cationic lipid, a non-cationic lipid, a PEG-modified lipid and cholesterol. In some embodiments, the pharmaceutical composition has a Dv50 of less than 500 nm, 300 nm, 200 nm, 150 nm, 125 nm, 120 nm, 100 nm, 75 nm, 50 nm, 25 nm or smaller upon reconstitution. In some embodiments, the pharmaceutical composition has a Dv90 of less than 750 nm, 700 nm, 500 nm, 300 nm, 200 nm, 150 nm, 125 nm, 100 nm, 75 nm, 50 nm, 25 nm or smaller upon reconstitution. In some embodiments, the pharmaceutical composition has a polydispersity index value of less than 1, 0.95, 0.9, 0.8, 0.75, 0.7, 0.6, 0.5, 0.4, 0.3, 0.25, 0.2, 0.1, 0.05 or less upon reconstitution. In some embodiments, the pharmaceutical composition has an average particle size of less than 500 nm, 400 nm, 300 nm, 200 nm, 175 nm, 150 nm, 125 nm, 100 nm, 75 nm, 50 nm, 25 nm or upon reconstitution.

In some embodiments, the lyophilized pharmaceutical composition further comprises one or more lyoprotectants, such as sucrose, trehalose, dextran or inulin. Typically, the lyoprotectant is sucrose. In some embodiments, the pharmaceutical composition is stable for at least 1 month or at least 6 months upon storage at 4° C., or for at least 6 months upon storage at 25° C. In some embodiments, the biologic activity of the mRNA of the reconstituted lyophilized pharmaceutical composition exceeds 75% of the biological activity observed prior to lyophilization of the composition.

Provided liposomes and compositions may be administered to any desired tissue. In some embodiments, the DNAH5 mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, 96 hours, 1 week, 2 weeks, or 1 month after administration of provided liposomes and/or compositions.

In some embodiments, a therapeutically effective dose of the provided composition, when administered regularly, results in a reduced methylmalonic acid level in a subject as compared to a baseline methylmalonic acid level before treatment.

In some embodiments, administering the provided composition results in an increased level of DNAH5 protein in a liver cell (e.g., a hepatocyte) of a subject as compared to a baseline level before treatment. Typically, the baseline level is measured immediately before treatment. In some embodiments, administering the provided composition results in an increased DNAH5 protein level in the liver cell by at least about 10%, 20%, 30%, 40%, 50%, 60%, 70%, 80%, 90%, or 95% as compared to a baseline level before treatment. In some embodiments, administering the provided composition results in an increased DNAH5 protein level in a liver cell as compared to the DNAH5 protein level a liver cell of subjects who are not treated.

In some embodiments, administering the provided composition results in an increased DNAH5 protein level in plasma or serum of subject as compared to a baseline level before treatment. Typically, the baseline level is measured immediately before treatment. In some embodiments, administering the provided composition results in an increased DNAH5 protein level in plasma or serum by at least about 10%, 20%, 30%, 40%, 50%, 60%, 70%, 80%, 90%, or 95% as compared to a baseline level before treatment. In some embodiments, administering the provided composition results in an increased DNAH5 protein level in plasma or serum as compared to a DNAH5 protein level in plasma or serum of subjects who are not treated.

In some embodiments, administering the provided composition results in increased DNAH5 enzyme activity in a biological sample from a subject as compared to the baseline level before treatment. Typically, the baseline level is measured immediately before treatment. Biological samples include, for example, whole blood, serum, plasma, urine and tissue samples (e.g., liver). In some embodiments, administering the provided composition results in an increased DNAH5 enzyme activity by at least about 10%, 20%, 30%, 40%, 50%, 60%, 70%, 80%, 90%, or 95% as compared to a baseline level immediately before treatment. In some embodiments, administering the provided composition results in an increased DNAH5 enzyme activity as compared to DNAH5 enzyme activity in subjects who are not treated.

In some embodiments the subject is a mammal. In some embodiments, the mammal is an adult. In some embodiments the mammal is an adolescent. In some embodiments the mammal is an infant or a young mammal. In some embodiments, the mammal is a primate. In some embodiments the mammal is a human. In some embodiments the subject is 6 years to 80 years old.

EXAMPLES

While certain compounds, compositions and methods of the present invention have been described with specificity in accordance with certain embodiments, the following examples serve only to illustrate the compounds of the invention and are not intended to limit the same.

Example 1. Exemplary Liposome Formulations for DNAH5 mRNA Delivery and Expression This example provides exemplary liposome formulations for effective delivery and expression of hDNAH5 mRNA in vivo.

Lipid Materials

The formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate human dynein axonemal heavy chain 5 (hDNAH5) mRNA. Unless otherwise specified, the multi-component lipid mixture used in the following Examples were ethanolic solutions of an imidazole cholesterol ester ("ICE") cationic lipid, a non-cationic lipid such as DOPE, and a PEGylated lipid such as DMG-PEG2K.

Messenger RNA Material

Codon-optimized hDNAH5 messenger RNA was synthesized by in vitro transcription from a plasmid DNA template encoding the gene. Following in vitro transcription, a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail were added. The poly(A) tail was approximately 135 nucleotides in length on average. The 5' and 3' untranslated regions present in each mRNA product are represented as X and Y, respectively, and defined as stated (vide infra).

```
Codon-Optimized hDNAH5 mRNA:
X-Coding region-Y
5′ and 3′ UTR Sequences
X (5′ UTR Sequence) =
                                            [SEQ ID NO.: 2]
AGACAGAUCGCCUGGAGACGCCAUCCACGCUGUUUUGACCUCCAUAGAA
GACACCGGGACCGAUCCAGCCUCCGCGGCCGGGAACGGUGCAUUGGAAC
GCGGAUUCCCCGUGCCAAGAGUGACUCACCGUCCUUGACACG
OR

                                            [SEQ ID NO.: 3]
GGACAGAUCGCCUGGAGACGCCAUCCACGCUGUUUUGACCUCCAUAGAA
GACACCGGGACCGAUCCAGCCUCCGCGGCCGGGAACGGUGCAUUGGAAC
GCGGAUUCCCCGUGCCAAGAGUGACUCACCGUCCUUGACACG

Y (3′ UTR Sequence) =
                                            [SEQ ID NO.: 4]
CGGGUGGCAUCCCUGUGACCCCUCCCCAGUGCCUCUCCUGGCCCUGGAA
GUUGCCACUCCAGUGCCCACCAGCCUUGUCCUAAUAAAAUUAAGUUGCA
UCAAGCU
OR

                                            [SEQ ID NO.: 5]
GGGUGGCAUCCCUGUGACCCCUCCCCAGUGCCUCUCCUGGCCCUGGAAG
UUGCCACUCCAGUGCCCACCAGCCUUGUCCUAAUAAAAUUAAGUUGCAU
CAAAGCU
```

Coding Regions

The MRT-1 codon-optimized hDNAH5 messenger RNA coding region comprised the sequence of SEQ ID NO. 6 or SEQ ID NO. 7. A 3'-GFP-tagged version of MRT-1 codon-optimized hDNA5 was likewise prepared, MRT-hDNA5-GFP using molecular cloning techniques well known in the art.

Formulation Protocol hDNAH5 mRNA was encapsulated in multi-component liposomes as described in WO 2018/089790, published May 17, 2018 (incorporated herein by reference), at an N/P ratio of approximately 10.

Example 2. In Vivo Administration and Delivery of hDNAH5 mRNA to the Lung and Expression of hDNAH5 Protein This example illustrates exemplary methods of administering hDNAH5 mRNA-loaded liposome nanoparticles and methods for analyzing delivered mRNA and subsequently expressed hDNAH5 protein in lung epithelium in vivo.

The studies in this Example were performed using male 129S1/SvimJ mice, which were of approximately 10-12 weeks of age. Three groups of mice (each n=5) were exposed by a single intratracheal aerosol administration via Microsprayer® (50 μL/animal) a test article (Groups 1 and 2) or a control. The test article for Group 1 was 10 μg/animal of MRT-1 hDNAH5 mRNA prepared as described in Example 1. The test article for Group 2 was 10 μg/animal (unless otherwise specified) of hDNAH5-GFP mRNA (i.e., a sequence including both MRT1 hDNAH5 mRNA and green fluorescent protein (GFP) mRNA) prepared as described in Example 1. The control included either saline administered at the same volume or an irrelevant mRNA in the same delivery vehicle as the test articles. Mice were euthanized at 24 hours (±5%) post dose administration.

Isolation of Plasma for Analysis

All animals were euthanized by isoflurane overdose via nose cone followed by thoracotomy and terminal blood collection. Whole blood (maximal obtainable volume) was collected via cardiac puncture on euthanized animals and discarded. The animals were then and perfused with saline.

Isolation of Organ Tissues for Analysis

Following perfusion, the liver and the entire airway (trachea to lungs) of each mouse was harvested. The entire airway for the top of the trachea to, and including, the lungs was dissected in one piece and then sagitally cut to provide left and right sections of the entire airway. FIG. 1A depicts the dissection scheme of the lung. The left section of the entire airway was fixed in buffer for subsequent immunohistochemical and histological analysis. The right section of the entire airway was snap-frozen and stored at −70° C. for subsequent qPCR analysis of the trachea (1), superior lobe (2), middle lobe (3), inferior lobe (4), and post-caval lobe (5). The liver also was snap-frozen and stored at −70° C.

qPCR Assay

Figure 1B:
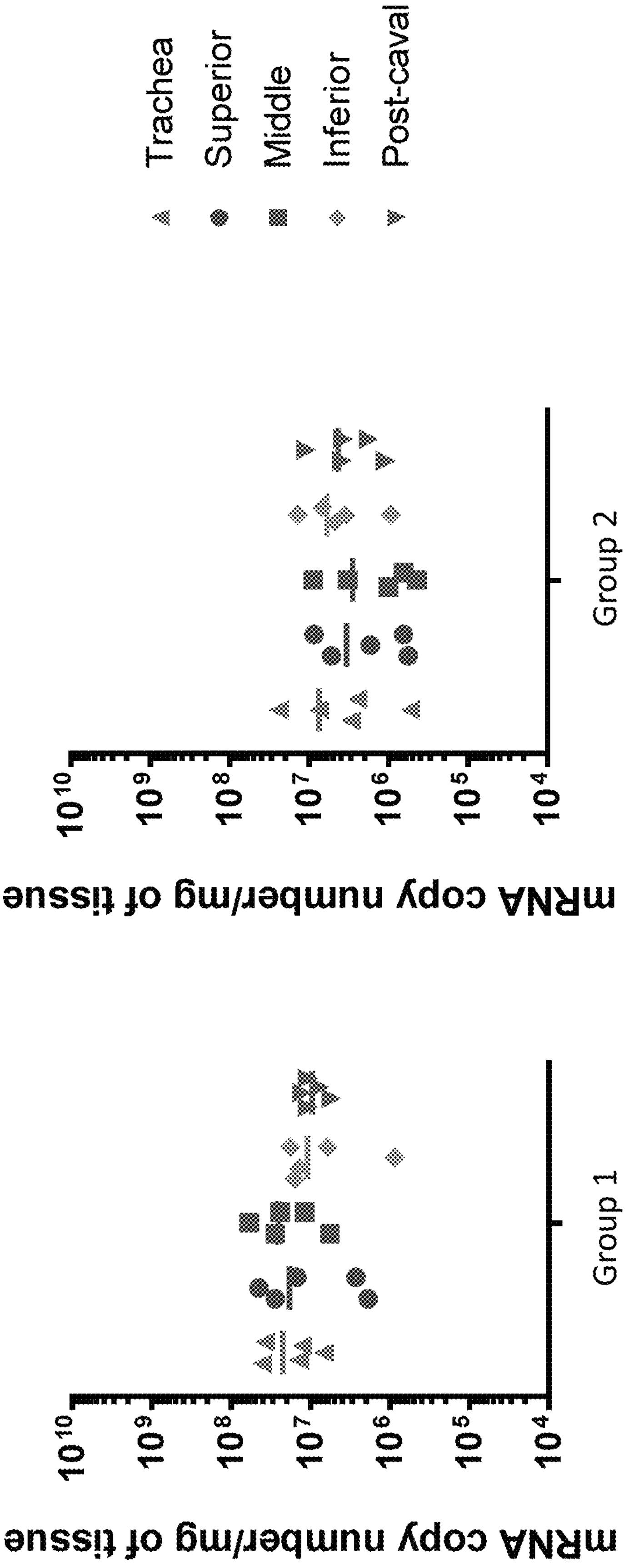
FIG. 1B (left) and (right), are graphs that show qPCR data for hDNA5 mRNA in the different regions of the respiratory system as indicated in the figure.

Mouse trachea and each lung lobes were homogenized in presence of trizol for complete lysis, followed by RNA extraction using silica-membrane based spin columns. The codon optimized hDNAH5 mRNA levels are determined using RT-qPCR. First, the purified RNA is reverse transcribed (RT) into cDNA using random primers. Then, a PCR reaction is performed using sequence specific primers and quantified in real-time using a tagman fluorophore probe (qPCR). Purified, in vitro transcribed hDNAH5 which is run as a reference in the qPCR assay is used to generate a standard curve and calculate hDNAH5 copy numbers per milligram of the analyzed tissue. Results of the qPCR analysis are shown in FIG. 1B.

Immunohistochemical (IHC) Analysis—DNAH5 or GFP

The hDNAH5 and GFP protein in the trachea and lungs was characterized by IHC staining. Briefly, the harvested tissues were fixed in formalin and embedded in paraffin blocks. Sections (5 micron thick) along the length of the tissues were mounted on glass slides for staining. Antigen retrieval was performed using EDTA based buffer, followed by blocking with hydrogen peroxide and goat serum. Primary antibodies against hDNAH5 (Ab122390) and GFP (Ab290) were incubated with respective samples overnight at 4° C. Enzyme-conjugated secondary antibodies were used for detection of the bound primary antibodies. The images of the stained slides were captured at 20× magnification. Results of the IHC analysis are shown in FIG. 2.

Results

Figure 2A:
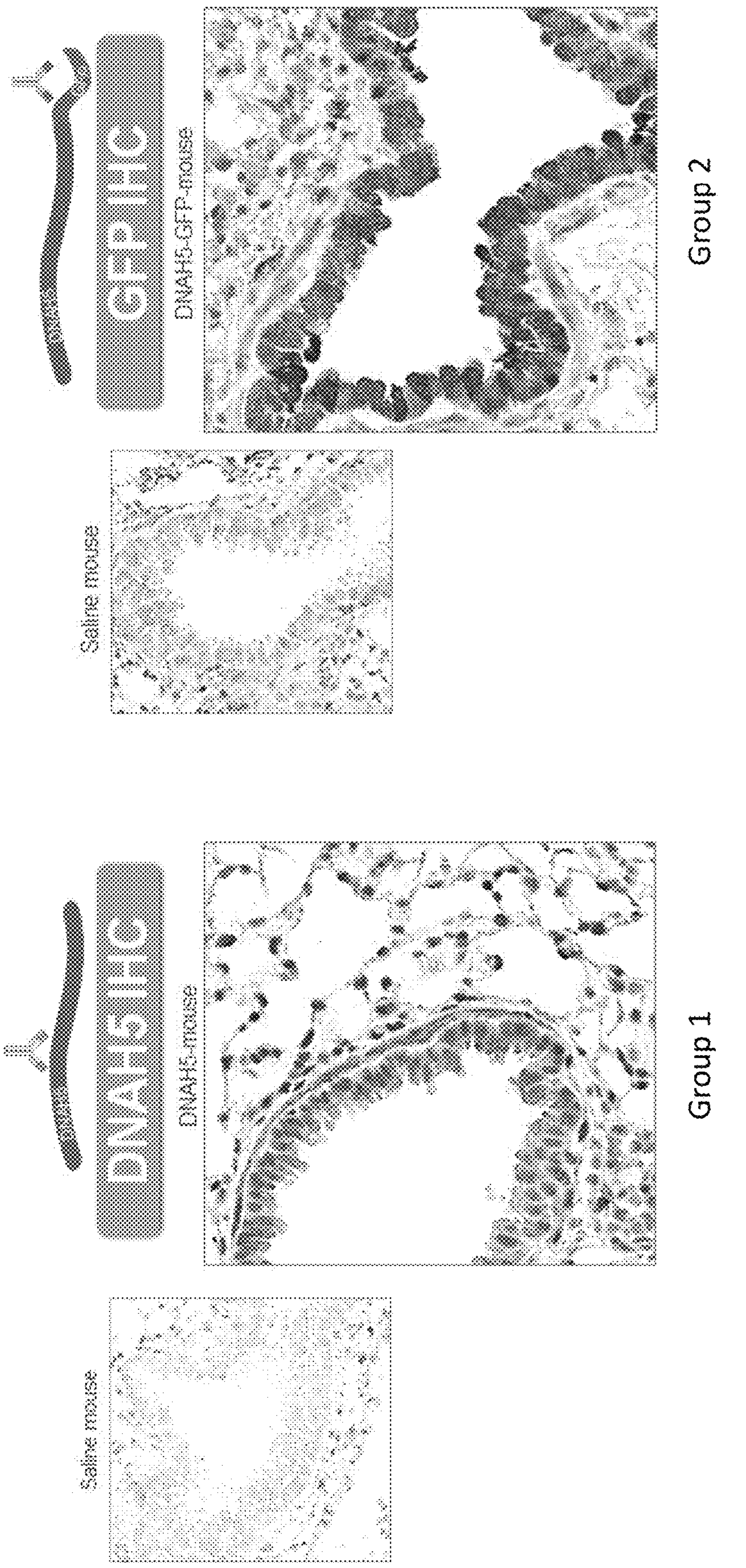
FIG. 2A and FIG. 2B show series of photomicrographs depicting results from IHC analysis for hDNA protein expression in the respiratory airways.
Figure 2B:
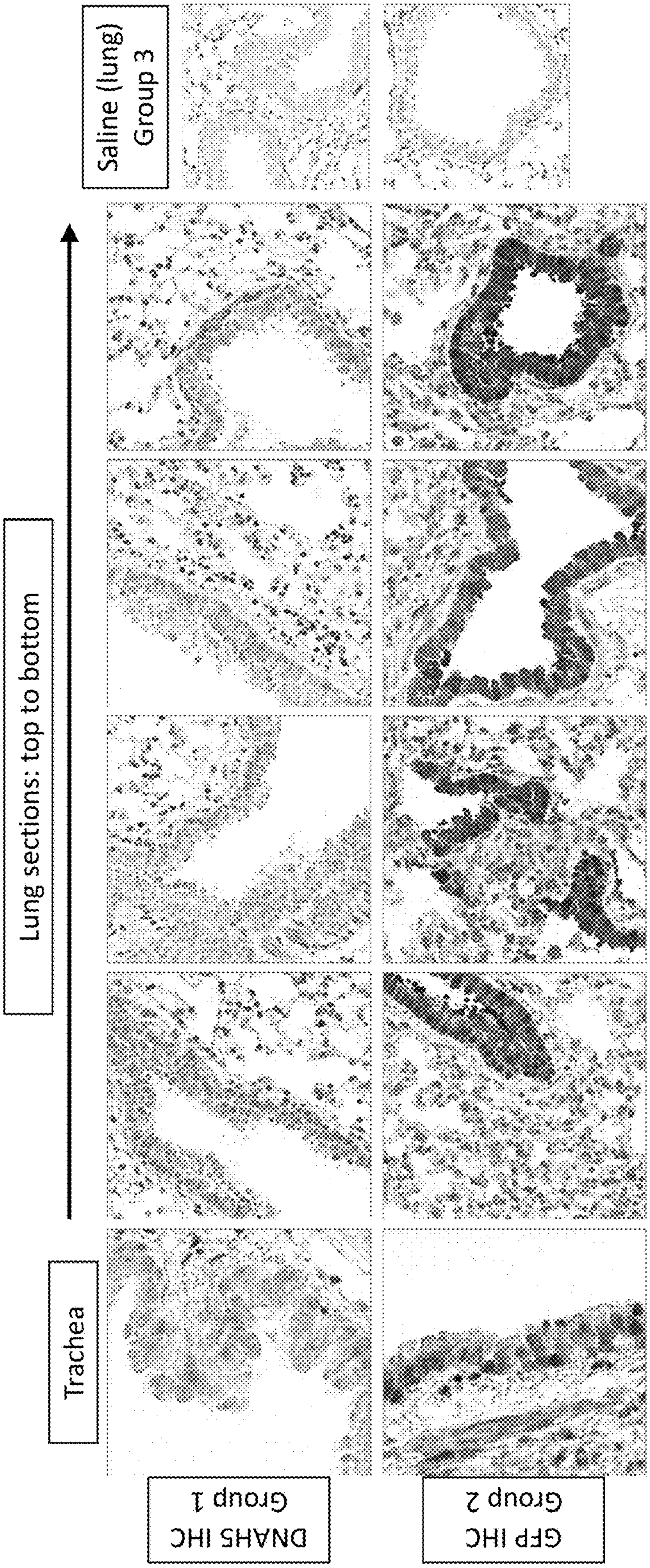

This Example shows the successful in vivo administration, delivery and expression of a greater than 10 kb therapeutic mRNA. In particular, in this Example, hDNAH5 mRNA, a 14 kb mRNA, was successfully encapsulated, administered by nebulization and delivered in vivo to the lung. FIG. 1B provides qPCR data showing successful hDNAH5 mRNA deposition in cells in each of the trachea (1), superior lobe (2), middle lobe (3), inferior lobe (4), and post-caval lobe (5) of the lung for each mouse in Groups 1 and 2. FIG. 2A provides exemplary IHC images showing positive staining for hDNAH5 protein expressed from the hDNAH5 mRNA lung tissue from mice in each of Groups 1 and 2. Further, FIG. 2B shows IHC images with positive staining for hDNAH5 protein, from mice in Groups 1 and 2, in tissue from the trachea as well as tissue across the entire lung, from top to bottom (left to right in FIG. 2B).

Exemplary Sequences

Exemplary codon-optimized mRNA sequences are shown in SEQ ID NO: 6-31. For the purpose of the sequence disclosure, U and T are used interchangeably.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of delivery of human dynein heavy chain 5 (DNAH5) for in vivo trachea expression comprising administering to a subject in need of delivery of an mRNA encoding a human DNAH5 protein encapsulated in a liposome, wherein the liposome comprises one or more cationic lipids, one or more non-cationic lipids, and one or more PEG-modified lipids, wherein the mRNA is administered via nebulization at an administration interval of once a week, twice a week, or once a day such that the administration results in sustained DNAH5 expression in the trachea of the subject.

2. The method of claim 1, wherein the liposome comprises one or more cholesterol based lipids.

3. The method of claim 1, wherein the administration results in DNAH5 expression in the lung.

4. The method of claim 1, wherein the liposome has a diameter of about 80 nm to 200 nm.

5. The method of claim 4, wherein the liposome has a diameter of about or less than 100 nm.

6. The method of claim 1, wherein the cationic lipid constitutes about 30-60% of the liposome by molar ratio.

7. The method of claim 1, wherein the mRNA encoding a human DNAH5 protein is codon optimized.

8. The method of claim 1, wherein the mRNA encoding a human DNAH5 protein comprises one or more modified nucleotides.

9. A method of delivery of human dynein heavy chain 5 (DNAH5) for in vivo trachea expression comprising administering to a subject in need of delivery of an mRNA encoding a human DNAH5 protein encapsulated in a liposome, wherein the liposome comprises one or more cationic lipids, one or more non-cationic lipids, and one or more PEG-modified lipids, wherein the mRNA is administered via nebulization at an administration interval of at least once a week, twice a week, or once a day such that the administration results in detectable DNAH5 expression encoded by the mRNA in the trachea of the subject 24 hours after the first administration.

10. The method of claim 9, wherein the liposome comprises one or more cholesterol based lipids.

11. The method of claim 9, wherein the administration results in DNAH5 expression in the lung.

12. The method of claim 9, wherein the liposome has a diameter of about 80 nm to 200 nm.

13. The method of claim 12, wherein the liposome has a diameter of about or less than 100 nm.

14. The method of claim 9, wherein the cationic lipid constitutes about 30-60% of the liposome by molar ratio.

15. The method of claim 9, wherein the mRNA encoding a human DNAH5 protein is codon optimized.

16. The method of claim 9, wherein the mRNA encoding a human DNAH5 protein comprises one or more modified nucleotides.

* * * * *